US012049514B2

(12) United States Patent
Bamdad et al.

(10) Patent No.: US 12,049,514 B2
(45) Date of Patent: *Jul. 30, 2024

(54) ANTI-NME ANTIBODY AND METHOD OF TREATING CANCER OR CANCER METASTASIS

(71) Applicant: Minerva Biotechnologies Corporation, Waltham, MA (US)

(72) Inventors: Cynthia Bamdad, Waltham, MA (US); Benoit Smagghe, Waltham, MA (US)

(73) Assignee: MINERVA BIOTECHNOLOGIES CORPORATION, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/000,249

(22) PCT Filed: Jun. 8, 2021

(86) PCT No.: PCT/US2021/036500
§ 371 (c)(1),
(2) Date: Nov. 29, 2022

(87) PCT Pub. No.: WO2021/252551
PCT Pub. Date: Dec. 16, 2021

(65) Prior Publication Data
US 2023/0279141 A1     Sep. 7, 2023

Related U.S. Application Data

(60) Provisional application No. 63/046,852, filed on Jul. 1, 2020, provisional application No. 63/044,670, filed on Jun. 26, 2020, provisional application No. 63/036,288, filed on Jun. 8, 2020.

(51) Int. Cl.
*C07K 16/30* (2006.01)
*A01K 67/0275* (2024.01)
*A61P 35/00* (2006.01)

(52) U.S. Cl.
CPC .......... *C07K 16/30* (2013.01); *A01K 67/0275* (2013.01); *A61P 35/00* (2018.01); *C07K 2317/24* (2013.01); *C07K 2317/35* (2013.01); *C07K 2317/55* (2013.01); *C07K 2317/565* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 5,631,271 A | 5/1997 | Serfontein | |
| 6,818,749 B1 | 11/2004 | Kashmiri et al. | |
| 9,814,782 B2 | 11/2017 | Park et al. | |
| 2003/0022306 A1 | 1/2003 | Bandman et al. | |
| 2003/0109690 A1 | 6/2003 | Ruben et al. | |
| 2004/0057952 A1 | 3/2004 | Payne et al. | |
| 2010/0316688 A1 | 12/2010 | Bamdad | |
| 2013/0287748 A1 | 10/2013 | June et al. | |
| 2014/0010861 A1 | 1/2014 | Bancel et al. | |
| 2015/0037371 A1 | 2/2015 | Landry | |
| 2015/0252430 A1 | 9/2015 | Bryant et al. | |
| 2017/0119903 A1 | 5/2017 | Park et al. | |
| 2017/0204196 A1 | 7/2017 | Bamdad et al. | |
| 2018/0230225 A1 | 8/2018 | Fan et al. | |
| 2018/0258186 A1 | 9/2018 | Bamdad et al. | |
| 2019/0031778 A1 | 1/2019 | Bamdad et al. | |
| 2019/0031779 A1 | 1/2019 | Bamdad et al. | |
| 2019/0290692 A1 | 9/2019 | Bamdad et al. | |
| 2019/0389956 A1 | 12/2019 | Zhang et al. | |
| 2020/0165354 A1 | 5/2020 | Liu et al. | |
| 2022/0259324 A1 | 8/2022 | Bamdad et al. | |
| 2022/0289865 A1 | 9/2022 | Bamdad et al. | |
| 2023/0242678 A1 | 8/2023 | Bamdad et al. | |

FOREIGN PATENT DOCUMENTS

| | | |
|---|---|---|
| CN | 101918844 A | 12/2010 |
| CN | 104220458 A | 12/2014 |
| WO | WO-2004050860 A2 | 6/2004 |
| WO | WO-2008157490 A1 | 12/2008 |
| WO | WO-2010031749 A1 | 3/2010 |
| WO | WO-2010042562 A2 | 4/2010 |
| WO | WO-2013059373 A2 | 4/2013 |
| WO | WO-2014018679 A2 | 1/2014 |
| WO | WO-2014028668 A2 | 2/2014 |
| WO | WO-2014052693 A2 | 4/2014 |
| WO | WO-2014130741 A2 | 8/2014 |
| WO | WO-2015157322 A2 | 10/2015 |
| WO | WO-2018071583 A2 | 4/2018 |
| WO | WO-2019104306 A1 | 5/2019 |
| WO | WO-2020163325 A1 | 8/2020 |
| WO | WO-2021252551 A2 | 12/2021 |
| WO | WO-2021263227 A2 | 12/2021 |

OTHER PUBLICATIONS

Stedman's Medical dictionary, 2000, lines 1-3 (Year: 2000).*
Apantaku et al. (Breast cancer diagnosis and screening, American Family Physician 2000) (Year: 2000).*
Martin et al (Journal of the National Cancer Institute, vol. 92, No. 14: pp. 1126-1135, Jul. 19, 2000) (Year: 2000).*
Desvignes et al., Nme protein family evolutionary history, a vertebrate perspective. BMC Evol Biol. 9:256 [1-25] (2009).
Expression of NME7 in cancer - Summary - The Human Protein Atlas, printed Mar. 2018.
Human Protein Atlas (2 pp.) printed Oct. 2, 2020.
Nm23-H7 (C-15): sc-82256 datasheet by Santa Cruz Biotechnology https://datasheets.scbt.com/sc-82256.pdf (ret. 2014).
PCT/US2015/024764 International Search Report and Written Opinion dated Oct. 28, 2015.
PCT/US2020/016570 International Search Report and Written Opinion dated May 21, 2020.

(Continued)

*Primary Examiner* — Meera Natarajan
(74) *Attorney, Agent, or Firm* — WILSON SONSINI GOODRICH & ROSATI

(57) ABSTRACT

The present application discloses anti-NME antibodies and their use in treating or preventing diseases.

16 Claims, 58 Drawing Sheets

Specification includes a Sequence Listing.

(56) References Cited

OTHER PUBLICATIONS

PCT/US2021/036500 International Search Report and Written Opinion dated Aug. 3, 2022.
PCT/US2021/039291 International Invitation to Pay Additional Fees dated Oct. 18, 2021.
PCT/US2021/039291 International Search Report and Written Opinion dated Dec. 30, 2021.
U.S. Appl. No. 17/719,302 Office Action dated Jun. 2, 2023.
Bendig. Humanization of rodent monoclonal antibodies by CDR grafting. Methods: A Companion to Methods in Enzymology 8:83-93 (1995).
Bonsignori et al. Maturation Pathway from Germline to Broad HIV-1 Neutralizer of a CD4-Mimic Antibody. Cell 165(2):449-463 (2016).
Panka et al. Variable region framework differences result in decreased or increased affinity of variant anti-digoxin antibodies. PNAS USA 85:3080-3084 (1988).
Paul. Fundamental Immunology, 3rd Edition, Chapter 9, pp. 292-295 (1993).
Rudikoff et al., Single Amino Acid Substitution Altering Antigen-binding Specificity. PNAS USA 79(6): 1979-1983 (Mar. 1982).
U.S. Appl. No. 17/392,981 Office Action dated Nov. 16, 2023.
U.S. Appl. No. 17/719,302 Office Action dated Jan. 30, 2024.
U.S. Appl. No. 17/719,302 Office Action dated Sep. 14, 2023.
U.S. Appl. No. 18/002,832 Office Action dated Nov. 6, 2023.

\* cited by examiner

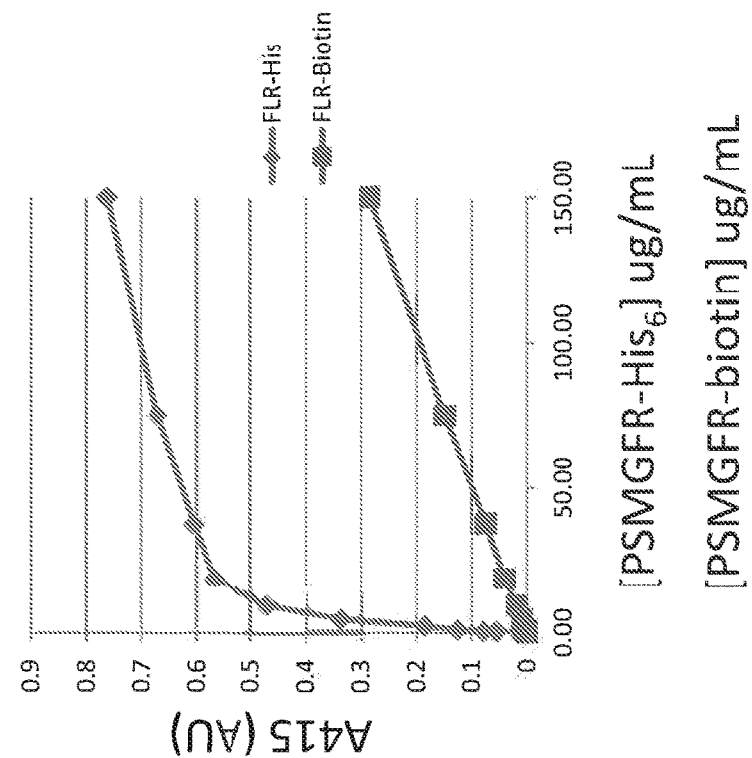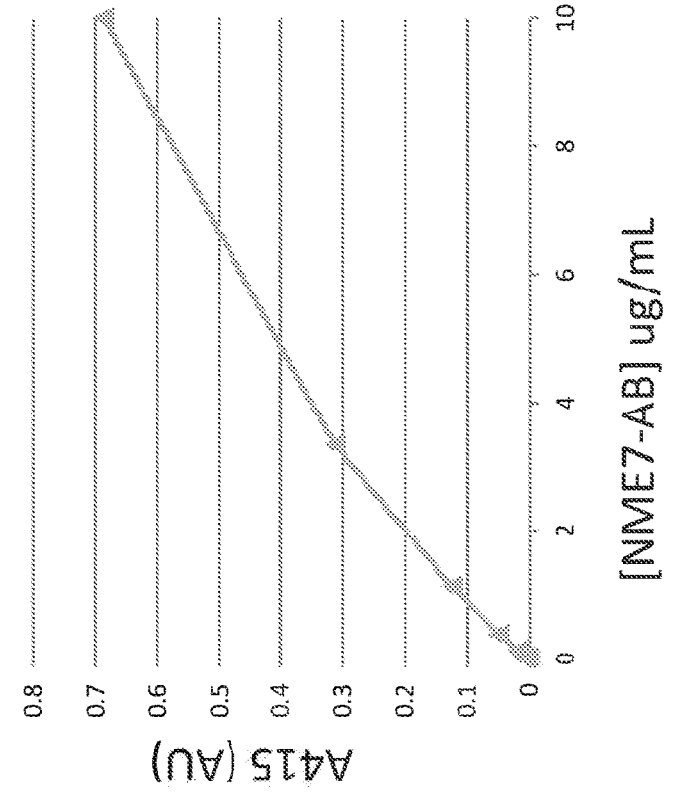
Fig. 1A
Fig. 1B
ELISA shows NME7 Dimerizes MUC1*
MUC1* extra cellular domain peptide immobilized on plate was bound by NME7 to saturation; a second MUC1* peptide with a C-terminal His-tag or Biotin tag was added and visualized by HRP labeled antibody to either His-tag or HRP labeled streptavidin

Figure 5
Sequence alignment of human NME1 to human NME7-A and –B domains

```
NME1      MANCERTFIAIKPDGVQRGLVGEIIKRFEQKGFRLVGLKFMQASEDLLKEHYVDLKDRPF 60
NME7A     -----EKTLALIKPDAISK---AGEIIEIINKAGFTITKLKMMMLSRKEALDFHVDHQSRPF 54
              *:*:  ****.:.: .****: ::: ** :. **:*  *..  :.:** :.***

NME1      FAGLVKYMHSGPVVAMVWEGLNVVKTGRVMLGETNP-----ADSKPGTIRGDFCIQVGPNII 117
NME7A     FNELIQFITTGPIIAMEILRDDAICEWKRLLGPANSGVARTDASESIRALFGTDGIRNAA  114
          *  *::::  :**::**      :.:    :  :** :*.   . . :**. *  :  **

NME1      HGSDSVESAEKEIGLWFHPEELVDYTSCAQNWIYE 152
NME7A     HGPDSFASAAREMELFF------------------ 131
          **.**. ** :*: *:*

NME1      MANCERTFIAIKPDGVQRGLVGEIIKRFEQKGFPLVGLKFMQASEDLLKEHYVDLK-DRP 59
NME7B     ----NCTCCIVKPHAVSEGLLGKILMAIRDAGFEISAMQMFNMDRVNVEEFYEVYKGVVT 56
              : *   :**..*..**:*:*   :.: **.: .:::::  ..   ::*.*   *  .

NME1      FFAGLVKYMHSGPVVAMVWEGLNVVKTGRVMLGETNPADS----KPGTIRGDFCIQVGRNI 116
NME7B     EYHDMVTEMYSGPCVAMEIQQNNATKTFREFCGPADPEIARHLRPGTLRAIFGKTKIQNA  116
           : .:*. *:*** ***   :   *..** * : * ::*   :   :***:*. *    :*

NME1      IHGSDSVESAEKEIGLWFHPEELVDYTSCAQNWIYE 152
NME7B     VHCTDLPEDGLLEVQYFFKILDN------------- 139
          :*  :*    *.. *: :*:    :
```

Figure 6

NME7 specific peptides for generating antibodies to inhibit NME7 for the treatment or prevention of cancers.

The following peptide sequences are identified as being immunogenic peptides giving rise to antibodies that target human NME7 but not human NME1. The sequences were chosen for their lack of sequence homology to human NME1.

1. LALIKPDA
2. MMMLSRKEALDFHVDHQS
3. ALDFHVDHQS
4. EILRDDAICEWKRL
5. FNELIQFITTGP
6. RDDAICEW
7. SGVARTDASESIRALFGTDGIRNAA
8. ELFFPSSGG
9. KFTNCTCCIVKPHAVSEGLLGKILMA
10. LMAIRDAGFEISAMQMFNMDRVNVEEFYEVYKGVVT
11. EFYEVYKGVVTEYHD
12. EIQQNNATKTFREFCGPADPEIARHLRPGTLRAIFGKTKIQNA
13. YSGPCVAM
14. FREFCGP
15. VHCTDLPEDGLLEVQYFFKILDN
16. IQNAVHCTD
17. TDLPEDGLLEVQYFFKILDN
18. PEDGLLEVQYFFK
19. EIINKAGFTITK
20. MLSRKEALDFHVDHQS
21. NELIQFITT
22. EILRDDAICEWKRL
23. SGVARTDASESIRALFGTDGI
24. SGVARTDASES

Figure 6 (Continued)

25. ALFGTDGI
26. NCTCCIVKPHAVSE
27. LGKILMAIRDA
28. EISAMQMFNMDRVNVE
29. EVYKGVVT
30. EYHDMVTE
31. EFCGPADPEIARHLR

Figure 7

NME7 specific peptides for generating antibodies to inhibit NME7 for the treatment or prevention of cancers.

The following are preferred as they are likely areas that are important for structural integrity or for binding to the MUC1* peptide. Bivalent antibodies wherein each variable region would bind to each one of a pair are preferred.

35. ICEWKRL
36. LGKILMAIRDA

37. HAVSEGLLGK
38. VTEMYSGP

39. NATKTFREF
40. AIRDAGFEI

41. AICEWKRLLGPAN
42. DHQSRPFF

43. AICEWKRLLGPAN
44. VDHQSRPF
45. PDSFAS
46. KAGEIIEIINKAGFTITK

Figure 8

The following peptide sequences are from human NME1 and were selected for their high homology to human NME7 as well as for their homology to other bacterial NME proteins that are able to mimic its function.

47. MANCERTFIAIKPDGVQRGLVGEIIKRFE
48. VDLKDRPF
49. HGSDSVESAEKEIGLWF

Especially preferred for their high homology to human NME7-A or -B and also to HSP 593 are:

50. ERTFIAIKPDGVQRGLVGEIIKRFE
51. VDLKDRPFFAGLVKYMHSGPVVAMVWEGLN
52. NIIHGSDSVESAEKEIGLWFHPEELV
53. KPDGVQRGLVGEII

Figure 9

NME7-AB specific peptides preferred for generating antibodies for the treatment or prevention of cancer.

NME7A peptide 1
MLSRKEALDFHVDHQS

NME7A peptide 2
SGVARTDASES

NME7B peptide 1
DAGFEISAMQMFNMDRVNVE

NME7B peptide 2 EVYKGVVTEYHDMVTE

NME7B peptide 3
AIFGKTKIQNAVHCTDLPEDGLLEVQYFF

NME7B peptide 3 Cys to Ser mutation
AIFGKTKIQNAVHSTDLPEDGLLEVQYFF

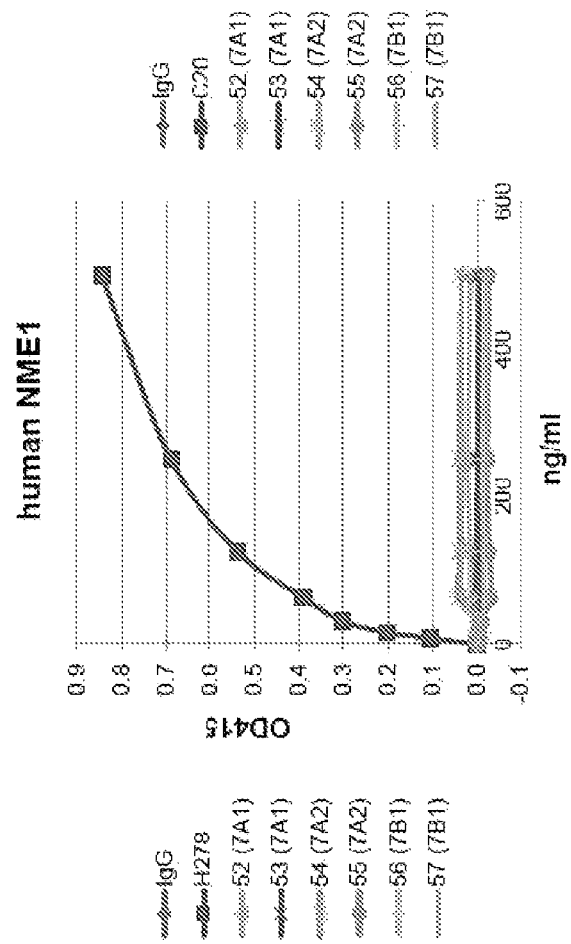
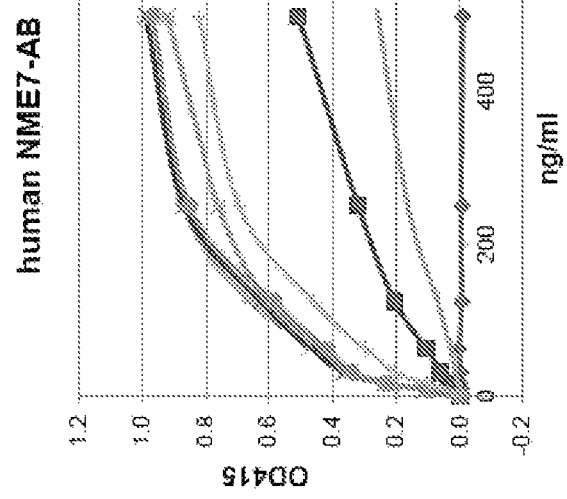
Fig. 10A, Fig. 10B. Anti-NME7 antibodies generated with peptides A1, A2, B1, B2 & B3 bind to NME7 (left) but not to NME1 (right); C20 is an anti-NME1 antibody Treating cancer cells with anti-NME7 antibodies inhibits transition to "floater" cells, which PCR shows have greatly increased expression of metastatic markers such as CXCR4; xenograft experiments show that the floater cells form a tumor at extremely low copy number – 50 – and thus fulfill the requirement for being classified cancer stem cells or metastatic cancer cells.

Fig. 14A

| Antibodies | Floater observation |
|---|---|
| Control IgG | 100% |
| 53, 55, 57 (A1, A2, B1) | 70% |
| 53, 57 (A1, B1) | 50% |
| 61 (B3) | 5% |

JR observations

The number of "Floater" cells, which are the ones that have higher expression of metastatic markers and that form tumors in animals at extremely low copy number is typically 20% of the amount of plated cells by Day 7. Here, we define 100% as the number of floater cells that results when a control antibody is added. Other percentages of floater cells is relative to the control in which a control IgG antibody was added.

Fig. 14B

| Antibodies | Floater observation |
|---|---|
| Control IgG | 100% |
| 53, 55, 57 (A1, A2, B1) | 65% |
| 53, 57 (A1, B1) | 40% |
| 61 (B3) | 5% |

VH observations

| Cell Line T47D | Medium | Total RNA ng/µL | Yield (µg) | EEF1A1 Threshold Cycle |
|---|---|---|---|---|
| CONTROLS | | | | |
| Control | RPMI + 10% FBS | 395.8 | 47.49 | 15.2 |
| 2i attached | MM + 2i | 387.8 | 11.64 | 14.5 |
| 2i Floaters | MM + 2i | 234.6 | 7.04 | 14.9 |
| NME7 attached | MM+NME7 4nM | 334.8 | 10.04 | 14.7 |
| NME7 Floaters | MM+NME7 4nM | 259.2 | 7.78 | 16.0 |
| 2i+ Antibody B3 rabbit 61 attached | MM + 2i | 2.7 | 0.08 | 25.9 |
| 2i+ Antibody B3 rabbit 61 Floaters | MM + 2i | 3.6 | 0.11 | 25.0 |
| 2i + Antibody Combination 3 attached | MM + 2i | 44.7 | 1.34 | 17.0 |
| 2i+ Antibody Combination 3 Floaters | MM + 2i | 39.0 | 1.17 | 15.9 |
| 2i+ Antibody Combination 2 attached | MM + 2i | 46.0 | 1.38 | 15.6 |
| 2i+ Antibody Combination 2 Floaters | MM + 2i | 77.8 | 2.33 | 16.3 |
| NME7+ Antibody B3 rabbit 61 attached | MM+NME7 4nM | 65.7 | 1.97 | 17.0 |
| NME7+ Antibody B3 rabbit 61 Floaters | MM+NME7 4nM | 15.8 | 0.47 | 19.9 |
| NME7+ Antibody Combination 3 attached | MM+NME7 4nM | 32.1 | 0.96 | 17.0 |
| NME7+ Antibody Combination 3 Floaters | MM+NME7 4nM | 109.2 | 3.28 | 16.1 |
| NME7+ Antibody Combination 2 attached | MM+NME7 4nM | 134.5 | 4.03 | 16.1 |
| NME7+ Antibody Combination 2 Floaters | MM+NME7 4nM | 139.5 | 4.19 | 18.6 |

Figure 16

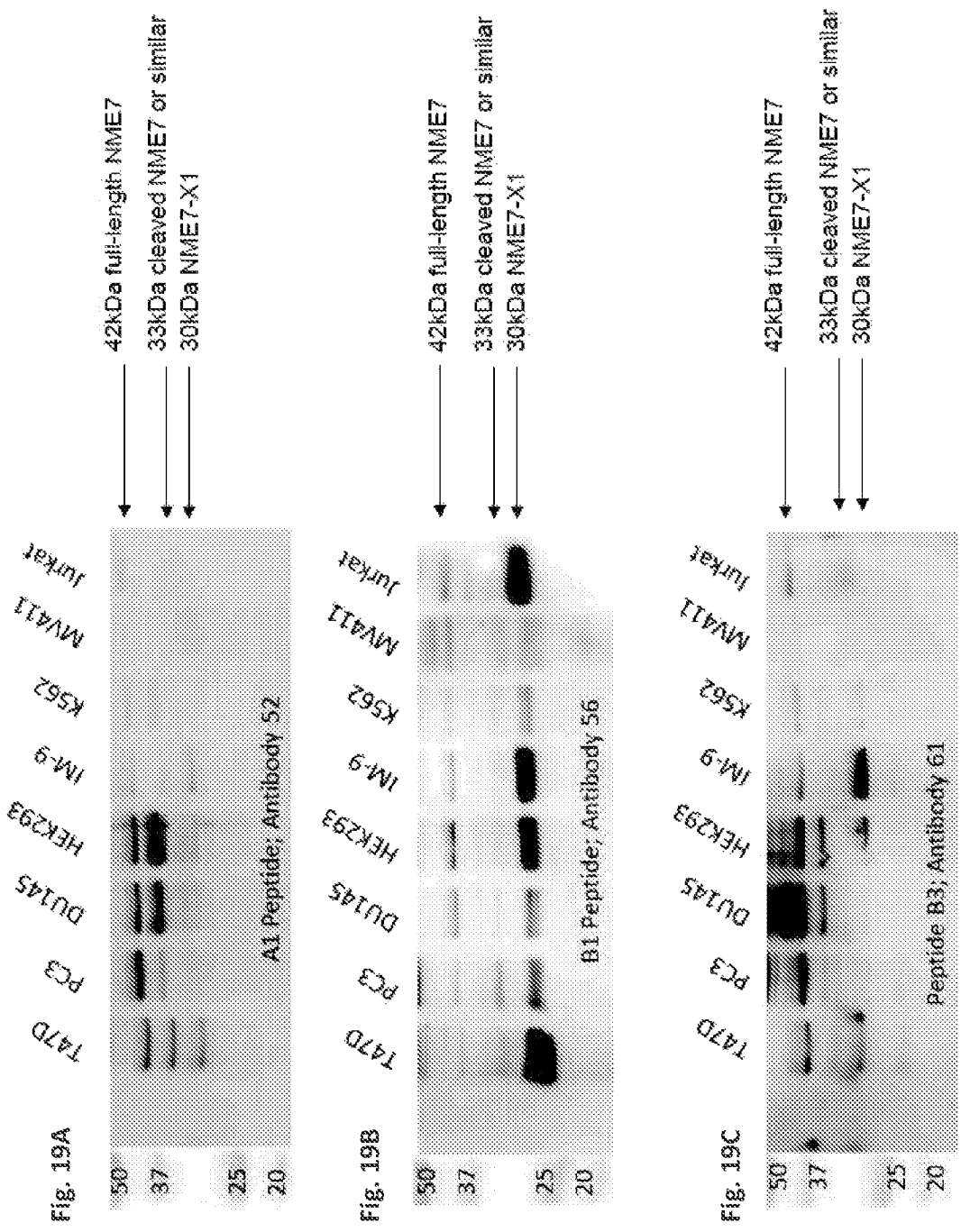

Various cancer cell lines express both full-length MUC1 and MUC1*

T47D – MUC1 positive breast cancer
PC3 – MUC1 negative prostate cancer
DU145 – MUC1 positive prostate cancer
BT-474 – HER2 positive breast cancer
CHL-1 – melanoma
A2058 – melanoma
CAPAN-2 – MUC1 positive pancreatic cancer
PANC-1 – MUC1 negative pancreatic cancer

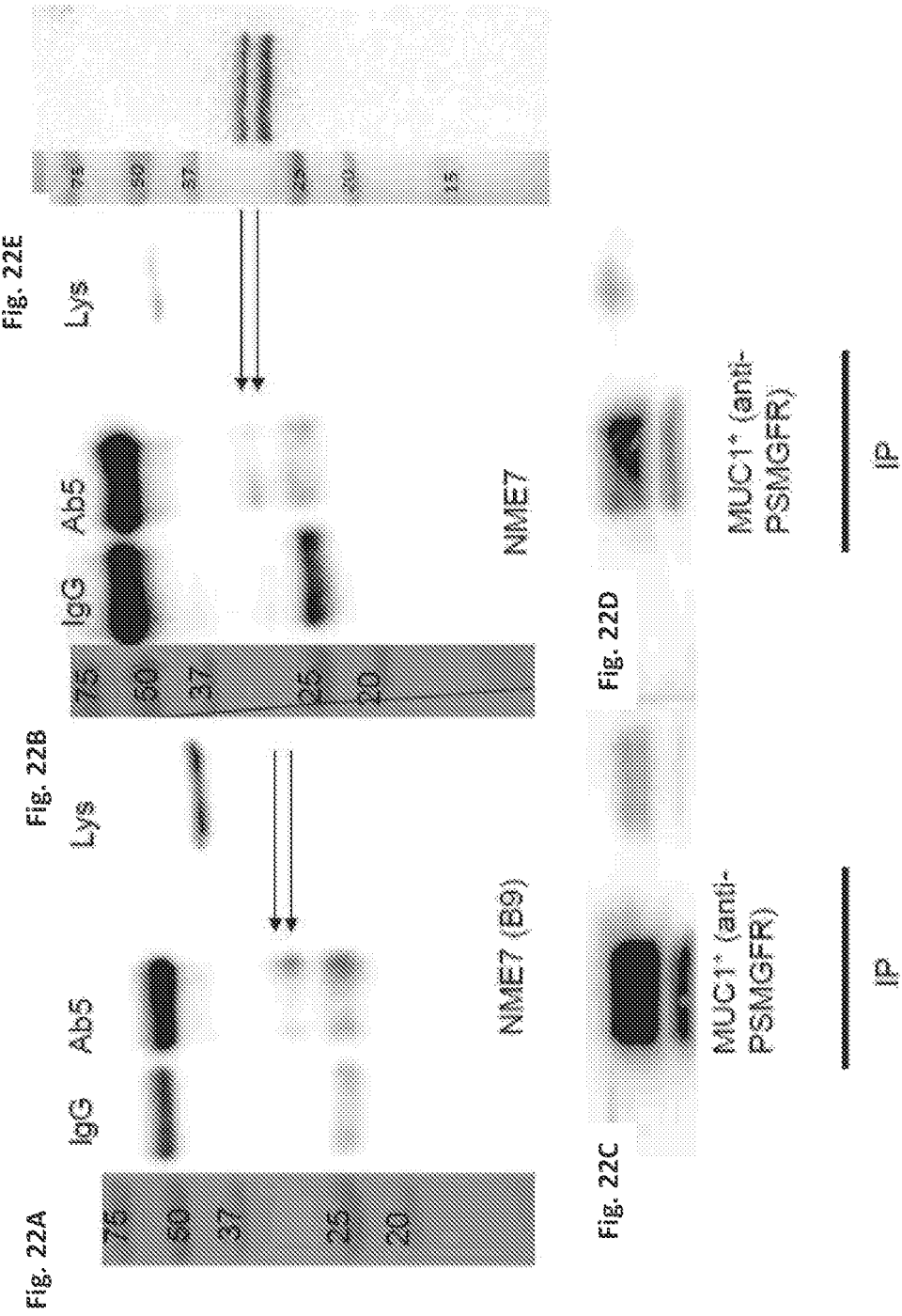

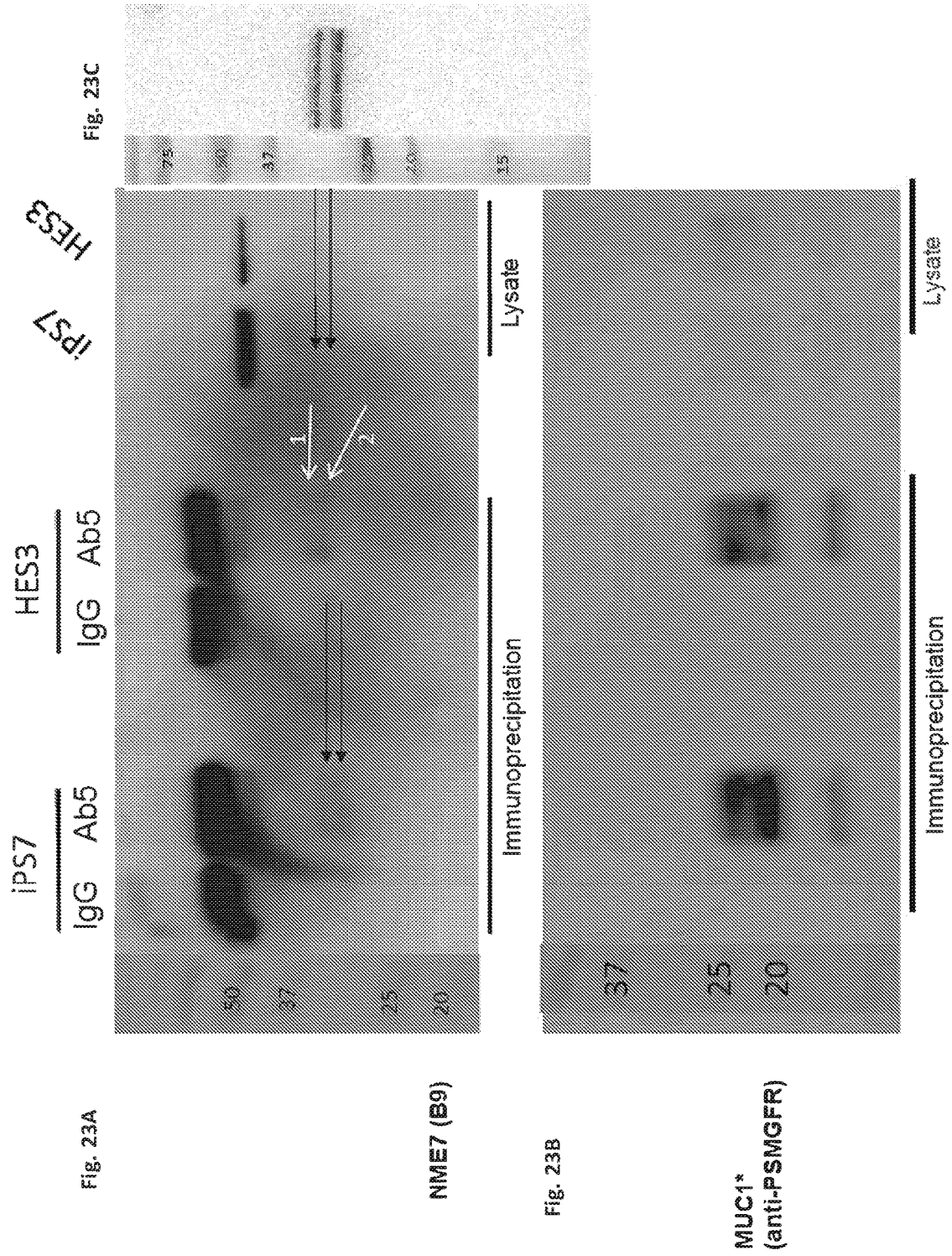

Onco-embryonic growth factor NME7 transforms cancer cells into metastatic cancer stem cells Day 6

500K T47D-wt breast cancer cells injected into tail vein

10K T47D breast cancer grown for 10 days in NME7 injected into tail vein

Day 10 T47D-CSC (cancer stem cells) @ 10K vs wt @ 500K +/- anti-NME7 treatment; Day 7 was 1st antibody injection but was done just after injection of NME7
Fig. 34A  Fig. 34B  Fig. 34C  Fig. 34D
T47D-wt
500K i.v.
Day 10
No Antibody
T47D-CSC
10K i.v.
Day 10
+ Antibody
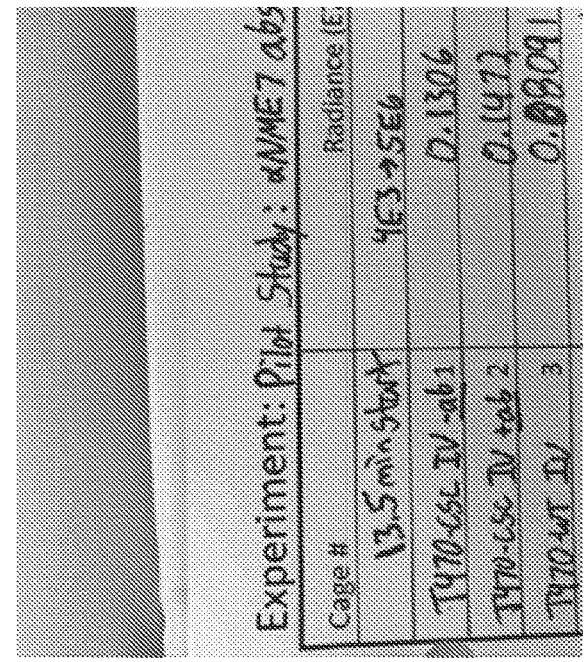
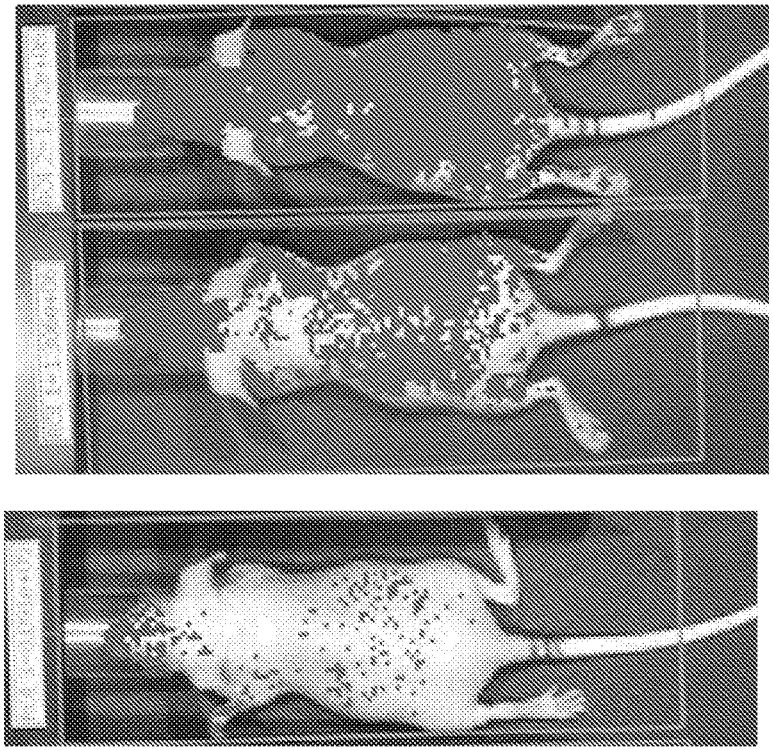

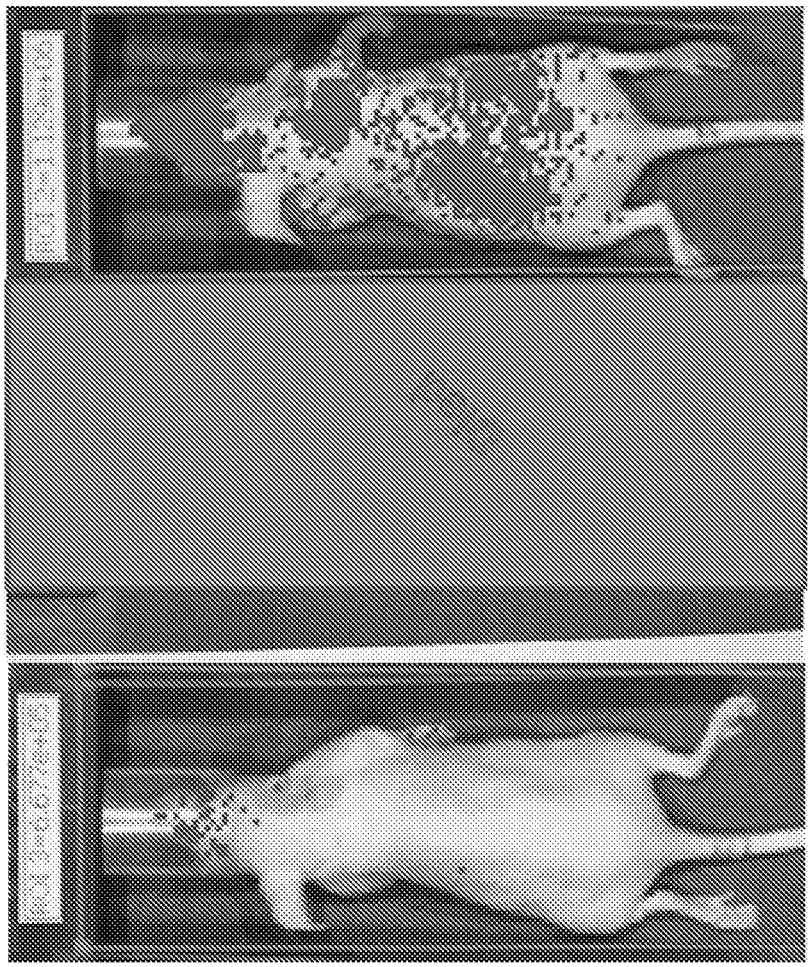

Day 14 T47D-CSC @ 10K vs wt @ 500K; CSC mouse had 3 anti-NME7 injections, although 1st injection was at same time as NME7 injection T47D-wt
500K i.v.
Day 14
No Antibody

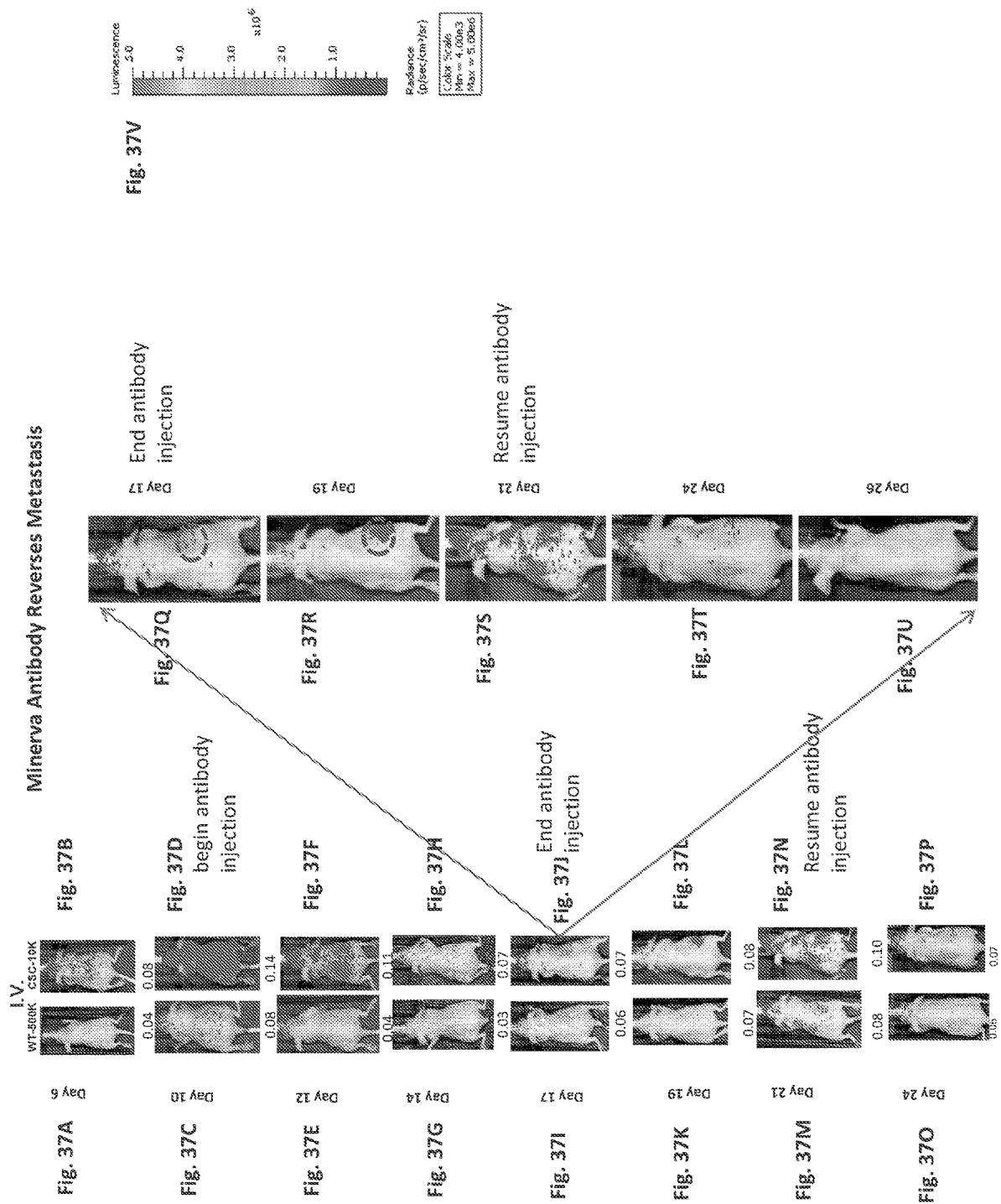

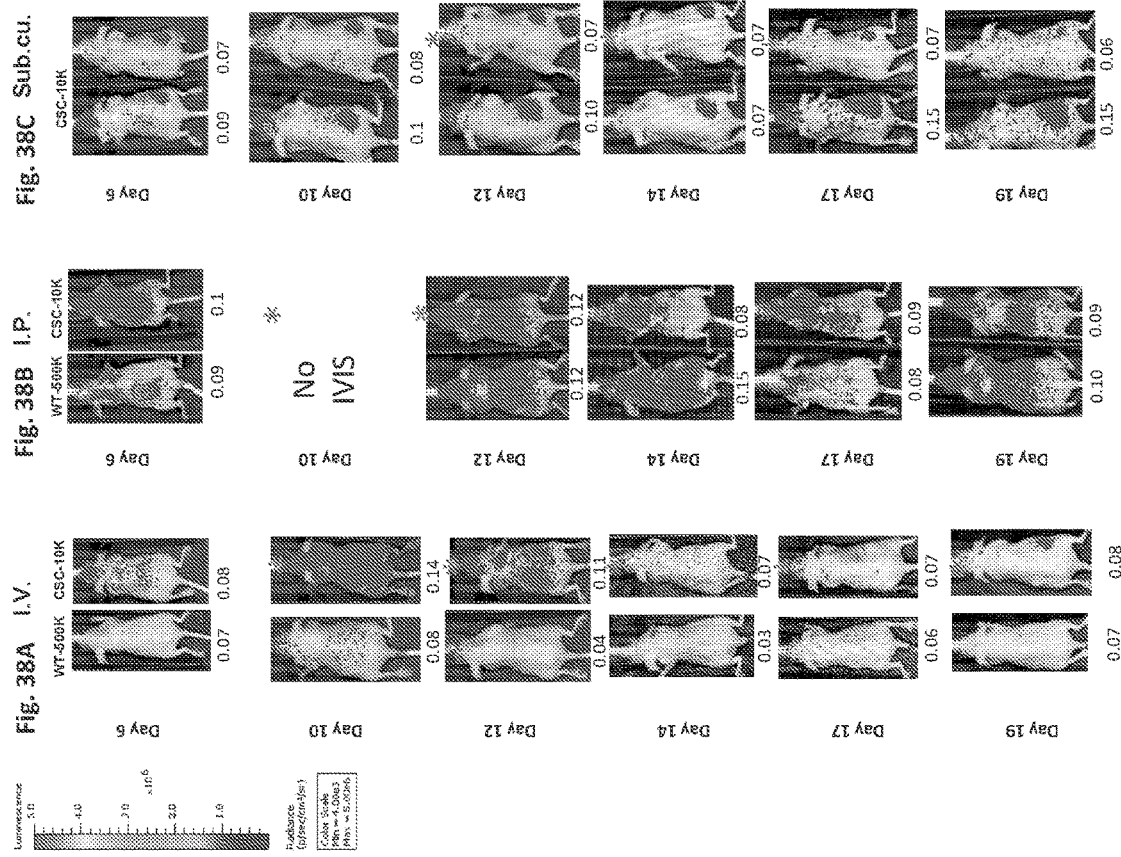

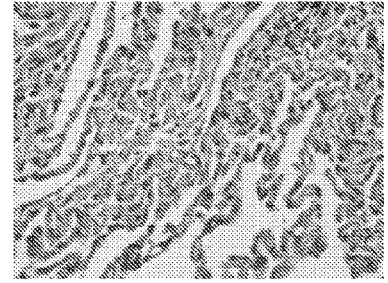 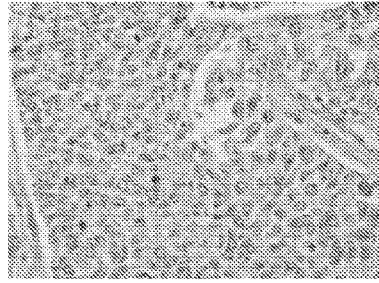 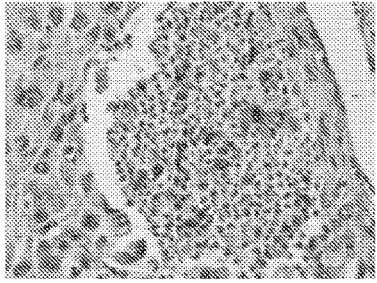
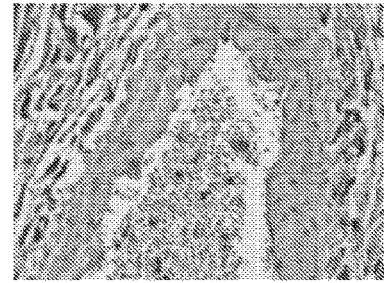 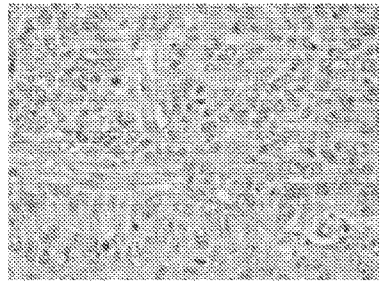 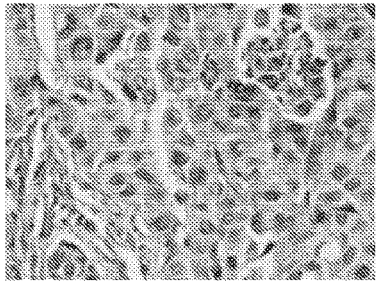
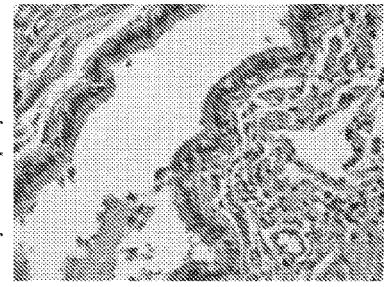 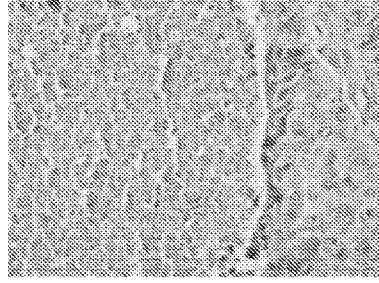 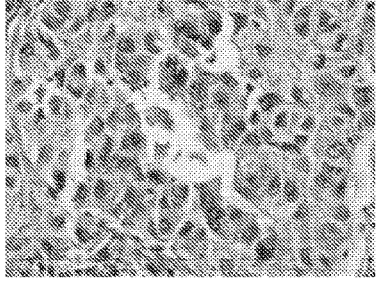
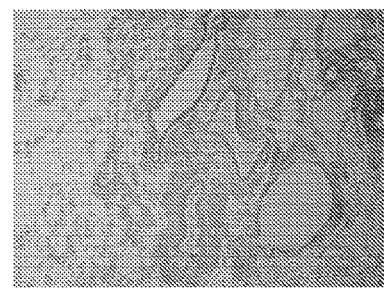 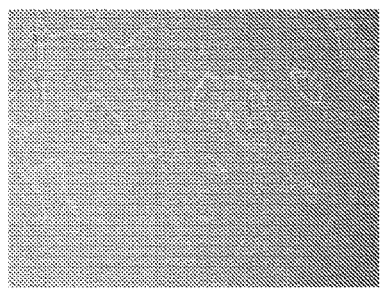 
Lung
Normal
61
10 ug/ml
61 = Minerva's anti-NME7 antibody
Fig. 39A
Tumor Grade 2
61
10 ug/ml
Fig. 39B
Tumor Grade 3
(T2N0M0) Clinical IB
61
10 ug/ml
Fig. 39C

Small Intestine
Normal
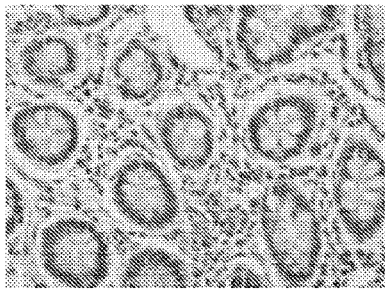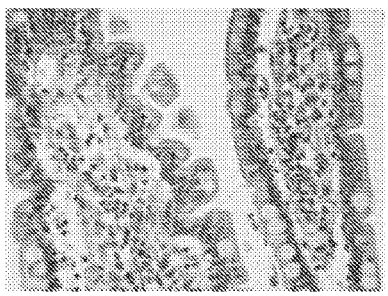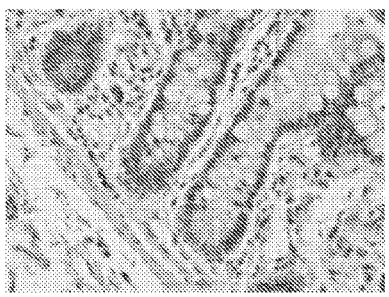
Fig. 40A
61
10 ug/ml
61 = Minerva's anti-NME7 antibody
Tumor Grade 2
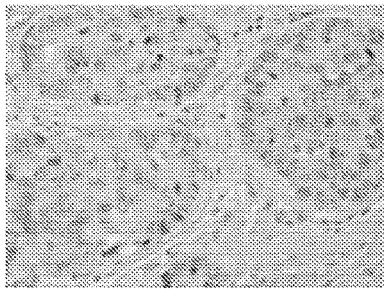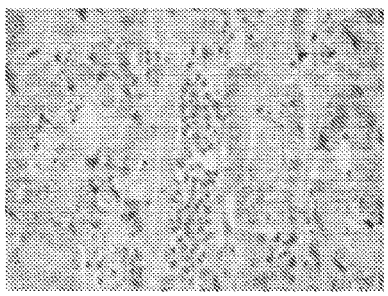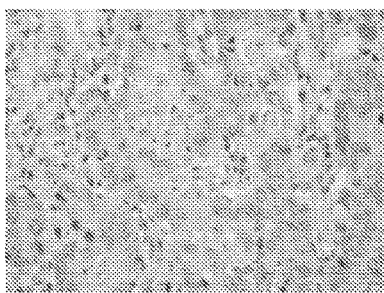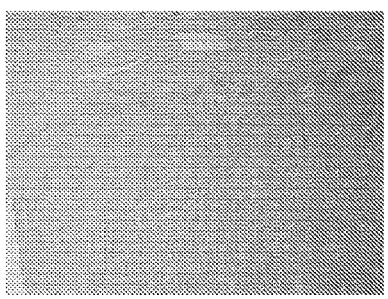
Fig. 40B
61
10 ug/ml
Tumor Grade 3
(T3N0M0) Clinical II
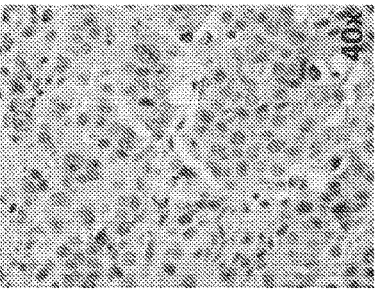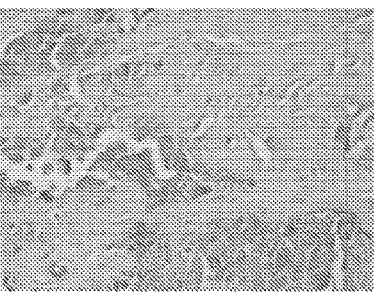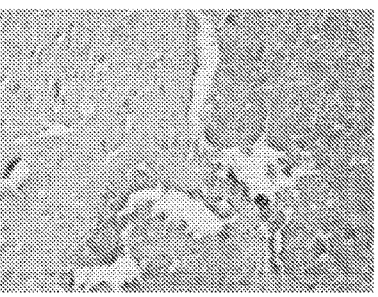
Fig. 40C
61
10 ug/ml

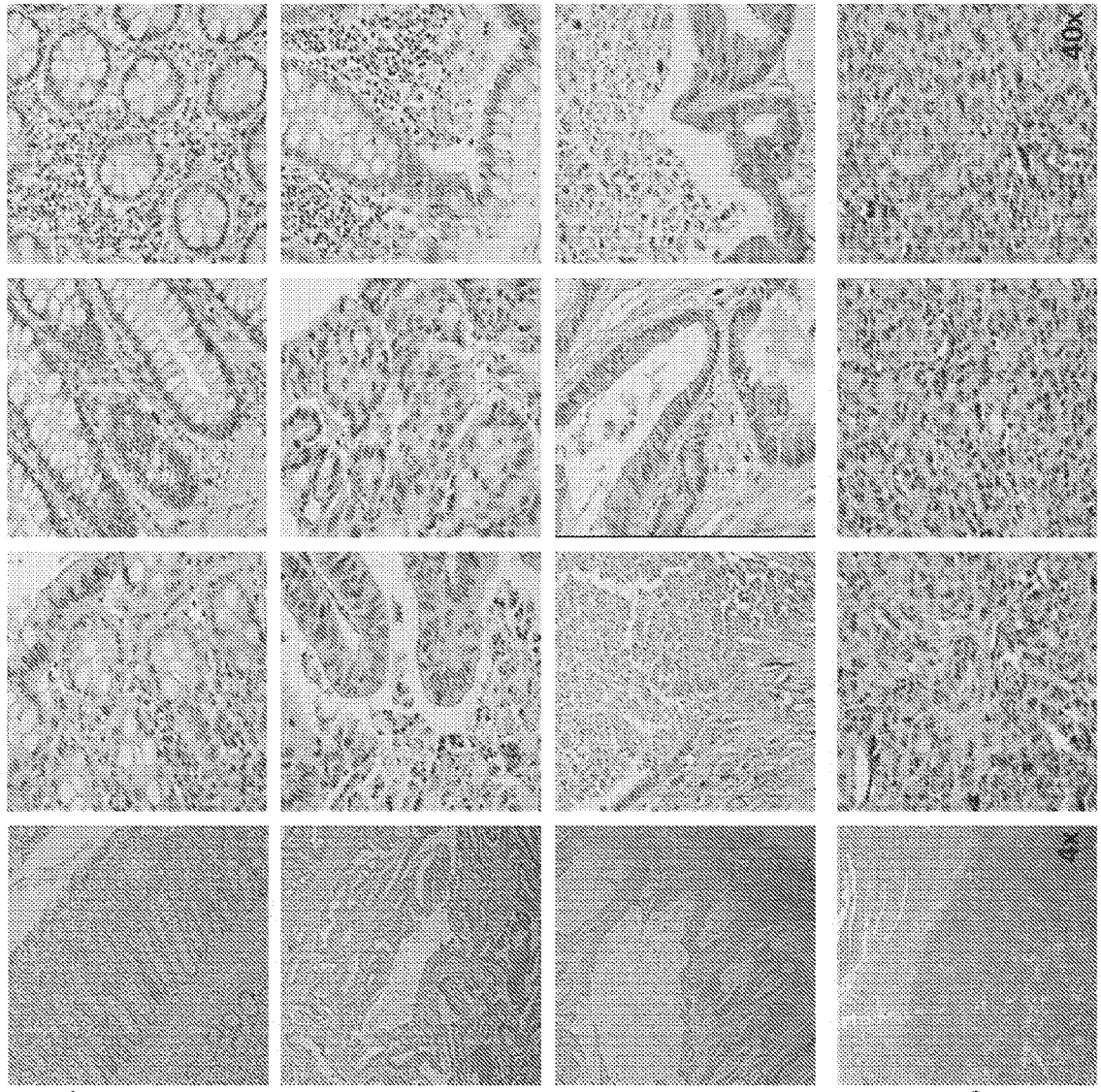
Fig. 41A Colon Normal, 61, 10 ug/ml, 61 = Minerva's anti-NME7 antibody
Fig. 41B Tumor Grade 1 (T4N1M1, Clinical IV), 61, 10 ug/ml
Fig. 41C Tumor Grade 2 (T4N0M0, Clinical IB), 61, 10 ug/ml
Fig. 41D Tumor Grade 3 (T3N1M1, Clinical IV), 61, 10 ug/ml

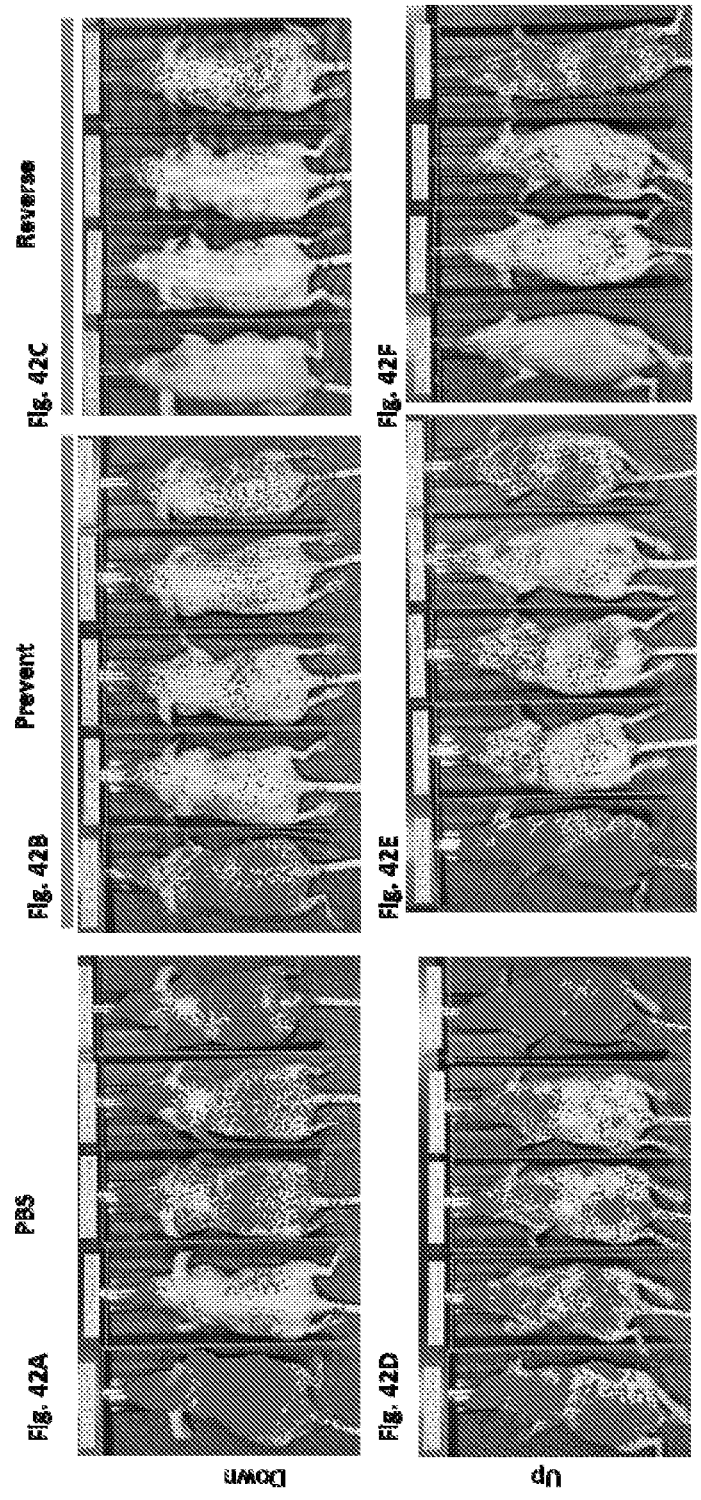

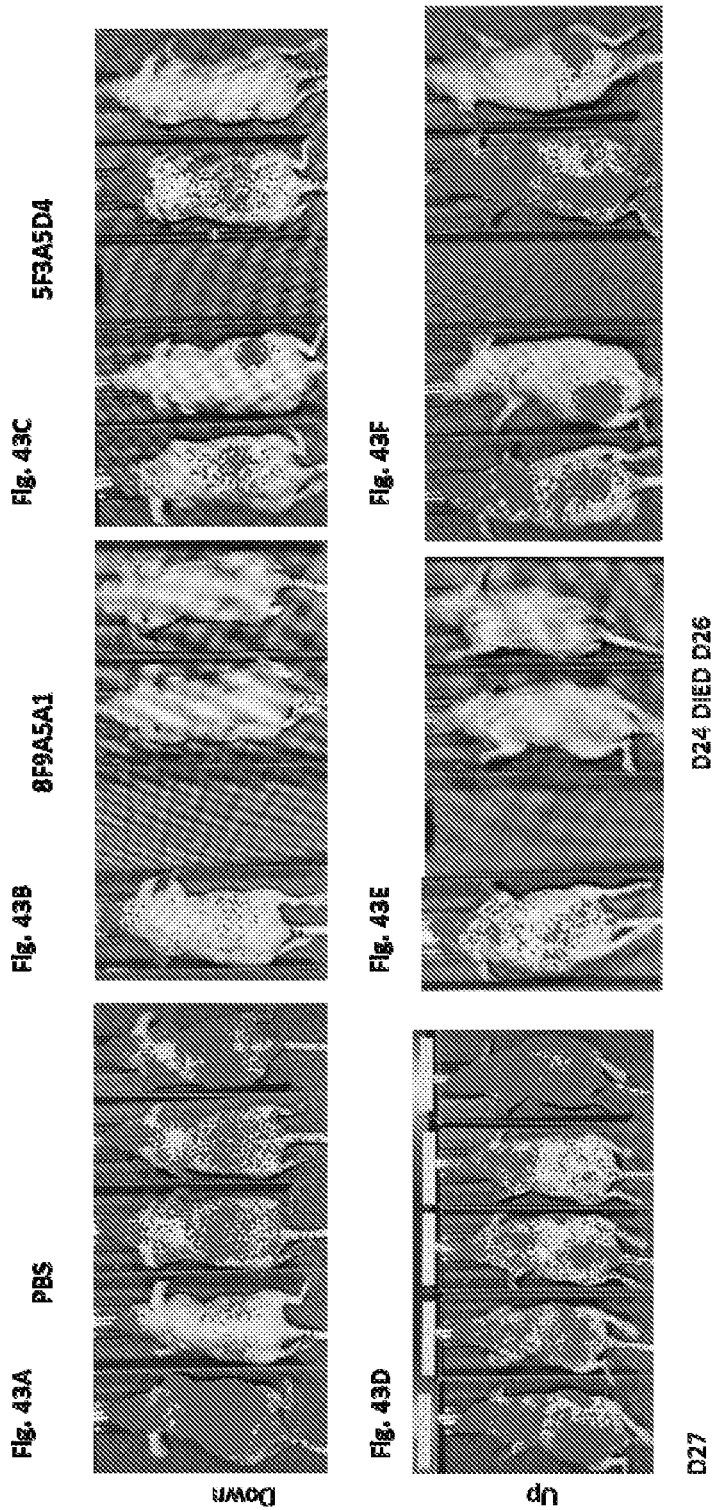

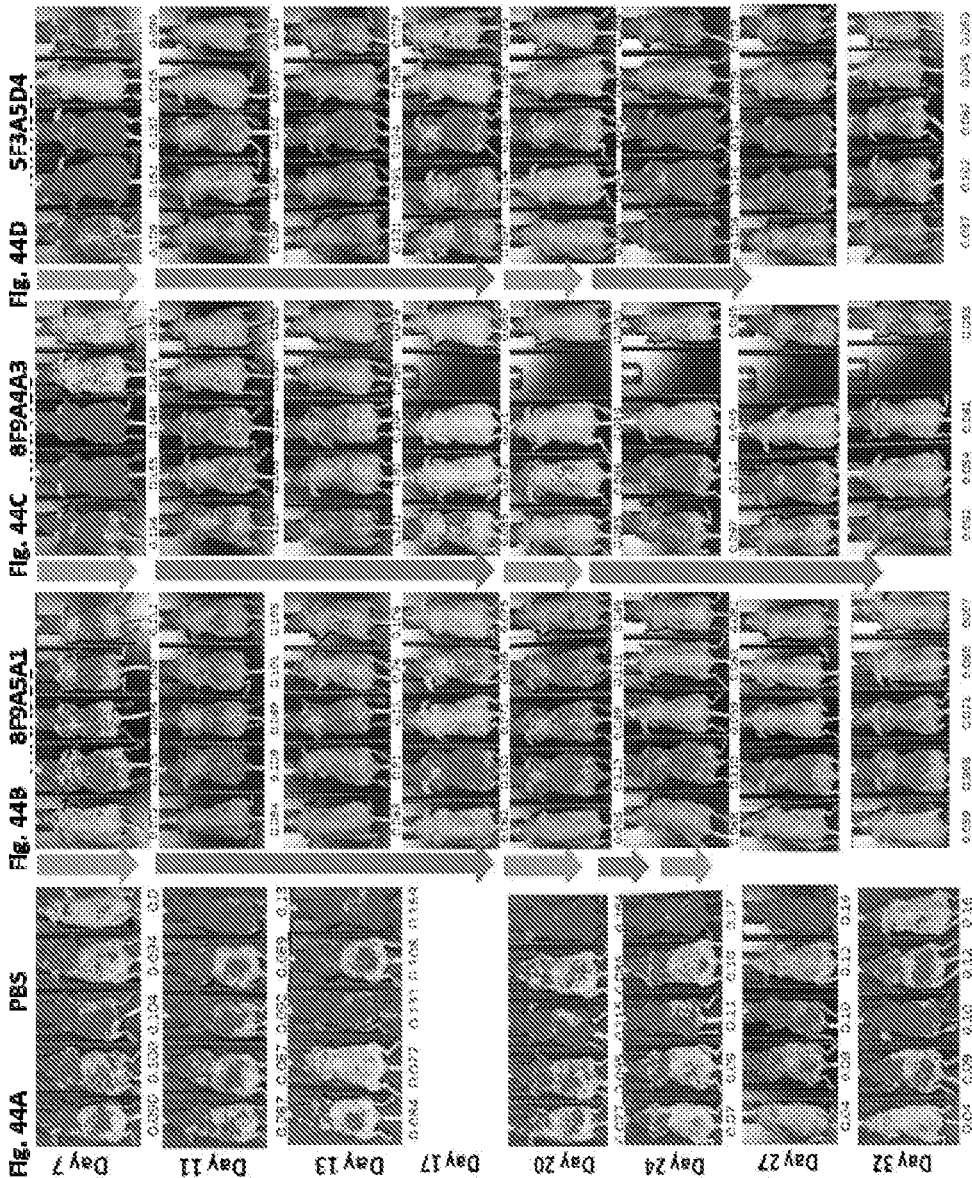

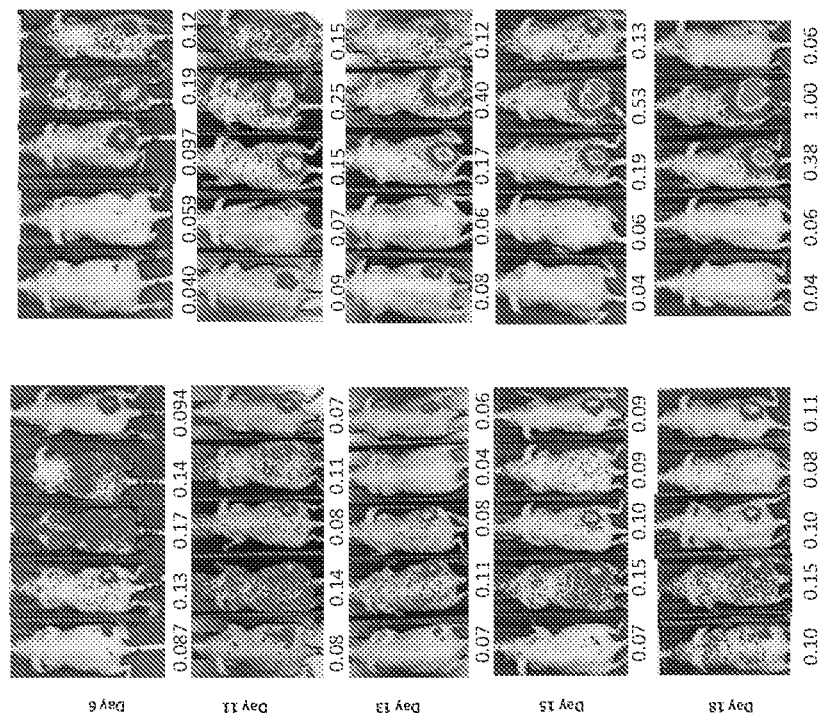
Fig. 45A Control  Fig. 45B Anti-NME7_AB Antibody
Sub-cu implantation of primary tumor comprised of T47D CSCs; conclusion: antibody cocktail inhibited metastases but did not inhibit growth of the primary

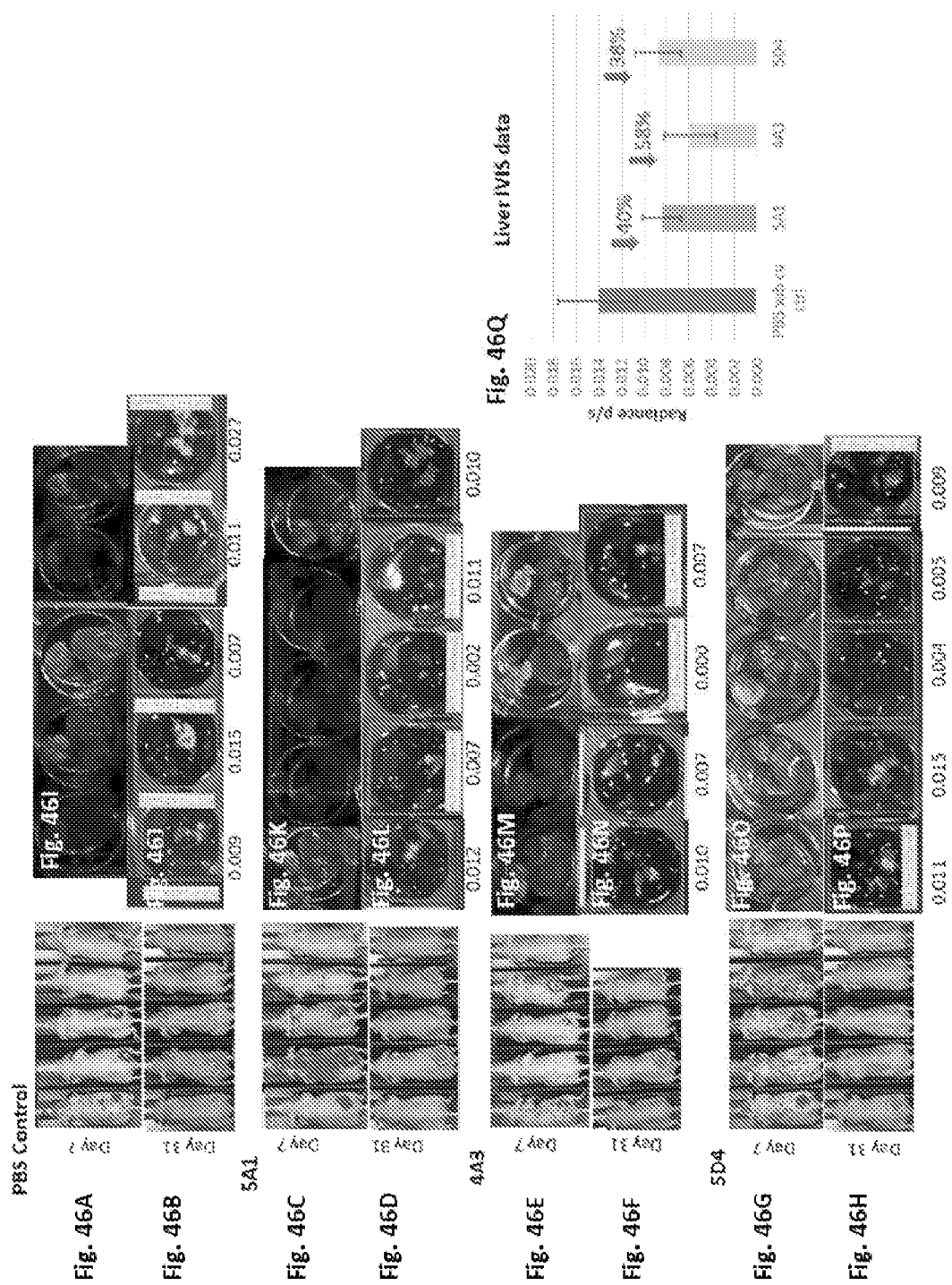

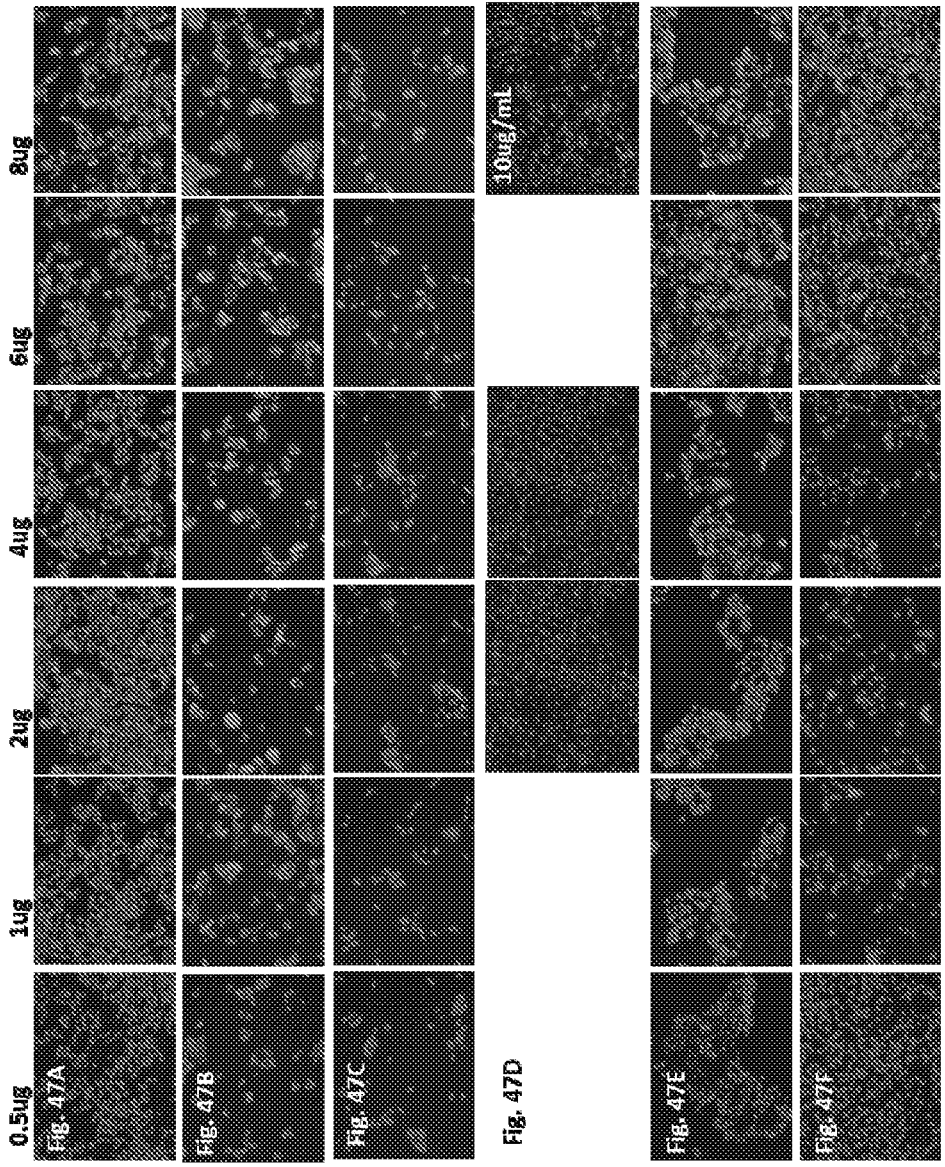

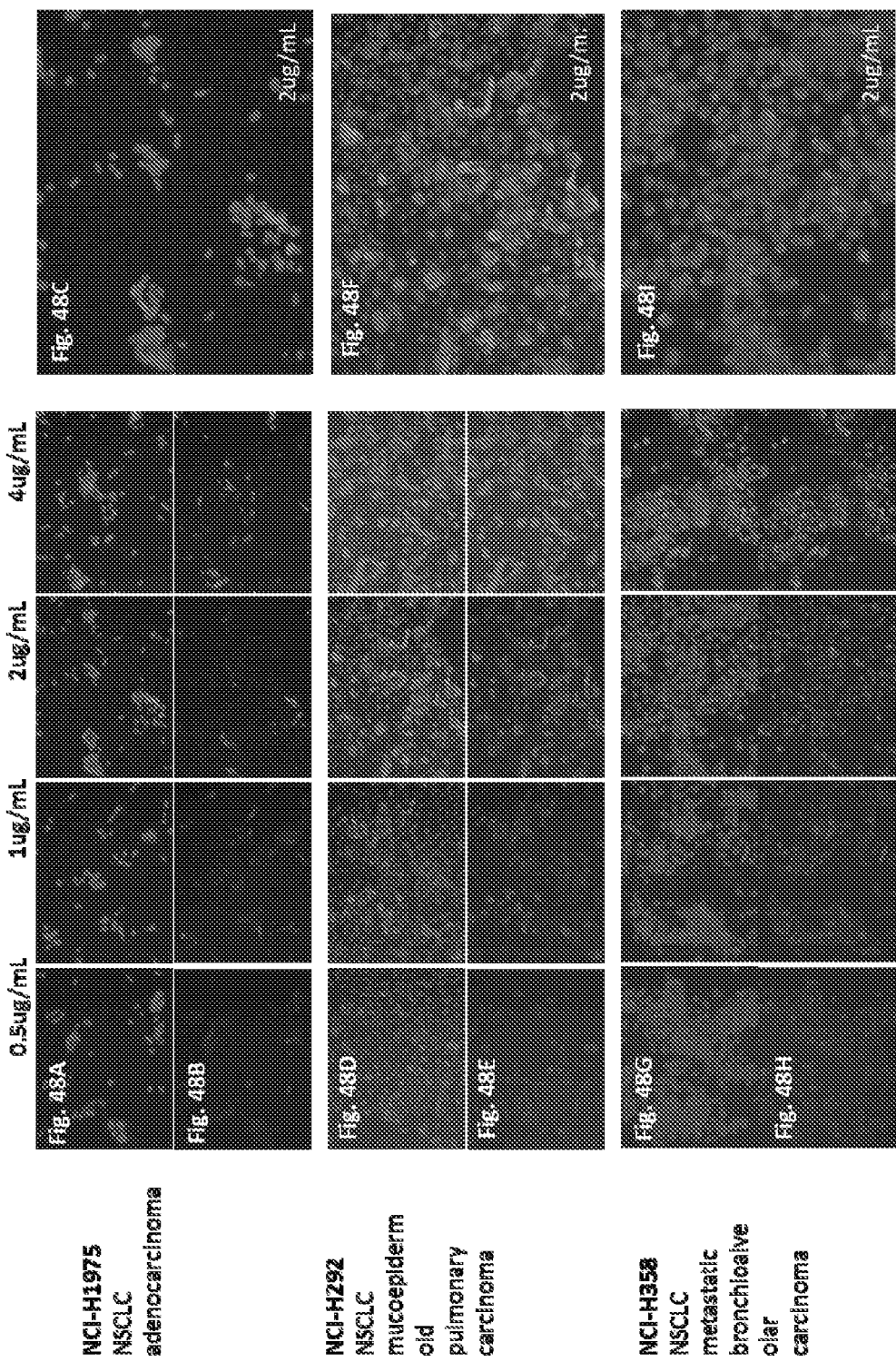

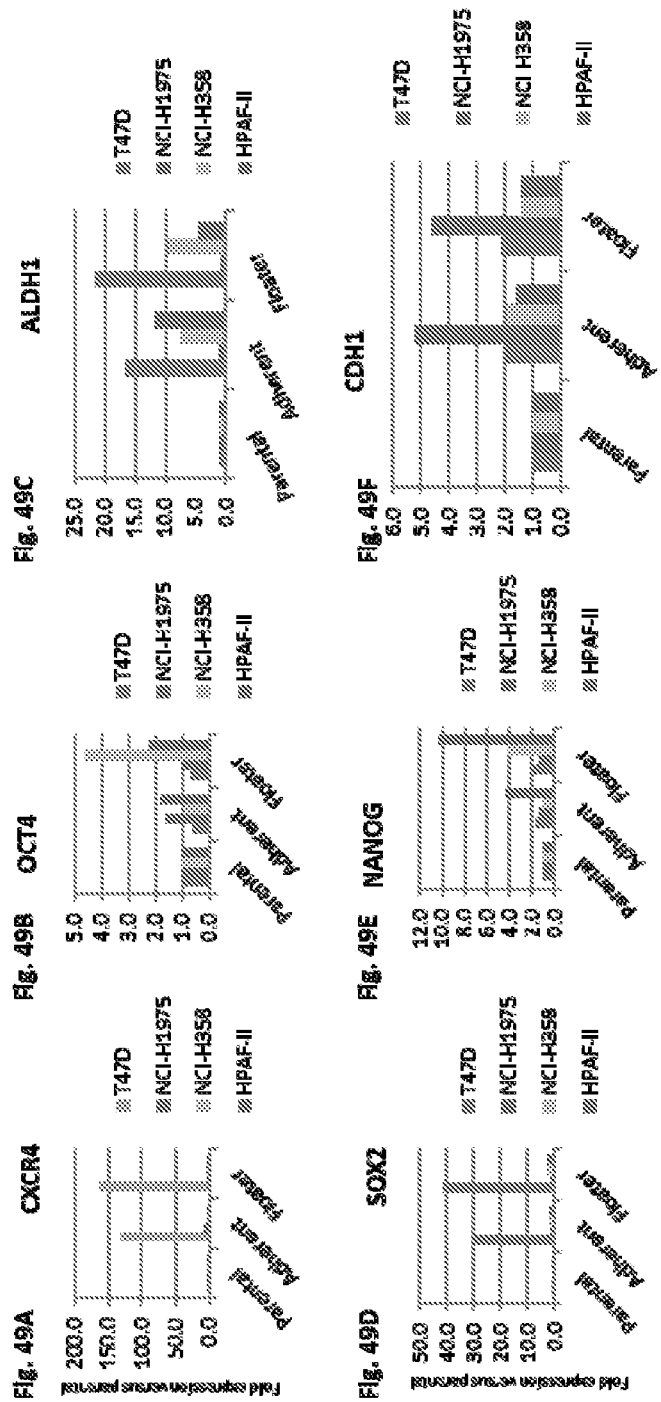

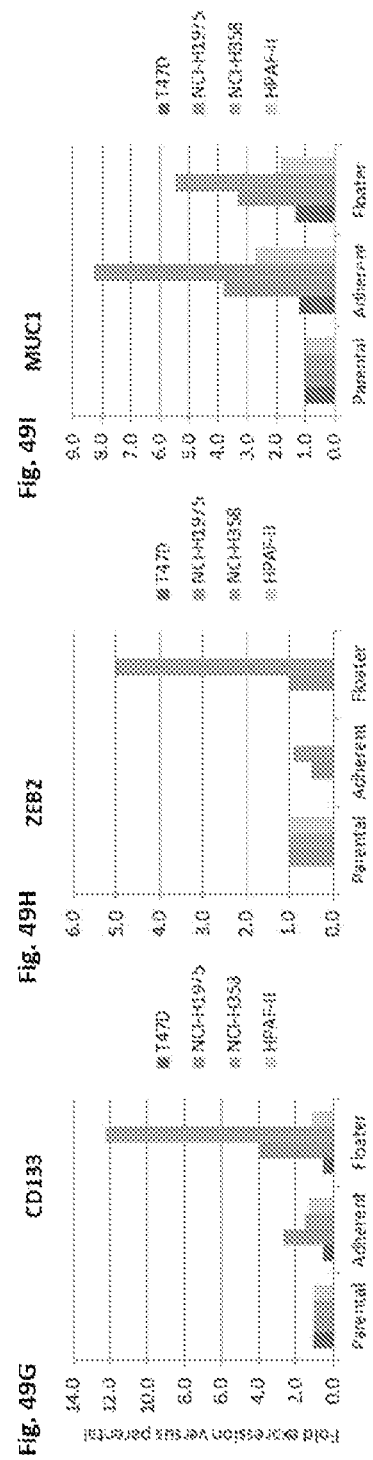

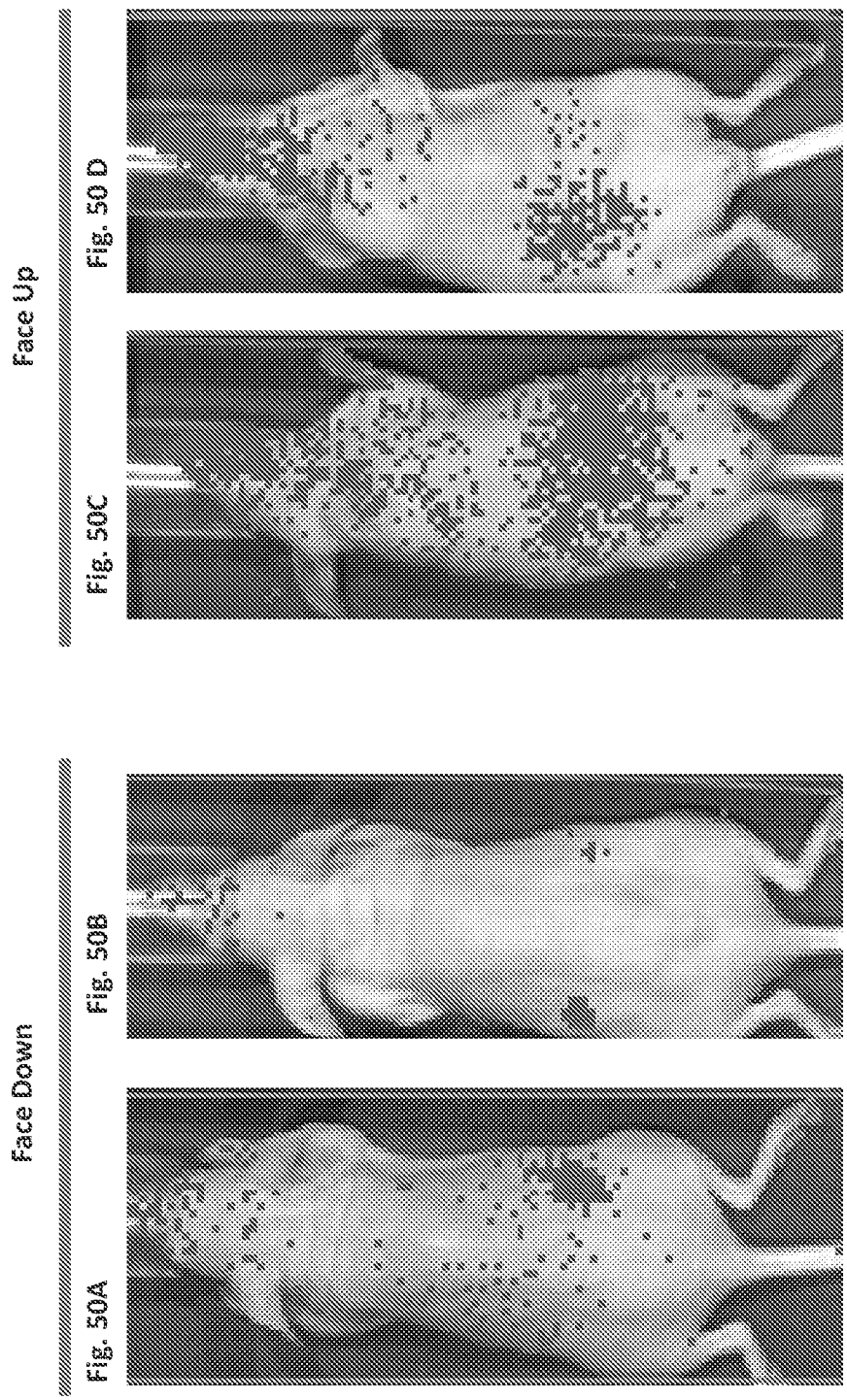

SEQUENCE LISTING

```
<160> NUMBER OF SEQ ID NOS: 1146

<210> SEQ ID NO 1
<211> LENGTH: 1255
<212> TYPE: PRT
<213> ORGANISM: Artificial Sequence
<220> FEATURE:
<223> OTHER INFORMATION: MUC1 Receptor - Mucin 1 precursor, Genbank
      Accession number: P15941

<400> SEQUENCE: 1

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Thr
    210                 215                 220

Arg Pro Ala Pro Gly Ser Thr Ala Pro Pro Ala His Gly Val Thr Ser
225                 230                 235                 240
```

-continued

Ala Pro Asp Thr Arg Pro Ala Pro Gly Ser Thr Ala Pro Pro Ala His
            245                 250                 255

Gly Val Thr Ser Ala Pro Asp Thr Arg Pro Ala Pro Gly Ser Thr Ala
            260                 265                 270

Pro Pro Ala His Gly Val Thr Ser Ala Pro Asp Thr Arg Pro Ala Pro
            275                 280                 285

Gly Ser Thr Ala Pro Pro Ala His Gly Val Thr Ser Ala Pro Asp Thr
            290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
            325                 330                 335

Gly Val Thr Ser Ala Pro Asp Thr Arg Pro Ala Pro Gly Ser Thr Ala
            340                 345                 350

Pro Pro Ala His Gly Val Thr Ser Ala Pro Asp Thr Arg Pro Ala Pro
            355                 360                 365

Gly Ser Thr Ala Pro Pro Ala His Gly Val Thr Ser Ala Pro Asp Thr
            370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
            405                 410                 415

Gly Val Thr Ser Ala Pro Asp Thr Arg Pro Ala Pro Gly Ser Thr Ala
            420                 425                 430

Pro Pro Ala His Gly Val Thr Ser Ala Pro Asp Thr Arg Pro Ala Pro
            435                 440                 445

Gly Ser Thr Ala Pro Pro Ala His Gly Val Thr Ser Ala Pro Asp Thr
            450                 455                 460

Arg Pro Ala Pro Gly Ser Thr Ala Pro Pro Ala His Gly Val Thr Ser
465                 470                 475                 480

Ala Pro Asp Thr Arg Pro Ala Pro Gly Ser Thr Ala Pro Pro Ala His
            485                 490                 495

Gly Val Thr Ser Ala Pro Asp Thr Arg Pro Ala Pro Gly Ser Thr Ala
            500                 505                 510

Pro Pro Ala His Gly Val Thr Ser Ala Pro Asp Thr Arg Pro Ala Pro
            515                 520                 525

Gly Ser Thr Ala Pro Pro Ala His Gly Val Thr Ser Ala Pro Asp Thr
            530                 535                 540

Arg Pro Ala Pro Gly Ser Thr Ala Pro Pro Ala His Gly Val Thr Ser
545                 550                 555                 560

Ala Pro Asp Thr Arg Pro Ala Pro Gly Ser Thr Ala Pro Pro Ala His
            565                 570                 575

Gly Val Thr Ser Ala Pro Asp Thr Arg Pro Ala Pro Gly Ser Thr Ala
            580                 585                 590

Pro Pro Ala His Gly Val Thr Ser Ala Pro Asp Thr Arg Pro Ala Pro
            595                 600                 605

Gly Ser Thr Ala Pro Pro Ala His Gly Val Thr Ser Ala Pro Asp Thr
            610                 615                 620

Arg Pro Ala Pro Gly Ser Thr Ala Pro Pro Ala His Gly Val Thr Ser
625                 630                 635                 640

Ala Pro Asp Thr Arg Pro Ala Pro Gly Ser Thr Ala Pro Pro Ala His
            645                 650                 655

```
Gly Val Thr Ser Ala Pro Asp Thr Arg Pro Ala Pro Gly Ser Thr Ala
            660                 665                 670

Pro Pro Ala His Gly Val Thr Ser Ala Pro Asp Thr Arg Pro Ala Pro
            675                 680                 685

Gly Ser Thr Ala Pro Pro Ala His Gly Val Thr Ser Ala Pro Asp Thr
            690                 695                 700

Arg Pro Ala Pro Gly Ser Thr Ala Pro Pro Ala His Gly Val Thr Ser
705                 710                 715                 720

Ala Pro Asp Thr Arg Pro Ala Pro Gly Ser Thr Ala Pro Pro Ala His
                725                 730                 735

Gly Val Thr Ser Ala Pro Asp Thr Arg Pro Ala Pro Gly Ser Thr Ala
            740                 745                 750

Pro Pro Ala His Gly Val Thr Ser Ala Pro Asp Thr Arg Pro Ala Pro
            755                 760                 765

Gly Ser Thr Ala Pro Pro Ala His Gly Val Thr Ser Ala Pro Asp Thr
            770                 775                 780

Arg Pro Ala Pro Gly Ser Thr Ala Pro Pro Ala His Gly Val Thr Ser
785                 790                 795                 800

Ala Pro Asp Thr Arg Pro Ala Pro Gly Ser Thr Ala Pro Pro Ala His
                805                 810                 815

Gly Val Thr Ser Ala Pro Asp Thr Arg Pro Ala Pro Gly Ser Thr Ala
            820                 825                 830

Pro Pro Ala His Gly Val Thr Ser Ala Pro Asp Thr Arg Pro Ala Pro
            835                 840                 845

Gly Ser Thr Ala Pro Pro Ala His Gly Val Thr Ser Ala Pro Asp Thr
            850                 855                 860

Arg Pro Ala Pro Gly Ser Thr Ala Pro Pro Ala His Gly Val Thr Ser
865                 870                 875                 880

Ala Pro Asp Thr Arg Pro Ala Pro Gly Ser Thr Ala Pro Pro Ala His
                885                 890                 895

Gly Val Thr Ser Ala Pro Asp Thr Arg Pro Ala Pro Gly Ser Thr Ala
            900                 905                 910

Pro Pro Ala His Gly Val Thr Ser Ala Pro Asp Thr Arg Pro Ala Pro
            915                 920                 925

Gly Ser Thr Ala Pro Pro Ala His Gly Val Thr Ser Ala Pro Asp Asn
            930                 935                 940

Arg Pro Ala Leu Gly Ser Thr Ala Pro Pro Val His Asn Val Thr Ser
945                 950                 955                 960

Ala Ser Gly Ser Ala Ser Gly Ser Ala Ser Thr Leu Val His Asn Gly
                965                 970                 975

Thr Ser Ala Arg Ala Thr Thr Thr Pro Ala Ser Lys Ser Thr Pro Phe
            980                 985                 990

Ser Ile Pro Ser His His Ser Asp Thr Pro Thr Thr Leu Ala Ser His
            995                 1000                1005

Ser Thr Lys Thr Asp Ala Ser Ser Thr His His Ser Ser Val Pro
            1010                1015                1020

Pro Leu Thr Ser Ser Asn His Ser Thr Ser Pro Gln Leu Ser Thr
            1025                1030                1035

Gly Val Ser Phe Phe Leu Ser Phe His Ile Ser Asn Leu Gln
            1040                1045                1050

Phe Asn Ser Ser Leu Glu Asp Pro Ser Thr Asp Tyr Tyr Gln Glu
            1055                1060                1065

Leu Gln Arg Asp Ile Ser Glu Met Phe Leu Gln Ile Tyr Lys Gln
```

```
                1070                1075                1080
Gly Gly Phe Leu Gly Leu Ser Asn Ile Lys Phe Arg Pro Gly Ser
        1085                1090                1095
Val Val Val Gln Leu Thr Leu Ala Phe Arg Glu Gly Thr Ile Asn
    1100                1105                1110
Val His Asp Val Glu Thr Gln Phe Asn Gln Tyr Lys Thr Glu Ala
    1115                1120                1125
Ala Ser Arg Tyr Asn Leu Thr Ile Ser Asp Val Ser Val Ser Asp
    1130                1135                1140
Val Pro Phe Pro Phe Ser Ala Gln Ser Gly Ala Gly Val Pro Gly
    1145                1150                1155
Trp Gly Ile Ala Leu Leu Val Leu Val Cys Val Leu Val Ala Leu
    1160                1165                1170
Ala Ile Val Tyr Leu Ile Ala Leu Ala Val Cys Gln Cys Arg Arg
    1175                1180                1185
Lys Asn Tyr Gly Gln Leu Asp Ile Phe Pro Ala Arg Asp Thr Tyr
    1190                1195                1200
His Pro Met Ser Glu Tyr Pro Thr Tyr His Thr His Gly Arg Tyr
    1205                1210                1215
Val Pro Pro Ser Ser Thr Asp Arg Ser Pro Tyr Glu Lys Val Ser
    1220                1225                1230
Ala Gly Asn Gly Gly Ser Ser Leu Ser Tyr Thr Asn Pro Ala Val
    1235                1240                1245
Ala Ala Ala Ser Ala Asn Leu
    1250                1255

<210> SEQ ID NO 2
<211> LENGTH: 19
<212> TYPE: PRT
<213> ORGANISM: Artificial Sequence
<220> FEATURE:
<223> OTHER INFORMATION: N-terminal MUC-1 signaling sequence

<400> SEQUENCE: 2

Met Thr Pro Gly Thr Gln Ser Pro Phe Phe Leu Leu Leu Leu Thr
1               5                   10                  15

Val Leu Thr

<210> SEQ ID NO 3
<211> LENGTH: 23
<212> TYPE: PRT
<213> ORGANISM: Artificial Sequence
<220> FEATURE:
<223> OTHER INFORMATION: N-terminal MUC-1 signaling sequence

<400> SEQUENCE: 3

Met Thr Pro Gly Thr Gln Ser Pro Phe Phe Leu Leu Leu Leu Thr
1               5                   10                  15

Val Leu Thr Val Val Thr Ala
            20

<210> SEQ ID NO 4
<211> LENGTH: 23
<212> TYPE: PRT
<213> ORGANISM: Artificial Sequence
<220> FEATURE:
<223> OTHER INFORMATION: N-terminal MUC-1 signaling sequence

<400> SEQUENCE: 4
```

Met Thr Pro Gly Thr Gln Ser Pro Phe Phe Leu Leu Leu Leu Thr
1               5                   10                  15

Val Leu Thr Val Val Thr Gly
            20

<210> SEQ ID NO 5
<211> LENGTH: 146
<212> TYPE: PRT
<213> ORGANISM: Artificial Sequence
<220> FEATURE:
<223> OTHER INFORMATION: Truncated MUC1 receptor isoform having
      nat-PSMGFR at its N-terminus and including the transmembrane and
      cytoplasmic sequences of a full-length MUC1 receptor

<400> SEQUENCE: 5

Gly Thr Ile Asn Val His Asp Val Glu Thr Gln Phe Asn Gln Tyr Lys
1               5                   10                  15

Thr Glu Ala Ala Ser Arg Tyr Asn Leu Thr Ile Ser Asp Val Ser Val
            20                  25                  30

Ser Asp Val Pro Phe Pro Phe Ser Ala Gln Ser Gly Ala Gly Val Pro
        35                  40                  45

Gly Trp Gly Ile Ala Leu Leu Val Leu Val Cys Val Leu Val Ala Leu
    50                  55                  60

Ala Ile Val Tyr Leu Ile Ala Leu Ala Val Cys Gln Cys Arg Arg Lys
65                  70                  75                  80

Asn Tyr Gly Gln Leu Asp Ile Phe Pro Ala Arg Asp Thr Tyr His Pro
                85                  90                  95

Met Ser Glu Tyr Pro Thr Tyr His Thr His Gly Arg Tyr Val Pro Pro
            100                 105                 110

Ser Ser Thr Asp Arg Ser Pro Tyr Glu Lys Val Ser Ala Gly Asn Gly
        115                 120                 125

Gly Ser Ser Leu Ser Tyr Thr Asn Pro Ala Val Ala Ala Ala Ser Ala
    130                 135                 140

Asn Leu
145

<210> SEQ ID NO 6
<211> LENGTH: 45
<212> TYPE: PRT
<213> ORGANISM: Artificial Sequence
<220> FEATURE:
<223> OTHER INFORMATION: PSMGFR sequence

<400> SEQUENCE: 6

Gly Thr Ile Asn Val His Asp Val Glu Thr Gln Phe Asn Gln Tyr Lys
1               5                   10                  15

Thr Glu Ala Ala Ser Arg Tyr Asn Leu Thr Ile Ser Asp Val Ser Val
            20                  25                  30

Ser Asp Val Pro Phe Pro Phe Ser Ala Gln Ser Gly Ala
        35                  40                  45

<210> SEQ ID NO 7
<211> LENGTH: 44
<212> TYPE: PRT
<213> ORGANISM: Artificial Sequence
<220> FEATURE:
<223> OTHER INFORMATION: PSMGFR sequence

<400> SEQUENCE: 7

Thr Ile Asn Val His Asp Val Glu Thr Gln Phe Asn Gln Tyr Lys Thr
1               5                   10                  15

Glu Ala Ala Ser Arg Tyr Asn Leu Thr Ile Ser Asp Val Ser Val Ser
            20                  25                  30

Asp Val Pro Phe Pro Phe Ser Ala Gln Ser Gly Ala
        35                  40

<210> SEQ ID NO 8
<211> LENGTH: 45
<212> TYPE: PRT
<213> ORGANISM: Artificial Sequence
<220> FEATURE:
<223> OTHER INFORMATION: PSMGFR sequence

<400> SEQUENCE: 8

Gly Thr Ile Asn Val His Asp Val Glu Thr Gln Phe Asn Gln Tyr Lys
1               5                   10                  15

Thr Glu Ala Ala Ser Pro Tyr Asn Leu Thr Ile Ser Asp Val Ser Val
            20                  25                  30

Ser Asp Val Pro Phe Pro Phe Ser Ala Gln Ser Gly Ala
        35                  40                  45

<210> SEQ ID NO 9
<211> LENGTH: 44
<212> TYPE: PRT
<213> ORGANISM: Artificial Sequence
<220> FEATURE:
<223> OTHER INFORMATION: PSMGFR sequence

<400> SEQUENCE: 9

Thr Ile Asn Val His Asp Val Glu Thr Gln Phe Asn Gln Tyr Lys Thr
1               5                   10                  15

Glu Ala Ala Ser Pro Tyr Asn Leu Thr Ile Ser Asp Val Ser Val Ser
            20                  25                  30

Asp Val Pro Phe Pro Phe Ser Ala Gln Ser Gly Ala
        35                  40

<210> SEQ ID NO 10
<211> LENGTH: 216
<212> TYPE: DNA
<213> ORGANISM: Artificial Sequence
<220> FEATURE:
<223> OTHER INFORMATION: MUC1 cytoplasmic domain nucleotide sequence

<400> SEQUENCE: 10
tgtcagtgcc gccgaaagaa ctacgggcag ctggacatct ttccagcccg ggatacctac      60
catcctatga gcgagtaccc cacctaccac acccatgggc gctatgtgcc ccctagcagt     120
accgatcgta gcccctatga gaaggtttct gcaggtaacg gtggcagcag cctctcttac     180
acaaacccag cagtggcagc cgcttctgcc aacttg                               216

<210> SEQ ID NO 11
<211> LENGTH: 72
<212> TYPE: PRT
<213> ORGANISM: Artificial Sequence
<220> FEATURE:
<223> OTHER INFORMATION: MUC1 cytoplasmic domain amino acid sequence

<400> SEQUENCE: 11

Cys Gln Cys Arg Arg Lys Asn Tyr Gly Gln Leu Asp Ile Phe Pro Ala
1               5                   10                  15

Arg Asp Thr Tyr His Pro Met Ser Glu Tyr Pro Thr Tyr His Thr His
            20                  25                  30

-continued

Gly Arg Tyr Val Pro Pro Ser Ser Thr Asp Arg Ser Pro Tyr Glu Lys
                35                  40                  45

Val Ser Ala Gly Asn Gly Ser Ser Leu Ser Tyr Thr Asn Pro Ala
 50                  55                  60

Val Ala Ala Ala Ser Ala Asn Leu
 65                  70

<210> SEQ ID NO 12
<211> LENGTH: 854
<212> TYPE: DNA
<213> ORGANISM: Artificial Sequence
<220> FEATURE:
<223> OTHER INFORMATION: NME7 nucleotide sequence (NME7: GENBANK
      ACCESSION AB209049)

<400> SEQUENCE: 12

```
gagatcctga gacaatgaat catagtgaaa gattcgtttt cattgcagag tggtatgatc    60
caaatgcttc acttcttcga cgttatgagc ttttatttta cccaggggat ggatctgttg   120
aaatgcatga tgtaaagaat catcgcacct ttttaaagcg accaaatat gataacctgc    180
acttggaaga tttatttata ggcaacaaag tgaatgtctt ttctcgacaa ctggtattaa   240
ttgactatgg ggatcaatat acagctcgcc agctgggcag taggaaagaa aaaacgctag   300
ccctaattaa accagatgca atatcaaagg ctggagaaat aattgaaata ataaacaaag   360
ctggatttac tataaccaaa ctcaaaatga tgatgctttc aaggaaagaa gcattggatt   420
ttcatgtaga tcaccagtca agacccttt tcaatgagct gatccagttt attacaactg    480
gtcctattat tgccatggag attttaagag atgatgctat atgtgaatgg aaaagactgc   540
tgggacctgc aaactctgga gtggcacgca cagatgcttc tgaaagcatt agagccctct   600
ttggaacaga tggcataaga aatgcagcgc atggccctga ttcttttgct ctgcggcca    660
gagaaatgga gttgtttttt ccttcaagtg gaggttgtgg gccggcaaac actgctaaat   720
ttactaattg tacctgttgc attgttaaac cccatgctgt cagtgaaggt atgttgaata   780
cactatattc agtacatttt gttaatagga gagcaatgtt tattttcttg atgtacttta   840
tgtatagaaa ataa                                                    854
```

<210> SEQ ID NO 13
<211> LENGTH: 283
<212> TYPE: PRT
<213> ORGANISM: Artificial Sequence
<220> FEATURE:
<223> OTHER INFORMATION: NME7 amino acid sequence (NME7: GENBANK
      ACCESSION AB209049)

<400> SEQUENCE: 13

Asp Pro Glu Thr Met Asn His Ser Glu Arg Phe Val Phe Ile Ala Glu
 1               5                  10                  15

Trp Tyr Asp Pro Asn Ala Ser Leu Leu Arg Arg Tyr Glu Leu Leu Phe
                20                  25                  30

Tyr Pro Gly Asp Gly Ser Val Glu Met His Asp Val Lys Asn His Arg
            35                  40                  45

Thr Phe Leu Lys Arg Thr Lys Tyr Asp Asn Leu His Leu Glu Asp Leu
         50                  55                  60

Phe Ile Gly Asn Lys Val Asn Val Phe Ser Arg Gln Leu Val Leu Ile
65                  70                  75                  80

Asp Tyr Gly Asp Gln Tyr Thr Ala Arg Gln Leu Gly Ser Arg Lys Glu
                85                  90                  95

```
Lys Thr Leu Ala Leu Ile Lys Pro Asp Ala Ile Ser Lys Ala Gly Glu
                100                 105                 110
Ile Ile Glu Ile Ile Asn Lys Ala Gly Phe Thr Ile Thr Lys Leu Lys
            115                 120                 125
Met Met Met Leu Ser Arg Lys Glu Ala Leu Asp Phe His Val Asp His
130                 135                 140
Gln Ser Arg Pro Phe Phe Asn Glu Leu Ile Gln Phe Ile Thr Thr Gly
145                 150                 155                 160
Pro Ile Ile Ala Met Glu Ile Leu Arg Asp Asp Ala Ile Cys Glu Trp
                165                 170                 175
Lys Arg Leu Leu Gly Pro Ala Asn Ser Gly Val Ala Arg Thr Asp Ala
                180                 185                 190
Ser Glu Ser Ile Arg Ala Leu Phe Gly Thr Asp Gly Ile Arg Asn Ala
                195                 200                 205
Ala His Gly Pro Asp Ser Phe Ala Ser Ala Ala Arg Glu Met Glu Leu
            210                 215                 220
Phe Phe Pro Ser Ser Gly Gly Cys Gly Pro Ala Asn Thr Ala Lys Phe
225                 230                 235                 240
Thr Asn Cys Thr Cys Cys Ile Val Lys Pro His Ala Val Ser Glu Gly
                245                 250                 255
Met Leu Asn Thr Leu Tyr Ser Val His Phe Val Asn Arg Arg Ala Met
                260                 265                 270
Phe Ile Phe Leu Met Tyr Phe Met Tyr Arg Lys
                275                 280
```

<210> SEQ ID NO 14
<211> LENGTH: 534
<212> TYPE: DNA
<213> ORGANISM: Artificial Sequence
<220> FEATURE:
<223> OTHER INFORMATION: NM23-H1 nucleotide sequence (NM23-H1: GENBANK ACCESSION AF487339)

<400> SEQUENCE: 14

```
atggtgctac tgtctacttt agggatcgtc tttcaaggcg aggggcctcc tatctcaagc    60
tgtgatacag gaaccatggc caactgtgag cgtaccttca ttgcgatcaa accagatggg   120
gtccagcggg gtcttgtggg agagattatc aagcgttttg agcagaaagg attccgcctt   180
gttggtctga aattcatgca agcttccgaa gatcttctca ggaacactac cgttgacctg   240
aaggaccgtc cattctttgc cggcctggtg aaatacatgc actcagggcc ggtagttgcc   300
atggtctggg aggggctgaa tgtggtgaag acgggccgag tcatgctcgg ggagaccaac   360
cctgcagact ccaagcctgg gaccatccgt ggagacttct gcatacaagt tggcaggaac   420
attatacatg gcagtgattc tgtggagagt gcagagaagg agatcggctt gtggtttcac   480
cctgaggaac tggtagatta cacgagctgt gctcagaact ggatctatga atga         534
```

<210> SEQ ID NO 15
<211> LENGTH: 177
<212> TYPE: PRT
<213> ORGANISM: Artificial Sequence
<220> FEATURE:
<223> OTHER INFORMATION: NM23-H1 describes amino acid sequence (NM23-H1: GENBANK ACCESSION AF487339)

<400> SEQUENCE: 15

```
Met Val Leu Leu Ser Thr Leu Gly Ile Val Phe Gln Gly Glu Gly Pro
1               5                   10                  15
```

```
Pro Ile Ser Ser Cys Asp Thr Gly Thr Met Ala Asn Cys Glu Arg Thr
            20                  25                  30

Phe Ile Ala Ile Lys Pro Asp Gly Val Gln Arg Gly Leu Val Gly Glu
        35                  40                  45

Ile Ile Lys Arg Phe Glu Gln Lys Gly Phe Arg Leu Val Gly Leu Lys
    50                  55                  60

Phe Met Gln Ala Ser Glu Asp Leu Leu Lys Glu His Tyr Val Asp Leu
65                  70                  75                  80

Lys Asp Arg Pro Phe Phe Ala Gly Leu Val Lys Tyr Met His Ser Gly
                85                  90                  95

Pro Val Val Ala Met Val Trp Glu Gly Leu Asn Val Val Lys Thr Gly
            100                 105                 110

Arg Val Met Leu Gly Glu Thr Asn Pro Ala Asp Ser Lys Pro Gly Thr
        115                 120                 125

Ile Arg Gly Asp Phe Cys Ile Gln Val Gly Arg Asn Ile Ile His Gly
    130                 135                 140

Ser Asp Ser Val Glu Ser Ala Glu Lys Glu Ile Gly Leu Trp Phe His
145                 150                 155                 160

Pro Glu Glu Leu Val Asp Tyr Thr Ser Cys Ala Gln Asn Trp Ile Tyr
                165                 170                 175

Glu

<210> SEQ ID NO 16
<211> LENGTH: 534
<212> TYPE: DNA
<213> ORGANISM: Artificial Sequence
<220> FEATURE:
<223> OTHER INFORMATION: NM23-H1 S120G mutant nucleotide sequence
      (NM23-H1: GENBANK ACCESSION AF487339)

<400> SEQUENCE: 16
atggtgctac tgtctacttt agggatcgtc tttcaaggcg aggggcctcc tatctcaagc      60
tgtgatacag gaaccatggc caactgtgag cgtaccttca ttgcgatcaa accagatggg     120
gtccagcggg gtcttgtggg agagattatc aagcgttttg agcagaaagg attccgcctt     180
gttggtctga aattcatgca agcttccgaa gatcttctca ggaacactac gttgacctg      240 aaggaccgtc cattctttgc cggcctggtg aaatacatgc actcagggcc ggtagttgcc     300
atggtctggg aggggctgaa tgtggtgaag acgggccgag tcatgctcgg ggagaccaac     360
cctgcagact ccaagcctgg gaccatccgt ggagacttct gcatacaagt tggcaggaac     420
attatacatg gcggtgattc tgtggagagt gcagagaagg agatcggctt gtggtttcac     480
cctgaggaac tggtagatta cacgagctgt gctcagaact ggatctatga atga          534

<210> SEQ ID NO 17
<211> LENGTH: 177
<212> TYPE: PRT
<213> ORGANISM: Artificial Sequence
<220> FEATURE:
<223> OTHER INFORMATION: NM23-H1 S120G mutant amino acid sequence
      (NM23-H1: GENBANK ACCESSION AF487339)

<400> SEQUENCE: 17

Met Val Leu Leu Ser Thr Leu Gly Ile Val Phe Gln Gly Glu Gly Pro
1               5                   10                  15

Pro Ile Ser Ser Cys Asp Thr Gly Thr Met Ala Asn Cys Glu Arg Thr
            20                  25                  30

Phe Ile Ala Ile Lys Pro Asp Gly Val Gln Arg Gly Leu Val Gly Glu
```

```
                35                  40                  45
Ile Ile Lys Arg Phe Glu Gln Lys Gly Phe Arg Leu Val Gly Leu Lys
 50                  55                  60

Phe Met Gln Ala Ser Glu Asp Leu Leu Lys Glu His Tyr Val Asp Leu
 65                  70                  75                  80

Lys Asp Arg Pro Phe Phe Ala Gly Leu Val Lys Tyr Met His Ser Gly
                 85                  90                  95

Pro Val Ala Met Val Trp Glu Gly Leu Asn Val Val Lys Thr Gly
            100                 105                 110

Arg Val Met Leu Gly Glu Thr Asn Pro Ala Asp Ser Lys Pro Gly Thr
            115                 120                 125

Ile Arg Gly Asp Phe Cys Ile Gln Val Gly Arg Asn Ile Ile His Gly
130                 135                 140

Gly Asp Ser Val Glu Ser Ala Glu Lys Glu Ile Gly Leu Trp Phe His
145                 150                 155                 160

Pro Glu Glu Leu Val Asp Tyr Thr Ser Cys Ala Gln Asn Trp Ile Tyr
                165                 170                 175

Glu

<210> SEQ ID NO 18
<211> LENGTH: 459
<212> TYPE: DNA
<213> ORGANISM: Artificial Sequence
<220> FEATURE:
<223> OTHER INFORMATION: NM23-H2 nucleotide sequence (NM23-H2: GENBANK
      ACCESSION AK313448)

<400> SEQUENCE: 18
atggccaacc tggagcgcac cttcatcgcc atcaagccgg acggcgtgca gcgcggcctg      60
gtgggcgaga tcatcaagcg cttcgagcag aagggattcc gcctcgtggc catgaagttc     120
ctccgggcct ctgaagaaca cctgaagcag cactacattg acctgaaaga ccgaccattc     180
ttccctgggc tggtgaagta catgaactca gggccggttg tggccatggt ctgggagggg     240
ctgaacgtgg tgaagacagg ccgagtgatg cttggggaga ccaatccagc agattcaaag     300
ccaggcacca ttcgtgggga cttctgcatt caggttggca ggaacatcat tcatggcagt     360
gattcagtaa aaagtgctga aaaagaaatc agcctatggt ttaagcctga gaactggtt      420 gactacaagt cttgtgctca tgactgggtc tatgaataa                            459

<210> SEQ ID NO 19
<211> LENGTH: 152
<212> TYPE: PRT
<213> ORGANISM: Artificial Sequence
<220> FEATURE:
<223> OTHER INFORMATION: NM23-H2 amino acid sequence (NM23-H2: GENBANK
      ACCESSION AK313448)

<400> SEQUENCE: 19

Met Ala Asn Leu Glu Arg Thr Phe Ile Ala Ile Lys Pro Asp Gly Val
 1               5                  10                  15

Gln Arg Gly Leu Val Gly Glu Ile Ile Lys Arg Phe Glu Gln Lys Gly
             20                  25                  30

Phe Arg Leu Val Ala Met Lys Phe Leu Arg Ala Ser Glu Glu His Leu
         35                  40                  45

Lys Gln His Tyr Ile Asp Leu Lys Asp Arg Pro Phe Phe Pro Gly Leu
 50                  55                  60

Val Lys Tyr Met Asn Ser Gly Pro Val Val Ala Met Val Trp Glu Gly
```

65                  70                  75                  80
Leu Asn Val Val Lys Thr Gly Arg Val Met Leu Gly Glu Thr Asn Pro
                        85                  90                  95

Ala Asp Ser Lys Pro Gly Thr Ile Arg Gly Asp Phe Cys Ile Gln Val
                100                 105                 110

Gly Arg Asn Ile Ile His Gly Ser Asp Ser Val Lys Ser Ala Glu Lys
            115                 120                 125

Glu Ile Ser Leu Trp Phe Lys Pro Glu Glu Leu Val Asp Tyr Lys Ser
130                 135                 140

Cys Ala His Asp Trp Val Tyr Glu
145                 150

<210> SEQ ID NO 20
<211> LENGTH: 1023
<212> TYPE: DNA
<213> ORGANISM: Artificial Sequence
<220> FEATURE:
<223> OTHER INFORMATION: Human NM23-H7-2 sequence optimized for E. coli
      expression

<400> SEQUENCE: 20
atgcatgacg ttaaaaatca ccgtaccttt ctgaaacgca cgaaatatga taatctgcat      60
ctggaagacc tgtttattgg caacaaagtc aatgtgttct ctcgtcagct ggtgctgatc     120
gattatggcg accagtacac cgcgcgtcaa ctgggtagtc gcaaagaaaa aacgctggcc     180
ctgattaaac cggatgcaat ctccaaagct ggcgaaatta tcgaaattat caacaaagcg     240
ggtttcacca tcacgaaact gaaaatgatg atgctgagcc gtaaagaagc cctggatttt     300
catgtcgacc accagtctcg cccgtttttc aatgaactga ttcaattcat caccacgggt     360
ccgattatcg caatggaaat tctgcgtgat gacgctatct gcgaatggaa acgcctgctg     420
ggcccggcaa actcaggtgt tgcgcgtacc gatgccagtg aatccattcg cgctctgttt     480
ggcaccgatg gtatccgtaa tgcagcacat ggtccggact cattcgcatc ggcagctcgt     540
gaaatggaac tgttttttcc gagctctggc ggttgcggtc cggcaaacac cgccaaattt     600
accaattgta cgtgctgtat tgtcaaaccg cacgcagtgt cagaaggcct gctgggtaaa     660
attctgatgg caatccgtga tgctggcttt gaaatctcgg ccatgcagat gttcaacatg     720
gaccgcgtta acgtcgaaga attctacgaa gtttacaaag cgtggttac cgaatatcac     780 gatatggtta cggaaatgta ctccggtccg tgcgtcgcga tggaaattca gcaaacaat     840 gccaccaaaa cgtttcgtga attctgtggt ccggcagatc cggaaatcgc acgtcatctg     900
cgtccgggta ccctgcgcgc aatttttggt aaaacgaaaa tccagaacgc tgtgcactgt     960
accgatctgc cggaagacgg tctgctggaa gttcaatact ttttcaaaat tctggataat    1020
tga                                                                  1023

<210> SEQ ID NO 21
<211> LENGTH: 340
<212> TYPE: PRT
<213> ORGANISM: Artificial Sequence
<220> FEATURE:
<223> OTHER INFORMATION: Human NM23-H7-2 sequence optimized for E. coli
      expression

<400> SEQUENCE: 21

Met His Asp Val Lys Asn His Arg Thr Phe Leu Lys Arg Thr Lys Tyr
1               5                   10                  15

Asp Asn Leu His Leu Glu Asp Leu Phe Ile Gly Asn Lys Val Asn Val

```
              20                  25                  30
Phe Ser Arg Gln Leu Val Leu Ile Asp Tyr Gly Asp Gln Tyr Thr Ala
             35                  40                  45
Arg Gln Leu Gly Ser Arg Lys Glu Lys Thr Leu Ala Leu Ile Lys Pro
         50                  55                  60
Asp Ala Ile Ser Lys Ala Gly Glu Ile Ile Glu Ile Ile Asn Lys Ala
 65                  70                  75                  80
Gly Phe Thr Ile Thr Lys Leu Lys Met Met Met Leu Ser Arg Lys Glu
                 85                  90                  95
Ala Leu Asp Phe His Val Asp His Gln Ser Arg Pro Phe Phe Asn Glu
             100                 105                 110
Leu Ile Gln Phe Ile Thr Thr Gly Pro Ile Ile Ala Met Glu Ile Leu
         115                 120                 125
Arg Asp Asp Ala Ile Cys Glu Trp Lys Arg Leu Gly Pro Ala Asn
130                 135                 140
Ser Gly Val Ala Arg Thr Asp Ala Ser Glu Ser Ile Arg Ala Leu Phe
145                 150                 155                 160
Gly Thr Asp Gly Ile Arg Asn Ala Ala His Gly Pro Asp Ser Phe Ala
                 165                 170                 175
Ser Ala Ala Arg Glu Met Glu Leu Phe Phe Pro Ser Ser Gly Gly Cys
             180                 185                 190
Gly Pro Ala Asn Thr Ala Lys Phe Thr Asn Cys Thr Cys Cys Ile Val
         195                 200                 205
Lys Pro His Ala Val Ser Glu Gly Leu Leu Gly Lys Ile Leu Met Ala
     210                 215                 220
Ile Arg Asp Ala Gly Phe Glu Ile Ser Ala Met Gln Met Phe Asn Met
225                 230                 235                 240
Asp Arg Val Asn Val Glu Glu Phe Tyr Glu Val Tyr Lys Gly Val Val
                 245                 250                 255
Thr Glu Tyr His Asp Met Val Thr Glu Met Tyr Ser Gly Pro Cys Val
             260                 265                 270
Ala Met Glu Ile Gln Gln Asn Asn Ala Thr Lys Thr Phe Arg Glu Phe
         275                 280                 285
Cys Gly Pro Ala Asp Pro Glu Ile Ala Arg His Leu Arg Pro Gly Thr
     290                 295                 300
Leu Arg Ala Ile Phe Gly Lys Thr Lys Ile Gln Asn Ala Val His Cys
305                 310                 315                 320
Thr Asp Leu Pro Glu Asp Gly Leu Leu Glu Val Gln Tyr Phe Phe Lys
                 325                 330                 335
Ile Leu Asp Asn
             340

<210> SEQ ID NO 22
<211> LENGTH: 399
<212> TYPE: DNA
<213> ORGANISM: Artificial Sequence
<220> FEATURE:
<223> OTHER INFORMATION: Human NME7-A

<400> SEQUENCE: 22
atggaaaaaa cgctagccct aattaaacca gatgcaatat caaaggctgg agaaataatt     60 gaataataa acaaagctgg atttactata accaaactca aatgatgat gctttcaagg    120 aaagaagcat tggattttca gtagatcac cagtcaagac ccttttcaa tgagctgatc    180 cagtttatta caactggtcc tattattgcc atggagattt taagagatga tgctatatgt    240
```

```
gaatggaaaa gactgctggg acctgcaaac tctggagtgg cacgcacaga tgcttctgaa      300
agcattagag ccctctttgg aacagatggc ataagaaatg cagcgcatgg ccctgattct      360
tttgcttctg cggccagaga aatggagttg ttttttttga                            399
```

<210> SEQ ID NO 23
<211> LENGTH: 132
<212> TYPE: PRT
<213> ORGANISM: Artificial Sequence
<220> FEATURE:
<223> OTHER INFORMATION: Human NME7-A

<400> SEQUENCE: 23

```
Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
            20                  25                  30

Leu Lys Met Met Met Leu Ser Arg Lys Glu Ala Leu Asp Phe His Val
        35                  40                  45

Asp His Gln Ser Arg Pro Phe Phe Asn Glu Leu Ile Gln Phe Ile Thr
    50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr
                85                  90                  95

Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Ala Arg Glu Met
        115                 120                 125

Glu Leu Phe Phe
    130
```

<210> SEQ ID NO 24
<211> LENGTH: 444
<212> TYPE: DNA
<213> ORGANISM: Artificial Sequence
<220> FEATURE:
<223> OTHER INFORMATION: Human NME7-A1

<400> SEQUENCE: 24

```
atggaaaaaa cgctagccct aattaaacca gatgcaatat caaaggctgg agaaataatt      60
gaaataataa acaagctgg atttactata accaaactca aaatgatgat gctttcaagg      120
aaagaagcat tggattttca tgtagatcac cagtcaagac ccttttttcaa tgagctgatc      180 cagtttatta caactggtcc tattattgcc atggagattt taagagatga tgctatatgt      240
gaatggaaaa gactgctggg acctgcaaac tctggagtgg cacgcacaga tgcttctgaa      300
agcattagag ccctctttgg aacagatggc ataagaaatg cagcgcatgg ccctgattct      360
tttgcttctg cggccagaga aatggagttg ttttttcctt caagtggagg ttgtgggccg      420
gcaaacactg ctaaatttac ttga                                             444
```

<210> SEQ ID NO 25
<211> LENGTH: 147
<212> TYPE: PRT
<213> ORGANISM: Artificial Sequence
<220> FEATURE:
<223> OTHER INFORMATION: Human NME7-A1

<400> SEQUENCE: 25

Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
                20                  25                  30

Leu Lys Met Met Met Leu Ser Arg Lys Glu Ala Leu Asp Phe His Val
            35                  40                  45

Asp His Gln Ser Arg Pro Phe Phe Asn Glu Leu Ile Gln Phe Ile Thr
        50                  55                  60

Thr Gly Pro Ile Ile Ala Met Glu Ile Leu Arg Asp Asp Ala Ile Cys
65              70                  75                  80

Glu Trp Lys Arg Leu Leu Gly Pro Ala Asn Ser Gly Val Ala Arg Thr
                85                  90                  95

Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Ala Arg Glu Met
        115                 120                 125

Glu Leu Phe Phe Pro Ser Ser Gly Gly Cys Gly Pro Ala Asn Thr Ala
    130                 135                 140

Lys Phe Thr
145

<210> SEQ ID NO 26
<211> LENGTH: 669
<212> TYPE: DNA
<213> ORGANISM: Artificial Sequence
<220> FEATURE:
<223> OTHER INFORMATION: Human NME7-A2

<400> SEQUENCE: 26
atgaatcata gtgaaagatt cgttttcatt gcagagtggt atgatccaaa tgcttcactt     60
cttcgacgtt atgagctttt attttaccca ggggatggat ctgttgaaat gcatgatgta    120
aagaatcatc gcacctttt aaagcggacc aaatatgata acctgcactt ggaagattta    180
tttataggca acaaagtgaa tgtcttttct cgacaactgg tattaattga ctatggggat    240
caatatacag ctcgccagct gggcagtagg aagaaaaaa cgctagccct aattaaacca    300
gatgcaatat caaaggctgg agaaataatt gaaataataa acaaagctgg atttactata    360
accaaactca aatgatgat gctttcaagg aagaagcat ggatttttca tgtagatcac    420
cagtcaagac ccttttttcaa tgagctgatc cagtttatta caactggtcc tattattgcc    480
atggagattt aagagatga tgctatatgt gaatggaaaa gactgctggg acctgcaaac    540
tctggagtgg cacgcacaga tgcttctgaa agcattagag ccctctttgg aacagatggc    600
ataagaaatg cagcgcatgg ccctgattct tttgcttctg cggccagaga aatggagttg    660
ttttttttga                                                            669

<210> SEQ ID NO 27
<211> LENGTH: 222
<212> TYPE: PRT
<213> ORGANISM: Artificial Sequence
<220> FEATURE:
<223> OTHER INFORMATION: Human NME7-A2

<400> SEQUENCE: 27

Met Asn His Ser Glu Arg Phe Val Phe Ile Ala Glu Trp Tyr Asp Pro
1               5                   10                  15

Asn Ala Ser Leu Leu Arg Arg Tyr Glu Leu Leu Phe Tyr Pro Gly Asp

```
                    20                  25                  30
Gly Ser Val Glu Met His Asp Val Lys Asn His Arg Thr Phe Leu Lys
             35                  40                  45

Arg Thr Lys Tyr Asp Asn Leu His Leu Glu Asp Leu Phe Ile Gly Asn
         50                  55                  60

Lys Val Asn Val Phe Ser Arg Gln Leu Val Leu Ile Asp Tyr Gly Asp
 65                  70                  75                  80

Gln Tyr Thr Ala Arg Gln Leu Gly Ser Arg Lys Glu Lys Thr Leu Ala
                 85                  90                  95

Leu Ile Lys Pro Asp Ala Ile Ser Lys Ala Gly Glu Ile Ile Glu Ile
            100                 105                 110

Ile Asn Lys Ala Gly Phe Thr Ile Thr Lys Leu Lys Met Met Met Leu
        115                 120                 125

Ser Arg Lys Glu Ala Leu Asp Phe His Val Asp His Gln Ser Arg Pro
    130                 135                 140

Phe Phe Asn Glu Leu Ile Gln Phe Ile Thr Thr Gly Pro Ile Ile Ala
145                 150                 155                 160

Met Glu Ile Leu Arg Asp Asp Ala Ile Cys Glu Trp Lys Arg Leu Leu
                165                 170                 175

Gly Pro Ala Asn Ser Gly Val Ala Arg Thr Asp Ala Ser Glu Ser Ile
            180                 185                 190

Arg Ala Leu Phe Gly Thr Asp Gly Ile Arg Asn Ala Ala His Gly Pro
        195                 200                 205

Asp Ser Phe Ala Ser Ala Ala Arg Glu Met Glu Leu Phe Phe
    210                 215                 220

<210> SEQ ID NO 28
<211> LENGTH: 714
<212> TYPE: DNA
<213> ORGANISM: Artificial Sequence
<220> FEATURE:
<223> OTHER INFORMATION: Human NME7-A3

<400> SEQUENCE: 28
atgaatcata gtgaaagatt cgttttcatt gcagagtggt atgatccaaa tgcttcactt     60
cttcgacgtt atgagctttt attttaccca ggggatggat ctgttgaaat gcatgatgta    120
aagaatcatc gcaccttttt aaagcggacc aaatatgata acctgcactt ggaagattta    180
tttataggca acaaagtgaa tgtcttttct cgacaactgg tattaattga ctatggggat    240
caatatacag ctcgccagct gggcagtagg aagaaaaaa cgctagccct aattaaacca    300
gatgcaatat caaaggctgg agaaataatt gaaataataa acaaagctgg atttactata    360
accaaactca aaatgatgat gctttcaagg aaagaagcat tggattttca tgtagatcac    420
cagtcaagac ccttttttcaa tgagctgatc cagtttatta caactggtcc tattattgcc    480
atggagattt taagagatga tgctatatgt gaatggaaaa gactgctggg acctgcaaac    540
tctggagtgg cacgcacaga tgcttctgaa agcattagag ccctctttgg aacagatggc    600
ataagaaatg cagcgcatgg ccctgattct tttgcttctg cggccagaga aatggagttg    660
ttttttcctt caagtggagg ttgtgggccg gcaaacactg ctaaatttac ttga          714

<210> SEQ ID NO 29
<211> LENGTH: 237
<212> TYPE: PRT
<213> ORGANISM: Artificial Sequence
<220> FEATURE:
<223> OTHER INFORMATION: Human NME7-A3
```

<400> SEQUENCE: 29

```
Met Asn His Ser Glu Arg Phe Val Phe Ile Ala Glu Trp Tyr Asp Pro
1               5                   10                  15

Asn Ala Ser Leu Leu Arg Arg Tyr Glu Leu Leu Phe Tyr Pro Gly Asp
            20                  25                  30

Gly Ser Val Glu Met His Asp Val Lys Asn His Arg Thr Phe Leu Lys
        35                  40                  45

Arg Thr Lys Tyr Asp Asn Leu His Leu Glu Asp Leu Phe Ile Gly Asn
    50                  55                  60

Lys Val Asn Val Phe Ser Arg Gln Leu Val Leu Ile Asp Tyr Gly Asp
65                  70                  75                  80

Gln Tyr Thr Ala Arg Gln Leu Gly Ser Arg Lys Glu Lys Thr Leu Ala
                85                  90                  95

Leu Ile Lys Pro Asp Ala Ile Ser Lys Ala Gly Glu Ile Ile Glu Ile
            100                 105                 110

Ile Asn Lys Ala Gly Phe Thr Ile Thr Lys Leu Lys Met Met Met Leu
        115                 120                 125

Ser Arg Lys Glu Ala Leu Asp Phe His Val Asp His Gln Ser Arg Pro
    130                 135                 140

Phe Phe Asn Glu Leu Ile Gln Phe Ile Thr Thr Gly Pro Ile Ile Ala
145                 150                 155                 160

Met Glu Ile Leu Arg Asp Asp Ala Ile Cys Glu Trp Lys Arg Leu Leu
                165                 170                 175

Gly Pro Ala Asn Ser Gly Val Ala Arg Thr Asp Ala Ser Glu Ser Ile
            180                 185                 190

Arg Ala Leu Phe Gly Thr Asp Gly Ile Arg Asn Ala Ala His Gly Pro
        195                 200                 205

Asp Ser Phe Ala Ser Ala Ala Arg Glu Met Glu Leu Phe Phe Pro Ser
    210                 215                 220

Ser Gly Gly Cys Gly Pro Ala Asn Thr Ala Lys Phe Thr
225                 230                 235
```

<210> SEQ ID NO 30
<211> LENGTH: 408
<212> TYPE: DNA
<213> ORGANISM: Artificial Sequence
<220> FEATURE:
<223> OTHER INFORMATION: Human NME7-B

<400> SEQUENCE: 30

```
atgaattgta cctgttgcat tgttaaaccc catgctgtca gtgaaggact gttgggaaag      60
atcctgatgg ctatccgaga tgcaggtttt gaaatctcag ctatgcagat gttcaatatg     120
gatcgggtta atgttgagga attctatgaa gtttataaag gagtagtgac cgaatatcat     180
gacatggtga cagaaatgta ttctggccct tgtgtagcaa tggagattca acagaataat     240
gctacaaaga catttcgaga attttgtgga cctgctgatc ctgaaattgc ccggcattta     300
cgccctggaa ctctcagagc aatctttggt aaaactaaga tccagaatgc tgttcactgt     360
actgatctgc cagaggatgg cctattagag gttcaatact tcttctga                 408
```

<210> SEQ ID NO 31
<211> LENGTH: 135
<212> TYPE: PRT
<213> ORGANISM: Artificial Sequence
<220> FEATURE:
<223> OTHER INFORMATION: Human NME7-B

<400> SEQUENCE: 31

Met Asn Cys Thr Cys Ile Val Lys Pro His Ala Val Ser Glu Gly
1               5                   10                  15

Leu Leu Gly Lys Ile Leu Met Ala Ile Arg Asp Ala Gly Phe Glu Ile
            20                  25                  30

Ser Ala Met Gln Met Phe Asn Met Asp Arg Val Asn Val Glu Glu Phe
                35                  40                  45

Tyr Glu Val Tyr Lys Gly Val Val Thr Glu Tyr His Asp Met Val Thr
50                  55                  60

Glu Met Tyr Ser Gly Pro Cys Val Ala Met Glu Ile Gln Gln Asn Asn
65                  70                  75                  80

Ala Thr Lys Thr Phe Arg Glu Phe Cys Gly Pro Ala Asp Pro Glu Ile
                85                  90                  95

Ala Arg His Leu Arg Pro Gly Thr Leu Arg Ala Ile Phe Gly Lys Thr
                100                 105                 110

Lys Ile Gln Asn Ala Val His Cys Thr Asp Leu Pro Glu Asp Gly Leu
            115                 120                 125

Leu Glu Val Gln Tyr Phe Phe
        130                 135

<210> SEQ ID NO 32
<211> LENGTH: 426
<212> TYPE: DNA
<213> ORGANISM: Artificial Sequence
<220> FEATURE:
<223> OTHER INFORMATION: Human NME7-B1

<400> SEQUENCE: 32
atgaattgta cctgttgcat tgttaaaccc catgctgtca gtgaaggact gttgggaaag      60
atcctgatgg ctatccgaga tgcaggtttt gaaatctcag ctatgcagat gttcaatatg     120
gatcgggtta atgttgagga attctatgaa gtttataaag gagtagtgac cgaatatcat     180
gacatggtga cagaaatgta ttctggccct gtgtagcaa tggagattca acagaataat      240
gctacaaaga catttcgaga attttgtgga cctgctgatc ctgaaattgc cggcattta      300 cgccctggaa ctctcagagc aatctttggt aaaactaaga tccagaatgc tgttcactgt     360
actgatctgc cagaggatgg cctattagag gttcaatact tcttcaagat cttggataat    420
tagtga                                                               426

<210> SEQ ID NO 33
<211> LENGTH: 140
<212> TYPE: PRT
<213> ORGANISM: Artificial Sequence
<220> FEATURE:
<223> OTHER INFORMATION: Human NME7-B1

<400> SEQUENCE: 33

Met Asn Cys Thr Cys Ile Val Lys Pro His Ala Val Ser Glu Gly
1               5                   10                  15

Leu Leu Gly Lys Ile Leu Met Ala Ile Arg Asp Ala Gly Phe Glu Ile
            20                  25                  30

Ser Ala Met Gln Met Phe Asn Met Asp Arg Val Asn Val Glu Glu Phe
                35                  40                  45

Tyr Glu Val Tyr Lys Gly Val Val Thr Glu Tyr His Asp Met Val Thr
50                  55                  60

Glu Met Tyr Ser Gly Pro Cys Val Ala Met Glu Ile Gln Gln Asn Asn

```
                65                  70                  75                  80
Ala Thr Lys Thr Phe Arg Glu Phe Cys Gly Pro Ala Asp Pro Glu Ile
                        85                  90                  95

Ala Arg His Leu Arg Pro Gly Thr Leu Arg Ala Ile Phe Gly Lys Thr
                    100                 105                 110

Lys Ile Gln Asn Ala Val His Cys Thr Asp Leu Pro Glu Asp Gly Leu
                115                 120                 125

Leu Glu Val Gln Tyr Phe Phe Lys Ile Leu Asp Asn
            130                 135                 140

<210> SEQ ID NO 34
<211> LENGTH: 453
<212> TYPE: DNA
<213> ORGANISM: Artificial Sequence
<220> FEATURE:
<223> OTHER INFORMATION: Human NME7-B2

<400> SEQUENCE: 34
atgccttcaa gtggaggttg tgggccggca acactgcta aatttactaa ttgtacctgt      60
tgcattgtta aacccatgc tgtcagtgaa ggactgttgg gaaagatcct gatggctatc    120
cgagatgcag gttttgaaat ctcagctatg cagatgttca atatggatcg gttaatgtt    180 gaggaattct atgaagttta taaggagta gtgaccgaat atcatgacat ggtgacagaa    240
atgtattctg gcccttgtgt agcaatggag attcaacaga ataatgctac aaagacattt    300
cgagaatttt gtggacctgc tgatcctgaa attgcccggc atttacgccc tggaactctc    360
agagcaatct ttggtaaaac taagatccag aatgctgttc actgtactga tctgccagag    420
gatggcctat tagaggttca atacttcttc tga                                  453

<210> SEQ ID NO 35
<211> LENGTH: 150
<212> TYPE: PRT
<213> ORGANISM: Artificial Sequence
<220> FEATURE:
<223> OTHER INFORMATION: Human NME7-B2

<400> SEQUENCE: 35

Met Pro Ser Ser Gly Gly Cys Gly Pro Ala Asn Thr Ala Lys Phe Thr
1               5                   10                  15

Asn Cys Thr Cys Cys Ile Val Lys Pro His Ala Val Ser Glu Gly Leu
                20                  25                  30

Leu Gly Lys Ile Leu Met Ala Ile Arg Asp Ala Gly Phe Glu Ile Ser
            35                  40                  45

Ala Met Gln Met Phe Asn Met Asp Arg Val Asn Val Glu Glu Phe Tyr
        50                  55                  60

Glu Val Tyr Lys Gly Val Val Thr Glu Tyr His Asp Met Val Thr Glu
65                  70                  75                  80

Met Tyr Ser Gly Pro Cys Val Ala Met Glu Ile Gln Gln Asn Asn Ala
                85                  90                  95

Thr Lys Thr Phe Arg Glu Phe Cys Gly Pro Ala Asp Pro Glu Ile Ala
            100                 105                 110

Arg His Leu Arg Pro Gly Thr Leu Arg Ala Ile Phe Gly Lys Thr Lys
        115                 120                 125

Ile Gln Asn Ala Val His Cys Thr Asp Leu Pro Glu Asp Gly Leu Leu
    130                 135                 140

Glu Val Gln Tyr Phe Phe
145                 150
```

<210> SEQ ID NO 36
<211> LENGTH: 471
<212> TYPE: DNA
<213> ORGANISM: Artificial Sequence
<220> FEATURE:
<223> OTHER INFORMATION: Human NME7-B3

<400> SEQUENCE: 36

```
atgccttcaa gtggaggttg tgggccggca acactgcta aatttactaa ttgtacctgt      60
tgcattgtta aaccccatgc tgtcagtgaa ggactgttgg gaaagatcct gatggctatc    120
cgagatgcag gttttgaaat ctcagctatg cagatgttca atatggatcg ggttaatgtt    180
gaggaattct atgaagttta taaggagta gtgaccgaat catgacat ggtgacagaa       240
atgtattctg gcccttgtgt agcaatggag attcaacaga ataatgctac aaagacattt    300
cgagaatttt gtggacctgc tgatcctgaa attgcccggc atttacgccc tggaactctc    360
agagcaatct tggtaaaaac taagatccag aatgctgttc actgtactga tctgccagag    420
gatggcctat tagaggttca atacttcttc aagatcttgg ataattagtg a            471
```

<210> SEQ ID NO 37
<211> LENGTH: 155
<212> TYPE: PRT
<213> ORGANISM: Artificial Sequence
<220> FEATURE:
<223> OTHER INFORMATION: Human NME7-B3

<400> SEQUENCE: 37

```
Met Pro Ser Ser Gly Gly Cys Gly Pro Ala Asn Thr Ala Lys Phe Thr
1               5                   10                  15
Asn Cys Thr Cys Cys Ile Val Lys Pro His Ala Val Ser Glu Gly Leu
            20                  25                  30
Leu Gly Lys Ile Leu Met Ala Ile Arg Asp Ala Gly Phe Glu Ile Ser
        35                  40                  45
Ala Met Gln Met Phe Asn Met Asp Arg Val Asn Val Glu Glu Phe Tyr
    50                  55                  60
Glu Val Tyr Lys Gly Val Val Thr Glu Tyr His Asp Met Val Thr Glu
65                  70                  75                  80
Met Tyr Ser Gly Pro Cys Val Ala Met Glu Ile Gln Gln Asn Asn Ala
                85                  90                  95
Thr Lys Thr Phe Arg Glu Phe Cys Gly Pro Ala Asp Pro Glu Ile Ala
            100                 105                 110
Arg His Leu Arg Pro Gly Thr Leu Arg Ala Ile Phe Gly Lys Thr Lys
        115                 120                 125
Ile Gln Asn Ala Val His Cys Thr Asp Leu Pro Glu Asp Gly Leu Leu
    130                 135                 140
Glu Val Gln Tyr Phe Phe Lys Ile Leu Asp Asn
145                 150                 155
```

<210> SEQ ID NO 38
<211> LENGTH: 864
<212> TYPE: DNA
<213> ORGANISM: Artificial Sequence
<220> FEATURE:
<223> OTHER INFORMATION: Human NME7-AB, also known as NME7AB

<400> SEQUENCE: 38

```
atggaaaaaa cgctagccct aattaaacca gatgcaatat caaaggctgg agaaataatt    60
```

-continued

```
gaaataataa acaaagctgg atttactata accaaactca aatgatgat gctttcaagg      120 aaagaagcat ggattttca tgtagatcac cagtcaagac cctttttcaa tgagctgatc      180
cagtttatta caactggtcc tattattgcc atggagattt aagagatga tgctatatgt      240 gaatggaaaa gactgctggg acctgcaaac tctggagtgg cacgcacaga tgcttctgaa      300
agcattagag ccctctttgg aacagatggc ataagaaatg cagcgcatgg ccctgattct      360
tttgcttctg cggccagaga aatggagttg ttttttcctt caagtggagg ttgtgggccg      420
gcaaacactg ctaaatttac taattgtacc tgttgcattg ttaaacccca tgctgtcagt      480
gaaggactgt tgggaaagat cctgatggct atccgagatg caggttttga aatctcagct      540
atgcagatgt tcaatatgga tcgggttaat gttgaggaat ctatgaagt ttataaagga      600 gtagtgaccg aatatcatga catggtgaca gaaatgtatt ctggcccttg tgtagcaatg      660
gagattcaac agaataatgc tacaaagaca tttcgagaat tttgtggacc tgctgatcct      720
gaaattgccc ggcatttacg ccctggaact ctcagagcaa tctttggtaa aactaagatc      780
cagaatgctg ttcactgtac tgatctgcca gaggatggcc tattagaggt tcaatacttc      840
ttcaagatct tggataatta gtga                                             864
```

<210> SEQ ID NO 39
<211> LENGTH: 286
<212> TYPE: PRT
<213> ORGANISM: Artificial Sequence
<220> FEATURE:
<223> OTHER INFORMATION: Human NME7-AB, also known as NME7AB

<400> SEQUENCE: 39

```
Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
            20                  25                  30

Leu Lys Met Met Met Leu Ser Arg Lys Glu Ala Leu Asp Phe His Val
        35                  40                  45

Asp His Gln Ser Arg Pro Phe Phe Asn Glu Leu Ile Gln Phe Ile Thr
    50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr
                85                  90                  95

Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Ala Arg Glu Met
        115                 120                 125

Glu Leu Phe Phe Pro Ser Ser Gly Gly Cys Gly Pro Ala Asn Thr Ala
    130                 135                 140

Lys Phe Thr Asn Cys Thr Cys Cys Ile Val Lys Pro His Ala Val Ser
145                 150                 155                 160

Glu Gly Leu Leu Gly Lys Ile Leu Met Ala Ile Arg Asp Ala Gly Phe
                165                 170                 175

Glu Ile Ser Ala Met Gln Met Phe Asn Met Asp Arg Val Asn Val Glu
            180                 185                 190

Glu Phe Tyr Glu Val Tyr Lys Gly Val Val Thr Glu Tyr His Asp Met
        195                 200                 205

Val Thr Glu Met Tyr Ser Gly Pro Cys Val Ala Met Glu Ile Gln Gln
    210                 215                 220
```

Asn Asn Ala Thr Lys Thr Phe Arg Glu Phe Cys Gly Pro Ala Asp Pro
225                 230                 235                 240

Glu Ile Ala Arg His Leu Arg Pro Gly Thr Leu Arg Ala Ile Phe Gly
                245                 250                 255

Lys Thr Lys Ile Gln Asn Ala Val His Cys Thr Asp Leu Pro Glu Asp
            260                 265                 270

Gly Leu Leu Glu Val Gln Tyr Phe Phe Lys Ile Leu Asp Asn
        275                 280                 285

<210> SEQ ID NO 40
<211> LENGTH: 846
<212> TYPE: DNA
<213> ORGANISM: Artificial Sequence
<220> FEATURE:
<223> OTHER INFORMATION: Human NME7-AB1

<400> SEQUENCE: 40

| | | | | | |
|---|---|---|---|---|---|
| atggaaaaaa | cgctagccct | aattaaacca | gatgcaatat | caaaggctgg | agaaataatt | 60 |
| gaataataa | acaaagctgg | atttactata | accaaactca | aaatgatgat | gctttcaagg | 120 |
| aaagaagcat | tggattttca | tgtagatcac | cagtcaagac | ccttttttcaa | tgagctgatc | 180 |
| cagtttatta | caactggtcc | tattattgcc | atggagattt | taagagatga | tgctatatgt | 240 |
| gaatggaaaa | gactgctggg | acctgcaaac | tctggagtgg | cacgcacaga | tgcttctgaa | 300 |
| agcattagag | ccctctttgg | aacagatggc | ataagaaatg | cagcgcatgg | ccctgattct | 360 |
| tttgcttctg | cggccagaga | aatggagttg | ttttttcctt | caagtggagg | ttgtgggccg | 420 |
| gcaaacactg | ctaaatttac | taattgtacc | tgttgcattg | ttaaacccca | tgctgtcagt | 480 |
| gaaggactgt | tgggaaagat | cctgatggct | atccgagatg | caggttttga | aatctcagct | 540 |
| atgcagatgt | tcaatatgga | tcgggttaat | gttgaggaat | tctatgaagt | ttataaagga | 600 |
| gtagtgaccg | aatatcatga | catggtgaca | gaaatgtatt | ctggcccttg | tgtagcaatg | 660 |
| gagattcaac | agaataatgc | tacaaagaca | tttcgagaat | tttgtggacc | tgctgatcct | 720 |
| gaaattgccc | ggcatttacg | ccctggaact | ctcagagcaa | tctttggtaa | aactaagatc | 780 |
| cagaatgctg | ttcactgtac | tgatctgcca | gaggatggcc | tattagaggt | tcaatacttc | 840 |
| ttctga | | | | | | 846 |

<210> SEQ ID NO 41
<211> LENGTH: 281
<212> TYPE: PRT
<213> ORGANISM: Artificial Sequence
<220> FEATURE:
<223> OTHER INFORMATION: Human NME7-AB1

<400> SEQUENCE: 41

Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
            20                  25                  30

Leu Lys Met Met Met Leu Ser Arg Lys Glu Ala Leu Asp Phe His Val
        35                  40                  45

Asp His Gln Ser Arg Pro Phe Phe Asn Glu Leu Ile Gln Phe Ile Thr
    50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr

```
                85                  90                  95
Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Ala Arg Glu Met
        115                 120                 125

Glu Leu Phe Phe Pro Ser Ser Gly Gly Cys Gly Pro Ala Asn Thr Ala
    130                 135                 140

Lys Phe Thr Asn Cys Thr Cys Cys Ile Val Lys Pro His Ala Val Ser
145                 150                 155                 160

Glu Gly Leu Leu Gly Lys Ile Leu Met Ala Ile Arg Asp Ala Gly Phe
                165                 170                 175

Glu Ile Ser Ala Met Gln Met Phe Asn Met Asp Arg Val Asn Val Glu
            180                 185                 190

Glu Phe Tyr Glu Val Tyr Lys Gly Val Val Thr Glu Tyr His Asp Met
        195                 200                 205

Val Thr Glu Met Tyr Ser Gly Pro Cys Val Ala Met Glu Ile Gln Gln
    210                 215                 220

Asn Asn Ala Thr Lys Thr Phe Arg Glu Phe Cys Gly Pro Ala Asp Pro
225                 230                 235                 240

Glu Ile Ala Arg His Leu Arg Pro Gly Thr Leu Arg Ala Ile Phe Gly
                245                 250                 255

Lys Thr Lys Ile Gln Asn Ala Val His Cys Thr Asp Leu Pro Glu Asp
            260                 265                 270

Gly Leu Leu Glu Val Gln Tyr Phe Phe
        275                 280

<210> SEQ ID NO 42
<211> LENGTH: 399
<212> TYPE: DNA
<213> ORGANISM: Artificial Sequence
<220> FEATURE:
<223> OTHER INFORMATION: Human NME7-A sequence optimized for E. coli
      expression

<400> SEQUENCE: 42
atggaaaaaa cgctggccct gattaaaccg gatgcaatct ccaaagctgg cgaaattatc      60
gaaattatca acaaagcggg tttcaccatc acgaaactga aaatgatgat gctgagccgt     120
aaagaagccc tggattttca gtcgaccacc agtctcgccc gttttttcaa tgaactgatt     180
caattcatca ccacgggtcc gattatcgca atggaaattc tgcgtgatga cgctatctgc     240
gaatggaaac gctgctgggg cccggcaaac tcaggtgttg cgcgtaccga tgccagtgaa     300
tccattcgcg ctctgtttgg caccgatggt atccgtaatg cagcacatgg tccggactca     360
ttcgcatcgg cagctcgtga atggaactg ttttctga                              399

<210> SEQ ID NO 43
<211> LENGTH: 132
<212> TYPE: PRT
<213> ORGANISM: Artificial Sequence
<220> FEATURE:
<223> OTHER INFORMATION: Human NME7-A sequence optimized for E. coli
      expression

<400> SEQUENCE: 43

Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
            20                  25                  30
```

Leu Lys Met Met Met Leu Ser Arg Lys Glu Ala Leu Asp Phe His Val
            35                  40                  45

Asp His Gln Ser Arg Pro Phe Phe Asn Glu Leu Ile Gln Phe Ile Thr
        50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr
                85                  90                  95

Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Ala Arg Glu Met
            115                 120                 125

Glu Leu Phe Phe
        130

<210> SEQ ID NO 44
<211> LENGTH: 444
<212> TYPE: DNA
<213> ORGANISM: Artificial Sequence
<220> FEATURE:
<223> OTHER INFORMATION: Human NME7-A1 sequence optimized for E. coli
      expression

<400> SEQUENCE: 44
atggaaaaaa cgctggccct gattaaaccg gatgcaatct ccaaagctgg cgaaattatc     60
gaaattatca caaagcggg tttcaccatc acgaaactga aatgatgat gctgagccgt      120 aaagaagccc tggattttca tgtcgaccac cagtctcgcc cgttttttcaa tgaactgatt   180 caattcatca ccacgggtcc gattatcgca atggaaattc tgcgtgatga cgctatctgc   240
gaatggaaac gcctgctggg cccggcaaac tcaggtgttg cgcgtaccga tgccagtgaa   300
tccattcgcg ctctgtttgg caccgatggt atccgtaatg cagcacatgg tccggactca   360
ttcgcatcgg cagctcgtga atggaactg ttttttcccga gctctggcgg ttgcggtccg   420
gcaaacaccg ccaaatttac ctga                                            444

<210> SEQ ID NO 45
<211> LENGTH: 147
<212> TYPE: PRT
<213> ORGANISM: Artificial Sequence
<220> FEATURE:
<223> OTHER INFORMATION: Human NME7-A1 sequence optimized for E. coli
      expression

<400> SEQUENCE: 45

Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
            20                  25                  30

Leu Lys Met Met Met Leu Ser Arg Lys Glu Ala Leu Asp Phe His Val
            35                  40                  45

Asp His Gln Ser Arg Pro Phe Phe Asn Glu Leu Ile Gln Phe Ile Thr
        50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr
                85                  90                  95

Asp Ala Ser Glu Ser Ile Arg Ala Leu Phe Gly Thr Asp Gly Ile Arg

```
              100                 105                 110
Asn Ala Ala His Gly Pro Asp Ser Phe Ala Ser Ala Ala Arg Glu Met
            115                 120                 125

Glu Leu Phe Phe Pro Ser Ser Gly Gly Cys Gly Pro Ala Asn Thr Ala
        130                 135                 140

Lys Phe Thr
145

<210> SEQ ID NO 46
<211> LENGTH: 669
<212> TYPE: DNA
<213> ORGANISM: Artificial Sequence
<220> FEATURE:
<223> OTHER INFORMATION: Human NME7-A2 sequence optimized for E. coli
      expression

<400> SEQUENCE: 46
atgaatcact ccgaacgctt tgtttttatc gccgaatggt atgacccgaa tgcttccctg    60
ctgcgccgct acgaactgct gttttatccg ggcgatggta gcgtggaaat gcatgacgtt   120
aaaaatcacc gtacctttct gaaacgcacg aaatatgata tcctgcatct ggaagacctg   180
tttattggca caaagtcaa tgtgttctct cgtcagctgg tgctgatcga ttatggcgac   240
cagtacaccg cgcgtcaact gggtagtcgc aagaaaaaa cgctggccct gattaaaccg   300
gatgcaatct ccaaagctgg cgaaattatc gaaattatca caaagcggg ttcaccatc    360 acgaaactga aaatgatgat gctgagccgt aagaagccc tggattttca tgtcgaccac   420
cagtctcgcc cgttttttcaa tgaactgatt caattcatca ccacgggtcc gattatcgca   480
atggaaattc tgcgtgatga cgctatctgc gaatggaaac gcctgctggg cccggcaaac   540
tcaggtgttg cgcgtaccga tgccagtgaa tccattcgcg ctctgtttgg caccgatggt   600
atccgtaatg cagcacatgg tccggactca ttcgcatcgg cagctcgtga atggaactg    660 ttttctga                                                           669

<210> SEQ ID NO 47
<211> LENGTH: 222
<212> TYPE: PRT
<213> ORGANISM: Artificial Sequence
<220> FEATURE:
<223> OTHER INFORMATION: Human NME7-A2 sequence optimized for E. coli
      expression

<400> SEQUENCE: 47

Met Asn His Ser Glu Arg Phe Val Phe Ile Ala Glu Trp Tyr Asp Pro
1               5                   10                  15

Asn Ala Ser Leu Leu Arg Arg Tyr Glu Leu Leu Phe Tyr Pro Gly Asp
            20                  25                  30

Gly Ser Val Glu Met His Asp Val Lys Asn His Arg Thr Phe Leu Lys
        35                  40                  45

Arg Thr Lys Tyr Asp Asn Leu His Leu Glu Asp Leu Phe Ile Gly Asn
    50                  55                  60

Lys Val Asn Val Phe Ser Arg Gln Leu Val Leu Ile Asp Tyr Gly Asp
65                  70                  75                  80

Gln Tyr Thr Ala Arg Gln Leu Gly Ser Arg Lys Glu Lys Thr Leu Ala
                85                  90                  95

Leu Ile Lys Pro Asp Ala Ile Ser Lys Ala Gly Glu Ile Ile Glu Ile
            100                 105                 110

Ile Asn Lys Ala Gly Phe Thr Ile Thr Lys Leu Lys Met Met Met Leu
```

```
                115                 120                 125
Ser Arg Lys Glu Ala Leu Asp Phe His Val Asp His Gln Ser Arg Pro
            130                 135                 140

Phe Phe Asn Glu Leu Ile Gln Phe Ile Thr Thr Gly Pro Ile Ile Ala
145                 150                 155                 160

Met Glu Ile Leu Arg Asp Asp Ala Ile Cys Glu Trp Lys Arg Leu Leu
                165                 170                 175

Gly Pro Ala Asn Ser Gly Val Ala Arg Thr Asp Ala Ser Glu Ser Ile
            180                 185                 190

Arg Ala Leu Phe Gly Thr Asp Gly Ile Arg Asn Ala Ala His Gly Pro
        195                 200                 205

Asp Ser Phe Ala Ser Ala Ala Arg Glu Met Glu Leu Phe Phe
        210                 215                 220
```

<210> SEQ ID NO 48
<211> LENGTH: 714
<212> TYPE: DNA
<213> ORGANISM: Artificial Sequence
<220> FEATURE:
<223> OTHER INFORMATION: Human NME7-A3 sequence optimized for E. coli
      expression

<400> SEQUENCE: 48

```
atgaatcact ccgaacgctt tgtttttatc gccgatggt atgacccgaa tgcttccctg      60
ctgcgccgct acgaactgct gttttatccg ggcgatggta gcgtggaaat gcatgacgtt    120
aaaaatcacc gtacctttct gaaacgcacg aaatatgata tctgcatct ggaagacctg    180
tttattggca acaaagtcaa tgtgttctct cgtcagctgg tgctgatcga ttatggcgac    240
cagtacaccg cgcgtcaact gggtagtcgc aaagaaaaaa cgctggccct gattaaaccg    300
gatgcaatct ccaaagctgg cgaaattatc gaaattatca caaagcgggg tttcaccatc    360
acgaaactga aaatgatgat gctgagccgt aaagaagccc tggattttca gtcgaccac    420
cagtctcgcc cgttttttcaa tgaactgatt caattcatca ccacgggtcc gattatcgca    480
atggaaattc tgcgtgatga cgctatctgc gaatggaaac gcctgctggg cccggcaaac    540
tcaggtgttg cgcgtaccga tgccagtgaa tccattcgcg ctctgtttgg caccgatggt    600
atccgtaatg cagcacatgg tccggactca ttcgcatcgg cagctcgtga atggaactg    660
ttttccccga gctctggcgg ttgcggtccg gcaaacaccg ccaaatttac ctga          714
```

<210> SEQ ID NO 49
<211> LENGTH: 237
<212> TYPE: PRT
<213> ORGANISM: Artificial Sequence
<220> FEATURE:
<223> OTHER INFORMATION: Human NME7-A3 sequence optimized for E. coli
      expression

<400> SEQUENCE: 49

```
Met Asn His Ser Glu Arg Phe Val Phe Ile Ala Glu Trp Tyr Asp Pro
1               5                   10                  15

Asn Ala Ser Leu Leu Arg Arg Tyr Glu Leu Leu Phe Tyr Pro Gly Asp
            20                  25                  30

Gly Ser Val Glu Met His Asp Val Lys Asn His Arg Thr Phe Leu Lys
        35                  40                  45

Arg Thr Lys Tyr Asp Asn Leu His Leu Glu Asp Leu Phe Ile Gly Asn
    50                  55                  60

Lys Val Asn Val Phe Ser Arg Gln Leu Val Leu Ile Asp Tyr Gly Asp
```

```
                65                  70                  75                  80
Gln Tyr Thr Ala Arg Gln Leu Gly Ser Arg Lys Glu Lys Thr Leu Ala
                    85                  90                  95
Leu Ile Lys Pro Asp Ala Ile Ser Lys Ala Gly Glu Ile Ile Glu Ile
                100                 105                 110
Ile Asn Lys Ala Gly Phe Thr Ile Thr Lys Leu Lys Met Met Met Leu
                115                 120                 125
Ser Arg Lys Glu Ala Leu Asp Phe His Val Asp His Gln Ser Arg Pro
130                 135                 140
Phe Phe Asn Glu Leu Ile Gln Phe Ile Thr Thr Gly Pro Ile Ile Ala
145                 150                 155                 160
Met Glu Ile Leu Arg Asp Asp Ala Ile Cys Glu Trp Lys Arg Leu Leu
                165                 170                 175
Gly Pro Ala Asn Ser Gly Val Ala Arg Thr Asp Ala Ser Glu Ser Ile
                180                 185                 190
Arg Ala Leu Phe Gly Thr Asp Gly Ile Arg Asn Ala Ala His Gly Pro
                195                 200                 205
Asp Ser Phe Ala Ser Ala Ala Arg Glu Met Glu Leu Phe Phe Pro Ser
    210                 215                 220
Ser Gly Gly Cys Gly Pro Ala Asn Thr Ala Lys Phe Thr
225                 230                 235

<210> SEQ ID NO 50
<211> LENGTH: 408
<212> TYPE: DNA
<213> ORGANISM: Artificial Sequence
<220> FEATURE:
<223> OTHER INFORMATION: Human NME7-B sequence optimized for E. coli
      expression

<400> SEQUENCE: 50
atgaattgta cgtgctgtat tgtcaaaccg cacgcagtgt cagaaggcct gctgggtaaa      60
attctgatgg caatccgtga tgctggcttt gaaatctcgg ccatgcagat gttcaacatg     120
gaccgcgtta acgtcgaaga attctacgaa gtttacaaag cgtggttac cgaatatcac      180 gatatggtta cggaaatgta ctccggtccg tgcgtcgcga tggaaattca gcaaaacaat     240
gccaccaaaa cgtttcgtga attctgtggt ccggcagatc cggaaatcgc acgtcatctg     300
cgtccgggta ccctgcgcgc aatttttggt aaaacgaaaa tccagaacgc tgtgcactgt     360
accgatctgc cggaagacgg tctgctggaa gttcaatact ttttctga                  408

<210> SEQ ID NO 51
<211> LENGTH: 135
<212> TYPE: PRT
<213> ORGANISM: Artificial Sequence
<220> FEATURE:
<223> OTHER INFORMATION: Human NME7-B sequence optimized for E. coli
      expression

<400> SEQUENCE: 51

Met Asn Cys Thr Cys Cys Ile Val Lys Pro His Ala Val Ser Glu Gly
1               5                   10                  15
Leu Leu Gly Lys Ile Leu Met Ala Ile Arg Asp Ala Gly Phe Glu Ile
                20                  25                  30
Ser Ala Met Gln Met Phe Asn Met Asp Arg Val Asn Val Glu Glu Phe
            35                  40                  45
Tyr Glu Val Tyr Lys Gly Val Val Thr Glu Tyr His Asp Met Val Thr
        50                  55                  60
```

Glu Met Tyr Ser Gly Pro Cys Val Ala Met Glu Ile Gln Gln Asn Asn
65                  70                  75                  80

Ala Thr Lys Thr Phe Arg Glu Phe Cys Gly Pro Ala Asp Pro Glu Ile
                85                  90                  95

Ala Arg His Leu Arg Pro Gly Thr Leu Arg Ala Ile Phe Gly Lys Thr
            100                 105                 110

Lys Ile Gln Asn Ala Val His Cys Thr Asp Leu Pro Glu Asp Gly Leu
        115                 120                 125

Leu Glu Val Gln Tyr Phe Phe
    130                 135

<210> SEQ ID NO 52
<211> LENGTH: 423
<212> TYPE: DNA
<213> ORGANISM: Artificial Sequence
<220> FEATURE:
<223> OTHER INFORMATION: Human NME7-B1 sequence optimized for E. coli
      expression

<400> SEQUENCE: 52
atgaattgta cgtgctgtat tgtcaaaccg cacgcagtgt cagaaggcct gctgggtaaa      60
attctgatgg caatccgtga tgctggcttt gaaatctcgg ccatgcagat gttcaacatg     120
gaccgcgtta acgtcgaaga attctacgaa gtttacaaag cgtggttac cgaatatcac     180 gatatggtta cggaaatgta ctccggtccg tgcgtcgcga tggaaattca gcaaacaat      240 gccaccaaaa cgtttcgtga attctgtggt ccggcagatc cggaaatcgc acgtcatctg     300
cgtccgggta ccctgcgcgc aattttttggt aaaacgaaaa tccagaacgc tgtgcactgt    360
accgatctgc cggaagacgg tctgctggaa gttcaatact ttttcaaaat tctggataat    420
tga                                                                    423

<210> SEQ ID NO 53
<211> LENGTH: 140
<212> TYPE: PRT
<213> ORGANISM: Artificial Sequence
<220> FEATURE:
<223> OTHER INFORMATION: Human NME7-B1 sequence optimized for E. coli
      expression

<400> SEQUENCE: 53

Met Asn Cys Thr Cys Cys Ile Val Lys Pro His Ala Val Ser Glu Gly
1               5                   10                  15

Leu Leu Gly Lys Ile Leu Met Ala Ile Arg Asp Ala Gly Phe Glu Ile
            20                  25                  30

Ser Ala Met Gln Met Phe Asn Met Asp Arg Val Asn Val Glu Glu Phe
        35                  40                  45

Tyr Glu Val Tyr Lys Gly Val Val Thr Glu Tyr His Asp Met Val Thr
    50                  55                  60

Glu Met Tyr Ser Gly Pro Cys Val Ala Met Glu Ile Gln Gln Asn Asn
65                  70                  75                  80

Ala Thr Lys Thr Phe Arg Glu Phe Cys Gly Pro Ala Asp Pro Glu Ile
                85                  90                  95

Ala Arg His Leu Arg Pro Gly Thr Leu Arg Ala Ile Phe Gly Lys Thr
            100                 105                 110

Lys Ile Gln Asn Ala Val His Cys Thr Asp Leu Pro Glu Asp Gly Leu
        115                 120                 125

Leu Glu Val Gln Tyr Phe Phe Lys Ile Leu Asp Asn

<210> SEQ ID NO 54
<211> LENGTH: 453
<212> TYPE: DNA
<213> ORGANISM: Artificial Sequence
<220> FEATURE:
<223> OTHER INFORMATION: Human NME7-B2 sequence optimized for E. coli
      expression

<400> SEQUENCE: 54
atgccgagct ctggcggttg cggtccggca acaccgcca aatttaccaa ttgtacgtgc      60
tgtattgtca aaccgcacgc agtgtcagaa ggcctgctgg gtaaaattct gatggcaatc     120
cgtgatgctg gctttgaaat ctcggccatg cagatgttca acatggaccg cgttaacgtc     180
gaagaattct acgaagttta caaaggcgtg gttaccgaat atcacgatat ggttacggaa     240
atgtactccg gtccgtgcgt cgcgatggaa attcagcaaa acaatgccac aaaaacgttt     300
cgtgaattct gtggtccggc agatccggaa atcgcacgtc atctgcgtcc gggtaccctg     360
cgcgcaattt ttggtaaaac gaaaatccag aacgctgtgc actgtaccga tctgccggaa     420
gacggtctgc tggaagttca atactttttc tga                                  453

<210> SEQ ID NO 55
<211> LENGTH: 150
<212> TYPE: PRT
<213> ORGANISM: Artificial Sequence
<220> FEATURE:
<223> OTHER INFORMATION: Human NME7-B2 sequence optimized for E. coli
      expression

<400> SEQUENCE: 55

Met Pro Ser Ser Gly Gly Cys Gly Pro Ala Asn Thr Ala Lys Phe Thr
1               5                   10                  15

Asn Cys Thr Cys Cys Ile Val Lys Pro His Ala Val Ser Glu Gly Leu
            20                  25                  30

Leu Gly Lys Ile Leu Met Ala Ile Arg Asp Ala Gly Phe Glu Ile Ser
        35                  40                  45

Ala Met Gln Met Phe Asn Met Asp Arg Val Asn Val Glu Glu Phe Tyr
    50                  55                  60

Glu Val Tyr Lys Gly Val Val Thr Glu Tyr His Asp Met Val Thr Glu
65                  70                  75                  80

Met Tyr Ser Gly Pro Cys Val Ala Met Glu Ile Gln Gln Asn Asn Ala
                85                  90                  95

Thr Lys Thr Phe Arg Glu Phe Cys Gly Pro Ala Asp Pro Glu Ile Ala
            100                 105                 110

Arg His Leu Arg Pro Gly Thr Leu Arg Ala Ile Phe Gly Lys Thr Lys
        115                 120                 125

Ile Gln Asn Ala Val His Cys Thr Asp Leu Pro Glu Asp Gly Leu Leu
    130                 135                 140

Glu Val Gln Tyr Phe Phe
145                 150

<210> SEQ ID NO 56
<211> LENGTH: 468
<212> TYPE: DNA
<213> ORGANISM: Artificial Sequence
<220> FEATURE:
<223> OTHER INFORMATION: Human NME7-B3 sequence optimized for E. coli
      expression -continued

<400> SEQUENCE: 56

```
atgccgagct ctggcggttg cggtccggca acaccgcca aatttaccaa ttgtacgtgc    60
tgtattgtca aaccgcacgc agtgtcagaa ggcctgctgg gtaaaattct gatggcaatc   120
cgtgatgctg gctttgaaat ctcggccatg cagatgttca acatggaccg cgttaacgtc   180
gaagaattct acgaagttta caaggcgtg gttaccgaat atcacgatat ggttacggaa    240
atgtactccg gtccgtgcgt cgcgatggaa attcagcaaa acaatgccac caaaacgttt   300
cgtgaattct gtggtccggc agatccggaa atcgcacgtc atctgcgtcc gggtaccctg   360
cgcgcaattt ttggtaaaac gaaaatccag aacgctgtgc actgtaccga tctgccggaa   420
gacggtctgc tggaagttca atactttttc aaaattctgg ataattga                468
```

<210> SEQ ID NO 57
<211> LENGTH: 155
<212> TYPE: PRT
<213> ORGANISM: Artificial Sequence
<220> FEATURE:
<223> OTHER INFORMATION: Human NME7-B3 sequence optimized for E. coli expression

<400> SEQUENCE: 57

```
Met Pro Ser Ser Gly Gly Cys Gly Pro Ala Asn Thr Ala Lys Phe Thr
1               5                   10                  15
Asn Cys Thr Cys Cys Ile Val Lys Pro His Ala Val Ser Glu Gly Leu
            20                  25                  30
Leu Gly Lys Ile Leu Met Ala Ile Arg Asp Ala Gly Phe Glu Ile Ser
        35                  40                  45
Ala Met Gln Met Phe Asn Met Asp Arg Val Asn Val Glu Glu Phe Tyr
    50                  55                  60
Glu Val Tyr Lys Gly Val Val Thr Glu Tyr His Asp Met Val Thr Glu
65                  70                  75                  80
Met Tyr Ser Gly Pro Cys Val Ala Met Glu Ile Gln Gln Asn Asn Ala
                85                  90                  95
Thr Lys Thr Phe Arg Glu Phe Cys Gly Pro Ala Asp Pro Glu Ile Ala
            100                 105                 110
Arg His Leu Arg Pro Gly Thr Leu Arg Ala Ile Phe Gly Lys Thr Lys
        115                 120                 125
Ile Gln Asn Ala Val His Cys Thr Asp Leu Pro Glu Asp Gly Leu Leu
    130                 135                 140
Glu Val Gln Tyr Phe Phe Lys Ile Leu Asp Asn
145                 150                 155
```

<210> SEQ ID NO 58
<211> LENGTH: 861
<212> TYPE: DNA
<213> ORGANISM: Artificial Sequence
<220> FEATURE:
<223> OTHER INFORMATION: Human NME7-AB, also known as NME7AB sequence optimized for E. coli expression

<400> SEQUENCE: 58

```
atggaaaaaa cgctggccct gattaaaccg gatgcaatct ccaaagctgg cgaaattatc    60
gaaattatca acaaagcggg tttcaccatc acgaaactga aatgatgat gctgagccgt   120
aaagaagccc tggattttca tgtcgaccac cagtctcgcc cgttttttcaa tgaactgatt   180
caattcatca ccacgggtcc gattatcgca atggaaattc tgcgtgatga cgctatctgc   240
gaatggaaac gcctgctggg cccggcaaac tcaggtgttg cgcgtaccga tgccagtgaa   300
```

-continued

```
tccattcgcg ctctgtttgg caccgatggt atccgtaatg cagcacatgg tccggactca    360
ttcgcatcgg cagctcgtga aatggaactg ttttcccga gctctggcgg ttgcggtccg     420
gcaaacaccg ccaaatttac caattgtacg tgctgtattg tcaaaccgca cgcagtgtca    480
gaaggcctgc tgggtaaaat tctgatggca atccgtgatg ctggctttga atctcggcc    540 atgcagatgt tcaacatgga ccgcgttaac gtcgaagaat tctacgaagt ttacaaaggc    600
gtggttaccg aatatcacga tatggttacg gaaatgtact ccggtccgtg cgtcgcgatg    660
gaaattcagc aaaacaatgc caccaaaacg tttcgtgaat tctgtggtcc ggcagatccg    720
gaaatcgcac gtcatctgcg tccgggtacc ctgcgcgcaa ttttggtaa acgaaaatc     780 cagaacgctg tgcactgtac cgatctgccg gaagacggtc tgctggaagt tcaatacttt    840
ttcaaaattc tggataattg a                                              861
```

```
<210> SEQ ID NO 59
<211> LENGTH: 286
<212> TYPE: PRT
<213> ORGANISM: Artificial Sequence
<220> FEATURE:
<223> OTHER INFORMATION: Human NME7-AB, also known as NME7AB sequence
      optimized for E. coli expression

<400> SEQUENCE: 59
```

| Met | Glu | Lys | Thr | Leu | Ala | Leu | Ile | Lys | Pro | Asp | Ala | Ile | Ser | Lys | Ala |
|---|---|---|---|---|---|---|---|---|---|---|---|---|---|---|---|
| 1 | | | | 5 | | | | | 10 | | | | | 15 | |
| Gly | Glu | Ile | Ile | Glu | Ile | Ile | Asn | Lys | Ala | Gly | Phe | Thr | Ile | Thr | Lys |
| | | | 20 | | | | | 25 | | | | | 30 | | |
| Leu | Lys | Met | Met | Met | Leu | Ser | Arg | Lys | Glu | Ala | Leu | Asp | Phe | His | Val |
| | | 35 | | | | | 40 | | | | | 45 | | | |
| Asp | His | Gln | Ser | Arg | Pro | Phe | Phe | Asn | Glu | Leu | Ile | Gln | Phe | Ile | Thr |
| | 50 | | | | | 55 | | | | | 60 | | | | |
| Thr | Gly | Pro | Ile | Ile | Ala | Met | Glu | Ile | Leu | Arg | Asp | Asp | Ala | Ile | Cys |
| 65 | | | | | 70 | | | | | 75 | | | | | 80 |
| Glu | Trp | Lys | Arg | Leu | Leu | Gly | Pro | Ala | Asn | Ser | Gly | Val | Ala | Arg | Thr |
| | | | | 85 | | | | | 90 | | | | | 95 | |
| Asp | Ala | Ser | Glu | Ser | Ile | Arg | Ala | Leu | Phe | Gly | Thr | Asp | Gly | Ile | Arg |
| | | | 100 | | | | | 105 | | | | | 110 | | |
| Asn | Ala | Ala | His | Gly | Pro | Asp | Ser | Phe | Ala | Ser | Ala | Ala | Arg | Glu | Met |
| | | | 115 | | | | | 120 | | | | | 125 | | |
| Glu | Leu | Phe | Phe | Pro | Ser | Ser | Gly | Gly | Cys | Gly | Pro | Ala | Asn | Thr | Ala |
| | 130 | | | | | 135 | | | | | 140 | | | | |
| Lys | Phe | Thr | Asn | Cys | Thr | Cys | Cys | Ile | Val | Lys | Pro | His | Ala | Val | Ser |
| 145 | | | | | 150 | | | | | 155 | | | | | 160 |
| Glu | Gly | Leu | Leu | Gly | Lys | Ile | Leu | Met | Ala | Ile | Arg | Asp | Ala | Gly | Phe |
| | | | | 165 | | | | | 170 | | | | | 175 | |
| Glu | Ile | Ser | Ala | Met | Gln | Met | Phe | Asn | Met | Asp | Arg | Val | Asn | Val | Glu |
| | | | 180 | | | | | 185 | | | | | 190 | | |
| Glu | Phe | Tyr | Glu | Val | Tyr | Lys | Gly | Val | Val | Thr | Glu | Tyr | His | Asp | Met |
| | | | 195 | | | | | 200 | | | | | 205 | | |
| Val | Thr | Glu | Met | Tyr | Ser | Gly | Pro | Cys | Val | Ala | Met | Glu | Ile | Gln | Gln |
| | 210 | | | | | 215 | | | | | 220 | | | | |
| Asn | Asn | Ala | Thr | Lys | Thr | Phe | Arg | Glu | Phe | Cys | Gly | Pro | Ala | Asp | Pro |
| 225 | | | | | 230 | | | | | 235 | | | | | 240 |
| Glu | Ile | Ala | Arg | His | Leu | Arg | Pro | Gly | Thr | Leu | Arg | Ala | Ile | Phe | Gly |
| | | | | 245 | | | | | 250 | | | | | 255 | |

Lys Thr Lys Ile Gln Asn Ala Val His Cys Thr Asp Leu Pro Glu Asp
            260                 265                 270

Gly Leu Leu Glu Val Gln Tyr Phe Phe Lys Ile Leu Asp Asn
        275                 280                 285

<210> SEQ ID NO 60
<211> LENGTH: 846
<212> TYPE: DNA
<213> ORGANISM: Artificial Sequence
<220> FEATURE:
<223> OTHER INFORMATION: Human NME7-AB1, also known as NME7AB1 sequence
      optimized for E. coli expression

<400> SEQUENCE: 60

| | | |
|---|---|---|
| atggaaaaaa cgctggccct gattaaaccg gatgcaatct ccaaagctgg cgaaattatc | 60 |
| gaaattatca acaaagcggg tttcaccatc acgaaactga aatgatgat gctgagccgt | 120 |
| aaagaagccc tggattttca tgtcgaccac cagtctcgcc cgttttcaa tgaactgatt | 180 |
| caattcatca ccacgggtcc gattatcgca atggaaattc tgcgtgatga cgctatctgc | 240 |
| gaatggaaac gcctgctggg cccggcaaac tcaggtgttg cgcgtaccga tgccagtgaa | 300 |
| tccattcgcg ctctgtttgg caccgatggt atccgtaatg cagcacatgg tccggactca | 360 |
| ttcgcatcgg cagctcgtga atggaactg ttttcccga gctctggcgg ttgcggtccg | 420 |
| gcaaacaccg ccaaatttac caattgtacg tgctgtattg tcaaaccgca cgcagtgtca | 480 |
| gaaggcctgc tgggtaaaat tctgatggca atccgtgatg ctggctttga atctcggcc | 540 |
| atgcagatgt tcaacatgga ccgcgttaac gtcgaagaat tctacgaagt ttacaaaggc | 600 |
| gtggttaccg aatatcacga tatggttacg gaaatgtact ccggtccgtg cgtcgcgatg | 660 |
| gaaattcagc aaaacaatgc caccaaaacg tttcgtgaat ctgtggtcc ggcagatccg | 720 |
| gaaatcgcac gtcatctgcg tccgggtacc ctgcgcgcaa ttttggtaa acgaaaatc | 780 |
| cagaacgctg tgcactgtac cgatctgccg gaagacggtc tgctggaagt tcaatacttt | 840 |
| ttctga | 846 |

<210> SEQ ID NO 61
<211> LENGTH: 281
<212> TYPE: PRT
<213> ORGANISM: Artificial Sequence
<220> FEATURE:
<223> OTHER INFORMATION: Human NME7-AB1, also known as NME7AB1 sequence
      optimized for E. coli expression

<400> SEQUENCE: 61

Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
            20                  25                  30

Leu Lys Met Met Met Leu Ser Arg Lys Glu Ala Leu Asp Phe His Val
        35                  40                  45

Asp His Gln Ser Arg Pro Phe Phe Asn Glu Leu Ile Gln Phe Ile Thr
    50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr
                85                  90                  95

Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Ala Arg Glu Met
        115                 120                 125

Glu Leu Phe Phe Pro Ser Ser Gly Gly Cys Gly Pro Ala Asn Thr Ala
    130                 135                 140

Lys Phe Thr Asn Cys Thr Cys Cys Ile Val Lys Pro His Ala Val Ser
145                 150                 155                 160

Glu Gly Leu Leu Gly Lys Ile Leu Met Ala Ile Arg Asp Ala Gly Phe
                165                 170                 175

Glu Ile Ser Ala Met Gln Met Phe Asn Met Asp Arg Val Asn Val Glu
            180                 185                 190

Glu Phe Tyr Glu Val Tyr Lys Gly Val Val Thr Glu Tyr His Asp Met
        195                 200                 205

Val Thr Glu Met Tyr Ser Gly Pro Cys Val Ala Met Glu Ile Gln Gln
    210                 215                 220

Asn Asn Ala Thr Lys Thr Phe Arg Glu Phe Cys Gly Pro Ala Asp Pro
225                 230                 235                 240

Glu Ile Ala Arg His Leu Arg Pro Gly Thr Leu Arg Ala Ile Phe Gly
                245                 250                 255

Lys Thr Lys Ile Gln Asn Ala Val His Cys Thr Asp Leu Pro Glu Asp
            260                 265                 270

Gly Leu Leu Glu Val Gln Tyr Phe Phe
        275                 280

<210> SEQ ID NO 62
<211> LENGTH: 570
<212> TYPE: DNA
<213> ORGANISM: Artificial Sequence
<220> FEATURE:
<223> OTHER INFORMATION: Mouse NME6

<400> SEQUENCE: 62
atgacctcca tcttgcgaag tccccaagct cttcagctca cactagccct gatcaagcct      60
gatgcagttg cccacccact gatcctggag gctgttcatc agcagattct gagcaacaag     120
ttcctcattg tacgaacgag ggaactgcag tggaagctgg aggactgccg gaggttttac     180
cgagagcatg aagggcgttt tttctatcag cggctggtgg agttcatgac aagtgggcca     240
atccgagcct atatccttgc cacaaagat gccatccaac tttggaggac actgatggga     300
cccaccagag tatttcgagc acgctatata gccccagatt caattcgtgg aagtttgggc     360
ctcactgaca cccgaaatac tacccatggc tcagactccg tggtttccgc agcagagag     420
attgcagcct tcttccctga cttcagtgaa cagcgctggt atgaggagga ggaaccccag     480
ctgcggtgtg gtcctgtgca ctacagtcca gaggaaggta tccactgtgc agctgaaaca     540
ggaggccaca aacaacctaa caaaacctag                                      570

<210> SEQ ID NO 63
<211> LENGTH: 189
<212> TYPE: PRT
<213> ORGANISM: Artificial Sequence
<220> FEATURE:
<223> OTHER INFORMATION: Mouse NME6

<400> SEQUENCE: 63

Met Thr Ser Ile Leu Arg Ser Pro Gln Ala Leu Gln Leu Thr Leu Ala
1               5                   10                  15

Leu Ile Lys Pro Asp Ala Val Ala His Pro Leu Ile Leu Glu Ala Val
            20                  25                  30

His Gln Gln Ile Leu Ser Asn Lys Phe Leu Ile Val Arg Thr Arg Glu
            35                  40                  45

Leu Gln Trp Lys Leu Glu Asp Cys Arg Arg Phe Tyr Arg Glu His Glu
    50                  55                  60

Gly Arg Phe Phe Tyr Gln Arg Leu Val Glu Phe Met Thr Ser Gly Pro
65                  70                  75                  80

Ile Arg Ala Tyr Ile Leu Ala His Lys Asp Ala Ile Gln Leu Trp Arg
                85                  90                  95

Thr Leu Met Gly Pro Thr Arg Val Phe Arg Ala Arg Tyr Ile Ala Pro
            100                 105                 110

Asp Ser Ile Arg Gly Ser Leu Gly Leu Thr Asp Thr Arg Asn Thr Thr
        115                 120                 125

His Gly Ser Asp Ser Val Val Ser Ala Ser Arg Glu Ile Ala Ala Phe
    130                 135                 140

Phe Pro Asp Phe Ser Glu Gln Arg Trp Tyr Glu Glu Glu Pro Gln
145                 150                 155                 160

Leu Arg Cys Gly Pro Val His Tyr Ser Pro Glu Gly Ile His Cys
                165                 170                 175

Ala Ala Glu Thr Gly Gly His Lys Gln Pro Asn Lys Thr
            180                 185

<210> SEQ ID NO 64
<211> LENGTH: 585
<212> TYPE: DNA
<213> ORGANISM: Artificial Sequence
<220> FEATURE:
<223> OTHER INFORMATION: Human NME6

<400> SEQUENCE: 64

```
atgacccaga atctggggag tgagatggcc tcaatcttgc gaagccctca ggctctccag      60
ctcactctag ccctgatcaa gcctgacgca gtcgcccatc cactgattct ggaggctgtt     120
catcagcaga ttctaagcaa caagttcctg attgtacgaa tgagagaact actgtggaga     180
aaggaagatt gccagaggtt ttaccgagag catgaagggc gtttttttcta tcagaggctg    240
gtggagttca tggccagcgg gccaatccga gcctacatcc ttgcccacaa ggatgccatc     300
cagctctgga ggacgctcat gggacccacc agagtgttcc gagcacgcca tgtggcccca     360
gattctatcc gtgggagttt cggcctcact gacacccgca acaccaccca tggttcggac     420
tctgtggttt cagccagcag agagattgca gccttcttcc ctgacttcag tgaacagcgc     480
tggtatgagg aggaagagcc ccagttgcgc tgtggccctg tgtgctatag cccagaggga     540
ggtgtccact atgtagctgg aacaggaggc ctaggaccag cctga                     585
```

<210> SEQ ID NO 65
<211> LENGTH: 194
<212> TYPE: PRT
<213> ORGANISM: Artificial Sequence
<220> FEATURE:
<223> OTHER INFORMATION: Human NME6

<400> SEQUENCE: 65

Met Thr Gln Asn Leu Gly Ser Glu Met Ala Ser Ile Leu Arg Ser Pro
1               5                   10                  15

Gln Ala Leu Gln Leu Thr Leu Ala Leu Ile Lys Pro Asp Ala Val Ala
            20                  25                  30

His Pro Leu Ile Leu Glu Ala Val His Gln Gln Ile Leu Ser Asn Lys
        35                  40                  45

```
Phe Leu Ile Val Arg Met Arg Glu Leu Leu Trp Arg Lys Glu Asp Cys
        50                  55                  60

Gln Arg Phe Tyr Arg Glu His Glu Gly Arg Phe Tyr Gln Arg Leu
 65              70                  75                  80

Val Glu Phe Met Ala Ser Gly Pro Ile Arg Ala Tyr Ile Leu Ala His
                85                  90                  95

Lys Asp Ala Ile Gln Leu Trp Arg Thr Leu Met Gly Pro Thr Arg Val
               100                 105                 110

Phe Arg Ala Arg His Val Ala Pro Asp Ser Ile Arg Gly Ser Phe Gly
               115                 120                 125

Leu Thr Asp Thr Arg Asn Thr Thr His Gly Ser Asp Ser Val Val Ser
           130                 135                 140

Ala Ser Arg Glu Ile Ala Ala Phe Phe Pro Asp Phe Ser Glu Gln Arg
145                 150                 155                 160

Trp Tyr Glu Glu Glu Pro Gln Leu Arg Cys Gly Pro Val Cys Tyr
                165                 170                 175

Ser Pro Glu Gly Gly Val His Tyr Val Ala Gly Thr Gly Leu Gly
               180                 185                 190

Pro Ala

<210> SEQ ID NO 66
<211> LENGTH: 525
<212> TYPE: DNA
<213> ORGANISM: Artificial Sequence
<220> FEATURE:
<223> OTHER INFORMATION: Human NME6 1

<400> SEQUENCE: 66
atgacccaga atctggggag tgagatggcc tcaatcttgc gaagccctca ggctctccag      60
ctcactctag ccctgatcaa gcctgacgca gtcgcccatc cactgattct ggaggctgtt    120
catcagcaga ttctaagcaa caagttcctg attgtacgaa tgagagaact actgtgggaga   180 aaggaagatt gccagaggtt ttaccgagag catgaagggc gttttttcta tcagaggctg    240
gtggagttca tggccagcgg gccaatccga gcctacatcc ttgcccacaa ggatgccatc    300
cagctctgga ggacgctcat gggacccacc agagtgttcc gagcacgcca tgtggcccca    360
gattctatcc gtgggagttt cggcctcact gacacccgca acaccaccca tggttcggac    420
tctgtggttt cagccagcag agagattgca gccttcttcc ctgacttcag tgaacagcgc    480
tggtatgagg aggaagagcc ccagttgcgc tgtggccctg tgtga                   525

<210> SEQ ID NO 67
<211> LENGTH: 174
<212> TYPE: PRT
<213> ORGANISM: Artificial Sequence
<220> FEATURE:
<223> OTHER INFORMATION: Human NME6 1

<400> SEQUENCE: 67

Met Thr Gln Asn Leu Gly Ser Glu Met Ala Ser Ile Leu Arg Ser Pro
  1               5                  10                  15

Gln Ala Leu Gln Leu Thr Leu Ala Leu Ile Lys Pro Asp Ala Val Ala
                20                  25                  30

His Pro Leu Ile Leu Glu Ala Val His Gln Gln Ile Leu Ser Asn Lys
            35                  40                  45

Phe Leu Ile Val Arg Met Arg Glu Leu Leu Trp Arg Lys Glu Asp Cys
        50                  55                  60
```

Gln Arg Phe Tyr Arg Glu His Glu Gly Arg Phe Phe Tyr Gln Arg Leu
 65                  70                  75                  80

Val Glu Phe Met Ala Ser Gly Pro Ile Arg Ala Tyr Ile Leu Ala His
             85                  90                  95

Lys Asp Ala Ile Gln Leu Trp Arg Thr Leu Met Gly Pro Thr Arg Val
            100                 105                 110

Phe Arg Ala Arg His Val Ala Pro Asp Ser Ile Arg Gly Ser Phe Gly
        115                 120                 125

Leu Thr Asp Thr Arg Asn Thr Thr His Gly Ser Asp Ser Val Val Ser
130                 135                 140

Ala Ser Arg Glu Ile Ala Ala Phe Phe Pro Asp Phe Ser Glu Gln Arg
145                 150                 155                 160

Trp Tyr Glu Glu Glu Pro Gln Leu Arg Cys Gly Pro Val
                165                 170

<210> SEQ ID NO 68
<211> LENGTH: 468
<212> TYPE: DNA
<213> ORGANISM: Artificial Sequence
<220> FEATURE:
<223> OTHER INFORMATION: Human NME6 2

<400> SEQUENCE: 68

| | | | | | |
|---|---|---|---|---|---|
| atgctcactc | tagccctgat | caagcctgac | gcagtcgccc | atccactgat | tctggaggct | 60 |
| gttcatcagc | agattctaag | caacaagttc | ctgattgtac | gaatgagaga | actactgtgg | 120 |
| agaaaggaag | attgccagag | gttttaccga | gagcatgaag | ggcgttttt | ctatcagagg | 180 |
| ctggtggagt | tcatggccag | cgggccaatc | cgagcctaca | tccttgccca | caaggatgcc | 240 |
| atccagctct | ggaggacgct | catgggaccc | accagagtgt | tccgagcacg | ccatgtggcc | 300 |
| ccagattcta | tccgtgggag | tttcggcctc | actgacaccc | gcaacaccac | ccatggttcg | 360 |
| gactctgtgg | tttcagccag | cagagagatt | gcagccttct | tccctgactt | cagtgaacag | 420 |
| cgctggtatg | aggaggaaga | gccccagttg | cgctgtggcc | ctgtgtga | | 468 |

<210> SEQ ID NO 69
<211> LENGTH: 155
<212> TYPE: PRT
<213> ORGANISM: Artificial Sequence
<220> FEATURE:
<223> OTHER INFORMATION: Human NME6 2

<400> SEQUENCE: 69

Met Leu Thr Leu Ala Leu Ile Lys Pro Asp Ala Val Ala His Pro Leu
  1               5                  10                  15

Ile Leu Glu Ala Val His Gln Gln Ile Leu Ser Asn Lys Phe Leu Ile
             20                  25                  30

Val Arg Met Arg Glu Leu Leu Trp Arg Lys Glu Asp Cys Gln Arg Phe
         35                  40                  45

Tyr Arg Glu His Glu Gly Arg Phe Phe Tyr Gln Arg Leu Val Glu Phe
     50                  55                  60

Met Ala Ser Gly Pro Ile Arg Ala Tyr Ile Leu Ala His Lys Asp Ala
 65                  70                  75                  80

Ile Gln Leu Trp Arg Thr Leu Met Gly Pro Thr Arg Val Phe Arg Ala
             85                  90                  95

Arg His Val Ala Pro Asp Ser Ile Arg Gly Ser Phe Gly Leu Thr Asp
            100                 105                 110

```
Thr Arg Asn Thr Thr His Gly Ser Asp Ser Val Val Ser Ala Ser Arg
        115                 120                 125

Glu Ile Ala Ala Phe Phe Pro Asp Phe Ser Glu Gln Arg Trp Tyr Glu
    130                 135                 140

Glu Glu Glu Pro Gln Leu Arg Cys Gly Pro Val
145                 150                 155

<210> SEQ ID NO 70
<211> LENGTH: 528
<212> TYPE: DNA
<213> ORGANISM: Artificial Sequence
<220> FEATURE:
<223> OTHER INFORMATION: Human NME6 3

<400> SEQUENCE: 70
atgctcactc tagccctgat caagcctgac gcagtcgccc atccactgat tctggaggct    60
gttcatcagc agattctaag caacaagttc ctgattgtac gaatgagaga actactgtgg   120
agaaaggaag attgccagag gttttaccga gagcatgaag gcgttttttt ctatcagagg   180
ctggtggagt tcatggccag cgggccaatc cgagcctaca tccttgccca caaggatgcc   240
atccagctct ggaggacgct catgggaccc accagagtgt tccgagcacg ccatgtggcc   300
ccagattcta tccgtgggag tttcggcctc actgacaccc gcaacaccac ccatggttcg   360
gactctgtgg tttcagccag cagagagatt gcagccttct tccctgactt cagtgaacag   420
cgctggtatg aggaggaaga gccccagttg cgctgtggcc ctgtgtgcta tagcccagag   480
ggaggtgtcc actatgtagc tggaacagga ggcctaggac cagcctga                 528

<210> SEQ ID NO 71
<211> LENGTH: 175
<212> TYPE: PRT
<213> ORGANISM: Artificial Sequence
<220> FEATURE:
<223> OTHER INFORMATION: Human NME6 3

<400> SEQUENCE: 71

Met Leu Thr Leu Ala Leu Ile Lys Pro Asp Ala Val Ala His Pro Leu
1               5                   10                  15

Ile Leu Glu Ala Val His Gln Gln Ile Leu Ser Asn Lys Phe Leu Ile
            20                  25                  30

Val Arg Met Arg Glu Leu Leu Trp Arg Lys Glu Asp Cys Gln Arg Phe
        35                  40                  45

Tyr Arg Glu His Glu Gly Arg Phe Phe Tyr Gln Arg Leu Val Glu Phe
    50                  55                  60

Met Ala Ser Gly Pro Ile Arg Ala Tyr Ile Leu Ala His Lys Asp Ala
65                  70                  75                  80

Ile Gln Leu Trp Arg Thr Leu Met Gly Pro Thr Arg Val Phe Arg Ala
                85                  90                  95

Arg His Val Ala Pro Asp Ser Ile Arg Gly Ser Phe Gly Leu Thr Asp
            100                 105                 110

Thr Arg Asn Thr Thr His Gly Ser Asp Ser Val Val Ser Ala Ser Arg
        115                 120                 125

Glu Ile Ala Ala Phe Phe Pro Asp Phe Ser Glu Gln Arg Trp Tyr Glu
    130                 135                 140

Glu Glu Glu Pro Gln Leu Arg Cys Gly Pro Val Cys Tyr Ser Pro Glu
145                 150                 155                 160

Gly Gly Val His Tyr Val Ala Gly Thr Gly Gly Leu Gly Pro Ala
                165                 170                 175
```

<210> SEQ ID NO 72
<211> LENGTH: 585
<212> TYPE: DNA
<213> ORGANISM: Artificial Sequence
<220> FEATURE:
<223> OTHER INFORMATION: Human NME6 sequence optimized for E. coli
      expression

<400> SEQUENCE: 72

```
atgacgcaaa atctgggctc ggaaatggca agtatcctgc gctccccgca agcactgcaa      60
ctgaccctgg ctctgatcaa accggacgct gttgctcatc cgctgattct ggaagcggtc     120
caccagcaaa ttctgagcaa caaatttctg atcgtgcgta tgcgcgaact gctgtggcgt     180
aaagaagatt gccagcgttt ttatcgcgaa catgaaggcc gttttctttta tcaacgcctg     240
gttgaattca tggcctctgg tccgattcgc gcatatatcc tggctcacaa agatgcgatt     300
cagctgtggc gtaccctgat gggtccgacg cgcgtctttc gtgcacgtca tgtggcaccg     360
gactcaatcc gtggctcgtt cggtctgacc gatacgcgca ataccacgca cggtagcgac     420
tctgttgtta gtgcgtcccg tgaaatcgcg gcctttttcc cggacttctc gaacagcgt      480
tggtacgaag aagaagaacc gcaactgcgc tgtggcccgg tctgttattc tccggaaggt     540
ggtgtccatt atgtggcggg cacgggtggt ctgggtccgg catga                     585
```

<210> SEQ ID NO 73
<211> LENGTH: 194
<212> TYPE: PRT
<213> ORGANISM: Artificial Sequence
<220> FEATURE:
<223> OTHER INFORMATION: Human NME6 sequence optimized for E. coli
      expression

<400> SEQUENCE: 73

```
Met Thr Gln Asn Leu Gly Ser Glu Met Ala Ser Ile Leu Arg Ser Pro
1               5                   10                  15

Gln Ala Leu Gln Leu Thr Leu Ala Leu Ile Lys Pro Asp Ala Val Ala
            20                  25                  30

His Pro Leu Ile Leu Glu Ala Val His Gln Gln Ile Leu Ser Asn Lys
        35                  40                  45

Phe Leu Ile Val Arg Met Arg Glu Leu Leu Trp Arg Lys Glu Asp Cys
    50                  55                  60

Gln Arg Phe Tyr Arg Glu His Glu Gly Arg Phe Phe Tyr Gln Arg Leu
65                  70                  75                  80

Val Glu Phe Met Ala Ser Gly Pro Ile Arg Ala Tyr Ile Leu Ala His
                85                  90                  95

Lys Asp Ala Ile Gln Leu Trp Arg Thr Leu Met Gly Pro Thr Arg Val
            100                 105                 110

Phe Arg Ala Arg His Val Ala Pro Asp Ser Ile Arg Gly Ser Phe Gly
        115                 120                 125

Leu Thr Asp Thr Arg Asn Thr Thr His Gly Ser Asp Ser Val Val Ser
    130                 135                 140

Ala Ser Arg Glu Ile Ala Ala Phe Phe Pro Asp Phe Ser Glu Gln Arg
145                 150                 155                 160

Trp Tyr Glu Glu Glu Pro Gln Leu Arg Cys Gly Pro Val Cys Tyr
                165                 170                 175

Ser Pro Glu Gly Gly Val His Tyr Val Ala Gly Thr Gly Gly Leu Gly
            180                 185                 190
```

<210> SEQ ID NO 74
<211> LENGTH: 525
<212> TYPE: DNA
<213> ORGANISM: Artificial Sequence
<220> FEATURE:
<223> OTHER INFORMATION: Human NME6 1 sequence optimized for E. coli expression

<400> SEQUENCE: 74

```
atgacgcaaa atctgggctc ggaaatggca agtatcctgc gctccccgca agcactgcaa      60
ctgacccctgg ctctgatcaa accggacgct gttgctcatc cgctgattct ggaagcggtc   120
caccagcaaa ttctgagcaa caaatttctg atcgtgcgta tgcgcgaact gctgtggcgt   180
aaagaagatt gccagcgttt ttatcgcgaa catgaaggcc gtttcttta tcaacgcctg   240
gttgaattca tggcctctgg tccgattcgc gcatatatcc tggctcacaa agatgcgatt   300
cagctgtggc gtaccctgat gggtccgacg cgcgtctttc gtgcacgtca tgtggcaccg   360
gactcaatcc gtggctcgtt cggtctgacc gatacgcgca ataccacgca cggtagcgac   420
tctgttgtta gtgcgtcccg tgaaatcgcg gccttttcc cggacttctc gaacagcgt   480
tggtacgaag aagaagaacc gcaactgcgc tgtggcccgg tctga                     525
```

<210> SEQ ID NO 75
<211> LENGTH: 174
<212> TYPE: PRT
<213> ORGANISM: Artificial Sequence
<220> FEATURE:
<223> OTHER INFORMATION: Human NME6 1 sequence optimized for E. coli expression

<400> SEQUENCE: 75

```
Met Thr Gln Asn Leu Gly Ser Glu Met Ala Ser Ile Leu Arg Ser Pro
1               5                   10                  15

Gln Ala Leu Gln Leu Thr Leu Ala Leu Ile Lys Pro Asp Ala Val Ala
            20                  25                  30

His Pro Leu Ile Leu Glu Ala Val His Gln Gln Ile Leu Ser Asn Lys
        35                  40                  45

Phe Leu Ile Val Arg Met Arg Glu Leu Leu Trp Arg Lys Glu Asp Cys
    50                  55                  60

Gln Arg Phe Tyr Arg Glu His Glu Gly Arg Phe Tyr Gln Arg Leu
65                  70                  75                  80

Val Glu Phe Met Ala Ser Gly Pro Ile Arg Ala Tyr Ile Leu Ala His
                85                  90                  95

Lys Asp Ala Ile Gln Leu Trp Arg Thr Leu Met Gly Pro Thr Arg Val
            100                 105                 110

Phe Arg Ala Arg His Val Ala Pro Asp Ser Ile Arg Gly Ser Phe Gly
        115                 120                 125

Leu Thr Asp Thr Arg Asn Thr Thr His Gly Ser Asp Ser Val Val Ser
    130                 135                 140

Ala Ser Arg Glu Ile Ala Ala Phe Phe Pro Asp Phe Ser Glu Gln Arg
145                 150                 155                 160

Trp Tyr Glu Glu Glu Glu Pro Gln Leu Arg Cys Gly Pro Val
                165                 170
```

<210> SEQ ID NO 76
<211> LENGTH: 468
<212> TYPE: DNA

<213> ORGANISM: Artificial Sequence
<220> FEATURE:
<223> OTHER INFORMATION: Human NME6 2 sequence optimized for E. coli expression

<400> SEQUENCE: 76

| | | | | | |
|---|---|---|---|---|---|
| atgctgaccc | tggctctgat | caaaccggac | gctgttgctc | atccgctgat | tctggaagcg | 60 |
| gtccaccagc | aaattctgag | caacaaattt | ctgatcgtgc | gtatgcgcga | actgctgtgg | 120 |
| cgtaaagaag | attgccagcg | tttttatcgc | gaacatgaag | gccgtttctt | ttatcaacgc | 180 |
| ctggttgaat | tcatggcctc | tggtccgatt | cgcgcatata | tcctggctca | aaagatgcg | 240 |
| attcagctgt | ggcgtaccct | gatgggtccg | acgcgcgtct | tcgtgcacg | tcatgtggca | 300 |
| ccggactcaa | tccgtggctc | gttcggtctg | accgatacgc | gcaataccac | gcacggtagc | 360 |
| gactctgttg | ttagtgcgtc | ccgtgaaatc | gcggcctttt | tcccggactt | ctccgaacag | 420 |
| cgttggtacg | aagaagaaga | accgcaactg | cgctgtggcc | cggtctga | | 468 |

<210> SEQ ID NO 77
<211> LENGTH: 155
<212> TYPE: PRT
<213> ORGANISM: Artificial Sequence
<220> FEATURE:
<223> OTHER INFORMATION: Human NME6 2 sequence optimized for E. coli expression

<400> SEQUENCE: 77

Met Leu Thr Leu Ala Leu Ile Lys Pro Asp Ala Val Ala His Pro Leu
1               5                   10                  15

Ile Leu Glu Ala Val His Gln Gln Ile Leu Ser Asn Lys Phe Leu Ile
                20                  25                  30

Val Arg Met Arg Glu Leu Leu Trp Arg Lys Glu Asp Cys Gln Arg Phe
            35                  40                  45

Tyr Arg Glu His Glu Gly Arg Phe Phe Tyr Gln Arg Leu Val Glu Phe
        50                  55                  60

Met Ala Ser Gly Pro Ile Arg Ala Tyr Ile Leu Ala His Lys Asp Ala
65                  70                  75                  80

Ile Gln Leu Trp Arg Thr Leu Met Gly Pro Thr Arg Val Phe Arg Ala
                85                  90                  95

Arg His Val Ala Pro Asp Ser Ile Arg Gly Ser Phe Gly Leu Thr Asp
            100                 105                 110

Thr Arg Asn Thr Thr His Gly Ser Asp Ser Val Val Ser Ala Ser Arg
        115                 120                 125

Glu Ile Ala Ala Phe Phe Pro Asp Phe Ser Glu Gln Arg Trp Tyr Glu
    130                 135                 140

Glu Glu Glu Pro Gln Leu Arg Cys Gly Pro Val
145                 150                 155

<210> SEQ ID NO 78
<211> LENGTH: 528
<212> TYPE: DNA
<213> ORGANISM: Artificial Sequence
<220> FEATURE:
<223> OTHER INFORMATION: Human NME6 3 sequence optimized for E. coli expression

<400> SEQUENCE: 78

| | | | | | |
|---|---|---|---|---|---|
| atgctgaccc | tggctctgat | caaaccggac | gctgttgctc | atccgctgat | tctggaagcg | 60 |
| gtccaccagc | aaattctgag | caacaaattt | ctgatcgtgc | gtatgcgcga | actgctgtgg | 120 |

```
cgtaaagaag attgccagcg tttttatcgc gaacatgaag gccgtttctt ttatcaacgc    180
ctggttgaat tcatggcctc tggtccgatt cgcgcatata tcctggctca caaagatgcg    240
attcagctgt ggcgtaccct gatgggtccg acgcgcgtct ttcgtgcacg tcatgtggca    300
ccggactcaa tccgtggctc gttcggtctg accgatacgc gcaataccac gcacggtagc    360
gactctgttg ttagtgcgtc ccgtgaaatc gcggccttt tcccggactt ctccgaacag     420
cgttggtacg aagaagaaga accgcaactg cgctgtggcc cggtctgtta ttctccggaa    480
ggtggtgtcc attatgtggc gggcacgggt ggtctgggtc cggcatga                 528
```

<210> SEQ ID NO 79
<211> LENGTH: 175
<212> TYPE: PRT
<213> ORGANISM: Artificial Sequence
<220> FEATURE:
<223> OTHER INFORMATION: Human NME6 3 sequence optimized for E. coli expression

<400> SEQUENCE: 79

```
Met Leu Thr Leu Ala Leu Ile Lys Pro Asp Ala Val Ala His Pro Leu
1               5                   10                  15
Ile Leu Glu Ala Val His Gln Gln Ile Leu Ser Asn Lys Phe Leu Ile
            20                  25                  30
Val Arg Met Arg Glu Leu Leu Trp Arg Lys Glu Asp Cys Gln Arg Phe
        35                  40                  45
Tyr Arg Glu His Glu Gly Arg Phe Phe Tyr Gln Arg Leu Val Glu Phe
    50                  55                  60
Met Ala Ser Gly Pro Ile Arg Ala Tyr Ile Leu Ala His Lys Asp Ala
65                  70                  75                  80
Ile Gln Leu Trp Arg Thr Leu Met Gly Pro Thr Arg Val Phe Arg Ala
                85                  90                  95
Arg His Val Ala Pro Asp Ser Ile Arg Gly Ser Phe Gly Leu Thr Asp
            100                 105                 110
Thr Arg Asn Thr Thr His Gly Ser Asp Ser Val Val Ser Ala Ser Arg
        115                 120                 125
Glu Ile Ala Ala Phe Phe Pro Asp Phe Ser Glu Gln Arg Trp Tyr Glu
    130                 135                 140
Glu Glu Glu Pro Gln Leu Arg Cys Gly Pro Val Cys Tyr Ser Pro Glu
145                 150                 155                 160
Gly Gly Val His Tyr Val Ala Gly Thr Gly Gly Leu Gly Pro Ala
                165                 170                 175
```

<210> SEQ ID NO 80
<211> LENGTH: 1306
<212> TYPE: DNA
<213> ORGANISM: Artificial Sequence
<220> FEATURE:
<223> OTHER INFORMATION: OriGene-NME7-1 full length

<400> SEQUENCE: 80

```
gacgttgtat acgactccta tagggcggcc gggaattcgt cgactggatc cggtaccgag    60
gagatctgcc gccgcgatcg ccatgaatca tagtgaaaga ttcgttttca ttgcagagtg    120
gtatgatcca aatgcttcac ttcttcgacg ttatgagctt tattttacc caggggatgg     180 atctgttgaa atgcatgatg taagaatca tcgcaccttt ttaaagcgga ccaaatatga    240
taacctgcac ttgaagatt tatttatagg caacaaagtg aatgtcttct ctcgacaact    300
ggtattaatt gactatgggg atcaatatac agctcgccag ctgggcagta ggaaagaaaa    360
```

```
aacgctagcc ctaattaaac cagatgcaat atcaaaggct ggagaaataa ttgaaataat    420
aaacaaagct ggatttacta taaccaaact caaaatgatg atgctttcaa ggaaagaagc    480
attggatttt catgtagatc accagtcaag acccttttc aatgagctga tccagtttat    540
tacaactggt cctattattg ccatggagat tttaagagat gatgctatat gtgaatggaa    600
aagactgctg ggacctgcaa actctggagt ggcacgcaca gatgcttctg aaagcattag    660
agccctcttt ggaacagatg gcataagaaa tgcagcgcat ggccctgatt cttttgcttc    720
tgcggccaga gaaatggagt tgttttttcc ttcaagtgga ggttgtgggc cggcaaacac    780
tgctaaattt actaattgta cctgttgcat tgttaaaccc catgctgtca gtgaaggact    840
gttgggaaag atcctgatgg ctatccgaga tgcaggtttt gaaatctcag ctatgcagat    900
gttcaatatg gatcgggtta atgttgagga attctatgaa gtttataaag gagtagtgac    960
cgaatatcat gacatggtga cagaaatgta ttctggcccct tgtgtagcaa tggagattca   1020
acagaataat gctacaaaga catttcgaga attttgtgga cctgctgatc ctgaaattgc   1080
ccggcattta cgccctggaa ctctcagagc aatctttggt aaaactaaga tccagaatgc   1140
tgttcactgt actgatctgc cagaggatgg cctattagag gttcaatact tcttcaagat   1200
cttggataat acgcgtacgc ggccgctcga gcagaaactc atctcagaag aggatctggc   1260
agcaaatgat atcctggatt acaaggatga cgacgataag gtttaa               1306
```

<210> SEQ ID NO 81
<211> LENGTH: 407
<212> TYPE: PRT
<213> ORGANISM: Artificial Sequence
<220> FEATURE:
<223> OTHER INFORMATION: OriGene-NME7-1 full length

<400> SEQUENCE: 81

```
Met Asn His Ser Glu Arg Phe Val Phe Ile Ala Glu Trp Tyr Asp Pro
1               5                  10                 15

Asn Ala Ser Leu Leu Arg Arg Tyr Glu Leu Phe Tyr Pro Gly Asp
            20                  25                  30

Gly Ser Val Glu Met His Asp Val Lys Asn His Arg Thr Phe Leu Lys
        35                  40                  45

Arg Thr Lys Tyr Asp Asn Leu His Leu Glu Asp Leu Phe Ile Gly Asn
    50                  55                  60

Lys Val Asn Val Phe Ser Arg Gln Leu Val Leu Ile Asp Tyr Gly Asp
65                  70                  75                  80

Gln Tyr Thr Ala Arg Gln Leu Gly Ser Arg Lys Glu Lys Thr Leu Ala
                85                  90                  95

Leu Ile Lys Pro Asp Ala Ile Ser Lys Ala Gly Glu Ile Ile Glu Ile
            100                 105                 110

Ile Asn Lys Ala Gly Phe Thr Ile Thr Lys Leu Lys Met Met Met Leu
        115                 120                 125

Ser Arg Lys Glu Ala Leu Asp Phe His Val Asp His Gln Ser Arg Pro
    130                 135                 140

Phe Phe Asn Glu Leu Ile Gln Phe Ile Thr Thr Gly Pro Ile Ile Ala
145                 150                 155                 160

Met Glu Ile Leu Arg Asp Asp Ala Ile Cys Glu Trp Lys Arg Leu Leu
                165                 170                 175

Gly Pro Ala Asn Ser Gly Val Ala Arg Thr Asp Ala Ser Glu Ser Ile
            180                 185                 190
```

```
Arg Ala Leu Phe Gly Thr Asp Gly Ile Arg Asn Ala Ala His Gly Pro
            195                 200                 205

Asp Ser Phe Ala Ser Ala Ala Arg Glu Met Glu Leu Phe Phe Pro Ser
        210                 215                 220

Ser Gly Gly Cys Gly Pro Ala Asn Thr Ala Lys Phe Thr Asn Cys Thr
225                 230                 235                 240

Cys Cys Ile Val Lys Pro His Ala Val Ser Glu Gly Leu Leu Gly Lys
                245                 250                 255

Ile Leu Met Ala Ile Arg Asp Ala Gly Phe Glu Ile Ser Ala Met Gln
            260                 265                 270

Met Phe Asn Met Asp Arg Val Asn Val Glu Glu Phe Tyr Glu Val Tyr
        275                 280                 285

Lys Gly Val Val Thr Glu Tyr His Asp Met Val Thr Glu Met Tyr Ser
290                 295                 300

Gly Pro Cys Val Ala Met Glu Ile Gln Gln Asn Asn Ala Thr Lys Thr
305                 310                 315                 320

Phe Arg Glu Phe Cys Gly Pro Ala Asp Pro Glu Ile Ala Arg His Leu
                325                 330                 335

Arg Pro Gly Thr Leu Arg Ala Ile Phe Gly Lys Thr Lys Ile Gln Asn
            340                 345                 350

Ala Val His Cys Thr Asp Leu Pro Glu Asp Gly Leu Leu Glu Val Gln
        355                 360                 365

Tyr Phe Phe Lys Ile Leu Asp Asn Thr Arg Thr Arg Arg Leu Glu Gln
    370                 375                 380

Lys Leu Ile Ser Glu Glu Asp Leu Ala Ala Asn Asp Ile Leu Asp Tyr
385                 390                 395                 400

Lys Asp Asp Asp Asp Lys Val
                405

<210> SEQ ID NO 82
<211> LENGTH: 376
<212> TYPE: PRT
<213> ORGANISM: Artificial Sequence
<220> FEATURE:
<223> OTHER INFORMATION: Abnova NME7-1 Full length

<400> SEQUENCE: 82

Met Asn His Ser Glu Arg Phe Val Phe Ile Ala Glu Trp Tyr Asp Pro
1               5                   10                  15

Asn Ala Ser Leu Leu Arg Arg Tyr Glu Leu Leu Phe Tyr Pro Gly Asp
            20                  25                  30

Gly Ser Val Glu Met His Asp Val Lys Asn His Arg Thr Phe Leu Lys
        35                  40                  45

Arg Thr Lys Tyr Asp Asn Leu His Leu Glu Asp Leu Phe Ile Gly Asn
    50                  55                  60

Lys Val Asn Val Phe Ser Arg Gln Leu Val Leu Ile Asp Tyr Gly Asp
65                  70                  75                  80

Gln Tyr Thr Ala Arg Gln Leu Gly Ser Arg Lys Glu Lys Thr Leu Ala
                85                  90                  95

Leu Ile Lys Pro Asp Ala Ile Ser Lys Ala Gly Glu Ile Ile Glu Ile
            100                 105                 110

Ile Asn Lys Ala Gly Phe Thr Ile Thr Lys Leu Lys Met Met Met Leu
        115                 120                 125

Ser Arg Lys Glu Ala Leu Asp Phe His Val Asp His Gln Ser Arg Pro
    130                 135                 140
```

```
Phe Phe Asn Glu Leu Ile Gln Phe Ile Thr Thr Gly Pro Ile Ile Ala
145                 150                 155                 160

Met Glu Ile Leu Arg Asp Asp Ala Ile Cys Glu Trp Lys Arg Leu Leu
                165                 170                 175

Gly Pro Ala Asn Ser Gly Val Ala Arg Thr Asp Ala Ser Glu Ser Ile
            180                 185                 190

Arg Ala Leu Phe Gly Thr Asp Gly Ile Arg Asn Ala Ala His Gly Pro
        195                 200                 205

Asp Ser Phe Ala Ser Ala Arg Glu Met Glu Leu Phe Phe Pro Ser
    210                 215                 220

Ser Gly Gly Cys Gly Pro Ala Asn Thr Ala Lys Phe Thr Asn Cys Thr
225                 230                 235                 240

Cys Cys Ile Val Lys Pro His Ala Val Ser Glu Gly Leu Leu Gly Lys
                245                 250                 255

Ile Leu Met Ala Ile Arg Asp Ala Gly Phe Glu Ile Ser Ala Met Gln
            260                 265                 270

Met Phe Asn Met Asp Arg Val Asn Val Glu Glu Phe Tyr Glu Val Tyr
        275                 280                 285

Lys Gly Val Val Thr Glu Tyr His Asp Met Val Thr Glu Met Tyr Ser
290                 295                 300

Gly Pro Cys Val Ala Met Glu Ile Gln Gln Asn Asn Ala Thr Lys Thr
305                 310                 315                 320

Phe Arg Glu Phe Cys Gly Pro Ala Asp Pro Glu Ile Ala Arg His Leu
                325                 330                 335

Arg Pro Gly Thr Leu Arg Ala Ile Phe Gly Lys Thr Lys Ile Gln Asn
            340                 345                 350

Ala Val His Cys Thr Asp Leu Pro Glu Asp Gly Leu Leu Glu Val Gln
        355                 360                 365

Tyr Phe Phe Lys Ile Leu Asp Asn
    370                 375

<210> SEQ ID NO 83
<211> LENGTH: 98
<212> TYPE: PRT
<213> ORGANISM: Artificial Sequence
<220> FEATURE:
<223> OTHER INFORMATION: Abnova Partial NME7-B

<400> SEQUENCE: 83

Asp Arg Val Asn Val Glu Glu Phe Tyr Glu Val Tyr Lys Gly Val Val
1               5                   10                  15

Thr Glu Tyr His Asp Met Val Thr Glu Met Tyr Ser Gly Pro Cys Val
            20                  25                  30

Ala Met Glu Ile Gln Gln Asn Asn Ala Thr Lys Thr Phe Arg Glu Phe
        35                  40                  45

Cys Gly Pro Ala Asp Pro Glu Ile Ala Arg His Leu Arg Pro Gly Thr
    50                  55                  60

Leu Arg Ala Ile Phe Gly Lys Thr Lys Ile Gln Asn Ala Val His Cys
65                  70                  75                  80

Thr Asp Leu Pro Glu Asp Gly Leu Leu Glu Val Gln Tyr Phe Phe Lys
                85                  90                  95

Ile Leu

<210> SEQ ID NO 84
<211> LENGTH: 27
<212> TYPE: DNA
```

-continued

```
<213> ORGANISM: Artificial Sequence
<220> FEATURE:
<223> OTHER INFORMATION: Histidine Tag

<400> SEQUENCE: 84
ctcgagcacc accaccacca ccactga                                          27

<210> SEQ ID NO 85
<211> LENGTH: 36
<212> TYPE: DNA
<213> ORGANISM: Artificial Sequence
<220> FEATURE:
<223> OTHER INFORMATION: Strept II Tag

<400> SEQUENCE: 85
accggttgga gccatcctca gttcgaaaag taatga                                36

<210> SEQ ID NO 86
<211> LENGTH: 35
<212> TYPE: PRT
<213> ORGANISM: Artificial Sequence
<220> FEATURE:
<223> OTHER INFORMATION: N-10 peptide

<400> SEQUENCE: 86

Gln Phe Asn Gln Tyr Lys Thr Glu Ala Ala Ser Arg Tyr Asn Leu Thr
1               5                   10                  15

Ile Ser Asp Val Ser Val Ser Asp Val Pro Phe Pro Phe Ser Ala Gln
            20                  25                  30

Ser Gly Ala
        35

<210> SEQ ID NO 87
<211> LENGTH: 35
<212> TYPE: PRT
<213> ORGANISM: Artificial Sequence
<220> FEATURE:
<223> OTHER INFORMATION: C-10 peptide

<400> SEQUENCE: 87

Gly Thr Ile Asn Val His Asp Val Glu Thr Gln Phe Asn Gln Tyr Lys
1               5                   10                  15

Thr Glu Ala Ala Ser Arg Tyr Asn Leu Thr Ile Ser Asp Val Ser Val
            20                  25                  30

Ser Asp Val
        35

<210> SEQ ID NO 88
<211> LENGTH: 8
<212> TYPE: PRT
<213> ORGANISM: Artificial Sequence
<220> FEATURE:
<223> OTHER INFORMATION: Peptide of NME7AB

<400> SEQUENCE: 88

Leu Ala Leu Ile Lys Pro Asp Ala
1               5

<210> SEQ ID NO 89
<211> LENGTH: 18
<212> TYPE: PRT
<213> ORGANISM: Artificial Sequence
<220> FEATURE:
<223> OTHER INFORMATION: Peptide of NME7AB
```

```
<400> SEQUENCE: 89

Met Met Met Leu Ser Arg Lys Glu Ala Leu Asp Phe His Val Asp His
1               5                   10                  15

Gln Ser

<210> SEQ ID NO 90
<211> LENGTH: 10
<212> TYPE: PRT
<213> ORGANISM: Artificial Sequence
<220> FEATURE:
<223> OTHER INFORMATION: Peptide of NME7AB

<400> SEQUENCE: 90

Ala Leu Asp Phe His Val Asp His Gln Ser
1               5                   10

<210> SEQ ID NO 91
<211> LENGTH: 14
<212> TYPE: PRT
<213> ORGANISM: Artificial Sequence
<220> FEATURE:
<223> OTHER INFORMATION: Peptide of NME7AB

<400> SEQUENCE: 91

Glu Ile Leu Arg Asp Asp Ala Ile Cys Glu Trp Lys Arg Leu
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Peptide of NME7AB

<400> SEQUENCE: 92

Phe Asn Glu Leu Ile Gln Phe Ile Thr Thr Gly Pro
1               5                   10

<210> SEQ ID NO 93
<211> LENGTH: 8
<212> TYPE: PRT
<213> ORGANISM: Artificial Sequence
<220> FEATURE:
<223> OTHER INFORMATION: Peptide of NME7AB

<400> SEQUENCE: 93

Arg Asp Asp Ala Ile Cys Glu Trp
1               5

<210> SEQ ID NO 94
<211> LENGTH: 25
<212> TYPE: PRT
<213> ORGANISM: Artificial Sequence
<220> FEATURE:
<223> OTHER INFORMATION: Peptide of NME7AB

<400> SEQUENCE: 94

Ser Gly Val Ala Arg Thr Asp Ala Ser Glu Ser Ile Arg Ala Leu Phe
1               5                   10                  15

Gly Thr Asp Gly Ile Arg Asn Ala Ala
            20                  25

<210> SEQ ID NO 95
<211> LENGTH: 9
<212> TYPE: PRT
```

<210> SEQ ID NO 95
<211> LENGTH: 8
<212> TYPE: PRT
<213> ORGANISM: Artificial Sequence
<220> FEATURE:
<223> OTHER INFORMATION: Peptide of NME7AB

<400> SEQUENCE: 95

Glu Leu Phe Phe Pro Ser Ser Gly Gly
1               5

<210> SEQ ID NO 96
<211> LENGTH: 26
<212> TYPE: PRT
<213> ORGANISM: Artificial Sequence
<220> FEATURE:
<223> OTHER INFORMATION: Peptide of NME7AB

<400> SEQUENCE: 96

Lys Phe Thr Asn Cys Thr Cys Cys Ile Val Lys Pro His Ala Val Ser
1               5                   10                  15

Glu Gly Leu Leu Gly Lys Ile Leu Met Ala
            20                  25

<210> SEQ ID NO 97
<211> LENGTH: 36
<212> TYPE: PRT
<213> ORGANISM: Artificial Sequence
<220> FEATURE:
<223> OTHER INFORMATION: Peptide of NME7AB

<400> SEQUENCE: 97

Leu Met Ala Ile Arg Asp Ala Gly Phe Glu Ile Ser Ala Met Gln Met
1               5                   10                  15

Phe Asn Met Asp Arg Val Asn Val Glu Glu Phe Tyr Glu Val Tyr Lys
            20                  25                  30

Gly Val Val Thr
        35

<210> SEQ ID NO 98
<211> LENGTH: 15
<212> TYPE: PRT
<213> ORGANISM: Artificial Sequence
<220> FEATURE:
<223> OTHER INFORMATION: Peptide of NME7AB

<400> SEQUENCE: 98

Glu Phe Tyr Glu Val Tyr Lys Gly Val Val Thr Glu Tyr His Asp
1               5                   10                  15

<210> SEQ ID NO 99
<211> LENGTH: 43
<212> TYPE: PRT
<213> ORGANISM: Artificial Sequence
<220> FEATURE:
<223> OTHER INFORMATION: Peptide of NME7AB

<400> SEQUENCE: 99

Glu Ile Gln Gln Asn Asn Ala Thr Lys Thr Phe Arg Glu Phe Cys Gly
1               5                   10                  15

Pro Ala Asp Pro Glu Ile Ala Arg His Leu Arg Pro Gly Thr Leu Arg
            20                  25                  30

Ala Ile Phe Gly Lys Thr Lys Ile Gln Asn Ala
        35                  40

<210> SEQ ID NO 100
<211> LENGTH: 8

```
<212> TYPE: PRT
<213> ORGANISM: Artificial Sequence
<220> FEATURE:
<223> OTHER INFORMATION: Peptide of NME7AB

<400> SEQUENCE: 100

Tyr Ser Gly Pro Cys Val Ala Met
1               5

<210> SEQ ID NO 101
<211> LENGTH: 7
<212> TYPE: PRT
<213> ORGANISM: Artificial Sequence
<220> FEATURE:
<223> OTHER INFORMATION: Peptide of NME7AB

<400> SEQUENCE: 101

Phe Arg Glu Phe Cys Gly Pro
1               5

<210> SEQ ID NO 102
<211> LENGTH: 23
<212> TYPE: PRT
<213> ORGANISM: Artificial Sequence
<220> FEATURE:
<223> OTHER INFORMATION: Peptide of NME7AB

<400> SEQUENCE: 102

Val His Cys Thr Asp Leu Pro Glu Asp Gly Leu Leu Glu Val Gln Tyr
1               5                   10                  15

Phe Phe Lys Ile Leu Asp Asn
            20

<210> SEQ ID NO 103
<211> LENGTH: 9
<212> TYPE: PRT
<213> ORGANISM: Artificial Sequence
<220> FEATURE:
<223> OTHER INFORMATION: Peptide of NME7AB

<400> SEQUENCE: 103

Ile Gln Asn Ala Val His Cys Thr Asp
1               5

<210> SEQ ID NO 104
<211> LENGTH: 20
<212> TYPE: PRT
<213> ORGANISM: Artificial Sequence
<220> FEATURE:
<223> OTHER INFORMATION: Peptide of NME7AB

<400> SEQUENCE: 104

Thr Asp Leu Pro Glu Asp Gly Leu Leu Glu Val Gln Tyr Phe Phe Lys
1               5                   10                  15

Ile Leu Asp Asn
            20

<210> SEQ ID NO 105
<211> LENGTH: 13
<212> TYPE: PRT
<213> ORGANISM: Artificial Sequence
<220> FEATURE:
<223> OTHER INFORMATION: Peptide of NME7AB

<400> SEQUENCE: 105

Pro Glu Asp Gly Leu Leu Glu Val Gln Tyr Phe Phe Lys
```

```
1               5                   10
```

<210> SEQ ID NO 106
<211> LENGTH: 12
<212> TYPE: PRT
<213> ORGANISM: Artificial Sequence
<220> FEATURE:
<223> OTHER INFORMATION: Peptide of NME7AB

<400> SEQUENCE: 106

```
Glu Ile Ile Asn Lys Ala Gly Phe Thr Ile Thr Lys
1               5                   10
```

<210> SEQ ID NO 107
<211> LENGTH: 16
<212> TYPE: PRT
<213> ORGANISM: Artificial Sequence
<220> FEATURE:
<223> OTHER INFORMATION: Peptide of NME7AB

<400> SEQUENCE: 107

```
Met Leu Ser Arg Lys Glu Ala Leu Asp Phe His Val Asp His Gln Ser
1               5                   10                  15
```

<210> SEQ ID NO 108
<211> LENGTH: 9
<212> TYPE: PRT
<213> ORGANISM: Artificial Sequence
<220> FEATURE:
<223> OTHER INFORMATION: Peptide of NME7AB

<400> SEQUENCE: 108

```
Asn Glu Leu Ile Gln Phe Ile Thr Thr
1               5
```

<210> SEQ ID NO 109
<211> LENGTH: 14
<212> TYPE: PRT
<213> ORGANISM: Artificial Sequence
<220> FEATURE:
<223> OTHER INFORMATION: Peptide of NME7AB

<400> SEQUENCE: 109

```
Glu Ile Leu Arg Asp Asp Ala Ile Cys Glu Trp Lys Arg Leu
1               5                   10
```

<210> SEQ ID NO 110
<211> LENGTH: 21
<212> TYPE: PRT
<213> ORGANISM: Artificial Sequence
<220> FEATURE:
<223> OTHER INFORMATION: Peptide of NME7AB

<400> SEQUENCE: 110

```
Ser Gly Val Ala Arg Thr Asp Ala Ser Glu Ser Ile Arg Ala Leu Phe
1               5                   10                  15

Gly Thr Asp Gly Ile
            20
```

<210> SEQ ID NO 111
<211> LENGTH: 11
<212> TYPE: PRT
<213> ORGANISM: Artificial Sequence
<220> FEATURE:
<223> OTHER INFORMATION: Peptide of NME7AB

<400> SEQUENCE: 111

Ser Gly Val Ala Arg Thr Asp Ala Ser Glu Ser
1               5                  10

<210> SEQ ID NO 112
<211> LENGTH: 8
<212> TYPE: PRT
<213> ORGANISM: Artificial Sequence
<220> FEATURE:
<223> OTHER INFORMATION: Peptide of NME7AB

<400> SEQUENCE: 112

Ala Leu Phe Gly Thr Asp Gly Ile
1               5

<210> SEQ ID NO 113
<211> LENGTH: 14
<212> TYPE: PRT
<213> ORGANISM: Artificial Sequence
<220> FEATURE:
<223> OTHER INFORMATION: Peptide of NME7AB

<400> SEQUENCE: 113

Asn Cys Thr Cys Cys Ile Val Lys Pro His Ala Val Ser Glu
1               5                  10

<210> SEQ ID NO 114
<211> LENGTH: 11
<212> TYPE: PRT
<213> ORGANISM: Artificial Sequence
<220> FEATURE:
<223> OTHER INFORMATION: Peptide of NME7AB

<400> SEQUENCE: 114

Leu Gly Lys Ile Leu Met Ala Ile Arg Asp Ala
1               5                  10

<210> SEQ ID NO 115
<211> LENGTH: 16
<212> TYPE: PRT
<213> ORGANISM: Artificial Sequence
<220> FEATURE:
<223> OTHER INFORMATION: Peptide of NME7AB

<400> SEQUENCE: 115

Glu Ile Ser Ala Met Gln Met Phe Asn Met Asp Arg Val Asn Val Glu
1               5                  10                  15

<210> SEQ ID NO 116
<211> LENGTH: 8
<212> TYPE: PRT
<213> ORGANISM: Artificial Sequence
<220> FEATURE:
<223> OTHER INFORMATION: Peptide of NME7AB

<400> SEQUENCE: 116

Glu Val Tyr Lys Gly Val Val Thr
1               5

<210> SEQ ID NO 117
<211> LENGTH: 8
<212> TYPE: PRT
<213> ORGANISM: Artificial Sequence
<220> FEATURE:
<223> OTHER INFORMATION: Peptide of NME7AB

<400> SEQUENCE: 117

```
Glu Tyr His Asp Met Val Thr Glu
1               5

<210> SEQ ID NO 118
<211> LENGTH: 15
<212> TYPE: PRT
<213> ORGANISM: Artificial Sequence
<220> FEATURE:
<223> OTHER INFORMATION: Peptide of NME7AB

<400> SEQUENCE: 118

Glu Phe Cys Gly Pro Ala Asp Pro Glu Ile Ala Arg His Leu Arg
1               5                   10                  15

<210> SEQ ID NO 119
<211> LENGTH: 12
<212> TYPE: PRT
<213> ORGANISM: Artificial Sequence
<220> FEATURE:
<223> OTHER INFORMATION: Peptide of NME7AB

<400> SEQUENCE: 119

Ala Ile Phe Gly Lys Thr Lys Ile Gln Asn Ala Val
1               5                   10

<210> SEQ ID NO 120
<211> LENGTH: 18
<212> TYPE: PRT
<213> ORGANISM: Artificial Sequence
<220> FEATURE:
<223> OTHER INFORMATION: Peptide of NME7AB

<400> SEQUENCE: 120

Leu Pro Glu Asp Gly Leu Leu Glu Val Gln Tyr Phe Phe Lys Ile Leu
1               5                   10                  15

Asp Asn

<210> SEQ ID NO 121
<211> LENGTH: 17
<212> TYPE: PRT
<213> ORGANISM: Artificial Sequence
<220> FEATURE:
<223> OTHER INFORMATION: Peptide of NME7AB

<400> SEQUENCE: 121

Gly Pro Asp Ser Phe Ala Ser Ala Ala Arg Glu Met Glu Leu Phe Phe
1               5                   10                  15

Pro

<210> SEQ ID NO 122
<211> LENGTH: 7
<212> TYPE: PRT
<213> ORGANISM: Artificial Sequence
<220> FEATURE:
<223> OTHER INFORMATION: Immunizing peptides derived from human NME7

<400> SEQUENCE: 122

Ile Cys Glu Trp Lys Arg Leu
1               5

<210> SEQ ID NO 123
<211> LENGTH: 11
<212> TYPE: PRT
<213> ORGANISM: Artificial Sequence
<220> FEATURE:
<223> OTHER INFORMATION: Immunizing peptides derived from human NME7
```

```
-continued

<400> SEQUENCE: 123

Leu Gly Lys Ile Leu Met Ala Ile Arg Asp Ala
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Immunizing peptides derived from human NME7

<400> SEQUENCE: 124

His Ala Val Ser Glu Gly Leu Leu Gly Lys
1               5                   10

<210> SEQ ID NO 125
<211> LENGTH: 8
<212> TYPE: PRT
<213> ORGANISM: Artificial Sequence
<220> FEATURE:
<223> OTHER INFORMATION: Immunizing peptides derived from human NME7

<400> SEQUENCE: 125

Val Thr Glu Met Tyr Ser Gly Pro
1               5

<210> SEQ ID NO 126
<211> LENGTH: 9
<212> TYPE: PRT
<213> ORGANISM: Artificial Sequence
<220> FEATURE:
<223> OTHER INFORMATION: Immunizing peptides derived from human NME7

<400> SEQUENCE: 126

Asn Ala Thr Lys Thr Phe Arg Glu Phe
1               5

<210> SEQ ID NO 127
<211> LENGTH: 9
<212> TYPE: PRT
<213> ORGANISM: Artificial Sequence
<220> FEATURE:
<223> OTHER INFORMATION: Immunizing peptides derived from human NME7

<400> SEQUENCE: 127

Ala Ile Arg Asp Ala Gly Phe Glu Ile
1               5

<210> SEQ ID NO 128
<211> LENGTH: 13
<212> TYPE: PRT
<213> ORGANISM: Artificial Sequence
<220> FEATURE:
<223> OTHER INFORMATION: Immunizing peptides derived from human NME7

<400> SEQUENCE: 128

Ala Ile Cys Glu Trp Lys Arg Leu Leu Gly Pro Ala Asn
1               5                   10

<210> SEQ ID NO 129
<211> LENGTH: 8
<212> TYPE: PRT
<213> ORGANISM: Artificial Sequence
<220> FEATURE:
<223> OTHER INFORMATION: Immunizing peptides derived from human NME7
```

```
<400> SEQUENCE: 129

Asp His Gln Ser Arg Pro Phe Phe
1               5

<210> SEQ ID NO 130
<211> LENGTH: 13
<212> TYPE: PRT
<213> ORGANISM: Artificial Sequence
<220> FEATURE:
<223> OTHER INFORMATION: Immunizing peptides derived from human NME7

<400> SEQUENCE: 130

Ala Ile Cys Glu Trp Lys Arg Leu Leu Gly Pro Ala Asn
1               5                   10

<210> SEQ ID NO 131
<211> LENGTH: 8
<212> TYPE: PRT
<213> ORGANISM: Artificial Sequence
<220> FEATURE:
<223> OTHER INFORMATION: Immunizing peptides derived from human NME7

<400> SEQUENCE: 131

Val Asp His Gln Ser Arg Pro Phe
1               5

<210> SEQ ID NO 132
<211> LENGTH: 6
<212> TYPE: PRT
<213> ORGANISM: Artificial Sequence
<220> FEATURE:
<223> OTHER INFORMATION: Immunizing peptides derived from human NME7

<400> SEQUENCE: 132

Pro Asp Ser Phe Ala Ser
1               5

<210> SEQ ID NO 133
<211> LENGTH: 18
<212> TYPE: PRT
<213> ORGANISM: Artificial Sequence
<220> FEATURE:
<223> OTHER INFORMATION: Immunizing peptides derived from human NME7

<400> SEQUENCE: 133

Lys Ala Gly Glu Ile Ile Glu Ile Ile Asn Lys Ala Gly Phe Thr Ile
1               5                   10                  15

Thr Lys

<210> SEQ ID NO 134
<211> LENGTH: 29
<212> TYPE: PRT
<213> ORGANISM: Artificial Sequence
<220> FEATURE:
<223> OTHER INFORMATION: Immunizing peptides derived from human NME1

<400> SEQUENCE: 134

Met Ala Asn Cys Glu Arg Thr Phe Ile Ala Ile Lys Pro Asp Gly Val
1               5                   10                  15

Gln Arg Gly Leu Val Gly Glu Ile Ile Lys Arg Phe Glu
            20                  25

<210> SEQ ID NO 135
<211> LENGTH: 8
<212> TYPE: PRT
```

<213> ORGANISM: Artificial Sequence
<220> FEATURE:
<223> OTHER INFORMATION: Immunizing peptides derived from human NME1

<400> SEQUENCE: 135

Val Asp Leu Lys Asp Arg Pro Phe
1               5

<210> SEQ ID NO 136
<211> LENGTH: 17
<212> TYPE: PRT
<213> ORGANISM: Artificial Sequence
<220> FEATURE:
<223> OTHER INFORMATION: Immunizing peptides derived from human NME1

<400> SEQUENCE: 136

His Gly Ser Asp Ser Val Glu Ser Ala Glu Lys Glu Ile Gly Leu Trp
1               5                   10                  15

Phe

<210> SEQ ID NO 137
<211> LENGTH: 25
<212> TYPE: PRT
<213> ORGANISM: Artificial Sequence
<220> FEATURE:
<223> OTHER INFORMATION: Immunizing peptides derived from human NME1

<400> SEQUENCE: 137

Glu Arg Thr Phe Ile Ala Ile Lys Pro Asp Gly Val Gln Arg Gly Leu
1               5                   10                  15

Val Gly Glu Ile Ile Lys Arg Phe Glu
            20                  25

<210> SEQ ID NO 138
<211> LENGTH: 30
<212> TYPE: PRT
<213> ORGANISM: Artificial Sequence
<220> FEATURE:
<223> OTHER INFORMATION: Immunizing peptides derived from human NME1

<400> SEQUENCE: 138

Val Asp Leu Lys Asp Arg Pro Phe Phe Ala Gly Leu Val Lys Tyr Met
1               5                   10                  15

His Ser Gly Pro Val Val Ala Met Val Trp Glu Gly Leu Asn
            20                  25                  30

<210> SEQ ID NO 139
<211> LENGTH: 26
<212> TYPE: PRT
<213> ORGANISM: Artificial Sequence
<220> FEATURE:
<223> OTHER INFORMATION: Immunizing peptides derived from human NME1

<400> SEQUENCE: 139

Asn Ile Ile His Gly Ser Asp Ser Val Glu Ser Ala Glu Lys Glu Ile
1               5                   10                  15

Gly Leu Trp Phe His Pro Glu Glu Leu Val
            20                  25

<210> SEQ ID NO 140
<211> LENGTH: 14
<212> TYPE: PRT
<213> ORGANISM: Artificial Sequence
<220> FEATURE:
<223> OTHER INFORMATION: Immunizing peptides derived from human NME1

```
<400> SEQUENCE: 140

Lys Pro Asp Gly Val Gln Arg Gly Leu Val Gly Glu Ile Ile
1               5                   10

<210> SEQ ID NO 141
<211> LENGTH: 16
<212> TYPE: PRT
<213> ORGANISM: Artificial Sequence
<220> FEATURE:
<223> OTHER INFORMATION: NME7A peptide 1 (A domain)

<400> SEQUENCE: 141

Met Leu Ser Arg Lys Glu Ala Leu Asp Phe His Val Asp His Gln Ser
1               5                   10                  15

<210> SEQ ID NO 142
<211> LENGTH: 11
<212> TYPE: PRT
<213> ORGANISM: Artificial Sequence
<220> FEATURE:
<223> OTHER INFORMATION: NME7A peptide 2 (A domain)

<400> SEQUENCE: 142

Ser Gly Val Ala Arg Thr Asp Ala Ser Glu Ser
1               5                   10

<210> SEQ ID NO 143
<211> LENGTH: 20
<212> TYPE: PRT
<213> ORGANISM: Artificial Sequence
<220> FEATURE:
<223> OTHER INFORMATION: NME7B peptide 1 (B domain)

<400> SEQUENCE: 143

Asp Ala Gly Phe Glu Ile Ser Ala Met Gln Met Phe Asn Met Asp Arg
1               5                   10                  15

Val Asn Val Glu
            20

<210> SEQ ID NO 144
<211> LENGTH: 16
<212> TYPE: PRT
<213> ORGANISM: Artificial Sequence
<220> FEATURE:
<223> OTHER INFORMATION: NME7B peptide 2 (B domain)

<400> SEQUENCE: 144

Glu Val Tyr Lys Gly Val Val Thr Glu Tyr His Asp Met Val Thr Glu
1               5                   10                  15

<210> SEQ ID NO 145
<211> LENGTH: 29
<212> TYPE: PRT
<213> ORGANISM: Artificial Sequence
<220> FEATURE:
<223> OTHER INFORMATION: NME7B peptide 3 (B domain)

<400> SEQUENCE: 145

Ala Ile Phe Gly Lys Thr Lys Ile Gln Asn Ala Val His Cys Thr Asp
1               5                   10                  15

Leu Pro Glu Asp Gly Leu Leu Glu Val Gln Tyr Phe Phe
            20                  25

<210> SEQ ID NO 146
```

<211> LENGTH: 1131
<212> TYPE: DNA
<213> ORGANISM: Artificial Sequence
<220> FEATURE:
<223> OTHER INFORMATION: Human NME7 a

<400> SEQUENCE: 146

```
atgaatcata gtgaaagatt cgttttcatt gcagagtggt atgatccaaa tgcttcactt      60
cttcgacgtt atgagctttt attttaccca ggggatggga ctgttgaaat gcatgatgta    120
aagaatcatc gcacctttt aaagcggacc aaatatgata acctgcactt ggaagattta     180
tttataggca acaaagtgaa tgtctttct cgacaactgg tattaattga ctatggggat     240
caatatacag ctcgccagct gggcagtagg aaagaaaaaa cgctagccct aattaaacca    300
gatgcaatat caaaggctgg agaaataatt gaaataataa acaaagctgg atttactata    360
accaaactca aaatgatgat gctttcaagg aaagaagcat tggattttca gtagatcac     420
cagtcaagac ccttttcaa tgagctgatc cagtttatta caactggtcc tattattgcc     480
atggagattt taagagatga tgctatatgt gaatggaaaa gactgctggg acctgcaaac    540
tctggagtgg cacgcacaga tgcttctgaa agcattagag ccctcttgg aacagatggc     600
ataagaaatg cagcgcatgg ccctgattct tttgcttctg cggccagaga atggagttg     660
tttttttcctt caagtggagg ttgtgggccg gcaaacactg ctaaatttac taattgtacc   720
tgttgcattg ttaaacccca tgctgtcagt gaaggactgt tggaaagat cctgatggct    780
atccgagatg caggtttga atctcagct atgcagatgt caatatgga tcgggttaat      840
gttgaggaat tctatgaagt ttataaagga gtagtgaccg aatatcatga catggtgaca    900
gaaatgtatt ctggcccttg tgtagcaatg gagattcaac agaataatgc tacaaagaca    960
tttcgagaat tttgtggacc tgctgatcct gaaattgccc ggcatttacg ccctggaact  1020
ctcagagcaa tctttggtaa aactaagatc cagaatgctg ttcactgtac tgatctgcca  1080
gaggatggcc tattagaggt tcaatacttc ttcaagatct tggataatta g           1131
```

<210> SEQ ID NO 147
<211> LENGTH: 376
<212> TYPE: PRT
<213> ORGANISM: Artificial Sequence
<220> FEATURE:
<223> OTHER INFORMATION: Human NME7 a

<400> SEQUENCE: 147

```
Met Asn His Ser Glu Arg Phe Val Phe Ile Ala Glu Trp Tyr Asp Pro
1               5                   10                  15

Asn Ala Ser Leu Leu Arg Arg Tyr Glu Leu Leu Phe Tyr Pro Gly Asp
            20                  25                  30

Gly Ser Val Glu Met His Asp Val Lys Asn His Arg Thr Phe Leu Lys
        35                  40                  45

Arg Thr Lys Tyr Asp Asn Leu His Leu Glu Asp Leu Phe Ile Gly Asn
    50                  55                  60

Lys Val Asn Val Phe Ser Arg Gln Leu Val Leu Ile Asp Tyr Gly Asp
65                  70                  75                  80

Gln Tyr Thr Ala Arg Gln Leu Gly Ser Arg Lys Glu Lys Thr Leu Ala
            85                  90                  95

Leu Ile Lys Pro Asp Ala Ile Ser Lys Ala Gly Glu Ile Ile Glu Ile
            100                 105                 110

Ile Asn Lys Ala Gly Phe Thr Ile Thr Lys Leu Lys Met Met Met Leu
        115                 120                 125
```

Ser Arg Lys Glu Ala Leu Asp Phe His Val Asp His Gln Ser Arg Pro
130                 135                 140

Phe Phe Asn Glu Leu Ile Gln Phe Ile Thr Thr Gly Pro Ile Ile Ala
145                 150                 155                 160

Met Glu Ile Leu Arg Asp Asp Ala Ile Cys Glu Trp Lys Arg Leu Leu
                165                 170                 175

Gly Pro Ala Asn Ser Gly Val Ala Arg Thr Asp Ala Ser Glu Ser Ile
            180                 185                 190

Arg Ala Leu Phe Gly Thr Asp Gly Ile Arg Asn Ala Ala His Gly Pro
        195                 200                 205

Asp Ser Phe Ala Ser Ala Arg Glu Met Glu Leu Phe Phe Pro Ser
210                 215                 220

Ser Gly Gly Cys Gly Pro Ala Asn Thr Ala Lys Phe Thr Asn Cys Thr
225                 230                 235                 240

Cys Cys Ile Val Lys Pro His Ala Val Ser Glu Gly Leu Leu Gly Lys
                245                 250                 255

Ile Leu Met Ala Ile Arg Asp Ala Gly Phe Glu Ile Ser Ala Met Gln
            260                 265                 270

Met Phe Asn Met Asp Arg Val Asn Val Glu Gly Phe Tyr Glu Val Tyr
        275                 280                 285

Lys Gly Val Val Thr Glu Tyr His Asp Met Val Thr Glu Met Tyr Ser
290                 295                 300

Gly Pro Cys Val Ala Met Glu Ile Gln Gln Asn Asn Ala Thr Lys Thr
305                 310                 315                 320

Phe Arg Glu Phe Cys Gly Pro Ala Asp Pro Glu Ile Ala Arg His Leu
                325                 330                 335

Arg Pro Gly Thr Leu Arg Ala Ile Phe Gly Lys Thr Lys Ile Gln Asn
            340                 345                 350

Ala Val His Cys Thr Asp Leu Pro Glu Asp Gly Leu Leu Glu Val Gln
        355                 360                 365

Tyr Phe Phe Lys Ile Leu Asp Asn
        370                 375

<210> SEQ ID NO 148
<211> LENGTH: 1023
<212> TYPE: DNA
<213> ORGANISM: Artificial Sequence
<220> FEATURE:
<223> OTHER INFORMATION: Human NME7 b

<400> SEQUENCE: 148
atgcatgatg taaagaatca tcgcaccttt ttaaagcgga ccaaatatga taacctgcac      60
ttggaagatt tatttatagg caacaaagtg aatgtctttt ctcgacaact ggtattaatt     120
gactatgggg atcaatatac agctcgccag ctgggcagta ggaaagaaaa aacgctagcc     180
ctaattaaac cagatgcaat atcaaaggct ggagaaataa ttgaaataat aaacaaagct     240
ggatttacta taaccaaact caaaatgatg atgctttcaa ggaaagaagc attggatttt     300
catgtagatc accagtcaag accctttttc aatgagctga tccagtttat tacaactggt     360
cctattattg ccatggagat tttaagagat gatgctatat gtgaatggaa agactgctg     420 ggacctgcaa actctggagt ggcacgcaca gatgcttctg aaagcattag agccctcttt     480
ggaacagatg gcataagaaa tgcagcgcat ggccctgatt cttttgcttc tgcggccaga     540
gaaatggagt tgttttttcc ttcaagtgga ggttgtgggc cggcaaacac tgctaaattt     600

```
actaattgta cctgttgcat tgttaaaccc catgctgtca gtgaaggact gttgggaaag    660
atcctgatgg ctatccgaga tgcaggtttt gaaatctcag ctatgcagat gttcaatatg    720
gatcgggtta atgttgagga attctatgaa gtttataaag gagtagtgac cgaatatcat    780
gacatggtga cagaaatgta ttctggccct tgtgtagcaa tggagattca acagaataat    840
gctacaaaga catttcgaga attttgtgga cctgctgatc ctgaaattgc ccggcattta    900
cgccctggaa ctctcagagc aatctttggt aaaactaaga tccagaatgc tgttcactgt    960
actgatctgc cagaggatgg cctattagag gttcaatact tcttcaagat cttggataat   1020
tag                                                                 1023
```

<210> SEQ ID NO 149  
<211> LENGTH: 340  
<212> TYPE: PRT  
<213> ORGANISM: Artificial Sequence  
<220> FEATURE:  
<223> OTHER INFORMATION: Human NME7 b

<400> SEQUENCE: 149

```
Met His Asp Val Lys Asn His Arg Thr Phe Leu Lys Arg Thr Lys Tyr
1               5                   10                  15

Asp Asn Leu His Leu Glu Asp Leu Phe Ile Gly Asn Lys Val Asn Val
            20                  25                  30

Phe Ser Arg Gln Leu Val Leu Ile Asp Tyr Gly Asp Gln Tyr Thr Ala
        35                  40                  45

Arg Gln Leu Gly Ser Arg Lys Glu Lys Thr Leu Ala Leu Ile Lys Pro
    50                  55                  60

Asp Ala Ile Ser Lys Ala Gly Glu Ile Ile Glu Ile Ile Asn Lys Ala
65                  70                  75                  80

Gly Phe Thr Ile Thr Lys Leu Lys Met Met Met Leu Ser Arg Lys Glu
                85                  90                  95

Ala Leu Asp Phe His Val Asp His Gln Ser Arg Pro Phe Phe Asn Glu
            100                 105                 110

Leu Ile Gln Phe Ile Thr Thr Gly Pro Ile Ile Ala Met Glu Ile Leu
        115                 120                 125

Arg Asp Asp Ala Ile Cys Glu Trp Lys Arg Leu Leu Gly Pro Ala Asn
    130                 135                 140

Ser Gly Val Ala Arg Thr Asp Ala Ser Glu Ser Ile Arg Ala Leu Phe
145                 150                 155                 160

Gly Thr Asp Gly Ile Arg Asn Ala Ala His Gly Pro Asp Ser Phe Ala
                165                 170                 175

Ser Ala Ala Arg Glu Met Glu Leu Phe Phe Pro Ser Ser Gly Gly Cys
            180                 185                 190

Gly Pro Ala Asn Thr Ala Lys Phe Thr Asn Cys Thr Cys Cys Ile Val
        195                 200                 205

Lys Pro His Ala Val Ser Glu Gly Leu Leu Gly Lys Ile Leu Met Ala
    210                 215                 220

Ile Arg Asp Ala Gly Phe Glu Ile Ser Ala Met Gln Met Phe Asn Met
225                 230                 235                 240

Asp Arg Val Asn Val Glu Glu Phe Tyr Glu Val Tyr Lys Gly Val Val
                245                 250                 255

Thr Glu Tyr His Asp Met Val Thr Glu Met Tyr Ser Gly Pro Cys Val
            260                 265                 270

Ala Met Glu Ile Gln Gln Asn Asn Ala Thr Lys Thr Phe Arg Glu Phe
        275                 280                 285
```

Cys Gly Pro Ala Asp Pro Glu Ile Ala Arg His Leu Arg Pro Gly Thr
            290                 295                 300

Leu Arg Ala Ile Phe Gly Lys Thr Lys Ile Gln Asn Ala Val His Cys
305                 310                 315                 320

Thr Asp Leu Pro Glu Asp Gly Leu Leu Glu Val Gln Tyr Phe Phe Lys
                325                 330                 335

Ile Leu Asp Asn
            340

<210> SEQ ID NO 150
<211> LENGTH: 861
<212> TYPE: DNA
<213> ORGANISM: Artificial Sequence
<220> FEATURE:
<223> OTHER INFORMATION: Human NME7-AB also known as NME7AB

<400> SEQUENCE: 150

| | | | | | |
|---|---|---|---|---|---|
| atggaaaaaa | cgctagccct | aattaaacca | gatgcaatat | caaaggctgg | agaaataatt | 60 |
| gaaataataa | acaaagctgg | atttactata | accaaactca | aaatgatgat | gctttcaagg | 120 |
| aaagaagcat | tggattttca | gtagatcac  | cagtcaagac | ccttttttcaa | tgagctgatc | 180 |
| cagtttatta | caactggtcc | tattattgcc | atggagattt | taagagatga | tgctatatgt | 240 |
| gaatggaaaa | gactgctggg | acctgcaaac | tctggagtgg | cacgcacaga | tgcttctgaa | 300 |
| agcattagag | ccctctttgg | aacagatggc | ataagaaatg | cagcgcatgg | ccctgattct | 360 |
| tttgcttctg | cggccagaga | aatggagttg | ttttttcctt | caagtggagg | ttgtgggccg | 420 |
| gcaaacactg | ctaaatttac | taattgtacc | tgttgcattg | ttaaacccca | tgctgtcagt | 480 |
| gaaggactgt | tgggaaagat | cctgatggct | atccgagatg | caggttttga | aatctcagct | 540 |
| atgcagatgt | tcaatatgga | tcgggttaat | gttgaggaat | ctatgaagt  | ttataaagga | 600 |
| gtagtgaccg | aatatcatga | catggtgaca | gaaatgtatt | ctggcccttg | tgtagcaatg | 660 |
| gagattcaac | agaataatgc | tacaaagaca | tttcgagaat | tttgtggacc | tgctgatcct | 720 |
| gaaattgccc | ggcatttacg | ccctggaact | ctcagagcaa | tctttggtaa | aactaagatc | 780 |
| cagaatgctg | ttcactgtac | tgatctgcca | gaggatggcc | tattagaggt | tcaatacttc | 840 |
| ttcaagatct | tggataatta | g | | | | 861 |

<210> SEQ ID NO 151
<211> LENGTH: 286
<212> TYPE: PRT
<213> ORGANISM: Artificial Sequence
<220> FEATURE:
<223> OTHER INFORMATION: Human NME7-AB also known as NME7AB

<400> SEQUENCE: 151

Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
                20                  25                  30

Leu Lys Met Met Met Leu Ser Arg Lys Glu Ala Leu Asp Phe His Val
            35                  40                  45

Asp His Gln Ser Arg Pro Phe Phe Asn Glu Leu Ile Gln Phe Ile Thr
        50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr

```
                 85                  90                  95
Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Ala Arg Glu Met
        115                 120                 125

Glu Leu Phe Phe Pro Ser Ser Gly Gly Cys Gly Pro Ala Asn Thr Ala
    130                 135                 140

Lys Phe Thr Asn Cys Thr Cys Cys Ile Val Lys Pro His Ala Val Ser
145                 150                 155                 160

Glu Gly Leu Leu Gly Lys Ile Leu Met Ala Ile Arg Asp Ala Gly Phe
                165                 170                 175

Glu Ile Ser Ala Met Gln Met Phe Asn Met Asp Arg Val Asn Val Glu
            180                 185                 190

Glu Phe Tyr Glu Val Tyr Lys Gly Val Val Thr Glu Tyr His Asp Met
        195                 200                 205

Val Thr Glu Met Tyr Ser Gly Pro Cys Val Ala Met Glu Ile Gln Gln
    210                 215                 220

Asn Asn Ala Thr Lys Thr Phe Arg Glu Phe Cys Gly Pro Ala Asp Pro
225                 230                 235                 240

Glu Ile Ala Arg His Leu Arg Pro Gly Thr Leu Arg Ala Ile Phe Gly
                245                 250                 255

Lys Thr Lys Ile Gln Asn Ala Val His Cys Thr Asp Leu Pro Glu Asp
            260                 265                 270

Gly Leu Leu Glu Val Gln Tyr Phe Phe Lys Ile Leu Asp Asn
        275                 280                 285

<210> SEQ ID NO 152
<211> LENGTH: 759
<212> TYPE: DNA
<213> ORGANISM: Artificial Sequence
<220> FEATURE:
<223> OTHER INFORMATION: Human NME7-X1

<400> SEQUENCE: 152
atgatgatgc tttcaaggaa agaagcattg gattttcatg tagatcacca gtcaagaccc      60 ttttttcaatg agctgatcca gtttattaca actggtccta ttattgccat ggagatttta     120
agagatgatg ctatatgtga atggaaaaga ctgctgggac tgcaaactc tggagtggca      180 cgcacagatg cttctgaaag cattagagcc ctctttggaa cagatggcat aagaaatgca     240
gcgcatggcc ctgattcttt tgcttctgcg gccagagaaa tggagttgtt ttttccttca     300
agtggaggtt gtgggccggc aaacactgct aaatttacta attgtacctg ttgcattgtt     360 aaacccccatg ctgtcagtga aggactgttg ggaaagatcc tgatggctat ccgagatgca    420
ggttttgaaa tctcagctat gcagatgttc aatatggatc gggttaatgt tgaggaattc     480
tatgaagttt ataaaggagt agtgaccgaa tatcatgaca tggtgacaga aatgtattct     540
ggcccttgtg tagcaatgga gattcaacag aataatgcta caaagacatt tcgagaattt     600
tgtggacctg ctgatcctga aattgcccgg catttacgcc ctggaactct cagagcaatc     660
tttggtaaaa ctaagatcca gaatgctgtt cactgtactg atctgccaga ggatggccta     720
ttagaggttc aatacttctt caagatcttg gataattag                             759

<210> SEQ ID NO 153
<211> LENGTH: 252
<212> TYPE: PRT
<213> ORGANISM: Artificial Sequence
```

```
<220> FEATURE:
<223> OTHER INFORMATION: Human NME7-X1

<400> SEQUENCE: 153

Met Met Met Leu Ser Arg Lys Glu Ala Leu Asp Phe His Val Asp His
1               5                   10                  15

Gln Ser Arg Pro Phe Phe Asn Glu Leu Ile Gln Phe Ile Thr Thr Gly
            20                  25                  30

Pro Ile Ile Ala Met Glu Ile Leu Arg Asp Asp Ala Ile Cys Glu Trp
        35                  40                  45

Lys Arg Leu Leu Gly Pro Ala Asn Ser Gly Val Ala Arg Thr Asp Ala
    50                  55                  60

Ser Glu Ser Ile Arg Ala Leu Phe Gly Thr Asp Gly Ile Arg Asn Ala
65                  70                  75                  80

Ala His Gly Pro Asp Ser Phe Ala Ser Ala Ala Arg Glu Met Glu Leu
                85                  90                  95

Phe Phe Pro Ser Ser Gly Gly Cys Gly Pro Ala Asn Thr Ala Lys Phe
            100                 105                 110

Thr Asn Cys Thr Cys Cys Ile Val Lys Pro His Ala Val Ser Glu Gly
        115                 120                 125

Leu Leu Gly Lys Ile Leu Met Ala Ile Arg Asp Ala Gly Phe Glu Ile
    130                 135                 140

Ser Ala Met Gln Met Phe Asn Met Asp Arg Val Asn Val Glu Glu Phe
145                 150                 155                 160

Tyr Glu Val Tyr Lys Gly Val Val Thr Glu Tyr His Asp Met Val Thr
                165                 170                 175

Glu Met Tyr Ser Gly Pro Cys Val Ala Met Glu Ile Gln Gln Asn Asn
            180                 185                 190

Ala Thr Lys Thr Phe Arg Glu Phe Cys Gly Pro Ala Asp Pro Glu Ile
        195                 200                 205

Ala Arg His Leu Arg Pro Gly Thr Leu Arg Ala Ile Phe Gly Lys Thr
    210                 215                 220

Lys Ile Gln Asn Ala Val His Cys Thr Asp Leu Pro Glu Asp Gly Leu
225                 230                 235                 240

Leu Glu Val Gln Tyr Phe Phe Lys Ile Leu Asp Asn
                245                 250

<210> SEQ ID NO 154
<211> LENGTH: 1128
<212> TYPE: DNA
<213> ORGANISM: Artificial Sequence
<220> FEATURE:
<223> OTHER INFORMATION: Human NME7 a (optimized for E coli expression)

<400> SEQUENCE: 154
atgaatcact ccgaacgctt tgtttttatc gccgaatggt atgacccgaa tgcttccctg      60
ctgcgccgct acgaactgct gttttatccg ggcgatggta gcgtggaaat gcatgacgtt     120
aaaaatcacc gtacctttct gaaacgcacg aaatatgata tctgcatctg gaagacctg     180 tttattggca acaaagtcaa tgtgttctct cgtcagctgg tgctgatcga ttatggcgac     240
cagtacaccg cgcgtcaact gggtagtcgc aagaaaaaa cgctggccct gattaaaccg     300
gatgcaatct ccaaagctgg cgaaattatc gaaattatca acaaagcggg tttcaccatc     360
acgaaactga aaatgatgat gctgagccgt aagaagccc tggattttca gtcgaccac      420 cagtctcgcc cgttttttcaa tgaactgatt caattcatca ccacgggtcc gattatcgca    480
```

-continued

```
atggaaattc tgcgtgatga cgctatctgc gaatggaaac gcctgctggg cccggcaaac    540
tcaggtgttg cgcgtaccga tgccagtgaa tccattcgcg ctctgtttgg caccgatggt    600
atccgtaatg cagcacatgg tccggactca ttcgcatcgg cagctcgtga atggaactg     660 ttttccccga gctctggcgg ttgcggtccg gcaaacaccg ccaaatttac caattgtacg    720
tgctgtattg tcaaaccgca cgcagtgtca gaaggcctgc tgggtaaaat tctgatggca    780
atccgtgatg ctggctttga aatctcggcc atgcagatgt caacatgga ccgcgttaac     840 gtcgaagaat tctacgaagt ttacaaaggc gtggttaccg aatatcacga tatggttacg    900
gaaatgtact ccggtccgtg cgtcgcgatg gaaattcagc aaaacaatgc caccaaaacg    960
tttcgtgaat tctgtggtcc ggcagatccg gaaatcgcac gtcatctgcg tccgggtacc   1020
ctgcgcgcaa ttttttggtaa aacgaaaatc cagaacgctg tgcactgtac cgatctgccg   1080
gaagacggtc tgctggaagt tcaatacttt ttcaaaattc tggataat                 1128
```

<210> SEQ ID NO 155
<211> LENGTH: 378
<212> TYPE: PRT
<213> ORGANISM: Artificial Sequence
<220> FEATURE:
<223> OTHER INFORMATION: Human NME7 a (optimized for E coli expression)

<400> SEQUENCE: 155

```
Met Asn His Ser Glu Arg Phe Val Phe Ile Ala Glu Trp Tyr Asp Pro
 1               5                  10                  15

Asn Ala Ser Leu Leu Arg Arg Tyr Glu Leu Leu Phe Tyr Pro Gly Asp
            20                  25                  30

Gly Ser Val Glu Met His Asp Val Lys Asn His Arg Thr Phe Leu Lys
        35                  40                  45

Arg Thr Lys Tyr Asp Asn Leu His Leu Glu Asp Leu Phe Ile Gly Asn
    50                  55                  60

Lys Val Asn Val Phe Ser Arg Gln Leu Val Leu Ile Asp Tyr Gly Asp
65                  70                  75                  80

Gln Tyr Thr Ala Arg Gln Leu Gly Ser Arg Lys Glu Lys Thr Leu Ala
                85                  90                  95

Leu Ile Lys Pro Asp Ala Ile Ser Lys Ala Gly Glu Ile Ile Glu Ile
            100                 105                 110

Ile Asn Lys Ala Gly Phe Thr Ile Thr Lys Leu Lys Met Met Met Leu
        115                 120                 125

Ser Arg Lys Glu Ala Leu Asp Phe His Val Asp His Gln Ser Arg Pro
    130                 135                 140

Phe Phe Asn Glu Leu Ile Gln Phe Ile Thr Thr Gly Pro Ile Ile Ala
145                 150                 155                 160

Met Glu Ile Leu Arg Asp Asp Ala Ile Cys Glu Trp Lys Arg Leu Leu
                165                 170                 175

Gly Pro Ala Asn Ser Gly Val Ala Arg Thr Asp Ala Ser Glu Ser Ile
            180                 185                 190

Arg Ala Leu Phe Gly Thr Asp Gly Ile Arg Asn Ala Ala His Gly Pro
        195                 200                 205

Asp Ser Phe Ala Ser Ala Ala Arg Glu Met Glu Leu Phe Phe Pro Ser
    210                 215                 220

Ser Gly Gly Cys Gly Pro Ala Asn Thr Ala Lys Phe Thr Asn Cys Thr
225                 230                 235                 240

Cys Cys Ile Val Lys Pro His Ala Val Ser Glu Gly Leu Leu Gly Lys
                245                 250                 255
```

Ile Leu Met Ala Ile Arg Asp Ala Gly Phe Glu Ile Ser Ala Met Gln
                260                 265                 270

Met Phe Asn Met Asp Arg Val Asn Val Glu Glu Phe Tyr Glu Val Tyr
            275                 280                 285

Lys Gly Val Val Thr Glu Tyr His Asp Met Val Thr Glu Met Tyr Ser
290                 295                 300

Gly Pro Cys Val Ala Met Glu Ile Gln Gln Asn Asn Ala Thr Lys Thr
305                 310                 315                 320

Phe Arg Glu Phe Cys Gly Pro Ala Asp Pro Glu Ile Ala Arg His Leu
                325                 330                 335

Arg Pro Gly Thr Leu Arg Ala Ile Phe Gly Lys Thr Lys Ile Gln Asn
            340                 345                 350

Ala Val His Cys Thr Asp Leu Pro Glu Asp Gly Leu Leu Glu Val Gln
        355                 360                 365

Tyr Phe Phe Lys Ile Leu Asp Asn Thr Gly
370                 375

<210> SEQ ID NO 156
<211> LENGTH: 1020
<212> TYPE: DNA
<213> ORGANISM: Artificial Sequence
<220> FEATURE:
<223> OTHER INFORMATION: Human NME7 b (optimized for E coli expression)

<400> SEQUENCE: 156

| | | |
|---|---|---|
| atgcatgacg ttaaaaatca ccgtaccttt ctgaaacgca cgaaatatga taatctgcat | 60 |
| ctggaagacc tgtttattgg caacaaagtc aatgtgttct ctcgtcagct ggtgctgatc | 120 |
| gattatggcg accagtacac cgcgcgtcaa ctgggtagtc gcaaagaaaa aacgctggcc | 180 |
| ctgattaaac cggatgcaat ctccaaagct ggcgaaatta tcgaaattat caacaaagcg | 240 |
| ggtttcacca tcacgaaact gaaaatgatg atgctgagcc gtaaagaagc cctggatttt | 300 |
| catgtcgacc accagtctcg cccgtttttc aatgaactga ttcaattcat caccacgggt | 360 |
| ccgattatcg caatggaaat tctgcgtgat gacgctatct gcgaatggaa acgcctgctg | 420 |
| ggcccggcaa actcaggtgt tgcgcgtacc gatgccagtg aatccattcg cgtctctgttt | 480 |
| ggcaccgatg gtatccgtaa tgcagcacat ggtccggact cattcgcatc ggcagctcgt | 540 |
| gaaatggaac tgttttttccc gagctctggc ggttgcggtc cggcaaacac cgccaaattt | 600 |
| accaattgta cgtgctgtat tgtcaaaccg cacgcagtgt cagaaggcct gctgggtaaa | 660 |
| attctgatgg caatccgtga tgctggcttt gaaatctcgg ccatgcagat gttcaacatg | 720 |
| gaccgcgtta acgtcgaaga attctacgaa gtttacaaag gcgtggttac cgaatatcac | 780 |
| gatatggtta cggaaatgta ctccggtccg tgcgtcgcga tggaaattca gcaaacaat | 840 |
| gccaccaaaa cgtttcgtga attctgtggt ccggcagatc cggaaatcgc acgtcatctg | 900 |
| cgtccgggta ccctgcgcgc aattttttggt aaaacgaaaa tccagaacgc tgtgcactgt | 960 |
| accgatctgc cggaagacgg tctgctggaa gttcaatact ttttcaaaat tctggataat | 1020 |

<210> SEQ ID NO 157
<211> LENGTH: 342
<212> TYPE: PRT
<213> ORGANISM: Artificial Sequence
<220> FEATURE:
<223> OTHER INFORMATION: Human NME7 b (optimized for E coli expression)

<400> SEQUENCE: 157

```
Met His Asp Val Lys Asn His Arg Thr Phe Leu Lys Arg Thr Lys Tyr
1               5                   10                  15

Asp Asn Leu His Leu Glu Asp Leu Phe Ile Gly Asn Lys Val Asn Val
            20                  25                  30

Phe Ser Arg Gln Leu Val Leu Ile Asp Tyr Gly Asp Gln Tyr Thr Ala
            35                  40                  45

Arg Gln Leu Gly Ser Arg Lys Glu Lys Thr Leu Ala Leu Ile Lys Pro
        50                  55                  60

Asp Ala Ile Ser Lys Ala Gly Glu Ile Ile Glu Ile Asn Lys Ala
65                  70                  75                  80

Gly Phe Thr Ile Thr Lys Leu Lys Met Met Met Leu Ser Arg Lys Glu
                    85                  90                  95

Ala Leu Asp Phe His Val Asp His Gln Ser Arg Pro Phe Phe Asn Glu
                100                 105                 110

Leu Ile Gln Phe Ile Thr Thr Gly Pro Ile Ile Ala Met Glu Ile Leu
            115                 120                 125

Arg Asp Asp Ala Ile Cys Glu Trp Lys Arg Leu Leu Gly Pro Ala Asn
130                 135                 140

Ser Gly Val Ala Arg Thr Asp Ala Ser Glu Ser Ile Arg Ala Leu Phe
145                 150                 155                 160

Gly Thr Asp Gly Ile Arg Asn Ala Ala His Gly Pro Asp Ser Phe Ala
                165                 170                 175

Ser Ala Ala Arg Glu Met Glu Leu Phe Phe Pro Ser Ser Gly Gly Cys
                180                 185                 190

Gly Pro Ala Asn Thr Ala Lys Phe Thr Asn Cys Thr Cys Cys Ile Val
            195                 200                 205

Lys Pro His Ala Val Ser Glu Gly Leu Leu Gly Lys Ile Leu Met Ala
210                 215                 220

Ile Arg Asp Ala Gly Phe Glu Ile Ser Ala Met Gln Met Phe Asn Met
225                 230                 235                 240

Asp Arg Val Asn Val Glu Glu Phe Tyr Glu Val Tyr Lys Gly Val Val
                245                 250                 255

Thr Glu Tyr His Asp Met Val Thr Glu Met Tyr Ser Gly Pro Cys Val
                260                 265                 270

Ala Met Glu Ile Gln Gln Asn Asn Ala Thr Lys Thr Phe Arg Glu Phe
            275                 280                 285

Cys Gly Pro Ala Asp Pro Glu Ile Ala Arg His Leu Arg Pro Gly Thr
            290                 295                 300

Leu Arg Ala Ile Phe Gly Lys Thr Lys Ile Gln Asn Ala Val His Cys
305                 310                 315                 320

Thr Asp Leu Pro Glu Asp Gly Leu Leu Glu Val Gln Tyr Phe Phe Lys
                325                 330                 335

Ile Leu Asp Asn Thr Gly
                340
```

<210> SEQ ID NO 158
<211> LENGTH: 858
<212> TYPE: DNA
<213> ORGANISM: Artificial Sequence
<220> FEATURE:
<223> OTHER INFORMATION: Human NME7-AB also known as NME7AB (optimized for E coli expression)

<400> SEQUENCE: 158
atggaaaaaa cgctggccct gattaaaccg gatgcaatct ccaaagctgg cgaaattatc     60

```
gaaattatca acaaagcggg tttcaccatc acgaaactga aaatgatgat gctgagccgt    120
aaagaagccc tggattttca tgtcgaccac cagtctcgcc cgttttttcaa tgaactgatt    180 caattcatca ccacgggtcc gattatcgca atggaaattc tgcgtgatga cgctatctgc    240
gaatggaaac gcctgctggg cccggcaaac tcaggtgttg cgcgtaccga tgccagtgaa    300
tccattcgcg ctctgtttgg caccgatggt atccgtaatg cagcacatgg tccggactca    360
ttcgcatcgg cagctcgtga atggaactg ttttcccga gctctggcgg ttgcggtccg    420
gcaaacaccg ccaaatttac caattgtacg tgctgtattg tcaaaccgca cgcagtgtca    480
gaaggcctgc tgggtaaaat tctgatggca atccgtgatg ctggctttga aatctcggcc    540
atgcagatgt tcaacatgga ccgcgttaac gtcgaagaat ctacgaagt ttacaaaggc    600 gtggttaccg aatatcacga tatggttacg gaaatgtact ccggtccgtg cgtcgcgatg    660
gaaattcagc aaaacaatgc caccaaaacg tttcgtgaat tctgtggtcc ggcagatccg    720
gaaatcgcac gtcatctgcg tccgggtacc ctgcgcgcaa ttttggtaa aacgaaaatc    780 cagaacgctg tgcactgtac cgatctgccg gaagacggtc tgctggaagt tcaatacttt    840
ttcaaaattc tggataat                                                 858
```

<210> SEQ ID NO 159
<211> LENGTH: 288
<212> TYPE: PRT
<213> ORGANISM: Artificial Sequence
<220> FEATURE:
<223> OTHER INFORMATION: Human NME7-AB also known as NME7AB (optimized for E coli expression)

<400> SEQUENCE: 159

```
Met Glu Lys Thr Leu Ala Leu Ile Lys Pro Asp Ala Ile Ser Lys Ala
1               5                   10                  15

Gly Glu Ile Ile Glu Ile Ile Asn Lys Ala Gly Phe Thr Ile Thr Lys
            20                  25                  30

Leu Lys Met Met Met Leu Ser Arg Lys Glu Ala Leu Asp Phe His Val
        35                  40                  45

Asp His Gln Ser Arg Pro Phe Phe Asn Glu Leu Ile Gln Phe Ile Thr
    50                  55                  60

Thr Gly Pro Ile Ile Ala Met Glu Ile Leu Arg Asp Asp Ala Ile Cys
65                  70                  75                  80

Glu Trp Lys Arg Leu Leu Gly Pro Ala Asn Ser Gly Val Ala Arg Thr
                85                  90                  95

Asp Ala Ser Glu Ser Ile Arg Ala Leu Phe Gly Thr Asp Gly Ile Arg
            100                 105                 110

Asn Ala Ala His Gly Pro Asp Ser Phe Ala Ser Ala Ala Arg Glu Met
        115                 120                 125

Glu Leu Phe Phe Pro Ser Ser Gly Cys Gly Pro Ala Asn Thr Ala
    130                 135                 140

Lys Phe Thr Asn Cys Thr Cys Cys Ile Val Lys Pro His Ala Val Ser
145                 150                 155                 160

Glu Gly Leu Leu Gly Lys Ile Leu Met Ala Ile Arg Asp Ala Gly Phe
                165                 170                 175

Glu Ile Ser Ala Met Gln Met Phe Asn Met Asp Arg Val Asn Val Glu
            180                 185                 190

Glu Phe Tyr Glu Val Tyr Lys Gly Val Val Thr Glu Tyr His Asp Met
        195                 200                 205

Val Thr Glu Met Tyr Ser Gly Pro Cys Val Ala Met Glu Ile Gln Gln
```

Asn Asn Ala Thr Lys Thr Phe Arg Glu Phe Cys Gly Pro Ala Asp Pro
225                 230                 235                 240

Glu Ile Ala Arg His Leu Arg Pro Gly Thr Leu Arg Ala Ile Phe Gly
            245                 250                 255

Lys Thr Lys Ile Gln Asn Ala Val His Cys Thr Asp Leu Pro Glu Asp
                260                 265                 270

Gly Leu Leu Glu Val Gln Tyr Phe Phe Lys Ile Leu Asp Asn Thr Gly
        275                 280                 285

<210> SEQ ID NO 160
<211> LENGTH: 756
<212> TYPE: DNA
<213> ORGANISM: Artificial Sequence
<220> FEATURE:
<223> OTHER INFORMATION: Human NME7-X1 (optimized for E coli expression)

<400> SEQUENCE: 160
atgatgatgc tgagccgtaa agaagccctg gattttcatg tcgaccacca gtctcgcccg      60 ttttcaatg aactgattca attcatcacc acgggtccga ttatcgcaat ggaaattctg     120
cgtgatgacg ctatctgcga atggaaacgc ctgctgggcc cggcaaactc aggtgttgcg     180
cgtaccgatg ccagtgaatc cattcgcgct ctgtttggca ccgatggtat ccgtaatgca     240
gcacatggtc cggactcatt cgcatcggca gctcgtgaaa tggaactgtt tttcccgagc     300
tctggcggtt gcggtccggc aaacaccgcc aaatttacca attgtacgtg ctgtattgtc     360
aaaccgcacg cagtgtcaga aggcctgctg gtaaaattc tgatggcaat ccgtgatgct     420
ggctttgaaa tctcggccat gcagatgttc aacatggacc gcgttaacgt cgaagaattc     480
tacgaagttt acaaggcgt ggttaccgaa atcacgata tggttacgga aatgtactcc     540
ggtccgtgcg tcgcgatgga aattcagcaa acaatgcca ccaaaacgtt cgtgaattc     600 tgtggtccgg cagatccgga aatcgcacgt catctgcgtc cgggtaccct gcgcgcaatt     660
tttggtaaaa cgaaaatcca gaacgctgtg cactgtaccg atctgccgga agacggtctg     720
ctggaagttc aatacttttt caaaattctg gataat                              756

<210> SEQ ID NO 161
<211> LENGTH: 254
<212> TYPE: PRT
<213> ORGANISM: Artificial Sequence
<220> FEATURE:
<223> OTHER INFORMATION: Human NME7-X1 (optimized for E coli expression)

<400> SEQUENCE: 161

Met Met Met Leu Ser Arg Lys Glu Ala Leu Asp Phe His Val Asp His
1               5                   10                  15

Gln Ser Arg Pro Phe Phe Asn Glu Leu Ile Gln Phe Ile Thr Thr Gly
            20                  25                  30

Pro Ile Ile Ala Met Glu Ile Leu Arg Asp Asp Ala Ile Cys Glu Trp
        35                  40                  45

Lys Arg Leu Leu Gly Pro Ala Asn Ser Gly Val Ala Arg Thr Asp Ala
    50                  55                  60

Ser Glu Ser Ile Arg Ala Leu Phe Gly Thr Asp Gly Ile Arg Asn Ala
65                  70                  75                  80

Ala His Gly Pro Asp Ser Phe Ala Ser Ala Ala Arg Glu Met Glu Leu
                85                  90                  95

Phe Phe Pro Ser Ser Gly Gly Cys Gly Pro Ala Asn Thr Ala Lys Phe

```
                100             105             110
Thr Asn Cys Thr Cys Cys Ile Val Lys Pro His Ala Val Ser Glu Gly
            115             120             125
Leu Leu Gly Lys Ile Leu Met Ala Ile Arg Asp Ala Gly Phe Glu Ile
            130             135             140
Ser Ala Met Gln Met Phe Asn Met Asp Arg Val Asn Val Glu Glu Phe
145             150             155             160
Tyr Glu Val Tyr Lys Gly Val Val Thr Glu Tyr His Asp Met Val Thr
            165             170             175
Glu Met Tyr Ser Gly Pro Cys Val Ala Met Glu Ile Gln Gln Asn Asn
            180             185             190
Ala Thr Lys Thr Phe Arg Glu Phe Cys Gly Pro Ala Asp Pro Glu Ile
            195             200             205
Ala Arg His Leu Arg Pro Gly Thr Leu Arg Ala Ile Phe Gly Lys Thr
            210             215             220
Lys Ile Gln Asn Ala Val His Cys Thr Asp Leu Pro Glu Asp Gly Leu
225             230             235             240
Leu Glu Val Gln Tyr Phe Phe Lys Ile Leu Asp Asn Thr Gly
            245             250

<210> SEQ ID NO 162
<211> LENGTH: 91
<212> TYPE: PRT
<213> ORGANISM: Artificial Sequence
<220> FEATURE:
<223> OTHER INFORMATION: DM10 domain of NME7

<400> SEQUENCE: 162

Met Asn His Ser Glu Arg Phe Val Phe Ile Ala Glu Trp Tyr Asp Pro
1               5                   10                  15
Asn Ala Ser Leu Leu Arg Arg Tyr Glu Leu Leu Phe Tyr Pro Gly Asp
            20                  25                  30
Gly Ser Val Glu Met His Asp Val Lys Asn His Arg Thr Phe Leu Lys
            35                  40                  45
Arg Thr Lys Tyr Asp Asn Leu His Leu Glu Asp Leu Phe Ile Gly Asn
50                  55                  60
Lys Val Asn Val Phe Ser Arg Gln Leu Val Leu Ile Asp Tyr Gly Asp
65                  70                  75                  80
Gln Tyr Thr Ala Arg Gln Leu Gly Ser Arg Lys
            85                  90

<210> SEQ ID NO 163
<211> LENGTH: 43
<212> TYPE: PRT
<213> ORGANISM: Artificial Sequence
<220> FEATURE:
<223> OTHER INFORMATION: Fragment or variation of PSMGFR peptide

<400> SEQUENCE: 163

Ser Asn Ile Lys Phe Arg Pro Gly Ser Val Val Gln Leu Thr Leu
1               5                   10                  15
Ala Phe Arg Glu Gly Thr Ile Asn Val His Asp Val Glu Thr Gln Phe
            20                  25                  30
Asn Gln Tyr Lys Thr Glu Ala Ala Ser Arg Tyr
            35                  40

<210> SEQ ID NO 164
<211> LENGTH: 35
```

```
<212> TYPE: PRT
<213> ORGANISM: Artificial Sequence
<220> FEATURE:
<223> OTHER INFORMATION: Fragment or variation of PSMGFR peptide

<400> SEQUENCE: 164

Ser Val Val Gln Leu Thr Leu Ala Phe Arg Glu Gly Thr Ile Asn
1               5                   10                  15

Val His Asp Val Glu Thr Gln Phe Asn Gln Tyr Lys Thr Glu Ala Ala
            20                  25                  30

Ser Arg Tyr
        35

<210> SEQ ID NO 165
<211> LENGTH: 24
<212> TYPE: PRT
<213> ORGANISM: Artificial Sequence
<220> FEATURE:
<223> OTHER INFORMATION: Fragment or variation of PSMGFR peptide

<400> SEQUENCE: 165

Val Gln Leu Thr Leu Ala Phe Arg Glu Gly Thr Ile Asn Val His Asp
1               5                   10                  15

Val Glu Thr Gln Phe Asn Gln Tyr
            20

<210> SEQ ID NO 166
<211> LENGTH: 24
<212> TYPE: PRT
<213> ORGANISM: Artificial Sequence
<220> FEATURE:
<223> OTHER INFORMATION: Fragment or variation of PSMGFR peptide

<400> SEQUENCE: 166

Ser Asn Ile Lys Phe Arg Pro Gly Ser Val Val Gln Leu Thr Leu
1               5                   10                  15

Ala Phe Arg Glu Gly Thr Ile Asn
            20

<210> SEQ ID NO 167
<211> LENGTH: 38
<212> TYPE: PRT
<213> ORGANISM: Artificial Sequence
<220> FEATURE:
<223> OTHER INFORMATION: Fragment or variation of PSMGFR peptide

<400> SEQUENCE: 167

Ser Asn Ile Lys Phe Arg Pro Gly Ser Val Val Gln Leu Thr Leu
1               5                   10                  15

Ala Phe Arg Glu Gly Thr Ile Asn Val His Asp Val Glu Thr Gln Phe
            20                  25                  30

Asn Gln Tyr Lys Thr Glu
        35

<210> SEQ ID NO 168
<211> LENGTH: 45
<212> TYPE: PRT
<213> ORGANISM: Artificial Sequence
<220> FEATURE:
<223> OTHER INFORMATION: Fragment or variation of PSMGFR peptide

<400> SEQUENCE: 168

Val Gln Leu Thr Leu Ala Phe Arg Glu Gly Thr Ile Asn Val His Asp
1               5                   10                  15
```

Val Glu Thr Gln Phe Asn Gln Tyr Lys Thr Glu Ala Ala Ser Arg Tyr
            20                  25                  30

Asn Leu Thr Ile Ser Asp Val Ser Val Ser Asp Val Pro
            35                  40                  45

<210> SEQ ID NO 169
<211> LENGTH: 29
<212> TYPE: PRT
<213> ORGANISM: Artificial Sequence
<220> FEATURE:
<223> OTHER INFORMATION: Ser of NME7B peptide 3 (B domain)

<400> SEQUENCE: 169

Ala Ile Phe Gly Lys Thr Lys Ile Gln Asn Ala Val His Ser Thr Asp
1               5                   10                  15

Leu Pro Glu Asp Gly Leu Leu Glu Val Gln Tyr Phe Phe
            20                  25

<210> SEQ ID NO 170
<211> LENGTH: 35
<212> TYPE: PRT
<213> ORGANISM: Artificial Sequence
<220> FEATURE:
<223> OTHER INFORMATION: N-10 peptide

<400> SEQUENCE: 170

Gln Phe Asn Gln Tyr Lys Thr Glu Ala Ala Ser Arg Tyr Asn Leu Thr
1               5                   10                  15

Ile Ser Asp Val Ser Val Ser Asp Val Pro Phe Pro Phe Ser Ala Gln
            20                  25                  30

Ser Gly Ala
        35

<210> SEQ ID NO 171
<211> LENGTH: 35
<212> TYPE: PRT
<213> ORGANISM: Artificial Sequence
<220> FEATURE:
<223> OTHER INFORMATION: C-10 peptide

<400> SEQUENCE: 171

Gly Thr Ile Asn Val His Asp Val Glu Thr Gln Phe Asn Gln Tyr Lys
1               5                   10                  15

Thr Glu Ala Ala Ser Arg Tyr Asn Leu Thr Ile Ser Asp Val Ser Val
            20                  25                  30

Ser Asp Val
        35

<210> SEQ ID NO 172
<211> LENGTH: 119
<212> TYPE: PRT
<213> ORGANISM: Artificial Sequence
<220> FEATURE:
<223> OTHER INFORMATION: 8F9A5A1H heavy chain

<400> SEQUENCE: 172

Ile Gln Leu Val Gln Ser Gly Pro Glu Leu Lys Lys Pro Gly Glu Thr
1               5                   10                  15

Val Lys Ile Ser Cys Lys Ala Ser Gly Tyr Thr Phe Thr Asn Tyr Gly
            20                  25                  30

Met Asn Trp Val Lys Gln Ala Pro Gly Lys Gly Leu Lys Trp Met Gly
            35                  40                  45

Trp Ile Asn Thr Tyr Thr Gly Glu Pro Thr Tyr Val Asp Asp Phe Lys
    50                  55                  60

Gly Arg Phe Ala Phe Ser Leu Glu Thr Ser Ala Thr Thr Ala Tyr Leu
65                  70                  75                  80

Gln Ile Asn Asn Leu Lys Asn Glu Asp Thr Ser Thr Tyr Phe Cys Ala
                85                  90                  95

Arg Leu Arg Gly Ile Arg Pro Gly Pro Leu Ala Tyr Trp Gly Gln Gly
            100                 105                 110

Thr Leu Val Thr Val Ser Ala
            115

<210> SEQ ID NO 173
<211> LENGTH: 121
<212> TYPE: PRT
<213> ORGANISM: Artificial Sequence
<220> FEATURE:
<223> OTHER INFORMATION: 8F9A4A3H heavy chain

<400> SEQUENCE: 173

Val Gln Leu Gln Gln Ser Gly Pro Glu Leu Val Lys Pro Gly Ala Ser
1               5                   10                  15

Val Lys Ile Ser Cys Lys Thr Ser Gly Asn Thr Phe Thr Glu Tyr Thr
                20                  25                  30

Met His Trp Val Lys Gln Ser His Gly Lys Ser Leu Glu Trp Ile Gly
            35                  40                  45

Gly Phe Asn Pro Asn Asn Gly Val Thr Asn Tyr Asn Gln Lys Phe Lys
    50                  55                  60

Gly Lys Ala Thr Leu Thr Val Asp Lys Ser Ser Ser Thr Ala Tyr Met
65                  70                  75                  80

Glu Leu Arg Ser Leu Thr Ser Glu Asp Ser Ala Val Tyr Tyr Cys Ala
                85                  90                  95

Arg Arg Tyr Tyr His Ser Leu Tyr Val Phe Tyr Phe Asp Tyr Trp Gly
            100                 105                 110

Gln Gly Thr Thr Leu Thr Val Ser Ser
            115                 120

<210> SEQ ID NO 174
<211> LENGTH: 116
<212> TYPE: PRT
<213> ORGANISM: Artificial Sequence
<220> FEATURE:
<223> OTHER INFORMATION: 5D9E2B11H

<400> SEQUENCE: 174

Val Gln Leu Gln Gln Ser Gly Pro Asp Leu Val Lys Pro Gly Thr Ser
1               5                   10                  15

Val Lys Ile Ser Cys Lys Thr Ser Gly Asn Thr Phe Thr Glu Tyr Thr
                20                  25                  30

Met His Trp Val Lys Gln Ser His Gly Lys Ser Leu Glu Trp Ile Gly
            35                  40                  45

Gly Phe Asn Pro Asn Asn Gly Val Thr Asn Tyr Asn Gln Lys Phe Lys
    50                  55                  60

Gly Lys Ala Thr Leu Thr Val Asp Lys Ser Ser Ser Thr Ala Tyr Met
65                  70                  75                  80

Glu Leu Arg Ser Leu Thr Ser Glu Asp Ser Ala Val Tyr Tyr Cys Ala
                85                  90                  95

Arg Arg Tyr Tyr His Ser Thr Tyr Val Phe Tyr Phe Asp Ser Trp Gly 100                 105                 110

Gln Gly Thr Thr
        115

<210> SEQ ID NO 175
<211> LENGTH: 121
<212> TYPE: PRT
<213> ORGANISM: Artificial Sequence
<220> FEATURE:
<223> OTHER INFORMATION: 5D9E10E4H

<400> SEQUENCE: 175

Val Gln Leu Gln Gln Ser Gly Pro Asp Leu Val Lys Pro Gly Thr Ser
1               5                   10                  15

Val Lys Ile Ser Cys Lys Thr Ser Gly Asn Thr Phe Thr Glu Tyr Thr
            20                  25                  30

Met His Trp Val Lys Gln Ser His Gly Lys Ser Leu Glu Trp Ile Gly
        35                  40                  45

Gly Phe Asn Pro Asn Asn Gly Val Thr Asn Tyr Asn Gln Lys Phe Lys
    50                  55                  60

Gly Lys Ala Thr Leu Thr Val Asp Lys Ser Ser Ser Thr Ala Tyr Met
65                  70                  75                  80

Glu Leu Arg Ser Leu Thr Ser Glu Asp Ser Ala Val Tyr Tyr Cys Ala
                85                  90                  95

Arg Arg Tyr Tyr His Ser Thr Tyr Val Phe Tyr Phe Asp Ser Trp Gly
            100                 105                 110

Gln Gly Thr Thr Leu Thr Val Ser Ser
        115                 120

<210> SEQ ID NO 176
<211> LENGTH: 121
<212> TYPE: PRT
<213> ORGANISM: Artificial Sequence
<220> FEATURE:
<223> OTHER INFORMATION: 5D9G2C4H

<400> SEQUENCE: 176

Val Gln Leu Gln Gln Ser Gly Pro Asp Leu Val Lys Pro Gly Thr Ser
1               5                   10                  15

Val Lys Ile Ser Cys Lys Thr Ser Gly Asn Thr Phe Thr Glu Tyr Thr
            20                  25                  30

Met His Trp Val Lys Gln Ser His Gly Lys Ser Leu Glu Trp Ile Gly
        35                  40                  45

Gly Phe Asn Pro Asn Asn Gly Val Thr Asn Tyr Asn Gln Lys Phe Lys
    50                  55                  60

Gly Lys Ala Thr Leu Thr Val Asp Lys Ser Ser Ser Thr Ala Tyr Met
65                  70                  75                  80

Glu Leu Arg Ser Leu Thr Ser Glu Asp Ser Ala Val Tyr Tyr Cys Ala
                85                  90                  95

Arg Arg Tyr Tyr His Ser Thr Tyr Val Phe Tyr Phe Asp Ser Trp Gly
            100                 105                 110

Gln Gly Thr Thr Leu Thr Val Ser Ser
        115                 120

<210> SEQ ID NO 177
<211> LENGTH: 121
<212> TYPE: PRT
<213> ORGANISM: Artificial Sequence
<220> FEATURE:

<223> OTHER INFORMATION: 5F3A5D4H

<400> SEQUENCE: 177

Val Gln Leu Gln Gln Ser Gly Pro Asp Leu Val Lys Pro Gly Thr Ser
1               5                   10                  15

Val Lys Ile Ser Cys Lys Thr Ser Gly Asn Thr Phe Thr Glu Tyr Thr
            20                  25                  30

Met His Trp Val Lys Gln Ser His Gly Lys Ser Leu Glu Trp Ile Gly
        35                  40                  45

Gly Phe Asn Pro Asn Asn Gly Val Thr Asn Tyr Asn Gln Lys Phe Lys
    50                  55                  60

Gly Lys Ala Thr Leu Thr Val Asp Lys Ser Ser Thr Ala Tyr Met
65                  70                  75                  80

Glu Leu Arg Ser Leu Thr Ser Glu Asp Ser Ala Val Tyr Tyr Cys Ala
                85                  90                  95

Arg Arg Tyr Tyr His Ser Thr Tyr Val Phe Tyr Phe Asp Ser Trp Gly
            100                 105                 110

Gln Gly Thr Thr Leu Thr Val Ser Ser
        115                 120

<210> SEQ ID NO 178
<211> LENGTH: 121
<212> TYPE: PRT
<213> ORGANISM: Artificial Sequence
<220> FEATURE:
<223> OTHER INFORMATION: 8H5H5G4H

<400> SEQUENCE: 178

Val Gln Leu Gln Gln Ser Gly Pro Asp Leu Val Lys Pro Gly Thr Ser
1               5                   10                  15

Val Lys Ile Ser Cys Lys Thr Ser Gly Asn Thr Phe Thr Glu Tyr Thr
            20                  25                  30

Met His Trp Val Lys Gln Ser His Gly Lys Ser Leu Glu Trp Ile Gly
        35                  40                  45

Gly Phe Asn Pro Asn Asn Gly Val Thr Asn Tyr Asn Gln Lys Phe Lys
    50                  55                  60

Gly Lys Ala Thr Leu Thr Val Asp Lys Ser Ser Ser Thr Ala Tyr Met
65                  70                  75                  80

Glu Leu Arg Ser Leu Thr Ser Glu Asp Ser Ala Val Tyr Tyr Cys Ala
                85                  90                  95

Arg Arg Tyr Tyr His Ser Thr Tyr Val Phe Tyr Phe Asp Ser Trp Gly
            100                 105                 110

Gln Gly Thr Thr Leu Thr Val Ser Ser
        115                 120

<210> SEQ ID NO 179
<211> LENGTH: 121
<212> TYPE: PRT
<213> ORGANISM: Artificial Sequence
<220> FEATURE:
<223> OTHER INFORMATION: 8F9A4A3H

<400> SEQUENCE: 179

Val Gln Leu Gln Gln Ser Gly Pro Glu Leu Val Lys Pro Gly Ala Ser
1               5                   10                  15

Val Lys Ile Ser Cys Lys Thr Ser Gly Asn Thr Phe Thr Glu Tyr Thr
            20                  25                  30

Met His Trp Val Lys Gln Ser His Gly Lys Ser Leu Glu Trp Ile Gly

```
                35                  40                  45
Gly Phe Asn Pro Asn Asn Gly Val Thr Asn Tyr Asn Gln Lys Phe Lys
 50                  55                  60

Gly Lys Ala Thr Leu Thr Val Asp Lys Ser Ser Ser Thr Ala Tyr Met
 65                  70                  75                  80

Glu Leu Arg Ser Leu Thr Ser Glu Asp Ser Ala Val Tyr Tyr Cys Ala
                 85                  90                  95

Arg Arg Tyr Tyr His Ser Leu Tyr Val Phe Tyr Phe Asp Tyr Trp Gly
                100                 105                 110

Gln Gly Thr Thr Leu Thr Val Ser Ser
            115                 120
```

<210> SEQ ID NO 180
<211> LENGTH: 116
<212> TYPE: PRT
<213> ORGANISM: Artificial Sequence
<220> FEATURE:
<223> OTHER INFORMATION: 5D9E2B11H

<400> SEQUENCE: 180

```
Val Gln Leu Gln Gln Ser Gly Pro Asp Leu Val Lys Pro Gly Thr Ser
 1               5                  10                  15

Val Lys Ile Ser Cys Lys Thr Ser Gly Asn Thr Phe Thr Glu Tyr Thr
             20                  25                  30

Met His Trp Val Lys Gln Ser His Gly Lys Ser Leu Glu Trp Ile Gly
         35                  40                  45

Gly Phe Asn Pro Asn Asn Gly Val Thr Asn Tyr Asn Gln Lys Phe Lys
 50                  55                  60

Gly Lys Ala Thr Leu Thr Val Asp Lys Ser Ser Ser Thr Ala Tyr Met
 65                  70                  75                  80

Glu Leu Arg Ser Leu Thr Ser Glu Asp Ser Ala Val Tyr Tyr Cys Ala
                 85                  90                  95

Arg Arg Tyr Tyr His Ser Thr Tyr Val Phe Tyr Phe Asp Ser Trp Gly
                100                 105                 110

Gln Gly Thr Thr
            115
```

<210> SEQ ID NO 181
<211> LENGTH: 121
<212> TYPE: PRT
<213> ORGANISM: Artificial Sequence
<220> FEATURE:
<223> OTHER INFORMATION: 5D9E10E4H

<400> SEQUENCE: 181

```
Val Gln Leu Gln Gln Ser Gly Pro Asp Leu Val Lys Pro Gly Thr Ser
 1               5                  10                  15

Val Lys Ile Ser Cys Lys Thr Ser Gly Asn Thr Phe Thr Glu Tyr Thr
             20                  25                  30

Met His Trp Val Lys Gln Ser His Gly Lys Ser Leu Glu Trp Ile Gly
         35                  40                  45

Gly Phe Asn Pro Asn Asn Gly Val Thr Asn Tyr Asn Gln Lys Phe Lys
 50                  55                  60

Gly Lys Ala Thr Leu Thr Val Asp Lys Ser Ser Ser Thr Ala Tyr Met
 65                  70                  75                  80

Glu Leu Arg Ser Leu Thr Ser Glu Asp Ser Ala Val Tyr Tyr Cys Ala
                 85                  90                  95
```

```
Arg Arg Tyr Tyr His Ser Thr Tyr Val Phe Tyr Phe Asp Ser Trp Gly
            100                 105                 110

Gln Gly Thr Thr Leu Thr Val Ser Ser
        115                 120

<210> SEQ ID NO 182
<211> LENGTH: 121
<212> TYPE: PRT
<213> ORGANISM: Artificial Sequence
<220> FEATURE:
<223> OTHER INFORMATION: 5D9G2C4H

<400> SEQUENCE: 182

Val Gln Leu Gln Gln Ser Gly Pro Asp Leu Val Lys Pro Gly Thr Ser
1               5                   10                  15

Val Lys Ile Ser Cys Lys Thr Ser Gly Asn Thr Phe Thr Glu Tyr Thr
            20                  25                  30

Met His Trp Val Lys Gln Ser His Gly Lys Ser Leu Glu Trp Ile Gly
        35                  40                  45

Gly Phe Asn Pro Asn Asn Gly Val Thr Asn Tyr Asn Gln Lys Phe Lys
    50                  55                  60

Gly Lys Ala Thr Leu Thr Val Asp Lys Ser Ser Ser Thr Ala Tyr Met
65                  70                  75                  80

Glu Leu Arg Ser Leu Thr Ser Glu Asp Ser Ala Val Tyr Tyr Cys Ala
                85                  90                  95

Arg Arg Tyr Tyr His Ser Thr Tyr Val Phe Tyr Phe Asp Ser Trp Gly
            100                 105                 110

Gln Gly Thr Thr Leu Thr Val Ser Ser
        115                 120

<210> SEQ ID NO 183
<211> LENGTH: 121
<212> TYPE: PRT
<213> ORGANISM: Artificial Sequence
<220> FEATURE:
<223> OTHER INFORMATION: 5F3A5D4H

<400> SEQUENCE: 183

Val Gln Leu Gln Gln Ser Gly Pro Asp Leu Val Lys Pro Gly Thr Ser
1               5                   10                  15

Val Lys Ile Ser Cys Lys Thr Ser Gly Asn Thr Phe Thr Glu Tyr Thr
            20                  25                  30

Met His Trp Val Lys Gln Ser His Gly Lys Ser Leu Glu Trp Ile Gly
        35                  40                  45

Gly Phe Asn Pro Asn Asn Gly Val Thr Asn Tyr Asn Gln Lys Phe Lys
    50                  55                  60

Gly Lys Ala Thr Leu Thr Val Asp Lys Ser Ser Ser Thr Ala Tyr Met
65                  70                  75                  80

Glu Leu Arg Ser Leu Thr Ser Glu Asp Ser Ala Val Tyr Tyr Cys Ala
                85                  90                  95

Arg Arg Tyr Tyr His Ser Thr Tyr Val Phe Tyr Phe Asp Ser Trp Gly
            100                 105                 110

Gln Gly Thr Thr Leu Thr Val Ser Ser
        115                 120

<210> SEQ ID NO 184
<211> LENGTH: 121
<212> TYPE: PRT
<213> ORGANISM: Artificial Sequence
```

```
<220> FEATURE:
<223> OTHER INFORMATION: 8H5H5G4H

<400> SEQUENCE: 184

Val Gln Leu Gln Gln Ser Gly Pro Asp Leu Val Lys Pro Gly Thr Ser
1               5                   10                  15

Val Lys Ile Ser Cys Lys Thr Ser Gly Asn Thr Phe Thr Glu Tyr Thr
            20                  25                  30

Met His Trp Val Lys Gln Ser His Gly Lys Ser Leu Glu Trp Ile Gly
        35                  40                  45

Gly Phe Asn Pro Asn Asn Gly Val Thr Asn Tyr Asn Gln Lys Phe Lys
    50                  55                  60

Gly Lys Ala Thr Leu Thr Val Asp Lys Ser Ser Ser Thr Ala Tyr Met
65                  70                  75                  80

Glu Leu Arg Ser Leu Thr Ser Glu Asp Ser Ala Val Tyr Tyr Cys Ala
                85                  90                  95

Arg Arg Tyr Tyr His Ser Thr Tyr Val Phe Tyr Phe Asp Ser Trp Gly
            100                 105                 110

Gln Gly Thr Thr Leu Thr Val Ser Ser
        115                 120

<210> SEQ ID NO 185
<211> LENGTH: 108
<212> TYPE: PRT
<213> ORGANISM: Artificial Sequence
<220> FEATURE:
<223> OTHER INFORMATION: 8F9A4A3L

<400> SEQUENCE: 185

Glu Thr Thr Val Thr Gln Ser Pro Ala Ser Leu Ser Met Ala Ile Gly
1               5                   10                  15

Glu Lys Val Thr Ile Arg Cys Ile Thr Ser Thr Asp Ile Asp Asp Asp
            20                  25                  30

Met Asn Trp Tyr Gln Gln Lys Pro Gly Glu Pro Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Pro Leu
                85                  90                  95

Thr Phe Gly Ser Gly Thr Lys Leu Glu Ile Lys Arg
            100                 105

<210> SEQ ID NO 186
<211> LENGTH: 108
<212> TYPE: PRT
<213> ORGANISM: Artificial Sequence
<220> FEATURE:
<223> OTHER INFORMATION: 5D9E2B11L

<400> SEQUENCE: 186

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Phe Gln Gln Lys Pro Asp Gly Thr Ile Lys Leu Leu Ile
        35                  40                  45
```

-continued

```
Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Val Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Ile Lys Arg
            100                 105

<210> SEQ ID NO 187
<211> LENGTH: 108
<212> TYPE: PRT
<213> ORGANISM: Artificial Sequence
<220> FEATURE:
<223> OTHER INFORMATION: 5D9E10E4L

<400> SEQUENCE: 187

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
                20                  25                  30

Leu Asn Trp Phe Gln Gln Lys Pro Asp Gly Thr Ile Lys Leu Leu Ile
            35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Val Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Ile Lys Arg
            100                 105

<210> SEQ ID NO 188
<211> LENGTH: 108
<212> TYPE: PRT
<213> ORGANISM: Artificial Sequence
<220> FEATURE:
<223> OTHER INFORMATION: 5D9G2C4L

<400> SEQUENCE: 188

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
                20                  25                  30

Leu Asn Trp Phe Gln Gln Lys Pro Asp Gly Thr Ile Lys Leu Leu Ile
            35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Val Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Ile Lys Arg
            100                 105

<210> SEQ ID NO 189
<211> LENGTH: 108
<212> TYPE: PRT
<213> ORGANISM: Artificial Sequence
```

```
<220> FEATURE:
<223> OTHER INFORMATION: 5F3A5D4L

<400> SEQUENCE: 189

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Phe Gln Gln Lys Pro Asp Gly Thr Ile Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Val Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Ile Lys Arg
            100                 105

<210> SEQ ID NO 190
<211> LENGTH: 108
<212> TYPE: PRT
<213> ORGANISM: Artificial Sequence
<220> FEATURE:
<223> OTHER INFORMATION: 8H5H5G4L

<400> SEQUENCE: 190

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Phe Gln Gln Lys Pro Asp Gly Thr Ile Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Val Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Ile Lys Arg
            100                 105

<210> SEQ ID NO 191
<211> LENGTH: 107
<212> TYPE: PRT
<213> ORGANISM: Artificial Sequence
<220> FEATURE:
<223> OTHER INFORMATION: 8F9A5A1L

<400> SEQUENCE: 191

Glu Ile Leu Leu Thr Gln Ser Pro Ala Ile Ala Ala Ser Pro Gly
1               5                   10                  15

Glu Lys Val Thr Ile Thr Cys Ser Ala Ser Ser Ser Val Ser Tyr Met
            20                  25                  30

Asn Trp Tyr Gln Gln Lys Pro Gly Ser Ser Pro Lys Ile Trp Ile Tyr
        35                  40                  45

Gly Ile Ser Asn Leu Ala Ser Gly Val Pro Ala Arg Phe Ser Gly Ser
    50                  55                  60
```

Gly Ser Gly Thr Ser Phe Ser Phe Thr Ile Asn Ser Met Glu Ala Glu
65                  70                  75                  80

Asp Val Ala Thr Tyr Tyr Cys Gln Gln Arg Ser Ser Tyr Pro Pro Thr
                85                  90                  95

Phe Gly Gly Gly Thr Lys Leu Glu Ile Lys Arg
            100                 105

<210> SEQ ID NO 192
<211> LENGTH: 108
<212> TYPE: PRT
<213> ORGANISM: Artificial Sequence
<220> FEATURE:
<223> OTHER INFORMATION: 5D9E2B11L

<400> SEQUENCE: 192

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
                20                  25                  30

Leu Asn Trp Phe Gln Gln Lys Pro Asp Gly Thr Ile Lys Leu Leu Ile
            35                  40                  45

Tyr Tyr Thr Ser Ser Leu His Ser Gly Val Pro Ser Arg Phe Ser Gly
50                  55                  60

Ser Gly Ser Gly Thr Asp Tyr Ser Leu Thr Ile Ser Asn Val Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Ile Lys Arg
            100                 105

<210> SEQ ID NO 193
<211> LENGTH: 108
<212> TYPE: PRT
<213> ORGANISM: Artificial Sequence
<220> FEATURE:
<223> OTHER INFORMATION: 5D9E10E4L

<400> SEQUENCE: 193

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
                20                  25                  30

Leu Asn Trp Phe Gln Gln Lys Pro Asp Gly Thr Ile Lys Leu Leu Ile
            35                  40                  45

Tyr Tyr Thr Ser Ser Leu His Ser Gly Val Pro Ser Arg Phe Ser Gly
50                  55                  60

Ser Gly Ser Gly Thr Asp Tyr Ser Leu Thr Ile Ser Asn Val Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Ile Lys Arg
            100                 105

<210> SEQ ID NO 194
<211> LENGTH: 108
<212> TYPE: PRT
<213> ORGANISM: Artificial Sequence
<220> FEATURE:
<223> OTHER INFORMATION: 5D9G2C4L -continued

<400> SEQUENCE: 194

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Phe Gln Gln Lys Pro Asp Gly Thr Ile Lys Leu Leu Ile
        35                  40                  45

Tyr Tyr Thr Ser Ser Leu His Ser Gly Val Pro Ser Arg Phe Ser Gly
50                  55                  60

Ser Gly Ser Gly Thr Asp Tyr Ser Leu Thr Ile Ser Asn Val Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Ile Lys Arg
            100                 105

<210> SEQ ID NO 195
<211> LENGTH: 108
<212> TYPE: PRT
<213> ORGANISM: Artificial Sequence
<220> FEATURE:
<223> OTHER INFORMATION: 5F3A5D4L

<400> SEQUENCE: 195

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Phe Gln Gln Lys Pro Asp Gly Thr Ile Lys Leu Leu Ile
        35                  40                  45

Tyr Tyr Thr Ser Ser Leu His Ser Gly Val Pro Ser Arg Phe Ser Gly
50                  55                  60

Ser Gly Ser Gly Thr Asp Tyr Ser Leu Thr Ile Ser Asn Val Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Ile Lys Arg
            100                 105

<210> SEQ ID NO 196
<211> LENGTH: 108
<212> TYPE: PRT
<213> ORGANISM: Artificial Sequence
<220> FEATURE:
<223> OTHER INFORMATION: 8H5H5G4L

<400> SEQUENCE: 196

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Phe Gln Gln Lys Pro Asp Gly Thr Ile Lys Leu Leu Ile
        35                  40                  45

Tyr Tyr Thr Ser Ser Leu His Ser Gly Val Pro Ser Arg Phe Ser Gly
50                  55                  60

Ser Gly Ser Gly Thr Asp Tyr Ser Leu Thr Ile Ser Asn Val Glu Pro
65                  70                  75                  80

Glu Asp Ile Ala Thr Tyr Tyr Cys Gln Gln Tyr Ser Lys Leu Pro Tyr
            85                  90                  95

Thr Phe Gly Gly Gly Thr Lys Leu Glu Ile Lys Arg
            100                 105

<210> SEQ ID NO 197
<211> LENGTH: 108
<212> TYPE: PRT
<213> ORGANISM: Artificial Sequence
<220> FEATURE:
<223> OTHER INFORMATION: 8F9A4A3L

<400> SEQUENCE: 197

Glu Thr Thr Val Thr Gln Ser Pro Ala Ser Leu Ser Met Ala Ile Gly
1               5                   10                  15

Glu Lys Val Thr Ile Arg Cys Ile Thr Ser Thr Asp Ile Asp Asp Asp
            20                  25                  30

Met Asn Trp Tyr Gln Gln Lys Pro Gly Glu Pro Pro Lys Leu Leu Ile
            35                  40                  45

Ser Glu Gly Asn Thr Leu Arg Pro Gly Val Pro Ser Arg Phe Ser Ser
        50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Pro Leu
            85                  90                  95

Thr Phe Gly Ser Gly Thr Lys Leu Glu Ile Lys Arg
            100                 105

<210> SEQ ID NO 198
<211> LENGTH: 107
<212> TYPE: PRT
<213> ORGANISM: Artificial Sequence
<220> FEATURE:
<223> OTHER INFORMATION: 8F9A5A1L

<400> SEQUENCE: 198

Glu Ile Leu Leu Thr Gln Ser Pro Ala Ile Ala Ala Ser Pro Gly
1               5                   10                  15

Glu Lys Val Thr Ile Thr Cys Ser Ala Ser Ser Val Ser Tyr Met
            20                  25                  30

Asn Trp Tyr Gln Gln Lys Pro Gly Ser Ser Pro Lys Ile Trp Ile Tyr
            35                  40                  45

Gly Ile Ser Asn Leu Ala Ser Gly Val Pro Ala Arg Phe Ser Gly Ser
        50                  55                  60

Gly Ser Gly Thr Ser Phe Ser Phe Thr Ile Asn Ser Met Glu Ala Glu
65                  70                  75                  80

Asp Val Ala Thr Tyr Tyr Cys Gln Gln Arg Ser Ser Tyr Pro Pro Thr
            85                  90                  95

Phe Gly Gly Gly Thr Lys Leu Glu Ile Lys Arg
            100                 105

<210> SEQ ID NO 199
<211> LENGTH: 131
<212> TYPE: PRT
<213> ORGANISM: Artificial Sequence
<220> FEATURE:
<223> OTHER INFORMATION: NME7A partial sequence

<400> SEQUENCE: 199

Glu Lys Thr Leu Ala Leu Ile Lys Pro Asp Ala Ile Ser Lys Ala Gly

-continued

```
                1               5                  10                 15
            Glu Ile Ile Glu Ile Ile Asn Lys Ala Gly Phe Thr Ile Thr Lys Leu
                            20                 25                 30

Lys Met Met Met Leu Ser Arg Lys Glu Ala Leu Asp Phe His Val Asp
                        35                 40                 45

His Gln Ser Arg Pro Phe Phe Asn Glu Leu Ile Gln Phe Ile Thr Thr
                    50                 55                 60

Gly Pro Ile Ile Ala Met Glu Ile Leu Arg Asp Asp Ala Ile Cys Glu
             65                 70                 75                 80

Trp Lys Arg Leu Leu Gly Pro Ala Asn Ser Gly Val Ala Arg Thr Asp
                            85                 90                 95

Ala Ser Glu Ser Ile Arg Ala Leu Phe Gly Thr Asp Gly Ile Arg Asn
                        100                105                110

Ala Ala His Gly Pro Asp Ser Phe Ala Ser Ala Ala Arg Glu Met Glu
                    115                120                125

Leu Phe Phe
                    130
```

<210> SEQ ID NO 200
<211> LENGTH: 152
<212> TYPE: PRT
<213> ORGANISM: Artificial Sequence
<220> FEATURE:
<223> OTHER INFORMATION: NME2 partial sequence

<400> SEQUENCE: 200

```
            Met Ala Asn Leu Glu Arg Thr Phe Ile Ala Ile Lys Pro Asp Gly Val
             1               5                  10                 15

Gln Arg Gly Leu Val Gly Glu Ile Ile Lys Arg Phe Glu Gln Lys Gly
                            20                 25                 30

Phe Arg Leu Val Ala Met Lys Phe Leu Arg Ala Ser Glu Glu His Leu
                        35                 40                 45

Lys Gln His Tyr Ile Asp Leu Lys Asp Arg Pro Phe Phe Pro Gly Leu
                    50                 55                 60

Val Lys Tyr Met Asn Ser Gly Pro Val Val Ala Met Val Trp Glu Gly
             65                 70                 75                 80

Leu Asn Val Val Lys Thr Gly Arg Val Met Leu Gly Glu Thr Asn Pro
                            85                 90                 95

Ala Asp Ser Lys Pro Gly Thr Ile Arg Gly Asp Phe Cys Ile Gln Val
                        100                105                110

Gly Arg Asn Ile Ile His Gly Ser Asp Ser Val Lys Ser Ala Glu Lys
                    115                120                125

Glu Ile Ser Leu Trp Phe Lys Pro Glu Glu Leu Val Asp Tyr Lys Ser
                    130                135                140

Cys Ala His Asp Trp Val Tyr Glu
            145                 150
```

<210> SEQ ID NO 201
<211> LENGTH: 134
<212> TYPE: PRT
<213> ORGANISM: Artificial Sequence
<220> FEATURE:
<223> OTHER INFORMATION: NME7B partial sequence

<400> SEQUENCE: 201

```
            Asn Cys Thr Cys Cys Ile Val Lys Pro His Ala Val Ser Glu Gly Leu
             1               5                  10                 15
```

```
Leu Gly Lys Ile Leu Met Ala Ile Arg Asp Ala Gly Phe Glu Ile Ser
            20                  25                  30

Ala Met Gln Met Phe Asn Met Asp Arg Val Asn Val Glu Glu Phe Tyr
        35                  40                  45

Glu Val Tyr Lys Gly Val Val Thr Glu Tyr His Asp Met Val Thr Glu
 50                  55                  60

Met Tyr Ser Gly Pro Cys Val Ala Met Glu Ile Gln Gln Asn Asn Ala
 65                  70                  75                  80

Thr Lys Thr Phe Arg Glu Phe Cys Gly Pro Ala Asp Pro Glu Ile Ala
                85                  90                  95

Arg His Leu Arg Pro Gly Thr Leu Arg Ala Ile Phe Gly Lys Thr Lys
                100                 105                 110

Ile Gln Asn Ala Val His Cys Thr Asp Leu Pro Glu Asp Gly Leu Leu
            115                 120                 125

Glu Val Gln Tyr Phe Phe
        130

<210> SEQ ID NO 202
<211> LENGTH: 152
<212> TYPE: PRT
<213> ORGANISM: Artificial Sequence
<220> FEATURE:
<223> OTHER INFORMATION: NME2 partial sequence

<400> SEQUENCE: 202

Met Ala Asn Leu Glu Arg Thr Phe Ile Ala Ile Lys Pro Asp Gly Val
 1               5                   10                  15

Gln Arg Gly Leu Val Gly Glu Ile Ile Lys Arg Phe Glu Gln Lys Gly
            20                  25                  30

Phe Arg Leu Val Ala Met Lys Phe Leu Arg Ala Ser Glu Glu His Leu
        35                  40                  45

Lys Gln His Tyr Ile Asp Leu Lys Asp Arg Pro Phe Phe Pro Gly Leu
 50                  55                  60

Val Lys Tyr Met Asn Ser Gly Pro Val Val Ala Met Val Trp Glu Gly
 65                  70                  75                  80

Leu Asn Val Val Lys Thr Gly Arg Val Met Leu Gly Glu Thr Asn Pro
                85                  90                  95

Ala Asp Ser Lys Pro Gly Thr Ile Arg Gly Asp Phe Cys Ile Gln Val
                100                 105                 110

Gly Arg Asn Ile Ile His Gly Ser Asp Ser Val Lys Ser Ala Glu Lys
            115                 120                 125

Glu Ile Ser Leu Trp Phe Lys Pro Glu Glu Leu Val Asp Tyr Lys Ser
        130                 135                 140

Cys Ala His Asp Trp Val Tyr Glu
145                 150

<210> SEQ ID NO 203
<211> LENGTH: 131
<212> TYPE: PRT
<213> ORGANISM: Artificial Sequence
<220> FEATURE:
<223> OTHER INFORMATION: NME7A partial sequence

<400> SEQUENCE: 203

Glu Lys Thr Leu Ala Leu Ile Lys Pro Asp Ala Ile Ser Lys Ala Gly
 1               5                   10                  15

Glu Ile Ile Glu Ile Ile Asn Lys Ala Gly Phe Thr Ile Thr Lys Leu
            20                  25                  30
```

```
Lys Met Met Met Leu Ser Arg Lys Glu Ala Leu Asp Phe His Val Asp
            35                  40                  45

His Gln Ser Arg Pro Phe Phe Asn Glu Leu Ile Gln Phe Ile Thr Thr
    50                  55                  60

Gly Pro Ile Ile Ala Met Glu Ile Leu Arg Asp Asp Ala Ile Cys Glu
65                  70                  75                  80

Trp Lys Arg Leu Leu Gly Pro Ala Asn Ser Gly Val Ala Arg Thr Asp
                85                  90                  95

Ala Ser Glu Ser Ile Arg Ala Leu Phe Gly Thr Asp Gly Ile Arg Asn
                100                 105                 110

Ala Ala His Gly Pro Asp Ser Phe Ala Ser Ala Ala Arg Glu Met Glu
        115                 120                 125

Leu Phe Phe
    130

<210> SEQ ID NO 204
<211> LENGTH: 130
<212> TYPE: PRT
<213> ORGANISM: Artificial Sequence
<220> FEATURE:
<223> OTHER INFORMATION: NME3 partial sequence

<400> SEQUENCE: 204

Glu Arg Thr Phe Leu Ala Val Lys Pro Asp Gly Val Gln Arg Arg Leu
1               5                   10                  15

Val Gly Glu Ile Val Arg Arg Phe Glu Arg Lys Gly Phe Lys Leu Val
                20                  25                  30

Ala Leu Lys Leu Val Gln Ala Ser Glu Glu Leu Leu Arg Glu His Tyr
            35                  40                  45

Val Glu Leu Arg Glu Arg Pro Phe Tyr Ser Arg Leu Val Lys Tyr Met
    50                  55                  60

Gly Ser Gly Pro Val Val Ala Met Val Trp Gln Gly Leu Asp Val Val
65                  70                  75                  80

Arg Ala Ser Arg Ala Leu Ile Gly Ala Thr Asp Pro Gly Asp Ala Thr
                85                  90                  95

Pro Gly Thr Ile Arg Gly Asp Phe Cys Val Glu Val Gly Lys Asn Val
                100                 105                 110

Ile His Gly Ser Asp Ser Val Glu Ser Ala Gln Arg Glu Ile Ala Leu
        115                 120                 125

Trp Phe
    130

<210> SEQ ID NO 205
<211> LENGTH: 134
<212> TYPE: PRT
<213> ORGANISM: Artificial Sequence
<220> FEATURE:
<223> OTHER INFORMATION: NME7B partial sequence

<400> SEQUENCE: 205

Asn Cys Thr Cys Cys Ile Val Lys Pro His Ala Val Ser Glu Gly Leu
1               5                   10                  15

Leu Gly Lys Ile Leu Met Ala Ile Arg Asp Ala Gly Phe Glu Ile Ser
                20                  25                  30

Ala Met Gln Met Phe Asn Met Asp Arg Val Asn Val Glu Glu Phe Tyr
            35                  40                  45

Glu Val Tyr Lys Gly Val Val Thr Glu Tyr His Asp Met Val Thr Glu
```

```
                    50                  55                  60
Met Tyr Ser Gly Pro Cys Val Ala Met Glu Ile Gln Gln Asn Asn Ala
 65                  70                  75                  80

Thr Lys Thr Phe Arg Glu Phe Cys Gly Pro Ala Asp Pro Glu Ile Ala
                     85                  90                  95

Arg His Leu Arg Pro Gly Thr Leu Arg Ala Ile Phe Gly Lys Thr Lys
                    100                 105                 110

Ile Gln Asn Ala Val His Cys Thr Asp Leu Pro Glu Asp Gly Leu Leu
                    115                 120                 125

Glu Val Gln Tyr Phe Phe
                    130

<210> SEQ ID NO 206
<211> LENGTH: 169
<212> TYPE: PRT
<213> ORGANISM: Artificial Sequence
<220> FEATURE:
<223> OTHER INFORMATION: NME3 partial sequence

<400> SEQUENCE: 206

Met Ile Cys Leu Val Leu Thr Ile Phe Ala Asn Leu Phe Pro Ser Ala
  1               5                  10                  15

Tyr Ser Gly Val Asn Glu Arg Thr Phe Leu Ala Val Lys Pro Asp Gly
                 20                  25                  30

Val Gln Arg Arg Leu Val Gly Glu Ile Val Arg Arg Phe Glu Arg Lys
             35                  40                  45

Gly Phe Lys Leu Val Ala Leu Lys Leu Val Gln Ala Ser Glu Glu Leu
 50                  55                  60

Leu Arg Glu His Tyr Val Glu Leu Arg Glu Arg Pro Phe Tyr Ser Arg
 65                  70                  75                  80

Leu Val Lys Tyr Met Gly Ser Gly Pro Val Val Ala Met Val Trp Gln
                 85                  90                  95

Gly Leu Asp Val Val Arg Ala Ser Arg Ala Leu Ile Gly Ala Thr Asp
            100                 105                 110

Pro Gly Asp Ala Thr Pro Gly Thr Ile Arg Gly Asp Phe Cys Val Glu
            115                 120                 125

Val Gly Lys Asn Val Ile His Gly Ser Asp Ser Val Glu Ser Ala Gln
130                 135                 140

Arg Glu Ile Ala Leu Trp Phe Arg Glu Asp Glu Leu Leu Cys Trp Glu
145                 150                 155                 160

Asp Ser Ala Gly His Trp Leu Tyr Glu
                165

<210> SEQ ID NO 207
<211> LENGTH: 131
<212> TYPE: PRT
<213> ORGANISM: Artificial Sequence
<220> FEATURE:
<223> OTHER INFORMATION: NME7A partial sequence

<400> SEQUENCE: 207

Glu Lys Thr Leu Ala Leu Ile Lys Pro Asp Ala Ile Ser Lys Ala Gly
  1               5                  10                  15

Glu Ile Ile Glu Ile Ile Asn Lys Ala Gly Phe Thr Ile Thr Lys Leu
                 20                  25                  30

Lys Met Met Met Leu Ser Arg Lys Glu Ala Leu Asp Phe His Val Asp
             35                  40                  45
```

-continued

His Gln Ser Arg Pro Phe Phe Asn Glu Leu Ile Gln Phe Ile Thr Thr
    50                  55                  60

Gly Pro Ile Ile Ala Met Glu Ile Leu Arg Asp Asp Ala Ile Cys Glu
65                  70                  75                  80

Trp Lys Arg Leu Leu Gly Pro Ala Asn Ser Gly Val Ala Arg Thr Asp
                85                  90                  95

Ala Ser Glu Ser Ile Arg Ala Leu Phe Gly Thr Asp Gly Ile Arg Asn
            100                 105                 110

Ala Ala His Gly Pro Asp Ser Phe Ala Ser Ala Ala Arg Glu Met Glu
        115                 120                 125

Leu Phe Phe
    130

<210> SEQ ID NO 208
<211> LENGTH: 130
<212> TYPE: PRT
<213> ORGANISM: Artificial Sequence
<220> FEATURE:
<223> OTHER INFORMATION: NME4 partial sequence

<400> SEQUENCE: 208

Glu Arg Thr Leu Val Ala Val Lys Pro Asp Gly Val Gln Arg Arg Leu
1               5                   10                  15

Val Gly Asp Val Ile Gln Arg Phe Glu Arg Arg Gly Phe Thr Leu Val
                20                  25                  30

Gly Met Lys Met Leu Gln Ala Pro Glu Ser Val Leu Ala Glu His Tyr
            35                  40                  45

Gln Asp Leu Arg Arg Lys Pro Phe Tyr Pro Ala Leu Ile Arg Tyr Met
        50                  55                  60

Ser Ser Gly Pro Val Val Ala Met Val Trp Glu Gly Tyr Asn Val Val
65                  70                  75                  80

Arg Ala Ser Arg Ala Met Ile Gly His Thr Asp Ser Ala Glu Ala Ala
                85                  90                  95

Pro Gly Thr Ile Arg Gly Asp Phe Ser Val His Ile Ser Arg Asn Val
            100                 105                 110

Ile His Ala Ser Asp Ser Val Glu Gly Ala Gln Arg Glu Ile Gln Leu
        115                 120                 125

Trp Phe
    130

<210> SEQ ID NO 209
<211> LENGTH: 132
<212> TYPE: PRT
<213> ORGANISM: Artificial Sequence
<220> FEATURE:
<223> OTHER INFORMATION: NME7B partial sequence

<400> SEQUENCE: 209

Thr Cys Cys Ile Val Lys Pro His Ala Val Ser Glu Gly Leu Leu Gly
1               5                   10                  15

Lys Ile Leu Met Ala Ile Arg Asp Ala Gly Phe Glu Ile Ser Ala Met
                20                  25                  30

Gln Met Phe Asn Met Asp Arg Val Asn Val Glu Glu Phe Tyr Glu Val
            35                  40                  45

Tyr Lys Gly Val Val Thr Glu Tyr His Asp Met Val Thr Glu Met Tyr
        50                  55                  60

Ser Gly Pro Cys Val Ala Met Glu Ile Gln Gln Asn Asn Ala Thr Lys
65                  70                  75                  80

```
Thr Phe Arg Glu Phe Cys Gly Pro Ala Asp Pro Glu Ile Ala Arg His
                 85                  90                  95

Leu Arg Pro Gly Thr Leu Arg Ala Ile Phe Gly Lys Thr Lys Ile Gln
            100                 105                 110

Asn Ala Val His Cys Thr Asp Leu Pro Glu Asp Gly Leu Leu Glu Val
            115                 120                 125

Gln Tyr Phe Phe
        130

<210> SEQ ID NO 210
<211> LENGTH: 128
<212> TYPE: PRT
<213> ORGANISM: Artificial Sequence
<220> FEATURE:
<223> OTHER INFORMATION: NME4 partial sequence

<400> SEQUENCE: 210

Thr Leu Val Ala Val Lys Pro Asp Gly Val Gln Arg Arg Leu Val Gly
1               5                   10                  15

Asp Val Ile Gln Arg Phe Glu Arg Arg Gly Phe Thr Leu Val Gly Met
            20                  25                  30

Lys Met Leu Gln Ala Pro Glu Ser Val Leu Ala Glu His Tyr Gln Asp
            35                  40                  45

Leu Arg Arg Lys Pro Phe Tyr Pro Ala Leu Ile Arg Tyr Met Ser Ser
        50                  55                  60

Gly Pro Val Val Ala Met Val Trp Glu Gly Tyr Asn Val Val Arg Ala
65                  70                  75                  80

Ser Arg Ala Met Ile Gly His Thr Asp Ser Ala Glu Ala Ala Pro Gly
                85                  90                  95

Thr Ile Arg Gly Asp Phe Ser Val His Ile Ser Arg Asn Val Ile His
            100                 105                 110

Ala Ser Asp Ser Val Glu Gly Ala Gln Arg Glu Ile Gln Leu Trp Phe
            115                 120                 125

<210> SEQ ID NO 211
<211> LENGTH: 131
<212> TYPE: PRT
<213> ORGANISM: Artificial Sequence
<220> FEATURE:
<223> OTHER INFORMATION: NME7A partial sequence

<400> SEQUENCE: 211

Glu Lys Thr Leu Ala Leu Ile Lys Pro Asp Ala Ile Ser Lys Ala Gly
1               5                   10                  15

Glu Ile Ile Glu Ile Ile Asn Lys Ala Gly Phe Thr Ile Thr Lys Leu
            20                  25                  30

Lys Met Met Met Leu Ser Arg Lys Glu Ala Leu Asp Phe His Val Asp
            35                  40                  45

His Gln Ser Arg Pro Phe Phe Asn Glu Leu Ile Gln Phe Ile Thr Thr
        50                  55                  60

Gly Pro Ile Ile Ala Met Glu Ile Leu Arg Asp Asp Ala Ile Cys Glu
65                  70                  75                  80

Trp Lys Arg Leu Leu Gly Pro Ala Asn Ser Gly Val Ala Arg Thr Asp
                85                  90                  95

Ala Ser Glu Ser Ile Arg Ala Leu Phe Gly Thr Asp Gly Ile Arg Asn
            100                 105                 110

Ala Ala His Gly Pro Asp Ser Phe Ala Ser Ala Ala Arg Glu Met Glu
```

```
                     115                 120                 125

Leu Phe Phe
    130

<210> SEQ ID NO 212
<211> LENGTH: 131
<212> TYPE: PRT
<213> ORGANISM: Artificial Sequence
<220> FEATURE:
<223> OTHER INFORMATION: NME5 partial sequence

<400> SEQUENCE: 212

Glu Lys Thr Leu Ala Ile Ile Lys Pro Asp Ile Val Asp Lys Glu Glu
1               5                   10                  15

Glu Ile Gln Asp Ile Ile Leu Arg Ser Gly Phe Thr Ile Val Gln Arg
            20                  25                  30

Arg Lys Leu Arg Leu Ser Pro Glu Gln Cys Ser Asn Phe Tyr Val Glu
        35                  40                  45

Lys Tyr Gly Lys Met Phe Phe Pro Asn Leu Thr Ala Tyr Met Ser Ser
    50                  55                  60

Gly Pro Leu Val Ala Met Ile Leu Ala Arg His Lys Ala Ile Ser Tyr
65                  70                  75                  80

Trp Leu Glu Leu Leu Gly Pro Asn Asn Ser Leu Val Ala Lys Glu Thr
                85                  90                  95

His Pro Asp Ser Leu Arg Ala Ile Tyr Gly Thr Asp Asp Leu Arg Asn
            100                 105                 110

Ala Leu His Gly Ser Asn Asp Phe Ala Ala Glu Arg Glu Ile Arg
        115                 120                 125

Phe Met Phe
    130

<210> SEQ ID NO 213
<211> LENGTH: 132
<212> TYPE: PRT
<213> ORGANISM: Artificial Sequence
<220> FEATURE:
<223> OTHER INFORMATION: NME7B partial sequence

<400> SEQUENCE: 213

Thr Cys Cys Ile Val Lys Pro His Ala Val Ser Glu Gly Leu Leu Gly
1               5                   10                  15

Lys Ile Leu Met Ala Ile Arg Asp Ala Gly Phe Glu Ile Ser Ala Met
            20                  25                  30

Gln Met Phe Asn Met Asp Arg Val Asn Val Glu Glu Phe Tyr Glu Val
        35                  40                  45

Tyr Lys Gly Val Val Thr Glu Tyr His Asp Met Val Thr Glu Met Tyr
    50                  55                  60

Ser Gly Pro Cys Val Ala Met Glu Ile Gln Gln Asn Asn Ala Thr Lys
65                  70                  75                  80

Thr Phe Arg Glu Phe Cys Gly Pro Ala Asp Pro Glu Ile Ala Arg His
                85                  90                  95

Leu Arg Pro Gly Thr Leu Arg Ala Ile Phe Gly Lys Thr Lys Ile Gln
            100                 105                 110

Asn Ala Val His Cys Thr Asp Leu Pro Glu Asp Gly Leu Leu Glu Val
        115                 120                 125

Gln Tyr Phe Phe
    130
```

-continued

<210> SEQ ID NO 214
<211> LENGTH: 129
<212> TYPE: PRT
<213> ORGANISM: Artificial Sequence
<220> FEATURE:
<223> OTHER INFORMATION: NME5 partial sequence

<400> SEQUENCE: 214

Thr Leu Ala Ile Ile Lys Pro Asp Ile Val Lys Glu Glu Glu Ile
1               5                   10                  15

Gln Asp Ile Ile Leu Arg Ser Gly Phe Thr Ile Val Gln Arg Lys
            20                  25                  30

Leu Arg Leu Ser Pro Glu Gln Cys Ser Asn Phe Tyr Val Glu Lys Tyr
        35                  40                  45

Gly Lys Met Phe Phe Pro Asn Leu Thr Ala Tyr Met Ser Ser Gly Pro
    50                  55                  60

Leu Val Ala Met Ile Leu Ala Arg His Lys Ala Ile Ser Tyr Trp Leu
65                  70                  75                  80

Glu Leu Leu Gly Pro Asn Asn Ser Leu Val Ala Lys Glu Thr His Pro
                85                  90                  95

Asp Ser Leu Arg Ala Ile Tyr Gly Thr Asp Leu Arg Asn Ala Leu
            100                 105                 110

His Gly Ser Asn Asp Phe Ala Ala Glu Arg Glu Ile Arg Phe Met
        115                 120                 125

Phe

<210> SEQ ID NO 215
<211> LENGTH: 129
<212> TYPE: PRT
<213> ORGANISM: Artificial Sequence
<220> FEATURE:
<223> OTHER INFORMATION: NME7A partial sequence

<400> SEQUENCE: 215

Thr Leu Ala Leu Ile Lys Pro Asp Ala Ile Ser Lys Ala Gly Glu Ile
1               5                   10                  15

Ile Glu Ile Ile Asn Lys Ala Gly Phe Thr Ile Thr Lys Leu Lys Met
            20                  25                  30

Met Met Leu Ser Arg Lys Glu Ala Leu Asp Phe His Val Asp His Gln
        35                  40                  45

Ser Arg Pro Phe Phe Asn Glu Leu Ile Gln Phe Ile Thr Thr Gly Pro
    50                  55                  60

Ile Ile Ala Met Glu Ile Leu Arg Asp Asp Ala Ile Cys Glu Trp Lys
65                  70                  75                  80

Arg Leu Leu Gly Pro Ala Asn Ser Gly Val Ala Arg Thr Asp Ala Ser
                85                  90                  95

Glu Ser Ile Arg Ala Leu Phe Gly Thr Asp Gly Ile Arg Asn Ala Ala
            100                 105                 110

His Gly Pro Asp Ser Phe Ala Ser Ala Ala Arg Glu Met Glu Leu Phe
        115                 120                 125

Phe

<210> SEQ ID NO 216
<211> LENGTH: 132
<212> TYPE: PRT
<213> ORGANISM: Artificial Sequence
<220> FEATURE:
<223> OTHER INFORMATION: NME6 partial sequence

<400> SEQUENCE: 216

Thr Leu Ala Leu Ile Lys Pro Asp Ala Val Ala His Pro Leu Ile Leu
1               5                   10                  15

Glu Ala Val His Gln Gln Ile Leu Ser Asn Lys Phe Leu Ile Val Arg
            20                  25                  30

Met Arg Glu Leu Leu Trp Arg Lys Glu Asp Cys Gln Arg Phe Tyr Arg
        35                  40                  45

Glu His Glu Gly Arg Phe Phe Tyr Gln Arg Leu Val Glu Phe Met Ala
    50                  55                  60

Ser Gly Pro Ile Arg Ala Tyr Ile Leu Ala His Lys Asp Ala Ile Gln
65                  70                  75                  80

Leu Trp Arg Thr Leu Met Gly Pro Thr Arg Val Phe Arg Ala Arg His
                85                  90                  95

Val Ala Pro Asp Ser Ile Arg Gly Ser Phe Gly Leu Thr Asp Thr Arg
            100                 105                 110

Asn Thr Thr His Gly Ser Asp Ser Val Val Ser Ala Ser Arg Glu Ile
        115                 120                 125

Ala Ala Phe Phe
    130

<210> SEQ ID NO 217
<211> LENGTH: 132
<212> TYPE: PRT
<213> ORGANISM: Artificial Sequence
<220> FEATURE:
<223> OTHER INFORMATION: NME7B partial sequence

<400> SEQUENCE: 217

Thr Cys Cys Ile Val Lys Pro His Ala Val Ser Glu Gly Leu Leu Gly
1               5                   10                  15

Lys Ile Leu Met Ala Ile Arg Asp Ala Gly Phe Glu Ile Ser Ala Met
            20                  25                  30

Gln Met Phe Asn Met Asp Arg Val Asn Val Glu Glu Phe Tyr Glu Val
        35                  40                  45

Tyr Lys Gly Val Val Thr Glu Tyr His Asp Met Val Thr Glu Met Tyr
    50                  55                  60

Ser Gly Pro Cys Val Ala Met Glu Ile Gln Gln Asn Asn Ala Thr Lys
65                  70                  75                  80

Thr Phe Arg Glu Phe Cys Gly Pro Ala Asp Pro Glu Ile Ala Arg His
                85                  90                  95

Leu Arg Pro Gly Thr Leu Arg Ala Ile Phe Gly Lys Thr Lys Ile Gln
            100                 105                 110

Asn Ala Val His Cys Thr Asp Leu Pro Glu Asp Gly Leu Leu Glu Val
        115                 120                 125

Gln Tyr Phe Phe
    130

<210> SEQ ID NO 218
<211> LENGTH: 132
<212> TYPE: PRT
<213> ORGANISM: Artificial Sequence
<220> FEATURE:
<223> OTHER INFORMATION: NME6 partial sequence

<400> SEQUENCE: 218

Thr Leu Ala Leu Ile Lys Pro Asp Ala Val Ala His Pro Leu Ile Leu
1               5                   10                  15

```
Glu Ala Val His Gln Gln Ile Leu Ser Asn Lys Phe Leu Ile Val Arg
            20                  25                  30

Met Arg Glu Leu Leu Trp Arg Lys Glu Asp Cys Gln Arg Phe Tyr Arg
        35                  40                  45

Glu His Glu Gly Arg Phe Phe Tyr Gln Arg Leu Val Glu Phe Met Ala
    50                  55                  60

Ser Gly Pro Ile Arg Ala Tyr Ile Leu Ala His Lys Asp Ala Ile Gln
65                  70                  75                  80

Leu Trp Arg Thr Leu Met Gly Pro Thr Arg Val Phe Arg Ala Arg His
                85                  90                  95

Val Ala Pro Asp Ser Ile Arg Gly Ser Phe Gly Leu Thr Asp Thr Arg
            100                 105                 110

Asn Thr Thr His Gly Ser Asp Ser Val Val Ser Ala Ser Arg Glu Ile
            115                 120                 125

Ala Ala Phe Phe
        130

<210> SEQ ID NO 219
<211> LENGTH: 131
<212> TYPE: PRT
<213> ORGANISM: Artificial Sequence
<220> FEATURE:
<223> OTHER INFORMATION: NME7A partial sequence

<400> SEQUENCE: 219

Glu Lys Thr Leu Ala Leu Ile Lys Pro Asp Ala Ile Ser Lys Ala Gly
1               5                   10                  15

Glu Ile Ile Glu Ile Ile Asn Lys Ala Gly Phe Thr Ile Thr Lys Leu
            20                  25                  30

Lys Met Met Met Leu Ser Arg Lys Glu Ala Leu Asp Phe His Val Asp
        35                  40                  45

His Gln Ser Arg Pro Phe Phe Asn Glu Leu Ile Gln Phe Ile Thr Thr
    50                  55                  60

Gly Pro Ile Ile Ala Met Glu Ile Leu Arg Asp Asp Ala Ile Cys Glu
65                  70                  75                  80

Trp Lys Arg Leu Leu Gly Pro Ala Asn Ser Gly Val Ala Arg Thr Asp
                85                  90                  95

Ala Ser Glu Ser Ile Arg Ala Leu Phe Gly Thr Asp Gly Ile Arg Asn
            100                 105                 110

Ala Ala His Gly Pro Asp Ser Phe Ala Ser Ala Ala Arg Glu Met Glu
            115                 120                 125

Leu Phe Phe
        130

<210> SEQ ID NO 220
<211> LENGTH: 133
<212> TYPE: PRT
<213> ORGANISM: Artificial Sequence
<220> FEATURE:
<223> OTHER INFORMATION: NME8 partial sequence

<400> SEQUENCE: 220

Glu Lys Thr Leu Ala Leu Leu Arg Pro Asn Leu Phe His Glu Arg Lys
1               5                   10                  15

Asp Asp Val Leu Arg Ile Ile Lys Asp Glu Asp Phe Lys Ile Leu Glu
            20                  25                  30

Gln Arg Gln Val Val Leu Ser Glu Lys Glu Ala Gln Ala Leu Cys Lys
```

```
            35                  40                  45
Glu Tyr Glu Asn Glu Asp Tyr Phe Asn Lys Leu Ile Glu Asn Met Thr
    50                  55                  60

Ser Gly Pro Ser Leu Ala Leu Val Leu Leu Arg Asp Asn Gly Leu Gln
65                  70                  75                  80

Tyr Trp Lys Gln Leu Leu Gly Pro Arg Thr Val Glu Glu Ala Ile Glu
                85                  90                  95

Tyr Phe Pro Glu Ser Leu Cys Ala Gln Phe Ala Met Asp Ser Leu Pro
            100                 105                 110

Val Asn Gln Leu Tyr Gly Ser Asp Ser Leu Glu Thr Ala Glu Arg Glu
                115                 120                 125

Ile Gln His Phe Phe
        130

<210> SEQ ID NO 221
<211> LENGTH: 127
<212> TYPE: PRT
<213> ORGANISM: Artificial Sequence
<220> FEATURE:
<223> OTHER INFORMATION: NME7B partial sequence

<400> SEQUENCE: 221

Glu Lys Thr Leu Ala Leu Ile Lys Pro Asp Ala Ile Ser Lys Ala Gly
1               5                   10                  15

Glu Ile Ile Glu Ile Ile Asn Lys Ala Gly Phe Thr Ile Thr Lys Leu
                20                  25                  30

Lys Met Met Met Leu Ser Arg Lys Glu Ala Leu Asp Phe His Val Asp
            35                  40                  45

His Gln Ser Arg Pro Phe Phe Asn Glu Leu Ile Gln Phe Ile Thr Thr
        50                  55                  60

Gly Pro Ile Ile Ala Met Glu Ile Leu Arg Asp Asp Ala Ile Cys Glu
65                  70                  75                  80

Trp Lys Arg Leu Leu Gly Pro Ala Asn Ser Gly Val Ala Arg Thr Asp
                85                  90                  95

Ala Ser Glu Ser Ile Arg Ala Leu Phe Gly Thr Asp Gly Ile Arg Asn
            100                 105                 110

Ala Ala His Gly Pro Asp Ser Phe Ala Ser Ala Arg Glu Met
        115                 120                 125

<210> SEQ ID NO 222
<211> LENGTH: 127
<212> TYPE: PRT
<213> ORGANISM: Artificial Sequence
<220> FEATURE:
<223> OTHER INFORMATION: NME8 partial sequence

<400> SEQUENCE: 222

Gln Ser Thr Leu Gly Leu Ile Lys Pro His Ala Thr Ser Glu Gln Arg
1               5                   10                  15

Glu Gln Ile Leu Lys Ile Val Lys Glu Ala Gly Phe Asp Leu Thr Gln
                20                  25                  30

Val Lys Lys Met Phe Leu Thr Pro Glu Gln Ile Glu Lys Ile Tyr Pro
            35                  40                  45

Lys Val Thr Gly Lys Asp Phe Tyr Lys Asp Leu Leu Glu Met Leu Ser
        50                  55                  60

Val Gly Pro Ser Met Val Met Ile Leu Thr Lys Trp Asn Ala Val Ala
65                  70                  75                  80
```

-continued

```
Glu Trp Arg Arg Leu Met Gly Pro Thr Asp Pro Glu Glu Ala Lys Leu
                 85                  90                  95

Leu Ser Pro Asp Ser Ile Arg Ala Gln Phe Gly Ile Ser Lys Leu Lys
            100                 105                 110

Asn Ile Val His Gly Ala Ser Asn Ala Tyr Glu Ala Lys Glu Val
        115                 120                 125

<210> SEQ ID NO 223
<211> LENGTH: 63
<212> TYPE: PRT
<213> ORGANISM: Artificial Sequence
<220> FEATURE:
<223> OTHER INFORMATION: NME7A partial sequence

<400> SEQUENCE: 223

Thr Leu Ala Leu Ile Lys Pro Asp Ala Ile Ser Lys Ala Gly Glu Ile
1               5                  10                  15

Ile Glu Ile Ile Asn Lys Ala Gly Phe Thr Ile Thr Lys Leu Lys Met
            20                  25                  30

Met Met Leu Ser Arg Lys Glu Ala Leu Asp Phe His Val Asp His Gln
        35                  40                  45

Ser Arg Pro Phe Phe Asn Glu Leu Ile Gln Phe Ile Thr Thr Gly
    50                  55                  60

<210> SEQ ID NO 224
<211> LENGTH: 65
<212> TYPE: PRT
<213> ORGANISM: Artificial Sequence
<220> FEATURE:
<223> OTHER INFORMATION: NME8 partial sequence

<400> SEQUENCE: 224

Ser Ile Ala Ile Ile Lys Pro Asp Ala Val Ile Ser Lys Lys Val Leu
1               5                  10                  15

Glu Ile Lys Arg Lys Ile Thr Lys Ala Gly Phe Ile Ile Glu Ala Glu
            20                  25                  30

His Lys Thr Val Leu Thr Glu Glu Gln Val Val Asn Phe Tyr Ser Arg
        35                  40                  45

Ile Ala Asp Gln Cys Asp Phe Glu Glu Phe Val Ser Phe Met Thr Ser
    50                  55                  60

Gly
65

<210> SEQ ID NO 225
<211> LENGTH: 116
<212> TYPE: PRT
<213> ORGANISM: Artificial Sequence
<220> FEATURE:
<223> OTHER INFORMATION: NME7B partial sequence

<400> SEQUENCE: 225

Thr Cys Cys Ile Val Lys Pro His Ala Val Ser Glu Gly Leu Leu Gly
1               5                  10                  15

Lys Ile Leu Met Ala Ile Arg Asp Ala Gly Phe Glu Ile Ser Ala Met
            20                  25                  30

Gln Met Phe Asn Met Asp Arg Val Asn Val Glu Glu Phe Tyr Glu Val
        35                  40                  45

Tyr Lys Gly Val Val Thr Glu Tyr His Asp Met Val Thr Glu Met Tyr
    50                  55                  60

Ser Gly Pro Cys Val Ala Met Glu Ile Gln Gln Asn Asn Ala Thr Lys
```

```
                65                  70                  75                  80
Thr Phe Arg Glu Phe Cys Gly Pro Ala Asp Pro Glu Ile Ala Arg His
                    85                  90                  95

Leu Arg Pro Gly Thr Leu Arg Ala Ile Phe Gly Lys Thr Lys Ile Gln
                100                 105                 110

Asn Ala Val His
            115

<210> SEQ ID NO 226
<211> LENGTH: 114
<212> TYPE: PRT
<213> ORGANISM: Artificial Sequence
<220> FEATURE:
<223> OTHER INFORMATION: NME8 partial sequence

<400> SEQUENCE: 226

Thr Leu Gly Leu Ile Lys Pro His Ala Thr Ser Glu Gln Arg Glu Gln
1               5                   10                  15

Ile Leu Lys Ile Val Lys Glu Ala Gly Phe Asp Leu Thr Gln Val Lys
                20                  25                  30

Lys Met Phe Leu Thr Pro Glu Gln Ile Glu Lys Ile Tyr Pro Lys Val
            35                  40                  45

Thr Gly Lys Asp Phe Tyr Lys Asp Leu Leu Glu Met Leu Ser Val Gly
        50                  55                  60

Pro Ser Met Val Met Ile Leu Thr Lys Trp Asn Ala Val Ala Glu Trp
65                  70                  75                  80

Arg Arg Leu Met Gly Pro Thr Asp Pro Glu Gly Ala Lys Leu Leu Ser
                85                  90                  95

Pro Asp Ser Ile Arg Ala Gln Phe Gly Ile Ser Lys Leu Lys Asn Ile
                100                 105                 110

Val His

<210> SEQ ID NO 227
<211> LENGTH: 115
<212> TYPE: PRT
<213> ORGANISM: Artificial Sequence
<220> FEATURE:
<223> OTHER INFORMATION: NME7A partial sequence

<400> SEQUENCE: 227

Ile Leu Met Ala Ile Arg Asp Ala Gly Phe Glu Ile Ser Ala Met Gln
1               5                   10                  15

Met Phe Asn Met Asp Arg Val Asn Val Glu Glu Phe Tyr Glu Val Tyr
                20                  25                  30

Lys Gly Val Val Thr Glu Tyr His Asp Met Val Thr Glu Met Tyr Ser
            35                  40                  45

Gly Pro Cys Val Ala Met Glu Ile Gln Gln Asn Asn Ala Thr Lys Thr
        50                  55                  60

Phe Arg Glu Phe Cys Gly Pro Ala Asp Pro Glu Ile Ala Arg His Leu
65                  70                  75                  80

Arg Pro Gly Thr Leu Arg Ala Ile Phe Gly Lys Thr Lys Ile Gln Asn
                85                  90                  95

Ala Val His Cys Thr Asp Leu Pro Glu Asp Gly Leu Leu Glu Val Gln
                100                 105                 110

Tyr Phe Phe
        115
```

```
<210> SEQ ID NO 228
<211> LENGTH: 115
<212> TYPE: PRT
<213> ORGANISM: Artificial Sequence
<220> FEATURE:
<223> OTHER INFORMATION: NME8 partial sequence

<400> SEQUENCE: 228

Val Leu Arg Ile Ile Lys Asp Glu Asp Phe Lys Ile Leu Glu Gln Arg
1               5                   10                  15

Gln Val Val Leu Ser Glu Lys Glu Ala Gln Ala Leu Cys Lys Glu Tyr
                20                  25                  30

Glu Asn Glu Asp Tyr Phe Asn Lys Leu Ile Glu Asn Met Thr Ser Gly
            35                  40                  45

Pro Ser Leu Ala Leu Val Leu Leu Arg Asp Asn Gly Leu Gln Tyr Trp
        50                  55                  60

Lys Gln Leu Leu Gly Pro Arg Thr Val Glu Glu Ala Ile Glu Tyr Phe
65                  70                  75                  80

Pro Glu Ser Leu Cys Ala Gln Phe Ala Met Asp Ser Leu Pro Val Asn
                85                  90                  95

Gln Leu Tyr Gly Ser Asp Ser Leu Glu Thr Ala Glu Arg Glu Ile Gln
            100                 105                 110

His Phe Phe
        115

<210> SEQ ID NO 229
<211> LENGTH: 100
<212> TYPE: PRT
<213> ORGANISM: Artificial Sequence
<220> FEATURE:
<223> OTHER INFORMATION: NME7B partial sequence

<400> SEQUENCE: 229

Ile Val Lys Pro His Ala Val Ser Glu Gly Leu Leu Gly Lys Ile Leu
1               5                   10                  15

Met Ala Ile Arg Asp Ala Gly Phe Glu Ile Ser Ala Met Gln Met Phe
                20                  25                  30

Asn Met Asp Arg Val Asn Val Glu Glu Phe Tyr Glu Val Tyr Lys Gly
            35                  40                  45

Val Val Thr Glu Tyr His Asp Met Val Thr Glu Met Tyr Ser Gly Pro
        50                  55                  60

Cys Val Ala Met Glu Ile Gln Gln Asn Asn Ala Thr Lys Thr Phe Arg
65                  70                  75                  80

Glu Phe Cys Gly Pro Ala Asp Pro Glu Ile Ala Arg His Leu Arg Pro
                85                  90                  95

Gly Thr Leu Arg
            100

<210> SEQ ID NO 230
<211> LENGTH: 110
<212> TYPE: PRT
<213> ORGANISM: Artificial Sequence
<220> FEATURE:
<223> OTHER INFORMATION: NME8 partial sequence

<400> SEQUENCE: 230

Ile Ile Lys Pro Asp Ala Val Ile Ser Lys Lys Val Leu Glu Ile Lys
1               5                   10                  15

Arg Lys Ile Thr Lys Ala Gly Phe Ile Ile Glu Ala Glu His Lys Thr
                20                  25                  30
```

Val Leu Thr Glu Glu Gln Val Val Asn Phe Tyr Ser Arg Ile Ala Asp
            35                  40                  45

Gln Cys Asp Phe Glu Glu Phe Val Ser Phe Met Thr Ser Gly Leu Ser
        50                  55                  60

Tyr Ile Leu Val Val Ser Gln Gly Ser Lys His Asn Pro Pro Ser Glu
65                  70                  75                  80

Glu Thr Glu Pro Gln Thr Asp Thr Glu Pro Asn Glu Arg Ser Glu Asp
                85                  90                  95

Gln Pro Glu Val Glu Ala Gln Val Thr Pro Gly Met Met Lys
            100                 105                 110

<210> SEQ ID NO 231
<211> LENGTH: 174
<212> TYPE: PRT
<213> ORGANISM: Artificial Sequence
<220> FEATURE:
<223> OTHER INFORMATION: NME9

<400> SEQUENCE: 231

Met Leu Ser Ser Lys Gly Leu Thr Val Val Asp Val Tyr Gln Gly Trp
1               5                   10                  15

Cys Gly Pro Cys Lys Pro Val Val Ser Leu Phe Gln Lys Met Arg Ile
            20                  25                  30

Glu Val Gly Leu Asp Leu Leu His Phe Ala Leu Ala Glu Ala Asp Arg
        35                  40                  45

Leu Asp Val Leu Glu Lys Tyr Arg Gly Lys Cys Glu Pro Thr Phe Leu
    50                  55                  60

Phe Tyr Ala Ile Lys Asp Glu Ala Leu Ser Asp Glu Asp Glu Cys Val
65                  70                  75                  80

Ser His Gly Lys Asn Asn Gly Glu Asp Glu Met Val Ser Ser Glu
                85                  90                  95

Arg Thr Cys Thr Leu Ala Ile Ile Lys Pro Asp Ala Val Ala His Gly
            100                 105                 110

Lys Thr Asp Glu Ile Ile Met Lys Ile Gln Glu Ala Gly Phe Glu Ile
        115                 120                 125

Leu Thr Asn Glu Glu Arg Thr Met Thr Glu Ala Glu Val Arg Leu Phe
    130                 135                 140

Tyr Gln His Lys Ala Gly Glu Ser Pro Ser Ser Val Arg His Arg Asn
145                 150                 155                 160

Ala Leu Gln Cys Arg Pro Trp Lys Pro Gly Gln Arg Arg Cys
                165                 170

<210> SEQ ID NO 232
<211> LENGTH: 58
<212> TYPE: PRT
<213> ORGANISM: Artificial Sequence
<220> FEATURE:
<223> OTHER INFORMATION: NME7A partial sequence

<400> SEQUENCE: 232

Thr Leu Ala Leu Ile Lys Pro Asp Ala Ile Ser Lys Ala Gly Glu Ile
1               5                   10                  15

Ile Glu Ile Ile Asn Lys Ala Gly Phe Thr Ile Thr Lys Leu Lys Met
            20                  25                  30

Met Met Leu Ser Arg Lys Glu Ala Leu Asp Phe His Ala Met Glu Ile
        35                  40                  45

Leu Arg Asp Asp Ala Ile Cys Glu Trp Lys

<210> SEQ ID NO 233
<211> LENGTH: 60
<212> TYPE: PRT
<213> ORGANISM: Artificial Sequence
<220> FEATURE:
<223> OTHER INFORMATION: NME9 partial sequence

<400> SEQUENCE: 233

Thr Leu Ala Ile Ile Lys Pro Asp Ala Val Ala His Gly Lys Thr Asp
1               5                   10                  15

Glu Ile Ile Met Lys Ile Gln Glu Ala Gly Phe Glu Ile Leu Thr Asn
            20                  25                  30

Glu Glu Arg Thr Met Thr Glu Ala Glu Val Arg Leu Phe Tyr Thr Leu
        35                  40                  45

Ala Ile Ile Lys Pro Asp Ala Val Ala His Gly Lys
    50                  55                  60

<210> SEQ ID NO 234
<211> LENGTH: 31
<212> TYPE: PRT
<213> ORGANISM: Artificial Sequence
<220> FEATURE:
<223> OTHER INFORMATION: NME7A partial sequence

<400> SEQUENCE: 234

Ile Ser Lys Ala Gly Glu Ile Glu Ile Ile Asn Lys Ala Gly Phe
1               5                   10                  15

Thr Ile Thr Lys Leu Lys Met Met Met Leu Ser Arg Lys Glu Ala
            20                  25                  30

<210> SEQ ID NO 235
<211> LENGTH: 29
<212> TYPE: PRT
<213> ORGANISM: Artificial Sequence
<220> FEATURE:
<223> OTHER INFORMATION: NME9 partial sequence

<400> SEQUENCE: 235

Ile Gln Glu Ala Gly Phe Glu Ile Leu Thr Asn Glu Glu Arg Thr Met
1               5                   10                  15

Thr Glu Ala Glu Val Arg Leu Phe Tyr Gln His Lys Ala
            20                  25

<210> SEQ ID NO 236
<211> LENGTH: 53
<212> TYPE: PRT
<213> ORGANISM: Artificial Sequence
<220> FEATURE:
<223> OTHER INFORMATION: NME7B partial sequence

<400> SEQUENCE: 236

Asn Cys Thr Cys Cys Ile Val Lys Pro His Ala Val Ser Glu Gly Leu
1               5                   10                  15

Leu Gly Lys Ile Leu Met Ala Ile Arg Asp Ala Gly Phe Glu Ile Ser
            20                  25                  30

Ala Met Gln Met Phe Asn Met Asp Arg Val Asn Val Glu Glu Phe Tyr
        35                  40                  45

Glu Val Tyr Lys Gly
    50

```
<210> SEQ ID NO 237
<211> LENGTH: 53
<212> TYPE: PRT
<213> ORGANISM: Artificial Sequence
<220> FEATURE:
<223> OTHER INFORMATION: NME9 partial sequence

<400> SEQUENCE: 237

Thr Cys Thr Leu Ala Ile Ile Lys Pro Asp Ala Val Ala His Gly Lys
1               5                   10                  15

Thr Asp Glu Ile Ile Met Lys Ile Gln Glu Ala Gly Phe Glu Ile Leu
            20                  25                  30

Thr Asn Glu Glu Arg Thr Met Thr Glu Ala Glu Val Arg Leu Phe Tyr
        35                  40                  45

Gln His Lys Ala Gly
    50

<210> SEQ ID NO 238
<211> LENGTH: 350
<212> TYPE: PRT
<213> ORGANISM: Artificial Sequence
<220> FEATURE:
<223> OTHER INFORMATION: NME10

<400> SEQUENCE: 238

Met Gly Cys Phe Phe Ser Lys Arg Arg Lys Ala Asp Lys Glu Ser Arg
1               5                   10                  15

Pro Glu Asn Glu Glu Glu Arg Pro Lys Gln Tyr Ser Trp Asp Gln Arg
            20                  25                  30

Glu Lys Val Asp Pro Lys Asp Tyr Met Phe Ser Gly Leu Lys Asp Glu
        35                  40                  45

Thr Val Gly Arg Leu Pro Gly Thr Val Ala Gly Gln Gln Phe Leu Ile
    50                  55                  60

Gln Asp Cys Glu Asn Cys Asn Ile Tyr Ile Phe Asp His Ser Ala Thr
65                  70                  75                  80

Val Thr Ile Asp Asp Cys Thr Asn Cys Ile Ile Phe Leu Gly Pro Val
                85                  90                  95

Lys Gly Ser Val Phe Phe Arg Asn Cys Arg Asp Cys Lys Cys Thr Leu
            100                 105                 110

Ala Cys Gln Gln Phe Arg Val Arg Asp Cys Arg Lys Leu Glu Val Phe
        115                 120                 125

Leu Cys Cys Ala Thr Gln Pro Ile Ile Glu Ser Ser Asn Ile Lys
    130                 135                 140

Phe Gly Cys Phe Gln Trp Tyr Tyr Pro Glu Leu Ala Phe Gln Phe Lys
145                 150                 155                 160

Asp Ala Gly Leu Ser Ile Phe Asn Asn Thr Trp Ser Asn Ile His Asp
                165                 170                 175

Phe Thr Pro Val Ser Gly Glu Leu Asn Trp Ser Leu Leu Pro Glu Asp
            180                 185                 190

Ala Val Val Gln Asp Tyr Val Pro Ile Pro Thr Thr Glu Glu Leu Lys
        195                 200                 205

Ala Val Arg Val Ser Thr Glu Ala Asn Arg Ser Ile Val Pro Ile Ser
    210                 215                 220

Arg Gly Gln Arg Gln Lys Ser Ser Asp Glu Ser Cys Leu Val Val Leu
225                 230                 235                 240

Phe Ala Gly Asp Tyr Thr Ile Ala Asn Ala Arg Lys Leu Ile Asp Glu
                245                 250                 255
```

```
Met Val Gly Lys Gly Phe Phe Leu Val Gln Thr Lys Glu Val Ser Met
            260                 265                 270

Lys Ala Glu Asp Ala Gln Arg Val Phe Arg Lys Ala Pro Asp Phe
        275                 280                 285

Leu Pro Leu Leu Asn Lys Gly Pro Val Ile Ala Leu Glu Phe Asn Gly
        290                 295                 300

Asp Gly Ala Val Glu Val Cys Gln Leu Ile Val Asn Glu Ile Phe Asn
305                 310                 315                 320

Gly Thr Lys Met Phe Val Ser Glu Ser Lys Thr Ala Ser Gly Asp
                325                 330                 335

Val Asp Ser Phe Tyr Asn Phe Ala Asp Ile Gln Met Gly Ile
            340                 345                 350
```

<210> SEQ ID NO 239
<211> LENGTH: 68
<212> TYPE: PRT
<213> ORGANISM: Artificial Sequence
<220> FEATURE:
<223> OTHER INFORMATION: NME7A partial sequence

<400> SEQUENCE: 239

```
Ala Ile Ser Lys Ala Gly Glu Ile Ile Glu Ile Asn Lys Ala Gly
1               5                   10                  15

Phe Thr Ile Thr Lys Leu Lys Met Met Met Leu Ser Arg Lys Glu Ala
            20                  25                  30

Leu Asp Phe His Val Asp His Gln Ser Arg Pro Phe Phe Asn Glu Leu
        35                  40                  45

Ile Gln Phe Ile Thr Thr Gly Pro Ile Ile Ala Met Glu Ile Leu Arg
    50                  55                  60

Asp Asp Ala Ile
65
```

<210> SEQ ID NO 240
<211> LENGTH: 63
<212> TYPE: PRT
<213> ORGANISM: Artificial Sequence
<220> FEATURE:
<223> OTHER INFORMATION: NME10 partial sequence

<400> SEQUENCE: 240

```
Thr Ile Ala Asn Ala Arg Lys Leu Ile Asp Glu Met Val Gly Lys Gly
1               5                   10                  15

Phe Phe Leu Val Gln Thr Lys Glu Val Ser Met Lys Ala Glu Asp Ala
            20                  25                  30

Gln Arg Val Phe Arg Glu Lys Ala Pro Asp Phe Leu Pro Leu Leu Asn
        35                  40                  45

Lys Gly Pro Val Ile Ala Leu Glu Phe Asn Gly Asp Gly Ala Val
    50                  55                  60
```

<210> SEQ ID NO 241
<211> LENGTH: 43
<212> TYPE: PRT
<213> ORGANISM: Artificial Sequence
<220> FEATURE:
<223> OTHER INFORMATION: NME7A partial sequence

<400> SEQUENCE: 241

```
Pro Ile Ile Ala Met Glu Ile Leu Arg Asp Asp Ala Ile Cys Glu Trp
1               5                   10                  15

Lys Arg Leu Leu Gly Pro Ala Asn Ser Gly Val Ala Arg Thr Asp Ala
```

```
            20                  25                  30

Ser Glu Ser Ile Arg Ala Leu Phe Gly Thr Asp
        35                  40

<210> SEQ ID NO 242
<211> LENGTH: 45
<212> TYPE: PRT
<213> ORGANISM: Artificial Sequence
<220> FEATURE:
<223> OTHER INFORMATION: NME10 partial sequence

<400> SEQUENCE: 242

Pro Ile Pro Thr Thr Glu Glu Leu Lys Ala Val Arg Val Ser Thr Glu
1               5                   10                  15

Ala Asn Arg Ser Ile Val Pro Ile Ser Arg Gly Gln Arg Gln Lys Ser
            20                  25                  30

Ser Asp Glu Ser Cys Leu Val Val Leu Phe Ala Gly Asp
        35                  40                  45

<210> SEQ ID NO 243
<211> LENGTH: 74
<212> TYPE: PRT
<213> ORGANISM: Artificial Sequence
<220> FEATURE:
<223> OTHER INFORMATION: NME7A partial sequence

<400> SEQUENCE: 243

Ile Lys Pro Asp Ala Ile Ser Lys Ala Gly Glu Ile Ile Glu Ile Ile
1               5                   10                  15

Asn Lys Ala Gly Phe Thr Ile Thr Lys Leu Lys Met Met Met Leu Ser
            20                  25                  30

Arg Lys Glu Ala Leu Asp Phe His Val Asp His Gln Ser Arg Pro Phe
        35                  40                  45

Phe Asn Glu Leu Ile Gln Phe Ile Thr Thr Gly Pro Ile Ile Ala Met
    50                  55                  60

Glu Ile Leu Arg Asp Asp Ala Ile Cys Glu
65                  70

<210> SEQ ID NO 244
<211> LENGTH: 75
<212> TYPE: PRT
<213> ORGANISM: Artificial Sequence
<220> FEATURE:
<223> OTHER INFORMATION: NME10 partial sequence

<400> SEQUENCE: 244

Val Asp Pro Lys Asp Tyr Met Phe Ser Gly Leu Lys Asp Glu Thr Val
1               5                   10                  15

Gly Arg Leu Pro Gly Thr Val Ala Gly Gln Gln Phe Leu Ile Gln Asp
            20                  25                  30

Cys Glu Asn Cys Asn Ile Tyr Ile Phe Asp His Ser Ala Thr Val Thr
        35                  40                  45

Ile Asp Asp Cys Thr Asn Cys Ile Ile Phe Leu Gly Pro Val Lys Gly
    50                  55                  60

Ser Val Phe Phe Arg Asn Cys Arg Asp Cys Lys
65                  70                  75

<210> SEQ ID NO 245
<211> LENGTH: 47
<212> TYPE: PRT
<213> ORGANISM: Artificial Sequence
```

<220> FEATURE:
<223> OTHER INFORMATION: NME7B partial sequence

<400> SEQUENCE: 245

Cys Cys Ile Val Lys Pro His Ala Val Ser Glu Gly Leu Leu Gly Lys
1               5                   10                  15

Ile Leu Met Ala Ile Arg Asp Ala Gly Phe Glu Ile Ser Ala Met Gln
            20                  25                  30

Met Phe Asn Met Asp Arg Val Asn Val Glu Glu Phe Tyr Glu Val
        35                  40                  45

<210> SEQ ID NO 246
<211> LENGTH: 51
<212> TYPE: PRT
<213> ORGANISM: Artificial Sequence
<220> FEATURE:
<223> OTHER INFORMATION: NME10 partial sequence

<400> SEQUENCE: 246

Cys Cys Ala Thr Gln Pro Ile Ile Glu Ser Ser Asn Ile Lys Phe
1               5                   10                  15

Gly Cys Phe Gln Trp Tyr Tyr Pro Glu Leu Ala Phe Gln Phe Lys Asp
            20                  25                  30

Ala Gly Leu Ser Ile Phe Asn Asn Thr Trp Ser Asn Ile His Asp Phe
        35                  40                  45

Thr Pro Val
        50

<210> SEQ ID NO 247
<211> LENGTH: 16
<212> TYPE: PRT
<213> ORGANISM: Artificial Sequence
<220> FEATURE:
<223> OTHER INFORMATION: NME2A1

<400> SEQUENCE: 247

Arg Ala Ser Glu Glu His Leu Lys Gln His Tyr Ile Asp Leu Lys Asp
1               5                   10                  15

<210> SEQ ID NO 248
<211> LENGTH: 8
<212> TYPE: PRT
<213> ORGANISM: Artificial Sequence
<220> FEATURE:
<223> OTHER INFORMATION: NME2A2

<400> SEQUENCE: 248

Pro Ala Asp Ser Lys Pro Gly Thr
1               5

<210> SEQ ID NO 249
<211> LENGTH: 20
<212> TYPE: PRT
<213> ORGANISM: Artificial Sequence
<220> FEATURE:
<223> OTHER INFORMATION: NME2B1

<400> SEQUENCE: 249

Gln Lys Gly Phe Arg Leu Val Ala Met Lys Phe Leu Arg Ala Ser Glu
1               5                   10                  15

Glu His Leu Lys
            20

```
<210> SEQ ID NO 250
<211> LENGTH: 14
<212> TYPE: PRT
<213> ORGANISM: Artificial Sequence
<220> FEATURE:
<223> OTHER INFORMATION: NME2B2

<400> SEQUENCE: 250

Ile Asp Leu Lys Asp Arg Pro Phe Pro Gly Leu Val Lys Tyr
1               5                   10

<210> SEQ ID NO 251
<211> LENGTH: 29
<212> TYPE: PRT
<213> ORGANISM: Artificial Sequence
<220> FEATURE:
<223> OTHER INFORMATION: NME2B3

<400> SEQUENCE: 251

Gly Asp Phe Cys Ile Gln Val Gly Arg Asn Ile Ile His Gly Ser Asp
1               5                   10                  15

Ser Val Lys Ser Ala Glu Lys Glu Ile Ser Leu Trp Phe
            20                  25

<210> SEQ ID NO 252
<211> LENGTH: 16
<212> TYPE: PRT
<213> ORGANISM: Artificial Sequence
<220> FEATURE:
<223> OTHER INFORMATION: NME3A1

<400> SEQUENCE: 252

Gln Ala Ser Glu Glu Leu Leu Arg Glu His Tyr Val Glu Leu Arg Glu
1               5                   10                  15

<210> SEQ ID NO 253
<211> LENGTH: 8
<212> TYPE: PRT
<213> ORGANISM: Artificial Sequence
<220> FEATURE:
<223> OTHER INFORMATION: NME3A1

<400> SEQUENCE: 253

Pro Gly Asp Ala Thr Pro Gly Thr
1               5

<210> SEQ ID NO 254
<211> LENGTH: 20
<212> TYPE: PRT
<213> ORGANISM: Artificial Sequence
<220> FEATURE:
<223> OTHER INFORMATION: NME3B1

<400> SEQUENCE: 254

Arg Lys Gly Phe Lys Leu Val Ala Leu Lys Leu Val Gln Ala Ser Glu
1               5                   10                  15

Glu Leu Leu Arg
            20

<210> SEQ ID NO 255
<211> LENGTH: 15
<212> TYPE: PRT
<213> ORGANISM: Artificial Sequence
<220> FEATURE:
<223> OTHER INFORMATION: NME3B2

<400> SEQUENCE: 255
```

```
Val Glu Leu Arg Glu Arg Pro Phe Tyr Ser Arg Leu Val Lys Tyr
1               5                   10                  15

<210> SEQ ID NO 256
<211> LENGTH: 29
<212> TYPE: PRT
<213> ORGANISM: Artificial Sequence
<220> FEATURE:
<223> OTHER INFORMATION: NME3B3

<400> SEQUENCE: 256

Gly Asp Phe Cys Val Glu Val Gly Lys Asn Val Ile His Gly Ser Asp
1               5                   10                  15

Ser Val Glu Ser Ala Gln Arg Glu Ile Ala Leu Trp Phe
            20                  25

<210> SEQ ID NO 257
<211> LENGTH: 16
<212> TYPE: PRT
<213> ORGANISM: Artificial Sequence
<220> FEATURE:
<223> OTHER INFORMATION: NME4A1

<400> SEQUENCE: 257

Gln Ala Pro Glu Ser Val Leu Ala Glu His Tyr Gln Asp Leu Arg Arg
1               5                   10                  15

<210> SEQ ID NO 258
<211> LENGTH: 8
<212> TYPE: PRT
<213> ORGANISM: Artificial Sequence
<220> FEATURE:
<223> OTHER INFORMATION: NME4A2

<400> SEQUENCE: 258

Ser Ala Glu Ala Ala Pro Gly Thr
1               5

<210> SEQ ID NO 259
<211> LENGTH: 20
<212> TYPE: PRT
<213> ORGANISM: Artificial Sequence
<220> FEATURE:
<223> OTHER INFORMATION: NME4B1

<400> SEQUENCE: 259

Arg Arg Gly Phe Thr Leu Val Gly Met Lys Met Leu Gln Ala Pro Glu
1               5                   10                  15

Ser Val Leu Ala
            20

<210> SEQ ID NO 260
<211> LENGTH: 15
<212> TYPE: PRT
<213> ORGANISM: Artificial Sequence
<220> FEATURE:
<223> OTHER INFORMATION: NME4B2

<400> SEQUENCE: 260

Gln Asp Leu Arg Arg Lys Pro Phe Tyr Pro Ala Leu Ile Arg Tyr
1               5                   10                  15

<210> SEQ ID NO 261
<211> LENGTH: 29
<212> TYPE: PRT
```

```
<213> ORGANISM: Artificial Sequence
<220> FEATURE:
<223> OTHER INFORMATION: NME4B3

<400> SEQUENCE: 261

Gly Asp Phe Ser Val His Ile Ser Arg Asn Val Ile His Ala Ser Asp
1               5                   10                  15

Ser Val Glu Gly Ala Gln Arg Glu Ile Gln Leu Trp Phe
            20                  25

<210> SEQ ID NO 262
<211> LENGTH: 16
<212> TYPE: PRT
<213> ORGANISM: Artificial Sequence
<220> FEATURE:
<223> OTHER INFORMATION: NME5A1

<400> SEQUENCE: 262

Arg Leu Ser Pro Glu Gln Cys Ser Asn Phe Tyr Val Glu Lys Tyr Gly
1               5                   10                  15

<210> SEQ ID NO 263
<211> LENGTH: 11
<212> TYPE: PRT
<213> ORGANISM: Artificial Sequence
<220> FEATURE:
<223> OTHER INFORMATION: NME5A2

<400> SEQUENCE: 263

Ser Leu Val Ala Lys Glu Thr His Pro Asp Ser
1               5                   10

<210> SEQ ID NO 264
<211> LENGTH: 20
<212> TYPE: PRT
<213> ORGANISM: Artificial Sequence
<220> FEATURE:
<223> OTHER INFORMATION: NME5B1

<400> SEQUENCE: 264

Arg Ser Gly Phe Thr Ile Val Gln Arg Arg Lys Leu Arg Leu Ser Pro
1               5                   10                  15

Glu Gln Cys Ser
            20

<210> SEQ ID NO 265
<211> LENGTH: 15
<212> TYPE: PRT
<213> ORGANISM: Artificial Sequence
<220> FEATURE:
<223> OTHER INFORMATION: NME5B2

<400> SEQUENCE: 265

Val Glu Lys Tyr Gly Lys Met Phe Phe Pro Asn Leu Thr Ala Tyr
1               5                   10                  15

<210> SEQ ID NO 266
<211> LENGTH: 29
<212> TYPE: PRT
<213> ORGANISM: Artificial Sequence
<220> FEATURE:
<223> OTHER INFORMATION: NME5B3

<400> SEQUENCE: 266

Ala Ile Tyr Gly Thr Asp Asp Leu Arg Asn Ala Leu His Gly Ser Asn
1               5                   10                  15
```

```
Asp Phe Ala Ala Ala Glu Arg Glu Ile Arg Phe Met Phe
            20                  25

<210> SEQ ID NO 267
<211> LENGTH: 16
<212> TYPE: PRT
<213> ORGANISM: Artificial Sequence
<220> FEATURE:
<223> OTHER INFORMATION: NME6A1

<400> SEQUENCE: 267

Leu Trp Arg Lys Glu Asp Cys Gln Arg Phe Tyr Arg Glu His Glu Gly
1               5                   10                  15

<210> SEQ ID NO 268
<211> LENGTH: 11
<212> TYPE: PRT
<213> ORGANISM: Artificial Sequence
<220> FEATURE:
<223> OTHER INFORMATION: NME6A2

<400> SEQUENCE: 268

Val Phe Arg Ala Arg His Val Ala Pro Asp Ser
1               5                   10

<210> SEQ ID NO 269
<211> LENGTH: 20
<212> TYPE: PRT
<213> ORGANISM: Artificial Sequence
<220> FEATURE:
<223> OTHER INFORMATION: NME6B1

<400> SEQUENCE: 269

Ser Asn Lys Phe Leu Ile Val Arg Met Arg Glu Leu Leu Trp Arg Lys
1               5                   10                  15

Glu Asp Cys Gln
            20

<210> SEQ ID NO 270
<211> LENGTH: 15
<212> TYPE: PRT
<213> ORGANISM: Artificial Sequence
<220> FEATURE:
<223> OTHER INFORMATION: NME6B2

<400> SEQUENCE: 270

Arg Glu His Glu Gly Arg Phe Phe Tyr Gln Arg Leu Val Glu Phe
1               5                   10                  15

<210> SEQ ID NO 271
<211> LENGTH: 29
<212> TYPE: PRT
<213> ORGANISM: Artificial Sequence
<220> FEATURE:
<223> OTHER INFORMATION: NME6B3

<400> SEQUENCE: 271

Gly Ser Phe Gly Leu Thr Asp Thr Arg Asn Thr Thr His Gly Ser Asp
1               5                   10                  15

Ser Val Val Ser Ala Ser Arg Glu Ile Ala Ala Phe Phe
            20                  25

<210> SEQ ID NO 272
<211> LENGTH: 16
<212> TYPE: PRT
```

```
<213> ORGANISM: Artificial Sequence
<220> FEATURE:
<223> OTHER INFORMATION: NME8A1

<400> SEQUENCE: 272

Val Leu Ser Glu Lys Glu Ala Gln Ala Leu Cys Lys Glu Tyr Glu Asn
1               5                   10                  15

<210> SEQ ID NO 273
<211> LENGTH: 11
<212> TYPE: PRT
<213> ORGANISM: Artificial Sequence
<220> FEATURE:
<223> OTHER INFORMATION: NME8A2

<400> SEQUENCE: 273

Val Glu Glu Ala Ile Glu Tyr Phe Pro Glu Ser
1               5                   10

<210> SEQ ID NO 274
<211> LENGTH: 16
<212> TYPE: PRT
<213> ORGANISM: Artificial Sequence
<220> FEATURE:
<223> OTHER INFORMATION: NME8A3

<400> SEQUENCE: 274

Phe Leu Thr Pro Glu Gln Ile Glu Lys Ile Tyr Pro Lys Val Thr Gly
1               5                   10                  15

<210> SEQ ID NO 275
<211> LENGTH: 11
<212> TYPE: PRT
<213> ORGANISM: Artificial Sequence
<220> FEATURE:
<223> OTHER INFORMATION: NME8A4

<400> SEQUENCE: 275

Pro Glu Glu Ala Lys Leu Leu Ser Pro Asp Ser
1               5                   10

<210> SEQ ID NO 276
<211> LENGTH: 16
<212> TYPE: PRT
<213> ORGANISM: Artificial Sequence
<220> FEATURE:
<223> OTHER INFORMATION: NME8A5

<400> SEQUENCE: 276

Val Leu Thr Glu Glu Gln Val Val Asn Phe Tyr Ser Arg Ile Ala Asp
1               5                   10                  15

<210> SEQ ID NO 277
<211> LENGTH: 20
<212> TYPE: PRT
<213> ORGANISM: Artificial Sequence
<220> FEATURE:
<223> OTHER INFORMATION: NME8B1

<400> SEQUENCE: 277

Glu Ala Gly Phe Asp Leu Thr Gln Val Lys Lys Met Phe Leu Thr Pro
1               5                   10                  15

Glu Gln Ile Glu
            20

<210> SEQ ID NO 278
```

```
<211> LENGTH: 15
<212> TYPE: PRT
<213> ORGANISM: Artificial Sequence
<220> FEATURE:
<223> OTHER INFORMATION: NME8B2

<400> SEQUENCE: 278

Pro Lys Val Thr Gly Lys Asp Phe Tyr Lys Asp Leu Leu Glu Met
1               5                   10                  15

<210> SEQ ID NO 279
<211> LENGTH: 13
<212> TYPE: PRT
<213> ORGANISM: Artificial Sequence
<220> FEATURE:
<223> OTHER INFORMATION: NME8B3

<400> SEQUENCE: 279

Ala Gln Phe Gly Ile Ser Lys Leu Lys Asn Ile Val His
1               5                   10

<210> SEQ ID NO 280
<211> LENGTH: 20
<212> TYPE: PRT
<213> ORGANISM: Artificial Sequence
<220> FEATURE:
<223> OTHER INFORMATION: NME8B4

<400> SEQUENCE: 280

Asp Glu Asp Phe Lys Ile Leu Glu Gln Arg Gln Val Val Leu Ser Glu
1               5                   10                  15

Lys Glu Ala Gln
            20

<210> SEQ ID NO 281
<211> LENGTH: 15
<212> TYPE: PRT
<213> ORGANISM: Artificial Sequence
<220> FEATURE:
<223> OTHER INFORMATION: NME8B5

<400> SEQUENCE: 281

Lys Glu Tyr Glu Asn Glu Asp Tyr Phe Asn Lys Leu Ile Glu Asn
1               5                   10                  15

<210> SEQ ID NO 282
<211> LENGTH: 30
<212> TYPE: PRT
<213> ORGANISM: Artificial Sequence
<220> FEATURE:
<223> OTHER INFORMATION: NME8B6

<400> SEQUENCE: 282

Ala Gln Phe Ala Met Asp Ser Leu Pro Val Asn Gln Leu Tyr Gly Ser
1               5                   10                  15

Asp Ser Leu Glu Thr Ala Glu Arg Glu Ile Gln His Phe Phe
            20                  25                  30

<210> SEQ ID NO 283
<211> LENGTH: 20
<212> TYPE: PRT
<213> ORGANISM: Artificial Sequence
<220> FEATURE:
<223> OTHER INFORMATION: NME8B7

<400> SEQUENCE: 283
```

```
Lys Ala Gly Phe Ile Ile Glu Ala Glu His Lys Thr Val Leu Thr Glu
1               5                   10                  15

Glu Gln Val Val
            20

<210> SEQ ID NO 284
<211> LENGTH: 15
<212> TYPE: PRT
<213> ORGANISM: Artificial Sequence
<220> FEATURE:
<223> OTHER INFORMATION: NME8B8

<400> SEQUENCE: 284

Ser Arg Ile Ala Asp Gln Cys Asp Phe Glu Glu Phe Val Ser Phe
1               5                   10                  15

<210> SEQ ID NO 285
<211> LENGTH: 11
<212> TYPE: PRT
<213> ORGANISM: Artificial Sequence
<220> FEATURE:
<223> OTHER INFORMATION: NME9A1

<400> SEQUENCE: 285

Thr Met Thr Glu Ala Glu Val Arg Leu Phe Tyr
1               5                   10

<210> SEQ ID NO 286
<211> LENGTH: 20
<212> TYPE: PRT
<213> ORGANISM: Artificial Sequence
<220> FEATURE:
<223> OTHER INFORMATION: NME9B1

<400> SEQUENCE: 286

Glu Ala Gly Phe Glu Ile Leu Thr Asn Glu Glu Arg Thr Met Thr Glu
1               5                   10                  15

Ala Glu Val Arg
            20

<210> SEQ ID NO 287
<211> LENGTH: 14
<212> TYPE: PRT
<213> ORGANISM: Artificial Sequence
<220> FEATURE:
<223> OTHER INFORMATION: NME10A1

<400> SEQUENCE: 287

Ser Met Lys Ala Glu Asp Ala Gln Arg Val Phe Arg Glu Lys
1               5                   10

<210> SEQ ID NO 288
<211> LENGTH: 10
<212> TYPE: PRT
<213> ORGANISM: Artificial Sequence
<220> FEATURE:
<223> OTHER INFORMATION: NME10A2

<400> SEQUENCE: 288

Gly Gln Arg Gln Lys Ser Ser Asp Glu Ser
1               5                   10

<210> SEQ ID NO 289
<211> LENGTH: 16
<212> TYPE: PRT
<213> ORGANISM: Artificial Sequence
```

```
<220> FEATURE:
<223> OTHER INFORMATION: NME10A3

<400> SEQUENCE: 289

Ile Gln Asp Cys Glu Asn Cys Asn Ile Tyr Ile Phe Asp His Ser Ala
1               5                   10                  15

<210> SEQ ID NO 290
<211> LENGTH: 22
<212> TYPE: PRT
<213> ORGANISM: Artificial Sequence
<220> FEATURE:
<223> OTHER INFORMATION: NME10B1

<400> SEQUENCE: 290

Glu Leu Ala Phe Gln Phe Lys Asp Ala Gly Leu Ser Ile Phe Asn Asn
1               5                   10                  15

Thr Trp Ser Asn Ile His
            20

<210> SEQ ID NO 291
<211> LENGTH: 23
<212> TYPE: PRT
<213> ORGANISM: Artificial Sequence
<220> FEATURE:
<223> OTHER INFORMATION: NME2A1

<400> SEQUENCE: 291

Arg Ala Ser Glu Glu His Leu Lys Gln His Tyr Ile Asp Leu Lys Asp
1               5                   10                  15

Arg Pro Phe Phe Pro Gly Leu
            20

<210> SEQ ID NO 292
<211> LENGTH: 18
<212> TYPE: PRT
<213> ORGANISM: Artificial Sequence
<220> FEATURE:
<223> OTHER INFORMATION: NME2A2

<400> SEQUENCE: 292

Leu Gly Glu Thr Asn Pro Ala Asp Ser Lys Pro Gly Thr Ile Arg Gly
1               5                   10                  15

Asp Phe

<210> SEQ ID NO 293
<211> LENGTH: 34
<212> TYPE: PRT
<213> ORGANISM: Artificial Sequence
<220> FEATURE:
<223> OTHER INFORMATION: NME2B1

<400> SEQUENCE: 293

Gly Leu Val Gly Glu Ile Ile Lys Arg Phe Glu Gln Lys Gly Phe Arg
1               5                   10                  15

Leu Val Ala Met Lys Phe Leu Arg Ala Ser Glu Glu His Leu Lys Gln
            20                  25                  30

His Tyr

<210> SEQ ID NO 294
<211> LENGTH: 25
<212> TYPE: PRT
<213> ORGANISM: Artificial Sequence
<220> FEATURE:
```

<223> OTHER INFORMATION: NME2B2

<400> SEQUENCE: 294

Tyr Ile Asp Leu Lys Asp Arg Pro Phe Phe Pro Gly Leu Val Lys Tyr
1               5                   10                  15

Met Asn Ser Gly Pro Val Val Ala Met
            20                  25

<210> SEQ ID NO 295
<211> LENGTH: 34
<212> TYPE: PRT
<213> ORGANISM: Artificial Sequence
<220> FEATURE:
<223> OTHER INFORMATION: NME2B3

<400> SEQUENCE: 295

Pro Gly Thr Ile Arg Gly Asp Phe Cys Ile Gln Val Gly Arg Asn Ile
1               5                   10                  15

Ile His Gly Ser Asp Ser Val Lys Ser Ala Glu Lys Glu Ile Ser Leu
            20                  25                  30

Trp Phe

<210> SEQ ID NO 296
<211> LENGTH: 27
<212> TYPE: PRT
<213> ORGANISM: Artificial Sequence
<220> FEATURE:
<223> OTHER INFORMATION: NME3A1

<400> SEQUENCE: 296

Leu Lys Leu Val Gln Ala Ser Glu Glu Leu Arg Glu His Tyr Val
1               5                   10                  15

Glu Leu Arg Glu Arg Pro Phe Tyr Ser Arg Leu
            20                  25

<210> SEQ ID NO 297
<211> LENGTH: 19
<212> TYPE: PRT
<213> ORGANISM: Artificial Sequence
<220> FEATURE:
<223> OTHER INFORMATION: NME3A1

<400> SEQUENCE: 297

Leu Ile Gly Ala Thr Asp Pro Gly Asp Ala Thr Pro Gly Thr Ile Arg
1               5                   10                  15

Gly Asp Phe

<210> SEQ ID NO 298
<211> LENGTH: 31
<212> TYPE: PRT
<213> ORGANISM: Artificial Sequence
<220> FEATURE:
<223> OTHER INFORMATION: NME3B1

<400> SEQUENCE: 298

Leu Val Gly Glu Ile Val Arg Arg Phe Glu Arg Lys Gly Phe Lys Leu
1               5                   10                  15

Val Ala Leu Lys Leu Val Gln Ala Ser Glu Glu Leu Leu Arg Glu
            20                  25                  30

<210> SEQ ID NO 299
<211> LENGTH: 27
<212> TYPE: PRT

<213> ORGANISM: Artificial Sequence
<220> FEATURE:
<223> OTHER INFORMATION: NME3B2

<400> SEQUENCE: 299

Glu His Tyr Val Glu Leu Arg Glu Arg Pro Phe Tyr Ser Arg Leu Val
1               5                   10                  15

Lys Tyr Met Gly Ser Gly Pro Val Val Ala Met
            20                  25

<210> SEQ ID NO 300
<211> LENGTH: 34
<212> TYPE: PRT
<213> ORGANISM: Artificial Sequence
<220> FEATURE:
<223> OTHER INFORMATION: NME3B3

<400> SEQUENCE: 300

Pro Gly Thr Ile Arg Gly Asp Phe Cys Val Glu Val Gly Lys Asn Val
1               5                   10                  15

Ile His Gly Ser Asp Ser Val Glu Ser Ala Gln Arg Glu Ile Ala Leu
            20                  25                  30

Trp Phe

<210> SEQ ID NO 301
<211> LENGTH: 29
<212> TYPE: PRT
<213> ORGANISM: Artificial Sequence
<220> FEATURE:
<223> OTHER INFORMATION: NME4A1

<400> SEQUENCE: 301

Gly Phe Thr Leu Val Gly Met Lys Met Leu Gln Ala Pro Glu Ser Val
1               5                   10                  15

Leu Ala Glu His Tyr Gln Asp Leu Arg Arg Lys Pro Phe
            20                  25

<210> SEQ ID NO 302
<211> LENGTH: 17
<212> TYPE: PRT
<213> ORGANISM: Artificial Sequence
<220> FEATURE:
<223> OTHER INFORMATION: NME4A2

<400> SEQUENCE: 302

Gly His Thr Asp Ser Ala Glu Ala Ala Pro Gly Thr Ile Arg Gly Asp
1               5                   10                  15

Phe

<210> SEQ ID NO 303
<211> LENGTH: 33
<212> TYPE: PRT
<213> ORGANISM: Artificial Sequence
<220> FEATURE:
<223> OTHER INFORMATION: NME4B1

<400> SEQUENCE: 303

Leu Val Gly Asp Val Ile Gln Arg Phe Glu Arg Arg Gly Phe Thr Leu
1               5                   10                  15

Val Gly Met Lys Met Leu Gln Ala Pro Glu Ser Val Leu Ala Glu His
            20                  25                  30

Tyr

```
<210> SEQ ID NO 304
<211> LENGTH: 27
<212> TYPE: PRT
<213> ORGANISM: Artificial Sequence
<220> FEATURE:
<223> OTHER INFORMATION: NME4B2

<400> SEQUENCE: 304

Glu His Tyr Gln Asp Leu Arg Arg Lys Pro Phe Tyr Pro Ala Leu Ile
1               5                   10                  15

Arg Tyr Met Ser Ser Gly Pro Val Val Ala Met
            20                  25

<210> SEQ ID NO 305
<211> LENGTH: 34
<212> TYPE: PRT
<213> ORGANISM: Artificial Sequence
<220> FEATURE:
<223> OTHER INFORMATION: NME4B3

<400> SEQUENCE: 305

Pro Gly Thr Ile Arg Gly Asp Phe Ser Val His Ile Ser Arg Asn Val
1               5                   10                  15

Ile His Ala Ser Asp Ser Val Glu Gly Ala Gln Arg Glu Ile Gln Leu
            20                  25                  30

Trp Phe

<210> SEQ ID NO 306
<211> LENGTH: 30
<212> TYPE: PRT
<213> ORGANISM: Artificial Sequence
<220> FEATURE:
<223> OTHER INFORMATION: NME5A1

<400> SEQUENCE: 306

Gly Phe Thr Ile Val Gln Arg Arg Lys Leu Arg Leu Ser Pro Glu Gln
1               5                   10                  15

Cys Ser Asn Phe Tyr Val Glu Lys Tyr Gly Lys Met Phe Phe
            20                  25                  30

<210> SEQ ID NO 307
<211> LENGTH: 25
<212> TYPE: PRT
<213> ORGANISM: Artificial Sequence
<220> FEATURE:
<223> OTHER INFORMATION: NME5A2

<400> SEQUENCE: 307

Leu Leu Gly Pro Asn Asn Ser Leu Val Ala Lys Glu Thr His Pro Asp
1               5                   10                  15

Ser Leu Arg Ala Ile Tyr Gly Thr Asp
            20                  25

<210> SEQ ID NO 308
<211> LENGTH: 29
<212> TYPE: PRT
<213> ORGANISM: Artificial Sequence
<220> FEATURE:
<223> OTHER INFORMATION: NME5B1

<400> SEQUENCE: 308

Ile Gln Asp Ile Ile Leu Arg Ser Gly Phe Thr Ile Val Gln Arg Arg
1               5                   10                  15
```

-continued

```
Lys Leu Arg Leu Ser Pro Glu Gln Cys Ser Asn Phe Tyr
            20                  25

<210> SEQ ID NO 309
<211> LENGTH: 26
<212> TYPE: PRT
<213> ORGANISM: Artificial Sequence
<220> FEATURE:
<223> OTHER INFORMATION: NME5B2

<400> SEQUENCE: 309

Phe Tyr Val Glu Lys Tyr Gly Lys Met Phe Phe Pro Asn Leu Thr Ala
1               5                   10                  15

Tyr Met Ser Ser Gly Pro Leu Val Ala Met
            20                  25

<210> SEQ ID NO 310
<211> LENGTH: 34
<212> TYPE: PRT
<213> ORGANISM: Artificial Sequence
<220> FEATURE:
<223> OTHER INFORMATION: NME5B3

<400> SEQUENCE: 310

Pro Asp Ser Leu Arg Ala Ile Tyr Gly Thr Asp Asp Leu Arg Asn Ala
1               5                   10                  15

Leu His Gly Ser Asn Asp Phe Ala Ala Ala Glu Arg Glu Ile Arg Phe
            20                  25                  30

Met Phe

<210> SEQ ID NO 311
<211> LENGTH: 32
<212> TYPE: PRT
<213> ORGANISM: Artificial Sequence
<220> FEATURE:
<223> OTHER INFORMATION: NME6A1

<400> SEQUENCE: 311

Phe Leu Ile Val Arg Met Arg Glu Leu Leu Trp Arg Lys Glu Asp Cys
1               5                   10                  15

Gln Arg Phe Tyr Arg Glu His Glu Gly Arg Phe Phe Tyr Gln Arg Leu
            20                  25                  30

<210> SEQ ID NO 312
<211> LENGTH: 23
<212> TYPE: PRT
<213> ORGANISM: Artificial Sequence
<220> FEATURE:
<223> OTHER INFORMATION: NME6A2

<400> SEQUENCE: 312

Leu Met Gly Pro Thr Arg Val Phe Arg Ala Arg His Val Ala Pro Asp
1               5                   10                  15

Ser Ile Arg Gly Ser Phe Gly
            20

<210> SEQ ID NO 313
<211> LENGTH: 25
<212> TYPE: PRT
<213> ORGANISM: Artificial Sequence
<220> FEATURE:
<223> OTHER INFORMATION: NME6B1

<400> SEQUENCE: 313
```

Ile Leu Ser Asn Lys Phe Leu Ile Val Arg Met Arg Glu Leu Leu Trp
1               5                   10                  15

Arg Lys Glu Asp Cys Gln Arg Phe Tyr
            20              25

<210> SEQ ID NO 314
<211> LENGTH: 25
<212> TYPE: PRT
<213> ORGANISM: Artificial Sequence
<220> FEATURE:
<223> OTHER INFORMATION: NME6B2

<400> SEQUENCE: 314

Phe Tyr Arg Glu His Glu Gly Arg Phe Phe Tyr Gln Arg Leu Val Glu
1               5                   10                  15

Phe Met Ala Ser Gly Pro Ile Arg Ala
            20              25

<210> SEQ ID NO 315
<211> LENGTH: 39
<212> TYPE: PRT
<213> ORGANISM: Artificial Sequence
<220> FEATURE:
<223> OTHER INFORMATION: NME6B3

<400> SEQUENCE: 315

Ala Arg His Val Ala Pro Asp Ser Ile Arg Gly Ser Phe Gly Leu Thr
1               5                   10                  15

Asp Thr Arg Asn Thr Thr His Gly Ser Asp Ser Val Val Ser Ala Ser
            20                  25                  30

Arg Glu Ile Ala Ala Phe Phe
        35

<210> SEQ ID NO 316
<211> LENGTH: 33
<212> TYPE: PRT
<213> ORGANISM: Artificial Sequence
<220> FEATURE:
<223> OTHER INFORMATION: NME8A1

<400> SEQUENCE: 316

Phe Lys Ile Leu Glu Gln Arg Gln Val Val Leu Ser Glu Lys Glu Ala
1               5                   10                  15

Gln Ala Leu Cys Lys Glu Tyr Glu Asn Glu Asp Tyr Phe Asn Lys Leu
            20                  25                  30

Ile

<210> SEQ ID NO 317
<211> LENGTH: 28
<212> TYPE: PRT
<213> ORGANISM: Artificial Sequence
<220> FEATURE:
<223> OTHER INFORMATION: NME8A2

<400> SEQUENCE: 317

Trp Lys Gln Leu Leu Gly Pro Arg Thr Val Glu Glu Ala Ile Glu Tyr
1               5                   10                  15

Phe Pro Glu Ser Leu Cys Ala Gln Phe Ala Met Asp
            20                  25

<210> SEQ ID NO 318
<211> LENGTH: 34
<212> TYPE: PRT

```
<213> ORGANISM: Artificial Sequence
<220> FEATURE:
<223> OTHER INFORMATION: NME8A3

<400> SEQUENCE: 318

Ala Gly Phe Asp Leu Thr Gln Val Lys Lys Met Phe Leu Thr Pro Glu
1               5                   10                  15

Gln Ile Glu Lys Ile Tyr Pro Lys Val Thr Gly Lys Asp Phe Tyr Lys
            20                  25                  30

Asp Leu

<210> SEQ ID NO 319
<211> LENGTH: 27
<212> TYPE: PRT
<213> ORGANISM: Artificial Sequence
<220> FEATURE:
<223> OTHER INFORMATION: NME8A4

<400> SEQUENCE: 319

Glu Trp Arg Arg Leu Met Gly Pro Thr Asp Pro Glu Glu Ala Lys Leu
1               5                   10                  15

Leu Ser Pro Asp Ser Ile Arg Ala Gln Phe Gly
            20                  25

<210> SEQ ID NO 320
<211> LENGTH: 34
<212> TYPE: PRT
<213> ORGANISM: Artificial Sequence
<220> FEATURE:
<223> OTHER INFORMATION: NME8A5

<400> SEQUENCE: 320

Lys Ala Gly Phe Ile Ile Glu Ala Glu His Lys Thr Val Leu Thr Glu
1               5                   10                  15

Glu Gln Val Val Asn Phe Tyr Ser Arg Ile Ala Asp Gln Cys Asp Phe
            20                  25                  30

Glu Glu

<210> SEQ ID NO 321
<211> LENGTH: 29
<212> TYPE: PRT
<213> ORGANISM: Artificial Sequence
<220> FEATURE:
<223> OTHER INFORMATION: NME8B1

<400> SEQUENCE: 321

Ile Leu Lys Ile Val Lys Glu Ala Gly Phe Asp Leu Thr Gln Val Lys
1               5                   10                  15

Lys Met Phe Leu Thr Pro Glu Gln Ile Glu Lys Ile Tyr
            20                  25

<210> SEQ ID NO 322
<211> LENGTH: 21
<212> TYPE: PRT
<213> ORGANISM: Artificial Sequence
<220> FEATURE:
<223> OTHER INFORMATION: NME8B2

<400> SEQUENCE: 322

Tyr Pro Lys Val Thr Gly Lys Asp Phe Tyr Lys Asp Leu Leu Glu Met
1               5                   10                  15

Leu Ser Val Gly Pro
            20
```

<210> SEQ ID NO 323
<211> LENGTH: 27
<212> TYPE: PRT
<213> ORGANISM: Artificial Sequence
<220> FEATURE:
<223> OTHER INFORMATION: NME8B3

<400> SEQUENCE: 323

Asp Pro Glu Glu Ala Lys Leu Leu Ser Pro Asp Ser Ile Arg Ala Gln
1               5                   10                  15

Phe Gly Ile Ser Lys Leu Lys Asn Ile Val His
            20                  25

<210> SEQ ID NO 324
<211> LENGTH: 25
<212> TYPE: PRT
<213> ORGANISM: Artificial Sequence
<220> FEATURE:
<223> OTHER INFORMATION: NME8B4

<400> SEQUENCE: 324

Leu Arg Ile Ile Lys Asp Glu Asp Phe Lys Ile Leu Glu Gln Arg Gln
1               5                   10                  15

Val Val Leu Ser Glu Lys Glu Ala Gln
            20                  25

<210> SEQ ID NO 325
<211> LENGTH: 23
<212> TYPE: PRT
<213> ORGANISM: Artificial Sequence
<220> FEATURE:
<223> OTHER INFORMATION: NME8B5

<400> SEQUENCE: 325

Lys Glu Tyr Glu Asn Glu Asp Tyr Phe Asn Lys Leu Ile Glu Asn Met
1               5                   10                  15

Thr Ser Gly Pro Ser Leu Ala
            20

<210> SEQ ID NO 326
<211> LENGTH: 35
<212> TYPE: PRT
<213> ORGANISM: Artificial Sequence
<220> FEATURE:
<223> OTHER INFORMATION: NME8B6

<400> SEQUENCE: 326

Pro Glu Ser Leu Cys Ala Gln Phe Ala Met Asp Ser Leu Pro Val Asn
1               5                   10                  15

Gln Leu Tyr Gly Ser Asp Ser Leu Glu Thr Ala Glu Arg Glu Ile Gln
            20                  25                  30

His Phe Phe
        35

<210> SEQ ID NO 327
<211> LENGTH: 29
<212> TYPE: PRT
<213> ORGANISM: Artificial Sequence
<220> FEATURE:
<223> OTHER INFORMATION: NME8B7

<400> SEQUENCE: 327

Ile Lys Arg Lys Ile Thr Lys Ala Gly Phe Ile Ile Glu Ala Glu His

```
1               5                   10                  15
Lys Thr Val Leu Thr Glu Glu Gln Val Val Asn Phe Tyr
            20                  25

<210> SEQ ID NO 328
<211> LENGTH: 21
<212> TYPE: PRT
<213> ORGANISM: Artificial Sequence
<220> FEATURE:
<223> OTHER INFORMATION: NME8B8

<400> SEQUENCE: 328

Phe Tyr Ser Arg Ile Ala Asp Gln Cys Asp Phe Glu Glu Phe Val Ser
1               5                   10                  15

Phe Met Thr Ser Gly
            20

<210> SEQ ID NO 329
<211> LENGTH: 22
<212> TYPE: PRT
<213> ORGANISM: Artificial Sequence
<220> FEATURE:
<223> OTHER INFORMATION: NME9A1

<400> SEQUENCE: 329

Ala Gly Phe Glu Ile Leu Thr Asn Glu Glu Arg Thr Met Thr Glu Ala
1               5                   10                  15

Glu Val Arg Leu Phe Tyr
            20

<210> SEQ ID NO 330
<211> LENGTH: 29
<212> TYPE: PRT
<213> ORGANISM: Artificial Sequence
<220> FEATURE:
<223> OTHER INFORMATION: NME9B1

<400> SEQUENCE: 330

Ile Ile Met Lys Ile Gln Glu Ala Gly Phe Glu Ile Leu Thr Asn Glu
1               5                   10                  15

Glu Arg Thr Met Thr Glu Ala Glu Val Arg Leu Phe Tyr
            20                  25

<210> SEQ ID NO 331
<211> LENGTH: 26
<212> TYPE: PRT
<213> ORGANISM: Artificial Sequence
<220> FEATURE:
<223> OTHER INFORMATION: NME10A1

<400> SEQUENCE: 331

Gly Phe Phe Leu Val Gln Thr Lys Glu Val Ser Met Lys Ala Glu Asp
1               5                   10                  15

Ala Gln Arg Val Phe Arg Glu Lys Ala Pro
            20                  25

<210> SEQ ID NO 332
<211> LENGTH: 30
<212> TYPE: PRT
<213> ORGANISM: Artificial Sequence
<220> FEATURE:
<223> OTHER INFORMATION: NME10A2

<400> SEQUENCE: 332
```

```
<210> SEQ ID NO 333
<211> LENGTH: 16
<212> TYPE: PRT
<213> ORGANISM: Artificial Sequence
<220> FEATURE:
<223> OTHER INFORMATION: NME10A3

<400> SEQUENCE: 333

Glu Ala Asn Arg Ser Ile Val Pro Ile Ser Arg Gly Gln Arg Gln Lys
1               5                   10                  15
Ser Ser Asp Glu Ser Cys Leu Val Val Leu Phe Ala Gly Asp
            20                  25                  30

<210> SEQ ID NO 333
<211> LENGTH: 16
<212> TYPE: PRT
<213> ORGANISM: Artificial Sequence
<220> FEATURE:
<223> OTHER INFORMATION: NME10A3

<400> SEQUENCE: 333

Ile Gln Asp Cys Glu Asn Cys Asn Ile Tyr Ile Phe Asp His Ser Ala
1               5                   10                  15

<210> SEQ ID NO 334
<211> LENGTH: 30
<212> TYPE: PRT
<213> ORGANISM: Artificial Sequence
<220> FEATURE:
<223> OTHER INFORMATION: NME10B1

<400> SEQUENCE: 334

Glu Leu Ala Phe Gln Phe Lys Asp Ala Gly Leu Ser Ile Phe Asn Asn
1               5                   10                  15
Thr Trp Ser Asn Ile His Asp Phe Thr Pro Val Asp Cys Thr
            20                  25                  30

<210> SEQ ID NO 335
<211> LENGTH: 363
<212> TYPE: DNA
<213> ORGANISM: Artificial Sequence
<220> FEATURE:
<223> OTHER INFORMATION: 8F9A4A3 Heavy chain variable region sequence
      mouse

<400> SEQUENCE: 335
gtccagctgc aacagtctgg acctgaactg gtgaagcctg ggcttcagt gaagatatcc      60 tgcaagactt ctggaaacac attcactgaa tacaccatgc actgggtgaa gcagagccat     120
ggaaagagcc ttgagtggat tggaggtttt aatcctaaca atggtgttac taactacaac    180
cagaagttca gggcaaggc cacattgact gtagacaagt cctccagcac agcctacatg     240
gagctccgca gcctgacatc tgaggattct gcagtctatt actgtgcaag acggtactac    300
catagtctct acgtgtttta ctttgactac tggggccaag gcaccactct cacagtctcc    360
tca                                                                  363

<210> SEQ ID NO 336
<211> LENGTH: 294
<212> TYPE: DNA
<213> ORGANISM: Artificial Sequence
<220> FEATURE:
<223> OTHER INFORMATION: IGHV1-24*01 V-REGION sequence human (closest
      match hu antibody sequence)

<400> SEQUENCE: 336
caggtccagc tggtacagtc tggggctgag gtgaagaagc ctggggcctc agtgaaggtc      60
tcctgcaagg tttccggata caccctcact gaattatcca tgcactgggt gcgacaggct    120
cctggaaaag gcttgagtg gatgggaggt tttgatcctg aagatggtga aacaatctac     180
gcacagaagt tccagggcag agtcaccatg accgaggaca catctacaga cacagcctac    240
```

```
atggagctga gcagcctgag atctgaggac acggccgtgt attactgtgc aaca      294
```

<210> SEQ ID NO 337
<211> LENGTH: 45
<212> TYPE: DNA
<213> ORGANISM: Artificial Sequence
<220> FEATURE:
<223> OTHER INFORMATION: IGHJ4*01 J-REGION sequence human (closest match hu antibody sequence)

<400> SEQUENCE: 337

```
tactttgact actggggcca aggaaccctg gtcaccgtct cctca                 45
```

<210> SEQ ID NO 338
<211> LENGTH: 366
<212> TYPE: DNA
<213> ORGANISM: Artificial Sequence
<220> FEATURE:
<223> OTHER INFORMATION: humanized 8F9A4A3 Heavy chain variable region sequence

<400> SEQUENCE: 338

```
caggtccagc tggtacagtc tggggctgag gtgaagaagc ctggggcctc agtgaaggtc      60
tcctgcaagg tttccggaaa cacattcact gaatacacca tgcactgggt gcgacaggct     120
cctggaaaag gcttgagtg gatgggaggt tttaatccta caatggtgt tactaactac      180
aaccagaagt tcaagggcag agtcaccatg accgaggaca catctacaga cacagcctac    240
atggagctga gcagcctgag atctgaggac acggccgtgt attactgtgc aagacggtac    300
taccatagtc tctacgtgtt ttactttgac tactggggcc aaggaaccct ggtcaccgtc    360
tcctca                                                               366
```

<210> SEQ ID NO 339
<211> LENGTH: 366
<212> TYPE: DNA
<213> ORGANISM: Artificial Sequence
<220> FEATURE:
<223> OTHER INFORMATION: humanized 8F9A4A3 Heavy chain variable region sequence (codon optimized)

<400> SEQUENCE: 339

```
caggttcagc tggttcagtc tggcgccgaa gtgaagaaac ctggcgcctc tgtgaaggtg      60
tcctgcaagg tgtccggaaa taccttcacc gagtacacca tgcactgggt ccgacaggcc    120
cctggcaaag gacttgaatg gatgggcggc ttcaacccca caacggcgt gaccaactac    180
aaccagaaat tcaagggccg cgtgaccatg accgaggaca aagcacaga caccgcctac    240
atggaactga gcagcctgag aagcgaggac accgccgtgt actactgcgc cagaaggtac    300
taccacagcc tgtacgtgtt ctacttcgac tactggggcc agggcaccct ggtcacagtt    360
tcttct                                                               366
```

<210> SEQ ID NO 340
<211> LENGTH: 366
<212> TYPE: DNA
<213> ORGANISM: Artificial Sequence
<220> FEATURE:
<223> OTHER INFORMATION: Modified humanized 8F9A4A3 Heavy chain variable region sequence)

<400> SEQUENCE: 340

```
caggtccagc tggtacagtc tggggctgag gtgaagaagc ctggggcctc agtgaaggtc      60
tcctgcaagg tttccggaaa cacattcact gaatacacca tgcactgggt gcgacaggct     120
```

```
cctggaaaag ggcttgagtg gattggaggt tttaatccta caatggtgt tactaactac    180 aaccagaagt tcaagggcaa agtcaccctg accgtggaca catctagcag cacagcctac    240
atggagctga gcagcctgag atctgaggac acggccgtgt attactgtgc aagacggtac    300
taccatagtc tctacgtgtt ttactttgac tactggggcc aaggaaccct ggtcaccgtc    360
tcctca                                                               366
```

<210> SEQ ID NO 341
<211> LENGTH: 366
<212> TYPE: DNA
<213> ORGANISM: Artificial Sequence
<220> FEATURE:
<223> OTHER INFORMATION: Modified humanized 8F9A4A3 Heavy chain variable
region sequence (codon optimized)

<400> SEQUENCE: 341

```
caggttcagc tggttcagtc tggcgccgaa gtgaagaaac ctggcgcctc tgtgaaggtg    60
tcctgcaagg tgtccggaaa taccttcacc gagtacacca tgcactgggt ccgacaggcc    120
cctggcaaag gactggaatg gatcggcggc ttcaacccca caacggcgt gaccaactac    180 aaccagaaat tcaagggcaa agtgaccctg accgtggaca ccagcagcag cacagcctac    240
atggaactga gcagcctgag aagcgaggac accgccgtgt actactgcgc cagaaggtac    300
taccacagcc tgtacgtgtt ctacttcgac tactggggcc agggcaccct ggtcacagtt    360
tcttct                                                               366
```

<210> SEQ ID NO 342
<211> LENGTH: 324
<212> TYPE: DNA
<213> ORGANISM: Artificial Sequence
<220> FEATURE:
<223> OTHER INFORMATION: 8F9A4A3 Light chain variable region sequence
mouse

<400> SEQUENCE: 342

```
gaaacaactg tgacccagtc tccagcatcc ctgtccatgg ctataggaga aaaagtcacc    60
atcagatgca taaccagcac tgatattgat gatgatatga actggtacca gcagaagcca    120
ggggaacctc ctaagctcct tatttcagaa ggcaatactc ttcgtcctgg agtcccatcc    180
cgattctcca gcagtggcta tggtacagat tttgtttta caattgaaaa catgctctca    240
gaagatgttg cagattacta ctgtttgcaa agtgataact gcctctcac gttcggctcg    300 gggacaaagt tggaaataaa acgg                                           324
```

<210> SEQ ID NO 343
<211> LENGTH: 264
<212> TYPE: DNA
<213> ORGANISM: Artificial Sequence
<220> FEATURE:
<223> OTHER INFORMATION: IGKV5-2*01 V-REGION sequence human (closest
match hu antibody sequence)

<400> SEQUENCE: 343

```
gaaacgacac tcacgcagtc tccagcattc atgtcagcga ctccaggaga caaagtcaac    60
atctcctgca aagccagcca agacattgat gatgatatga actggtacca acagaaacca    120
ggagaagctg ctatttcat tattcaagaa gctactactc tcgttcctgg aatcccacct    180
cgattcagtg gcagcgggta tggaacagat tttaccctca caattaataa catagaatct    240
gaggatgctg catattactt ctgt                                           264
```

<210> SEQ ID NO 344
<211> LENGTH: 36
<212> TYPE: DNA
<213> ORGANISM: Artificial Sequence
<220> FEATURE:
<223> OTHER INFORMATION: IGKJ4*02 J-REGION sequence human (closest match hu antibody sequence)

<400> SEQUENCE: 344
ctcacgttcg gcggagggac caaggtggag atcaaa                                 36

<210> SEQ ID NO 345
<211> LENGTH: 324
<212> TYPE: DNA
<213> ORGANISM: Artificial Sequence
<220> FEATURE:
<223> OTHER INFORMATION: humanized 8F9A4A3 Light chain variable region sequence

<400> SEQUENCE: 345
gaaacgacac tcacgcagtc tccagcattc atgtcagcga ctccaggaga caaagtcaac        60
atctcctgca taaccagcac tgatattgat gatgatatga actggtacca acagaaacca      120
ggagaagctg ctattttcat tattcaagaa ggcaatactc ttcgtcctgg aatcccacct      180
cgattcagtg gcagcgggta tggaacagat tttacccctca caattaataa catagaatct     240
gaggatgctg catattactt ctgtttgcaa agtgataact tgcctctcac gttcggcgga      300
gggaccaagg tggagatcaa acgg                                             324

<210> SEQ ID NO 346
<211> LENGTH: 324
<212> TYPE: DNA
<213> ORGANISM: Artificial Sequence
<220> FEATURE:
<223> OTHER INFORMATION: humanized 8F9A4A3 Light chain variable region sequence (codon optimized)

<400> SEQUENCE: 346
gagacaaccc tgacacagag ccctgccttc atgtctgcca cacctggcga caaagtgaac        60
atcagctgca tcaccagcac cgacatcgac gacgacatga ctggtatca gcagaagcct       120 ggcgaggccg ccatcttcat catccaagag ggcaacacac tgcggcctgg catccctcct      180
agattttctg gcagcggcta cggcaccgac ttcaccctga ccatcaacaa catcgagagc      240
gaggacgccg cctactactt ctgcctgcaa agcgacaacc tgcctctgac ctttggcgga      300
ggcaccaagg tggaaatcaa gcgg                                             324

<210> SEQ ID NO 347
<211> LENGTH: 324
<212> TYPE: DNA
<213> ORGANISM: Artificial Sequence
<220> FEATURE:
<223> OTHER INFORMATION: Modified humanized 8F9A4A3 Light chain variable region sequence

<400> SEQUENCE: 347
gaaacgacag tgacgcagtc tccagcattc atgtcagcga ctccaggaga caaagtcacc        60
atctcctgca taaccagcac tgatattgat gatgatatga actggtacca acagaaacca      120
ggagaagctg ctattctgct gattagcgaa ggcaatactc ttcgtcctgg aatcccacct      180
cgattcagta gcagcgggta tggaacagat tttacccctca caattaataa catagaatct     240

```
gaggatgctg catattactt ctgtttgcaa agtgataact tgcctctcac gttcggcgga      300
gggaccaagg tggagatcaa acgg                                             324
```

<210> SEQ ID NO 348
<211> LENGTH: 324
<212> TYPE: DNA
<213> ORGANISM: Artificial Sequence
<220> FEATURE:
<223> OTHER INFORMATION: Modified humanized 8F9A4A3 Light chain variable
      region sequence (codon optimized)

<400> SEQUENCE: 348

```
gagacaaccg tgacacagag ccctgccttc atgtctgcca cacctggcga caaagtgacc      60
atcagctgca tcaccagcac cgacatcgac gacgacatga actggtatca gcagaagcct     120
ggcgaggccg ccatcctgct tatctctgag ggaaacacac tgcggcctgg catccctcct     180
agattttcca gcagcggcta cggcaccgac ttcaccctga ccatcaacaa catcgagagc     240
gaggacgccg cctactactt ctgcctgcaa agcgacaacc tgcctctgac ctttggcgga     300
ggcaccaagg tggaaatcaa gcgg                                            324
```

<210> SEQ ID NO 349
<211> LENGTH: 735
<212> TYPE: DNA
<213> ORGANISM: Artificial Sequence
<220> FEATURE:
<223> OTHER INFORMATION: Modified humanized 8F9A4A3 sequence (codon
      optimized) - humanized heavy and light chains joined via a
      flexible linker

<400> SEQUENCE: 349

```
caggttcagc tggttcagtc tggcgccgaa gtgaagaaac tggcgcctc tgtgaaggtg       60 tcctgcaagg tgtccggaaa taccttcacc gagtacacca tgcactgggt ccgacaggcc     120
cctggcaaag gactggaatg gatcggcggc ttcaacccca caacggcgt gaccaactac      180 aaccagaaat tcaagggcaa agtgaccctg accgtggaca ccagcagcag cacagcctac     240
atggaactga gcagcctgag aagcgaggac accgccgtgt actactgcgc cagaaggtac     300
taccacagcc tgtacgtgtt ctacttcgac tactgggggcc agggcaccct ggtcacagtt     360
tcttctggcg gtggcggaag cggaggcggt ggctccggtg gcggaggcag cgaaacgaca     420
gtgacgcagt ctccagcatt catgtcagcg actccaggag acaaagtcac catctcctgc     480
ataaccagca ctgatattga tgatgatatg aactggtacc aacagaaacc aggagaagct     540
gctattctgc tgattagcga aggcaatact cttcgtcctg gaatcccacc tcgattcagt     600
agcagcgggt atggaacaga ttttaccctc acaattaata acatagaatc tgaggatgct     660
gcatattact tctgtttgca aagtgataac ttgcctctca cgttcggcgg agggaccaag     720
gtggagatca aacgg                                                      735
```

<210> SEQ ID NO 350
<211> LENGTH: 357
<212> TYPE: DNA
<213> ORGANISM: Artificial Sequence
<220> FEATURE:
<223> OTHER INFORMATION: 8F9A5A1 Heavy chain variable region sequence

<400> SEQUENCE: 350

```
atccagttgg tgcagtctgg acctgagctg aagaagcctg agagacagt caagatctcc       60 tgcaaggctt ctgggtatac cttcacaaac tatggaatga ctgggtgaa gcaggctcca     120
```

```
ggaaagggtt taaagtggat gggctggata acaccctaca ctggagagcc aacatatgtt    180
gatgacttca agggacggtt tgccttctct ttggaaacct ctgccaccac tgcctatttg    240
cagatcaaca acctcaaaaa tgaggacacg tctacatatt tctgtgcaag attgagggggg    300 atacgaccgg gtcccttggc ttactggggc aagggactc tggtcactgt ctctgca        357
```

<210> SEQ ID NO 351
<211> LENGTH: 294
<212> TYPE: DNA
<213> ORGANISM: Artificial Sequence
<220> FEATURE:
<223> OTHER INFORMATION: IGHV7-81*01 V-REGION sequence

<400> SEQUENCE: 351

```
caggtgcagc tggtgcagtc tggccatgag gtgaagcagc tggggcctc agtgaaggtc     60 tcctgcaagg cttctggtta cagtttcacc acctatggta tgaattgggt gccacaggcc    120
cctggacaag gcttgagtg gatgggatgg ttcaacacct acactgggaa cccaacatat    180
gcccagggct tcacaggacg gtttgtcttc tccatgacca cctctgccag cacagcatac    240
ctgcagatca gcagcctaaa ggctgaggac atggccatgt attactgtgc gaga           294
```

<210> SEQ ID NO 352
<211> LENGTH: 45
<212> TYPE: DNA
<213> ORGANISM: Artificial Sequence
<220> FEATURE:
<223> OTHER INFORMATION: IGHJ4*03 J-REGION sequence

<400> SEQUENCE: 352

```
tactttgact actggggcca agggaccctg gtcaccgtct cctca                     45
```

<210> SEQ ID NO 353
<211> LENGTH: 360
<212> TYPE: DNA
<213> ORGANISM: Artificial Sequence
<220> FEATURE:
<223> OTHER INFORMATION: humanized 8F9A5A1 Heavy chain variable region
      sequence

<400> SEQUENCE: 353

```
caggtgcagc tggtgcagtc tggccatgag gtgaagcagc tggggcctc agtgaaggtc     60 tcctgcaagg cttctgggta taccttcaca aactatggaa tgaactgggt gccacaggcc    120
cctggacaag gcttgagtg gatgggatgg ataaacacct acactggaga gccaacatat    180
gttgatgact tcaagggacg gtttgtcttc tccatgacca cctctgccag cacagcatac    240
ctgcagatca gcagcctaaa ggctgaggac atggccatgt attactgtgc aagattgagg    300
gggatacgac cgggtccctt ggcttactgg ggccaaggga ccctggtcac cgtctcctca    360
```

<210> SEQ ID NO 354
<211> LENGTH: 360
<212> TYPE: DNA
<213> ORGANISM: Artificial Sequence
<220> FEATURE:
<223> OTHER INFORMATION: humanized 8F9A5A1 Heavy chain variable region
      sequence (codon optimized)

<400> SEQUENCE: 354

```
caggttcagc tggtgcagtc tggccacgaa gtgaaacagc tggcgcctc tgtgaaggtg     60 tcctgtaaag ccagcggcta cacctttacc aactacggaa tgaactgggt gcccaggct    120 cctggacaag gcttggaatg gatgggctgg atcaacacct acaccggcga gcctacctac    180
```

```
gtggacgact tcaagggcag attcgtgttc agcatggaca ccagcgccag cacagcctac    240
ctgcagatca gctctctgaa ggccgaggat atggccatgt actactgcgc cagactgaga    300
ggcatcagac ctggacctct ggcctattgg ggacagggca cactggtcac agtgtcctct    360
```

<210> SEQ ID NO 355
<211> LENGTH: 360
<212> TYPE: DNA
<213> ORGANISM: Artificial Sequence
<220> FEATURE:
<223> OTHER INFORMATION: Modified humanized 8F9A5A1 Heavy chain variable
      region sequence

<400> SEQUENCE: 355

```
cagatccagc tggtgcagtc tggccccgag gtgaagcagc ctggggcctc agtgaaggtc    60
tcctgcaagg cttctgggta taccttcaca aactatggaa tgaactgggt gaagcaggcc    120
cctggacaag gcttgagtg gatgggatgg ataaacacct acactggaga gccaacatat    180
gttgatgact caagggacg gtttgccttc tccatggaca cctctgccag cacagcatac    240
ctgcagatca gcagcctaaa ggctgaggac accgccacct attactgtgc aagattgagg    300
gggatacgac cggtcccctt ggcttactgg ggccaaggga ccctggtcac cgtctcctca    360
```

<210> SEQ ID NO 356
<211> LENGTH: 360
<212> TYPE: DNA
<213> ORGANISM: Artificial Sequence
<220> FEATURE:
<223> OTHER INFORMATION: Modified humanized 8F9A5A1 Heavy chain variable
      region sequence (codon optimized)

<400> SEQUENCE: 356

```
cagattcagc tggtgcagtc tggccccgaa gtgaaacaac ctggcgcctc tgtgaaggtg    60
tcctgcaagg ccagcggcta cacctttacc aactacggca tgaactgggt caagcaggcc    120
cctggacaag gcctggaatg gatgggctgg atcaacacct acaccggcga gcctacctac    180
gtggacgact tcaagggcag attcgccttc agcatggaca ccagcgccag cacagcctac    240
ctgcagatca gctctctgaa ggccgaggac accgccacct actactgtgc cagactgaga    300
ggcatcagac ccggacctct ggcctattgg ggacagggaa cactggtcac cgtgtcctct    360
```

<210> SEQ ID NO 357
<211> LENGTH: 321
<212> TYPE: DNA
<213> ORGANISM: Artificial Sequence
<220> FEATURE:
<223> OTHER INFORMATION: 8F9A5A1 Light chain variable region sequence

<400> SEQUENCE: 357

```
gaaattttgc tcacccagtc tccagcaatc atagctgcat ctcctgggga aaggtcacc    60 atcacctgca gtgccagctc aagtgtaagt tacatgaact ggtaccagca gaaaccagga    120
tcctccccca aaatatggat ttatggtata tccaacctgg cttctggagt tcctgctcgc    180
ttcagtggca gtgggtctgg gacatctttc tctttcacaa tcaacagcat ggaggctgaa    240
gatgttgcca cttattactg tcagcaaagg agtagttacc cacccacgtt cggagggggg    300
accaagctgg aaataaaacg g                                              321
```

<210> SEQ ID NO 358
<211> LENGTH: 279
<212> TYPE: DNA

<213> ORGANISM: Artificial Sequence
<220> FEATURE:
<223> OTHER INFORMATION: IGKV3D-15*02 V-REGION sequence

<400> SEQUENCE: 358

```
gaaatagtga tgatgcagtc tccagccacc ctgtctgtgt ctccagggga aagagccacc      60
ctctcctgca gggccagtca gagtgttagc agcaacttag cctggtacca gcagaaacct    120
ggccaggctc ccaggctcct catctatggt gcatccacca gggccactgg catcccagcc    180
aggttcagtg gcagtgggtc tgggacagag ttcactctca ccatcagcag cctgcagtct    240
gaagattttg cagtttatta ctgtcagcag tataataac                            279
```

<210> SEQ ID NO 359
<211> LENGTH: 36
<212> TYPE: DNA
<213> ORGANISM: Artificial Sequence
<220> FEATURE:
<223> OTHER INFORMATION: IGKJ4*02 J-REGION sequence

<400> SEQUENCE: 359

```
ctcacgttcg gcgagggac caaggtggag atcaaa                                 36
```

<210> SEQ ID NO 360
<211> LENGTH: 321
<212> TYPE: DNA
<213> ORGANISM: Artificial Sequence
<220> FEATURE:
<223> OTHER INFORMATION: humanized 8F9A5A1 Light chain variable region
      sequence

<400> SEQUENCE: 360

```
gaaatagtga tgatgcagtc tccagccacc ctgtctgtgt ctccagggga aagagccacc      60
ctctcctgca gtgccagctc aagtgtaagt tacatgaact ggtaccagca gaaacctggc    120
caggctccca ggctcctcat ctatggtata tccaacctgg cttctggcat cccagccagg    180
ttcagtggca gtgggtctgg gacagagttc actctcacca tcagcagcct gcagtctgaa    240
gattttgcag tttattactg tcagcaaagg agtagttacc cacccacgtt cggcggaggg    300
accaaggtgg agatcaaacg g                                               321
```

<210> SEQ ID NO 361
<211> LENGTH: 321
<212> TYPE: DNA
<213> ORGANISM: Artificial Sequence
<220> FEATURE:
<223> OTHER INFORMATION: humanized 8F9A5A1 Light chain variable region
      sequence (codon optimized)

<400> SEQUENCE: 361

```
gagatcgtga tgatgcagag ccccgccaca ctgagtgtgt ctccaggcga aagagccaca      60
ctgtcctgta gcgccagcag cagcgtgtcc tacatgaact ggtatcagca gaagcccgga    120
caggccccta gactgctgat ctacggcatc agcaatctgg ccagcggcat ccctgccaga    180
ttttctggct ctggctccgg caccgagttc accctgacaa tctctagcct gcagagcgag    240
gacttcgccg tgtactactg ccagcagaga agcagctacc ctcctacctt tggcggaggc    300
accaaggtgg aaatcaagcg g                                               321
```

<210> SEQ ID NO 362
<211> LENGTH: 321
<212> TYPE: DNA
<213> ORGANISM: Artificial Sequence

```
<220> FEATURE:
<223> OTHER INFORMATION: Modified humanized 8F9A5A1 Light chain variable
      region sequence

<400> SEQUENCE: 362
gaaatagtgc tgacccagtc tccagccacc ctgtctgtgt ctccagggga aagagccacc      60
ctctcctgca gtgccagctc aagtgtaagt tacatgaact ggtaccagca gaaacctggc     120
caggctccca ggctctggat ctatggtata tccaacctgg cttctggcat cccagccagg     180
ttcagtggca gtgggtctgg acaagcttc agcctcacca tcagcagcct gcagtctgaa      240
gattttgcag tttattactg tcagcaaagg agtagttacc cacccacgtt cggcggaggg     300
accaaggtgg agatcaaacg g                                                321

<210> SEQ ID NO 363
<211> LENGTH: 321
<212> TYPE: DNA
<213> ORGANISM: Artificial Sequence
<220> FEATURE:
<223> OTHER INFORMATION: Modified humanized 8F9A5A1 Light chain variable
      region sequence (codon optimized)

<400> SEQUENCE: 363
gagatcgtgc tgacacagtc tcccgccaca ctgagtgtgt ctccaggcga aagagccaca     60
ctgtcctgta gcgccagcag cagcgtgtcc tacatgaact ggtatcagca gaagcccgga    120
caggccccta gactgtggat ctacggcatc agcaatctgg ccagcggcat ccctgccaga    180
ttttctggct ctggctccgg caccagcttc agcctgacaa tcagcagcct gcagagcgag    240
gacttcgccg tgtactactg ccagcagaga agcagctacc ctcctacctt tggcggaggc    300
accaaggtgg aaatcaagcg g                                                321

<210> SEQ ID NO 364
<211> LENGTH: 726
<212> TYPE: DNA
<213> ORGANISM: Artificial Sequence
<220> FEATURE:
<223> OTHER INFORMATION: Modified humanized 8F9A5A1 scFV sequence (codon
      optimized)

<400> SEQUENCE: 364
cagattcagc tggtgcagtc tggccccgaa gtgaaacaac tggcgcctc tgtgaaggtg      60 tcctgcaagg ccagcggcta cacctttacc aactacggca tgaactgggt caagcaggcc    120
cctggacaag gcctggaatg gatgggctgg atcaacacct acaccggcga gcctacctac    180
gtggacgact tcaagggcag attcgccttc agcatggaca ccagcgccag cacagcctac    240
ctgcagatca gctctctgaa ggccgaggac accgccacct actactgtgc cagactgaga    300
ggcatcagac ccggacctct ggcctattgg ggacagggaa cactggtcac cgtgtcctct    360
ggcggtggcg gaagcggagg cggtggctcc ggtggcggag cagcgagat cgtgctgaca    420 cagtctcccg ccacactgag tgtgtctcca ggcgaaagag ccacactgtc ctgtagcgcc    480
agcagcagcg tgtcctacat gaactggtat cagcagaagc ccggacaggc cctagactg     540 tggatctacg gcatcagcaa tctggccagc ggcatccctg ccagatttc tggctctggc    600 tccggcacca gcttcagcct gacaatcagc agcctgcaga gcgaggactt cgccgtgtac    660
tactgccagc agagaagcag ctaccctcct acctttggcg gaggcaccaa ggtggaaatc    720
aagcgg                                                                 726
```

```
<210> SEQ ID NO 365
<211> LENGTH: 363
<212> TYPE: DNA
<213> ORGANISM: Artificial Sequence
<220> FEATURE:
<223> OTHER INFORMATION: 8H5H5G4 Heavy chain variable region sequence

<400> SEQUENCE: 365
gtccagctgc aacagtctgg acctgatctg gtgaagcctg ggacttcagt gaagatatcc      60
tgtaagactt ctggaaacac attcactgaa tacaccatgc actgggtgaa gcagagccat     120
ggaaagagcc ttgagtggat tggaggtttt aatcctaaca tggtgttac taactacaac      180 cagaagttca gggcaaggc cacattgact gtagacaagt cctccagcac agcctacatg      240
gagctccgca gcctgacatc tgaggattct gcagtctatt actgtgcaag acgttactac     300
catagtacct acgtgttcta ctttgactcc tggggccaag gcaccactct cacagtctcc     360
tca                                                                  363

<210> SEQ ID NO 366
<211> LENGTH: 294
<212> TYPE: DNA
<213> ORGANISM: Artificial Sequence
<220> FEATURE:
<223> OTHER INFORMATION: IGHV1-24*01 V-REGION sequence

<400> SEQUENCE: 366
caggtccagc tggtacagtc tggggctgag gtgaagaagc ctggggcctc agtgaaggtc      60
tcctgcaagg tttccggata caccctcact gaattatcca tgcactgggt gcgacaggct     120
cctggaaaag gcttgagtg gatgggaggt tttgatcctg aagatggtga acaatctac       180 gcacagaagt tccagggcag agtcaccatg accgaggaca catctacaga cacagcctac     240
atggagctga gcagcctgag atctgaggac acggccgtgt attactgtgc aaca           294

<210> SEQ ID NO 367
<211> LENGTH: 45
<212> TYPE: DNA
<213> ORGANISM: Artificial Sequence
<220> FEATURE:
<223> OTHER INFORMATION: IGHJ4*03 J-REGION sequence

<400> SEQUENCE: 367
tactttgact actggggcca agggaccctg gtcaccgtct cctca                      45

<210> SEQ ID NO 368
<211> LENGTH: 366
<212> TYPE: DNA
<213> ORGANISM: Artificial Sequence
<220> FEATURE:
<223> OTHER INFORMATION: Humanized 8H5H5G4 Heavy chain variable region
      sequence

<400> SEQUENCE: 368
caggtccagc tggtacagtc tggggctgag gtgaagaagc ctggggcctc agtgaaggtc      60
tcctgcaagg tttccggaaa cacattcact gaatacacca tgcactgggt gcgacaggct     120
cctggaaaag gcttgagtg gatgggaggt tttaatccta acaatggtgt tactaactac      180
aaccagaagt tcaagggcag agtcaccatg accgaggaca catctacaga cacagcctac     240
atggagctga gcagcctgag atctgaggac acggccgtgt attactgtgc aagacgttac     300
taccatagta cctacgtgtt ctactttgac tcctggggcc aagggaccct ggtcaccgtc     360
tcctca                                                               366
```

<210> SEQ ID NO 369
<211> LENGTH: 366
<212> TYPE: DNA
<213> ORGANISM: Artificial Sequence
<220> FEATURE:
<223> OTHER INFORMATION: Humanized 8H5H5G4 Heavy chain variable region
    sequence (codon optimized)

<400> SEQUENCE: 369

```
caggttcagc tggttcagtc tggcgccgaa gtgaagaaac ctggcgcctc tgtgaaggtg      60
tcctgcaagg tgtccggaaa taccttcacc gagtacacca tgcactgggt ccgacaggcc     120
cctggcaaag acttgaatg gatgggcggc ttcaacccca caacggcgt gaccaactac      180
aaccagaaat tcaagggccg cgtgaccatg accgaggaca agcacaga caccgcctac      240
atggaactga gcagcctgag aagcgaggac accgccgtgt actactgcgc cagaaggtac      300
taccacagca cctacgtgtt ctacttcgac agctggggcc agggcacact ggtcacagtt     360
tcttct                                                                366
```

<210> SEQ ID NO 370
<211> LENGTH: 366
<212> TYPE: DNA
<213> ORGANISM: Artificial Sequence
<220> FEATURE:
<223> OTHER INFORMATION: Modified Humanized 8H5H5G4 Heavy chain variable
    region sequence

<400> SEQUENCE: 370

```
caggtccagc tggtacagtc tggggctgag gtgaagaagc ctggggcctc agtgaaggtc      60
tcctgcaagg tttccggaaa cacattcact gaatacacca tgcactgggt gcgacaggct     120
cctggaaaag ggcttgagtg gatcggaggt tttaatccta caatggtgt tactaactac      180
aaccagaagt tcaagggcaa ggtcaccctg accgtggaca catctagcag cacagcctac      240
atggagctga gcagcctgag atctgaggac acggccgtgt attactgtgc aagacgttac      300
taccatagta cctacgtgtt ctactttgac tcctggggcc aagggaccct ggtcaccgtc      360
tcctca                                                                366
```

<210> SEQ ID NO 371
<211> LENGTH: 366
<212> TYPE: DNA
<213> ORGANISM: Artificial Sequence
<220> FEATURE:
<223> OTHER INFORMATION: Modified Humanized 8H5H5G4 Heavy chain variable
    region sequence (codon optimized)

<400> SEQUENCE: 371

```
caggttcagc tggttcagtc tggcgccgaa gtgaagaaac ctggcgcctc tgtgaaggtg      60
tcctgcaagg tgtccggaaa taccttcacc gagtacacca tgcactgggt ccgacaggcc     120
cctggcaaag actggaatg gatcggcggc ttcaacccca caacggcgt gaccaactac      180
aaccagaaat tcaagggcaa agtgaccctg accgtggaca ccagcagcag cacagcctac      240
atggaactga gcagcctgag aagcgaggac accgccgtgt actactgcgc cagaaggtac      300
taccacagca cctacgtgtt ctacttcgac agctggggcc agggcacact ggtcacagtt     360
tcttct                                                                366
```

<210> SEQ ID NO 372
<211> LENGTH: 324

<212> TYPE: DNA
<213> ORGANISM: Artificial Sequence
<220> FEATURE:
<223> OTHER INFORMATION: 8H5H5G4 Light chain variable region sequence

<400> SEQUENCE: 372

```
gatatccaga tgacacagac tacatcctcc ctgtctgcct ctctgggaga cagagtcacc    60
atcagttgca gtgcaagtca gggcattagc aattatttaa actggtttca gcagaaacca   120
gatggaacta ttaagctcct gatctattac acatcaagtt tacattcagg agtcccatca   180
aggttcagtg gcagtgggtc tgggacagat tattctctca ccatcagtaa tgtggaacct   240
gaagatattg ccacttacta ttgtcagcag tatagtaagc ttccttacac gttcggaggg   300
gggaccaagc tggagataaa acgg                                          324
```

<210> SEQ ID NO 373
<211> LENGTH: 285
<212> TYPE: DNA
<213> ORGANISM: Artificial Sequence
<220> FEATURE:
<223> OTHER INFORMATION: IGKV1-27*01 V-REGION sequence

<400> SEQUENCE: 373

```
gacatccaga tgacccagtc tccatcctcc ctgtctgcat ctgtaggaga cagagtcacc    60
atcacttgcc gggcgagtca gggcattagc aattatttag cctggtatca gcagaaacca   120
gggaaagttc ctaagctcct gatctatgct gcatccactt gcaatcagg ggtcccatct   180
cggttcagtg gcagtggatc tgggacagat ttcactctca ccatcagcag cctgcagcct   240
gaagatgttg caacttatta ctgtcaaaag tataacagtg ccct                    285
```

<210> SEQ ID NO 374
<211> LENGTH: 36
<212> TYPE: DNA
<213> ORGANISM: Artificial Sequence
<220> FEATURE:
<223> OTHER INFORMATION: IGKJ4*02 J-REGION sequence

<400> SEQUENCE: 374

```
ctcacgttcg gcggagggac caaggtggag atcaaa                              36
```

<210> SEQ ID NO 375
<211> LENGTH: 324
<212> TYPE: DNA
<213> ORGANISM: Artificial Sequence
<220> FEATURE:
<223> OTHER INFORMATION: humanized 8H5H5G4 Light chain variable region
      sequence

<400> SEQUENCE: 375

```
gacatccaga tgacccagtc tccatcctcc ctgtctgcat ctgtaggaga cagagtcacc    60
atcacttgca gtgcaagtca gggcattagc aattatttaa actggtatca gcagaaacca   120
gggaaagttc ctaagctcct gatctattac acatcaagtt tacattcagg ggtcccatct   180
cggttcagtg gcagtggatc tgggacagat ttcactctca ccatcagcag cctgcagcct   240
gaagatgttg caacttatta ctgtcagcag tatagtaagc ttccttacac gttcggcgga   300
gggaccaagg tggagatcaa acgg                                          324
```

<210> SEQ ID NO 376
<211> LENGTH: 324
<212> TYPE: DNA
<213> ORGANISM: Artificial Sequence
<220> FEATURE:
<223> OTHER INFORMATION: humanized 8H5H5G4 Light chain variable region sequence (codon optimized)

<400> SEQUENCE: 376
gacatccaga tgacacagag ccctagcagc ctgtctgcca gcgtgggaga cagagtgacc    60
atcacatgta gcgccagcca gggcatcagc aactacctga actggtatca gcagaaaccc   120
ggcaaggtgc ccaagctgct gatctactac accagcagcc tgcacagcgg cgtgccaagc   180 agatttctg gcagcggctc tggcaccgac ttcaccctga ccatatctag cctgcagcct    240
gaggacgtgg ccacctacta ctgtcagcag tacagcaagc tgccctacac ctttggcgga   300
ggcaccaagg tggaaatcaa gcgg                                           324

<210> SEQ ID NO 377
<211> LENGTH: 324
<212> TYPE: DNA
<213> ORGANISM: Artificial Sequence
<220> FEATURE:
<223> OTHER INFORMATION: Modified humanized 8H5H5G4 Light chain variable region sequence

<400> SEQUENCE: 377
gacatccaga tgacccagtc tccatcctcc ctgtctgcat ctgtaggaga cagagtcacc    60
atcacttgca gtgcaagtca gggcattagc aattatttaa actggtatca gcagaaacca   120
gggaaagttc ctaagctcct gatctattac acatcaagtt tacattcagg ggtcccatct   180
cggttcagtg gcagtggatc tgggacagat tacactctca ccatcagcag cctgcagcct   240
gaagatgttg caacttatta ctgtcagcag tatagtaagc ttccttacac gttcggcgga   300
gggaccaagg tggagatcaa acgg                                           324

<210> SEQ ID NO 378
<211> LENGTH: 324
<212> TYPE: DNA
<213> ORGANISM: Artificial Sequence
<220> FEATURE:
<223> OTHER INFORMATION: Modified humanized 8H5H5G4 Light chain variable region sequence (codon optimized)

<400> SEQUENCE: 378
gacatccaga tgacacagag ccctagcagc ctgtctgcca gcgtgggaga cagagtgacc    60
atcacatgta gcgccagcca gggcatcagc aactacctga actggtatca gcagaaaccc   120
ggcaaggtgc ccaagctgct gatctactac accagcagcc tgcacagcgg cgtgccaagc   180 agatttctg gcagcggctc tggcaccgac tacaccctga ccatatctag cctgcagcct    240
gaggacgtgg ccacctacta ctgtcagcag tacagcaagc tgccctacac ctttggcgga   300
ggcaccaagg tggaaatcaa gcgg                                           324

<210> SEQ ID NO 379
<211> LENGTH: 735
<212> TYPE: DNA
<213> ORGANISM: Artificial Sequence
<220> FEATURE:
<223> OTHER INFORMATION: Modified humanized 8H5H5G4 scFV sequence (codon optimized)

<400> SEQUENCE: 379
caggttcagc tggttcagtc tggcgccgaa gtgaagaaac ctggcgcctc tgtgaaggtg    60
tcctgcaagg tgtccggaaa taccttcacc gagtacacca tgcactgggt ccgacaggcc   120

```
cctggcaaag gactggaatg gatcggcggc ttcaacccca caacggcgt gaccaactac    180 aaccagaaat tcaagggcaa agtgaccctg accgtggaca ccagcagcag cacagcctac    240
atggaactga gcagcctgag aagcgaggac accgccgtgt actactgcgc cagaaggtac    300
taccacagca cctacgtgtt ctacttcgac agctggggcc agggcacact ggtcacagtt    360
tcttctggcg gtggcggaag cggaggcggt ggctccggtg gcggaggcag cgacatccag    420
atgacacaga gccctagcag cctgtctgcc agcgtgggag acagagtgac catcacatgt    480
agcgccagcc agggcatcag caactacctg aactggtatc agcagaaacc cggcaaggtg    540
cccaagctgc tgatctacta caccagcagc ctgcacagcg gcgtgccaag cagattttct    600
ggcagcggct ctggcaccga ctacaccctg accatatcta gcctgcagcc tgaggacgtg    660
gccacctact actgtcagca gtacagcaag ctgccctaca cctttggcgg aggcaccaag    720
gtggaaatca agcgg                                                    735

<210> SEQ ID NO 380
<211> LENGTH: 993
<212> TYPE: DNA
<213> ORGANISM: Artificial Sequence
<220> FEATURE:
<223> OTHER INFORMATION: Human IgG1 heavy chain constant region
      sequence: (for making full antibody - pair with either kappa or
      lambda constant region; 2 plasmids, express together)

<400> SEQUENCE: 380
gctagcacca agggcccatc ggtcttcccc ctggcaccct cctccaagag cacctctggg    60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgaca gtgccctcca gcagcttggg cacccagacc    240
tacatctgca acgtgaatca caagcccagc aacaccaagg tggacaagaa agttgagccc    300
aaatcttgtg acaaaactca cacatgccca ccgtgcccag cacctgaact cctggggggga    360 ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag gcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa tga                                993

<210> SEQ ID NO 381
<211> LENGTH: 981
<212> TYPE: DNA
<213> ORGANISM: Artificial Sequence
<220> FEATURE:
<223> OTHER INFORMATION: Human IgG2 heavy chain constant region
      sequence: (for making full antibody - pair with either kappa or
      lambda constant region; 2 plasmids, express together)

<400> SEQUENCE: 381
```

```
gcctccacca agggcccatc ggtcttcccc ctggcgccct gctccaggag cacctccgag    60
agcacagccg ccctgggctg cctggtcaag gactacttcc ccgaaccggt gacggtgtcg   120
tggaactcag gcgctctgac cagcggcgtg cacaccttcc cagctgtcct acagtcctca   180
ggactctact ccctcagcag cgtggtgacc gtgccctcca gcaacttcgg cacccagacc   240
tacacctgca acgtagatca caagcccagc aacaccaagg tggacaagac agttgagcgc   300
aaatgttgtg tcgagtgccc accgtgccca gcaccacctg tggcaggacc gtcagtcttc   360
ctcttccccc caaaacccaa ggacaccctc atgatctccc ggacccctga ggtcacgtgc   420
gtggtggtgg acgtgagcca cgaagacccc gaggtccagt tcaactggta cgtggacggc   480
gtggaggtgc ataatgccaa gacaaagcca cgggaggagc agttcaacag cacgttccgt   540
gtggtcagcg tcctcaccgt tgtgcaccag gactggctga acggcaagga gtacaagtgc   600
aaggtctcca acaaaggcct cccagccccc atcgagaaaa ccatctccaa aaccaaaggg   660
cagccccgag aaccacaggt gtacaccctg cccccatccc gggaggagat gaccaagaac   720
caggtcagcc tgacctgcct ggtcaaaggc ttctaccccc gcgacatcgc cgtggagtgg   780
gagagcaatg ggcagccgga gaacaactac aagaccacac ctcccatgct ggactccgac   840
ggctccttct tcctctacag caagctcacc gtggacaaga gcaggtggca gcaggggaac   900
gtcttctcat gctccgtgat gcatgaggct ctgcacaacc actacacgca gaagagcctc   960
tccctgtctc cgggtaaata g                                              981

<210> SEQ ID NO 382
<211> LENGTH: 324
<212> TYPE: DNA
<213> ORGANISM: Artificial Sequence
<220> FEATURE:
<223> OTHER INFORMATION: Human Kappa light chain constant region
      sequence

<400> SEQUENCE: 382
aggacggtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgcccc ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg ttag                                          324

<210> SEQ ID NO 383
<211> LENGTH: 321
<212> TYPE: DNA
<213> ORGANISM: Artificial Sequence
<220> FEATURE:
<223> OTHER INFORMATION: Human Lambda light chain constant region
      sequence

<400> SEQUENCE: 383
ggtcagccca aggctgcccc ctcggtcact ctgttcccgc cctcctctga ggagcttcaa    60
gccaacaagg ccacactggt gtgtctcata agtgacttct acccgggagc cgtgacagtg   120
gcctggaagg cagatagcag ccccgtcaag gcgggagtgg agaccaccac accctccaaa   180
caaagcaaca acaagtacgc ggccagcagc tatctgagcc tgacgcctga gcagtggaag   240
tcccacagaa gctacagctg ccaggtcacg catgaaggga gcaccgtgga agagacagtg   300
```
gcccctacag aatgttcata g        321

<210> SEQ ID NO 384
<211> LENGTH: 699
<212> TYPE: DNA
<213> ORGANISM: Artificial Sequence
<220> FEATURE:
<223> OTHER INFORMATION: Human IgG1 Fc region sequence: (to be fused to
      scFv for homo-dimerizes)

<400> SEQUENCE: 384
gagcccaaat cttgtgacaa aactcacaca tgcccaccgt gcccagcacc tgaactcctg        60
gggggaccgt cagtcttcct cttccccca aacccaagg acaccctcat gatctcccgg        120
accctgagg tcacatgcgt ggtggtggac gtgagccacg aagaccctga ggtcaagttc        180
aactggtacg tggacggcgt ggaggtgcat aatgccaaga caaagccgcg ggaggagcag        240
tacaacagca cgtaccgtgt ggtcagcgtc ctcaccgtcc tgcaccagga ctggctgaat        300
ggcaaggagt acaagtgcaa ggtctccaac aaagccctcc cagcccccat cgagaaaacc        360
atctccaaag ccaaagggca gccccgagaa ccacaggtgt acaccctgcc cccatcccgg        420
gaggagatga ccaagaacca ggtcagcctg acctgcctgg tcaaaggctt ctatcccagc        480
gacatcgccg tggagtggga gagcaatggg cagccggaga caactacaa gaccacgcct        540
cccgtgctgg actccgacgg ctccttcttc ctctacagca agctcaccgt ggacaagagc        600
aggtggcagc aggggaacgt cttctcatgc tccgtgatgc atgaggctct gcacaaccac        660
tacacgcaga gagcctctc cctgtctccg ggtaaatga        699

<210> SEQ ID NO 385
<211> LENGTH: 687
<212> TYPE: DNA
<213> ORGANISM: Artificial Sequence
<220> FEATURE:
<223> OTHER INFORMATION: Human IgG2 Fc region sequence

<400> SEQUENCE: 385
gagcgcaaat gttgtgtcga gtgcccaccg tgcccagcac cacctgtggc aggaccgtca        60
gtcttcctct tccccccaaa acccaaggac accctcatga tctcccggac ccctgaggtc        120
acgtgcgtgg tggtggacgt gagccacgaa gaccccgagg tccagttcaa ctggtacgtg        180
gacggcgtgg aggtgcataa tgccaagaca agccacggg aggagcagtt caacagcacg        240
ttccgtgtgg tcagcgtcct caccgttgtg caccaggact ggctgaacgg caaggagtac        300
aagtgcaagg tctccaacaa ggcctccca gcccccatcg agaaaaccat ctccaaaacc        360
aaagggcagc cccgagaacc acaggtgtac accctgcccc catcccggga ggagatgacc        420
aagaaccagg tcagcctgac ctgcctggtc aaaggcttct accccagcga catcgccgtg        480
gagtgggaga gcaatgggca gccggagaac aactacaaga ccacacctcc catgctggac        540
tccgacggct ccttcttcct ctacagcaag ctcaccgtgg acaagagcag gtggcagcag        600
gggaacgtct tctcatgctc cgtgatgcat gaggctctgc acaaccacta cacgcagaag        660
agcctctccc tgtctccggg taaatag        687

<210> SEQ ID NO 386
<211> LENGTH: 363
<212> TYPE: DNA
<213> ORGANISM: Artificial Sequence
<220> FEATURE:
<223> OTHER INFORMATION: Monoclonal antibody 8F9A4A3 - Heavy chain
      variable region sequence - H-1,8,9,10,11

<400> SEQUENCE: 386

```
gtccagctgc aacagtctgg acctgaactg gtgaagcctg gggcttcagt gaagatatcc      60
tgcaagactt ctggaaacac attcactgaa taccatgc actgggtgaa gcagagccat       120
ggaaagagcc ttgagtggat tggaggtttt aatcctaaca atggtgttac taactacaac     180
cagaagttca aggcaaggc cacattgact gtagacaagt cctccagcac agcctacatg      240
gagctccgca gcctgacatc tgaggattct gcagtctatt actgtgcaag acggtactac    300
catagtctct acgtgtttta ctttgactac tggggccaag caccactct cacagtctcc     360
tca                                                                    363
```

<210> SEQ ID NO 387
<211> LENGTH: 121
<212> TYPE: PRT
<213> ORGANISM: Artificial Sequence
<220> FEATURE:
<223> OTHER INFORMATION: Monoclonal antibody 8F9A4A3 Translated protein, wherein the underlined sequence is the complementarity determining region (CDR)

<400> SEQUENCE: 387

```
Val Gln Leu Gln Gln Ser Gly Pro Glu Leu Val Lys Pro Gly Ala Ser
1               5                   10                  15

Val Lys Ile Ser Cys Lys Thr Ser Gly Asn Thr Phe Thr Glu Tyr Thr
            20                  25                  30

Met His Trp Val Lys Gln Ser His Gly Lys Ser Leu Glu Trp Ile Gly
        35                  40                  45

Gly Phe Asn Pro Asn Asn Gly Val Thr Asn Tyr Asn Gln Lys Phe Lys
    50                  55                  60

Gly Lys Ala Thr Leu Thr Val Asp Lys Ser Ser Ser Thr Ala Tyr Met
65                  70                  75                  80

Glu Leu Arg Ser Leu Thr Ser Glu Asp Ser Ala Val Tyr Tyr Cys Ala
                85                  90                  95

Arg Arg Tyr Tyr His Ser Leu Tyr Val Phe Tyr Phe Asp Tyr Trp Gly
            100                 105                 110

Gln Gly Thr Thr Leu Thr Val Ser Ser
        115                 120
```

<210> SEQ ID NO 388
<211> LENGTH: 9
<212> TYPE: PRT
<213> ORGANISM: Artificial Sequence
<220> FEATURE:
<223> OTHER INFORMATION: Monoclonal antibody 8F9A4A3 Heavy chain variable region CDR1

<400> SEQUENCE: 388

```
Asn Thr Phe Thr Glu Tyr Thr Met His
1               5
```

<210> SEQ ID NO 389
<211> LENGTH: 17
<212> TYPE: PRT
<213> ORGANISM: Artificial Sequence
<220> FEATURE:
<223> OTHER INFORMATION: Monoclonal antibody 8F9A4A3 Heavy chain variable region CDR2

<400> SEQUENCE: 389

Gly Phe Asn Pro Asn Asn Gly Val Thr Asn Tyr Asn Gln Lys Phe Lys

Gly

<210> SEQ ID NO 390
<211> LENGTH: 13
<212> TYPE: PRT
<213> ORGANISM: Artificial Sequence
<220> FEATURE:
<223> OTHER INFORMATION: Monoclonal antibody 8F9A4A3 Heavy chain
      variable region CDR3

<400> SEQUENCE: 390

Arg Tyr Tyr His Ser Leu Tyr Val Phe Tyr Phe Asp Tyr
1               5                   10

<210> SEQ ID NO 391
<211> LENGTH: 324
<212> TYPE: DNA
<213> ORGANISM: Artificial Sequence
<220> FEATURE:
<223> OTHER INFORMATION: Monoclonal antibody 8F9A4A3 Light chain
      variable region sequence - K-3,4,9,10,11

<400> SEQUENCE: 391
gaaacaactg tgacccagtc tccagcatcc ctgtccatgg ctataggaga aaaagtcacc    60
atcagatgca taaccagcac tgatattgat gatgatatga actggtacca gcagaagcca   120
ggggaacctc ctaagctcct tatttcagaa ggcaatactc ttcgtcctgg agtcccatcc   180
cgattctcca gcagtggcta tggtacagat tttgttttta caattgaaaa catgctctca   240
gaagatgttg cagattacta ctgtttgcaa agtgataact gcctctcac gttcggctcg    300 gggacaaagt tggaaataaa acgg                                         324

<210> SEQ ID NO 392
<211> LENGTH: 108
<212> TYPE: PRT
<213> ORGANISM: Artificial Sequence
<220> FEATURE:
<223> OTHER INFORMATION: Monoclonal antibody 8F9A4A3 Translated protein,
      wherein the underlined sequence is the complementarity determining
      region (CDR)

<400> SEQUENCE: 392

Glu Thr Thr Val Thr Gln Ser Pro Ala Ser Leu Ser Met Ala Ile Gly
1               5                   10                  15

Glu Lys Val Thr Ile Arg Cys Ile Thr Ser Thr Asp Ile Asp Asp Asp
                20                  25                  30

Met Asn Trp Tyr Gln Gln Lys Pro Gly Glu Pro Pro Lys Leu Leu Ile
            35                  40                  45

Ser Glu Gly Asn Thr Leu Arg Pro Gly Val Pro Ser Arg Phe Ser Ser
        50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Pro Leu
                85                  90                  95

Thr Phe Gly Ser Gly Thr Lys Leu Glu Ile Lys Arg
            100                 105

<210> SEQ ID NO 393
<211> LENGTH: 11
<212> TYPE: PRT
<213> ORGANISM: Artificial Sequence
<220> FEATURE:
<223> OTHER INFORMATION: Monoclonal antibody 8F9A4A3 Light chain
    variable region CDR1

<400> SEQUENCE: 393

Ser Ala Ser Gln Gly Ile Ser Asn Tyr Leu Asn
1               5                   10

<210> SEQ ID NO 394
<211> LENGTH: 7
<212> TYPE: PRT
<213> ORGANISM: Artificial Sequence
<220> FEATURE:
<223> OTHER INFORMATION: Monoclonal antibody 8F9A4A3 Light chain
    variable region CDR2

<400> SEQUENCE: 394

Tyr Thr Ser Ser Leu His Ser
1               5

<210> SEQ ID NO 395
<211> LENGTH: 9
<212> TYPE: PRT
<213> ORGANISM: Artificial Sequence
<220> FEATURE:
<223> OTHER INFORMATION: Monoclonal antibody 8F9A4A3 Light chain
    variable region CDR3

<400> SEQUENCE: 395

Gln Gln Tyr Ser Lys Leu Pro Tyr Thr
1               5

<210> SEQ ID NO 396
<211> LENGTH: 363
<212> TYPE: DNA
<213> ORGANISM: Artificial Sequence
<220> FEATURE:
<223> OTHER INFORMATION: Monoclonal antibody 5D9E2B11 - Heavy chain
    variable region sequence - H-1,4,7,8,12

<400> SEQUENCE: 396
gtccagctgc aacagtctgg acctgatctg gtgaagcctg ggacttcagt gaagatatcc      60
tgtaagactt ctggaaacac attcactgaa taccatgc actgggtgaa gcagagccat      120
ggaaagagcc ttgagtggat tggaggtttt aatcctaaca atggtgttac taactacaac      180
cagaagttca aggcaaggc acattgact gtagacaagt cctccagcac agcctacatg      240
gagctccgca gcctgacatc tgaggattct gcagtctatt actgtgcaag acgttactac      300
catagtacct acgtgttcta ctttgactcc tggggccaag gcaccactct cacagtctcc      360
tca                                                                    363

<210> SEQ ID NO 397
<211> LENGTH: 121
<212> TYPE: PRT
<213> ORGANISM: Artificial Sequence
<220> FEATURE:
<223> OTHER INFORMATION: Monoclonal antibody 5D9E2B11 Translated
    protein, wherein the underlined sequence is the complementarity
    determining region (CDR)

<400> SEQUENCE: 397

Val Gln Leu Gln Gln Ser Gly Pro Asp Leu Val Lys Pro Gly Thr Ser
1               5                   10                  15

Val Lys Ile Ser Cys Lys Thr Ser Gly Asn Thr Phe Thr Glu Tyr Thr
            20                  25                  30

Met His Trp Val Lys Gln Ser His Gly Lys Ser Leu Glu Trp Ile Gly
         35                  40                  45

Gly Phe Asn Pro Asn Asn Gly Val Thr Asn Tyr Asn Gln Lys Phe Lys
     50                  55                  60

Gly Lys Ala Thr Leu Thr Val Asp Lys Ser Ser Thr Ala Tyr Met
65                  70                  75                  80

Glu Leu Arg Ser Leu Thr Ser Glu Asp Ser Ala Val Tyr Tyr Cys Ala
                 85                  90                  95

Arg Arg Tyr Tyr His Ser Thr Tyr Val Phe Tyr Phe Asp Ser Trp Gly
            100                 105                 110

Gln Gly Thr Thr Leu Thr Val Ser Ser
        115                 120

<210> SEQ ID NO 398
<211> LENGTH: 9
<212> TYPE: PRT
<213> ORGANISM: Artificial Sequence
<220> FEATURE:
<223> OTHER INFORMATION: Monoclonal antibody 5D9E2B11 Heavy chain
      variable region CDR1

<400> SEQUENCE: 398

Asn Thr Phe Thr Glu Tyr Thr Met His
1               5

<210> SEQ ID NO 399
<211> LENGTH: 17
<212> TYPE: PRT
<213> ORGANISM: Artificial Sequence
<220> FEATURE:
<223> OTHER INFORMATION: Monoclonal antibody 5D9E2B11 Heavy chain
      variable region CDR2

<400> SEQUENCE: 399

Gly Phe Asn Pro Asn Asn Gly Val Thr Asn Tyr Asn Gln Lys Phe Lys
1               5                   10                  15

Gly

<210> SEQ ID NO 400
<211> LENGTH: 13
<212> TYPE: PRT
<213> ORGANISM: Artificial Sequence
<220> FEATURE:
<223> OTHER INFORMATION: Monoclonal antibody 5D9E2B11 Heavy chain
      variable region CDR3

<400> SEQUENCE: 400

Arg Tyr Tyr His Ser Thr Tyr Val Phe Tyr Phe Asp Ser
1               5                   10

<210> SEQ ID NO 401
<211> LENGTH: 324
<212> TYPE: DNA
<213> ORGANISM: Artificial Sequence
<220> FEATURE:
<223> OTHER INFORMATION: Monoclonal antibody 5D9E2B11 Light chain
      variable region sequence - K-3,4,5,6,12

<400> SEQUENCE: 401
gatatccaga tgacacagac tacatcctcc ctgtctgcct ctctgggaga cagagtcacc      60
atcagttgca gtgcaagtca gggcattagc aattatttaa actggtttca gcagaaacca     120
gatggaacta ttaagctcct gatctattac acatcaagtt tacattcagg agtcccatca     180

```
aggttcagtg gcagtgggtc tgggacagat tattctctca ccatcagtaa tgtggaacct    240
gaagatattg ccacttacta ttgtcagcag tatagtaagc ttccttacac gttcggaggg    300
gggaccaagc tggagataaa acgg                                          324
```

<210> SEQ ID NO 402
<211> LENGTH: 108
<212> TYPE: PRT
<213> ORGANISM: Artificial Sequence
<220> FEATURE:
<223> OTHER INFORMATION: Monoclonal antibody 5D9E2B11 Translated protein

<400> SEQUENCE: 402

```
Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Phe Gln Gln Lys Pro Asp Gly Thr Ile Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Val Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Ile Lys Arg
            100                 105
```

<210> SEQ ID NO 403
<211> LENGTH: 108
<212> TYPE: PRT
<213> ORGANISM: Artificial Sequence
<220> FEATURE:
<223> OTHER INFORMATION: Monoclonal antibody 5D9E2B11 Translated
    protein, wherein the underlined sequence is the complementarity
    determining region (CDR)

<400> SEQUENCE: 403

```
Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Phe Gln Gln Lys Pro Asp Gly Thr Ile Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Val Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Ile Lys Arg
            100                 105
```

<210> SEQ ID NO 404
<211> LENGTH: 11
<212> TYPE: PRT
<213> ORGANISM: Artificial Sequence
<220> FEATURE:
<223> OTHER INFORMATION: Monoclonal antibody 5D9E2B11 Light chain
    variable region CDR 1

<400> SEQUENCE: 404

Ser Ala Ser Gln Gly Ile Ser Asn Tyr Leu Asn
1               5                   10

<210> SEQ ID NO 405
<211> LENGTH: 7
<212> TYPE: PRT
<213> ORGANISM: Artificial Sequence
<220> FEATURE:
<223> OTHER INFORMATION: Monoclonal antibody 5D9E2B11 Light chain
      variable region CDR2

<400> SEQUENCE: 405

Tyr Thr Ser Ser Leu His Ser
1               5

<210> SEQ ID NO 406
<211> LENGTH: 9
<212> TYPE: PRT
<213> ORGANISM: Artificial Sequence
<220> FEATURE:
<223> OTHER INFORMATION: Monoclonal antibody 5D9E2B11 Light chain
      variable region CDR3

<400> SEQUENCE: 406

Gln Gln Tyr Ser Lys Leu Pro Tyr Thr
1               5

<210> SEQ ID NO 407
<211> LENGTH: 363
<212> TYPE: DNA
<213> ORGANISM: Artificial Sequence
<220> FEATURE:
<223> OTHER INFORMATION: Monoclonal antibody 5D9E10E4 - Heavy chain
      variable region sequence - H-2,4,7,10,12

<400> SEQUENCE: 407
gtccagctgc aacagtctgg acctgatctg gtgaagcctg ggacttcagt gaagatatcc      60
tgtaagactt ctggaaacac attcactgaa tacaccatgc actgggtgaa gcagagccat     120
ggaaagagcc ttgagtggat tggaggtttt aatcctaaca atggtgttac taactacaac     180
cagaagttca gggcaaggc acattgact gtagacaagt cctccagcac agcctacatg      240
gagctccgca gcctgacatc tgaggattct gcagtctatt actgtgcaag acgttactac     300
catagtacct acgtgttcta ctttgactcc tggggccaag gcaccactct cacagtctcc     360
tca                                                                    363

<210> SEQ ID NO 408
<211> LENGTH: 121
<212> TYPE: PRT
<213> ORGANISM: Artificial Sequence
<220> FEATURE:
<223> OTHER INFORMATION: Monoclonal antibody 5D9E10E4 Translated
      protein, wherein the underlined sequence is the complementarity
      determining region (CDR)

<400> SEQUENCE: 408

Val Gln Leu Gln Gln Ser Gly Pro Asp Leu Val Lys Pro Gly Thr Ser
1               5                   10                  15

Val Lys Ile Ser Cys Lys Thr Ser Gly Asn Thr Phe Thr Glu Tyr Thr
            20                  25                  30

Met His Trp Val Lys Gln Ser His Gly Lys Ser Leu Glu Trp Ile Gly
        35                  40                  45

-continued

Gly Phe Asn Pro Asn Asn Gly Val Thr Asn Tyr Asn Gln Lys Phe Lys
            50                  55                  60

Gly Lys Ala Thr Leu Thr Val Asp Lys Ser Ser Ser Thr Ala Tyr Met
 65                  70                  75                  80

Glu Leu Arg Ser Leu Thr Ser Glu Asp Ser Ala Val Tyr Tyr Cys Ala
                85                  90                  95

Arg Arg Tyr Tyr His Ser Thr Tyr Val Phe Tyr Phe Asp Ser Trp Gly
            100                 105                 110

Gln Gly Thr Thr Leu Thr Val Ser Ser
        115                 120

<210> SEQ ID NO 409
<211> LENGTH: 9
<212> TYPE: PRT
<213> ORGANISM: Artificial Sequence
<220> FEATURE:
<223> OTHER INFORMATION: Monoclonal antibody 5D9E10E4 Heavy chain
      variable region CDR1

<400> SEQUENCE: 409

Asn Thr Phe Thr Glu Tyr Thr Met His
 1               5

<210> SEQ ID NO 410
<211> LENGTH: 17
<212> TYPE: PRT
<213> ORGANISM: Artificial Sequence
<220> FEATURE:
<223> OTHER INFORMATION: Monoclonal antibody 5D9E10E4 Heavy chain
      variable region CDR2

<400> SEQUENCE: 410

Gly Phe Asn Pro Asn Asn Gly Val Thr Asn Tyr Asn Gln Lys Phe Lys
 1               5                   10                  15

Gly

<210> SEQ ID NO 411
<211> LENGTH: 13
<212> TYPE: PRT
<213> ORGANISM: Artificial Sequence
<220> FEATURE:
<223> OTHER INFORMATION: Monoclonal antibody 5D9E10E4 Heavy chain
      variable region CDR3

<400> SEQUENCE: 411

Arg Tyr Tyr His Ser Thr Tyr Val Phe Tyr Phe Asp Ser
 1               5                   10

<210> SEQ ID NO 412
<211> LENGTH: 324
<212> TYPE: DNA
<213> ORGANISM: Artificial Sequence
<220> FEATURE:
<223> OTHER INFORMATION: Monoclonal antibody 5D9E10E4 Light chain
      variable region sequence - K-2,6,8,14,15

<400> SEQUENCE: 412
gatatccaga tgacacagac tacatcctcc ctgtctgcct ctctgggaga cagagtcacc      60
atcagttgca gtgcaagtca gggcattagc aattatttaa actggtttca gcagaaacca     120
gatggaacta ttaagctcct gatctattac acatcaagtt acattcagg agtcccatca      180 aggttcagtg gcagtgggtc tgggacagat tattctctca ccatcagtaa tgtggaacct     240

```
gaagatattg ccacttacta ttgtcagcag tatagtaagc ttccttacac gttcggaggg      300
gggaccaagc tggagataaa acgg                                             324
```

<210> SEQ ID NO 413
<211> LENGTH: 108
<212> TYPE: PRT
<213> ORGANISM: Artificial Sequence
<220> FEATURE:
<223> OTHER INFORMATION: Monoclonal antibody 5D9E10E4 Translated
      protein, wherein the underlined sequence is the complementarity
      determining region (CDR)

<400> SEQUENCE: 413

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Phe Gln Gln Lys Pro Asp Gly Thr Ile Lys Leu Leu Ile
        35                  40                  45

Tyr Tyr Thr Ser Ser Leu His Ser Gly Val Pro Ser Arg Phe Ser Gly
50                  55                  60

Ser Gly Ser Gly Thr Asp Tyr Ser Leu Thr Ile Ser Asn Val Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Ile Lys Arg
            100                 105

<210> SEQ ID NO 414
<211> LENGTH: 11
<212> TYPE: PRT
<213> ORGANISM: Artificial Sequence
<220> FEATURE:
<223> OTHER INFORMATION: Monoclonal antibody 5D9E10E4 Light chain
      variable region CDR 1

<400> SEQUENCE: 414

Ser Ala Ser Gln Gly Ile Ser Asn Tyr Leu Asn
1               5                   10

<210> SEQ ID NO 415
<211> LENGTH: 7
<212> TYPE: PRT
<213> ORGANISM: Artificial Sequence
<220> FEATURE:
<223> OTHER INFORMATION: Monoclonal antibody 5D9E10E4 Light chain
      variable region CDR2

<400> SEQUENCE: 415

Tyr Thr Ser Ser Leu His Ser
1               5

<210> SEQ ID NO 416
<211> LENGTH: 9
<212> TYPE: PRT
<213> ORGANISM: Artificial Sequence
<220> FEATURE:
<223> OTHER INFORMATION: Monoclonal antibody 5D9E10E4 Light chain
      variable region CDR3

<400> SEQUENCE: 416

Gln Gln Tyr Ser Lys Leu Pro Tyr Thr
1               5

<210> SEQ ID NO 417
<211> LENGTH: 363
<212> TYPE: DNA
<213> ORGANISM: Artificial Sequence
<220> FEATURE:
<223> OTHER INFORMATION: Monoclonal antibody 5D9G2C4 - Heavy chain
      variable region sequence - H-4,9,10,11,13

<400> SEQUENCE: 417

```
gtccagctgc aacagtctgg acctgatctg gtgaagcctg ggacttcagt gaagatatcc    60
tgtaagactt ctggaaacac attcactgaa taccatgc actgggtgaa gcagagccat     120
ggaaagagcc ttgagtggat tggaggtttt aatcctaaca atggtgttac taactacaac    180
cagaagttca aggcaaggc acattgact gtagacaagt cctccagcac agcctacatg     240
gagctccgca gcctgacatc tgaggattct gcagtctatt actgtgcaag acgttactac    300
catagtacct acgtgttcta ctttgactcc tggggccaag gcaccactct cacagtctcc    360
tca                                                                  363
```

<210> SEQ ID NO 418
<211> LENGTH: 121
<212> TYPE: PRT
<213> ORGANISM: Artificial Sequence
<220> FEATURE:
<223> OTHER INFORMATION: Monoclonal antibody 5D9G2C4 Translated protein,
      wherein the underlined sequence is the complementarity determining
      region (CDR)

<400> SEQUENCE: 418

```
Val Gln Leu Gln Gln Ser Gly Pro Asp Leu Val Lys Pro Gly Thr Ser
1               5                   10                  15

Val Lys Ile Ser Cys Lys Thr Ser Gly Asn Thr Phe Thr Glu Tyr Thr
            20                  25                  30

Met His Trp Val Lys Gln Ser His Gly Lys Ser Leu Glu Trp Ile Gly
        35                  40                  45

Gly Phe Asn Pro Asn Asn Gly Val Thr Asn Tyr Asn Gln Lys Phe Lys
    50                  55                  60

Gly Lys Ala Thr Leu Thr Val Asp Lys Ser Ser Ser Thr Ala Tyr Met
65                  70                  75                  80

Glu Leu Arg Ser Leu Thr Ser Glu Asp Ser Ala Val Tyr Tyr Cys Ala
                85                  90                  95

Arg Arg Tyr Tyr His Ser Thr Tyr Val Phe Tyr Phe Asp Ser Trp Gly
            100                 105                 110

Gln Gly Thr Thr Leu Thr Val Ser Ser
        115                 120
```

<210> SEQ ID NO 419
<211> LENGTH: 9
<212> TYPE: PRT
<213> ORGANISM: Artificial Sequence
<220> FEATURE:
<223> OTHER INFORMATION: Monoclonal antibody 5D9G2C4 Heavy chain
      variable region CDR1

<400> SEQUENCE: 419

```
Asn Thr Phe Thr Glu Tyr Thr Met His
1               5
```

<210> SEQ ID NO 420
<211> LENGTH: 17
<212> TYPE: PRT

```
<213> ORGANISM: Artificial Sequence
<220> FEATURE:
<223> OTHER INFORMATION: Monoclonal antibody 5D9G2C4 Heavy chain
      variable region CDR2

<400> SEQUENCE: 420

Gly Phe Asn Pro Asn Asn Gly Val Thr Asn Tyr Asn Gln Lys Phe Lys
1               5                   10                  15

Gly

<210> SEQ ID NO 421
<211> LENGTH: 13
<212> TYPE: PRT
<213> ORGANISM: Artificial Sequence
<220> FEATURE:
<223> OTHER INFORMATION: Monoclonal antibody 5D9G2C4 Heavy chain
      variable region CDR3

<400> SEQUENCE: 421

Arg Tyr Tyr His Ser Thr Tyr Val Phe Tyr Phe Asp Ser
1               5                   10

<210> SEQ ID NO 422
<211> LENGTH: 324
<212> TYPE: DNA
<213> ORGANISM: Artificial Sequence
<220> FEATURE:
<223> OTHER INFORMATION: Monoclonal antibody 5D9G2C4 Light chain
      variable region sequence - K-4,6,7,8,10

<400> SEQUENCE: 422
gatatccaga tgacacagac tacatcctcc ctgtctgcct ctctgggaga cagagtcacc     60
atcagttgca gtgcaagtca gggcattagc aattatttaa actggtttca gcagaaacca    120
gatggaacta ttaagctcct gatctattac acatcaagtt tacattcagg agtcccatca    180
aggttcagtg gcagtgggtc tgggacagat tattctctca ccatcagtaa tgtggaacct    240
gaagatattg ccacttacta ttgtcagcag tatagtaagc ttccttacac gttcggaggg    300
gggaccaagc tggagataaa acgg                                           324

<210> SEQ ID NO 423
<211> LENGTH: 108
<212> TYPE: PRT
<213> ORGANISM: Artificial Sequence
<220> FEATURE:
<223> OTHER INFORMATION: Monoclonal antibody 5D9G2C4 Translated protein,
      wherein the underlined sequence is the complementarity determining
      region (CDR)

<400> SEQUENCE: 423

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
                20                  25                  30

Leu Asn Trp Phe Gln Gln Lys Pro Asp Gly Thr Ile Lys Leu Leu Ile
            35                  40                  45

Tyr Tyr Thr Ser Ser Leu His Ser Gly Val Pro Ser Arg Phe Ser Gly
        50                  55                  60

Ser Gly Ser Gly Thr Asp Tyr Ser Leu Thr Ile Ser Asn Val Glu Pro
65                  70                  75                  80

Glu Asp Ile Ala Thr Tyr Tyr Cys Gln Gln Tyr Ser Lys Leu Pro Tyr
                85                  90                  95
```

Thr Phe Gly Gly Gly Thr Lys Leu Glu Ile Lys Arg
            100                 105

<210> SEQ ID NO 424
<211> LENGTH: 11
<212> TYPE: PRT
<213> ORGANISM: Artificial Sequence
<220> FEATURE:
<223> OTHER INFORMATION: Monoclonal antibody 5D9G2C4 Light chain
      variable region CDR 1

<400> SEQUENCE: 424

Ser Ala Ser Gln Gly Ile Ser Asn Tyr Leu Asn
1               5                   10

<210> SEQ ID NO 425
<211> LENGTH: 7
<212> TYPE: PRT
<213> ORGANISM: Artificial Sequence
<220> FEATURE:
<223> OTHER INFORMATION: Monoclonal antibody 5D9G2C4 Light chain
      variable region CDR2

<400> SEQUENCE: 425

Tyr Thr Ser Ser Leu His Ser
1               5

<210> SEQ ID NO 426
<211> LENGTH: 9
<212> TYPE: PRT
<213> ORGANISM: Artificial Sequence
<220> FEATURE:
<223> OTHER INFORMATION: Monoclonal antibody 5D9G2C4 Light chain
      variable region CDR3

<400> SEQUENCE: 426

Gln Gln Tyr Ser Lys Leu Pro Tyr Thr
1               5

<210> SEQ ID NO 427
<211> LENGTH: 363
<212> TYPE: DNA
<213> ORGANISM: Artificial Sequence
<220> FEATURE:
<223> OTHER INFORMATION: Monoclonal antibody 5F3A5D4 - Heavy chain
      variable region sequence - H-2,3,4,13,15

<400> SEQUENCE: 427
gtccagctgc aacagtctgg acctgatctg gtgaagcctg ggacttcagt gaagatatcc      60
tgtaagactt ctggaaacac attcactgaa taccatgcc actgggtgaa gcagagccat     120
ggaaagagcc ttgagtggat tggaggtttt aatcctaaca atggtgttac taactacaac     180
cagaagttca gggcaaggc cacattgact gtagacaagt cctccagcac agcctacatg     240
gagctccgca gcctgacatc tgaggattct gcagtctatt actgtgcaag acgttactac     300
catagtacct acgtgttcta ctttgactcc tggggccaag gcaccactct cacagtctcc     360
tca                                                                  363

<210> SEQ ID NO 428
<211> LENGTH: 121
<212> TYPE: PRT
<213> ORGANISM: Artificial Sequence
<220> FEATURE:
<223> OTHER INFORMATION: Monoclonal antibody 5F3A5D4 Translated protein,
      wherein the underlined sequence is the complementarity determining
      region (CDR)

<400> SEQUENCE: 428

Val Gln Leu Gln Gln Ser Gly Pro Asp Leu Val Lys Pro Gly Thr Ser
1               5                   10                  15

Val Lys Ile Ser Cys Lys Thr Ser Gly Asn Thr Phe Thr Glu Tyr Thr
            20                  25                  30

Met His Trp Val Lys Gln Ser His Gly Lys Ser Leu Glu Trp Ile Gly
        35                  40                  45

Gly Phe Asn Pro Asn Asn Gly Val Thr Asn Tyr Asn Gln Lys Phe Lys
    50                  55                  60

Gly Lys Ala Thr Leu Thr Val Asp Lys Ser Ser Ser Thr Ala Tyr Met
65                  70                  75                  80

Glu Leu Arg Ser Leu Thr Ser Glu Asp Ser Ala Val Tyr Tyr Cys Ala
                85                  90                  95

Arg Arg Tyr Tyr His Ser Thr Tyr Val Phe Tyr Phe Asp Ser Trp Gly
            100                 105                 110

Gln Gly Thr Thr Leu Thr Val Ser Ser
        115                 120

<210> SEQ ID NO 429
<211> LENGTH: 9
<212> TYPE: PRT
<213> ORGANISM: Artificial Sequence
<220> FEATURE:
<223> OTHER INFORMATION: Monoclonal antibody 5F3A5D4 Heavy chain
      variable region CDR1

<400> SEQUENCE: 429

Asn Thr Phe Thr Glu Tyr Thr Met His
1               5

<210> SEQ ID NO 430
<211> LENGTH: 17
<212> TYPE: PRT
<213> ORGANISM: Artificial Sequence
<220> FEATURE:
<223> OTHER INFORMATION: Monoclonal antibody 5F3A5D4 Heavy chain
      variable region CDR2

<400> SEQUENCE: 430

Gly Phe Asn Pro Asn Asn Gly Val Thr Asn Tyr Asn Gln Lys Phe Lys
1               5                   10                  15

Gly

<210> SEQ ID NO 431
<211> LENGTH: 13
<212> TYPE: PRT
<213> ORGANISM: Artificial Sequence
<220> FEATURE:
<223> OTHER INFORMATION: Monoclonal antibody 5F3A5D4 Heavy chain
      variable region CDR3

<400> SEQUENCE: 431

Arg Tyr Tyr His Ser Thr Tyr Val Phe Tyr Phe Asp Ser
1               5                   10

<210> SEQ ID NO 432
<211> LENGTH: 324
<212> TYPE: DNA
<213> ORGANISM: Artificial Sequence
<220> FEATURE:
<223> OTHER INFORMATION: Monoclonal antibody 5F3A5D4 Light chain
      variable region sequence - K-1,2,3,4,9

-continued

<400> SEQUENCE: 432

```
gatatccaga tgacacagac tacatcctcc ctgtctgcct ctctgggaga cagagtcacc    60
atcagttgca gtgcaagtca gggcattagc aattatttaa actggtttca gcagaaacca   120
gatggaacta ttaagctcct gatctattac acatcaagtt tacattcagg agtcccatca   180
aggttcagtg gcagtgggtc tgggacagat tattctctca ccatcagtaa tgtggaacct   240
gaagatattg ccacttacta ttgtcagcag tatagtaagc ttccttacac gttcggaggg   300
gggaccaagc tggagataaa acgg                                          324
```

<210> SEQ ID NO 433
<211> LENGTH: 108
<212> TYPE: PRT
<213> ORGANISM: Artificial Sequence
<220> FEATURE:
<223> OTHER INFORMATION: Monoclonal antibody 5F3A5D4 Translated protein, wherein the underlined sequence is the complementarity determining region (CDR)

<400> SEQUENCE: 433

```
Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Phe Gln Gln Lys Pro Asp Gly Thr Ile Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Val Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Ile Lys Arg
            100                 105
```

<210> SEQ ID NO 434
<211> LENGTH: 11
<212> TYPE: PRT
<213> ORGANISM: Artificial Sequence
<220> FEATURE:
<223> OTHER INFORMATION: Monoclonal antibody 5F3A5D4 Light chain variable region CDR1

<400> SEQUENCE: 434

```
Ser Ala Ser Gln Gly Ile Ser Asn Tyr Leu Asn
1               5                   10
```

<210> SEQ ID NO 435
<211> LENGTH: 7
<212> TYPE: PRT
<213> ORGANISM: Artificial Sequence
<220> FEATURE:
<223> OTHER INFORMATION: Monoclonal antibody 5F3A5D4 Light chain variable region CDR2

<400> SEQUENCE: 435

```
Tyr Thr Ser Ser Leu His Ser
1               5
```

<210> SEQ ID NO 436
<211> LENGTH: 9

```
<212> TYPE: PRT
<213> ORGANISM: Artificial Sequence
<220> FEATURE:
<223> OTHER INFORMATION: Monoclonal antibody 5F3A5D4 Light chain
      variable region CDR3

<400> SEQUENCE: 436

Gln Gln Tyr Ser Lys Leu Pro Tyr Thr
1               5

<210> SEQ ID NO 437
<211> LENGTH: 357
<212> TYPE: DNA
<213> ORGANISM: Artificial Sequence
<220> FEATURE:
<223> OTHER INFORMATION: Monoclonal antibody 8F9A5A1 - Heavy chain
      variable region sequence - H-3,4,6,10,11

<400> SEQUENCE: 437
atccagttgg tgcagtctgg acctgagctg aagaagcctg gagagacagt caagatctcc      60
tgcaaggctt ctgggtatac cttcacaaac tatggaatga actgggtgaa gcaggctcca     120
ggaaagggtt taaagtggat gggctggata aacacctaca ctggagagcc aacatatgtt     180
gatgacttca aggacggttt gccttctct ttggaaacct ctgccaccac tgcctatttg      240
cagatcaaca acctcaaaaa tgaggacacg tctacatatt tctgtgcaag attgaggggg     300
atacgaccgg gtcccttggc ttactggggc caagggactc tggtcactgt ctctgca        357

<210> SEQ ID NO 438
<211> LENGTH: 119
<212> TYPE: PRT
<213> ORGANISM: Artificial Sequence
<220> FEATURE:
<223> OTHER INFORMATION: Monoclonal antibody 8F9A5A1 Translated protein,
      wherein the underlined sequence is the complementarity determining
      region (CDR)

<400> SEQUENCE: 438

Ile Gln Leu Val Gln Ser Gly Pro Glu Leu Lys Lys Pro Gly Glu Thr
1               5                   10                  15

Val Lys Ile Ser Cys Lys Ala Ser Gly Tyr Thr Phe Thr Asn Tyr Gly
            20                  25                  30

Met Asn Trp Val Lys Gln Ala Pro Gly Lys Gly Leu Lys Trp Met Gly
        35                  40                  45

Trp Ile Asn Thr Tyr Thr Gly Glu Pro Thr Tyr Val Asp Asp Phe Lys
    50                  55                  60

Gly Arg Phe Ala Phe Ser Leu Glu Thr Ser Ala Thr Thr Ala Tyr Leu
65                  70                  75                  80

Gln Ile Asn Asn Leu Lys Asn Glu Asp Thr Ser Thr Tyr Phe Cys Ala
                85                  90                  95

Arg Leu Arg Gly Ile Arg Pro Gly Pro Leu Ala Tyr Trp Gly Gln Gly
            100                 105                 110

Thr Leu Val Thr Val Ser Ala
        115

<210> SEQ ID NO 439
<211> LENGTH: 9
<212> TYPE: PRT
<213> ORGANISM: Artificial Sequence
<220> FEATURE:
<223> OTHER INFORMATION: Monoclonal antibody 8F9A5A1 Heavy chain
      variable region CDR1
```

<400> SEQUENCE: 439

Tyr Thr Phe Thr Asn Tyr Gly Met Asn
1               5

<210> SEQ ID NO 440
<211> LENGTH: 17
<212> TYPE: PRT
<213> ORGANISM: Artificial Sequence
<220> FEATURE:
<223> OTHER INFORMATION: Monoclonal antibody 8F9A5A1 Heavy chain
      variable region CDR2

<400> SEQUENCE: 440

Trp Ile Asn Thr Tyr Thr Gly Glu Pro Thr Tyr Val Asp Asp Phe Lys
1               5                   10                  15

Gly

<210> SEQ ID NO 441
<211> LENGTH: 11
<212> TYPE: PRT
<213> ORGANISM: Artificial Sequence
<220> FEATURE:
<223> OTHER INFORMATION: Monoclonal antibody 8F9A5A1 Heavy chain
      variable region CDR3

<400> SEQUENCE: 441

Leu Arg Gly Ile Arg Pro Gly Pro Leu Ala Tyr
1               5                   10

<210> SEQ ID NO 442
<211> LENGTH: 321
<212> TYPE: DNA
<213> ORGANISM: Artificial Sequence
<220> FEATURE:
<223> OTHER INFORMATION: Monoclonal antibody 8F9A5A1 Light chain
      variable region sequence - K-1,2,3,4,5

<400> SEQUENCE: 442
gaaattttgc tcacccagtc tccagcaatc atagctgcat ctcctgggga gaaggtcacc      60
atcacctgca gtgccagctc aagtgtaagt tacatgaact ggtaccagca gaaaccagga     120
tcctccccca aaatatggat ttatggtata tccaacctgg cttctggagt tcctgctcgc     180
ttcagtggca gtgggtctgg gacatctttc tctttcacaa tcaacagcat ggaggctgaa     240
gatgttgcca cttattactg tcagcaaagg agtagttacc acccacgtt cggaggggg       300 accaagctgg aaataaaacg g                                               321

<210> SEQ ID NO 443
<211> LENGTH: 107
<212> TYPE: PRT
<213> ORGANISM: Artificial Sequence
<220> FEATURE:
<223> OTHER INFORMATION: Monoclonal antibody 8F9A5A1 Translated protein,
      wherein the underlined sequence is the complementarity determining
      region (CDR)

<400> SEQUENCE: 443

Glu Ile Leu Leu Thr Gln Ser Pro Ala Ile Ile Ala Ala Ser Pro Gly
1               5                   10                  15

Glu Lys Val Thr Ile Thr Cys Ser Ala Ser Ser Ser Val Ser Tyr Met
                20                  25                  30

Asn Trp Tyr Gln Gln Lys Pro Gly Ser Ser Pro Lys Ile Trp Ile Tyr
            35                  40                  45

```
Gly Ile Ser Asn Leu Ala Ser Gly Val Pro Ala Arg Phe Ser Gly Ser
 50                  55                  60
Gly Ser Gly Thr Ser Phe Ser Phe Thr Ile Asn Ser Met Glu Ala Glu
 65                  70                  75                  80
Asp Val Ala Thr Tyr Tyr Cys Gln Gln Arg Ser Ser Tyr Pro Pro Thr
                 85                  90                  95
Phe Gly Gly Gly Thr Lys Leu Glu Ile Lys Arg
            100                 105

<210> SEQ ID NO 444
<211> LENGTH: 10
<212> TYPE: PRT
<213> ORGANISM: Artificial Sequence
<220> FEATURE:
<223> OTHER INFORMATION: Monoclonal antibody 8F9A5A1 Light chain
      variable region CDR 1

<400> SEQUENCE: 444

Ser Ala Ser Ser Ser Val Ser Tyr Met Asn
1               5                   10

<210> SEQ ID NO 445
<211> LENGTH: 7
<212> TYPE: PRT
<213> ORGANISM: Artificial Sequence
<220> FEATURE:
<223> OTHER INFORMATION: Monoclonal antibody 8F9A5A1 Light chain
      variable region CDR2

<400> SEQUENCE: 445

Gly Ile Ser Asn Leu Ala Ser
1               5

<210> SEQ ID NO 446
<211> LENGTH: 9
<212> TYPE: PRT
<213> ORGANISM: Artificial Sequence
<220> FEATURE:
<223> OTHER INFORMATION: Monoclonal antibody 8F9A5A1 Light chain
      variable region CDR3

<400> SEQUENCE: 446

Gln Gln Arg Ser Ser Tyr Pro Pro Thr
1               5

<210> SEQ ID NO 447
<211> LENGTH: 363
<212> TYPE: DNA
<213> ORGANISM: Artificial Sequence
<220> FEATURE:
<223> OTHER INFORMATION: Monoclonal antibody 8H5H5G4 - Heavy chain
      variable region sequence - H-1,3,5,6,10

<400> SEQUENCE: 447
gtccagctgc aacagtctgg acctgatctg gtgaagcctg ggacttcagt gaagatatcc      60
tgtaagactt ctggaaacac attcactgaa taccatgca ctgggtgaa gcagagccat      120 ggaaagagcc ttgagtggat tgaggttttt aatcctaaca atggtgttac taactacaac      180
cagaagttca gggcaaggc cacattgact gtagacaagt cctccagcac agcctacatg      240
gagctccgca gcctgacatc tgaggattct gcagtctatt actgtgcaag acgttactac      300
catagtacct acgtgttcta ctttgactcc tggggccaag gcaccactct cacagtctcc      360
tca                                                                   363
```

-continued

<210> SEQ ID NO 448
<211> LENGTH: 121
<212> TYPE: PRT
<213> ORGANISM: Artificial Sequence
<220> FEATURE:
<223> OTHER INFORMATION: Monoclonal antibody 8H5H5G4 Translated protein,
      wherein the underlined sequence is the complementarity determining
      region (CDR)

<400> SEQUENCE: 448

Val Gln Leu Gln Gln Ser Gly Pro Asp Leu Val Lys Pro Gly Thr Ser
1               5                   10                  15

Val Lys Ile Ser Cys Lys Thr Ser Gly Asn Thr Phe Thr Glu Tyr Thr
            20                  25                  30

Met His Trp Val Lys Gln Ser His Gly Lys Ser Leu Glu Trp Ile Gly
        35                  40                  45

Gly Phe Asn Pro Asn Asn Gly Val Thr Asn Tyr Asn Gln Lys Phe Lys
    50                  55                  60

Gly Lys Ala Thr Leu Thr Val Asp Lys Ser Ser Ser Thr Ala Tyr Met
65                  70                  75                  80

Glu Leu Arg Ser Leu Thr Ser Glu Asp Ser Ala Val Tyr Tyr Cys Ala
                85                  90                  95

Arg Arg Tyr Tyr His Ser Thr Tyr Val Phe Tyr Phe Asp Ser Trp Gly
            100                 105                 110

Gln Gly Thr Thr Leu Thr Val Ser Ser
        115                 120

<210> SEQ ID NO 449
<211> LENGTH: 9
<212> TYPE: PRT
<213> ORGANISM: Artificial Sequence
<220> FEATURE:
<223> OTHER INFORMATION: Monoclonal antibody 8H5H5G4 Heavy chain
      variable region CDR1

<400> SEQUENCE: 449

Asn Thr Phe Thr Glu Tyr Thr Met His
1               5

<210> SEQ ID NO 450
<211> LENGTH: 17
<212> TYPE: PRT
<213> ORGANISM: Artificial Sequence
<220> FEATURE:
<223> OTHER INFORMATION: Monoclonal antibody 8H5H5G4 Heavy chain
      variable region CDR2

<400> SEQUENCE: 450

Gly Phe Asn Pro Asn Asn Gly Val Thr Asn Tyr Asn Gln Lys Phe Lys
1               5                   10                  15

Gly

<210> SEQ ID NO 451
<211> LENGTH: 13
<212> TYPE: PRT
<213> ORGANISM: Artificial Sequence
<220> FEATURE:
<223> OTHER INFORMATION: Monoclonal antibody 8H5H5G4 Heavy chain
      variable region CDR3

<400> SEQUENCE: 451

Arg Tyr Tyr His Ser Thr Tyr Val Phe Tyr Phe Asp Ser
1               5                   10

<210> SEQ ID NO 452
<211> LENGTH: 324
<212> TYPE: DNA
<213> ORGANISM: Artificial Sequence
<220> FEATURE:
<223> OTHER INFORMATION: Monoclonal antibody 8H5H5G4 Light chain
      variable region sequence - K-2,5,8,9,15

<400> SEQUENCE: 452
gatatccaga tgacacagac tacatcctcc ctgtctgcct ctctgggaga cagagtcacc      60
atcagttgca gtgcaagtca gggcattagc aattatttaa actggtttca gcagaaacca     120
gatggaacta ttaagctcct gatctattac acatcaagtt tacattcagg agtcccatca     180
aggttcagtg gcagtgggtc tgggacagat tattctctca ccatcagtaa tgtgaacct      240 gaagatattg ccacttacta ttgtcagcag tatagtaagc ttccttacac gttcggaggg     300
gggaccaagc tggagataaa acgg                                            324

<210> SEQ ID NO 453
<211> LENGTH: 108
<212> TYPE: PRT
<213> ORGANISM: Artificial Sequence
<220> FEATURE:
<223> OTHER INFORMATION: Monoclonal antibody 8H5H5G4 Translated protein,
      wherein the underlined sequence is the complementarity determining
      region (CDR)

<400> SEQUENCE: 453

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Phe Gln Gln Lys Pro Asp Gly Thr Ile Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Val Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Ile Lys Arg
            100                 105

<210> SEQ ID NO 454
<211> LENGTH: 11
<212> TYPE: PRT
<213> ORGANISM: Artificial Sequence
<220> FEATURE:
<223> OTHER INFORMATION: Monoclonal antibody 8H5H5G4 Light chain
      variable region CDR 1

<400> SEQUENCE: 454

Ser Ala Ser Gln Gly Ile Ser Asn Tyr Leu Asn
1               5                   10

<210> SEQ ID NO 455
<211> LENGTH: 7
<212> TYPE: PRT
<213> ORGANISM: Artificial Sequence
<220> FEATURE:
<223> OTHER INFORMATION: Monoclonal antibody 8H5H5G4 Light chain
      variable region CDR2

<400> SEQUENCE: 455

Tyr Thr Ser Ser Leu His Ser
1               5

<210> SEQ ID NO 456
<211> LENGTH: 9
<212> TYPE: PRT
<213> ORGANISM: Artificial Sequence
<220> FEATURE:
<223> OTHER INFORMATION: Monoclonal antibody 8H5H5G4 Light chain
      variable region CDR3

<400> SEQUENCE: 456

Gln Gln Tyr Ser Lys Leu Pro Tyr Thr
1               5

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

<210> SEQ ID NO 461

<400> SEQUENCE: 461

000

<210> SEQ ID NO 462

<400> SEQUENCE: 462

000

<210> SEQ ID NO 463

<400> SEQUENCE: 463

000

<210> SEQ ID NO 464

<400> SEQUENCE: 464

000

<210> SEQ ID NO 465

<400> SEQUENCE: 465

000

<210> SEQ ID NO 466

<400> SEQUENCE: 466

000

<210> SEQ ID NO 467

<400> SEQUENCE: 467

000

<210> SEQ ID NO 468

<400> SEQUENCE: 468

000

<210> SEQ ID NO 469

<400> SEQUENCE: 469

000

<210> SEQ ID NO 470

<400> SEQUENCE: 470

000

<210> SEQ ID NO 471

<400> SEQUENCE: 471

000

<210> SEQ ID NO 472

<400> SEQUENCE: 472

000

<210> SEQ ID NO 473

<400> SEQUENCE: 473

000

<210> SEQ ID NO 474

<400> SEQUENCE: 474

000

<210> SEQ ID NO 475

<400> SEQUENCE: 475

000

<210> SEQ ID NO 476

<400> SEQUENCE: 476

000

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481

<400> SEQUENCE: 481

000

<210> SEQ ID NO 482

<400> SEQUENCE: 482

000

<210> SEQ ID NO 483

<400> SEQUENCE: 483

000

<210> SEQ ID NO 484

<400> SEQUENCE: 484

000

<210> SEQ ID NO 485

<400> SEQUENCE: 485

000

<210> SEQ ID NO 486

<400> SEQUENCE: 486

000

<210> SEQ ID NO 487

<400> SEQUENCE: 487

000

-continued

<210> SEQ ID NO 488
<400> SEQUENCE: 488
000

<210> SEQ ID NO 489
<400> SEQUENCE: 489
000

<210> SEQ ID NO 490
<400> SEQUENCE: 490
000

<210> SEQ ID NO 491
<400> SEQUENCE: 491
000

<210> SEQ ID NO 492
<400> SEQUENCE: 492
000

<210> SEQ ID NO 493
<400> SEQUENCE: 493
000

<210> SEQ ID NO 494
<400> SEQUENCE: 494
000

<210> SEQ ID NO 495
<400> SEQUENCE: 495
000

<210> SEQ ID NO 496
<400> SEQUENCE: 496
000

<210> SEQ ID NO 497
<400> SEQUENCE: 497
000

<210> SEQ ID NO 498
<400> SEQUENCE: 498
000

<210> SEQ ID NO 499

<400> SEQUENCE: 499

000

<210> SEQ ID NO 500

<400> SEQUENCE: 500

000

<210> SEQ ID NO 501

<400> SEQUENCE: 501

000

<210> SEQ ID NO 502

<400> SEQUENCE: 502

000

<210> SEQ ID NO 503

<400> SEQUENCE: 503

000

<210> SEQ ID NO 504

<400> SEQUENCE: 504

000

<210> SEQ ID NO 505

<400> SEQUENCE: 505

000

<210> SEQ ID NO 506

<400> SEQUENCE: 506

000

<210> SEQ ID NO 507

<400> SEQUENCE: 507

000

<210> SEQ ID NO 508

<400> SEQUENCE: 508

000

<210> SEQ ID NO 509

<400> SEQUENCE: 509

000

<210> SEQ ID NO 510

<400> SEQUENCE: 510

000

<210> SEQ ID NO 511

<400> SEQUENCE: 511

000

<210> SEQ ID NO 512

<400> SEQUENCE: 512

000

<210> SEQ ID NO 513

<400> SEQUENCE: 513

000

<210> SEQ ID NO 514

<400> SEQUENCE: 514

000

<210> SEQ ID NO 515

<400> SEQUENCE: 515

000

<210> SEQ ID NO 516

<400> SEQUENCE: 516

000

<210> SEQ ID NO 517

<400> SEQUENCE: 517

000

<210> SEQ ID NO 518

<400> SEQUENCE: 518

000

<210> SEQ ID NO 519

<400> SEQUENCE: 519

000

<210> SEQ ID NO 520

<400> SEQUENCE: 520

000

<210> SEQ ID NO 521

<400> SEQUENCE: 521

000

<210> SEQ ID NO 522

<400> SEQUENCE: 522

000

<210> SEQ ID NO 523

<400> SEQUENCE: 523

000

<210> SEQ ID NO 524

<400> SEQUENCE: 524

000

<210> SEQ ID NO 525

<400> SEQUENCE: 525

000

<210> SEQ ID NO 526

<400> SEQUENCE: 526

000

<210> SEQ ID NO 527

<400> SEQUENCE: 527

000

<210> SEQ ID NO 528

<400> SEQUENCE: 528

000

<210> SEQ ID NO 529

<400> SEQUENCE: 529

000

<210> SEQ ID NO 530

<400> SEQUENCE: 530

000

<210> SEQ ID NO 531

<400> SEQUENCE: 531

000

<210> SEQ ID NO 532

<400> SEQUENCE: 532

000

<210> SEQ ID NO 533

<400> SEQUENCE: 533

000

<210> SEQ ID NO 534

<400> SEQUENCE: 534

000

<210> SEQ ID NO 535

<400> SEQUENCE: 535

000

<210> SEQ ID NO 536

<400> SEQUENCE: 536

000

<210> SEQ ID NO 537

<400> SEQUENCE: 537

000

<210> SEQ ID NO 538

<400> SEQUENCE: 538

000

<210> SEQ ID NO 539

<400> SEQUENCE: 539

000

<210> SEQ ID NO 540

<400> SEQUENCE: 540

000

<210> SEQ ID NO 541

<400> SEQUENCE: 541

000

<210> SEQ ID NO 542

<400> SEQUENCE: 542

000

<210> SEQ ID NO 543

<400> SEQUENCE: 543

000

<210> SEQ ID NO 544

<400> SEQUENCE: 544

000

<210> SEQ ID NO 545

<400> SEQUENCE: 545

000

<210> SEQ ID NO 546

<400> SEQUENCE: 546

000

<210> SEQ ID NO 547

<400> SEQUENCE: 547

000

<210> SEQ ID NO 548

<400> SEQUENCE: 548

000

<210> SEQ ID NO 549

<400> SEQUENCE: 549

000

<210> SEQ ID NO 550

<400> SEQUENCE: 550

000

<210> SEQ ID NO 551

<400> SEQUENCE: 551

000

<210> SEQ ID NO 552

<400> SEQUENCE: 552

000

<210> SEQ ID NO 553

<400> SEQUENCE: 553

000

<210> SEQ ID NO 554

<400> SEQUENCE: 554

000

<210> SEQ ID NO 555

<400> SEQUENCE: 555

000

<210> SEQ ID NO 556

<400> SEQUENCE: 556

000

<210> SEQ ID NO 557

<400> SEQUENCE: 557

000

<210> SEQ ID NO 558

<400> SEQUENCE: 558

000

<210> SEQ ID NO 559

<400> SEQUENCE: 559

000

<210> SEQ ID NO 560

<400> SEQUENCE: 560

000

<210> SEQ ID NO 561

<400> SEQUENCE: 561

000

<210> SEQ ID NO 562

<400> SEQUENCE: 562

000

<210> SEQ ID NO 563

<400> SEQUENCE: 563

000

<210> SEQ ID NO 564

<400> SEQUENCE: 564

000

<210> SEQ ID NO 565

<400> SEQUENCE: 565

000

<210> SEQ ID NO 566

<400> SEQUENCE: 566

000

-continued

<210> SEQ ID NO 567

<400> SEQUENCE: 567

000

<210> SEQ ID NO 568

<400> SEQUENCE: 568

000

<210> SEQ ID NO 569

<400> SEQUENCE: 569

000

<210> SEQ ID NO 570

<400> SEQUENCE: 570

000

<210> SEQ ID NO 571

<400> SEQUENCE: 571

000

<210> SEQ ID NO 572

<400> SEQUENCE: 572

000

<210> SEQ ID NO 573

<400> SEQUENCE: 573

000

<210> SEQ ID NO 574

<400> SEQUENCE: 574

000

<210> SEQ ID NO 575

<400> SEQUENCE: 575

000

<210> SEQ ID NO 576

<400> SEQUENCE: 576

000

<210> SEQ ID NO 577

<400> SEQUENCE: 577

000

<210> SEQ ID NO 578

<400> SEQUENCE: 578

000

<210> SEQ ID NO 579

<400> SEQUENCE: 579

000

<210> SEQ ID NO 580

<400> SEQUENCE: 580

000

<210> SEQ ID NO 581

<400> SEQUENCE: 581

000

<210> SEQ ID NO 582

<400> SEQUENCE: 582

000

<210> SEQ ID NO 583

<400> SEQUENCE: 583

000

<210> SEQ ID NO 584

<400> SEQUENCE: 584

000

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

<400> SEQUENCE: 590

000

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

<210> SEQ ID NO 594

<400> SEQUENCE: 594

000

<210> SEQ ID NO 595

<400> SEQUENCE: 595

000

<210> SEQ ID NO 596

<400> SEQUENCE: 596

000

<210> SEQ ID NO 597

<400> SEQUENCE: 597

000

<210> SEQ ID NO 598

<400> SEQUENCE: 598

000

<210> SEQ ID NO 599

<400> SEQUENCE: 599

000

<210> SEQ ID NO 600

<400> SEQUENCE: 600

000

<210> SEQ ID NO 601

<400> SEQUENCE: 601

000

<210> SEQ ID NO 602

<400> SEQUENCE: 602

000

<210> SEQ ID NO 603

<400> SEQUENCE: 603

000

<210> SEQ ID NO 604

<400> SEQUENCE: 604

000

<210> SEQ ID NO 605

<400> SEQUENCE: 605

000

<210> SEQ ID NO 606

<400> SEQUENCE: 606

000

<210> SEQ ID NO 607

<400> SEQUENCE: 607

000

<210> SEQ ID NO 608

<400> SEQUENCE: 608

000

<210> SEQ ID NO 609

<400> SEQUENCE: 609

000

<210> SEQ ID NO 610

<400> SEQUENCE: 610

000

<210> SEQ ID NO 611

<400> SEQUENCE: 611

000

<210> SEQ ID NO 612

<400> SEQUENCE: 612

000

<210> SEQ ID NO 613

<400> SEQUENCE: 613

000

<210> SEQ ID NO 614

<400> SEQUENCE: 614

000

<210> SEQ ID NO 615

<400> SEQUENCE: 615

000

<210> SEQ ID NO 616

<400> SEQUENCE: 616

000

<210> SEQ ID NO 617

<400> SEQUENCE: 617

000

<210> SEQ ID NO 618

<400> SEQUENCE: 618

000

<210> SEQ ID NO 619

<400> SEQUENCE: 619

000

<210> SEQ ID NO 620

<400> SEQUENCE: 620

000

<210> SEQ ID NO 621

<400> SEQUENCE: 621

000

<210> SEQ ID NO 622

<400> SEQUENCE: 622

000

<210> SEQ ID NO 623

<400> SEQUENCE: 623

000

<210> SEQ ID NO 624

<400> SEQUENCE: 624

000

<210> SEQ ID NO 625

<400> SEQUENCE: 625

000

<210> SEQ ID NO 626

<400> SEQUENCE: 626

000

<210> SEQ ID NO 627

<400> SEQUENCE: 627

000

<210> SEQ ID NO 628

<400> SEQUENCE: 628

000

<210> SEQ ID NO 629

<400> SEQUENCE: 629

000

<210> SEQ ID NO 630

<400> SEQUENCE: 630

000

<210> SEQ ID NO 631

<400> SEQUENCE: 631

000

<210> SEQ ID NO 632

<400> SEQUENCE: 632

000

<210> SEQ ID NO 633

<400> SEQUENCE: 633

000

<210> SEQ ID NO 634

<400> SEQUENCE: 634

000

<210> SEQ ID NO 635

<400> SEQUENCE: 635

000

<210> SEQ ID NO 636

<400> SEQUENCE: 636

000

<210> SEQ ID NO 637

<400> SEQUENCE: 637

000

<210> SEQ ID NO 638

<400> SEQUENCE: 638

000

<210> SEQ ID NO 639

<400> SEQUENCE: 639

000

<210> SEQ ID NO 640

<400> SEQUENCE: 640

000

<210> SEQ ID NO 641

<400> SEQUENCE: 641

000

<210> SEQ ID NO 642

<400> SEQUENCE: 642

000

<210> SEQ ID NO 643

<400> SEQUENCE: 643

000

<210> SEQ ID NO 644

<400> SEQUENCE: 644

000

<210> SEQ ID NO 645

<400> SEQUENCE: 645

000

<210> SEQ ID NO 646

<400> SEQUENCE: 646

000

<210> SEQ ID NO 647

<400> SEQUENCE: 647

000

<210> SEQ ID NO 648

<400> SEQUENCE: 648

000

<210> SEQ ID NO 649

<400> SEQUENCE: 649

000

<210> SEQ ID NO 650

<400> SEQUENCE: 650

000

<210> SEQ ID NO 651

<400> SEQUENCE: 651

000

<210> SEQ ID NO 652

<400> SEQUENCE: 652

000

<210> SEQ ID NO 653

<400> SEQUENCE: 653

000

<210> SEQ ID NO 654

<400> SEQUENCE: 654

000

<210> SEQ ID NO 655

<400> SEQUENCE: 655

000

<210> SEQ ID NO 656

<400> SEQUENCE: 656

000

<210> SEQ ID NO 657

<400> SEQUENCE: 657

000

<210> SEQ ID NO 658

<400> SEQUENCE: 658

000

<210> SEQ ID NO 659

<400> SEQUENCE: 659

000

<210> SEQ ID NO 660

<400> SEQUENCE: 660

000

<210> SEQ ID NO 661

<400> SEQUENCE: 661

000

<210> SEQ ID NO 662

<400> SEQUENCE: 662

000

<210> SEQ ID NO 663

<400> SEQUENCE: 663

000

<210> SEQ ID NO 664

<400> SEQUENCE: 664

000

<210> SEQ ID NO 665

<400> SEQUENCE: 665

000

<210> SEQ ID NO 666

<400> SEQUENCE: 666

000

<210> SEQ ID NO 667

<400> SEQUENCE: 667

000

<210> SEQ ID NO 668

<400> SEQUENCE: 668

000

<210> SEQ ID NO 669

<400> SEQUENCE: 669

000

<210> SEQ ID NO 670

<400> SEQUENCE: 670

000

<210> SEQ ID NO 671

<400> SEQUENCE: 671

000

<210> SEQ ID NO 672

<400> SEQUENCE: 672

000

<210> SEQ ID NO 673

<400> SEQUENCE: 673

000

<210> SEQ ID NO 674

<400> SEQUENCE: 674

000

<210> SEQ ID NO 675

<400> SEQUENCE: 675

000

<210> SEQ ID NO 676

<400> SEQUENCE: 676

000

<210> SEQ ID NO 677

<400> SEQUENCE: 677

000

<210> SEQ ID NO 678

<400> SEQUENCE: 678

000

<210> SEQ ID NO 679

<400> SEQUENCE: 679

000

<210> SEQ ID NO 680

<400> SEQUENCE: 680

000

<210> SEQ ID NO 681

<400> SEQUENCE: 681

000

<210> SEQ ID NO 682

<400> SEQUENCE: 682

000

<210> SEQ ID NO 683

<400> SEQUENCE: 683

000

<210> SEQ ID NO 684

<400> SEQUENCE: 684

000

<210> SEQ ID NO 685

<400> SEQUENCE: 685

000

<210> SEQ ID NO 686

<400> SEQUENCE: 686

000

<210> SEQ ID NO 687

<400> SEQUENCE: 687

000

<210> SEQ ID NO 688

<400> SEQUENCE: 688

000

<210> SEQ ID NO 689

<400> SEQUENCE: 689

000

<210> SEQ ID NO 690

<400> SEQUENCE: 690

000

-continued

<210> SEQ ID NO 691

<400> SEQUENCE: 691

000

<210> SEQ ID NO 692

<400> SEQUENCE: 692

000

<210> SEQ ID NO 693

<400> SEQUENCE: 693

000

<210> SEQ ID NO 694

<400> SEQUENCE: 694

000

<210> SEQ ID NO 695

<400> SEQUENCE: 695

000

<210> SEQ ID NO 696

<400> SEQUENCE: 696

000

<210> SEQ ID NO 697

<400> SEQUENCE: 697

000

<210> SEQ ID NO 698

<400> SEQUENCE: 698

000

<210> SEQ ID NO 699

<400> SEQUENCE: 699

000

<210> SEQ ID NO 700

<400> SEQUENCE: 700

000

<210> SEQ ID NO 701

<400> SEQUENCE: 701

000

<210> SEQ ID NO 702

```
<400> SEQUENCE: 702

000

<210> SEQ ID NO 703

<400> SEQUENCE: 703

000

<210> SEQ ID NO 704

<400> SEQUENCE: 704

000

<210> SEQ ID NO 705

<400> SEQUENCE: 705

000

<210> SEQ ID NO 706

<400> SEQUENCE: 706

000

<210> SEQ ID NO 707

<400> SEQUENCE: 707

000

<210> SEQ ID NO 708

<400> SEQUENCE: 708

000

<210> SEQ ID NO 709

<400> SEQUENCE: 709

000

<210> SEQ ID NO 710

<400> SEQUENCE: 710

000

<210> SEQ ID NO 711

<400> SEQUENCE: 711

000

<210> SEQ ID NO 712

<400> SEQUENCE: 712

000

<210> SEQ ID NO 713

<400> SEQUENCE: 713
```

000

<210> SEQ ID NO 714

<400> SEQUENCE: 714

000

<210> SEQ ID NO 715

<400> SEQUENCE: 715

000

<210> SEQ ID NO 716

<400> SEQUENCE: 716

000

<210> SEQ ID NO 717

<400> SEQUENCE: 717

000

<210> SEQ ID NO 718

<400> SEQUENCE: 718

000

<210> SEQ ID NO 719

<400> SEQUENCE: 719

000

<210> SEQ ID NO 720

<400> SEQUENCE: 720

000

<210> SEQ ID NO 721

<400> SEQUENCE: 721

000

<210> SEQ ID NO 722

<400> SEQUENCE: 722

000

<210> SEQ ID NO 723

<400> SEQUENCE: 723

000

<210> SEQ ID NO 724

<400> SEQUENCE: 724

000

<210> SEQ ID NO 725

<400> SEQUENCE: 725

000

<210> SEQ ID NO 726

<400> SEQUENCE: 726

000

<210> SEQ ID NO 727

<400> SEQUENCE: 727

000

<210> SEQ ID NO 728

<400> SEQUENCE: 728

000

<210> SEQ ID NO 729

<400> SEQUENCE: 729

000

<210> SEQ ID NO 730

<400> SEQUENCE: 730

000

<210> SEQ ID NO 731

<400> SEQUENCE: 731

000

<210> SEQ ID NO 732

<400> SEQUENCE: 732

000

<210> SEQ ID NO 733

<400> SEQUENCE: 733

000

<210> SEQ ID NO 734

<400> SEQUENCE: 734

000

<210> SEQ ID NO 735

<400> SEQUENCE: 735

000

<210> SEQ ID NO 736

-continued

<400> SEQUENCE: 736

000

<210> SEQ ID NO 737

<400> SEQUENCE: 737

000

<210> SEQ ID NO 738

<400> SEQUENCE: 738

000

<210> SEQ ID NO 739

<400> SEQUENCE: 739

000

<210> SEQ ID NO 740

<400> SEQUENCE: 740

000

<210> SEQ ID NO 741

<400> SEQUENCE: 741

000

<210> SEQ ID NO 742

<400> SEQUENCE: 742

000

<210> SEQ ID NO 743

<400> SEQUENCE: 743

000

<210> SEQ ID NO 744

<400> SEQUENCE: 744

000

<210> SEQ ID NO 745

<400> SEQUENCE: 745

000

<210> SEQ ID NO 746

<400> SEQUENCE: 746

000

<210> SEQ ID NO 747

<400> SEQUENCE: 747

000

<210> SEQ ID NO 748

<400> SEQUENCE: 748

000

<210> SEQ ID NO 749

<400> SEQUENCE: 749

000

<210> SEQ ID NO 750

<400> SEQUENCE: 750

000

<210> SEQ ID NO 751

<400> SEQUENCE: 751

000

<210> SEQ ID NO 752

<400> SEQUENCE: 752

000

<210> SEQ ID NO 753

<400> SEQUENCE: 753

000

<210> SEQ ID NO 754

<400> SEQUENCE: 754

000

<210> SEQ ID NO 755

<400> SEQUENCE: 755

000

<210> SEQ ID NO 756

<400> SEQUENCE: 756

000

<210> SEQ ID NO 757

<400> SEQUENCE: 757

000

<210> SEQ ID NO 758

<400> SEQUENCE: 758

000

<210> SEQ ID NO 759

<400> SEQUENCE: 759

000

<210> SEQ ID NO 760

<400> SEQUENCE: 760

000

<210> SEQ ID NO 761

<400> SEQUENCE: 761

000

<210> SEQ ID NO 762

<400> SEQUENCE: 762

000

<210> SEQ ID NO 763

<400> SEQUENCE: 763

000

<210> SEQ ID NO 764

<400> SEQUENCE: 764

000

<210> SEQ ID NO 765

<400> SEQUENCE: 765

000

<210> SEQ ID NO 766

<400> SEQUENCE: 766

000

<210> SEQ ID NO 767

<400> SEQUENCE: 767

000

<210> SEQ ID NO 768

<400> SEQUENCE: 768

000

<210> SEQ ID NO 769

<400> SEQUENCE: 769

000

<210> SEQ ID NO 770

<400> SEQUENCE: 770

000

<210> SEQ ID NO 771

<400> SEQUENCE: 771

000

<210> SEQ ID NO 772

<400> SEQUENCE: 772

000

<210> SEQ ID NO 773

<400> SEQUENCE: 773

000

<210> SEQ ID NO 774

<400> SEQUENCE: 774

000

<210> SEQ ID NO 775

<400> SEQUENCE: 775

000

<210> SEQ ID NO 776

<400> SEQUENCE: 776

000

<210> SEQ ID NO 777

<400> SEQUENCE: 777

000

<210> SEQ ID NO 778

<400> SEQUENCE: 778

000

<210> SEQ ID NO 779

<400> SEQUENCE: 779

000

<210> SEQ ID NO 780

<400> SEQUENCE: 780

000

<210> SEQ ID NO 781

<400> SEQUENCE: 781

000

<210> SEQ ID NO 782

<400> SEQUENCE: 782

000

<210> SEQ ID NO 783

<400> SEQUENCE: 783

000

<210> SEQ ID NO 784

<400> SEQUENCE: 784

000

<210> SEQ ID NO 785

<400> SEQUENCE: 785

000

<210> SEQ ID NO 786

<400> SEQUENCE: 786

000

<210> SEQ ID NO 787

<400> SEQUENCE: 787

000

<210> SEQ ID NO 788

<400> SEQUENCE: 788

000

<210> SEQ ID NO 789

<400> SEQUENCE: 789

000

<210> SEQ ID NO 790

<400> SEQUENCE: 790

000

<210> SEQ ID NO 791

<400> SEQUENCE: 791

000

<210> SEQ ID NO 792

<400> SEQUENCE: 792

000

<210> SEQ ID NO 793
<400> SEQUENCE: 793
000

<210> SEQ ID NO 794
<400> SEQUENCE: 794
000

<210> SEQ ID NO 795
<400> SEQUENCE: 795
000

<210> SEQ ID NO 796
<400> SEQUENCE: 796
000

<210> SEQ ID NO 797
<400> SEQUENCE: 797
000

<210> SEQ ID NO 798
<400> SEQUENCE: 798
000

<210> SEQ ID NO 799
<400> SEQUENCE: 799
000

<210> SEQ ID NO 800
<400> SEQUENCE: 800
000

<210> SEQ ID NO 801
<400> SEQUENCE: 801
000

<210> SEQ ID NO 802
<400> SEQUENCE: 802
000

<210> SEQ ID NO 803
<400> SEQUENCE: 803
000

<210> SEQ ID NO 804

<400> SEQUENCE: 804

000

<210> SEQ ID NO 805

<400> SEQUENCE: 805

000

<210> SEQ ID NO 806

<400> SEQUENCE: 806

000

<210> SEQ ID NO 807

<400> SEQUENCE: 807

000

<210> SEQ ID NO 808

<400> SEQUENCE: 808

000

<210> SEQ ID NO 809

<400> SEQUENCE: 809

000

<210> SEQ ID NO 810

<400> SEQUENCE: 810

000

<210> SEQ ID NO 811

<400> SEQUENCE: 811

000

<210> SEQ ID NO 812

<400> SEQUENCE: 812

000

<210> SEQ ID NO 813

<400> SEQUENCE: 813

000

<210> SEQ ID NO 814

<400> SEQUENCE: 814

000

<210> SEQ ID NO 815

<400> SEQUENCE: 815

000

<210> SEQ ID NO 816

<400> SEQUENCE: 816

000

<210> SEQ ID NO 817

<400> SEQUENCE: 817

000

<210> SEQ ID NO 818

<400> SEQUENCE: 818

000

<210> SEQ ID NO 819

<400> SEQUENCE: 819

000

<210> SEQ ID NO 820

<400> SEQUENCE: 820

000

<210> SEQ ID NO 821

<400> SEQUENCE: 821

000

<210> SEQ ID NO 822

<400> SEQUENCE: 822

000

<210> SEQ ID NO 823

<400> SEQUENCE: 823

000

<210> SEQ ID NO 824

<400> SEQUENCE: 824

000

<210> SEQ ID NO 825

<400> SEQUENCE: 825

000

<210> SEQ ID NO 826

<400> SEQUENCE: 826

-continued

000

<210> SEQ ID NO 827

<400> SEQUENCE: 827

000

<210> SEQ ID NO 828

<400> SEQUENCE: 828

000

<210> SEQ ID NO 829

<400> SEQUENCE: 829

000

<210> SEQ ID NO 830

<400> SEQUENCE: 830

000

<210> SEQ ID NO 831

<400> SEQUENCE: 831

000

<210> SEQ ID NO 832

<400> SEQUENCE: 832

000

<210> SEQ ID NO 833

<400> SEQUENCE: 833

000

<210> SEQ ID NO 834

<400> SEQUENCE: 834

000

<210> SEQ ID NO 835

<400> SEQUENCE: 835

000

<210> SEQ ID NO 836

<400> SEQUENCE: 836

000

<210> SEQ ID NO 837

<400> SEQUENCE: 837

000

<210> SEQ ID NO 838

<400> SEQUENCE: 838

000

<210> SEQ ID NO 839

<400> SEQUENCE: 839

000

<210> SEQ ID NO 840

<400> SEQUENCE: 840

000

<210> SEQ ID NO 841

<400> SEQUENCE: 841

000

<210> SEQ ID NO 842

<400> SEQUENCE: 842

000

<210> SEQ ID NO 843

<400> SEQUENCE: 843

000

<210> SEQ ID NO 844

<400> SEQUENCE: 844

000

<210> SEQ ID NO 845

<400> SEQUENCE: 845

000

<210> SEQ ID NO 846

<400> SEQUENCE: 846

000

<210> SEQ ID NO 847

<400> SEQUENCE: 847

000

<210> SEQ ID NO 848

<400> SEQUENCE: 848

000

<210> SEQ ID NO 849

<400> SEQUENCE: 849

000

<210> SEQ ID NO 850

<400> SEQUENCE: 850

000

<210> SEQ ID NO 851

<400> SEQUENCE: 851

000

<210> SEQ ID NO 852

<400> SEQUENCE: 852

000

<210> SEQ ID NO 853

<400> SEQUENCE: 853

000

<210> SEQ ID NO 854

<400> SEQUENCE: 854

000

<210> SEQ ID NO 855

<400> SEQUENCE: 855

000

<210> SEQ ID NO 856

<400> SEQUENCE: 856

000

<210> SEQ ID NO 857

<400> SEQUENCE: 857

000

<210> SEQ ID NO 858

<400> SEQUENCE: 858

000

<210> SEQ ID NO 859

<400> SEQUENCE: 859

000

<210> SEQ ID NO 860

<400> SEQUENCE: 860

000

<210> SEQ ID NO 861

<400> SEQUENCE: 861

000

<210> SEQ ID NO 862

<400> SEQUENCE: 862

000

<210> SEQ ID NO 863

<400> SEQUENCE: 863

000

<210> SEQ ID NO 864

<400> SEQUENCE: 864

000

<210> SEQ ID NO 865

<400> SEQUENCE: 865

000

<210> SEQ ID NO 866

<400> SEQUENCE: 866

000

<210> SEQ ID NO 867

<400> SEQUENCE: 867

000

<210> SEQ ID NO 868

<400> SEQUENCE: 868

000

<210> SEQ ID NO 869

<400> SEQUENCE: 869

000

<210> SEQ ID NO 870

<400> SEQUENCE: 870

000

<210> SEQ ID NO 871

<400> SEQUENCE: 871

000

<210> SEQ ID NO 872

<400> SEQUENCE: 872

000

<210> SEQ ID NO 873

<400> SEQUENCE: 873

000

<210> SEQ ID NO 874

<400> SEQUENCE: 874

000

<210> SEQ ID NO 875

<400> SEQUENCE: 875

000

<210> SEQ ID NO 876

<400> SEQUENCE: 876

000

<210> SEQ ID NO 877

<400> SEQUENCE: 877

000

<210> SEQ ID NO 878

<400> SEQUENCE: 878

000

<210> SEQ ID NO 879

<400> SEQUENCE: 879

000

<210> SEQ ID NO 880

<400> SEQUENCE: 880

000

<210> SEQ ID NO 881

<400> SEQUENCE: 881

000

<210> SEQ ID NO 882

<400> SEQUENCE: 882

000

-continued

<210> SEQ ID NO 883
<400> SEQUENCE: 883
000

<210> SEQ ID NO 884
<400> SEQUENCE: 884
000

<210> SEQ ID NO 885
<400> SEQUENCE: 885
000

<210> SEQ ID NO 886
<400> SEQUENCE: 886
000

<210> SEQ ID NO 887
<400> SEQUENCE: 887
000

<210> SEQ ID NO 888
<400> SEQUENCE: 888
000

<210> SEQ ID NO 889
<400> SEQUENCE: 889
000

<210> SEQ ID NO 890
<400> SEQUENCE: 890
000

<210> SEQ ID NO 891
<400> SEQUENCE: 891
000

<210> SEQ ID NO 892
<400> SEQUENCE: 892
000

<210> SEQ ID NO 893
<400> SEQUENCE: 893
000

<210> SEQ ID NO 894

```
<400> SEQUENCE: 894
000

<210> SEQ ID NO 895
<400> SEQUENCE: 895
000

<210> SEQ ID NO 896
<400> SEQUENCE: 896
000

<210> SEQ ID NO 897
<400> SEQUENCE: 897
000

<210> SEQ ID NO 898
<400> SEQUENCE: 898
000

<210> SEQ ID NO 899
<400> SEQUENCE: 899
000

<210> SEQ ID NO 900
<400> SEQUENCE: 900
000

<210> SEQ ID NO 901
<400> SEQUENCE: 901
000

<210> SEQ ID NO 902
<400> SEQUENCE: 902
000

<210> SEQ ID NO 903
<400> SEQUENCE: 903
000

<210> SEQ ID NO 904
<400> SEQUENCE: 904
000

<210> SEQ ID NO 905
<400> SEQUENCE: 905
```

000

<210> SEQ ID NO 906

<400> SEQUENCE: 906

000

<210> SEQ ID NO 907

<400> SEQUENCE: 907

000

<210> SEQ ID NO 908

<400> SEQUENCE: 908

000

<210> SEQ ID NO 909

<400> SEQUENCE: 909

000

<210> SEQ ID NO 910

<400> SEQUENCE: 910

000

<210> SEQ ID NO 911

<400> SEQUENCE: 911

000

<210> SEQ ID NO 912

<400> SEQUENCE: 912

000

<210> SEQ ID NO 913

<400> SEQUENCE: 913

000

<210> SEQ ID NO 914

<400> SEQUENCE: 914

000

<210> SEQ ID NO 915

<400> SEQUENCE: 915

000

<210> SEQ ID NO 916

<400> SEQUENCE: 916

000

<210> SEQ ID NO 917

<400> SEQUENCE: 917

000

<210> SEQ ID NO 918

<400> SEQUENCE: 918

000

<210> SEQ ID NO 919

<400> SEQUENCE: 919

000

<210> SEQ ID NO 920

<400> SEQUENCE: 920

000

<210> SEQ ID NO 921

<400> SEQUENCE: 921

000

<210> SEQ ID NO 922

<400> SEQUENCE: 922

000

<210> SEQ ID NO 923

<400> SEQUENCE: 923

000

<210> SEQ ID NO 924

<400> SEQUENCE: 924

000

<210> SEQ ID NO 925

<400> SEQUENCE: 925

000

<210> SEQ ID NO 926

<400> SEQUENCE: 926

000

<210> SEQ ID NO 927

<400> SEQUENCE: 927

000

<210> SEQ ID NO 928

<400> SEQUENCE: 928

000

<210> SEQ ID NO 929

<400> SEQUENCE: 929

000

<210> SEQ ID NO 930

<400> SEQUENCE: 930

000

<210> SEQ ID NO 931

<400> SEQUENCE: 931

000

<210> SEQ ID NO 932

<400> SEQUENCE: 932

000

<210> SEQ ID NO 933

<400> SEQUENCE: 933

000

<210> SEQ ID NO 934

<400> SEQUENCE: 934

000

<210> SEQ ID NO 935

<400> SEQUENCE: 935

000

<210> SEQ ID NO 936

<400> SEQUENCE: 936

000

<210> SEQ ID NO 937

<400> SEQUENCE: 937

000

<210> SEQ ID NO 938

<400> SEQUENCE: 938

000

<210> SEQ ID NO 939

```
<400> SEQUENCE: 939
000

<210> SEQ ID NO 940
<400> SEQUENCE: 940
000

<210> SEQ ID NO 941
<400> SEQUENCE: 941
000

<210> SEQ ID NO 942
<400> SEQUENCE: 942
000

<210> SEQ ID NO 943
<400> SEQUENCE: 943
000

<210> SEQ ID NO 944
<400> SEQUENCE: 944
000

<210> SEQ ID NO 945
<400> SEQUENCE: 945
000

<210> SEQ ID NO 946
<400> SEQUENCE: 946
000

<210> SEQ ID NO 947
<400> SEQUENCE: 947
000

<210> SEQ ID NO 948
<400> SEQUENCE: 948
000

<210> SEQ ID NO 949
<400> SEQUENCE: 949
000

<210> SEQ ID NO 950
<400> SEQUENCE: 950
```

000

<210> SEQ ID NO 951

<400> SEQUENCE: 951

000

<210> SEQ ID NO 952

<400> SEQUENCE: 952

000

<210> SEQ ID NO 953

<400> SEQUENCE: 953

000

<210> SEQ ID NO 954

<400> SEQUENCE: 954

000

<210> SEQ ID NO 955

<400> SEQUENCE: 955

000

<210> SEQ ID NO 956

<400> SEQUENCE: 956

000

<210> SEQ ID NO 957

<400> SEQUENCE: 957

000

<210> SEQ ID NO 958

<400> SEQUENCE: 958

000

<210> SEQ ID NO 959

<400> SEQUENCE: 959

000

<210> SEQ ID NO 960

<400> SEQUENCE: 960

000

<210> SEQ ID NO 961

<400> SEQUENCE: 961

000

-continued

<210> SEQ ID NO 962
<400> SEQUENCE: 962
000

<210> SEQ ID NO 963
<400> SEQUENCE: 963
000

<210> SEQ ID NO 964
<400> SEQUENCE: 964
000

<210> SEQ ID NO 965
<400> SEQUENCE: 965
000

<210> SEQ ID NO 966
<400> SEQUENCE: 966
000

<210> SEQ ID NO 967
<400> SEQUENCE: 967
000

<210> SEQ ID NO 968
<400> SEQUENCE: 968
000

<210> SEQ ID NO 969
<400> SEQUENCE: 969
000

<210> SEQ ID NO 970
<400> SEQUENCE: 970
000

<210> SEQ ID NO 971
<400> SEQUENCE: 971
000

<210> SEQ ID NO 972
<400> SEQUENCE: 972
000

<210> SEQ ID NO 973

<400> SEQUENCE: 973

000

<210> SEQ ID NO 974

<400> SEQUENCE: 974

000

<210> SEQ ID NO 975

<400> SEQUENCE: 975

000

<210> SEQ ID NO 976

<400> SEQUENCE: 976

000

<210> SEQ ID NO 977

<400> SEQUENCE: 977

000

<210> SEQ ID NO 978

<400> SEQUENCE: 978

000

<210> SEQ ID NO 979

<400> SEQUENCE: 979

000

<210> SEQ ID NO 980

<400> SEQUENCE: 980

000

<210> SEQ ID NO 981

<400> SEQUENCE: 981

000

<210> SEQ ID NO 982

<400> SEQUENCE: 982

000

<210> SEQ ID NO 983

<400> SEQUENCE: 983

000

<210> SEQ ID NO 984

<400> SEQUENCE: 984

000

<210> SEQ ID NO 985

<400> SEQUENCE: 985

000

<210> SEQ ID NO 986

<400> SEQUENCE: 986

000

<210> SEQ ID NO 987

<400> SEQUENCE: 987

000

<210> SEQ ID NO 988

<400> SEQUENCE: 988

000

<210> SEQ ID NO 989

<400> SEQUENCE: 989

000

<210> SEQ ID NO 990

<400> SEQUENCE: 990

000

<210> SEQ ID NO 991

<400> SEQUENCE: 991

000

<210> SEQ ID NO 992

<400> SEQUENCE: 992

000

<210> SEQ ID NO 993

<400> SEQUENCE: 993

000

<210> SEQ ID NO 994

<400> SEQUENCE: 994

000

<210> SEQ ID NO 995

<400> SEQUENCE: 995

000

<210> SEQ ID NO 996

<400> SEQUENCE: 996

000

<210> SEQ ID NO 997

<400> SEQUENCE: 997

000

<210> SEQ ID NO 998

<400> SEQUENCE: 998

000

<210> SEQ ID NO 999

<400> SEQUENCE: 999

000

<210> SEQ ID NO 1000

<400> SEQUENCE: 1000

000

<210> SEQ ID NO 1001
<211> LENGTH: 121
<212> TYPE: PRT
<213> ORGANISM: Artificial Sequence
<220> FEATURE:
<223> OTHER INFORMATION: Anti-NME7 B3 peptide monoclonal antibodies -
      8F9A4A3 Heavy chain variable region sequence mouse

<400> SEQUENCE: 1001

```
Val Gln Leu Gln Gln Ser Gly Pro Glu Leu Val Lys Pro Gly Ala Ser
1               5                   10                  15

Val Lys Ile Ser Cys Lys Thr Ser Gly Asn Thr Phe Thr Glu Tyr Thr
            20                  25                  30

Met His Trp Val Lys Gln Ser His Gly Lys Ser Leu Glu Trp Ile Gly
        35                  40                  45

Gly Phe Asn Pro Asn Asn Gly Val Thr Asn Tyr Asn Gln Lys Phe Lys
    50                  55                  60

Gly Lys Ala Thr Leu Thr Val Asp Lys Ser Ser Ser Thr Ala Tyr Met
65                  70                  75                  80

Glu Leu Arg Ser Leu Thr Ser Glu Asp Ser Ala Val Tyr Tyr Cys Ala
                85                  90                  95

Arg Arg Tyr Tyr His Ser Leu Tyr Val Phe Tyr Phe Asp Tyr Trp Gly
            100                 105                 110

Gln Gly Thr Thr Leu Thr Val Ser Ser
        115                 120
```

<210> SEQ ID NO 1002
<211> LENGTH: 98
<212> TYPE: PRT
<213> ORGANISM: Artificial Sequence
<220> FEATURE:
<223> OTHER INFORMATION: IGHV1-24*01 V-REGION sequence human (closest
      match hu antibody sequence)

<400> SEQUENCE: 1002

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr

<210> SEQ ID NO 1003
<211> LENGTH: 15
<212> TYPE: PRT
<213> ORGANISM: Artificial Sequence
<220> FEATURE:
<223> OTHER INFORMATION: IGHJ4*01 J-REGION sequence human (closest match
      hu antibody sequence)

<400> SEQUENCE: 1003

Tyr Phe Asp Tyr Trp Gly Gln Gly Thr Leu Val Thr Val Ser Ser
1               5                   10                  15

<210> SEQ ID NO 1004
<211> LENGTH: 122
<212> TYPE: PRT
<213> ORGANISM: Artificial Sequence
<220> FEATURE:
<223> OTHER INFORMATION: humanized 8F9A4A3 Heavy chain variable region
      sequence

<400> SEQUENCE: 1004

Gln Val Gln Leu Val Gln Ser Gly Ala Glu Val Lys Lys Pro Gly Ala
1               5                   10                  15

Ser Val Lys Val Ser Cys Lys Val Ser Gly Asn Thr Phe Thr Glu Tyr
            20                  25                  30

Thr Met His Trp Val Arg Gln Ala Pro Gly Lys Gly Leu Glu Trp Met
        35                  40                  45

Gly Gly Phe Asn Pro Asn Asn Gly Val Thr Asn Tyr Asn Gln Lys Phe
    50                  55                  60

Lys Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Tyr Tyr His Ser Leu Tyr Val Phe Tyr Phe Asp Tyr Trp
            100                 105                 110

Gly Gln Gly Thr Leu Val Thr Val Ser Ser
        115                 120

<210> SEQ ID NO 1005
<211> LENGTH: 122
<212> TYPE: PRT
<213> ORGANISM: Artificial Sequence
<220> FEATURE:
<223> OTHER INFORMATION: humanized 8F9A4A3 Heavy chain variable region -continued sequence (codon optimized)

<400> SEQUENCE: 1005

Gln Val Gln Leu Val Gln Ser Gly Ala Glu Val Lys Lys Pro Gly Ala
1               5                   10                  15

Ser Val Lys Val Ser Cys Lys Val Ser Gly Asn Thr Phe Thr Glu Tyr
            20                  25                  30

Thr Met His Trp Val Arg Gln Ala Pro Gly Lys Gly Leu Glu Trp Met
        35                  40                  45

Gly Gly Phe Asn Pro Asn Asn Gly Val Thr Asn Tyr Asn Gln Lys Phe
    50                  55                  60

Lys Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Tyr Tyr His Ser Leu Tyr Val Phe Tyr Phe Asp Tyr Trp
            100                 105                 110

Gly Gln Gly Thr Leu Val Thr Val Ser Ser
        115                 120

<210> SEQ ID NO 1006
<211> LENGTH: 122
<212> TYPE: PRT
<213> ORGANISM: Artificial Sequence
<220> FEATURE:
<223> OTHER INFORMATION: Modified humanized 8F9A4A3 Heavy chain variable
      region sequence)

<400> SEQUENCE: 1006

Gln Val Gln Leu Val Gln Ser Gly Ala Glu Val Lys Lys Pro Gly Ala
1               5                   10                  15

Ser Val Lys Val Ser Cys Lys Val Ser Gly Asn Thr Phe Thr Glu Tyr
            20                  25                  30

Thr Met His Trp Val Arg Gln Ala Pro Gly Lys Gly Leu Glu Trp Ile
        35                  40                  45

Gly Gly Phe Asn Pro Asn Asn Gly Val Thr Asn Tyr Asn Gln Lys Phe
    50                  55                  60

Lys Gly Lys Val Thr Leu Thr Val Asp Thr Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Tyr Tyr His Ser Leu Tyr Val Phe Tyr Phe Asp Tyr Trp
            100                 105                 110

Gly Gln Gly Thr Leu Val Thr Val Ser Ser
        115                 120

<210> SEQ ID NO 1007
<211> LENGTH: 122
<212> TYPE: PRT
<213> ORGANISM: Artificial Sequence
<220> FEATURE:
<223> OTHER INFORMATION: Modified humanized 8F9A4A3 Heavy chain variable
      region sequence (codon optimized)

<400> SEQUENCE: 1007

Gln Val Gln Leu Val Gln Ser Gly Ala Glu Val Lys Lys Pro Gly Ala
1               5                   10                  15

Ser Val Lys Val Ser Cys Lys Val Ser Gly Asn Thr Phe Thr Glu Tyr
            20                  25                  30

```
Thr Met His Trp Val Arg Gln Ala Pro Gly Lys Gly Leu Glu Trp Ile
        35                  40                  45

Gly Gly Phe Asn Pro Asn Asn Gly Val Thr Asn Tyr Asn Gln Lys Phe
    50                  55                  60

Lys Gly Lys Val Thr Leu Thr Val Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Tyr Tyr His Ser Leu Tyr Val Phe Tyr Phe Asp Tyr Trp
                100                 105                 110

Gly Gln Gly Thr Leu Val Thr Val Ser Ser
            115                 120

<210> SEQ ID NO 1008
<211> LENGTH: 108
<212> TYPE: PRT
<213> ORGANISM: Artificial Sequence
<220> FEATURE:
<223> OTHER INFORMATION: 8F9A4A3 Light chain variable region sequence
      mouse

<400> SEQUENCE: 1008

Glu Thr Thr Val Thr Gln Ser Pro Ala Ser Leu Ser Met Ala Ile Gly
1               5                   10                  15

Glu Lys Val Thr Ile Arg Cys Ile Thr Ser Thr Asp Ile Asp Asp Asp
                20                  25                  30

Met Asn Trp Tyr Gln Gln Lys Pro Gly Glu Pro Pro Lys Leu Leu Ile
            35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Pro Leu
                85                  90                  95

Thr Phe Gly Ser Gly Thr Lys Leu Glu Ile Lys Arg
            100                 105

<210> SEQ ID NO 1009
<211> LENGTH: 88
<212> TYPE: PRT
<213> ORGANISM: Artificial Sequence
<220> FEATURE:
<223> OTHER INFORMATION: IGKV5-2*01 V-REGION sequence human (closest
      match hu antibody sequence)

<400> SEQUENCE: 1009

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
                20                  25                  30

Met Asn Trp Tyr Gln Gln Lys Pro Gly Glu Ala Ala Ile Phe Ile Ile
            35                  40                  45

Gln Glu Ala Thr Thr Leu Val Pro Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys
                85
```

<210> SEQ ID NO 1010
<211> LENGTH: 12
<212> TYPE: PRT
<213> ORGANISM: Artificial Sequence
<220> FEATURE:
<223> OTHER INFORMATION: IGKJ4*02 J-REGION sequence human (closest match hu antibody sequence)

<400> SEQUENCE: 1010

```
Leu Thr Phe Gly Gly Gly Thr Lys Val Glu Ile Lys
1               5                   10
```

<210> SEQ ID NO 1011
<211> LENGTH: 108
<212> TYPE: PRT
<213> ORGANISM: Artificial Sequence
<220> FEATURE:
<223> OTHER INFORMATION: humanized 8F9A4A3 Light chain variable region sequence

<400> SEQUENCE: 1011

```
Glu Thr Thr Leu Thr Gln Ser Pro Ala Phe Met Ser Ala Thr Pro Gly
1               5                   10                  15

Asp Lys Val Asn Ile Ser Cys Ile Thr Ser Thr Asp Ile Asp Asp Asp
                20                  25                  30

Met Asn Trp Tyr Gln Gln Lys Pro Gly Glu Ala Ala Ile Phe Ile Ile
            35                  40                  45

Gln Glu Gly Asn Thr Leu Arg Pro Gly Ile Pro Pro Arg Phe Ser Gly
        50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln Ser Asp Asn Leu Pro Leu
                85                  90                  95

Thr Phe Gly Gly Gly Thr Lys Val Glu Ile Lys Arg
            100                 105
```

<210> SEQ ID NO 1012
<211> LENGTH: 108
<212> TYPE: PRT
<213> ORGANISM: Artificial Sequence
<220> FEATURE:
<223> OTHER INFORMATION: humanized 8F9A4A3 Light chain variable region sequence (codon optimized)

<400> SEQUENCE: 1012

```
Glu Thr Thr Leu Thr Gln Ser Pro Ala Phe Met Ser Ala Thr Pro Gly
1               5                   10                  15

Asp Lys Val Asn Ile Ser Cys Ile Thr Ser Thr Asp Ile Asp Asp Asp
                20                  25                  30

Met Asn Trp Tyr Gln Gln Lys Pro Gly Glu Ala Ala Ile Phe Ile Ile
            35                  40                  45

Gln Glu Gly Asn Thr Leu Arg Pro Gly Ile Pro Pro Arg Phe Ser Gly
        50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln Ser Asp Asn Leu Pro Leu
                85                  90                  95

Thr Phe Gly Gly Gly Thr Lys Val Glu Ile Lys Arg
            100                 105
```

<210> SEQ ID NO 1013
<211> LENGTH: 108
<212> TYPE: PRT
<213> ORGANISM: Artificial Sequence
<220> FEATURE:
<223> OTHER INFORMATION: Modified humanized 8F9A4A3 Light chain variable
      region sequence

<400> SEQUENCE: 1013

Glu Thr Thr Val Thr Gln Ser Pro Ala Phe Met Ser Ala Thr Pro Gly
1               5                   10                  15

Asp Lys Val Thr Ile Ser Cys Ile Thr Ser Thr Asp Ile Asp Asp Asp
                20                  25                  30

Met Asn Trp Tyr Gln Gln Lys Pro Gly Glu Ala Ala Ile Leu Leu Ile
            35                  40                  45

Ser Glu Gly Asn Thr Leu Arg Pro Gly Ile Pro Pro Arg Phe Ser Ser
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln Ser Asp Asn Leu Pro Leu
                85                  90                  95

Thr Phe Gly Gly Gly Thr Lys Val Glu Ile Lys Arg
                100                 105

<210> SEQ ID NO 1014
<211> LENGTH: 108
<212> TYPE: PRT
<213> ORGANISM: Artificial Sequence
<220> FEATURE:
<223> OTHER INFORMATION: Modified humanized 8F9A4A3 Light chain variable
      region sequence (codon optimized)

<400> SEQUENCE: 1014

Glu Thr Thr Val Thr Gln Ser Pro Ala Phe Met Ser Ala Thr Pro Gly
1               5                   10                  15

Asp Lys Val Thr Ile Ser Cys Ile Thr Ser Thr Asp Ile Asp Asp Asp
                20                  25                  30

Met Asn Trp Tyr Gln Gln Lys Pro Gly Glu Ala Ala Ile Leu Leu Ile
            35                  40                  45

Ser Glu Gly Asn Thr Leu Arg Pro Gly Ile Pro Pro Arg Phe Ser Ser
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln Ser Asp Asn Leu Pro Leu
                85                  90                  95

Thr Phe Gly Gly Gly Thr Lys Val Glu Ile Lys Arg
                100                 105

<210> SEQ ID NO 1015
<211> LENGTH: 245
<212> TYPE: PRT
<213> ORGANISM: Artificial Sequence
<220> FEATURE:
<223> OTHER INFORMATION: Modified humanized 8F9A4A3 sequence (codon
      optimized) - humanized heavy and light chains joined via a
      flexible linker

<400> SEQUENCE: 1015

Gln Val Gln Leu Val Gln Ser Gly Ala Glu Val Lys Lys Pro Gly Ala
1               5                   10                  15

```
Ser Val Lys Val Ser Cys Lys Val Ser Gly Asn Thr Phe Thr Glu Tyr
            20                  25                  30

Thr Met His Trp Val Arg Gln Ala Pro Gly Lys Gly Leu Glu Trp Ile
            35                  40                  45

Gly Gly Phe Asn Pro Asn Asn Gly Val Thr Asn Tyr Asn Gln Lys Phe
 50                  55                  60

Lys Gly Lys Val Thr Leu Thr Val Asp Thr Ser Ser Thr Ala Tyr
 65                  70                  75                  80

Met Glu Leu Ser Ser Leu Arg Ser Glu Asp Thr Ala Val Tyr Tyr Cys
            85                  90                  95

Ala Arg Arg Tyr Tyr His Ser Leu Tyr Val Phe Tyr Phe Asp Tyr Trp
           100                 105                 110

Gly Gln Gly Thr Leu Val Thr Val Ser Ser Gly Gly Gly Ser Gly
           115                 120                 125

Gly Gly Gly Ser Gly Gly Gly Ser Glu Thr Thr Val Thr Gln Ser
       130                 135                 140

Pro Ala Phe Met Ser Ala Thr Pro Gly Asp Lys Val Thr Ile Ser Cys
145                 150                 155                 160

Ile Thr Ser Thr Asp Ile Asp Asp Met Asn Trp Tyr Gln Gln Lys
                165                 170                 175

Pro Gly Glu Ala Ala Ile Leu Leu Ile Ser Glu Gly Asn Thr Leu Arg
           180                 185                 190

Pro Gly Ile Pro Pro Arg Phe Ser Ser Gly Tyr Gly Thr Asp Phe
           195                 200                 205

Thr Leu Thr Ile Asn Asn Ile Glu Ser Glu Asp Ala Ala Tyr Tyr Phe
210                 215                 220

Cys Leu Gln Ser Asp Asn Leu Pro Leu Thr Phe Gly Gly Gly Thr Lys
225                 230                 235                 240

Val Glu Ile Lys Arg
                245

<210> SEQ ID NO 1016
<211> LENGTH: 119
<212> TYPE: PRT
<213> ORGANISM: Artificial Sequence
<220> FEATURE:
<223> OTHER INFORMATION: 8F9A5A1 Heavy chain variable region sequence

<400> SEQUENCE: 1016

Ile Gln Leu Val Gln Ser Gly Pro Glu Leu Lys Lys Pro Gly Glu Thr
 1               5                  10                  15

Val Lys Ile Ser Cys Lys Ala Ser Gly Tyr Thr Phe Thr Asn Tyr Gly
            20                  25                  30

Met Asn Trp Val Lys Gln Ala Pro Gly Lys Gly Leu Lys Trp Met Gly
            35                  40                  45

Trp Ile Asn Thr Tyr Thr Gly Glu Pro Thr Tyr Val Asp Asp Phe Lys
 50                  55                  60

Gly Arg Phe Ala Phe Ser Leu Glu Thr Ser Ala Thr Thr Ala Tyr Leu
 65                  70                  75                  80

Gln Ile Asn Asn Leu Lys Asn Glu Asp Thr Ser Thr Tyr Phe Cys Ala
            85                  90                  95

Arg Leu Arg Gly Ile Arg Pro Gly Pro Leu Ala Tyr Trp Gly Gln Gly
           100                 105                 110

Thr Leu Val Thr Val Ser Ala
       115
```

<210> SEQ ID NO 1017
<211> LENGTH: 98
<212> TYPE: PRT
<213> ORGANISM: Artificial Sequence
<220> FEATURE:
<223> OTHER INFORMATION: IGHV7-81*01 V-REGION sequence

<400> SEQUENCE: 1017

Gln Val Gln Leu Val Gln Ser Gly His Glu Val Lys Gln Pro Gly Ala
1               5                   10                  15

Ser Val Lys Val Ser Cys Lys Ala Ser Gly Tyr Ser Phe Thr Thr Tyr
            20                  25                  30

Gly Met Asn Trp Val Pro Gln Ala Pro Gly Gln Gly Leu Glu Trp Met
        35                  40                  45

Gly Trp Phe Asn Thr Tyr Thr Gly Asn Pro Thr Tyr Ala Gln Gly Phe
    50                  55                  60

Thr Gly Arg Phe Val Phe Ser Met Asp Thr Ser Ala Ser Thr Ala Tyr
65                  70                  75                  80

Leu Gln Ile Ser Ser Leu Lys Ala Glu Asp Met Ala Met Tyr Tyr Cys
                85                  90                  95

Ala Arg

<210> SEQ ID NO 1018
<211> LENGTH: 15
<212> TYPE: PRT
<213> ORGANISM: Artificial Sequence
<220> FEATURE:
<223> OTHER INFORMATION: IGHJ4*03 J-REGION sequence

<400> SEQUENCE: 1018

Tyr Phe Asp Tyr Trp Gly Gln Gly Thr Leu Val Thr Val Ser Ser
1               5                   10                  15

<210> SEQ ID NO 1019
<211> LENGTH: 120
<212> TYPE: PRT
<213> ORGANISM: Artificial Sequence
<220> FEATURE:
<223> OTHER INFORMATION: humanized 8F9A5A1 Heavy chain variable region
      sequence

<400> SEQUENCE: 1019

Gln Val Gln Leu Val Gln Ser Gly His Glu Val Lys Gln Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Pro Gln Ala Pro Gly Gln Gly Leu Glu Trp Met
        35                  40                  45

Gly Trp Ile Asn Thr Tyr Thr Gly Glu Pro Thr Tyr Val Asp Asp Phe
    50                  55                  60

Lys Gly Arg Phe Val Phe Ser Met Asp Thr Ser Ala Ser Thr Ala Tyr
65                  70                  75                  80

Leu Gln Ile Ser Ser Leu Lys Ala Glu Asp Met Ala Met Tyr Tyr Cys
                85                  90                  95

Ala Arg Leu Arg Gly Ile Arg Pro Gly Pro Leu Ala Tyr Trp Gly Gln
            100                 105                 110

Gly Thr Leu Val Thr Val Ser Ser
        115                 120

<210> SEQ ID NO 1020
<211> LENGTH: 120
<212> TYPE: PRT
<213> ORGANISM: Artificial Sequence
<220> FEATURE:
<223> OTHER INFORMATION: humanized 8F9A5A1 Heavy chain variable region sequence (codon optimized)

<400> SEQUENCE: 1020

Gln Val Gln Leu Val Gln Ser Gly His Glu Val Lys Gln Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Pro Gln Ala Pro Gly Gln Gly Leu Glu Trp Met
            35                  40                  45

Gly Trp Ile Asn Thr Tyr Thr Gly Glu Pro Thr Tyr Val Asp Asp Phe
        50                  55                  60

Lys Gly Arg Phe Val Phe Ser Met Asp Thr Ser Ala Ser Thr Ala Tyr
65                  70                  75                  80

Leu Gln Ile Ser Ser Leu Lys Ala Glu Asp Met Ala Met Tyr Tyr Cys
                85                  90                  95

Ala Arg Leu Arg Gly Ile Arg Pro Gly Pro Leu Ala Tyr Trp Gly Gln
            100                 105                 110

Gly Thr Leu Val Thr Val Ser Ser
        115                 120

<210> SEQ ID NO 1021
<211> LENGTH: 120
<212> TYPE: PRT
<213> ORGANISM: Artificial Sequence
<220> FEATURE:
<223> OTHER INFORMATION: Modified humanized 8F9A5A1 Heavy chain variable region sequence

<400> SEQUENCE: 1021

Gln Ile Gln Leu Val Gln Ser Gly Pro Glu Val Lys Gln Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Lys Gln Ala Pro Gly Gln Gly Leu Glu Trp Met
            35                  40                  45

Gly Trp Ile Asn Thr Tyr Thr Gly Glu Pro Thr Tyr Val Asp Asp Phe
        50                  55                  60

Lys Gly Arg Phe Ala Phe Ser Met Asp Thr Ser Ala Ser Thr Ala Tyr
65                  70                  75                  80

Leu Gln Ile Ser Ser Leu Lys Ala Glu Asp Thr Ala Thr Tyr Tyr Cys
                85                  90                  95

Ala Arg Leu Arg Gly Ile Arg Pro Gly Pro Leu Ala Tyr Trp Gly Gln
            100                 105                 110

Gly Thr Leu Val Thr Val Ser Ser
        115                 120

<210> SEQ ID NO 1022
<211> LENGTH: 120
<212> TYPE: PRT
<213> ORGANISM: Artificial Sequence
<220> FEATURE:
<223> OTHER INFORMATION: Modified humanized 8F9A5A1 Heavy chain variable region sequence (codon optimized)

<400> SEQUENCE: 1022

```
Gln Ile Gln Leu Val Gln Ser Gly Pro Glu Val Lys Gln Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Glu Trp Met
            35                  40                  45

Gly Trp Ile Asn Thr Tyr Thr Gly Glu Pro Thr Tyr Val Asp Asp Phe
50                  55                  60

Lys Gly Arg Phe Ala Phe Ser Met Asp Thr Ser Ala Ser Thr Ala Tyr
65                  70                  75                  80

Leu Gln Ile Ser Ser Leu Lys Ala Glu Asp Thr Ala Tyr Tyr Cys
                85                  90                  95

Ala Arg Leu Arg Gly Ile Arg Pro Gly Pro Leu Ala Tyr Trp Gly Gln
            100                 105                 110

Gly Thr Leu Val Thr Val Ser Ser
            115                 120

<210> SEQ ID NO 1023
<211> LENGTH: 107
<212> TYPE: PRT
<213> ORGANISM: Artificial Sequence
<220> FEATURE:
<223> OTHER INFORMATION: 8F9A5A1 Light chain variable region sequence

<400> SEQUENCE: 1023

Glu Ile Leu Leu Thr Gln Ser Pro Ala Ile Ala Ala Ser Pro Gly
1               5                   10                  15

Glu Lys Val Thr Ile Thr Cys Ser Ala Ser Ser Ser Val Ser Tyr Met
            20                  25                  30

Asn Trp Tyr Gln Gln Lys Pro Gly Ser Ser Pro Lys Ile Trp Ile Tyr
            35                  40                  45

Gly Ile Ser Asn Leu Ala Ser Gly Val Pro Ala Arg Phe Ser Gly Ser
    50                  55                  60

Gly Ser Gly Thr Ser Phe Ser Phe Thr Ile Asn Ser Met Glu Ala Glu
65                  70                  75                  80

Asp Val Ala Thr Tyr Tyr Cys Gln Gln Arg Ser Ser Tyr Pro Pro Thr
                85                  90                  95

Phe Gly Gly Gly Thr Lys Leu Glu Ile Lys Arg
            100                 105

<210> SEQ ID NO 1024
<211> LENGTH: 93
<212> TYPE: PRT
<213> ORGANISM: Artificial Sequence
<220> FEATURE:
<223> OTHER INFORMATION: IGKV3D-15*02 V-REGION sequence

<400> SEQUENCE: 1024

Glu Ile Val Met Met Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
```

```
                65                  70                  75                  80
Glu Asp Phe Ala Val Tyr Tyr Cys Gln Gln Tyr Asn Asn
                    85                  90

<210> SEQ ID NO 1025
<211> LENGTH: 12
<212> TYPE: PRT
<213> ORGANISM: Artificial Sequence
<220> FEATURE:
<223> OTHER INFORMATION: IGKJ4*02 J-REGION sequence

<400> SEQUENCE: 1025

Leu Thr Phe Gly Gly Gly Thr Lys Val Glu Ile Lys
1               5                   10

<210> SEQ ID NO 1026
<211> LENGTH: 107
<212> TYPE: PRT
<213> ORGANISM: Artificial Sequence
<220> FEATURE:
<223> OTHER INFORMATION: humanized 8F9A5A1 Light chain variable region
      sequence

<400> SEQUENCE: 1026

Glu Ile Val Met Met Gln Ser Pro Ala Thr Leu Ser Val Ser Pro Gly
1               5                   10                  15

Glu Arg Ala Thr Leu Ser Cys Ser Ala Ser Ser Val Ser Tyr Met
            20                  25                  30

Asn Trp Tyr Gln Gln Lys Pro Gly Gln Ala Pro Arg Leu Leu Ile Tyr
        35                  40                  45

Gly Ile Ser Asn Leu Ala Ser Gly Ile Pro Ala Arg Phe Ser Gly Ser
    50                  55                  60

Gly Ser Gly Thr Glu Phe Thr Leu Thr Ile Ser Ser Leu Gln Ser Glu
65                  70                  75                  80

Asp Phe Ala Val Tyr Tyr Cys Gln Gln Arg Ser Ser Tyr Pro Pro Thr
                85                  90                  95

Phe Gly Gly Gly Thr Lys Val Glu Ile Lys Arg
            100                 105

<210> SEQ ID NO 1027
<211> LENGTH: 107
<212> TYPE: PRT
<213> ORGANISM: Artificial Sequence
<220> FEATURE:
<223> OTHER INFORMATION: humanized 8F9A5A1 Light chain variable region
      sequence (codon optimized)

<400> SEQUENCE: 1027

Glu Ile Val Met Met Gln Ser Pro Ala Thr Leu Ser Val Ser Pro Gly
1               5                   10                  15

Glu Arg Ala Thr Leu Ser Cys Ser Ala Ser Ser Val Ser Tyr Met
            20                  25                  30

Asn Trp Tyr Gln Gln Lys Pro Gly Gln Ala Pro Arg Leu Leu Ile Tyr
        35                  40                  45

Gly Ile Ser Asn Leu Ala Ser Gly Ile Pro Ala Arg Phe Ser Gly Ser
    50                  55                  60

Gly Ser Gly Thr Glu Phe Thr Leu Thr Ile Ser Ser Leu Gln Ser Glu
65                  70                  75                  80

Asp Phe Ala Val Tyr Tyr Cys Gln Gln Arg Ser Ser Tyr Pro Pro Thr
                85                  90                  95
```

Phe Gly Gly Gly Thr Lys Val Glu Ile Lys Arg
            100                 105

<210> SEQ ID NO 1028
<211> LENGTH: 107
<212> TYPE: PRT
<213> ORGANISM: Artificial Sequence
<220> FEATURE:
<223> OTHER INFORMATION: Modified humanized 8F9A5A1 Light chain variable
      region sequence

<400> SEQUENCE: 1028

Glu Ile Val Leu Thr Gln Ser Pro Ala Thr Leu Ser Val Ser Pro Gly
1               5                   10                  15

Glu Arg Ala Thr Leu Ser Cys Ser Ala Ser Ser Val Ser Tyr Met
            20                  25                  30

Asn Trp Tyr Gln Gln Lys Pro Gly Gln Ala Pro Arg Leu Trp Ile Tyr
            35                  40                  45

Gly Ile Ser Asn Leu Ala Ser Gly Ile Pro Ala Arg Phe Ser Gly Ser
        50                  55                  60

Gly Ser Gly Thr Ser Phe Ser Leu Thr Ile Ser Ser Leu Gln Ser Glu
65                  70                  75                  80

Asp Phe Ala Val Tyr Tyr Cys Gln Gln Arg Ser Ser Tyr Pro Pro Thr
                85                  90                  95

Phe Gly Gly Gly Thr Lys Val Glu Ile Lys Arg
            100                 105

<210> SEQ ID NO 1029
<211> LENGTH: 107
<212> TYPE: PRT
<213> ORGANISM: Artificial Sequence
<220> FEATURE:
<223> OTHER INFORMATION: Modified humanized 8F9A5A1 Light chain variable
      region sequence (codon optimized)

<400> SEQUENCE: 1029

Glu Ile Val Leu Thr Gln Ser Pro Ala Thr Leu Ser Val Ser Pro Gly
1               5                   10                  15

Glu Arg Ala Thr Leu Ser Cys Ser Ala Ser Ser Val Ser Tyr Met
            20                  25                  30

Asn Trp Tyr Gln Gln Lys Pro Gly Gln Ala Pro Arg Leu Trp Ile Tyr
            35                  40                  45

Gly Ile Ser Asn Leu Ala Ser Gly Ile Pro Ala Arg Phe Ser Gly Ser
        50                  55                  60

Gly Ser Gly Thr Ser Phe Ser Leu Thr Ile Ser Ser Leu Gln Ser Glu
65                  70                  75                  80

Asp Phe Ala Val Tyr Tyr Cys Gln Gln Arg Ser Ser Tyr Pro Pro Thr
                85                  90                  95

Phe Gly Gly Gly Thr Lys Val Glu Ile Lys Arg
            100                 105

<210> SEQ ID NO 1030
<211> LENGTH: 242
<212> TYPE: PRT
<213> ORGANISM: Artificial Sequence
<220> FEATURE:
<223> OTHER INFORMATION: Modified humanized 8F9A5A1 scFV sequence (codon
      optimized)

<400> SEQUENCE: 1030

Gln Ile Gln Leu Val Gln Ser Gly Pro Glu Val Lys Gln Pro Gly Ala

-continued

```
1               5                   10                  15
Ser Val Lys Val Ser Cys Lys Ala Ser Gly Tyr Thr Phe Thr Asn Tyr
                20                  25                  30

Gly Met Asn Trp Val Lys Gln Ala Pro Gly Gln Gly Leu Glu Trp Met
                35                  40                  45

Gly Trp Ile Asn Thr Tyr Thr Gly Glu Pro Thr Tyr Val Asp Asp Phe
            50                  55                  60

Lys Gly Arg Phe Ala Phe Ser Met Asp Thr Ser Ala Ser Thr Ala Tyr
65                  70                  75                  80

Leu Gln Ile Ser Ser Leu Lys Ala Glu Asp Thr Ala Thr Tyr Tyr Cys
                85                  90                  95

Ala Arg Leu Arg Gly Ile Arg Pro Gly Pro Leu Ala Tyr Trp Gly Gln
                100                 105                 110

Gly Thr Leu Val Thr Val Ser Ser Gly Gly Gly Ser Gly Gly Gly
                115                 120                 125

Gly Ser Gly Gly Gly Gly Ser Glu Ile Val Leu Thr Gln Ser Pro Ala
            130                 135                 140

Thr Leu Ser Val Ser Pro Gly Glu Arg Ala Thr Leu Ser Cys Ser Ala
145                 150                 155                 160

Ser Ser Ser Val Ser Tyr Met Asn Trp Tyr Gln Gln Lys Pro Gly Gln
                165                 170                 175

Ala Pro Arg Leu Trp Ile Tyr Gly Ile Ser Asn Leu Ala Ser Gly Ile
                180                 185                 190

Pro Ala Arg Phe Ser Gly Ser Gly Ser Gly Thr Ser Phe Ser Leu Thr
                195                 200                 205

Ile Ser Ser Leu Gln Ser Glu Asp Phe Ala Val Tyr Tyr Cys Gln Gln
                210                 215                 220

Arg Ser Ser Tyr Pro Pro Thr Phe Gly Gly Gly Thr Lys Val Glu Ile
225                 230                 235                 240

Lys Arg
```

<210> SEQ ID NO 1031
<211> LENGTH: 121
<212> TYPE: PRT
<213> ORGANISM: Artificial Sequence
<220> FEATURE:
<223> OTHER INFORMATION: 8H5H5G4 Heavy chain variable region sequence

<400> SEQUENCE: 1031

```
Val Gln Leu Gln Gln Ser Gly Pro Asp Leu Val Lys Pro Gly Thr Ser
1               5                   10                  15

Val Lys Ile Ser Cys Lys Thr Ser Gly Asn Thr Phe Thr Glu Tyr Thr
                20                  25                  30

Met His Trp Val Lys Gln Ser His Gly Lys Ser Leu Glu Trp Ile Gly
                35                  40                  45

Gly Phe Asn Pro Asn Asn Gly Val Thr Asn Tyr Asn Gln Lys Phe Lys
            50                  55                  60

Gly Lys Ala Thr Leu Thr Val Asp Lys Ser Ser Ser Thr Ala Tyr Met
65                  70                  75                  80

Glu Leu Arg Ser Leu Thr Ser Glu Asp Ser Ala Val Tyr Tyr Cys Ala
                85                  90                  95

Arg Arg Tyr Tyr His Ser Thr Tyr Val Phe Tyr Phe Asp Ser Trp Gly
                100                 105                 110

Gln Gly Thr Thr Leu Thr Val Ser Ser
                115                 120
```

<210> SEQ ID NO 1032
<211> LENGTH: 98
<212> TYPE: PRT
<213> ORGANISM: Artificial Sequence
<220> FEATURE:
<223> OTHER INFORMATION: IGHV1-24*01 V-REGION sequence

<400> SEQUENCE: 1032

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr

<210> SEQ ID NO 1033
<211> LENGTH: 15
<212> TYPE: PRT
<213> ORGANISM: Artificial Sequence
<220> FEATURE:
<223> OTHER INFORMATION: IGHJ4*03 J-REGION sequence

<400> SEQUENCE: 1033

Tyr Phe Asp Tyr Trp Gly Gln Gly Thr Leu Val Thr Val Ser Ser
1               5                   10                  15

<210> SEQ ID NO 1034
<211> LENGTH: 122
<212> TYPE: PRT
<213> ORGANISM: Artificial Sequence
<220> FEATURE:
<223> OTHER INFORMATION: Humanized 8H5H5G4 Heavy chain variable region
    sequence

<400> SEQUENCE: 1034

Gln Val Gln Leu Val Gln Ser Gly Ala Glu Val Lys Lys Pro Gly Ala
1               5                   10                  15

Ser Val Lys Val Ser Cys Lys Val Ser Gly Asn Thr Phe Thr Glu Tyr
            20                  25                  30

Thr Met His Trp Val Arg Gln Ala Pro Gly Lys Gly Leu Glu Trp Met
        35                  40                  45

Gly Gly Phe Asn Pro Asn Asn Gly Val Thr Asn Tyr Asn Gln Lys Phe
    50                  55                  60

Lys Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Tyr Tyr His Ser Thr Tyr Val Phe Tyr Phe Asp Ser Trp
            100                 105                 110

Gly Gln Gly Thr Leu Val Thr Val Ser Ser
        115                 120

<210> SEQ ID NO 1035
<211> LENGTH: 122
<212> TYPE: PRT
<213> ORGANISM: Artificial Sequence
<220> FEATURE:
<223> OTHER INFORMATION: Humanized 8H5H5G4 Heavy chain variable region
      sequence (codon optimized)

<400> SEQUENCE: 1035

Gln Val Gln Leu Val Gln Ser Gly Ala Glu Val Lys Lys Pro Gly Ala
1               5                   10                  15

Ser Val Lys Val Ser Cys Lys Val Ser Gly Asn Thr Phe Thr Glu Tyr
            20                  25                  30

Thr Met His Trp Val Arg Gln Ala Pro Gly Lys Gly Leu Glu Trp Met
        35                  40                  45

Gly Gly Phe Asn Pro Asn Asn Gly Val Thr Asn Tyr Asn Gln Lys Phe
    50                  55                  60

Lys Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Tyr Tyr His Ser Thr Tyr Val Phe Tyr Phe Asp Ser Trp
            100                 105                 110

Gly Gln Gly Thr Leu Val Thr Val Ser Ser
        115                 120

<210> SEQ ID NO 1036
<211> LENGTH: 122
<212> TYPE: PRT
<213> ORGANISM: Artificial Sequence
<220> FEATURE:
<223> OTHER INFORMATION: Modified Humanized 8H5H5G4 Heavy chain variable
      region sequence

<400> SEQUENCE: 1036

Gln Val Gln Leu Val Gln Ser Gly Ala Glu Val Lys Lys Pro Gly Ala
1               5                   10                  15

Ser Val Lys Val Ser Cys Lys Val Ser Gly Asn Thr Phe Thr Glu Tyr
            20                  25                  30

Thr Met His Trp Val Arg Gln Ala Pro Gly Lys Gly Leu Glu Trp Ile
        35                  40                  45

Gly Gly Phe Asn Pro Asn Asn Gly Val Thr Asn Tyr Asn Gln Lys Phe
    50                  55                  60

Lys Gly Lys Val Thr Leu Thr Val Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Tyr Tyr His Ser Thr Tyr Val Phe Tyr Phe Asp Ser Trp
            100                 105                 110

Gly Gln Gly Thr Leu Val Thr Val Ser Ser
        115                 120

<210> SEQ ID NO 1037
<211> LENGTH: 122
<212> TYPE: PRT
<213> ORGANISM: Artificial Sequence
<220> FEATURE:
<223> OTHER INFORMATION: Modified Humanized 8H5H5G4 Heavy chain variable
      region sequence (codon optimized)

-continued

```
<400> SEQUENCE: 1037

Gln Val Gln Leu Val Gln Ser Gly Ala Glu Val Lys Lys Pro Gly Ala
1               5                   10                  15

Ser Val Lys Val Ser Cys Lys Val Ser Gly Asn Thr Phe Thr Glu Tyr
            20                  25                  30

Thr Met His Trp Val Arg Gln Ala Pro Gly Lys Gly Leu Glu Trp Ile
        35                  40                  45

Gly Gly Phe Asn Pro Asn Asn Gly Val Thr Asn Tyr Asn Gln Lys Phe
    50                  55                  60

Lys Gly Lys Val Thr Leu Thr Val Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Tyr Tyr His Ser Thr Tyr Val Phe Tyr Phe Asp Ser Trp
            100                 105                 110

Gly Gln Gly Thr Leu Val Thr Val Ser Ser
        115                 120

<210> SEQ ID NO 1038
<211> LENGTH: 108
<212> TYPE: PRT
<213> ORGANISM: Artificial Sequence
<220> FEATURE:
<223> OTHER INFORMATION: 8H5H5G4 Light chain variable region sequence

<400> SEQUENCE: 1038

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Phe Gln Gln Lys Pro Asp Gly Thr Ile Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Val Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Ile Lys Arg
            100                 105

<210> SEQ ID NO 1039
<211> LENGTH: 95
<212> TYPE: PRT
<213> ORGANISM: Artificial Sequence
<220> FEATURE:
<223> OTHER INFORMATION: IGKV1-27*01 V-REGION sequence

<400> SEQUENCE: 1039

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro
                 85                  90                  95

<210> SEQ ID NO 1040
<211> LENGTH: 12
<212> TYPE: PRT
<213> ORGANISM: Artificial Sequence
<220> FEATURE:
<223> OTHER INFORMATION: IGKJ4*02 J-REGION sequence

<400> SEQUENCE: 1040

Leu Thr Phe Gly Gly Gly Thr Lys Val Glu Ile Lys
 1               5                  10

<210> SEQ ID NO 1041
<211> LENGTH: 108
<212> TYPE: PRT
<213> ORGANISM: Artificial Sequence
<220> FEATURE:
<223> OTHER INFORMATION: humanized 8H5H5G4 Light chain variable region
      sequence

<400> SEQUENCE: 1041

Asp Ile Gln Met Thr Gln Ser Pro Ser Ser Leu Ser Ala Ser Val Gly
 1               5                  10                  15

Asp Arg Val Thr Ile Thr Cys Ser Ala Ser Gln Gly Ile Ser Asn Tyr
                 20                  25                  30

Leu Asn Trp Tyr Gln Gln Lys Pro Gly Lys Val Pro Lys Leu Leu Ile
             35                  40                  45

Tyr Tyr Thr Ser Ser Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Gln Tyr Ser Lys Leu Pro Tyr
                 85                  90                  95

Thr Phe Gly Gly Gly Thr Lys Val Glu Ile Lys Arg
            100                 105

<210> SEQ ID NO 1042
<211> LENGTH: 108
<212> TYPE: PRT
<213> ORGANISM: Artificial Sequence
<220> FEATURE:
<223> OTHER INFORMATION: humanized 8H5H5G4 Light chain variable region
      sequence (codon optimized)

<400> SEQUENCE: 1042

Asp Ile Gln Met Thr Gln Ser Pro Ser Ser Leu Ser Ala Ser Val Gly
 1               5                  10                  15

Asp Arg Val Thr Ile Thr Cys Ser Ala Ser Gln Gly Ile Ser Asn Tyr
                 20                  25                  30

Leu Asn Trp Tyr Gln Gln Lys Pro Gly Lys Val Pro Lys Leu Leu Ile
             35                  40                  45

Tyr Tyr Thr Ser Ser Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Gln Tyr Ser Lys Leu Pro Tyr
                 85                  90                  95
```

```
Thr Phe Gly Gly Gly Thr Lys Val Glu Ile Lys Arg
            100                 105
```

<210> SEQ ID NO 1043
<211> LENGTH: 108
<212> TYPE: PRT
<213> ORGANISM: Artificial Sequence
<220> FEATURE:
<223> OTHER INFORMATION: Modified humanized 8H5H5G4 Light chain variable
      region sequence

<400> SEQUENCE: 1043

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Val Pro Lys Leu Leu Ile
        35                  40                  45

Tyr Tyr Thr Ser Ser Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Gln Tyr Ser Lys Leu Pro Tyr
                85                  90                  95

Thr Phe Gly Gly Gly Thr Lys Val Glu Ile Lys Arg
            100                 105
```

<210> SEQ ID NO 1044
<211> LENGTH: 108
<212> TYPE: PRT
<213> ORGANISM: Artificial Sequence
<220> FEATURE:
<223> OTHER INFORMATION: Modified humanized 8H5H5G4 Light chain variable
      region sequence (codon optimized)

<400> SEQUENCE: 1044

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Val Pro Lys Leu Leu Ile
        35                  40                  45

Tyr Tyr Thr Ser Ser Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Gln Tyr Ser Lys Leu Pro Tyr
                85                  90                  95

Thr Phe Gly Gly Gly Thr Lys Val Glu Ile Lys Arg
            100                 105
```

<210> SEQ ID NO 1045
<211> LENGTH: 245
<212> TYPE: PRT
<213> ORGANISM: Artificial Sequence
<220> FEATURE:
<223> OTHER INFORMATION: Modified humanized 8H5H5G4 scFV sequence (codon
      optimized)

<400> SEQUENCE: 1045

```
Gln Val Gln Leu Val Gln Ser Gly Ala Glu Val Lys Lys Pro Gly Ala
1               5                   10                  15

Ser Val Lys Val Ser Cys Lys Val Ser Gly Asn Thr Phe Thr Glu Tyr
            20                  25                  30

Thr Met His Trp Val Arg Gln Ala Pro Gly Lys Gly Leu Glu Trp Ile
        35                  40                  45

Gly Gly Phe Asn Pro Asn Asn Gly Val Thr Asn Tyr Asn Gln Lys Phe
    50                  55                  60

Lys Gly Lys Val Thr Leu Thr Val Asp Thr Ser Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Arg Tyr Tyr His Ser Thr Tyr Val Phe Tyr Phe Asp Ser Trp
            100                 105                 110

Gly Gln Gly Thr Leu Val Thr Val Ser Ser Gly Gly Gly Ser Gly
            115                 120                 125

Gly Gly Gly Ser Gly Gly Gly Ser Asp Ile Gln Met Thr Gln Ser
130                 135                 140

Pro Ser Ser Leu Ser Ala Ser Val Gly Asp Arg Val Thr Ile Thr Cys
145                 150                 155                 160

Ser Ala Ser Gln Gly Ile Ser Asn Tyr Leu Asn Trp Tyr Gln Gln Lys
            165                 170                 175

Pro Gly Lys Val Pro Lys Leu Leu Ile Tyr Tyr Thr Ser Ser Leu His
            180                 185                 190

Ser Gly Val Pro Ser Arg Phe Ser Gly Ser Gly Ser Gly Thr Asp Tyr
            195                 200                 205

Thr Leu Thr Ile Ser Ser Leu Gln Pro Glu Asp Val Ala Thr Tyr Tyr
210                 215                 220

Cys Gln Gln Tyr Ser Lys Leu Pro Tyr Thr Phe Gly Gly Gly Thr Lys
225                 230                 235                 240

Val Glu Ile Lys Arg
                245

<210> SEQ ID NO 1046
<211> LENGTH: 330
<212> TYPE: PRT
<213> ORGANISM: Artificial Sequence
<220> FEATURE:
<223> OTHER INFORMATION: Human IgG1 heavy chain constant region
      sequence: (for making full antibody - pair with either kappa or
      lambda constant region; 2 plasmids, express together)

<400> SEQUENCE: 1046

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
```

```
                100             105             110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 1047
<211> LENGTH: 326
<212> TYPE: PRT
<213> ORGANISM: Artificial Sequence
<220> FEATURE:
<223> OTHER INFORMATION: Human IgG2 heavy chain constant region
      sequence: (for making full antibody - pair with either kappa or
      lambda constant region; 2 plasmids, express together)

<400> SEQUENCE: 1047

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Cys Val Glu Cys Pro Pro Cys Pro Ala Pro
            100                 105                 110
Pro Val Ala Gly Pro Ser Val Phe Leu Phe Pro Pro Lys Pro Lys Asp
        115                 120                 125
```

```
Thr Leu Met Ile Ser Arg Thr Pro Glu Val Thr Cys Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 1048
<211> LENGTH: 107
<212> TYPE: PRT
<213> ORGANISM: Artificial Sequence
<220> FEATURE:
<223> OTHER INFORMATION: Human Kappa light chain constant region
      sequence

<400> SEQUENCE: 1048

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 1049
<211> LENGTH: 106
<212> TYPE: PRT
<213> ORGANISM: Artificial Sequence
<220> FEATURE:
<223> OTHER INFORMATION: Human Lambda light chain constant region
```

```
                         sequence

<400> SEQUENCE: 1049

Gly Gln Pro Lys Ala Ala Pro Ser Val Thr Leu Phe Pro Pro Ser Ser
1               5                  10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 1050
<211> LENGTH: 232
<212> TYPE: PRT
<213> ORGANISM: Artificial Sequence
<220> FEATURE:
<223> OTHER INFORMATION: Human IgG1 Fc region sequence: (to be fused to
      scFv for homo-dimerizes)

<400> SEQUENCE: 1050

Glu Pro Lys Ser Cys Asp Lys Thr His Thr Cys Pro Pro Cys Pro Ala
1               5                  10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
```

<210> SEQ ID NO 1051
<211> LENGTH: 228
<212> TYPE: PRT
<213> ORGANISM: Artificial Sequence
<220> FEATURE:
<223> OTHER INFORMATION: Human IgG2 Fc region sequence

<400> SEQUENCE: 1051

```
Glu Arg Lys Cys Cys Val Glu Cys Pro Pro Cys Pro Ala Pro Pro Val
 1               5                  10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225
```

<210> SEQ ID NO 1052

<400> SEQUENCE: 1052

000

<210> SEQ ID NO 1053

<400> SEQUENCE: 1053

000

<210> SEQ ID NO 1054

<400> SEQUENCE: 1054

000

```
<210> SEQ ID NO 1055

<400> SEQUENCE: 1055

000

<210> SEQ ID NO 1056

<400> SEQUENCE: 1056

000

<210> SEQ ID NO 1057

<400> SEQUENCE: 1057

000

<210> SEQ ID NO 1058

<400> SEQUENCE: 1058

000

<210> SEQ ID NO 1059

<400> SEQUENCE: 1059

000

<210> SEQ ID NO 1060

<400> SEQUENCE: 1060

000

<210> SEQ ID NO 1061

<400> SEQUENCE: 1061

000

<210> SEQ ID NO 1062

<400> SEQUENCE: 1062

000

<210> SEQ ID NO 1063

<400> SEQUENCE: 1063

000

<210> SEQ ID NO 1064

<400> SEQUENCE: 1064

000

<210> SEQ ID NO 1065

<400> SEQUENCE: 1065

000

<210> SEQ ID NO 1066
```

<400> SEQUENCE: 1066

000

<210> SEQ ID NO 1067

<400> SEQUENCE: 1067

000

<210> SEQ ID NO 1068

<400> SEQUENCE: 1068

000

<210> SEQ ID NO 1069

<400> SEQUENCE: 1069

000

<210> SEQ ID NO 1070

<400> SEQUENCE: 1070

000

<210> SEQ ID NO 1071

<400> SEQUENCE: 1071

000

<210> SEQ ID NO 1072

<400> SEQUENCE: 1072

000

<210> SEQ ID NO 1073

<400> SEQUENCE: 1073

000

<210> SEQ ID NO 1074

<400> SEQUENCE: 1074

000

<210> SEQ ID NO 1075

<400> SEQUENCE: 1075

000

<210> SEQ ID NO 1076

<400> SEQUENCE: 1076

000

<210> SEQ ID NO 1077

<400> SEQUENCE: 1077

000

<210> SEQ ID NO 1078

<400> SEQUENCE: 1078

000

<210> SEQ ID NO 1079

<400> SEQUENCE: 1079

000

<210> SEQ ID NO 1080

<400> SEQUENCE: 1080

000

<210> SEQ ID NO 1081

<400> SEQUENCE: 1081

000

<210> SEQ ID NO 1082

<400> SEQUENCE: 1082

000

<210> SEQ ID NO 1083

<400> SEQUENCE: 1083

000

<210> SEQ ID NO 1084

<400> SEQUENCE: 1084

000

<210> SEQ ID NO 1085

<400> SEQUENCE: 1085

000

<210> SEQ ID NO 1086

<400> SEQUENCE: 1086

000

<210> SEQ ID NO 1087

<400> SEQUENCE: 1087

000

<210> SEQ ID NO 1088

<400> SEQUENCE: 1088

000

<210> SEQ ID NO 1089

<400> SEQUENCE: 1089

000

<210> SEQ ID NO 1090

<400> SEQUENCE: 1090

000

<210> SEQ ID NO 1091

<400> SEQUENCE: 1091

000

<210> SEQ ID NO 1092

<400> SEQUENCE: 1092

000

<210> SEQ ID NO 1093

<400> SEQUENCE: 1093

000

<210> SEQ ID NO 1094

<400> SEQUENCE: 1094

000

<210> SEQ ID NO 1095

<400> SEQUENCE: 1095

000

<210> SEQ ID NO 1096

<400> SEQUENCE: 1096

000

<210> SEQ ID NO 1097

<400> SEQUENCE: 1097

000

<210> SEQ ID NO 1098

<400> SEQUENCE: 1098

000

<210> SEQ ID NO 1099

<400> SEQUENCE: 1099

000

<210> SEQ ID NO 1100

<400> SEQUENCE: 1100

000

<210> SEQ ID NO 1101
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1101
caagtgcagc tggtgcagag cggcgccgag gtgaagaaac ctggcgccag cgtgaaagtg     60
tcctgcaagg ccagcggcaa tacattcacc gagtacacaa tgcactgggt cagacaggcc    120
cccggccagg gcctggaatg gatcggcgga tttaacccca acaacggcgt gacaaactac    180
aaccagaagt tcaagggcaa ggtgaccatc acaagagaca ccagcagcag caccgtgtac    240
atggaactgt cttctctgcg gagcgaggat accgccgtgt actattgtgc cagacggtac    300
taccacagcc tgtacgtgtt ctacttcgac tactggggac agggcaccct ggttaccgtg    360
tcctct                                                               366

<210> SEQ ID NO 1102
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1102

Gln Val Gln Leu Val Gln Ser Gly Ala Glu Val Lys Lys Pro Gly Ala
1               5                   10                  15

Ser Val Lys Val Ser Cys Lys Ala Ser Gly Asn Thr Phe Thr Glu Tyr
            20                  25                  30

Thr Met His Trp Val Arg Gln Ala Pro Gly Gln Gly Leu Glu Trp Ile
        35                  40                  45

Gly Gly Phe Asn Pro Asn Asn Gly Val Thr Asn Tyr Asn Gln Lys Phe
    50                  55                  60

Lys Gly Lys Val Thr Ile Thr Arg Asp Thr Ser Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Tyr Tyr His Ser Leu Tyr Val Phe Tyr Phe Asp Tyr Trp
            100                 105                 110

Gly Gln Gly Thr Leu Val Thr Val Ser Ser
        115                 120

<210> SEQ ID NO 1103
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1103
gatatccaga tgacacagag ccctagctcc ctgagcgcca gcgtgggcga ccgggtcacc     60
attacatgca gcgcttctca gggcatctcc aactacctga actggtacca gcagaaaccc    120

```
ggcaaggccc ctaagctgct gatcttctac accagctctc tgcacagcgg cgtgccatct    180
agattcagcg gatctggcag cggcaccgac tacaccctga ccatcagctc cctccagcct    240
gaggacttcg ccacctacta ctgtcagcaa tacagcaagc tgccttatac ctttggcggc    300
ggaacaaagg tggaaatcaa g                                              321
```

```
<210> SEQ ID NO 1104
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1104

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Ala Pro Lys Leu Leu Ile
        35                  40                  45

Phe Tyr Thr Ser Ser Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Lys Leu Pro Tyr
                85                  90                  95

Thr Phe Gly Gly Gly Thr Lys Val Glu Ile Lys
            100                 105
```

```
<210> SEQ ID NO 1105
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1105
caagtgcagc tgcaggagag cggacctggc ctggttaagc ctggaggcac cctgtctctg     60
acatgtgctg tgtctggcaa taccttacc gagtacacca tgcactgggt gcggcagcct    120
ccaggcaagg cctggaatg atcggcggc ttcaaccca caacggcgt gacaaattac        180 aaccagaaat tcaagggaaa agtgaccatc accgtggata agtccaagaa caccttcagc    240
ctcaagctga gcagcgtgac agccgccgac accgccgtgt actactgcgc cagaagatac    300
tatcacagcc tgtacgtgtt ctacttcgac tactggggcc agggcacact ggtcaccgtg    360
tccagc                                                               366
```

```
<210> SEQ ID NO 1106
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1106

Gln Val Gln Leu Gln Glu Ser Gly Pro Gly Leu Val Lys Pro Gly Gly
1               5                   10                  15
```

Thr Leu Ser Leu Thr Cys Ala Val Ser Gly Asn Thr Phe Thr Glu Tyr
            20                  25                  30

Thr Met His Trp Val Arg Gln Pro Gly Lys Gly Leu Glu Trp Ile
        35                  40                  45

Gly Gly Phe Asn Pro Asn Asn Gly Val Thr Asn Tyr Asn Gln Lys Phe
50                  55                  60

Lys Gly Lys Val Thr Ile Thr Val Asp Lys Ser Lys Asn Thr Phe Ser
65                  70                  75                  80

Leu Lys Leu Ser Ser Val Thr Ala Ala Asp Thr Ala Val Tyr Tyr Cys
                85                  90                  95

Ala Arg Arg Tyr Tyr His Ser Leu Tyr Val Phe Tyr Phe Asp Tyr Trp
            100                 105                 110

Gly Gln Gly Thr Leu Val Thr Val Ser Ser
            115                 120

<210> SEQ ID NO 1107
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1107
gatatcgtga tgacccagag cccagacagc ctggcagtga gtctgggtga gcgtgctaca      60
atcaactgca gcgccagcca gggcatctcc aactacctga attggtatca gcagaaacct     120
ggccaggctc ctaagctgct gatcttctac accagcagcc tgcacagcgg cgtgccagat     180
agattcagcg gcagcggatc tggcaccgac tacacactga ccatttcttc tctccaggcc     240
gaggacgtgg ccgtctacta ctgtcagcaa tacagcaagc tgccttacac ctttggcgga     300
ggcacaaagg tggaaatcaa g                                               321

<210> SEQ ID NO 1108
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1108

Asp Ile Val Met Thr Gln Ser Pro Asp Ser Leu Ala Val Ser Leu Gly
1               5                   10                  15

Glu Arg Ala Thr Ile Asn Cys Ser Ala Ser Gln Gly Ile Ser Asn Tyr
            20                  25                  30

Leu Asn Trp Tyr Gln Gln Lys Pro Gly Gln Ala Pro Lys Leu Leu Ile
        35                  40                  45

Phe Tyr Thr Ser Ser Leu His Ser Gly Val Pro Asp Arg Phe Ser Gly
50                  55                  60

Ser Gly Ser Gly Thr Asp Tyr Thr Leu Thr Ile Ser Ser Leu Gln Ala
65                  70                  75                  80

Glu Asp Val Ala Val Tyr Tyr Cys Gln Gln Tyr Ser Lys Leu Pro Tyr
                85                  90                  95

Thr Phe Gly Gly Gly Thr Lys Val Glu Ile Lys
            100                 105

<210> SEQ ID NO 1109

<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1109

Asp Ile Gln Met Thr Gln Thr Thr Ser Ser Leu Ser Ala Ser Leu Gly
1               5                   10                  15

Asp Arg Val Thr Leu Ser Cys Ser Ala Ser Gln Gly Ile Ser Asn Tyr
            20                  25                  30

Leu Asn Trp Tyr Gln Gln Lys Pro Asp Gly Thr Val Glu Leu Leu Ile
        35                  40                  45

Phe Tyr Thr Ser Ser Leu His Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Ile Lys
            100                 105

<210> SEQ ID NO 1110
<211> LENGTH: 187
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1110

Met Gly Gly Leu Phe Trp Arg Ser Ala Leu Arg Gly Leu Arg Cys Gly
1               5                   10                  15

Pro Arg Ala Pro Gly Pro Ser Leu Leu Val Arg His Gly Ser Gly Gly
            20                  25                  30

Pro Ser Trp Thr Arg Glu Arg Thr Leu Val Ala Val Lys Pro Asp Gly
        35                  40                  45

Val Gln Arg Arg Leu Val Gly Asp Val Ile Gln Arg Phe Glu Arg Arg
50                  55                  60

Gly Phe Thr Leu Val Gly Met Lys Met Leu Gln Ala Pro Glu Ser Val
65                  70                  75                  80

Leu Ala Glu His Tyr Gln Asp Leu Arg Arg Lys Pro Phe Tyr Pro Ala
                85                  90                  95

Leu Ile Arg Tyr Met Ser Ser Gly Pro Val Val Ala Met Val Trp Glu
            100                 105                 110

Gly Tyr Asn Val Val Arg Ala Ser Arg Ala Met Ile Gly His Thr Asp
        115                 120                 125

Ser Ala Glu Ala Ala Pro Gly Thr Ile Arg Gly Asp Phe Ser Val His
    130                 135                 140

Ile Ser Arg Asn Val Ile His Ala Ser Asp Ser Val Glu Gly Ala Gln
145                 150                 155                 160

Arg Glu Ile Gln Leu Trp Phe Gln Ser Ser Glu Leu Val Ser Trp Ala
                165                 170                 175

Asp Gly Gly Gln His Ser Ser Ile His Pro Ala
            180                 185

<210> SEQ ID NO 1111

```
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1111
```

Met Glu Ile Ser Met Pro Pro Gln Ile Tyr Val Glu Lys Thr Leu
1               5                   10                  15

Ala Ile Ile Lys Pro Asp Ile Val Asp Lys Glu Glu Ile Gln Asp
                20                  25                  30

Ile Ile Leu Arg Ser Gly Phe Thr Ile Val Gln Arg Arg Lys Leu Arg
            35                  40                  45

Leu Ser Pro Glu Gln Cys Ser Asn Phe Tyr Val Glu Lys Tyr Gly Lys
50                  55                  60

Met Phe Phe Pro Asn Leu Thr Ala Tyr Met Ser Ser Gly Pro Leu Val
65                  70                  75                  80

Ala Met Ile Leu Ala Arg His Lys Ala Ile Ser Tyr Trp Leu Glu Leu
                85                  90                  95

Leu Gly Pro Asn Asn Ser Leu Val Ala Lys Glu Thr His Pro Asp Ser
                100                 105                 110

Leu Arg Ala Ile Tyr Gly Thr Asp Asp Leu Arg Asn Ala Leu His Gly
            115                 120                 125

Ser Asn Asp Phe Ala Ala Ala Glu Arg Glu Ile Arg Phe Met Phe Pro
130                 135                 140

Glu Val Ile Val Glu Pro Ile Pro Ile Gly Gln Ala Ala Lys Asp Tyr
145                 150                 155                 160

Leu Asn Leu His Ile Met Pro Thr Leu Leu Glu Gly Leu Thr Glu Leu
                165                 170                 175

Cys Lys Gln Lys Pro Ala Asp Pro Leu Phe Trp Tyr Met Cys Cys Arg
            180                 185                 190

Arg Glu His Trp Thr Leu Arg Ser Ile Leu Leu Val Cys Met Ser Gly
        195                 200                 205

Ile Arg Met Ser Leu Pro His Cys Ala Asp Tyr Cys Ser Phe Val Glu
210                 215                 220

Gly Phe Glu Ile Trp Leu Ala Asp Trp Leu Leu Lys Asn Asn Pro Asn
225                 230                 235                 240

Lys Pro Lys Leu Cys His His Pro Ile Val Glu Glu Pro Tyr
                245                 250

```
<210> SEQ ID NO 1112
<211> LENGTH: 588
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1112
```

Met Ala Ser Lys Lys Arg Glu Val Gln Leu Gln Thr Val Ile Asn Asn
1               5                   10                  15

Gln Ser Leu Trp Asp Glu Met Leu Gln Asn Lys Gly Leu Thr Val Ile
                20                  25                  30

Asp Val Tyr Gln Ala Trp Cys Gly Pro Cys Arg Ala Met Gln Pro Leu
            35                  40                  45

Phe Arg Lys Leu Lys Asn Glu Leu Asn Glu Asp Glu Ile Leu His Phe
50                  55                  60

```
Ala Val Ala Glu Ala Asp Asn Ile Val Thr Leu Gln Pro Phe Arg Asp
 65                  70                  75                  80

Lys Cys Glu Pro Val Phe Leu Phe Ser Val Asn Gly Lys Ile Ile Glu
                 85                  90                  95

Lys Ile Gln Gly Ala Asn Ala Pro Leu Val Asn Lys Lys Val Ile Asn
            100                 105                 110

Leu Ile Asp Glu Glu Arg Lys Ile Ala Ala Gly Glu Met Ala Arg Pro
        115                 120                 125

Gln Tyr Pro Glu Ile Pro Leu Val Asp Ser Asp Ser Glu Val Ser Glu
    130                 135                 140

Glu Ser Pro Cys Glu Ser Val Gln Glu Leu Tyr Ser Ile Ala Ile Ile
145                 150                 155                 160

Lys Pro Asp Ala Val Ile Ser Lys Lys Val Leu Glu Ile Lys Arg Lys
                165                 170                 175

Ile Thr Lys Ala Gly Phe Ile Ile Glu Ala Glu His Lys Thr Val Leu
            180                 185                 190

Thr Glu Glu Gln Val Val Asn Phe Tyr Ser Arg Ile Ala Asp Gln Cys
        195                 200                 205

Asp Phe Glu Glu Phe Val Ser Phe Met Thr Ser Gly Leu Ser Tyr Ile
210                 215                 220

Leu Val Val Ser Gln Gly Ser Lys His Asn Pro Ser Glu Glu Thr
225                 230                 235                 240

Glu Pro Gln Thr Asp Thr Glu Pro Asn Glu Arg Ser Glu Asp Gln Pro
                245                 250                 255

Glu Val Glu Ala Gln Val Thr Pro Gly Met Met Lys Asn Lys Gln Asp
            260                 265                 270

Ser Leu Gln Glu Tyr Leu Glu Arg Gln His Leu Ala Gln Leu Cys Asp
        275                 280                 285

Ile Glu Glu Asp Ala Ala Asn Val Ala Lys Phe Met Asp Ala Phe Phe
    290                 295                 300

Pro Asp Phe Lys Lys Met Lys Ser Met Lys Leu Glu Lys Thr Leu Ala
305                 310                 315                 320

Leu Leu Arg Pro Asn Leu Phe His Glu Arg Lys Asp Asp Val Leu Arg
                325                 330                 335

Ile Ile Lys Asp Glu Asp Phe Lys Ile Leu Glu Gln Arg Gln Val Val
            340                 345                 350

Leu Ser Glu Lys Glu Ala Gln Ala Leu Cys Lys Glu Tyr Glu Asn Glu
        355                 360                 365

Asp Tyr Phe Asn Lys Leu Ile Glu Asn Met Thr Ser Gly Pro Ser Leu
    370                 375                 380

Ala Leu Val Leu Leu Arg Asp Asn Gly Leu Gln Tyr Trp Lys Gln Leu
385                 390                 395                 400

Leu Gly Pro Arg Thr Val Glu Glu Ala Ile Glu Tyr Phe Pro Glu Ser
                405                 410                 415

Leu Cys Ala Gln Phe Ala Met Asp Ser Leu Pro Val Asn Gln Leu Tyr
            420                 425                 430

Gly Ser Asp Ser Leu Glu Thr Ala Glu Arg Glu Ile Gln His Phe Phe
        435                 440                 445

Pro Leu Gln Ser Thr Leu Gly Leu Ile Lys Pro His Ala Thr Ser Glu
    450                 455                 460

Gln Arg Glu Gln Ile Leu Lys Ile Val Lys Glu Ala Gly Phe Asp Leu
465                 470                 475                 480
```

```
Thr Gln Val Lys Lys Met Phe Leu Thr Pro Glu Gln Ile Glu Lys Ile
            485                 490                 495

Tyr Pro Lys Val Thr Gly Lys Asp Phe Tyr Lys Asp Leu Leu Glu Met
        500                 505                 510

Leu Ser Val Gly Pro Ser Met Val Met Ile Leu Thr Lys Trp Asn Ala
        515                 520                 525

Val Ala Glu Trp Arg Arg Leu Met Gly Pro Thr Asp Pro Glu Glu Ala
        530                 535                 540

Lys Leu Leu Ser Pro Asp Ser Ile Arg Ala Gln Phe Gly Ile Ser Lys
545                 550                 555                 560

Leu Lys Asn Ile Val His Gly Ala Ser Asn Ala Tyr Glu Ala Lys Glu
            565                 570                 575

Val Val Asn Arg Leu Phe Glu Asp Pro Glu Glu Asn
            580                 585

<210> SEQ ID NO 1113
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1113
gaggtccagc tgcaacagtc tggacctgaa ctggtgaagc tggggcttc agtgaagata         60 tcctgcaaga cttctgga                                                     78

<210> SEQ ID NO 1114
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1114

Glu Val Gln Leu Gln Gln Ser Gly Pro Glu Leu Val Lys Pro Gly Ala
1               5                   10                  15

Ser Val Lys Ile Ser Cys Lys Thr Ser Gly
            20                  25

<210> SEQ ID NO 1115
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1115
aacacattca ctgaatacac catgcac                                            27

<210> SEQ ID NO 1116
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1116
tgggtgaagc agagccatgg aaagagcctt gagtggattg ga                           42
```

<210> SEQ ID NO 1117
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1117

Trp Val Lys Gln Ser His Gly Lys Ser Leu Glu Trp Ile Gly
1               5                   10

<210> SEQ ID NO 1118
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1118
ggttttaatc ctaacaatgg tgttactaac tacaaccaga agttcaaggg c            51

<210> SEQ ID NO 1119
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1119
aaggccacat tgactgtaga caagtcctcc agcacagcct acatggagct ccgcagcctg   60
acatctgagg attctgcagt ctattactgt gcaaga                             96

<210> SEQ ID NO 1120
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1120

Lys Ala Thr Leu Thr Val Asp Lys Ser Ser Thr Ala Tyr Met Glu
1               5                   10                  15

Leu Arg Ser Leu Thr Ser Glu Asp Ser Ala Val Tyr Tyr Cys Ala Arg
            20                  25                  30

<210> SEQ ID NO 1121
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1121
cggtactacc atagtctcta cgtgttttac tttgactac                          39

<210> SEQ ID NO 1122
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1122
gatatccaga tgacacagac tacatcctcc ctgtctgcct ctctgggaga cagagtcacc    60
ctcagttgc    69

<210> SEQ ID NO 1123
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1123

Asp Ile Gln Met Thr Gln Thr Thr Ser Ser Leu Ser Ala Ser Leu Gly
1               5                   10                  15

Asp Arg Val Thr Leu Ser Cys
            20

<210> SEQ ID NO 1124
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1124
agtgcaagtc agggcattag caattattta aac    33

<210> SEQ ID NO 1125
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1125
tggtatcagc agaaaccaga tggaactgtt gaactcctga tcttt    45

<210> SEQ ID NO 1126
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1126

Trp Tyr Gln Gln Lys Pro Asp Gly Thr Val Glu Leu Leu Ile Phe
1               5                   10                  15

<210> SEQ ID NO 1127
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1127
tacacatcaa gtttacactc a    21

```
<210> SEQ ID NO 1128
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1128
ggagtcccat caaggttcag tggcagtggg tctgggacag attattctct caccatcagc    60
aacctggaac ctgaagatat tgccacttac tattgt                              96

<210> SEQ ID NO 1129
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1129

Gly Val Pro Ser Arg Phe Ser Gly Ser Gly Ser Gly Thr Asp Tyr Ser
1               5                   10                  15

Leu Thr Ile Ser Asn Leu Glu Pro Glu Asp Ile Ala Thr Tyr Tyr Cys
            20                  25                  30

<210> SEQ ID NO 1130
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1130
cagcagtata gtaagcttcc ttacacg                                        27

<210> SEQ ID NO 1131
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1131
caggttcagc tggtttcagtc tggtgcagaa gtgaagaaac ctggcgcctc tgtgaaggtg    60
tcctgcaagg tgtccggaaa taccttcacc gagtacacca tgcactgggt ccgacaggcc   120
cctggcaaag gacttgaatg gatgggcggc ttcaacccca caacggcgt gaccaactac    180 aaccagaaat tcaagggccg cgtgaccatg accgaggaca caagcacaga caccgcctac   240
atggaactga gcagcctgag aagcgaggac accgccgtgt actactgcgc cagaaggtac   300
taccacagcc tgtacgtgtt ctacttcgac tactggggcc agggcaccct ggtcacagtt   360
tcttct                                                             366

<210> SEQ ID NO 1132
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1132
```

```
gaggtgcagc tggtggaaag cggcggcggc ctggttaagc ctggcggatc tctgagactg      60
agctgtgccg cttctggcaa taccttcacc gagtacacca tgcactgggt gcggcaggcc     120
cctggaaaag gcctggaatg gatcggcgga tttaacccca acaacggcgt gacaaattac     180
aaccagaaat tcaagggcaa gttcaccatc acaagagata gagcaagaa cacccctgtac     240 ctgcaaatga acagcctgaa gtccgaggac accgccgtgt actactgcgc agacggtac     300 taccacagcc tctatgtgtt ctacttcgac tactggggcc agggcacact ggtcaccgtg     360
tccagc                                                                366
```

```
<210> SEQ ID NO 1133
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1133
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Asn Thr Phe Thr Glu Tyr
            20                  25                  30

Thr Met His Trp Val Arg Gln Ala Pro Gly Lys Gly Leu Glu Trp Ile
        35                  40                  45

Gly Gly Phe Asn Pro Asn Asn Gly Val Thr Asn Tyr Asn Gln Lys Phe
    50                  55                  60

Lys Gly Lys Phe Thr Ile Thr Arg Asp Lys Ser Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Arg Arg Tyr Tyr His Ser Leu Tyr Val Phe Tyr Phe Asp Tyr Trp
            100                 105                 110

Gly Gln Gly Thr Leu Val Thr Val Ser Ser
        115                 120

```
<210> SEQ ID NO 1134
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1134
```

```
gagatcgtga tgacccagag cccagctaca cttagtgtga gtccaggtga acgggctacc      60
ctgtcctgca gcgccagcca gggcatcagc aactacctga actggtacca gcagaaacct     120
ggccaggccc ctagactgct gatcttctac accagcagcc tgcacagcgg catcccccgcc    180 agattcagcg gcagcggctc tggaacagac tacaccctga caatctctag cctgcagtct     240
gaagattttg ccgtctacta ctgtcagcaa tacagcaagc tgccttatac cttcggcggc     300
ggaaccaagg tggaaattaa g                                               321
```

```
<210> SEQ ID NO 1135
<211> LENGTH: 107
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 1135

Glu Ile Val Met Thr Gln Ser Pro Ala Thr Leu Ser Val Ser Pro Gly
1               5                   10                  15

Glu Arg Ala Thr Leu Ser Cys Ser Ala Ser Gln Gly Ile Ser Asn Tyr
            20                  25                  30

Leu Asn Trp Tyr Gln Gln Lys Pro Gly Gln Ala Pro Arg Leu Leu Ile
        35                  40                  45

Phe Tyr Thr Ser Ser Leu His Ser Gly Ile Pro Ala Arg Phe Ser Gly
50                  55                  60

Ser Gly Ser Gly Thr Asp Tyr Thr Leu Thr Ile Ser Ser Leu Gln Ser
65                  70                  75                  80

Glu Asp Phe Ala Val Tyr Tyr Cys Gln Gln Tyr Ser Lys Leu Pro Tyr
                85                  90                  95

Thr Phe Gly Gly Gly Thr Lys Val Glu Ile Lys
            100                 105

<210> SEQ ID NO 1136
<211> LENGTH: 321
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 1136
gatatccaga tgacacagac tacatcctcc ctgtctgcct ctctgggaga cagagtcacc        60
ctcagttgca gtgcaagtca gggcattagc aattatttaa actggtatca gcagaaacca      120
gatggaactg ttgaactcct gatcttttac acatcaagtt tacactcagg agtcccatca      180
aggttcagtg gcagtgggtc tgggacagat tattctctca ccatcagcaa cctggaacct      240
gaagatattg ccacttacta ttgtcagcag tatagtaagc ttccttacac gttcggaggg      300
gggaccaagc tggaaataaa a                                                321

<210> SEQ ID NO 1137
<211> LENGTH: 152
<212> TYPE: PRT
<213> ORGANISM: Homo sapiens

<400> SEQUENCE: 1137

Met Ala Asn Cys Glu Arg Thr Phe Ile Ala Ile Lys Pro Asp Gly Val
1               5                   10                  15

Gln Arg Gly Leu Val Gly Glu Ile Ile Lys Arg Phe Glu Gln Lys Gly
            20                  25                  30

Phe Arg Leu Val Gly Leu Lys Phe Met Gln Ala Ser Glu Asp Leu Leu
        35                  40                  45

Lys Glu His Tyr Val Asp Leu Lys Asp Arg Pro Phe Phe Ala Gly Leu
    50                  55                  60

Val Lys Tyr Met His Ser Gly Pro Val Val Ala Met Val Trp Glu Gly
65                  70                  75                  80

Leu Asn Val Val Lys Thr Gly Arg Val Met Leu Gly Glu Thr Asn Pro
                85                  90                  95

Ala Asp Ser Lys Pro Gly Thr Ile Arg Gly Asp Phe Cys Ile Gln Val
            100                 105                 110

Gly Arg Asn Ile Ile His Gly Ser Asp Ser Val Glu Ser Ala Glu Lys

```
            115                 120                 125
Glu Ile Gly Leu Trp Phe His Pro Glu Glu Leu Val Asp Tyr Thr Ser
        130                 135                 140
Cys Ala Gln Asn Trp Ile Tyr Glu
145                 150
```

<210> SEQ ID NO 1138
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1138

```
gaggtccagc tgcaacagtc tggacctgaa ctggtgaagc tggggcttc agtgaagata    60 tcctgcaaga cttctggaaa cacattcact gaatacacca tgcactgggt gaagcagagc  120
catggaaaga gccttgagtg gattggaggt tttaatccta caatggtgt tactaactac  180 aaccagaagt tcaagggcaa ggccacattg actgtagaca gtcctccag cacagcctac  240 atggagctcc gcagcctgac atctgaggat tctgcagtct attactgtgc aagacggtac  300
taccatagtc tctacgtgtt ttactttgac tactggggcc aaggcaccac tctcacagtc  360
tcctca                                                             366
```

<210> SEQ ID NO 1139
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1139

```
Glu Val Gln Leu Gln Gln Ser Gly Pro Glu Leu Val Lys Pro Gly Ala
1               5                   10                  15

Ser Val Lys Ile Ser Cys Lys Thr Ser Gly Asn Thr Phe Thr Glu Tyr
            20                  25                  30

Thr Met His Trp Val Lys Gln Ser His Gly Lys Ser Leu Glu Trp Ile
        35                  40                  45

Gly Gly Phe Asn Pro Asn Asn Gly Val Thr Asn Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Arg Tyr Tyr His Ser Leu Tyr Val Phe Tyr Phe Asp Tyr Trp
            100                 105                 110

Gly Gln Gly Thr Thr Leu Thr Val Ser Ser
        115                 120
```

<210> SEQ ID NO 1140
<211> LENGTH: 131
<212> TYPE: PRT
<213> ORGANISM: Homo sapiens

<400> SEQUENCE: 1140

```
Glu Lys Thr Leu Ala Leu Ile Lys Pro Asp Ala Ile Ser Lys Ala Gly
1               5                   10                  15
```

Glu Ile Ile Glu Ile Ile Asn Lys Ala Gly Phe Thr Ile Thr Lys Leu
                20                  25                  30

Lys Met Met Met Leu Ser Arg Lys Glu Ala Leu Asp Phe His Val Asp
        35                  40                  45

His Gln Ser Arg Pro Phe Phe Asn Glu Leu Ile Gln Phe Ile Thr Thr
    50                  55                  60

Gly Pro Ile Ile Ala Met Glu Ile Leu Arg Asp Asp Ala Ile Cys Glu
65                  70                  75                  80

Trp Lys Arg Leu Leu Gly Pro Ala Asn Ser Gly Val Ala Arg Thr Asp
                85                  90                  95

Ala Ser Glu Ser Ile Arg Ala Leu Phe Gly Thr Asp Gly Ile Arg Asn
            100                 105                 110

Ala Ala His Gly Pro Asp Ser Phe Ala Ser Ala Arg Glu Met Glu
        115                 120                 125

Leu Phe Phe
    130

<210> SEQ ID NO 1141
<211> LENGTH: 376
<212> TYPE: PRT
<213> ORGANISM: Homo sapiens

<400> SEQUENCE: 1141

Met Asn His Ser Glu Arg Phe Val Phe Ile Ala Glu Trp Tyr Asp Pro
1               5                   10                  15

Asn Ala Ser Leu Leu Arg Arg Tyr Glu Leu Leu Phe Tyr Pro Gly Asp
                20                  25                  30

Gly Ser Val Glu Met His Asp Val Lys Asn His Arg Thr Phe Leu Lys
            35                  40                  45

Arg Thr Lys Tyr Asp Asn Leu His Leu Glu Asp Leu Phe Ile Gly Asn
        50                  55                  60

Lys Val Asn Val Phe Ser Arg Gln Leu Val Leu Ile Asp Tyr Gly Asp
65                  70                  75                  80

Gln Tyr Thr Ala Arg Gln Leu Gly Ser Arg Lys Glu Lys Thr Leu Ala
                85                  90                  95

Leu Ile Lys Pro Asp Ala Ile Ser Lys Ala Gly Glu Ile Ile Glu Ile
            100                 105                 110

Ile Asn Lys Ala Gly Phe Thr Ile Thr Lys Leu Lys Met Met Met Leu
        115                 120                 125

Ser Arg Lys Glu Ala Leu Asp Phe His Val Asp His Gln Ser Arg Pro
130                 135                 140

Phe Phe Asn Glu Leu Ile Gln Phe Ile Thr Thr Gly Pro Ile Ile Ala
145                 150                 155                 160

Met Glu Ile Leu Arg Asp Asp Ala Ile Cys Glu Trp Lys Arg Leu Leu
                165                 170                 175

Gly Pro Ala Asn Ser Gly Val Ala Arg Thr Asp Ala Ser Glu Ser Ile
            180                 185                 190

Arg Ala Leu Phe Gly Thr Asp Gly Ile Arg Asn Ala Ala His Gly Pro
        195                 200                 205

Asp Ser Phe Ala Ser Ala Ala Arg Glu Met Glu Leu Phe Phe Pro Ser
    210                 215                 220

Ser Gly Gly Cys Gly Pro Ala Asn Thr Ala Lys Phe Thr Asn Cys Thr
225                 230                 235                 240

Cys Cys Ile Val Lys Pro His Ala Val Ser Glu Gly Leu Leu Gly Lys
                245                 250                 255

Ile Leu Met Ala Ile Arg Asp Ala Gly Phe Glu Ile Ser Ala Met Gln
            260                 265                 270

Met Phe Asn Met Asp Arg Val Asn Val Glu Glu Phe Tyr Glu Val Tyr
            275                 280                 285

Lys Gly Val Val Thr Glu Tyr His Asp Met Val Thr Glu Met Tyr Ser
        290                 295                 300

Gly Pro Cys Val Ala Met Glu Ile Gln Gln Asn Asn Ala Thr Lys Thr
305                 310                 315                 320

Phe Arg Glu Phe Cys Gly Pro Ala Asp Pro Glu Ile Ala Arg His Leu
                325                 330                 335

Arg Pro Gly Thr Leu Arg Ala Ile Phe Gly Lys Thr Lys Ile Gln Asn
            340                 345                 350

Ala Val His Cys Thr Asp Leu Pro Glu Asp Gly Leu Leu Glu Val Gln
            355                 360                 365

Tyr Phe Phe Lys Ile Leu Asp Asn
        370                 375

<210> SEQ ID NO 1142
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1142

Ala Ile Phe Gly Lys Thr Lys Ile Gln Asn Ala Val His Cys Thr Asp
1               5                   10                  15

Leu Pro Glu Asp Gly Leu Leu Glu Val Gln Tyr Phe Phe Cys
            20                  25                  30

<210> SEQ ID NO 1143
<211> LENGTH: 139
<212> TYPE: PRT
<213> ORGANISM: Homo sapiens

<400> SEQUENCE: 1143

Asn Cys Thr Cys Cys Ile Val Lys Pro His Ala Val Ser Glu Gly Leu
1               5                   10                  15

Leu Gly Lys Ile Leu Met Ala Ile Arg Asp Ala Gly Phe Glu Ile Ser
            20                  25                  30

Ala Met Gln Met Phe Asn Met Asp Arg Val Asn Val Glu Glu Phe Tyr
        35                  40                  45

Glu Val Tyr Lys Gly Val Val Thr Glu Tyr His Asp Met Val Thr Glu
    50                  55                  60

Met Tyr Ser Gly Pro Cys Val Ala Met Glu Ile Gln Gln Asn Asn Ala
65                  70                  75                  80

Thr Lys Thr Phe Arg Glu Phe Cys Gly Pro Ala Asp Pro Glu Ile Ala
                85                  90                  95

Arg His Leu Arg Pro Gly Thr Leu Arg Ala Ile Phe Gly Lys Thr Lys
            100                 105                 110

Ile Gln Asn Ala Val His Cys Thr Asp Leu Pro Glu Asp Gly Leu Leu
        115                 120                 125

Glu Val Gln Tyr Phe Phe Lys Ile Leu Asp Asn
    130                 135

<210> SEQ ID NO 1144

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1144

Ile Thr Ser Thr Asp Ile Asp Asp Met Asn
1               5                   10

<210> SEQ ID NO 1145
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1145

Glu Gly Asn Thr Leu Arg Pro
1               5

<210> SEQ ID NO 1146
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1146

Leu Gln Ser Asp Asn Leu Pro Leu Thr
1               5
```

ANTI-NME ANTIBODY AND METHOD OF TREATING CANCER OR CANCER METASTASIS

SEQUENCE LISTING

The instant application contains a Sequence Listing which has been submitted electronically in ASCII format and is hereby incorporated by reference in its entirety. Said ASCII copy, created on May 15, 2023, is named 56699-743_831_SL.txt and is 465,564 bytes in size.

BACKGROUND OF THE INVENTION

Field of the Invention

The present application relates to NME proteins, peptides derived from NME proteins, and antibodies generated from the peptides thereof or antibody or antibody fragments selected by virtue of their ability to bind to said peptides. The present application also relates to treating or preventing diseases associated with the expression of NME in a patient.

2. General Background and State of the Art

NDPK (nucleoside diphosphate protein kinase) proteins are a family of proteins grouped together because they all contain an NDPK domain. The first NME proteins discovered, previously called NM23 proteins, were NM23-H1 and NM23-H2. For decades it was unclear whether they induced differentiation or prevented differentiation of hematopoietic cells. The inventors previously discovered that NM23-H1 prevents differentiation when it is a dimer, which binds to the MUC1* growth factor receptor, but at higher concentrations NM23-H1 becomes a hexamer, which does not bind to MUC1*, and it induces differentiation. NM23 used to be called a metastasis suppressor when it was found that it was under-expressed in some very aggressive cancers. The present inventors previously disclosed that NM23-H1 dimers bind to and dimerize the extracellular domain of the MUC1* growth factor receptor that is over expressed on the vast majority of cancers and such binding promotes the growth of cancer cells. Conversely, at higher concentrations, NM23 forms tetramers and hexamers that do not bind to MUC1* and do not promote tumorigenesis. Very recently more NME family proteins (NME 1-10) have been discovered although until now, their functions have not been elucidated. NME7 is a newly discovered NME family protein, but its NDPK domain has no enzymatic activity, unlike other NME family members. NME7 is either not expressed at all in adult tissues or is expressed at extremely low levels.

SUMMARY OF THE INVENTION

The present application is directed to a method of treating or preventing cancer in a subject, comprising administering to the subject an antibody made against a member of the NME family. The NME family may be NME7 family. The antibody may bind to NME7. The antibody may bind to NME7AB or NME7AB-like protein. The antibody may bind to NME7-X1. The antibody may inhibit binding between NME7 and its cognate binding partner. The cognate binding partner may be MUC1*. The cognate binding partner may be PSMGFR portion of the MUC1* extracellular domain. In one aspect, the antibody may be generated or selected for its ability to bind to a peptide selected from those listed in FIGS. 6-9 (SEQ ID NOS:88 to 145). Preferably, the peptide may be selected from those listed in FIG. 9 (SEQ ID NOS:141 to 145).

The peptide may be highly homologous to, or to which is added or subtracted up to 7, up to 6, up to 5, up to 4, up to 3, up to 2, or up to 1 amino acid residues at the N-terminus or C-terminus, of the peptides listed in FIG. 6-9 (SEQ ID NOS:88 to 145). In one aspect, the antibody may be selected for its ability to bind to NME7AB or NME7-X1 but not to NME1. The antibody may be polyclonal, monoclonal, bivalent, monovalent, bispecific, an antibody fragment containing the variable region, or an antibody mimic. The antibody may be human or humanized. The antibody may be a single chain scFv.

In another aspect, the invention is directed to a method of treating or preventing cancer in a subject, comprising administering to the subject a peptide that is highly homologous or identical to regions of NME7AB. The peptide may be at least 80% homologous to one or more of the peptides listed in FIG. 6. The peptide may be at least 80% homologous to one or more of the peptides listed in FIG. 7. The peptide may be at least 80% homologous to one or more of the peptides listed in FIG. 8. The peptide may be at least 80% homologous to one or more of the peptides listed in FIG. 9. The peptide may be selected from peptides listed in FIG. 6-9 (SEQ ID NOS:88 to 145). The peptide may be selected from those listed in FIG. 9 (SEQ ID NOS:141 to 145). Or, the peptide may be highly homologous to, or to which is added or subtracted up to 7, up to 6, up to 5, up to 4, up to 3, up to 2, or up to 1 amino acid residues at the N-terminus or C-terminus, of the peptides listed in FIG. 6-9 (SEQ ID NOS:88 to 145). The peptide may be connected to another peptide via a spacer or linker.

In another aspect, the invention is directed to a chimeric antigen receptor (CAR), for the treatment or prevention of cancer wherein the targeting extracellular portion of the CAR comprises at least a peptide fragment of a member of the NME family. NME family may be NME7 family. The member of the NME7 family may be NME7. Or, the member of the NME7 family may be NME7AB or NME7AB-like protein. The member of the NME7 family may be also NME7-X1. The targeting extracellular portion of the CAR may include a peptide of the peptides listed in FIG. 6-9 (SEQ ID NOS:88 to 145). The peptide may be selected from those listed in FIG. 9 (SEQ ID NOS:141 to 145). The peptide may include a peptide, which is highly homologous to, or to which is added or subtracted up to 7, up to 6, up to 5, up to 4, up to 3, up to 2, or up to 1 amino acid residues at the N-terminus or C-terminus, of the peptides listed in FIG. 6-9 (SEQ ID NOS:88 to 145). The peptide may be connected to another peptide via a spacer or linker.

In yet another aspect, the invention is directed to a method of treating or preventing cancer or cancer metastasis, comprising engineering the chimeric antigen receptor according to claim 3, into an immune system cell and administering the cell to a subject in need thereof.

In another aspect, the invention is directed to a chimeric antigen receptor (CAR), for the treatment or prevention of cancer, wherein the targeting extracellular portion of the chimeric antigen receptor comprises a portion of an antibody that binds to NME7AB, NME7AB-like protein or NME7-X1. The portion of the antibody may be a single chain scFv or may be human or humanized.

In yet another aspect, the invention is directed to a method of vaccinating a person against cancer or metastatic cancer comprising immunizing the person with a peptide fragment of a member of the NME family. The NME family may be NME7 family. The member of the NME7 family may be NME7 or NME7b. The member of the NME7 family may be NME7AB or NME7AB-like protein. The NME7 family may be NME7-X1. The immunizing peptide may be a peptide from the peptides listed in FIG. 6-9 (SEQ ID NOS:88 to 145). Preferably, the peptide may be selected from those listed in FIG. 9 (SEQ ID NOS:141 to 145). The immunizing peptide may include a peptide, which is highly homologous to, or to which is added or subtracted up to 7, up to 6, up to 5, up to 4, up to 3, up to 2, or up to 1 amino acid residues at the N-terminus or C-terminus, of the peptides listed in FIG. 6-9 (SEQ ID NOS:88 to 145). The immunizing peptide may be connected to another peptide via a spacer or linker.

In yet another aspect, the invention is directed to a method of treating or preventing cancer in a subject, comprising administering to the subject a nucleic acid that inhibits the expression of NME7, NME7b, NME7AB-like protein or NME7-X1. The nucleic acid may be an anti-sense nucleic acid that suppresses expression of NME7, NME7AB-like protein or NME7-X1. The nucleic acid may be an inhibitory RNA, siRNA, RNAi, or shRNA that inhibits expression of NME7, NME7AB-like protein or NME7-X1.

In another aspect, the invention is directed to a method of treating or preventing cancer in a subject, comprising administering to the subject genetically edited nucleic acids that inhibit expression of NME7, NME7b, NME7AB-like protein or NME7-X1. The genetically edited nucleic acids that inhibit expression of NME7, NME7b, NME7AB-like protein or NME7-X1 may be inserted into cells that may be then administered to the patient. The genetically edited nucleic acids that inhibit expression of NME7, NME7b, NME7AB-like protein or NME7-X1 may be inserted into cells using a viral vector. The viral vector may be a lentiviral system.

In another aspect, the invention is directed to a method of growing cancer cells comprising contacting the cells with NME7AB, NME7b, NME7AB-like protein or NME7-X1, 2i or 5i. The method may include culturing the cells in a medium that contains NME7AB, NME7b, NME7AB-like protein or NME7-X1, 2i or 5i, or growing cells in an animal that expresses human NME7AB, NME7b, NME7AB-like protein or NME7-X1, or to which NME7AB, NME7b, NME7AB-like protein or NME7-X1 is administered. The cancer cells may be breast, prostate, ovarian, colorectal, pancreatic, liver, melanoma or brain cancer cells. Drug candidates may be tested on the cells. The efficacy of the drugs may be assessed by comparing cancer growth to a no drug control or comparing expression levels of metastatic markers or stem cell markers to a no drug control or comparing the ability of the resultant cells to form tumors in animals from low cell copy number compared to a no drug control and determining the efficacy of a candidate drug for the treatment of cancer or metastasis. The cells may be obtained from a patient being assessed for treatment for cancer and drugs that would be effective for that patient are selected based on results using methods described above. The cells may not be obtained from a patient being assessed for treatment for cancer but drugs that would be effective for that patient are selected based on results using the methods described above.

In another aspect, the invention is directed to a method of generating antibodies or antibody-like molecules from peptides or peptide mimics having a sequence derived from the sequence of NME. The NME may be NME7. The peptide may be used as an immunogen to generate antibodies or antibody-like molecules. The peptide may be administered to an animal to generate anti-NME7 antibodies. The peptide may be administered to a human to generate anti-NME7 antibodies. The peptide may have a sequence listed in FIG. 6-9 (SEQ ID NOS:88 to 145). Preferably, the peptide may be selected from those listed in FIG. 9 (SEQ ID NOS:141 to 145). The peptide may include a peptide, which is highly homologous to, or to which is added or subtracted up to 7, up to 6, up to 5, up to 4, up to 3, up to 2, or up to 1 amino acid residues at the N-terminus or C-terminus, of the peptides listed in FIG. 6-9 (SEQ ID NOS:88 to 145).

In another aspect, the invention is directed to a method of detecting presence of cancer or the progression of cancer, comprising the steps of:
1) obtaining a sample from a patient having cancer or at risk of developing a cancer;
2) subjecting that sample to an assay capable of detecting or measuring levels of a member of the NME7 family, or levels of nucleic acids encoding a member of the NME7 family;
3) comparing levels of the measured member of the NME7 family or the member of the NME7 family-encoding nucleic acids in the test sample to levels in control patients or control cells;
4) determining that the levels of the member of the NME7 family or nucleic acids encoding the member of the NME7 family are elevated compared to the controls; and
5) concluding that the donor of the test sample has cancer or has had a progression of cancer if the control to which the test was compared came from a donor previously diagnosed with a cancer. In this method, the detection of the member of the NME7 family in circulation or in a tissue may be an indicator of cancer in a patient. The member of the NME7 family may be NME7, NME7b, NME7-X1, or NME7AB-like protein.

In yet another aspect, the invention is directed to a method comprising:
detecting presence of a member of the NME7 family or MUC1* in a patient; and
administering anti-NME7 or anti-MUC1* antibody or antibodies to the patient exhibiting the member of the NME7 family or MUC1* expression. The member of the NME7 family may be NME7, NME7b, NME7-X1, or NME7AB-like protein.

In yet another aspect, the invention is directed to a method for treating or preventing cancer comprising:
1) obtaining a sample from a patient suspected of having a cancer or at risk of developing a cancer or at risk of developing a metastatic cancer;
2) measuring an amount of the member of an NME7 family or a member of the NME7 family encoding nucleic acid, wherein the measured levels are significantly above those measured in a control sample;
3) determining that the patient has a cancer or has developed a more aggressive or a metastatic cancer;
4) administering to the patient an effective amount of a therapeutic agent that suppresses expression of the member of the NME7 family, inhibits cleavage of NME7 or inhibits NME7 binding to its targets. The target of the member of the NME7 family may be MUC1*. The target of the member of the NME7 family may be PSMGFR portion of the MUC1* extracellular domain. The member of the NME7 family may be NME7, NME7b, NME7-X1, or NME7AB-like protein.

In any of the methods above regarding cancer, cancer may include breast, prostate, ovarian, colorectal, pancreatic, liver, melanoma or brain cancer.

In one aspect, the invention is directed to an NME7 specific antibody or fragment thereof that binds to the NME7 B3 peptide of SEQ ID NO:145 or SEQ ID NO:169. The antibody may be monoclonal antibody or bivalent, monovalent, an Fab, or a single chain variable fragment antibody (scFv). The antibody may be linked to an antibody drug conjugate. The drug may be linked to a toxin or pro-toxin.

The invention is also directed to an isolated nucleic acid encoding the antibody.

The invention is also directed to an isolated hybridoma expressing the monoclonal antibody discussed above. The antibody may specifically bind to NME7AB or NME7-X1, but not to NME1. The antibody may disrupt interaction between NME7AB and MUC1* extra cellular domain or between NME7-X1 and MUC1* extra cellular domain. Or, the antibody may disrupt binding between NME7AB and PSMGFR or between NME7-X1 and PSMGFR. Further, the antibody may disrupt binding between NME7AB and N-10 or between NME7-X1 and N-10.

In another aspect, the antibody may not disrupt interaction between NME7AB and MUC1* extra cellular domain or between NME7-X1 and MUC1* extra cellular domain. NME7$_{AB}$ or NME7-X1 may bind to the N-10 peptide (SEQ ID NO:170) but not to a C-10 peptide (SEQ ID NO:171). In particular, the antibody may be 5A1, 4A3, 5D4, or 4P3.

The antibody may comprise an amino acid sequence in the heavy chain variable region comprising the following:
 in the CDR1 region YTFTNYGMN (SEQ ID NO:439);
 in the CDR2 region WINTYTGEPTYVDDFKG (SEQ ID NO:440); and
 in the CDR3 region LRGIRPGPLAY (SEQ ID NO:441); and
an amino acid sequence in the light chain variable region comprising the following:
 in the CDR1 region SASSSVSYMN (SEQ ID NO:444);
 in the CDR2 region GISNLAS (SEQ ID NO:445); and
 in the CDR3 region QQRSSYPPT (SEQ ID NO:446).
An example of such an antibody above is 5A1.

In another aspect, the antibody may comprise an amino acid sequence in the heavy chain variable region comprising the following:
 in the CDR1 region NTFTEYTMH (SEQ ID NO:429);
 in the CDR2 region GFNPNNGVTNYNQKFKG (SEQ ID NO:430); and
 in the CDR3 region RYYHSTYVFYFDS (SEQ ID NO:431); and
an amino acid sequence in the light chain variable region comprising the following:
 in the CDR1 region SASQGISNYLN (SEQ ID NO:434);
 in the CDR2 region YTSSLHS (SEQ ID NO:435); and
 in the CDR3 region QQYSKLPYT (SEQ ID NO:436).
An example of such an antibody above is 5D4.

In another aspect, the antibody may comprise an amino acid sequence in the heavy chain variable region comprising the following:
 in the CDR1 region NTFTEYTMH (SEQ ID NO:388);
 in the CDR2 region GFNPNNGVTNYNQKFKG (SEQ ID NO:389); and
 in the CDR3 region RYYHSLYVFYFDY (SEQ ID NO:390); and
an amino acid sequence in the light chain variable region comprising the following:
 in the CDR1 region SASQGISNYLN (SEQ ID NO:393);
 in the CDR2 region YTSSLHS (SEQ ID NO:394); and
 in the CDR3 region QQYSKLPYT (SEQ ID NO:395).
An example of such an antibody above is 4A3.

In another aspect, the antibody may comprise an amino acid sequence in the heavy chain variable region comprising the following:
 in the CDR1 region NTFTEYTMH (SEQ ID NO:388);
 in the CDR2 region GFNPNNGVTNYNQKFKG (SEQ ID NO:389); and
 in the CDR3 region RYYHSLYVFYFDY (SEQ ID NO:390); and
an amino acid sequence in the light chain variable region comprising the following:
 in the CDR1 region ITSTDIDDDMN (SEQ ID NO: 1144);
 in the CDR2 region EGNTLRP (SEQ ID NO: 1145); and
 in the CDR3 region LQSDNLPLT (SEQ ID NO: 1146).
An example of such an antibody above is 4P3.

The antibody may be human, humanized or an engineered antibody mimic.

The antibody may be non-human, such as murine or camelid.

The invention is also directed to a method of administering to a patient for prevention or treatment of cancer comprising administering to the patient a composition comprising the antibody described above.

The invention is also directed to a method for preventing or treating cancer metastasis in a patient, comprising administering to the patient a composition comprising the antibody described above.

The invention is also directed to a method for diagnosing cancer or cancer metastasis comprising contacting a patient specimen and normal specimen with the antibody above, and comparing the results from both specimen, wherein presence of positive binding to the antibody in the patient specimen indicates the presence of cancer or cancer metastasis in the patient. The antibody may be linked to an imaging agent. The patient specimen may be blood, bodily fluid, tissue, circulating cells, in vitro, in vivo, including intra-operative.

The invention is also directed to a cell that is engineered to express an anti-NME7$_{AB}$ antibody or fragment thereof. The cell may be an immune cell, such as T cell or NK cell, or a stem or progenitor cell, preferably stem or progenitor cell that is then differentiated to become a T cell.

The cell may comprise a chimeric antigen receptor (CAR) that recognizes tumor associated antigen. Expression of the anti-NME7 antibody may be inducible. Nucleic acid encoding an anti-NME7$_{AB}$ antibody may be inserted into the Foxp3 enhancer or promoter. The anti-NME7$_{AB}$ antibody may be in an NFAT-inducible system. NFATc1 response element may be inserted upstream of the antibody sequence that is inserted into Foxp3 enhancer or promoter region.

The anti-NME7$_{AB}$ antibody or fragment thereof may bind to the NME7 B3 peptide, or disrupt binding of NME7$_{AB}$ or NME7-X1 to the PSMGFR peptide of the MUC1* extra cellular domain.

The CAR may recognize a tumor associated antigen and an anti-NME7 antibody. The tumor associated antigen may be MUC1*.

The invention is also directed to an anti-cancer vaccine comprising a composition comprising one or more peptides derived from NME7$_{AB}$ listed in FIG. 6-FIG. 9 or a peptide having at least 80%, 85%, 90%, 95%, 97% sequence identity thereof as the immunogenicity eliciting portion. The peptide may be a peptide of SEQ ID NOS:141-145 or a peptide having at least 80%, 85%, 90%, 95%, 97% sequence identity thereof. The peptide may be a peptide of SEQ ID NO: 145 or a peptide having at least 80%, 85%, 90%, 95%, 97% sequence identity thereof.

In another aspect, the invention is directed to a BiTE comprising the above-described antibody.

In yet another aspect, the invention is directed to a method of generating anti-NME7$_{AB}$ antibodies wherein Cysteine residue in the NME7 B3 peptide is mutated to avoid disulfide bonding.

In yet another aspect, the invention is directed to a method of generating cells with enhanced metastatic potential comprising culturing the cells with NME7$_{AB}$ or NME7-X1.

The invention is also directed to a cell that is engineered to express NME7$_{AB}$ or NME7-X1, a transgenic animal that expresses NME7$_{AB}$ or NME7-X1, wherein the NME7$_{AB}$ or NME7-X1 may be human, and also wherein expression of NME7$_{AB}$ or NME7-X1 may be inducible.

BRIEF DESCRIPTION OF THE DRAWINGS

The patent or application file contains at least one drawing executed in color. Copies of this patent or patent application publication with color drawings will be provided by the Office upon request and payment of the necessary fee.

The present invention will become more fully understood from the detailed description given herein below, and the accompanying drawings which are given by way of illustration only, and thus are not limitative of the present invention, and wherein;

FIG. 1 shows a graph of HRP signal from ELISA sandwich assay showing NME7-AB dimerizes MUC1* extra cellular domain peptide.

FIG. 5 is a sequence alignment between human NME1 and human NME7-A or -B domain. Figure discloses SEQ ID NOS 1137, 1140, 1137 and 1143, respectively, in order of appearance.

FIG. 6 lists immunogenic peptides from human NME7 with low sequence identity to NME1 and selected for their ability to generate therapeutic anti-NME7 antibodies for the treatment or prevention of cancers. Figure discloses SEQ ID NOS 88-108, 91, and 110-118, respectively, in order of appearance.

FIG. 7 lists immunogenic peptides from human NME7 that may be important for structural integrity or for binding to MUC1* selected for their ability to generate therapeutic anti-NME7 antibodies for the treatment or prevention of cancers. Figure discloses SEQ ID NOS 122, 114, 124-129, 128, and 131-133, respectively, in order of appearance.

FIG. 8 lists immunogenic peptides from human NME1 that may be important for structural integrity or for binding to MUC1* and selected for their ability to generate therapeutic anti-NME7 antibodies for the treatment or prevention of cancers. Figure discloses SEQ ID NOS 134-140, respectively, in order of appearance.

FIG. 9 lists immunogenic peptides from human NME7 selected for their low sequence identity to NME1 and for their homology to bacterial NME1 proteins that have been implicated in cancers. These peptides are preferred for their ability to generate therapeutic anti-NME7 antibodies for the treatment or prevention of cancers. The peptides shown in this Figure include and added Cysteine covalently bound at the C-terminal end. Figure discloses SEQ ID NOS 107, 111, 143-145, and 169, respectively, in order of appearance.

FIGS. 10A-10B show graphs of ELISA assays in which either NME7-AB (FIG. 10A) or NME1 (FIG. 10B) is adsorbed to the plate and anti-NME7 antibodies generated by NME7 peptides A1, A2, B1, B2 and B3 are tested for their ability to bind to NME7 but not to NME1. C20 is an anti-NME1 antibody.

FIGS. 14A-14B show tables of scientist observations when cancer cells were grown in either NME7-AB or 2i inhibitors, which both are able to transform cancer cells to a more metastatic state, and in the presence or absence of NME7 derived peptides A1, A2, B1, B2 and B3. The NME7-AB peptides inhibited the transition of adherent cancer cells to the floater cells, which RT-PCR measurements show have increased expression of metastatic markers, especially CXCR4.

FIG. 15A shows PCR graph of CXCR4 expression of T47D cancer cells grown in NME7$_{AB}$ or 2i in the presence or absence of anti-NME7 antibodies. FIG. 15B shows a graph of RT-PCR measurements of CXCR4, CHD1 and SOX2 expression in T47D breast cancer cells that were grown in 2i inhibitors for 72 hours or 144 hours, in the presence of NME7$_{AB}$ immunizing peptides and shows the peptides are themselves inhibitory to the metastatic transformation. Peptides A1, A2 and B1 which were used in the inhibitory Combo 2 and 3 in FIG. 15A are also inhibitory as peptides. Peptide B3 is the most inhibitory and is the immunizing peptide for antibody 61 which was the most inhibitory antibody tested in FIG. 15A. FIG. 15C shows the graph of FIG. 15B with the scale of the Y-axis reduced.

FIG. 16 shows a table of recorded RNA levels in samples that were used for RT-PCR measurement of CXCR4 in FIG.

31 as well as the threshold cycle number for CXCR4 expression as well as for the control housekeeping gene.

Figure 17:
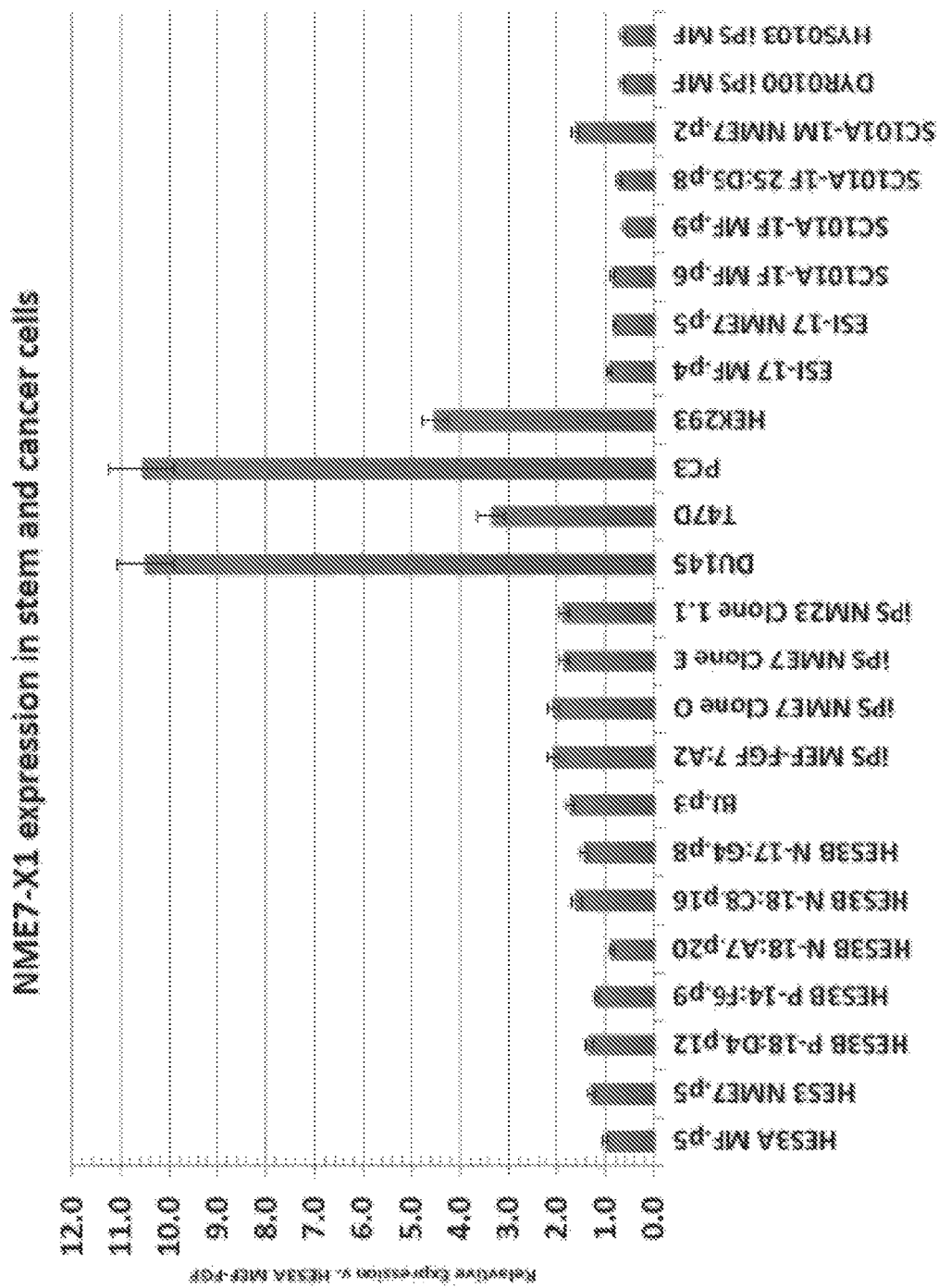

FIG. 17 shows a graph of RT-PCR measurement of the expression of NME7-X1 in a panel of human stem cells and cancer cells.

Figure 18:
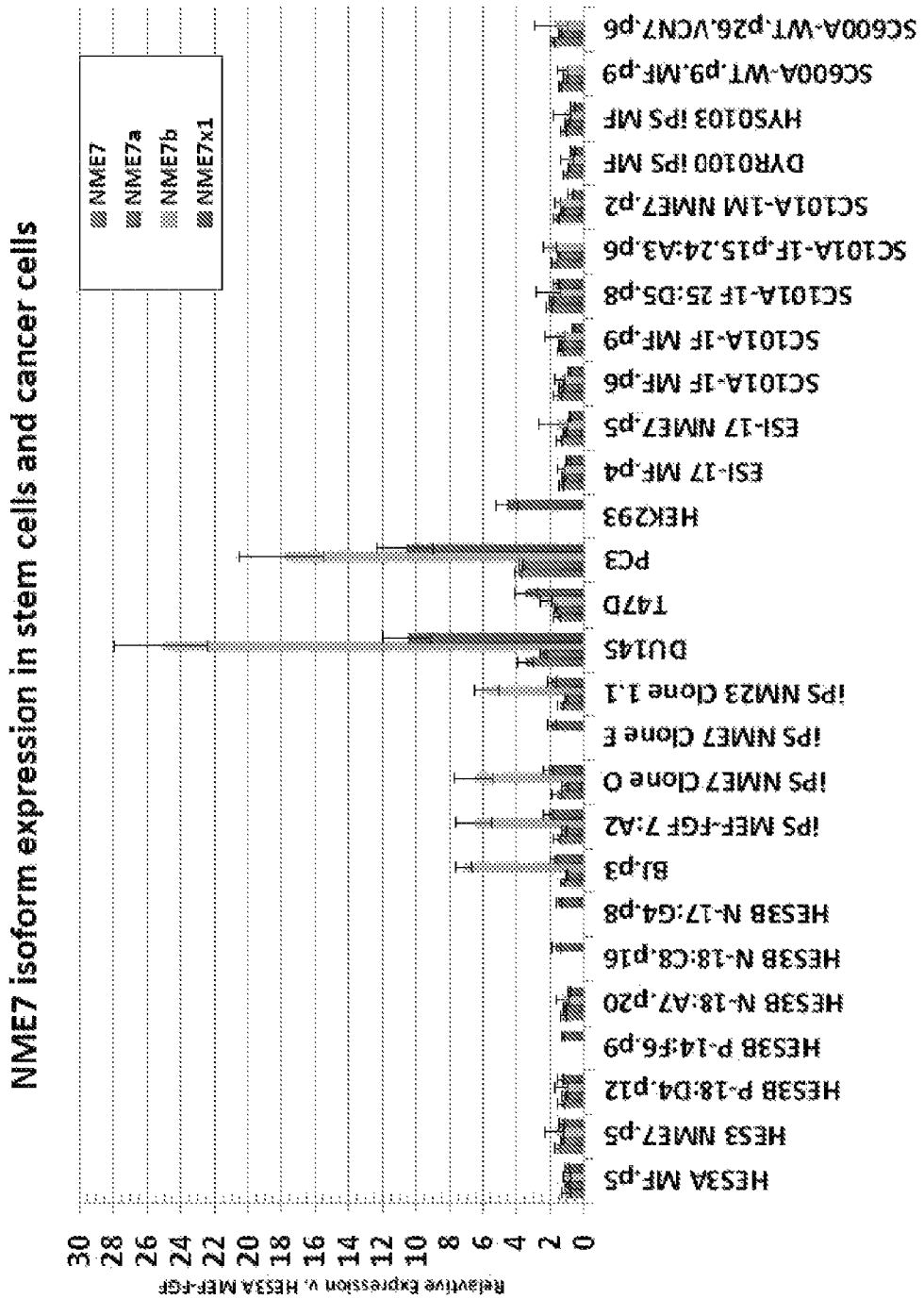

FIG. 18 shows a graph of RT-PCR measurement of the expression of NME7, NME7a, NME7b and NME7-X1 in a panel of human stem cells and cancer cells. NME7a is full-length NME7, NME7b is missing a small portion of the DM10 domain, NME7-X1 is missing all of the DM10 domain and a small portion of the N-terminus of the first NDPK A domain. The bar labeled NME7 means that primers were used that detected both NME7a and NME7b.

Figure 19E:
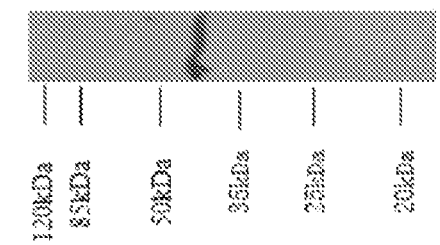

FIGS. 19A-19F show photographs of Western blots in which various cancer cell lines are probed for expression of NME7 species using antibodies generated by immunization with NME7 derived peptides. FIG. 19A shows Western blot wherein antibody 52 that binds to the A1 peptide is used to probe a panel of cells for the presence of full-length NME7, NME7$_{AB}$ or NME7-X1. FIG. 19B shows Western blot wherein antibody 56 that binds to the B1 peptide is used to probe a panel of cells for the presence of full-length NME7, NME7$_{AB}$ or NME7-X1.

Figure 19D:
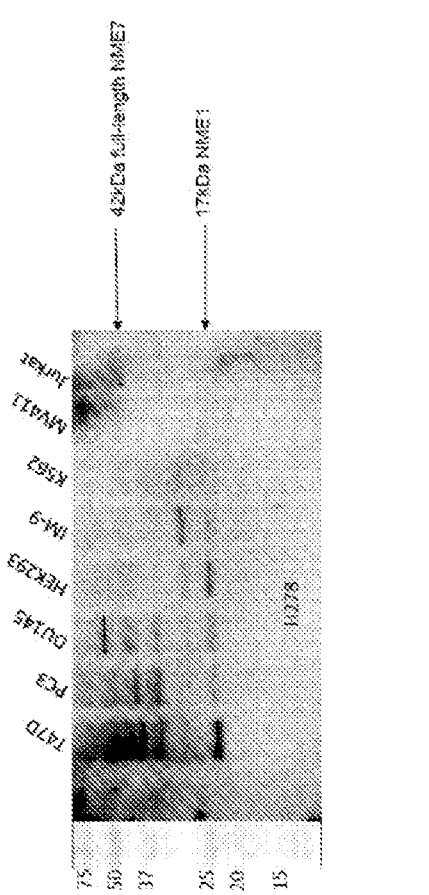
Figure 19F:
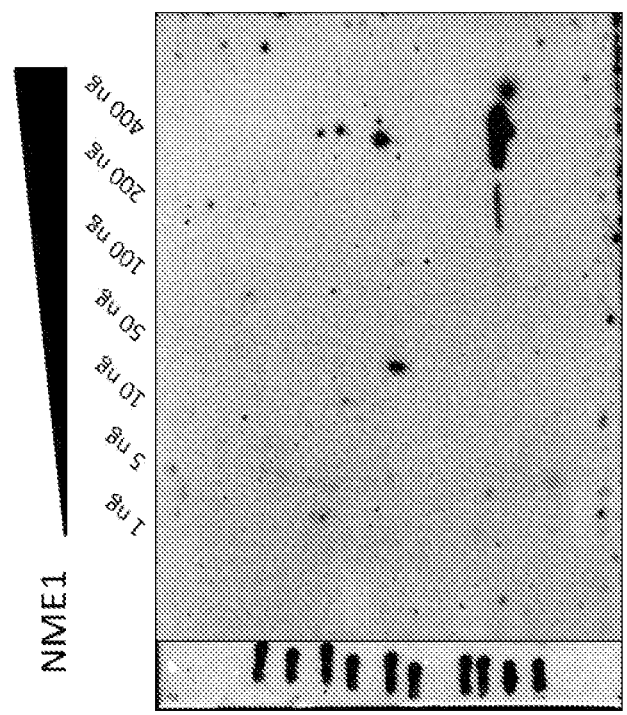

FIG. 19C shows Western blot wherein antibody 61 that binds to the B3 peptide is used to probe a panel of cells for the presence of full-length NME7, NME7$_{AB}$ or NME7-X1. FIG. 19D shows Western blot wherein commercially available polyclonal antibody H278, raised against both the NME7 A and B domain, is used to probe a panel of cells for the presence of NME7. As the figure shows, antibody H278 also recognizes NME1. FIG. 19E shows a gel published on website for commercially available anti-NME7 antibody B9, showing it binds to a species with an apparent molecular weight of full-length NME7. FIG. 19F shows a Western blot in which we used anti-NME7 antibody B9 to probe a gel that was loaded only with NME1. As can be seen in the figure, antibody B9 recognizes NME1 as well as full-length NME7. This is not surprising because like antibody H278, B9 was raised against both A and B domains of NME7 where the A domain of NME1 is highly homologous to the A domain of NME7$_{AB}$.

Figure 20B:
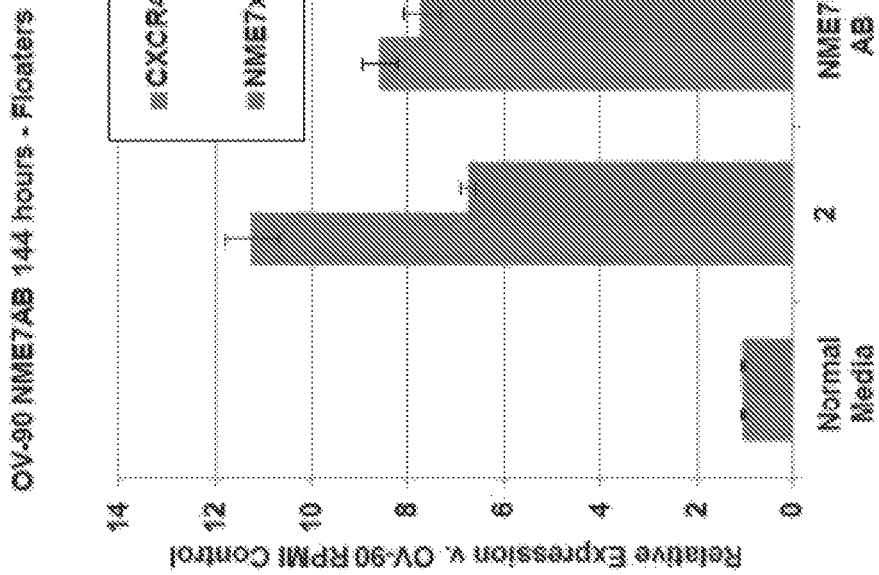
Figure 20A:
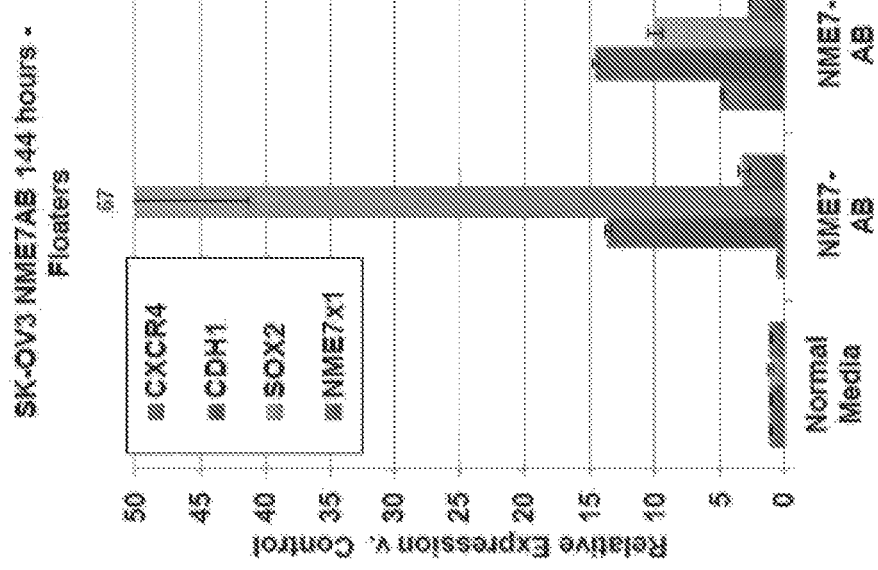
Figure 20C:
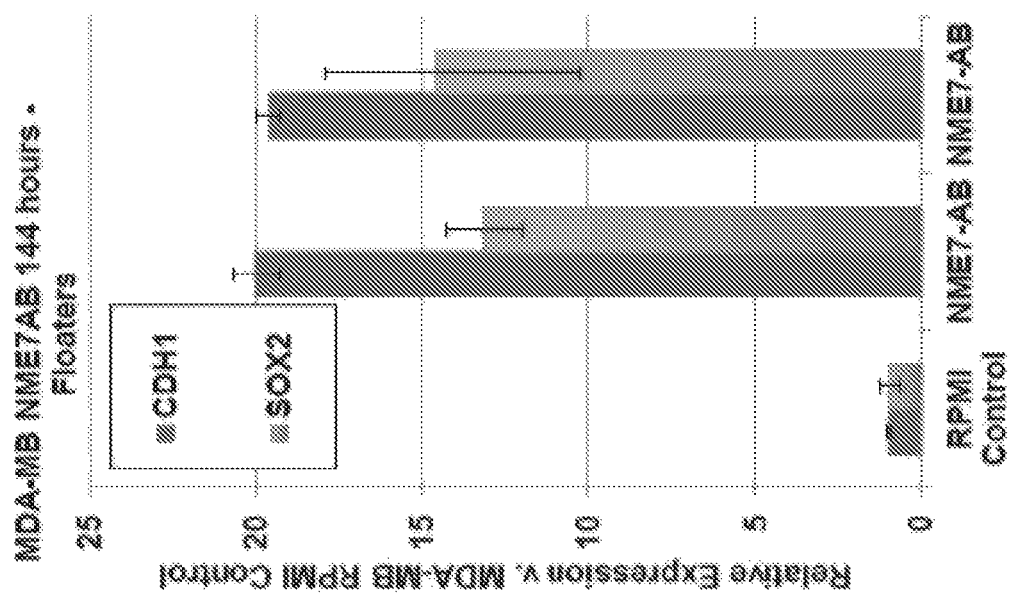

FIGS. 20A-20C show graphs of RT-PCR measurements of metastatic markers in cancer cells after being cultured in a serum-free media containing NME7-AB compared to the standard media. FIG. 20A shows SK-OV3, a MUC1-positive ovarian cancer cell line increased expression of metastatic markers CXCR4, CDH1 aka E-cadherin, SOX2 and NME7-X1; FIG. 20B shows OV-90 a MUC1-negative ovarian cancer cell line increased expression of metastatic markers CXCR4 and NME7-X1; FIG. 20C shows MDA-MB a breast cancer cell line that expresses minimal levels of MUC1 increased expression of metastatic markers CDH1 aka E-cadherin and SOX2.

Figure 21A:
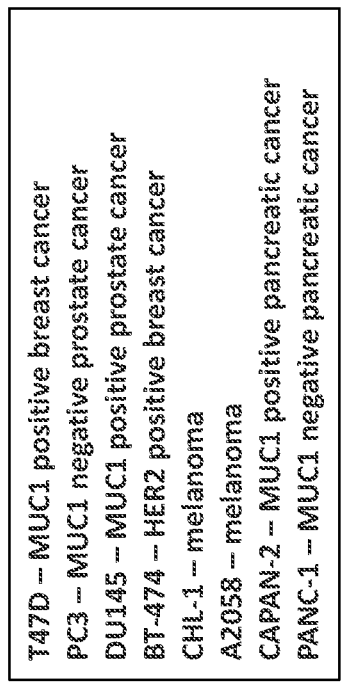
Figure 21B:
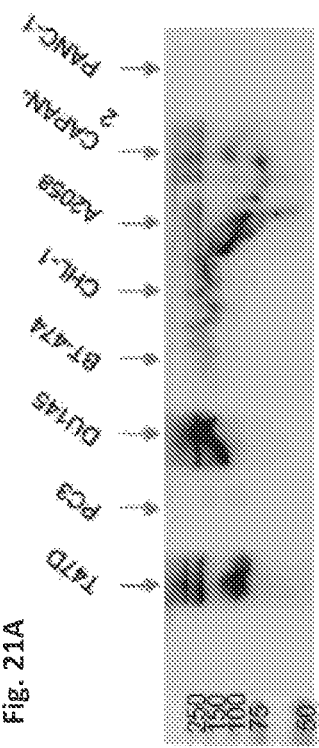
Figure 21C:
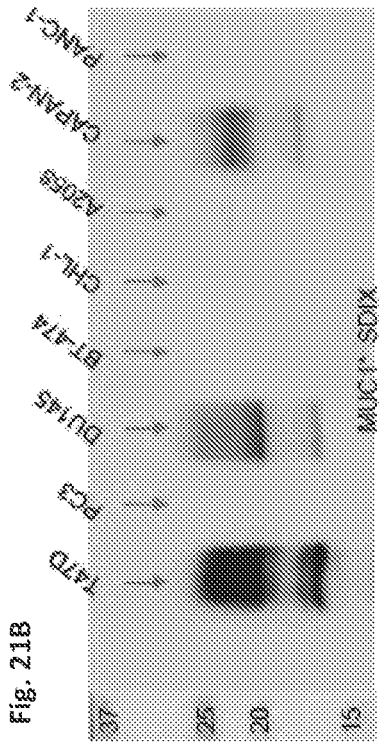
Figure 21D:
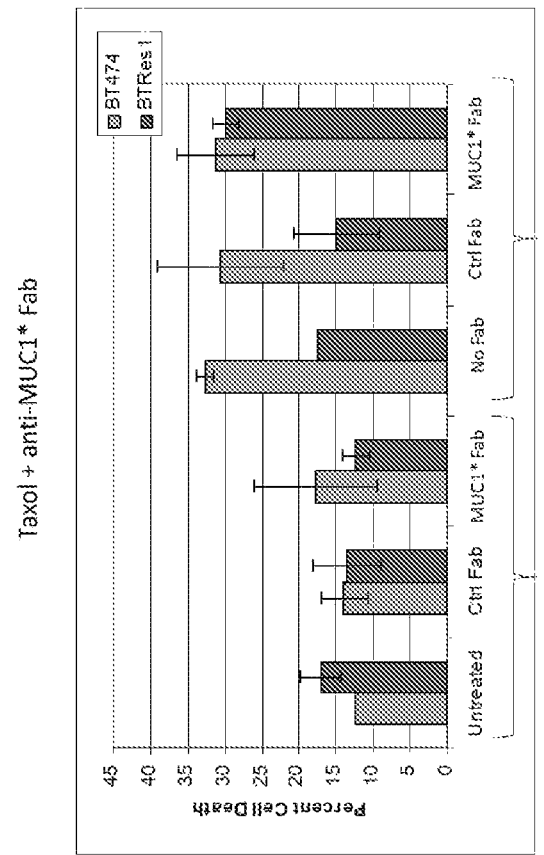
Figure 21E:
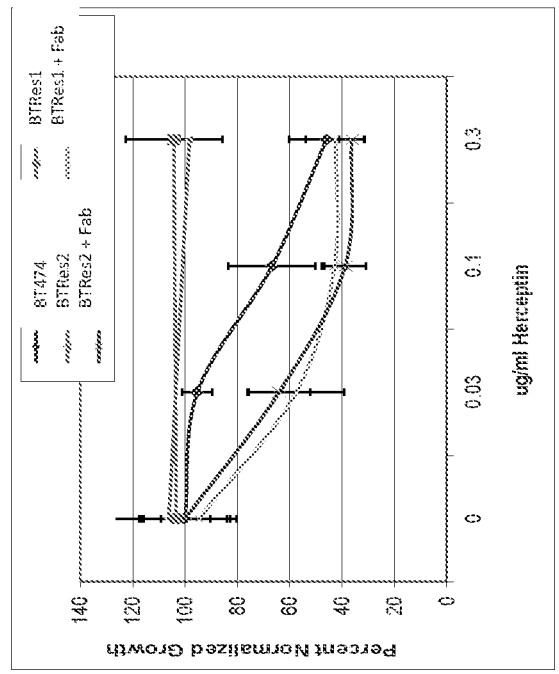
Figure 21F:
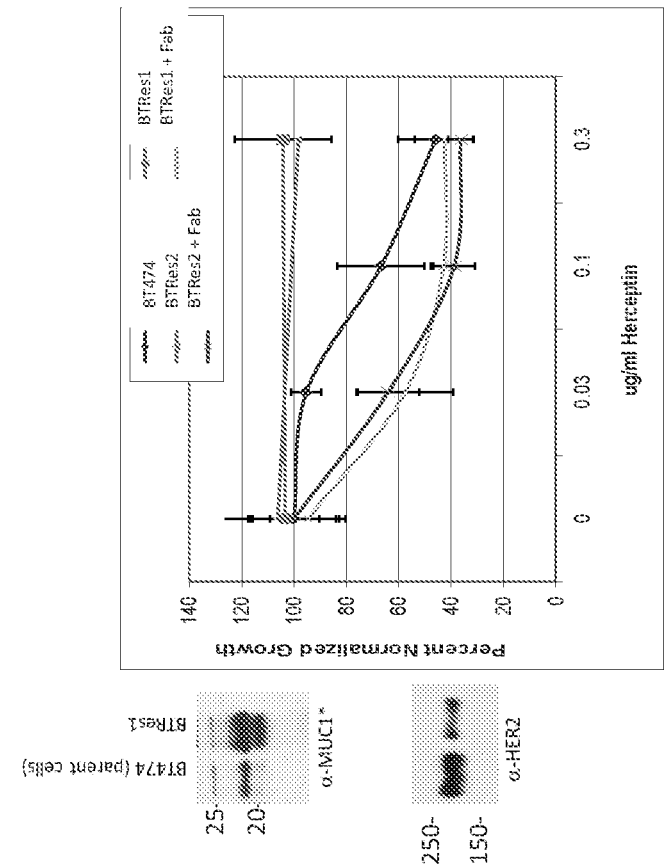

FIGS. 21A-21F show photographs of Western blots and description of cancer cell lines analyzed. For Western blots in FIGS. 21A and 21B, all cancer samples were normalized such that they were loaded onto gel at a concentration of 40 ug/mL. In FIG. 21A, various cancer cell lines are probed for the expression of full-length MUC1 using an anti-tandem repeat monoclonal antibody VU4H5. In FIG. 21B, various cancer cell lines are probed for the expression of cleaved form MUC1* using a polyclonal anti-PSMGFR antibody. FIG. 21C is a description of the cancer cell lines analyzed. FIG. 21D shows that HER2 positive BT474 breast cancer cells, marked "BT474 (parent cells)" express little to no MUC1 or MUC1* until they acquire resistance to Herceptin and other chemotherapy drugs, marked "BTRes1" in figure. Parent cells were made resistant to Herceptin, Taxol, Doxorubicin and cyclophosphamide by culturing the cells in sub-lethal levels of Herceptin. FIG. 21D shows that the expression level of HER2 has not changed but expression of MUC1* has dramatically increased as the cells acquired resistance to Herceptin. FIG. 21E shows a graph of the growth of the parent BT474 cells compared to the drug resistant metastatic cells in response to treatment with Herceptin in the presence or absence of an anti-MUC1* Fab. As can be seen in the figure, the BT474 parent cells show a Herceptin concentration dependent decrease in cell growth, whereas the two Herceptin resistant cell lines, BTRes 1 and BTRes2, show no decrease in cancer cell growth in response to treatment with Herceptin. However, when treated with an anti-MUC1* Fab, the resistant cell lines show a Herceptin concentration dependent decrease in cancer cell growth. FIG. 21F shows a graph of the percent cell death of the parent BT474 cells compared to the drug resistant BTRes1 cells, in response to treatment with Taxol in the presence or absence of an anti-MUC1* Fab.

FIGS. 22A-22E show photographs of Western blots of a co-immunoprecipitation experiment. T47D breast cancer cell extracts were incubated with an antibody against the MUC1 cytoplasmic tail, Ab-5, or a control antibody, IgG, and co-immunoprecipitated. The gels were blotted with two different commercially available anti-NME7 antibodies B9 (FIG. 22A) and CF7 (FIG. 22B). Both gels show unique NME7 bands at ~33 kDa and ~30 kDa. The gels were stripped and re-probed with an antibody against the extracellular domain of MUC1*, anti-PSMGFR (FIG. 22C) and (FIG. 22D), which shows that the NME7 species and MUC1* interact. A recombinant NME7-AB and a recombinant NME7-X1 were mixed together and run on a gel, then probed with an anti-NME7 antibody, showing that the two unique NME7 species that are naturally occurring in breast cancer cells and that interact with MUC1* are an NME7-AB-like species and NME7-X1 (FIG. 22E).

FIGS. 23A-23C show photographs of Western blots of a co-immunoprecipitation experiment. Human induced pluripotent stem, iPS7, or embryonic stem, HES3, cell extracts were incubated with an antibody against the MUC1 cytoplasmic tail, Ab-5, or a control antibody, IgG, and co-immunoprecipitated. The gel was blotted with a commercially available anti-NME7 antibody B9 (FIG. 23A). Both cell types show unique NME7 bands at ~33 kDa and ~30 kDa. The gel was stripped and re-probed with an antibody against the extracellular domain of MUC1*, anti-PSMGFR (FIG. 23B), which shows that the NME7 species and MUC1* interact. A recombinant NME7-AB and a recombinant NME7-X1 were mixed together and run on a gel, then probed with an anti-NME7 antibody, showing that the two unique NME7 species that are naturally occurring in breast cancer cells and that interact with MUC1* are an NME7-AB-like species and NME7-X1 (FIG. 23C).

Figure 24:
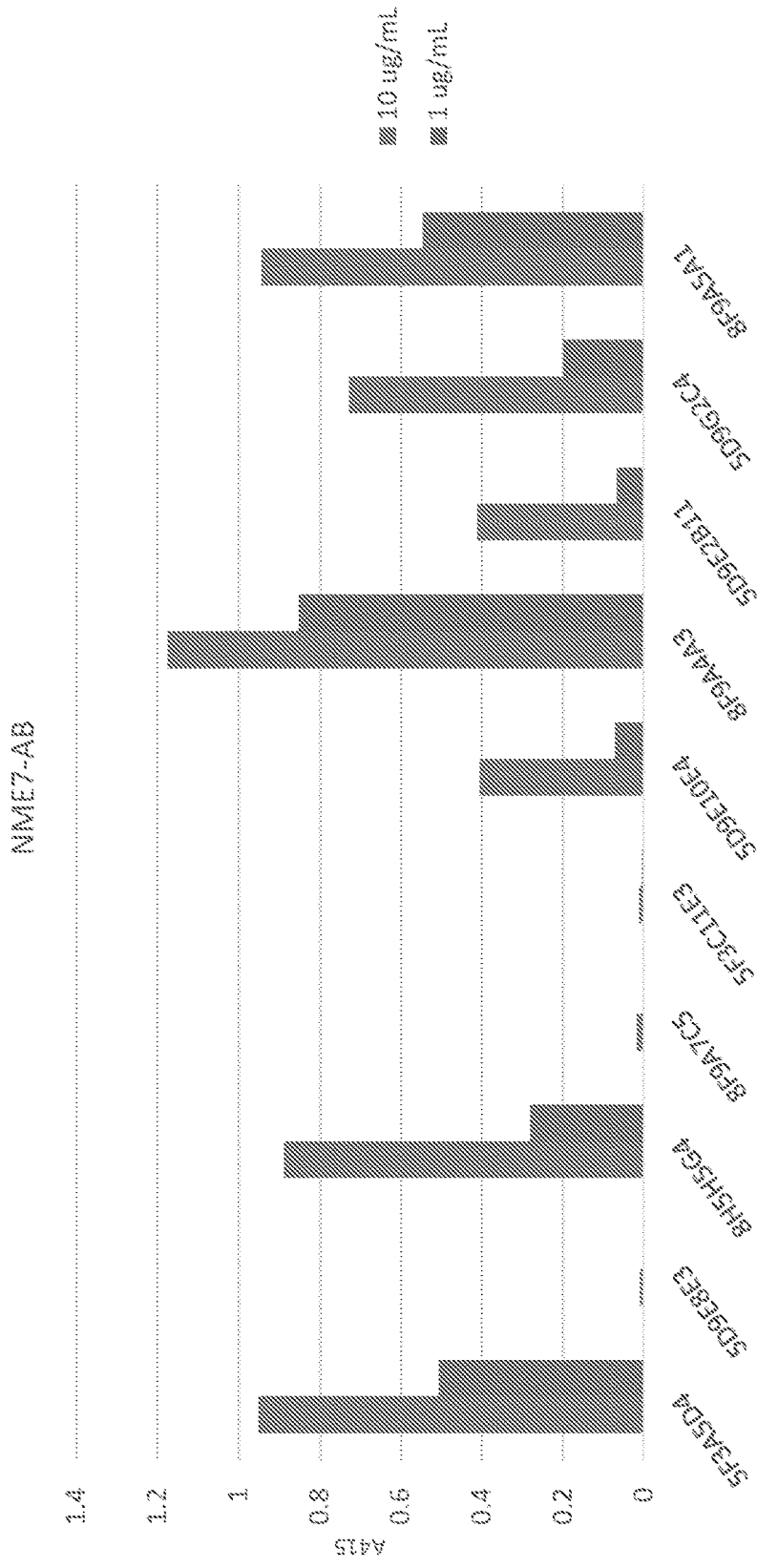

FIG. 24 shows a graph of an ELISA experiment assaying new anti-NME7 antibodies for their ability to bind to NME7-AB. NME7-AB is known to bind to the extra cellular domain of MUC1*. The surface of the multi-well plate was coated with a recombinant NME7-AB. Anti-NME7-AB antibodies were separately added to wells. Standard washes were performed and visualized by adding an HRP-conjugated secondary antibody. As can be seen, 7 of the 10 new anti-NME7 antibodies bound strongly to NME7-AB.

Figure 25:
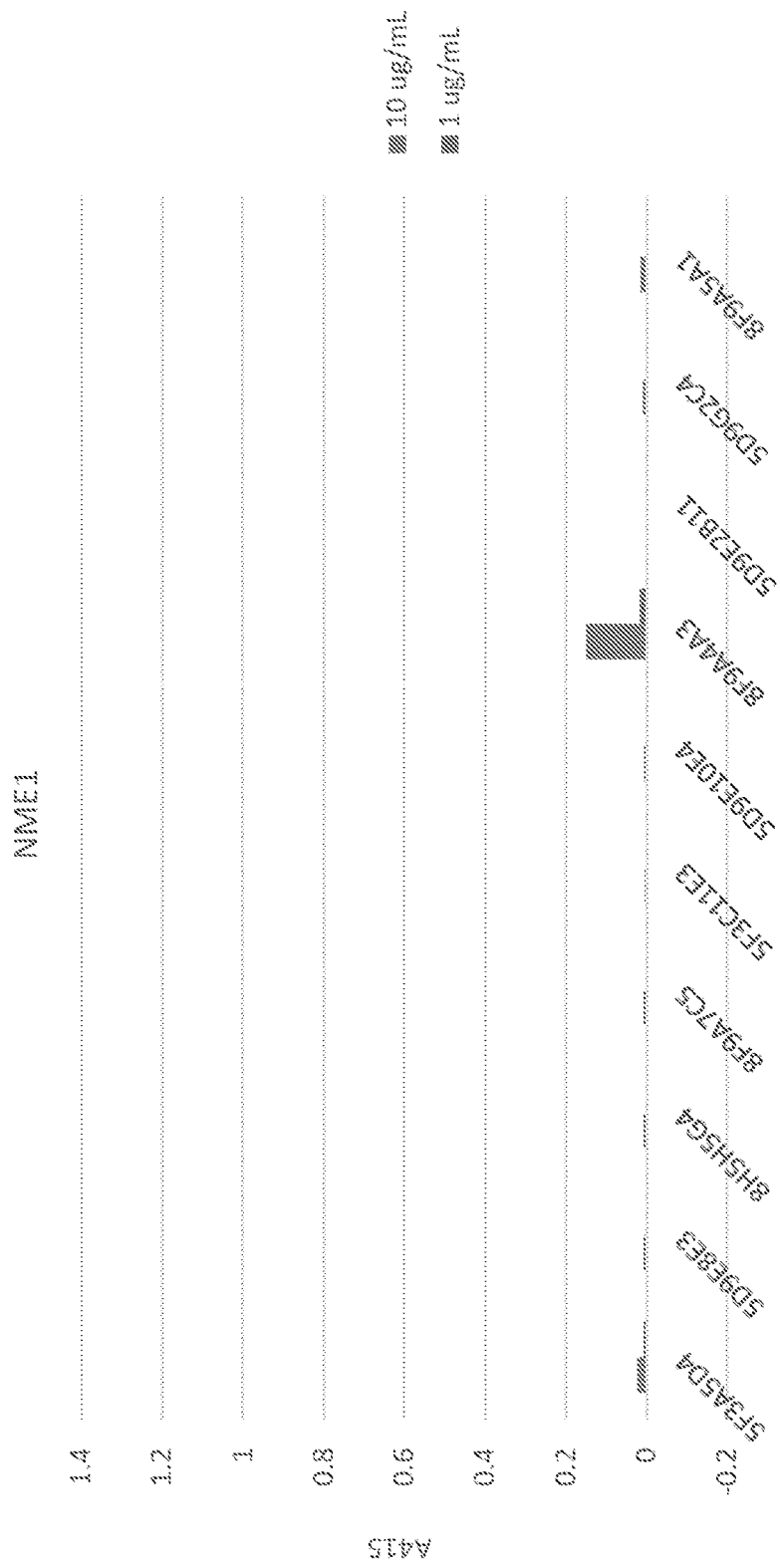

FIG. 25 shows a graph of an ELISA experiment assaying new anti-NME7 antibodies for their ability, or preferably inability, to bind to NME1. The surface of the multi-well plate was coated with a recombinant NME1-S120G dimers, which are also known to bind to the MUC1* extra cellular domain. Anti-NME7-AB antibodies were separately added to wells. Standard washes were performed and visualized by adding an HRP-conjugated secondary antibody. As can be seen only one antibody showed just minimal binding to NME1.

Figure 26:
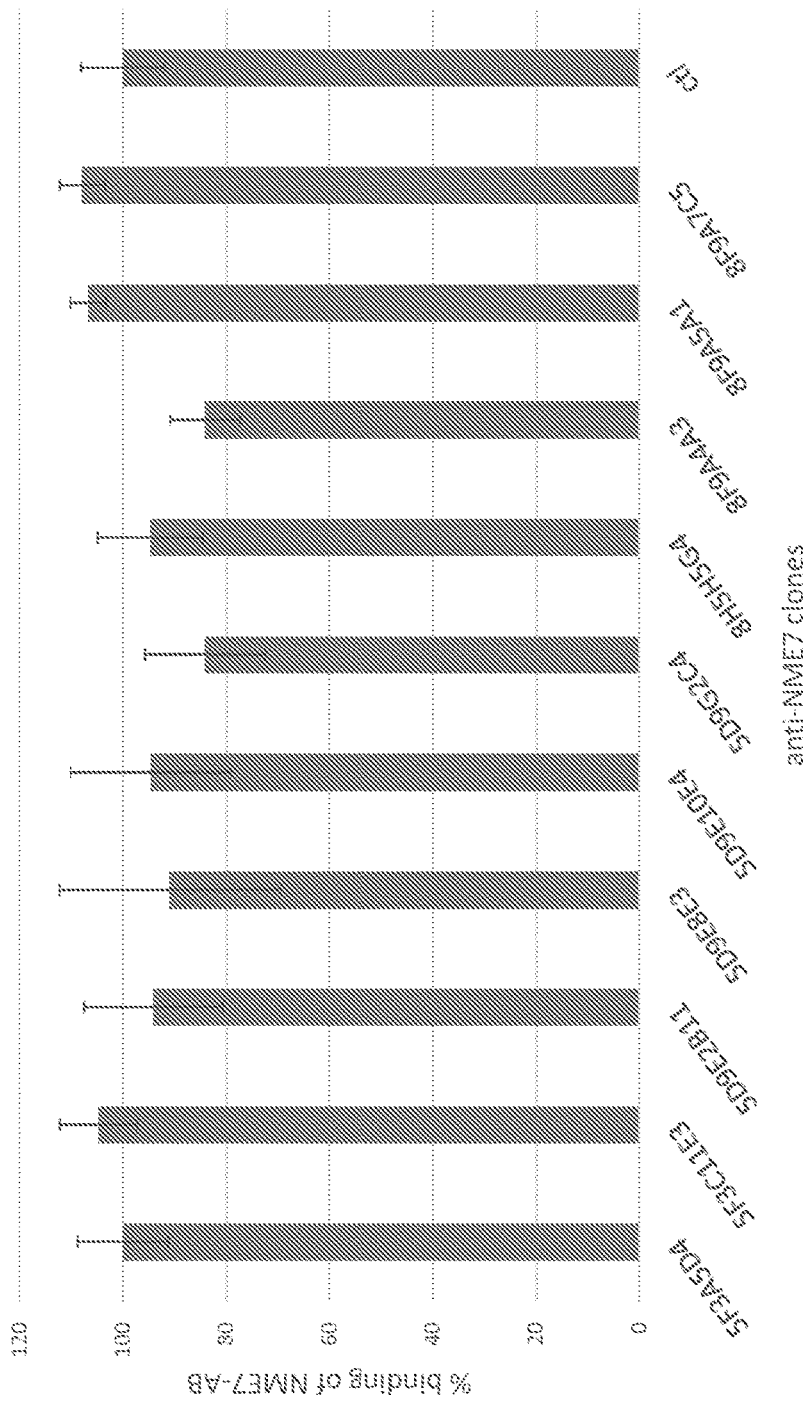

FIG. 26 shows a graph of an ELISA competitive inhibition assay. NME7-AB/anti-NME7 antibody complexes were made before adding to a multi-well plate coated with MUC1* extra cellular domain peptide, PSMGFR. Recall that NME7-AB has two pseudo-identical domains A and B that are each able to bind to MUC1* extra cellular domain. Antibodies that bind to the NME7 B3 peptide, which is in the B domain, do not bind to the NME7 A domain. Therefore, only partial inhibition of the NME7-AB/MUC1* interaction is expected.

Figure 27:
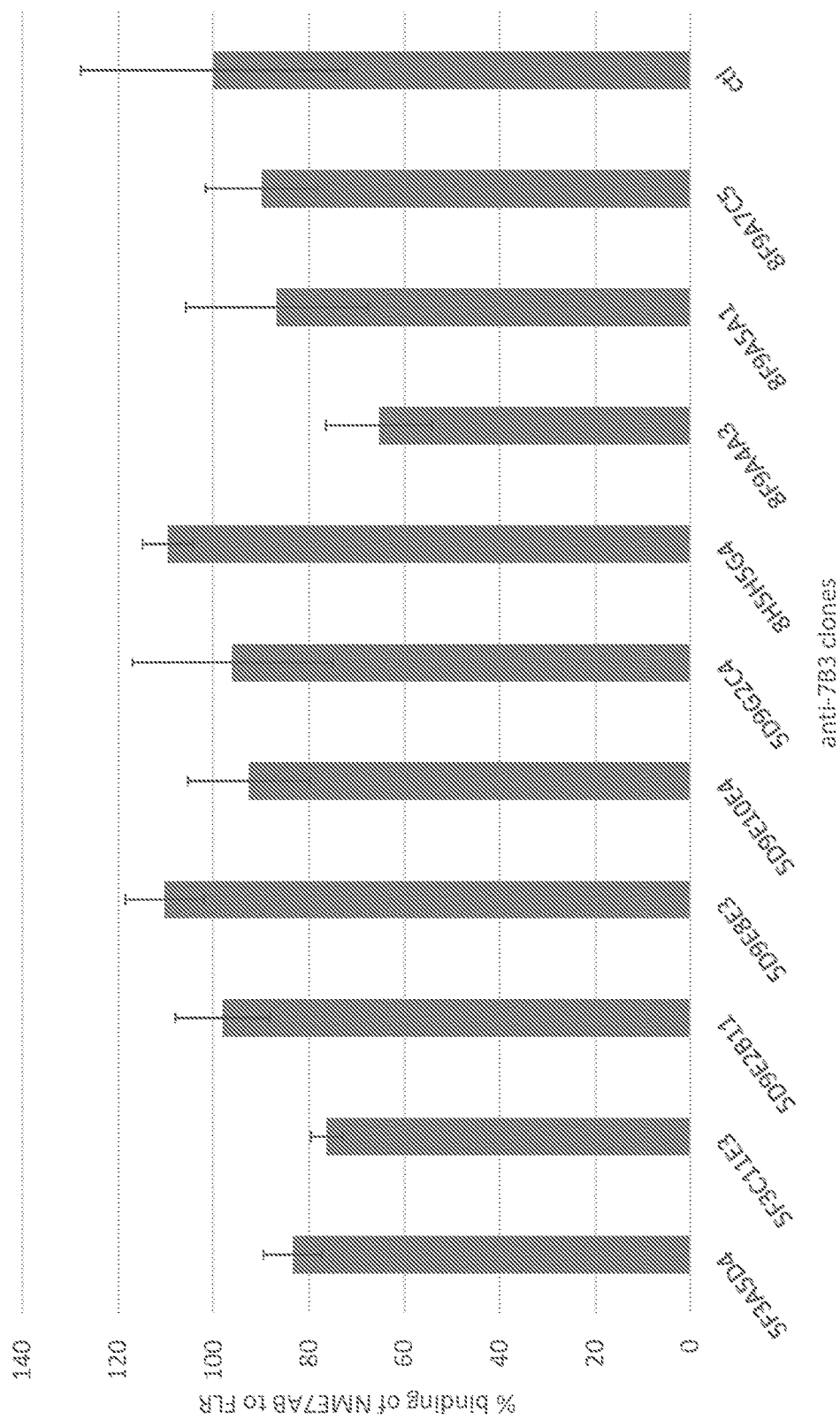

FIG. 27 shows a graph of an ELISA displacement assay. NME7-AB was first bound to surface-immobilized MUC1* extra cellular domain peptide on the plate, then disrupted by the addition of anti-NME7 antibodies.

Figure 28:
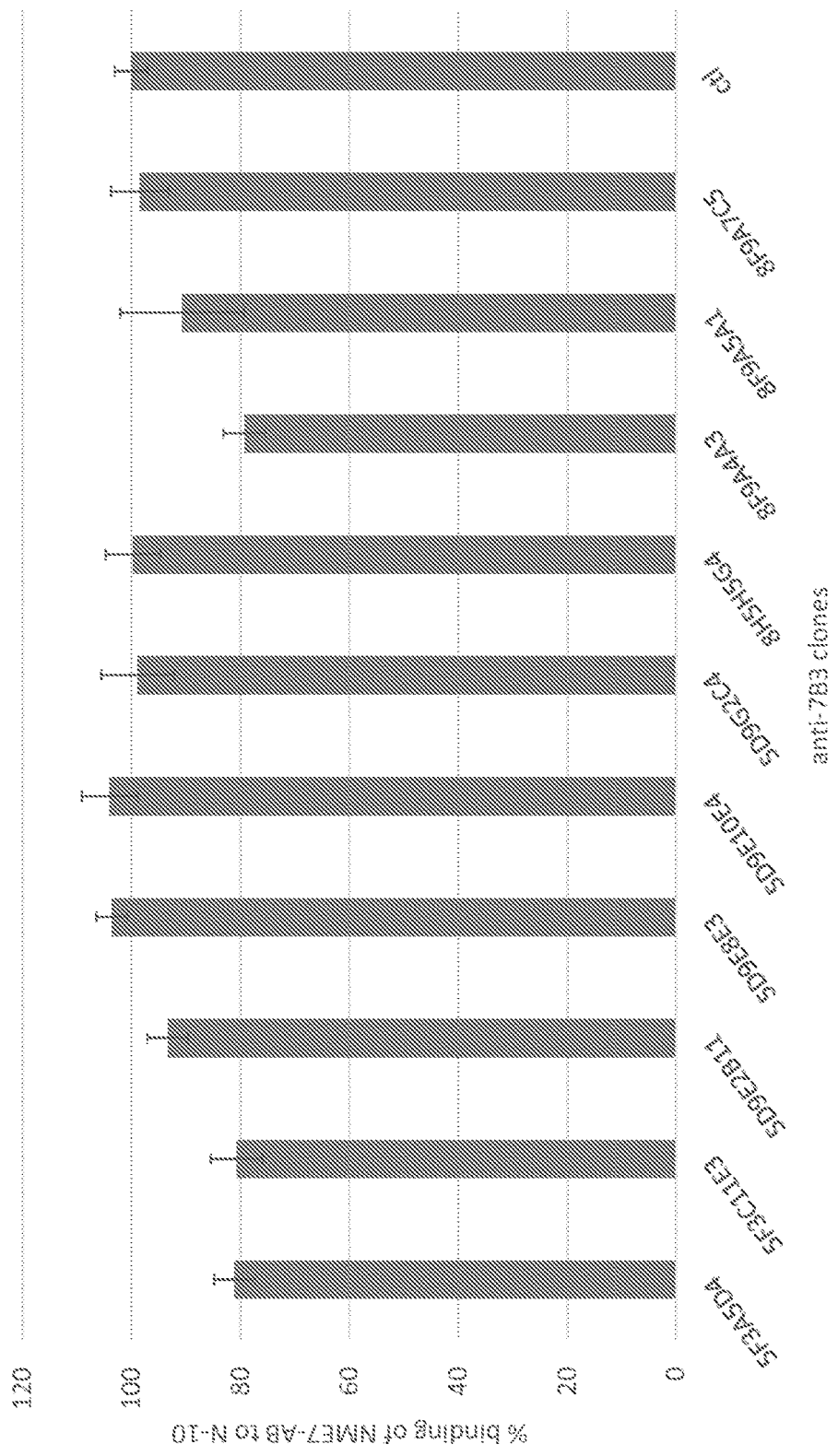

FIG. 28 shows a graph of an ELISA displacement assay. In this case, the multi-well plate was coated with a truncated MUC1* peptide, N-10, which has the 10 N-terminal amino acids missing of the PSMGFR sequence. NME7-AB is known to bind to the N-10 peptide. NME7-AB was bound to surface-immobilized N-10 peptide on the plate, then disrupted by the addition of anti-NME7 antibodies.

Figure 29:
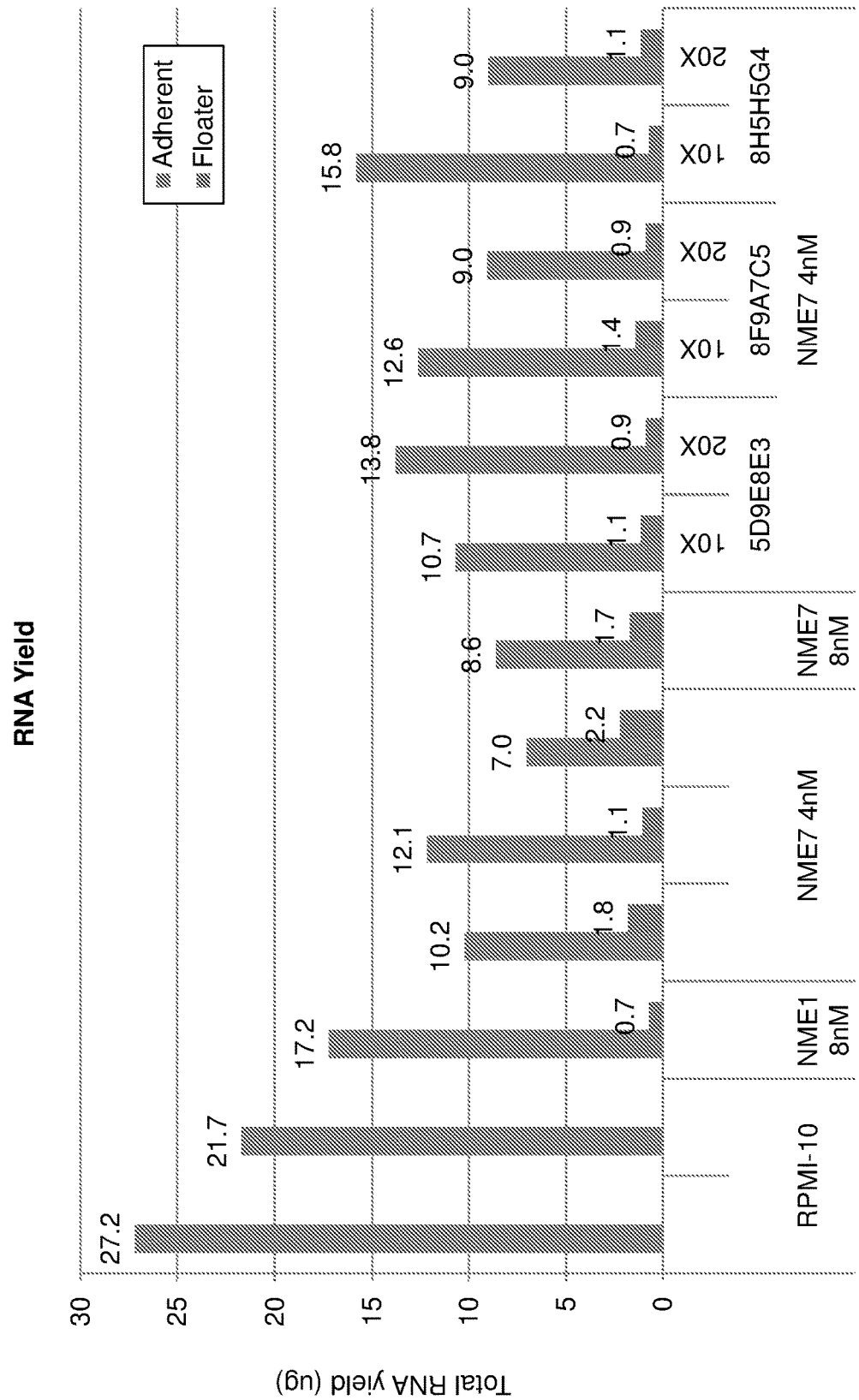

FIG. 29 shows a graph of the amount of RNA present in samples of T47D breast cancer cells were cultured in either their normal recommended media, RMPI, serum-free media containing only NME7-AB as the growth factor at 4 nM, which is optimal, or 8 nM, or serum-free media containing only NME1 S120G dimers as the growth factor at 8 nM; because NME1 is a homodimer and NME7-AB is a monomer comprised of two pseudo-identical domains, 8 nM NME1 is the molar equivalent of 4 nM NME7-AB. The cancer cells were cultured in the presence or absence of anti-NME7 B3 antibodies. In this experiment, floating cells were separated from the adherent cells and analyzed separately. Significant data argues that the floater cells are the cancer stem cells. An increase or decrease in the amount of RNA in a sample argues that an agent increased or decreased, respectively, the number of cells in a given population that were generated.

Figure 30:
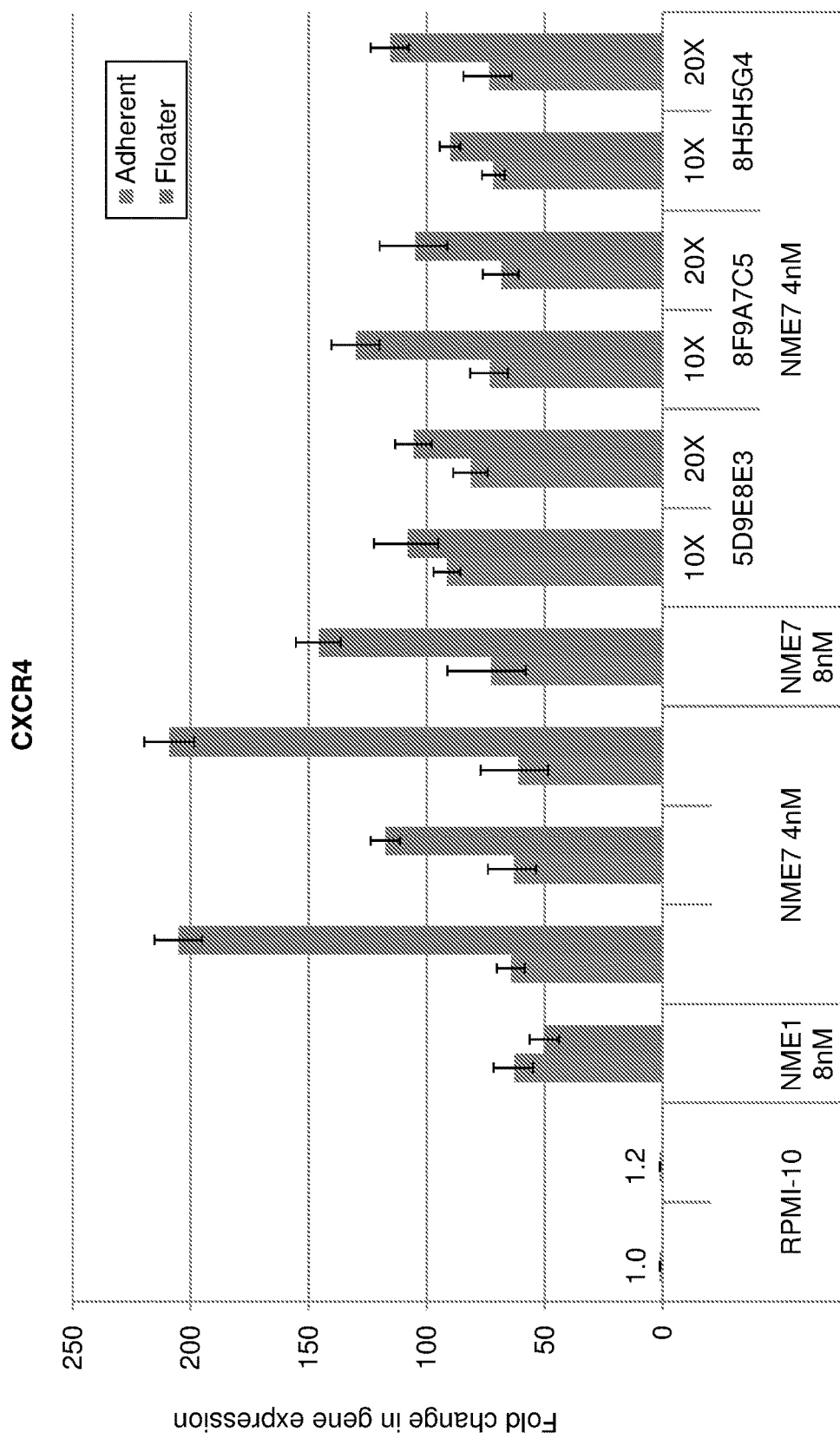

FIG. 30 shows a graph of a PCR measurement of metastatic marker CXCR4 in T47D breast cancer cells that were cultured in either their normal recommended media, RPMI, serum-free media containing only NME7-AB as the growth factor at 4 nM, which is optimal, or 8 nM, or serum-free media containing only NME1 S120G dimers as the growth factor at 8 nM; because NME1 is a homodimer and NME7-AB is a monomer comprised of two pseudo-identical domains, 8 nM NME1 is the molar equivalent of 4 nM NME7-AB. The cancer cells were cultured in the presence or absence of anti-NME7 B3 antibodies. In this experiment, floating cells were separated from the adherent cells and analyzed separately. Significant data argues that the floater cells are the cancer stem cells. As can be seen in the figure, growth in NME7-AB media increases CXCR4 in the floater population of cells and anti-NME7 B3 antibodies decreased its expression, arguing that anti-NME7 antibodies decreased generation of cancer stem cells.

Figure 31:
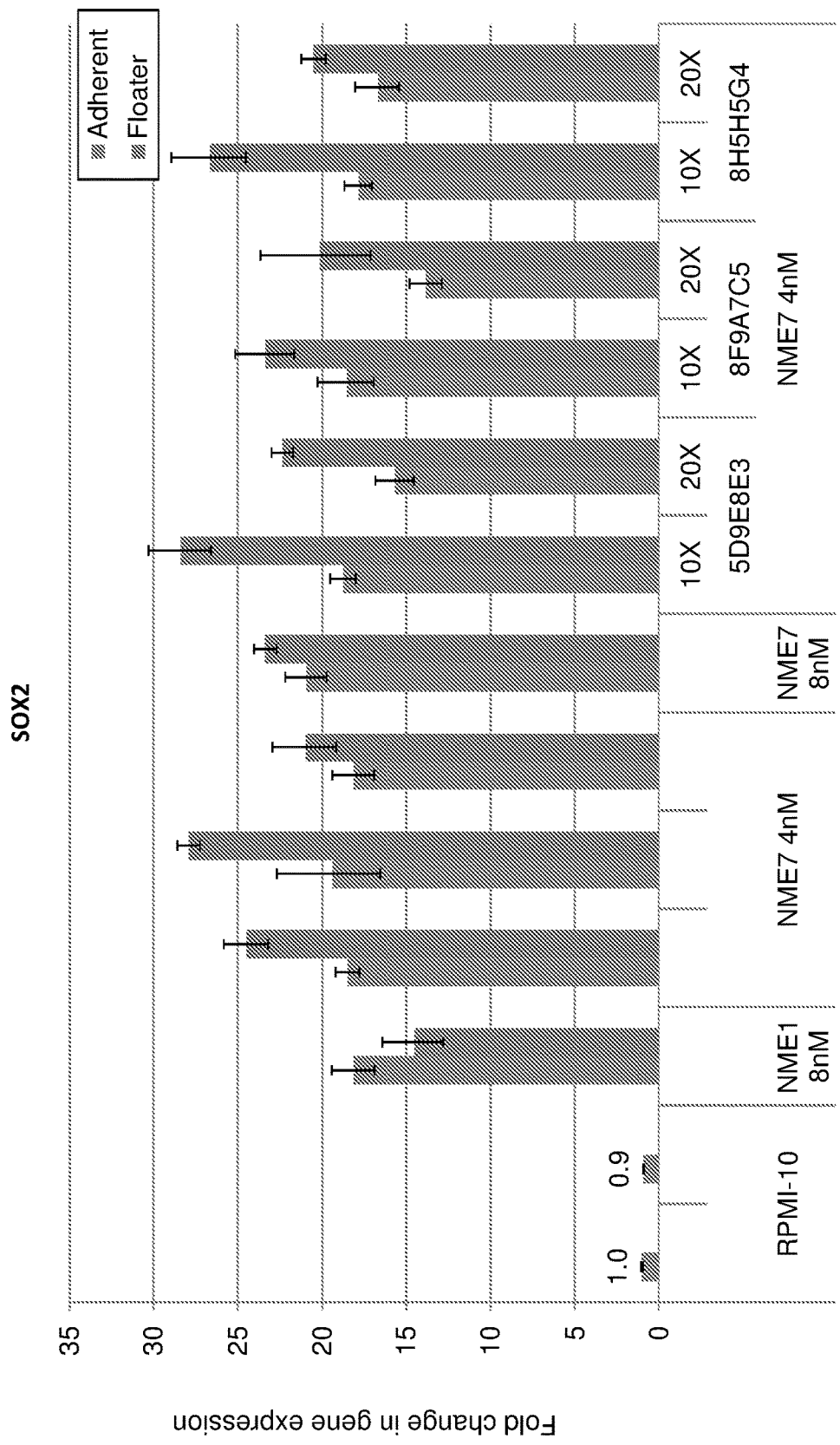

FIG. 31 shows a graph of a PCR measurement of stem cell marker and metastatic marker SOX2 in T47D breast cancer cells that were cultured in either their normal recommended media, RMPI, serum-free media containing only NME7-AB as the growth factor at 4 nM, which is optimal, or 8 nM, or serum-free media containing only NME1 S120G dimers as the growth factor at 8 nM; because NME1 is a homodimer and NME7-AB is a monomer comprised of two pseudo-identical domains, 8 nM NME1 is the molar equivalent of 4 nM NME7-AB. The cancer cells were cultured in the presence or absence of anti-NME7 B3 antibodies. In this experiment, floating cells were separated from the adherent cells and analyzed separately. Significant data argues that the floater cells are the cancer stem cells. As can be seen in the figure, growth in NME7-AB media increases SOX2 expression in the floater population of cells and anti-NME7 B3 antibodies decreased its expression, arguing that anti-NME7 antibodies decreased generation of cancer stem cells.

Figure 32:
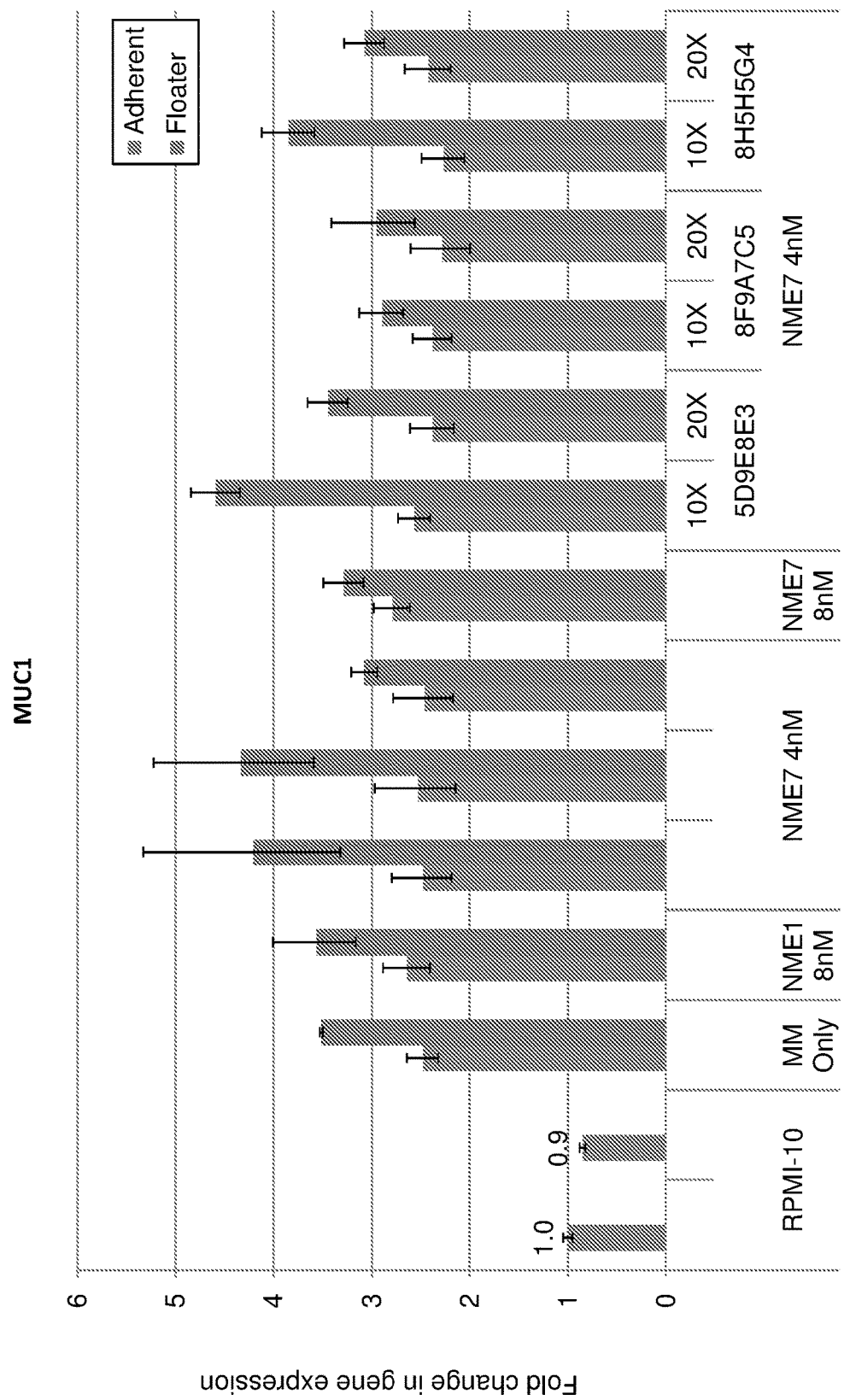

FIG. 32 shows a graph of a PCR measurement of stem cell marker and metastatic growth factor receptor MUC1 in T47D breast cancer cells that were cultured in either their normal recommended media, RMPI, serum-free media containing only NME7-AB as the growth factor at 4 nM, which is optimal, or 8 nM, or serum-free media containing only NME1 S120G dimers as the growth factor at 8 nM; because NME1 is a homodimer and NME7-AB is a monomer comprised of two pseudo-identical domains, 8 nM NME1 is the molar equivalent of 4 nM NME7-AB. The cancer cells were cultured in the presence or absence of anti-NME7 B3 antibodies. In this experiment, floating cells were separated from the adherent cells and analyzed separately. Significant data argues that the floater cells are the cancer stem cells. As can be seen in the figure, growth in NME7-AB media increases MUC1 expression in the floater population of cells and anti-NME7 B3 antibodies decreased its expression, arguing that anti-NME7 antibodies decreased generation of cancer stem cells.

Figure 33A:
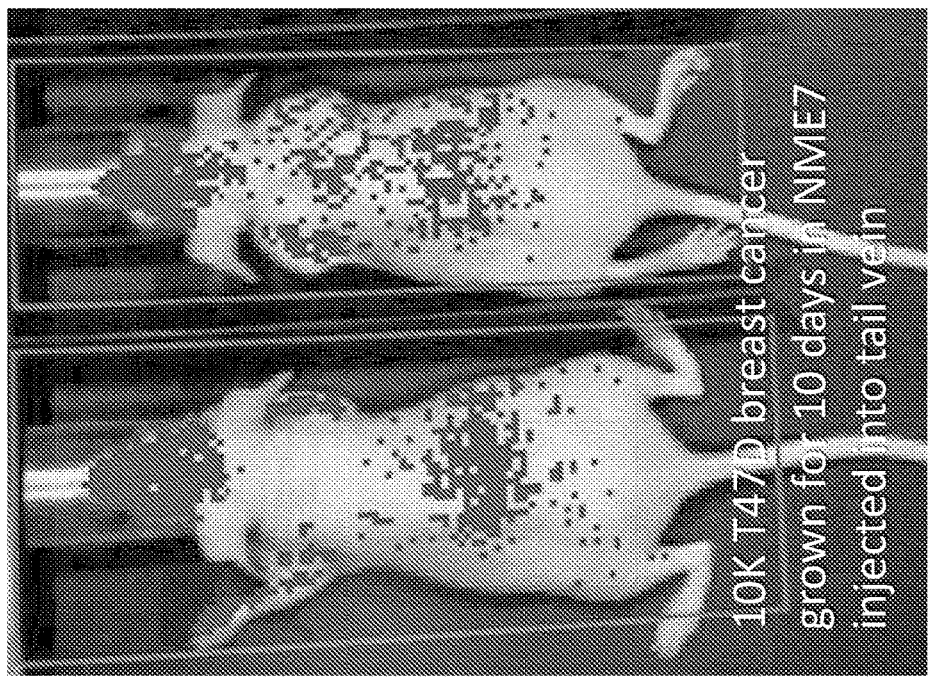
Figure 33B:
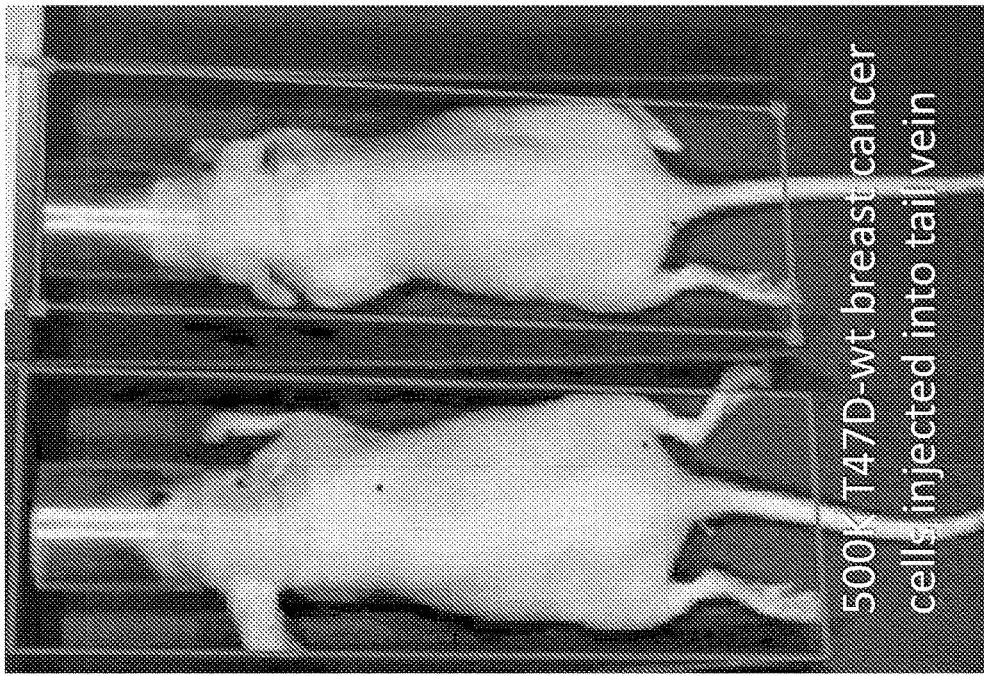

FIGS. 33A-33B show IVIS photographs of immune compromised nu/nu mice Day 6 post tail vein injection of cancer cells. FIG. 33A shows IVIS photographs of mice injected with 500,000 T47D-wt breast cancer cells. FIG. 33B shows IVIS photographs of mice injected with 10,000 T47D breast cancer cells that were grown for 10 days in NME7-AB in a minimal media. The floating cells were collected. These floating cells are referred to herein as cancer stem cells, CSCs. As can be seen in the figure, the mice injected with wild type cancer cells show no signs of metastasis. However, the mice injected with 50-times less cells, but cancer stem cells, show that the injected cancer cells are clearly metastasizing.

FIGS. 34A-34D show IVIS photographs of immune compromised nu/nu mice Day 10 post tail vein injection of cancer cells. FIG. 34A shows IVIS photographs of mouse injected with 500,000 T47D-wt breast cancer cells. FIG. 34B shows IVIS photographs of mouse injected with 10,000 T47D-CSC (cancer stem cells). FIG. 34C shows IVIS photographs of mouse injected with 10,000 T47D-CSC (cancer stem cells) and injected on Day 7 with anti-NME7 antibody. FIG. 34D shows the hand recording of the IVIS measure of emitted photons. As can be seen in the figure, the mouse chosen for treatment is more metastatic than the comparable T47D-CSC mouse. The efficacy of the first antibody injection may have been blocked by the Day 6 injection of free NME7-AB. Control mouse injected with 500,000 T47D-wt cells shows some weak emission of photons that may be background or surviving cancer cells.

FIG. 35A-35C shows IVIS photographs of immune compromised nu/nu mice Day 12 post tail vein injection of cancer cells. FIG. 35A shows IVIS photographs of mouse injected with 500,000 T47D-wt breast cancer cells. FIG. 35B shows that mouse injected with 10,000 T47D-CSC (cancer stem cells) that was not treated with anti-NME7 antibody died from excess tumor burden before IVIS photograph could be taken. FIG. 35C shows IVIS photographs of mouse injected with 10,000 T47D-CSC (cancer stem cells) and injected on Day 7 and Day 10 with anti-NME7 antibody. As can be seen in the figure, the mouse treated with anti-NME7 antibody is clearing away the cancer metastases. Control mouse injected with 500,000 T47D-wt cells shows less photon emissions indicating fewer surviving cancer cells or may be background.

Figures 36A, 36B:
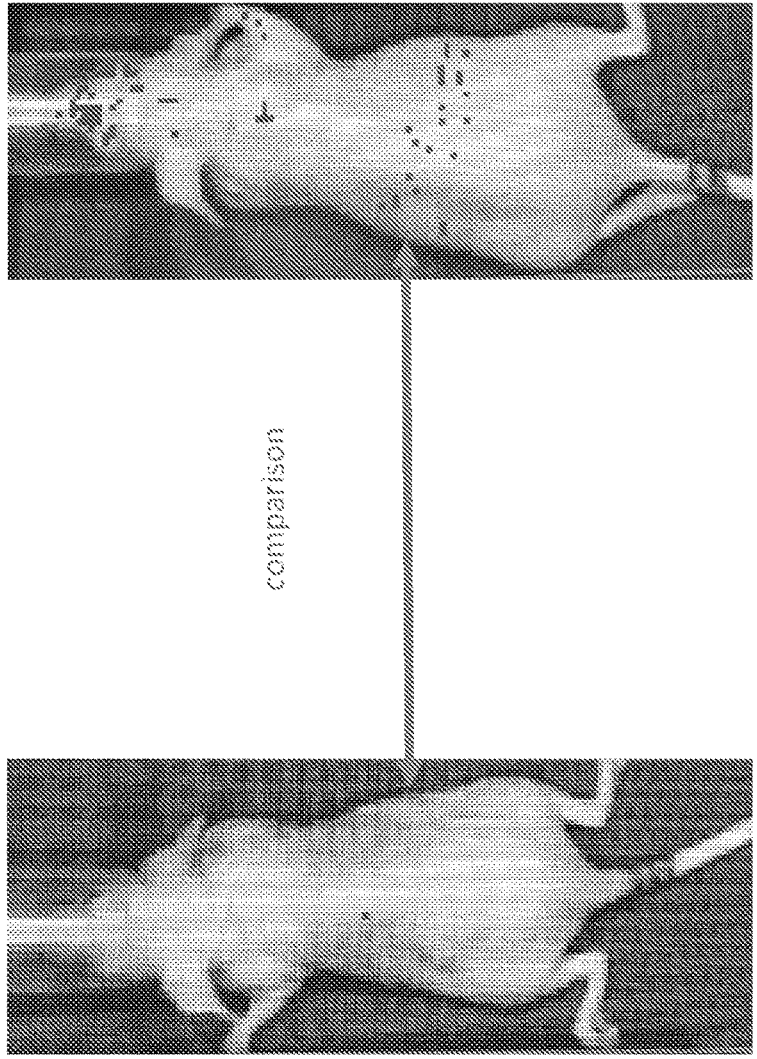

FIGS. 36A-36B shows IVIS photographs of immune compromised nu/nu mice Day 14 post tail vein injection of cancer cells. FIG. 36A shows IVIS photographs of mouse injected with 500,000 T47D-wt breast cancer cells. FIG. 36B shows IVIS photographs of mouse injected with 10,000 T47D-CSC (cancer stem cells) and injected on Day 7, Day 10, and Day 12 with anti-NME7 antibody. As can be seen in the figure, the mouse treated with anti-NME7 antibody nearly completely free of cancer cell metastases. Control mouse injected with 500,000 T47D-wt cells shows no photon emissions.

FIGS. 37A-37V shows time course of IVIS photographs of immune compromised nu/nu mice from Day 6 to Day 26 post cancer cell tail vein injection. FIGS. 37A, 37C, 37E, 37G, 37I, 37K, 37M and 37O show IVIS photographs of mouse that had been injected Day 0 into the tail vein with 500,000 T47D-wt cells. FIGS. 37B, 37D, 37F, 37H, 37J, 37L, 37N and 37P show IVIS photographs of mouse that had been injected Day 0 into the tail vein with 10,000 T47D cancer stem cells, to which anti-NME7 antibody was administered from Day 7 to Day 17, whereupon treatment was suspended, then resumed on Day 21. FIGS. 37Q, 37R, 37S, 37T, and 37U show enlarged IVIS photographs of the treated mouse between Day 17, when anti-NME7 antibody treatment was suspended, through Day 21, when antibody treatment was resumed to Day 26. FIG. 37V shows the scale bar of the IVIS measurements. As can be seen in this time course, cancer cells that had been grown in NME7 readily metastasize and such metastasis can be effectively treated, prevented or reversed by treatment with an antibody that binds to NME7.

FIG. 38A-38C shows time course of IVIS photographs of immune compromised nu/nu mice from Day 6 to Day 19 post injection with either 500,000 T47D wild type breast cancer cells or 10,000 T47D cancer stem cells. FIG. 38A shows mice that were injected into the tail vein (i.v.). FIG. 38B shows mice that were injected intra-peritonealy (i.p.). FIG. 38C shows mice that were injected sub-cutaneously (s.c.).

FIGS. 39A-39C shows human lung tissue specimens stained with an anti-NME7 antibody that binds to the B3 peptide. The figure shows lack of NME7 expression on normal tissues, increasing expression of NME7 as tumor grade and metastasis increase.

FIGS. 40A-40C shows human small intestine tissue specimens stained with an anti-NME7 antibody that binds to the B3 peptide. The figure shows lack of NME7 expression on normal tissues, increasing expression of NME7 as tumor grade and metastasis increase.

FIGS. 41A-41D show human colon tissue specimens stained with an anti-NME7 antibody that binds to the B3 peptide. The figure shows lack of NME7 expression on normal tissues, increasing expression of NME7 as tumor grade and metastasis increase.

FIGS. 42A-42F shows photographs of female nu/nu mice weighing approximately 20 g each, which were injected into the tail vein with 10,000 Luciferase positive T47D metastatic breast cancer stem cells and treated with the anti-NME7$_{AB}$ antibody 4A3 also known as 8F9A4A3. To image cancer cells, the Luciferase substrate, Luciferin, is intraperitoneally injected 10 minutes before being photographed in IVIS instrument. FIGS. 42A-42C show IVIS photographs with animals face down. FIG. 42D-42F show IVIS photographs with animals face up. FIGS. 42A and 42D show control animals injected with phosphate buffered saline solution. FIGS. 42B and 42E show a prevention model in which animals were injected with anti-NME7$_{AB}$ antibody 4A3 24 hrs before injection of the metastatic cancer cells, then approximately every other day for a total of 12 antibody injections over 22 days. FIGS. 42C and 42F show a reversal model in which animals were injected with anti-NME7$_{AB}$ antibody 4A3 24 hrs after injection of the metastatic cancer cells, then approximately every other day for a total of 11 antibody injections over 20 days.

FIGS. 43A-43F shows photographs of female nu/nu mice weighing approximately 20 g each, which were injected into the tail vein with 10,000 Luciferase positive T47D metastatic breast cancer stem cells and treated with the anti-NME7$_{AB}$ antibodies 5A1, also known as 8F9A5A1, or 5D4, also known as 5F3A5D4. To image cancer cells, the Luciferase substrate, Luciferin, is intraperitoneally injected 10 minutes before being photographed in IVIS instrument. FIGS. 43A-43C show IVIS photographs with animals face down. FIGS. 43D-43F show IVIS photographs with animals face up. FIGS. 43A and 43D show control animals injected with phosphate buffered saline solution. FIGS. 43B, 43E, 43C and 43F show a prevention model in which animals were injected with anti-NME7$_{AB}$ antibodies 24 hours before injection of the metastatic cancer cells, then approximately every other day for a total of 12 antibody injections over 22 days. Images were taken on Day 27.

FIGS. 44A-44D shows photographs of female nu/nu mice that on Day 0 were injected into the tail vein with 10,000 Luciferase positive T47D metastatic breast cancer stem cells mixed with NME7$_{AB}$ to a final concentration of 32 nM. On Day 1 and Day 2 animals were injected into the tail vein with more 32 nM NME7$_{AB}$, which we have shown increases metastases. This is a system to demonstrate reversion of established metastases. On Day 7 animals were treated with individual anti-NME7$_{AB}$ antibodies 8F9A5A1, 8F9A4A3, or 5F3A5D4. FIG. 44A shows control animals injected with phosphate buffered saline solution. FIG. 44B shows animals treated with anti-NME7$_{AB}$ monoclonal antibody 8F9A5A1, also known as 5A1. FIG. 44C shows animals treated with anti-NME7$_{AB}$ monoclonal antibody 8F9A4A3, also known as 4A3. FIG. 44D shows animals treated with anti-NME7$_{AB}$ monoclonal antibody 5F3A5D4, also known as 5D4. Green arrows indicate low antibody dosage (5-7 mg/kg) over the indicated period and Red arrows indicate high dosage (15 mg/kg). As can be seen in the figure, animals treated with anti-NME7$_{AB}$ antibodies have less metastases than the control animals even though many of the animals in the groups to be treated with antibody have more metastasis before any treatment. Higher concentrations of anti-NME7$_{AB}$ antibody are more effective than low concentrations. For example between Day 11 and Day 17, animals were treated with high dose and most of the treated animals have cleared metastases by about Day 17. However, 1 low dose of antibody resulted in metastasis recurrence. Animals again respond to high dose treatment by Day 32.

FIGS. 45A-45B shows photographs of female nu/nu mice that on Day 0 were injected sub-cutaneously into the right flank with 10,000 Luciferase positive T47D metastatic breast cancer stem cells, mixed with NME7$_{AB}$ to a final concentration of 32 nM, then mixed in a 1:1 vol:vol with Matrigel. Tumor engraftment was allowed to progress Day 0-Day 6. Animals were then treated i.v. by tail vein injection with anti-NME7$_{AB}$ antibodies. Control animals were injected with PBS. FIG. 45A shows IVIS photographs of control animals. FIG. 45B shows IVIS photographs of animals injected into tail vein with a cocktail of anti-NME7$_{AB}$ antibodies 5A1, 4A3 and 5D4 to a total concentration of 15 mg/kg. Antibodies or PBS were administered 4 times between Day 7 and Day 18. As can be seen in the figure, the anti-NME7$_{AB}$ antibody treated animals show less metastases than the control group. In the treated group, 2 of the 5 animals have primary tumors that are larger than those in the control group. This could be because the anti-NME7$_{AB}$ antibodies prevented the spread of the cancer cells, so they remained concentrated in the primary tumor. In this experiment, PCR analysis showed that after 11 days in culture with NME7$_{AB}$, the T47D breast cancer cells had upregulated CXCR4 by 109-fold, OCT4 by 2-fold, NANOG by 3.5-fold and MUC1 by 2.7-fold.

FIGS. 46A-46Q shows photographs of female nu/nu mice that on Day 0 were injected sub-cutaneously into the right flank with 10,000 Luciferase positive T47D metastatic breast cancer stem cells, mixed with NME7$_{AB}$ to a final concentration of 32 nM, then mixed in a 1:1 vol:vol with Matrigel. Tumor engraftment was allowed to progress Day 0-Day 6. Animals were then treated i.v., by tail vein injection, with anti-NME7$_{AB}$ antibodies. Control animals were injected with PBS. On Day 38 animals were sacrificed and livers harvested then analyzed by IVIS to detect cancer cells that had metastasized to the liver. FIGS. 46A-46B show whole body IVIS photographs of control animals that were injected with only PBS. FIGS. 46C-46D show whole body IVIS photographs of control animals that were injected with the anti-NME7$_{AB}$ antibody 5A1. FIGS. 46E-46F show whole body IVIS photographs of control animals that were injected with the anti-NME7$_{AB}$ antibody 4A3. FIGS. 46G-46H show whole body IVIS photographs of control animals that were injected with the anti-NME7$_{AB}$ antibody 5D4. FIGS. 46A, 46C, 46E, and 46G are IVIS photographs taken at Day 7 before any treatment. FIGS. 46B, 46D, 46F, and 46H are IVIS photographs taken at Day 31 after anti-NME7$_{AB}$ antibody treatment or mock treatment. As can be seen in the figure, animals in the PBS control group show metastasis (blue dots) in the whole body IVIS photographs, while animals treated with anti-NME7$_{AB}$ antibodies do not. FIGS. 46I-46P show photographs and IVIS photographs of livers and lung harvested from animals after sacrifice. FIGS. 46I, 46K, 46M, and 46O are regular photographs. FIGS. 46J, 46L, 46N, and 46P are IVIS photographs, illuminating the cancer cells that have metastasized there. As can be seen in the figure, the anti-NME7$_{AB}$ antibodies greatly inhibited metastasis to the liver, which is a primary site for breast cancer metastasis. FIG. 46Q is a bar graph of the measured photons emitted and enumerated by IVIS instrument for livers harvested from control animals versus the treated animals.

FIGS. 47A-47F shows photographs of immunofluorescent experiments in which various cancer cell lines are stained for the presence of NME7$_{AB}$. FIG. 47A shows T47D breast cancer cells stained with varying concentrations of anti-NME7$_{AB}$ antibody 5D4. FIG. 47B shows ZR-75-1 breast cancer cells, also known as 1500s, stained with varying concentrations of anti-NME7$_{AB}$ antibody 5D4. FIG. 47C shows H1975 non-small cell lung cancer cells stained with varying concentrations of anti-NME7$_{AB}$ antibody 5D4. FIG. 47D shows H292 non-small cell lung cancer cells stained with varying concentrations of anti-NME7$_{AB}$ antibody 5D4. FIG. 47E shows HPAFII pancreatic cancer cells stained with varying concentrations of anti-NME7$_{AB}$ antibody 5D4. FIG. 47F shows DU145 prostate cancer cells stained with varying concentrations of anti-NME7$_{AB}$ antibody 5D4. As can be seen in the figure, all the cancer cell lines we tested show strong and membranous staining for NME7$_{AB}$. The monoclonal antibody used in these experiments was 5D4. In parallel, NME7$_{AB}$ antibodies 5A1 and 4A3 were used to stain the same cell lines and produced the same results.

FIGS. 48A-48I shows photographs of immunofluorescent experiments in which various lung cancer cell lines are stained for the presence of NME7$_{AB}$. FIGS. 48A-48C shows H1975 non-small cell lung cancer cells, which are an adenocarcinoma, stained with varying concentrations of anti-NME7$_{AB}$ antibody 5D4. FIG. 48A is an overlay of DAPI and anti-NME7$_{AB}$ staining. FIG. 48B shows anti-NME7$_{AB}$ staining alone. FIG. 48C is a magnified view of the overlay of DAPI and anti-NME7$_{AB}$ staining. FIGS. 48D-48F shows H292 non-small cell lung cancer cells, which are a mucoepidermoid pulmonary carcinoma, stained with varying concentrations of anti-NME7$_{AB}$ antibody 5D4. FIG. 48D is an overlay of DAPI and anti-NME7$_{AB}$ staining. FIG. 48E shows anti-NME7$_{AB}$ staining alone. FIG. 48F is a magnified view of the overlay of DAPI and anti-NME7$_{AB}$ staining. FIGS. 48G-48I shows H358 non-small cell lung cancer cells, which are a metastatic bronchioalveolar carcinoma, stained with varying concentrations of anti-NME7$_{AB}$ antibody 5D4. FIG. 48G is an overlay of DAPI and anti-NME7$_{AB}$ staining. FIG. 48H shows anti-NME7$_{AB}$ staining alone. FIG. 48I is a magnified view of the overlay of DAPI and anti-NME7$_{AB}$ staining.

FIG. 49A-49I shows PCR graphs of cancer cell lines, breast T47D, Lung H1975, lung H358 and pancreatic HPAFII before and after culture in NME7$_{AB}$. FIG. 49A measured breast metastatic marker CXCR4. FIG. 49B measured stem cell marker OCT4. FIG. 49C measured metastatic marker ALDH1. FIG. 49D measured stem cell marker SOX2. FIG. 49E measured stem cell marker NANOG. FIG. 49F measured marker CDH1, also known as E-cadherin. FIG. 49G measured metastatic marker CD133. FIG. 49H measured stem cell marker ZEB2. FIG. 49I measured stem, cancer and metastatic marker MUC1. The floater cells, also known as tumor spheres become able to grow anchorage independently and show markers of metastasis that are more elevated than the adherent cells. Animals injected with cancer stem cells are those injected with the NME7$_{AB}$ grown floater cells. As can be seen in the figure markers of metastasis, stem cell markers, or markers of epithelial to mesenchymal transition (EMT) are elevated after culture in NME7$_{AB}$, indicating a transition to a more metastatic state.

FIG. 50A-50D shows IVIS photographs of NSG mice injected into the tail vein with 10,000 cancer cells that were either NCI-H358 parent cells or NCI-H358 cells after 10 days in culture with NME7$_{AB}$. FIGS. 50A and 50C show IVIS photographs of the mouse that was injected with the NCI-H358 lung cancer cells that had been grown in NME7$_{AB}$ for 10 days. FIGS. 50B and 50D show IVIS photographs of the mouse that was injected with the parental NCI-H358 cells. FIGS. 50A and 50B show the IVIS photographs where mice are imaged face down. FIGS. 50C and 50D show the IVIS photographs where mice are imaged face up. As can be seen in the figure, the NME7$_{AB}$ grown cells have greatly increased metastatic potential.

Figure 51:
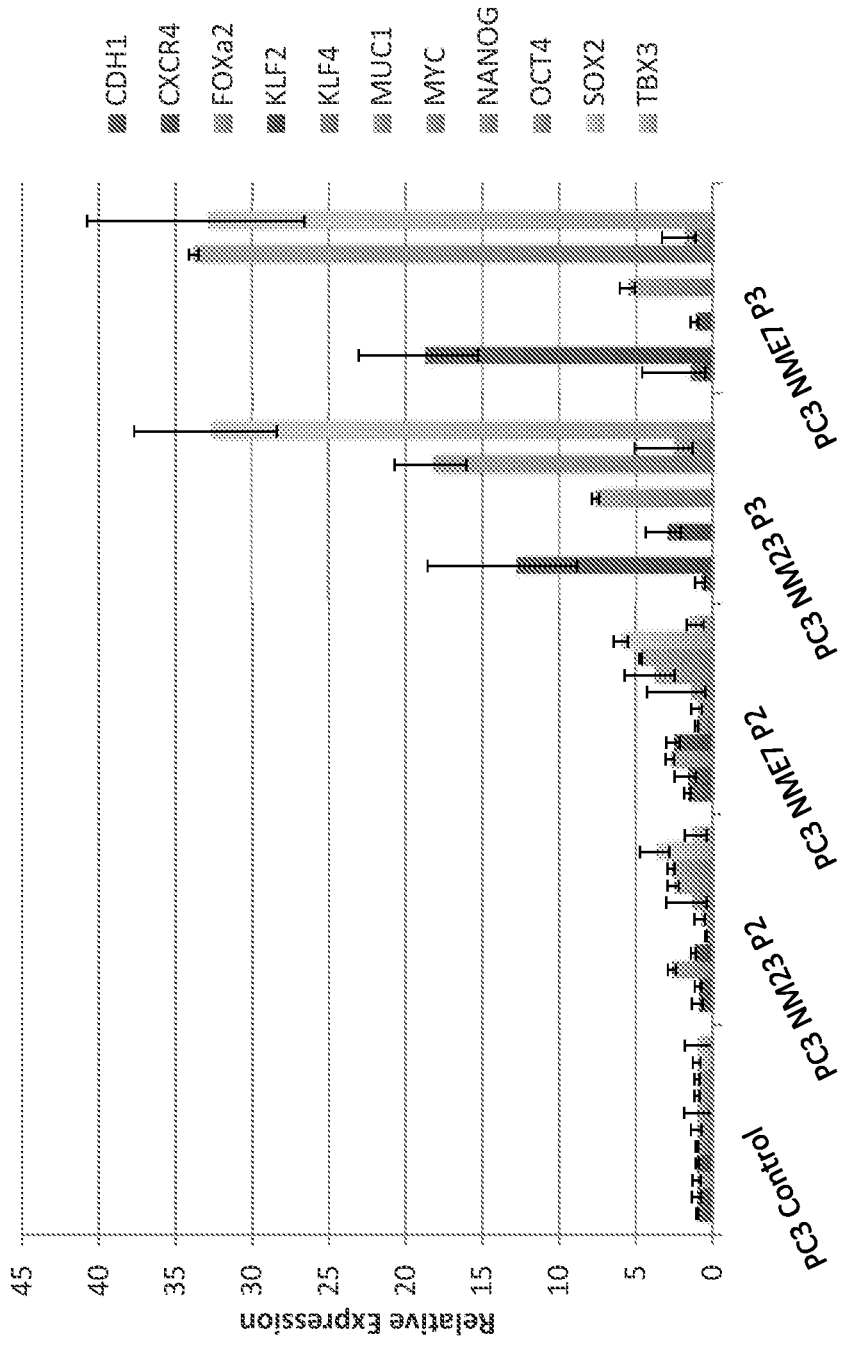

FIG. 51 shows PCR graph of a MUC1 negative prostate cancer line PC3 before and after 2 or 3 passages in culture in either dimeric NM23-H1, also known as NME1, or NME7$_{AB}$. The graph shows the fold difference in markers of stem cells, cancer cells as well as metastatic markers. As can be seen in the figure, repeated culture in NME1 or NME7$_{AB}$ induces upregulation of stem, cancer and metastatic markers but also upregulates expression of MUC1 by 5-8 times.

DETAILED DESCRIPTION OF THE PREFERRED EMBODIMENTS

Definitions

In the present application, "a" and "an" are used to refer to both single and a plurality of objects.

As used herein, "about" or "substantially" generally provides a leeway from being limited to an exact number. For example, as used in the context of the length of a polypeptide sequence, "about" or "substantially" indicates that the polypeptide is not to be limited to the recited number of amino acids. A few amino acids add to or subtracted from the N-terminus or C-terminus may be included so long as the functional activity such as its binding activity is present.

As used herein, administration "in combination with" one or more further therapeutic agents includes simultaneous (concurrent) and consecutive administration in any order.

As used herein, "amino acid" and "amino acids" refer to all naturally occurring L-α-amino acids. This definition is meant to include norleucine, ornithine, and homocysteine.

As used herein, in general, the term "amino acid sequence variant" refers to molecules with some differences in their amino acid sequences as compared to a reference (e.g. native sequence) polypeptide. The amino acid alterations may be substitutions, insertions, deletions or any desired combinations of such changes in a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, and so on.

Insertional variants are those with one or more amino acids inserted immediately adjacent to an amino acid at a particular position in a native amino acid sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule.

As used herein, "fragments" or "functional derivatives" refers to biologically active amino acid sequence variants and fragments of the polypeptide of the present invention, as well as covalent modifications, including derivatives obtained by reaction with organic derivatizing agents, post-translational modifications, derivatives with nonproteinaceous polymers, and immunoadhesins.

As used herein, "carriers" include pharmaceutically acceptable carriers, excipients, or stabilizers which are non-toxic to the cell or mammal being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

As used herein "pharmaceutically acceptable carrier and/or diluent" includes any and all solvents, dispersion media, coatings antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form. A unit dosage form can, for example, contain the principal active compound in amounts ranging from 0.5 μg to about 2000 mg. Expressed in proportions, the active compound is generally present in from about 0.5 μg/ml of carrier. In the case of compositions containing supplementary active ingredients, the dosages are determined by reference to the usual dose and manner of administration of the said ingredients.

As used herein, "vector", "polynucleotide vector", "construct" and "polynucleotide construct" are used interchangeably herein. A polynucleotide vector of this invention may be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-structures, such as polyamides.

As used herein, "host cell" includes an individual cell or cell culture which can be or has been a recipient of a vector of this invention. Host cells include progeny of a single host cell, and the progeny may not necessarily be completely identical (in morphology or in total DNA complement) to the original parent cell due to natural, accidental, or deliberate mutation and/or change.

As used herein, "subject" is a vertebrate, preferably a mammal, more preferably a human.

As used herein, "mammal" for purposes of treatment refers to any animal classified as a mammal, including humans, domestic and farm animals, and zoo, sports, or pet animals, such as dogs, cats, cattle, horses, sheep, pigs, and so on. Preferably, the mammal is human.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" refers to both therapeutic treatment and prophylactic or preventative measures. Those in need of treatment include those already with the disorder as well as those in which the disorder is to be prevented. "Palliating" a disease means that the extent and/or undesirable clinical manifestations of a disease state are lessened and/or the time course of the progression is slowed or lengthened, as compared to a situation without treatment.

As used herein, "A1" peptide, "A2" peptide, "B1" peptide, "B2" peptide and "B3" peptide refer to peptides derived from NME7 that are used to generate or select antibodies that bind to human NME7$_{AB}$, but not (or significantly less) to human NME1. The peptides used to generate these antibodies are common to both NME7$_{AB}$ and NME7-X1, and are set forth as below.

```
A1 is NME7A peptide 1 (A domain):
                                (SEQ ID NO: 141)
MLSRKEALDFHVDHQS A2 is NME7A peptide 2 (A domain):
                                (SEQ ID NO: 142)
SGVARTDASES B1 is NME7B peptide 1 (B domain):
                                (SEQ ID NO: 143)
DAGFEISAMQMFNMDRVNVE B2 is NME7B peptide 2 (B domain):
                                (SEQ ID NO: 144)
EVYKGVVTEYHDMVTE B3 is NME7B peptide 3 (B domain):
                                (SEQ ID NO: 145)
AIFGKTKIQNAVHCTDLPEDGLLEVQYFF
```

Further, for the sake of clarity, NME7A (with capital letter "A") refers to the subunit A portion of NME7. NME7a (with small letter "a") refers to the full-length NME7 that is described elsewhere in this application. And, NME7B (with capital letter "B") refers to the subunit B portion of NME7. NME7b (with small letter "b") refers to a species of NME7 that is partially devoid of the DM10 region, which is described elsewhere in this application.

As used herein, the term "antibody-like" means a molecule that may be engineered such that it contains portions of antibodies but is not an antibody that would naturally occur in nature. Examples include but are not limited to CAR (chimeric antigen receptor) T cell technology and the Ylanthia® technology. The CAR technology uses an antibody epitope fused to a portion of a T cell so that the body's immune system is directed to attack a specific target protein or cell. The Ylanthia® technology consists of an "antibody-like" library that is a collection of synthetic human fabs that are then screened for binding to peptide epitopes from target proteins. The selected Fab regions can then be engineered into a scaffold or framework so that they resemble antibodies.

As used herein, an "effective amount of an agent to inhibit an NME family member protein" refers to the effective amount of the agent in hindering the activating interaction between the NME family member protein and its cognate receptor such as As used herein, "NME derived fragment" refers to a peptide sequence that is either a fragment of the NME or is highly homologous to the peptide sequence that is a fragment of the NME.

As used herein, the "MUC1*" extra cellular domain is defined primarily by the PSMGFR sequence (GTINVHDVETQFNQYKTEAAS-RYNLTISDVSVSDVPFPFSAQSGA (SEQ ID NO:6)). Because the exact site of MUC1 cleavage depends on the enzyme that clips it, and that the cleavage enzyme varies depending on cell type, tissue type or the time in the evolution of the cell, the exact sequence of the MUC1* extra cellular domain may vary at the N-terminus.

As used herein, the term "PSMGFR" is an acronym for Primary Sequence of MUC1 Growth Factor Receptor as set forth as GTINVHDVETQFNQYKTEAAS-RYNLTISDVSVSDVPFPFSAQSGA (SEQ ID NO:6). In this regard, the "N-number" as in "N-10 PSMGFR" or simply "N-10", "N-15 PSMGFR" or simply "N-15", or "N-20 PSMGFR" or simply "N-20" refers to the number of amino acid residues that have been deleted at the N-terminal end of PSMGFR. Likewise "C-number" as in "C-10 PSMGFR" or simply "C-10", "C-15 PSMGFR" or simply "C-15", or "C-20 PSMGFR" or simply "C-20" refers to the number of amino acid residues that have been deleted at the C-terminal end of PSMGFR. A mixture of deletions and additions is also possible. For instance, N+20/C-27 refers to a peptide fragment of wild-type MUC1 in which 20 amino acids are added to the PSMGFR at the N-terminus and 27 amino acids are deleted from the C-terminus.

As used herein, the "extracellular domain of MUC1*" refers to the extracellular portion of a MUC1 protein that is devoid of the tandem repeat domain. In most cases, MUC1* is a cleavage product wherein the MUC1* portion consists of a short extracellular domain devoid of tandem repeats, a transmembrane domain and a cytoplasmic tail. The precise location of cleavage of MUC1 is not known perhaps because it appears that it can be cleaved by more than one enzyme. The extracellular domain of MUC1* will include most of the PSMGFR sequence but may have an additional 10-20 N-terminal amino acids.

As used herein, "high homology" is considered to be at least 30%, 35%, 40%, 45%, 50%, 55%, 60%, 65%, 70%, 75%, 80%, 85%, 90%, 95%, or 97% identity in a designated overlapping region between any two polypeptides.

As used herein, "NME family proteins" or "NME family member proteins", numbered 1-10, are proteins grouped together because they all have at least one NDPK (nucleotide diphosphate kinase) domain. In some cases, the NDPK domain is not functional in terms of being able to catalyze the conversion of ATP to ADP. NME proteins were formerly known as NM23 proteins, numbered H1 and H2. Recently, as many as ten (10) NME family members have been identified. Herein, the terms NM23 and NME are interchangeable. Herein, terms NME1, NME2, NME5, NME6, NME7, NME8 and NME9 are used to refer to the native protein as well as NME variants. In some cases these variants are more soluble, express better in *E. coli* or are more soluble than the native sequence protein. For example, NME7 as used in the specification can mean the native protein or a variant, such as $NME7_{AB}$ that has superior commercial applicability because variations allow high yield expression of the soluble, properly folded protein in *E. coli*. $NME7_{AB}$ consists primarily of the NME7 A and B domains but is devoid of most of the DM10 domain (SEQ ID NO:39), which is at the N-terminus of the native protein. "NME1" as referred to herein is interchangeable with "NM23-H1". It is also intended that the invention not be limited by the exact sequence of the NME proteins. The mutant NME1-5120G, also called NM23-5120G, are used interchangeably throughout the application. The 5120G mutants and the P96S mutant are preferred because of their preference for dimer formation, but may be referred to herein as NM23 dimers, NME1 dimers, or dimeric NME1, or dimeric NM23.

NME7 as referred to herein is intended to mean native NME7 having a molecular weight of about 42 kDa.

A "family of NME7" refers to full length NME7 as well as naturally occurring or artificially created cleaved form having a molecular weight about 30 kDa, 33 kDa, or a cleaved form having a molecular weight of about 25 kDa, a variant devoid or partially devoid of the DM10 leader sequence (SEQ ID NO:162), which is NME7 amino acids 1-91 of NME7 represented by SEQ ID NO:82 or 147, such as NME7b, NME7-X1, $NME7_{AB}$ or a recombinant NME7 protein, or variants thereof whose sequence may be altered to allow for efficient expression or that increase yield, solubility or other characteristics that make the NME7 more effective or commercially more viable. The "family of NME7" may also include "$NME7_{AB}$-like" protein, which is a protein in the range of 30 to 33 kDa that is expressed in cancer cells.

As used herein, an "an agent that maintains stem cells in the naïve state or reverts primed stem cells to the naïve state" refers to a protein, small molecule or nucleic acid that alone or in combination maintains stem cells in the naïve state, resembling cells of the inner cell mass of an embryo. Examples include but are not limited to human NME1 dimers, bacterial, fungal, yeast, viral or parasitic NME proteins that have high sequence identity to human NME proteins, especially NME1, NME7, NME7-X1, $NME7_{AB}$, NME6, 2i (Silva J et al, 2008; Hanna et al, 2010), 5i (Theunissen T W et al, 2014), nucleic acids such as siRNA that suppress expression of MBD3, CHD4 (Rais Y1 et al, 2013), BRD4, or JMJD6 (Liu W et al 2013).

As used herein, the terms "$NME7_{AB}$", "$NME7_{AB}$" and "NME-AB" are used interchangeably.

As used herein, an "agent that promotes pluripotency" or "reverts somatic cells to a stem-like or cancer-like state" refers to a protein, small molecule or nucleic acid that alone or in combination induces expression of or suppresses expression of certain genes such that the genetic signature shifts to one that more closely resembles stem cells or cancer cells. Examples include but are not limited to NME1 dimers, NME7, NME7-X1, $NME7_{AB}$, 2i, 5i, nucleic acids such as siRNA that suppress expression of MBD3, CHD4, BRD4, or JMJD6, microbial NME proteins that have high sequence homology to human NME1, NME2, NME5, NME6, NME7, NME8, or NME9, preferably with the regions that house NDPK domains.

As used herein, in reference to an agent being referred to as a "small molecule", it may be a synthetic chemical or chemically based molecule having a molecular weight between 50 Da and 2000 Da, more preferably between 150 Da and 1000 Da, still more preferably between 200 Da and 750 Da.

As used herein, in reference to an agent being referred to as a "natural product", it may be chemical molecule or a biological molecule, so long as the molecule exists in nature.

As used herein, FGF, FGF-2 or bFGF refer to fibroblast growth factor (Xu R H et al, 2005; Xu C et al, 2005).

As used herein, "Rho associated kinase inhibitors" may be small molecules, peptides or proteins (Rath N, et al, 2012). Rho kinase inhibitors are abbreviated here and elsewhere as ROCi or ROCKi, or Ri. The use of specific rho kinase inhibitors are meant to be exemplary and can be substituted for any other rho kinase inhibitor.

As used herein, the term "cancer stem cells" or "tumor initiating cells" refers to cancer cells that express levels of genes that have been linked to a more metastatic state or more aggressive cancers. The terms "cancer stem cells" or "tumor initiating cells" can also refer to cancer cells for which far fewer cells are required to give rise to a tumor when transplanted into an animal. Cancer stem cells and tumor initiating cells are often resistant to chemotherapy drugs.

As used herein, the terms "stem/cancer", "cancer-like", "stem-like" refers to a state in which cells acquire characteristics of stem cells or cancer cells, share important elements of the gene expression profile of stem cells, cancer cells or cancer stem cells. Stem-like cells may be somatic cells undergoing induction to a less mature state, such as increasing expression of pluripotency genes. Stem-like cells also refers to cells that have undergone some dedifferentiation or are in a meta-stable state from which they can alter their terminal differentiation. Cancer like cells may be cancer cells that have not yet been fully characterized but display morphology and characteristics of cancer cells, such as being able to grow anchorage-independently or being able to give rise to a tumor in an animal.

As used herein, "spacers" or "linkers" of different lengths can be incorporated anywhere in the peptide. Spacer attachment is usually through an amide linkage but other functionalities are possible.

NME, NME7 and Protein Family of NME7

The present inventors discovered that NME7 and NME7-X1 are highly expressed in early human stem cells and also in most cancer cells (FIG. 17, FIG. 18, FIG. 19A-FIG. 19F, FIG. 22, FIG. 23, FIG. 39, FIG. 40, FIG. 41, FIG. 47, FIG. 48. FIG. 17 shows a graph of RT-PCR measurement of the expression of NME7-X1 in a panel of human stem cells and cancer cells. FIG. 18 shows a graph of RT-PCR measurement of the expression of NME7, NME7a, NME7b and NME7-X1 in a panel of human stem cells and cancer cells. NME7a is full-length NME7, NME7b is missing a small portion of the DM10 domain, NME7-X1 is missing all of the DM10 domain and a small portion of the N-terminus of the first NDPK A domain. The bar labeled NME7 means that primers were used that detected both NME7a and NME7b. FIGS. 19A-19F show photographs of Western blots in which various cancer cell lines are probed for expression of NME7 species using antibodies generated by immunization with NME7 derived short peptides. FIG. 19A shows Western probed with antibody of the invention #52 which binds to NME7 derived peptide A1. FIG. 19B shows Western probed with antibody of the invention #56 which binds to NME7 derived peptide B1. FIG. 19C shows Western probed with antibody of the invention #61 which binds to NME7 derived peptide B3. FIGS. 22A-22E show photographs of Western blots of a co-immunoprecipitation experiment. T47D breast cancer cell extracts were incubated with an antibody against the MUC1 cytoplasmic tail, Ab-5, or a control antibody, IgG, and co-immunoprecipitated. The gels were blotted with two different commercially available anti-NME7 antibodies B9 (FIG. 22A) and CF7 (FIG. 22B). Both gels show unique NME7 bands at ~33 kDa and ~30 kDa. The gels were stripped and re-probed with an antibody against the extracellular domain of MUC1*, anti-PSMGFR (FIG. 22C) and (FIG. 22D), which shows that the NME7 species and MUC1* interact. A recombinant NME7-AB and a recombinant NME7-X1 were mixed together and run on a gel, then probed with an anti-NME7 antibody, showing that the two unique NME7 species that are naturally occurring in breast cancer cells and that interact with MUC1* are an NME7-AB-like species and NME7-X1 (FIG. 22E). FIGS. 23A-23C show photographs of Western blots of a co-immunoprecipitation experiment. Human induced pluripotent stem, iPS7, or embryonic stem, HES3, cell extracts were incubated with an antibody against the MUC1 cytoplasmic tail, Ab-5, or a control antibody, IgG, and co-immunoprecipitated. The gel was blotted with a commercially available anti-NME7 antibody B9 (FIG. 23A). Both cell types show unique NME7 bands at ~33 kDa and ~30 kDa. The gel was stripped and re-probed with an antibody against the extracellular domain of MUC1*, anti-PSMGFR (FIG. 23B), which shows that the NME7 species and MUC1* interact. A recombinant NME7-AB and a recombinant NME7-X1 were mixed together and run on a gel, then probed with an anti-NME7 antibody, showing that the two unique NME7 species that are naturally occurring in breast cancer cells and that interact with MUC1* are an NME7-AB-like species and NME7-X1 (FIG. 23C). FIGS. 39A-39C shows human lung tissue specimens stained with an anti-NME7 antibody that binds to the B3 peptide. The figure shows lack of NME7 expression on normal tissues, increasing expression of NME7 as tumor grade and metastasis increase. FIGS. 40A-40C shows human small intestine tissue specimens stained with an anti-NME7 antibody that binds to the B3 peptide. The figure shows lack of NME7 expression on normal tissues, increasing expression of NME7 as tumor grade and metastasis increase. FIGS. 41A-41D show human colon tissue specimens stained with an anti-NME7 antibody that binds to the B3 peptide. The figure shows lack of NME7 expression on normal tissues, increasing expression of NME7 as tumor grade and metastasis increase. FIG. 47 and FIG. 48 show immunofluorescent photographs showing that NME7 is secreted by and binds to an extra cellular receptor of a wide variety of cancer cell lines.

Further, we demonstrated that like NM23-H1, NME7 binds to and dimerizes the MUC1* growth factor receptor on both stem cells and cancer cells (FIG. 1). FIG. 5 shows a sequence alignment of NME1 and NME7 A and B domains.

The inventors recently discovered that NME7 is a primitive form of NME1 (NM23-H1) that is expressed in very early embryonic stem cells. NME7 is either not expressed at all, or is expressed at extremely low levels, in adult tissues. However, the inventors discovered that NME7 is expressed at high levels in cancerous cells and tissues and at even higher levels in metastatic cancer cells and tissues. A cleaved form of NME7 may be a secreted form allowing it to bind to and activate extracellular receptors. We detect full-length NME7, MW 42 kDa, as well as NME7 species that are approximately 33 kDa and 30 kDa. The 33 kDa and 30 kDa species are secreted from cancer cells. Western blots detect full-length NME7 in cell lysates, but smaller 30-33kDaNME7 species in their conditioned media. Western blots probed with either an antibody that recognizes NME7 or an antibody that only recognizes the DM10 domain show that the lower molecular weight NME7 species that are secreted into the conditioned media are devoid of the DM10 domain. These data are consistent with the idea that naturally occurring NME7 species are comparable to the recombinant $NME7_{AB}$ we generated as they have nearly the same molecular weight, both are secreted and are both devoid of the 91 amino acids of the DM10 domain which may keep the protein retained within the cell.

We discovered a new NME7 isoform, NME7-X1, and also discovered that it is over-expressed in stem cells and cancer cells and is particularly over-expressed in prostate cancers (FIG. 17, FIG. 18, FIG. 19, and FIG. 22). NME7-X1, molecular weight ~30 kDa, comprises NME7 amino acids 125-376, whereas the recombinant $NME7_{AB}$, molecular weight ~33 kDa, that we generated spans amino acids 92-376, so includes 33 more N-terminal amino acids. NME7b spans amino acids 37-376 and is devoid of only 37 amino acids of the DM10 domain is also overexpressed in prostate cancers (FIG. 18). We generated a human recombinant NME7-X1 and show that it is the secreted 30 kDa NME7 species in cancer cells that runs just lower than a naturally occurring ~33kDaNME7 species that appears to be a naturally occurring "$NME7_{AB}$-like" protein that is a cleavage product or alternative isoform.

We tested a panel of cancer cell lines and found that they express high levels of NME7 and lower molecular weight species that may be truncations similar to $NME7_{AB}$, such as $NME7_{AB}$-like protein, or alternate isoforms such as NME7-X1.

Whereas NM23-H1 (aka NME1) has to be a dimer, NME7 is a monomer with two binding sites for MUC1* extracellular domain. We generated a recombinant human NME7 that is devoid of the DM10 domain, which we call $NME7_{AB}$. A sandwich ELISA binding assay that shows that a recombinant $NME7_{AB}$ simultaneously binds to two PSMGFR peptides wherein the extracellular domain of MUC1* is comprised of most or all of the PSMGFR sequence (FIG. 1). In a nanoparticle binding assay, NME7 was also shown to be able to bind to and dimerize the PSMGFR portion of the MUC1* extracellular domain.

Agents that disable NME7, block its interaction with its binding partners or suppress its expression are potent anticancer therapeutics. Such agents may be antibodies, small molecules or nucleic acids. They may act on NME7 directly, on molecules that regulate NME7 expression, or on enzymes that cleave NME7 to cancer-promoting forms.

We discovered that like NM23-H1 dimers, a recombinant $NME7_{AB}$ monomer was fully able to support pluripotent human stem cell growth in the absence of any other growth factor, cytokine or serum. Competitively inhibiting the interaction between NME7 and MUC1* extracellular domain, comprised essentially of the PSMGFR sequence, induced differentiation of stem cells, showing that it is the interaction of NME7 and MUC1* that promotes stem cell growth and inhibits differentiation.

Figure 12:
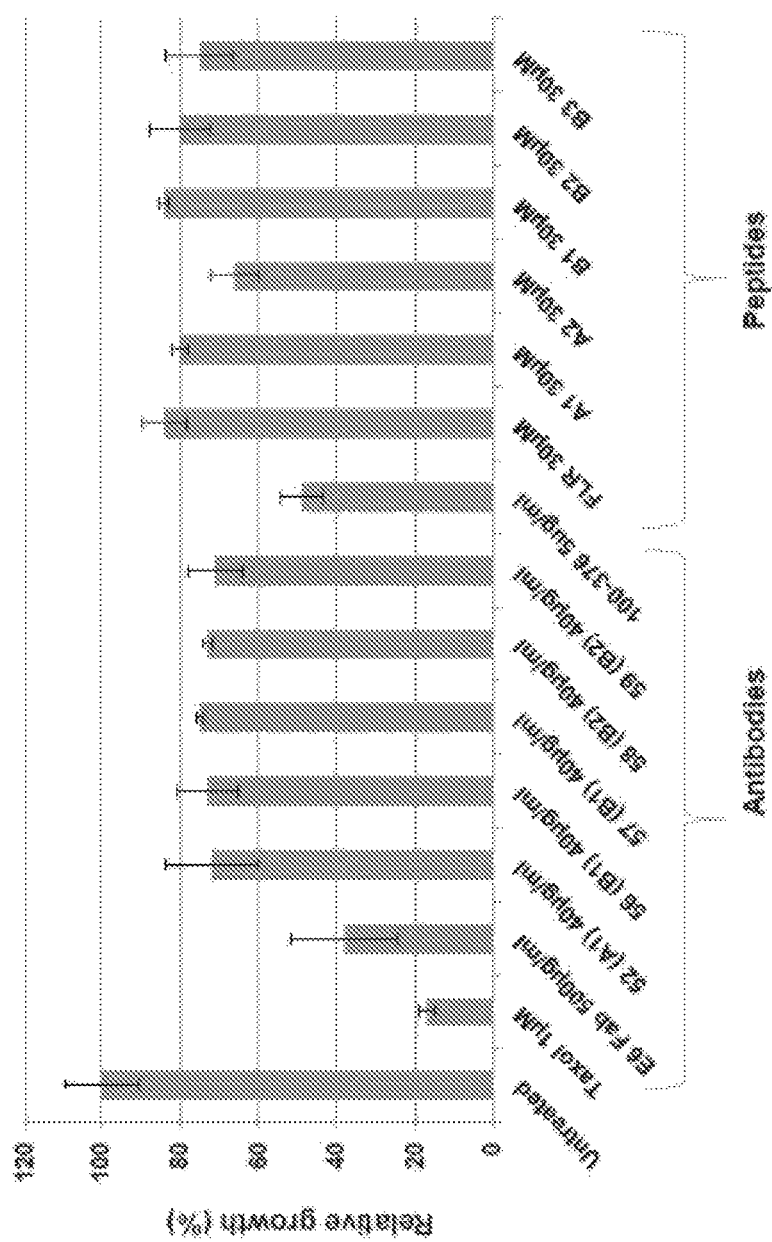
FIG. 12 shows a graph of a cancer cell growth experiment in which breast cancer cells were grown in the presence or absence of NME7 antibodies or short peptides derived from NME7, which were used to generate or select the antibodies. In addition, an antibody generated by immunization with nearly the entire NME7-AB peptide, amino acids 100-376, was shown to inhibit cancer cell growth.
Figure 13:
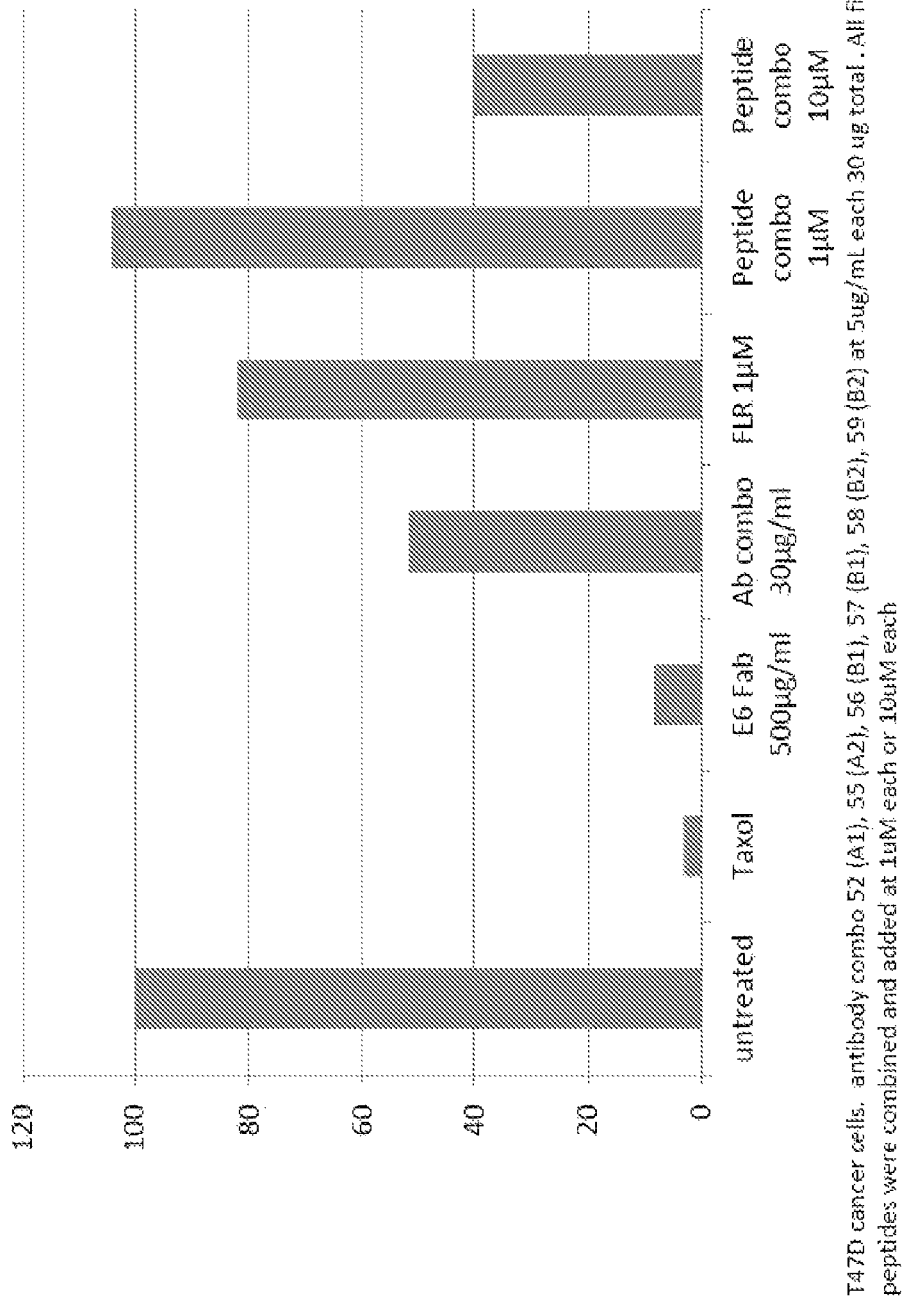
FIG. 13 shows a graph of a cancer cell growth experiment in which breast cancer cells were grown in the presence or absence of combinations of NME7 antibodies or combinations of the short peptides derived from NME7, which were used to generate or select the antibodies. Both antibodies as well as their immunizing NME7-AB peptides inhibited growth of cancer cells.

Next, we showed that $NME7_{AB}$ alone is also able to fully support human cancer cell growth. $NME7_{AB}$, when added to regular cancer cell growth media, stimulated cancer cell growth and in particular the growth of MUC1-positive and MUC1*-positive cancer cells. Inhibiting the interaction of NME7 with MUC1* inhibited cancer cell growth. Blocking the MUC1* growth factor receptor with an anti-MUC1* Fab potently inhibited cancer cell growth. Similarly, antibodies that bind to NME7 inhibit cancer cell growth. In one example of inhibition of cancer growth by anti-NME7 antibody, the polyclonal antibody was generated from immunizing an animal with the portion of NME7 that spans amino acids 100-376 (FIG. 12 and FIG. 13). However, we found that antibodies generated from immunizing with shorter peptides from $NME7_{AB}$ or from NME7-X1 also inhibit cancer growth. In particular, they inhibit the growth of MUC1 and MUC1*-positive cancers. Anti-NME7 antibodies of the invention inhibited the formation of the non-adherent "floater" cells that are able to form tumor spheres and which can travel from primary tumor and metastasize (FIG. 14, FIG. 16, FIG. 29). Anti-NME7 antibodies of the invention inhibited the upregulation of metastatic and stem cell markers, now believed to also be characteristic of metastasis (FIG. 15, FIG. 30, FIG. 31, FIG. 32).

NME7 Causes Cancer Metastasis

The inventors further discovered that culturing cancer cells in a minimal media containing $NME7_{AB}$ induced a wide variety of cancer cells to become transformed to a more metastatic state. Evidence of this induced metastatic state include a change from adherent cell growth to non-adherent cell growth, aka, "floater" cells and accompanying up-regulation of specific metastatic markers that were especially upregulated in the floating cells. These metastatic markers that are upregulated after culture in $NME7_{AB}$ include but are not limited to CXCR4, CHD1 aka E-cadherin, MUC1, ALDH1, CD44, and pluripotent stem cell markers such as OCT4, SOX2, NANOG, KLF2/4, FOXa2, TBX3, ZEB2 and c-Myc (FIG. 2, FIG. 3, FIG. 20, FIG. 49, FIG. 51). Cancer cells cultured in $NME7_{AB}$ had dramatically higher engraftment rates when xenografted into test animals, which were over 90%. In addition, very low numbers of implanted cancer cells formed tumors in the test animals, which is evidence that $NME7_{AB}$ had transformed them into cancer stem cells also known as metastatic cancer cells. Cancer cells cultured in $NME7_{AB}$ and injected into the tail vein of NOD/SCID/GAMMA mice bearing estrogen release pellets metastasized in animals from low numbers of cells compared to the parent cells, grown in regular media (FIG. 33-FIG. 38). Because cancer cells make either an NME7 cleavage product or alternative isoform that is essentially equivalent to $NME7_{AB}$, the methods described here are not limited to using $NME7_{AB}$; other NME7 species could work as well. For example, we discovered another NME7 isoform, NME7-X1, is expressed by cancer cells. It is identical to our recombinant $NME7_{AB}$ with the exception that the X1 isoform is missing 33 amino acids from the N-terminus. NME7-X1 is expected to function like $NME7_{AB}$. "$NME7_{AB}$-like" protein has also been detected in cancer cells as being about 33 Da species.

We note that the inventors' previous work showed that $NME7_{AB}$ alone is able to revert human stem cells to an earlier naïve state. We discovered that culturing cancer cells in the presence of other reagents that make stem cells revert to a more naïve state, makes the cancer cells transform to a more metastatic state. We demonstrated that culturing cancer cells $NME7_{AB}$ (FIG. 2), or in dimeric NME1 (FIG. 3), or "2i" inhibitors (FIG. 4), are each able to transform regular cancer cells into metastatic cancer cells, which are also called cancer stem cells "CSCs" or tumor initiating cells "TICs". However, $NME7_{AB}$ induced cancer cells to enter a more metastatic state better than NME1, also known as NM23-H1, which was better than 2i.

2i is the name given to two biochemical inhibitors that researchers found made human stem cells revert to a more naïve state. 2i are MEK and GSK3-beta inhibitors PD0325901 and CHIR99021, which are added to culture medium to final concentrations of about 1 mM and 3 mM, respectively. $NME7_{AB}$ and NME7-X1 are at a final concentration of about 4 nM when added to separate batches of minimal medium to make cancer cells transform to metastatic cells, although lower and higher concentrations also work well in the range of about 1 nM to 16 nM. Human or bacterial NME1 dimers are used at a final concentration of 4 nM to 32 nM, with 16 nM typically used in these experiments, wherein the human NME bears the S120G mutation. Lower concentrations may be required if using wild type. It is not intended that these exact concentrations are important. It is important that the NME1 proteins are dimers and the range of concentrations over which this happens is in the low nanomolar range although certain mutations allow higher concentrations to remain as dimers. Similarly, the concentrations of NME7 proteins can vary. $NME7_{AB}$ and NME7-X1 are monomers and concentrations used to transform cancer cells to metastatic cells should allow the proteins to remain as monomers.

In addition to NME7, $NME7_{AB}$, NME7-X1, and the 2i inhibitors MEKi and GSK3i, other reagents and inhibitors have been shown by others to cause stem cells to revert to a more naïve state. These inhibitors, "i's" include JNKi, p38i, PKCi, ROCKi, BMPi, BRAFi, SRCi as well as growth factors activing and LIF (Gafni et al 2013, Chan et al 2013, Valamehr et al 2014, Ware et al 2014, Theunissen et al 2014). These reagents can also be used to make cancer cells progress to a more metastatic state. Cells that have been induced to transform to a more metastatic state using any single factor or combination of the inhibitors or growth factors, that make stem cells revert to a more naïve state, can then be used as discovery tools to identify or test drugs to treat or prevent cancer metastasis.

Various molecular markers have been proposed as being indicators of metastatic cancer cells. Different cancer types may have different molecules that are up-regulated. For example, the receptor CXCR4 is up-regulated in metastatic breast cancers while E-cadherin, also known as CHD1, is up-regulated more in metastatic prostate cancers. In addition to these specific metastasis markers, typical markers of pluripotency such as OCT4, SOX2, NANOG, and KLF4 are up-regulated as cancers become metastatic. The starting cancer cells and the later metastatic cancer cells are assayed by PCR to measure expression levels of these genes. We demonstrated that these cancer cells, cultured in agents such as $NME7_{AB}$ that cause them to be transformed to a more metastatic state, as evidenced by increased expression of metastatic markers and pluripotent stem cell markers, function as metastatic cancer cells.

A functional test of whether or not a population of cancer cells is metastatic is to implant very low numbers, e.g. 200, of the cells in immuno-compromised mice and see if they develop into a tumor. Typically 5-6 million cancer cells are required to form a tumor in an immuno-compromised mouse. We showed that as few as 50 of the NME-induced metastatic cancer cells formed tumors in mice. In addition, mice that were injected throughout the test period with human $NME7_{AB}$, NME1, or NME7-X1 developed remote metastases.

In one particular experiment, T47D human breast cancer cells were cultured in standard RPMI media for 14 days with media changes every 48 hours and passed by trypsinization when approximately 75% confluent. The cells were then plated into 6-well plates and cultured in minimal stem cell media (see Example 1) that was supplemented with 4 nM NME7$_{AB}$ B. Media was changed every 48 hours. By about Day 4, some cells become detached from the surface and float. Media is carefully changed so as to retain the "floaters" as these are the cells that have the highest metastatic potential as evidence by RT-PCR measurement of metastatic markers. On Day 7 or 8, the floaters are harvested and counted. Samples are retained for RT-PCR measurement. The key marker measured is CXCR4, which is up-regulated by 40-200-times after being briefly cultured in NME7$_{AB}$.

The freshly harvested floater metastatic cells were xenografted into the flank of female nu/nu athymic mice that have been implanted with 90-day slow release estrogen pellets. Floater cells were xenografted with 10,000, 1,000, 100 or 50 cells each. Half of the mice in each group of 6 were also injected daily with 32 nM NME7$_{AB}$ near the original implantation site. The parent T47D cells that were cultured in RPMI media without NME7$_{AB}$ were also implanted into mice at 6 million, 10,000 or 100 as controls. Mice implanted with the NME7-induced floater cells developed tumors even when as few as 50 cells were implanted. Mice that were implanted with the floater cells and that received daily injections of NME7$_{AB}$ also developed remote tumors or remote metastases in various organs. 11 out of the 12 mice, or 92%, that were injected with human NME7$_{AB}$ after implantation of the NME7$_{AB}$ cultured cancer cells developed tumors at the injection site. Only 7 out of the 12 mice, or 58%, that were not injected with human NME7$_{AB}$ after implantation developed tumors. 9 out of the 11 mice, or 82%, that exhibited tumors and were injected with human NME7$_{AB}$ developed multiple tumors remote from the injection site. None of the mice that were not injected with NME7$_{AB}$ developed multiple, visible tumors.

After sacrifice, RT-PCR and Western blots showed that the remote bumps on the mice injected with NME7$_{AB}$ were indeed human breast tumors. Similar analysis of their organs showed that in addition to remote bumps, mice had randomly metastasized to the liver and lung with human breast cancer characteristic of the human breast cancer cells that were implanted. As expected, only the mice implanted with 6 million cells grew tumors.

Figure 2:
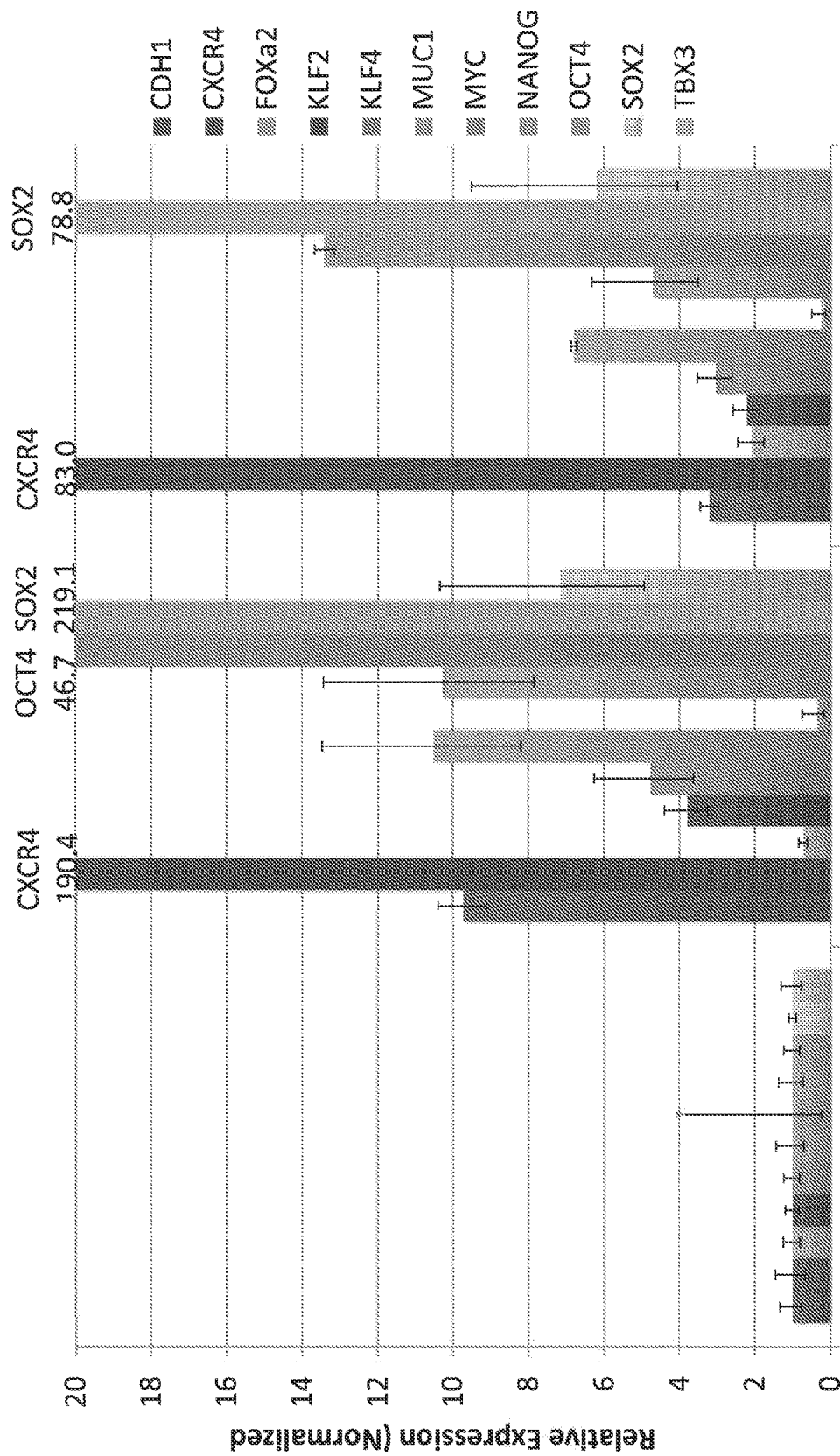
FIG. 2 is a graph of RT-PCR measurements of gene expression for stem cell markers and cancer stem cell markers for T47D cancer cells after being cultured in traditional media or a media containing NME7, wherein cells that became non-adherent (floaters) were analyzed separate from those that remained adherent.

We have demonstrated that human recombinant NME7$_{AB}$ is comparable in size and sequence to NME7-X1 and to a 30-33 kDa NME7 cleavage product. We have shown that NME7$_{AB}$ promotes cancerous growth and causes cancer cells to accelerate to the highly metastatic cancer stem cell (CSC) state also called tumor initiating cells (TIC). Therefore, we conclude that NME7-X1 and an NME7 cleavage product that removes the DM10 domain also promote cancerous growth and causes cancer cells to accelerate to the highly metastatic cancer stem cell (CSC) state also called tumor initiating cells (TIC). In one example, NME7$_{AB}$ was added to cancer cells in a serum-free media and in the absence of any other growth factors or cytokines. Within 7-10 days, the cancer cells had reverted to the highly metastatic CSCs/TICs as evidenced by more than 100-fold increase in the expression of molecular markers such as CXCR4, which are indicators of metastatic cancer cells. In one example, T47D breast cancer cells were cultured in either standard RPMI media or in a Minimal Stem Cell Media (Example 1) to which was added recombinant NME7$_{AB}$ to a final concentration of 16 nM. After 10 days cells were collected and analyzed by RT-PCR for expression of molecular markers of CSCs which were elevated by 10-200-times (FIG. 2). This is a specific, detailed example of how we transformed one cancer cell type to a more metastatic state. It is not intended that the invention be limited by these details as there are a range of cancer cells that are transformed in this way, a range of reagents that revert stem cells to a more naïve state that also progress cancer cells to a more metastatic state and a range of concentrations over which the added reagents transform the cancer cells. Other types of cancer cells have required longer periods of culture in NME7$_{AB}$ for dramatic upregulation of metastatic markers and ability to form tumors from very low numbers of cancer cells implanted. For example, prostate cancer cells cultured in NME7$_{AB}$, 2i, human NME1 or bacterial NME1 that has high homology to human NME1 or human NME7 showed dramatic increase in metastatic markers after 2-3 passages.

Metastasis marker CXCR4 is particularly elevated in metastatic breast cancer cells, while CHD1 is particularly elevated in metastatic prostate cancer. Here we show that pluripotent stem cell markers such as OCT4, SOX2, NANOG, KLF2/4 and TBX3 are also up-regulated when cancer cells transform to more metastatic cells.

Figure 3:
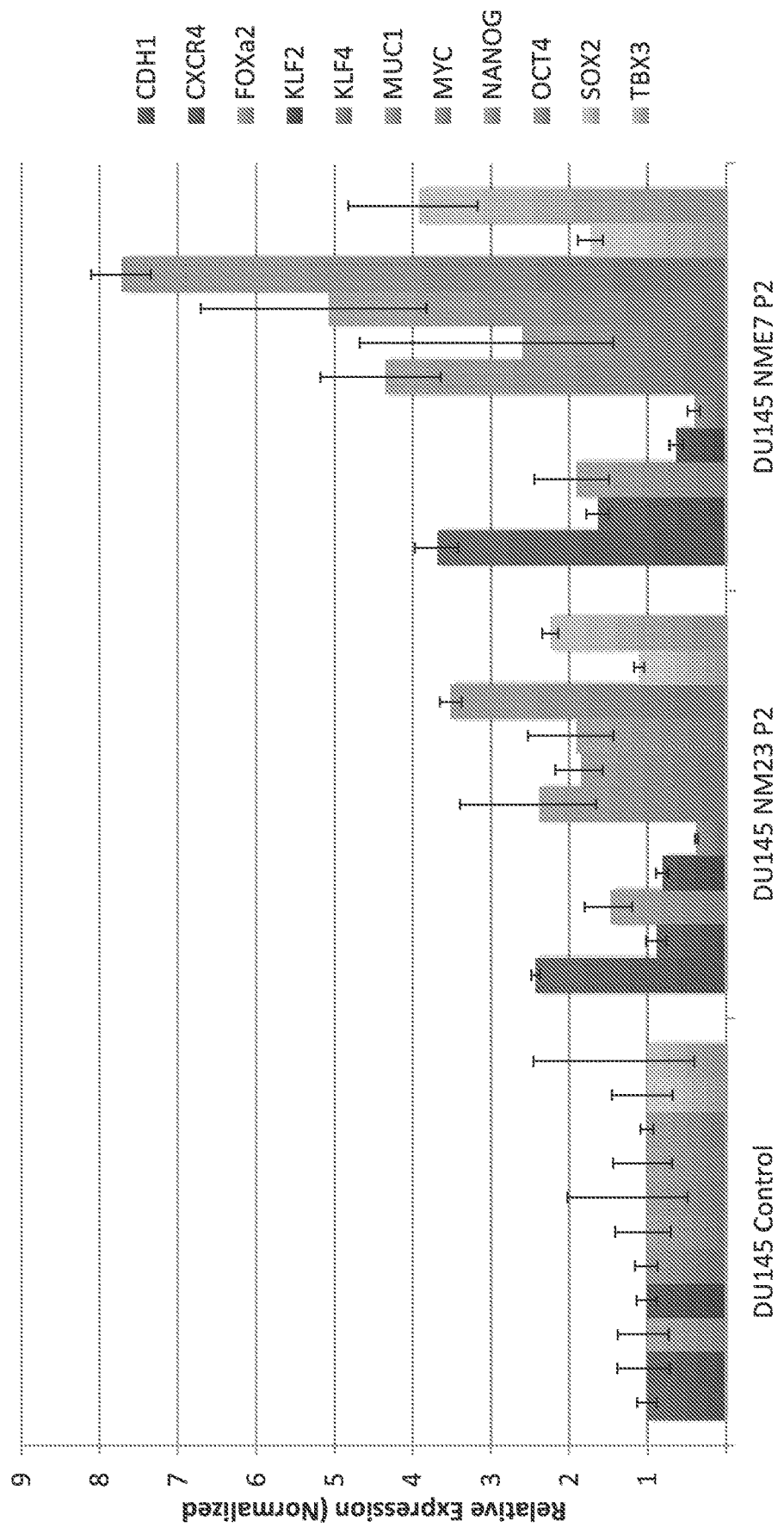
FIG. 3 is a graph of RT-PCR measurements of gene expression for a variety of stem and putative cancer stem cell markers for DU145 prostate cancer cells. Cells were cultured either in traditional media or a media containing NME1 dimers ("NM23") or NME7 (NME7-AB). Rho kinase inhibitor was not used because by passage 2, cells remained adherent.

DU145 prostate cancer cells were cultured similarly and those cells cultured in NME7$_{AB}$ also showed dramatic increases in expression of CSC markers (FIG. 3). In prostate cancer cells, CHD1 (aka E-cadherin) and CXCR4 were up-regulated compared to the control cancer cells, which were not grown in NME7$_{AB}$, along with other pluripotent stem cell markers. FIG. 20A-20C shows that ovarian cancer cell lines SK-OV3, OV-90 and breast cancer cell line MDA-MB all transitioned from adherent to non-adherent floater cells and increased expression of metastatic markers after 72 or 144 hours in culture with NME7$_{AB}$. Ovarian, prostate, pancreatic cancer cells and melanoma cells were also cultured in NME7$_{AB}$ and were transformed to a more metastatic state after as few as 3 days in culture. FIG. 21 shows that breast, ovarian, prostate, pancreatic cancer cells and melanoma cells express MUC1 and MUC1*.

Here we have shown that NME7$_{AB}$ transforms a wide range of cancer cells to a more metastatic state. We have also shown that cancer cells express a naturally occurring species that is approximately the same molecular weight as recombinant NME7$_{AB}$ 33 kDa (FIG. 17, FIG. 18. FIG. 19, and FIG. 22 and is also devoid of the DM10 domain like NME7$_{AB}$ and also express an alternative isoform NME7-X1 30 kDa which is the same sequence as NME7$_{AB}$ except is missing 33 amino acids from the N-terminus. A co-immunoprecipitation experiment was performed on T47D breast cancer cells, wherein the cell extracts were incubated with an antibody against the MUC1 cytoplasmic tail, Ab-5, or a control antibody, IgG, and co-immunoprecipitated. The immunoprecipitated species were separated by gel electrophoresis. The gels were blotted with two different commercially available anti-NME7 antibodies. Both gels show unique NME7 bands at ~33 kDa and ~30 kDa (FIG. 22A-22B). The gels were stripped and re-probed with an antibody against the extracellular domain of MUC1*, anti-PSMGFR (FIG. 22C-22D), which shows that the NME7 species and MUC1* interact. A recombinant NME7$_{AB}$ and a recombinant NME7-X1 that we made were mixed together and run on a gel, then probed with an anti-NME7 antibody, showing that the two unique NME7 species that are naturally occurring in breast cancer cells and that interact with MUC1* are an NME7$_{AB}$-like species and NME7-X1 (FIG. 22E). A similar experiment was carried out in human stem cells. FIG. 23A-23C show photographs of Western blots of a co-immunoprecipitation experiment. Human induced pluripotent stem, iPS7, or embryonic stem, HES3, cell extracts were incubated with an antibody against the MUC1 cytoplasmic tail, Ab-5, or a control antibody, IgG, and co-immunoprecipitated. The gel was blotted with a commercially available anti-NME7 antibody B9 (FIG. 23A). Both cell types show unique NME7 bands at ~33 kDa and ~30 kDa. The gel was stripped and re-probed with an antibody against the extracellular domain of MUC1*, anti-PSMGFR (FIG. 23B), which shows that the NME7 species and MUC1* interact. A recombinant $NME7_{AB}$ and a recombinant NME7-X1 that we made were mixed together and run on a gel, then probed with an anti-NME7 antibody, showing that the two unique NME7 species that are naturally occurring in breast cancer cells and that interact with MUC1* are an $NME7_{AB}$-like species and NME7-X1 (FIG. 23C). Because $NME7_{AB}$ is a recombinant protein, we do not know if the naturally occurring species may contain an extra 1-15 additional amino acids or devoid of 1-15 additional amino acids than the recombinant $NME7_{AB}$, yet run with the same apparent molecular weight. By "$NME7_{AB}$-like", we mean an NME7 species that runs with an apparent molecular weight of approximately 33 kDa that is able to function the way the recombinant $NME7_{AB}$ does, in that it is able to stimulate cancer cell growth, induce transition of cancer cells to a more metastatic state and is able to fully support pluripotent growth of human stem cells.

We conclude that cancer cell lines and cancer cell populations that express NME7 and lower molecular weight NME7 species contain some cancer cells that are CSCs or metastatic cancer cells. These cancers can be made more metastatic or increase the population of cells that are metastatic by culturing the cells in $NME7_{AB}$, NME7-X1 or lower molecular weight NME7 species. FIG. 19 shows a Western blot of a panel of cancer cells all expressing NME7 as well as lower molecular weight species $NME7_{AB}$-like at 33 kDa and NME7-X1 at 30 kDa. FIG. 21 shows that cancer cell lines T47D breast cancer, PC3 and DU145 prostate cancer, BT-474 breast cancer, CHL-1 and A2058 both melanoma cell lines and CAPAN-2 and PANC-1 both pancreatic cell lines all express MUC1 and MUC1*. In FIG. 21A, BT474 cells appear not to express MUC1 or MUC1* however, we previously showed (Fessler et al 2009) that when these HER2 positive breast cancer cells become resistant to chemotherapy drugs, i.e. metastatic, they do so by increasing expression of MUC1* (FIG. 21D). Blocking the MUC1* receptor with an anti-MUC1* Fab reversed their resistance to Herceptin (FIG. 21E), Taxol (FIG. 21F) as well as other chemo agents. These cancer types and other cancer types that express NME7 and lower molecular weight NME7 species such as 33 kDa, 30 kDa can be made more metastatic or increase the population of cells that are metastatic by culturing the cells in $NME7_{AB}$, NME7-X1 or lower molecular weight NME7 species.

Conversely, the metastatic potential of these and other cancer types that express NME7 and lower molecular weight NME7 species such as 33 kDa or 30 kDa can be reversed by treating the cells with anti-NME7 antibodies. Anti-NME7 antibodies or antibodies that bind to $NME7_{AB}$ or NME7-X1 are administered to a patient for the treatment or prevention of cancers including breast, prostate, ovarian, pancreatic and liver cancers. Because we have shown that $NME7_{AB}$ exerts its tumorigenic effects by binding to and activating the MUC1* growth factor receptor, anti-NME7 antibodies will be effective against any MUC1*-positive cancers, which include but are not limited to breast, lung, liver, pancreatic, gastric colorectal, prostate, brain, melanoma, kidney and others. Anti-NME7, anti-$NME7_{AB}$ or anti-NME7-X1 antibodies are administered to patients for the treatment or prevention of cancers that are $NME7_{AB}$, $NME7_{AB}$-like, or NME7-X1 positive or a MUC1* positive.

Testing Patient Cancer Cells for Effective Therapies $NME7_{AB}$, NME7-X1 as well as 2i and other reagents that revert stem cells to a more naïve state also induce cancer cells to transform to a more metastatic state. After treatment with any one or combination of these reagents, cancer cells have a higher engraftment rate and require up to 100,000-times less cells to cause a tumor to form in a test animal. Therefore, methods described in this disclosure can be used to enable xenografting of a patient's primary tumor cells into a test animal.

Candidate therapeutic agents can then be tested on the recipient animal. Effective therapeutic agents identified in this way can be used to treat the donor patient or other patients with similar cancers. In one embodiment, a method of identifying effective therapeutics for a particular patient or a particular type of cancer comprises the steps of: 1) cancer cells are obtained from a cell line, a patient or a patient to whom the therapeutic being tested will be administered; 2) cancer cells are cultured in $NME7_{AB}$, NME7-X1, human NME1, bacterial NME1 that has high homology to human NME1 or NME7, 2i, or other reagents shown to revert stem cells to a more naïve state; 3) resultant cancer cells are implanted into a test animal to which human $NME7_{AB}$, NME7-X1, human NME1, bacterial NME1 that has high homology to human NME1 or NME7, 2i, or other reagents shown to revert stem cells to a more naïve state may also be administered or animal is transgenic for human $NME7_{AB}$ or NME7-X1; 4) candidate anti-cancer therapeutic agents are administered to the animal; 5) efficacy of the therapeutic agents are assessed; and 6) effective therapeutic agent is administered to the donor patient or to another patient with similar cancer.

Anti-NME7 Antibodies

Anti-NME7 antibodies are potent anti-cancer agents. NME7 is a growth factor that promotes the growth of cancer cells and also promotes their progression to a more metastatic state or a more aggressive state. NME7 and a truncated form of NME7 that is ~33 kDa or 30 kDa have been shown to fully support cancer growth even in serum-free media devoid of any other growth factors or cytokines. In pull-down assays, ELISAs and nanoparticle binding experiments, we have shown that the growth factor receptor MUC1* is a binding partner of NME7 and $NME7_{AB}$. Promotion of this interaction by eliminating all other growth factors or cytokines increased expression of cancer stem cell markers. Blocking this interaction even in the presence of serum, using a polyclonal antibody that specifically binds to NME7 actively killed the cancer cells. Thus, anti-NME7 or anti-$NME7_{AB}$ antibodies are potent anti-cancer agents that can be administered to a patient for the treatment or prevention of cancers. More than 75% of all cancers are MUC1* positive. MUC1* is the transmembrane cleavage product of MUC1 wherein most of the extracellular domain has been shed, leaving a portion of the extracellular domain that contains most of the PSMGFR sequence and may contain 9-20 additional amino acids N-terminal to the boundary of the of the PSMGFR sequence.

One aspect of the invention is a method of treating or preventing cancer in a subject, comprising administering to the subject an effective amount of an anti-NME7 antibody. In one instance, the anti-NME7 antibody is able to bind to $NME7_{AB}$. In another instance, the anti-NME7 antibody is able to bind to NME7-X1. In yet another instance, the anti-NME7 antibody that is administered to a patient inhibits or prevents its binding to its target in the promotion of cancers. In one case, the target is the extracellular domain of a cleaved MUC1. More specifically, the NME7 target that promotes cancer is the PSMGFR region of the MUC1* extracellular domain. In one aspect, an effective therapeutic agent is one that disrupts or prevents the interaction between an NME7 species and MUC1* extracellular domain, consisting primarily of the PSMGFR portion of MUC1* or the PSMGFR peptide. Agents for the treatment or prevention of cancers are those agents that directly or indirectly inhibit the expression or function of NME7, an $NME7_{AB}$-like cleavage product or alternative isoform, including NME7-X1. In one case an effective anti-cancer therapeutic agent is one that binds to the NME7 species or disables its tumorigenic activity. An effective therapeutic agent for the treatment or prevention of cancers is an agent that binds to or disables NME7, an $NME7_{AB}$-like cleavage product or alternative isoform, or NME7-X1. In one aspect, the therapeutic agents that binds to the NME7 species is an antibody. The antibody may be polyclonal, monoclonal, bispecific, bivalent, monovalent, single chain, scFv, or an antibody mimic that may be animal in origin, human-animal chimera, humanized or human. The antibody can be generated by inoculation or immunization with an NME7 species or fragment thereof or selected, for example from a library or a pool of antibodies, for their ability to bind to an NME7 species, including NME7, an $NME7_{AB}$-like cleavage product or alternative isoform, including NME7-X1.

Generation of Anti-NME7 Antibodies

Anti-NME7 antibodies can be generated outside of the patient such as in a host animal or in a patient. Antibodies can be generated by immunization of NME7 or NME7 fragments or selected from a library or pool of antibodies that may be natural, synthetic, whole or antibody fragments based on their ability to bind to desired NME7 species such as $NME7_{AB}$ or NME7-X1. In one aspect, the antibody is generated from immunization with, or selected for its ability to bind to, a peptide selected from those listed in FIG. 6-9. In another aspect, the antibody is generated from peptides whose sequences are not identical to those of human NME1 or the antibodies are selected for their ability to bind to NME7 species and their inability to bind to human NME1.

One method used to identify NME7 or NME7-X1 derived peptides that give rise to antibodies that inhibit cancer growth and inhibit transition to metastasis or peptides that are themselves inhibitory is as follows: 1) protein sequences of human NME1, human NME7, human NME7-X1 and several bacterial or fungal NME proteins that have high sequence homology to either human NME1 or human NME7 are aligned; 2) regions of high sequence homology among all the NMEs are identified; 3) peptide sequences that are unique to NME7 or NME7-X1 but are flanking the regions of high sequence homology are identified. The peptides are then synthesized and used to generate antibodies in a human or host animal. The resultant antibodies are selected for therapeutic use if: 1) they bind to $NME7_{AB}$ or NME7-X1, but not to NME1; 2) have the ability to inhibit cancer growth; 3) have the ability to inhibit the transition of cancer cells to a more metastatic state; or 4) inhibit metastasis in vivo. In some cases, antibodies for therapeutic use are selected for their ability to disrupt binding of $NME7_{AB}$ or NME7-X1 to the MUC1* extra cellular domain, to the PSMGFR peptide or to the N-10 peptide.

Use of Anti-NME7 Antibody for Treatment of Cancer

Figure 11:
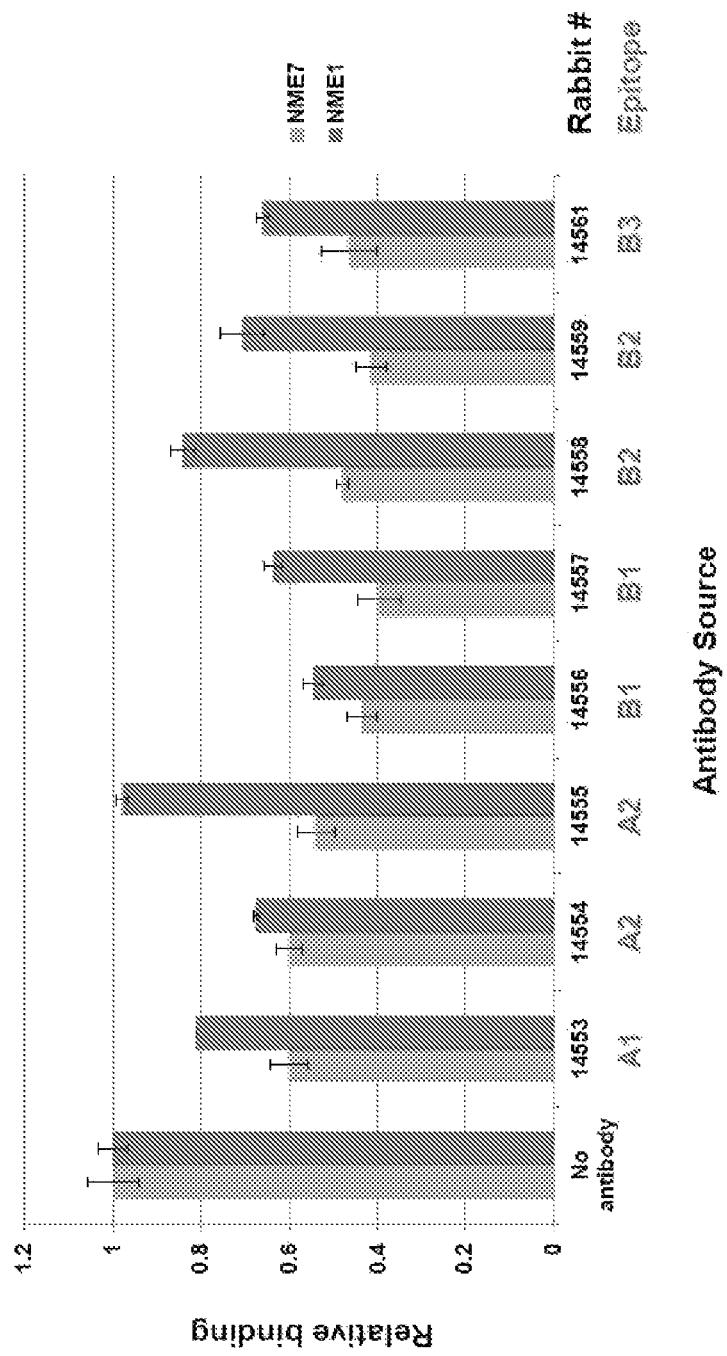
FIG. 11 shows graphs of ELISA assays in which anti-NME7 antibodies generated are tested for their ability to inhibit binding of NME7-AB to a surface immobilized MUC1* peptide but not inhibit binding of NME1.
Figure 15A:
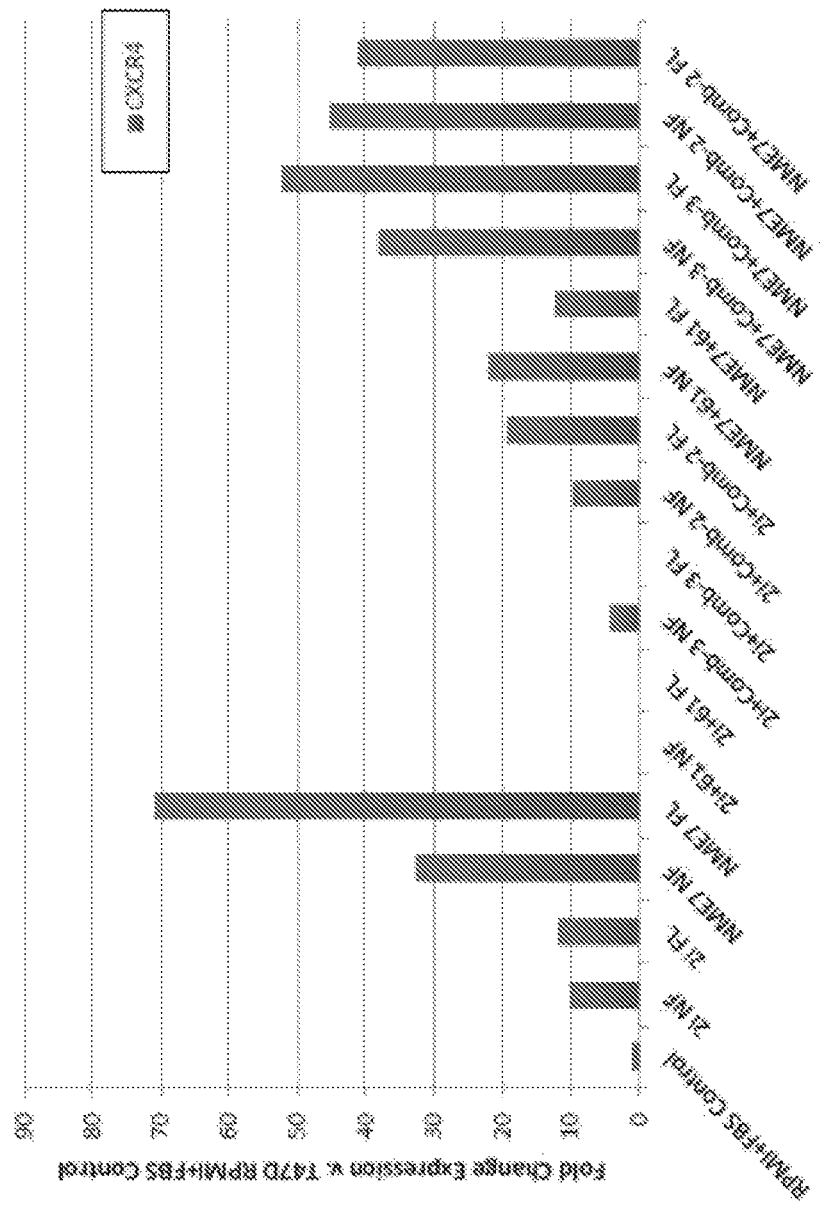
FIGS. 15A-15C show graphs of RT-PCR measurements of expression of CXCR4 and other metastatic markers in T47D breast cancer cells that were grown in either NME7-AB or 2i inhibitors, each of which transform cancer cells to a more metastatic state, and the inhibitory effect of anti-NME7 antibodies on the metastatic transformation.

Those antibodies that inhibit cancer growth or transition to a more metastatic state are selected for use as anti-cancer therapeutics and may be administered to a patient for the treatment or prevention of cancers. Selected antibodies may be further optimized for example by engineering or making human chimera antibodies or fully human antibodies. To demonstrate the efficacy of this approach, we selected NME7 peptides from regions of NME7 suspected to be critical to its cancerous function. We then generated antibodies using these peptides and then tested both the resultant antibodies as well as the immunizing peptides for their ability to: a) inhibit cancerous growth; and b) inhibit the induced transition from cancer cells to metastatic cancer cells. NME7 peptides were selected as immunizing agents for antibody production and as inhibitory agents themselves (FIG. 9, Example 7). Peptides A1 (SEQ ID NO:141), A2 (SEQ ID NO:142), B1 (SEQ ID NO:143), B2 (SEQ ID NO:144) and B3 (SEQ ID NO:145), wherein A refers to the domain from which the peptide is derived, i.e. the NDPK A domain and the B denotes that the peptide is derived from the NDPK B domain (FIG. 5). Each peptide was used as an immunogen and injected into 2 rabbits each for production of polyclonal antibodies. The antibodies that were harvested from the blood of the immunized rabbits were purified over a column derivatized with the immunizing peptide. The purified antibodies were then tested for their ability to bind to human NME7. All of the resultant antibodies bound to human NME7 but not human NME1 as desired (FIG. 10A-10B, Example 8). These results show that by choosing peptides whose sequence is found in NME7 but not exactly identical in NME1, antibodies are generated that specifically bind to NME7 but not NME1. Because NME1 has healthy function, it is in most cases desirable to generate antibodies that do not interfere with NME1. The antibodies were also tested for their ability to inhibit the binding of NME7 to a MUC1* extracellular domain peptide. The ELISA experiment shown in FIG. 11 shows that the antibodies inhibited the binding of $NME7_{AB}$ to a MUC1* extracellular domain peptide much more than they inhibited binding of NME1. Recall that each of the NME7 A domain and B domain can bind to a PSMGFR peptide. Therefore, complete inhibition of $NME7_{AB}$ binding to a PSMGFR peptide cannot be accomplished with a single antibody or peptide that is derived from just one domain. These antibodies and their respective immunizing peptides also inhibited cancer cell growth (FIG. 12-13). These antibodies also inhibited the formation of non-adherent "floater" cells that result from growing cancer cells in $NME7_{AB}$ (FIG. 14). As can be seen in the figure, the polyclonal antibody generated by immunization with the B3 peptide reduced the number of metastatic floater cells by 95%, indicating that anti-NME7 antibodies that bind to the B3 peptide are most effective at inhibiting cancer metastasis. Similarly, the antibodies inhibited the expression of metastatic marker CXCR4 (FIG. 15A). Again, the B3 antibodies were most efficient at inhibiting expression of CXCR4; bar labeled NME7 FL (NME7 floater cells) shows 70-fold increase in CXCR4 that B3 antibody 61 decreased to 20-fold (bar labeled NME7+61 FL). In addition, the immunizing peptides themselves inhibited the upregulation of CXCR4 and other metastatic markers when T47D cancer cells were grown in $NME7_{AB}$ or 2i.

This is but one example of selecting peptides that generate antibodies that inhibit the cancerous function of NME7 and NME7 species. Sequence alignment among human NME1, human NME7, human NME7-X1 and bacterial NME proteins that had high sequence homology to human NME1 or NME7 identified five regions of homology. The fact that peptides A1, A2, B1, B2 and B3 all generated antibodies that inhibited cancer growth or their transition to a metastatic state means that the five regions from which these peptides were derived are regions of NME7 that are important for its function in the promotion of cancer. Other peptides from these regions will also give rise to anti-NME7 antibodies that will inhibit cancer growth and metastasis and are therefore potent anti-cancer therapeutics. Antibodies generated from peptides A1, A2, B1, B2 and B3 were shown to inhibit cancer growth and inhibited the transition to a more metastatic state. Monoclonal antibodies generated by immunization with the same or similar peptides and subsequent testing of the monoclonals will identify antibodies that, after humanizing or other engineering known to those skilled in the art, would be administered to a patient for the treatment or prevention of cancers.

In a particular experiment, the antibodies generated by immunization with peptides A1, A2, B1, B2 and B3, as well as the immunizing peptides themselves, were added to cancer cells in culture to see if the addition of the antibodies or the immunizing peptides would inhibit cancer cell growth. At low concentrations and added separately, the antibodies as well as the immunizing peptides inhibited cancer cells growth (FIG. 12 for one example). However, when added at higher concentrations or combined, the antibodies as well as the immunizing peptides robustly inhibited cancer cell growth (FIG. 13). The corresponding human NME7 amino acid numbers of immunizing peptides A1, A2, B1, B2 and B3 are 127-142, 181-191, 263-282, 287-301, 343-371, respectively, from human full-length NME7 having SEQ ID NO:82 or 147.

To clarify, when residue numbers of NME7 are discussed, they refer to the residue numbers of NME7 as set forth in SEQ ID NO:82 or 147.

The antibody used in cancer growth inhibition experiments and one of the antibodies shown in FIG. 12 was generated by immunizing with NME7 peptide corresponding to amino acids 100-376 of NME7 (SEQ ID NO:82 or 147). To generate higher affinity and specific anti-NME7 antibodies, the following steps are followed: immunize animal with a peptide containing human NME7 amino acids 100-376, then: 1) de-select those antibodies that bind to human NME1; 2) select those antibodies that inhibit $NME7_{AB}$, 2i, or other NME induced transition of cancer cells to a more metastatic state; 3) select those antibodies that inhibit the growth of cancer cells; 4) select those antibodies that inhibit the growth of MUC1* positive cancer cells; 5) select those antibodies that inhibit binding of $NME7_{AB}$ or NME7-X1 to MUC1* extracellular domain, essentially inhibit binding to the PSMGFR peptide; and/or 6) select those antibodies that bind to one or more of the peptides listed in FIG. 9—A1, A2, B1, B2 or B3 peptides.

Higher affinity monoclonal antibodies or monoclonal antibodies generated from longer peptides may be more effective antibody therapeutics. Alternatively, combinations of anti-NME7, anti-$NME7_{AB}$ or anti-NME7-X1 antibodies are administered to a patient to increase efficacy.

Anti-NME7 Antibodies Inhibit the Transition of Cancer Cells to Metastatic Cancer Cells.

Anti-NME7 antibodies inhibit transition of cancer cells to metastatic cancer cells also called cancer stem cells (CSCs) or tumor initiating cells (TICs). Recall that we have demonstrated that culturing a wide variety of cancer cells in the presence of $NME7_{AB}$ causes them to transition from regular cancer cells to the metastatic CSCs or TICs. Thus, antibodies that bind to NME7, $NME7_{AB}$ or NME7-X1 will inhibit the progression of cancer cells to a more metastatic state.

Cancer cells transform to a more metastatic state when cultured in the presence of agents that revert stem cells to a more naïve state. We have demonstrated that culturing cancer cells in $NME7_{AB}$, human NME1 dimers, bacterial NME1 dimers or MEK and GSK3-beta inhibitors, called "2i", causes the cells to become more metastatic. As the cells transition to a more metastatic state, they become non-adherent or less adherent and float off of the culture plate. These floating cells, "floaters" were collected separately from those that were adherent and were shown to: a) express much higher levels of metastatic genes; and b) generated tumors when xenografted into mice at very low copy number. RT-PCR measurement of specific metastatic markers such as CXCR4 for breast cancers, CHD1 for prostate cancer, and other pluripotent stem cell markers such as OCT4, SOX2, NANOG, KLF4 and others were dramatically over-expressed in cancer cells that were cultured in $NME7_{AB}$ and most over-expressed in the cells that became non-adherent, called "floaters" here and in figures.

In one example, $NME7_{AB}$ specific antibodies, generated by immunization with NME7-derived peptides A1, A2, B1, B2 and B3, as well as the immunizing peptides themselves, were added into the media along with either $NME7_{AB}$ or 2i to determine if they inhibited the transformation of regular cancer cells to metastatic cancer stem cells. Antibodies and peptides were separately added along with the agent that causes metastatic transformation; in this case $NME7_{AB}$ or the 2i inhibitors PD0325901 and CHIR99021. $NME7_{AB}$ and 2i were separately used to induce the cancer cells to be transformed to a more aggressive metastatic state. 2i was used so that it could not be argued that the antibodies that were added to the media simply sopped up all of the $NME7_{AB}$ so that the causative agent effectively was not there (Example 10).

Figure 15B:
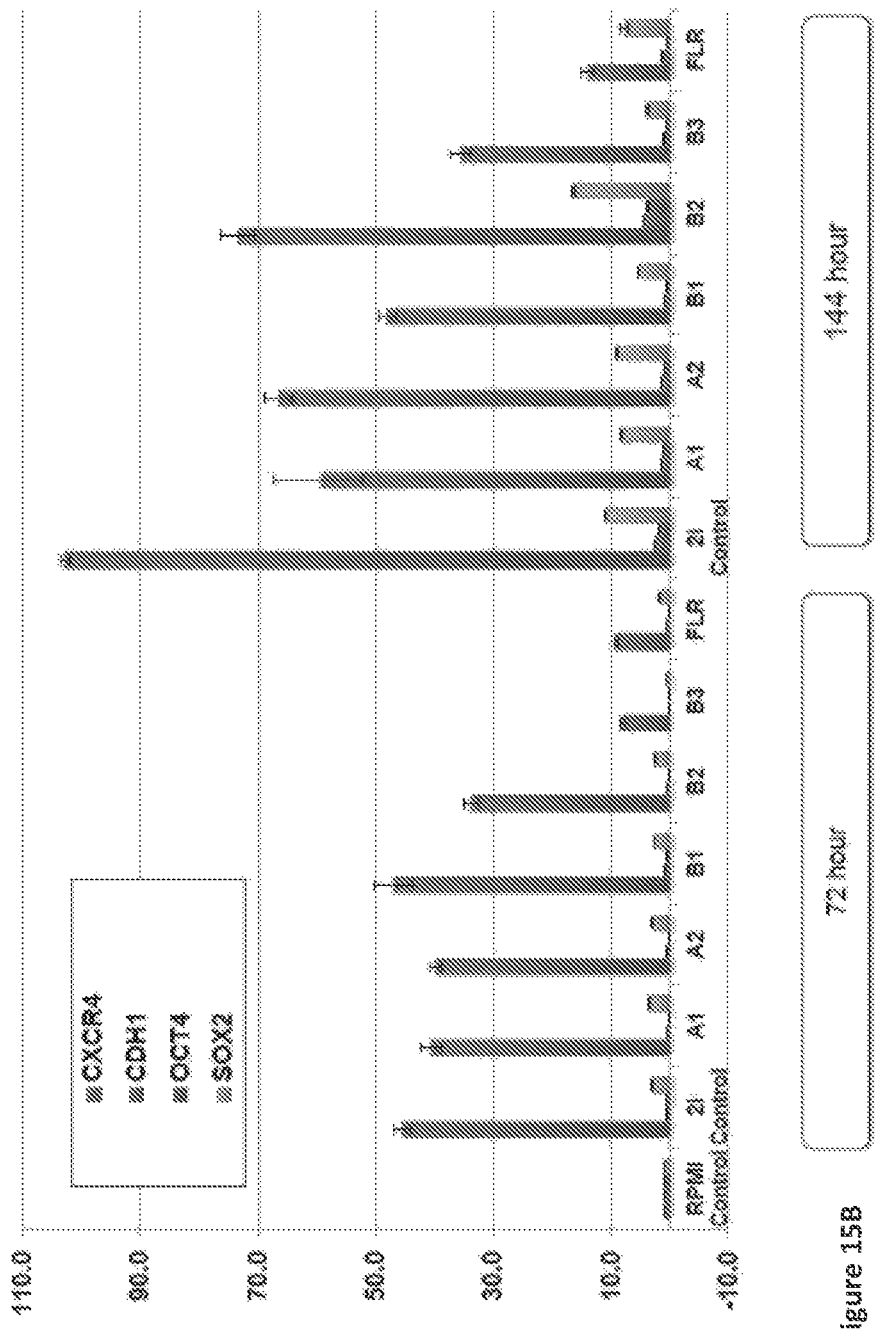
Figure 15C:
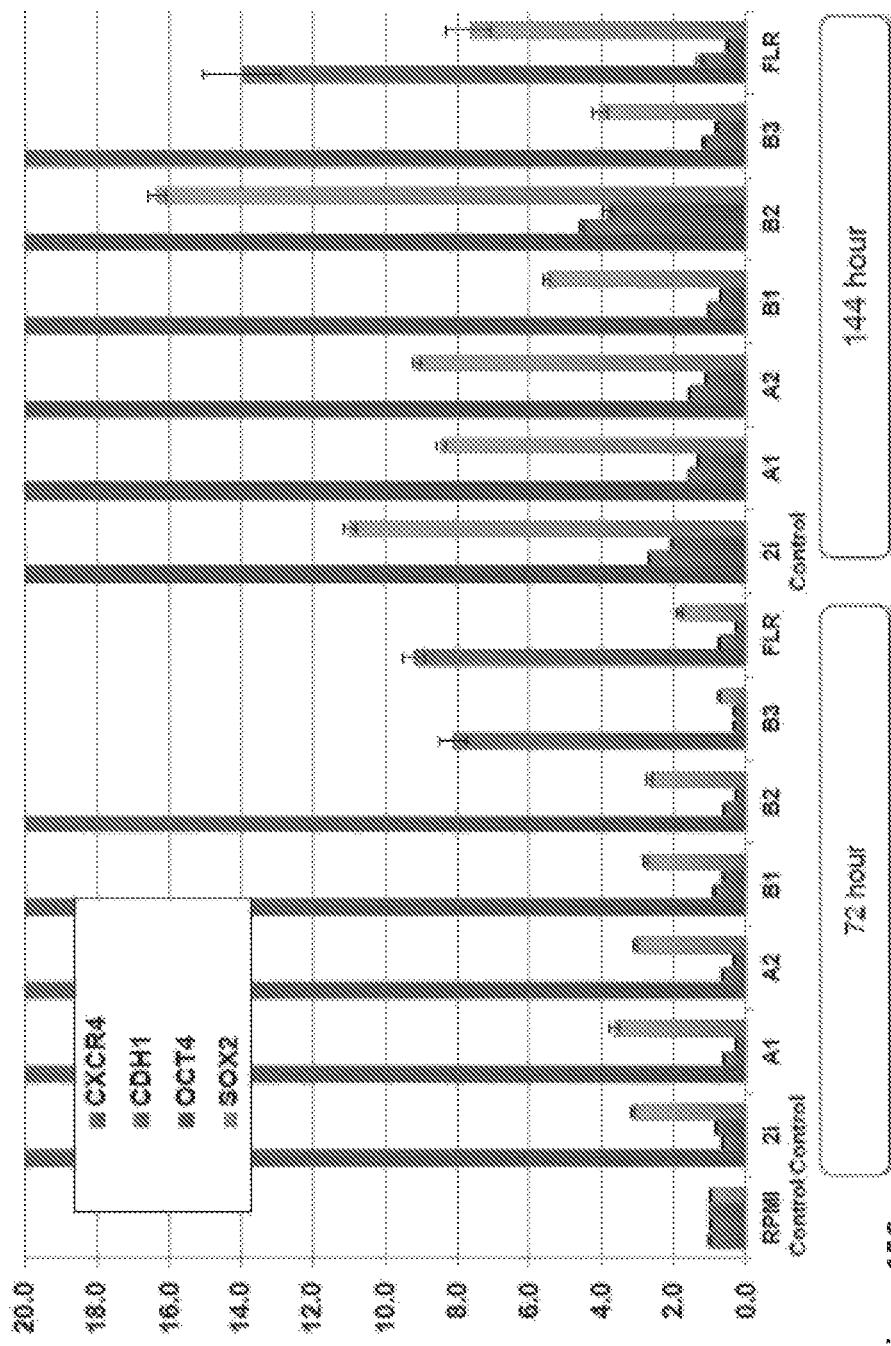

Visual observation was independently recorded by two scientists as the experiment progressed (FIG. 14). The most striking observation was that the antibodies and the peptides dramatically reduced the number of floater cells, which was the first indication that the antibodies and peptides inhibit the transformation to metastatic cancer cells. In particular, cells to which the antibody generated from immunization with the B3 peptide barely generated any floater cells. mRNA was extracted from both the floater cells, the adherent cells and the control cancer cells. The amount of mRNA, which indicates cell viability and growth, was measured. Cells that were treated with antibody had much less mRNA, indicating less live dividing cells (FIG. 16), which confirms that anti-$NME7_{AB}$ antibodies inhibit cancer cell growth as well as their transition to a more metastatic state. RT-PCR was used to measure expression levels of metastatic markers, including CXCR4. Treatment with the anti-NME7 antibodies greatly reduced the amount of metastatic markers, such as CXCR4, indicating that the anti-NME7 antibodies or peptides inhibit the transition to metastatic cancer (FIG. 15A-15C). These results show that antibodies that bind to $NME7_{AB}$ can be administered to a patient for the treatment or prevention of metastatic cancers.

Peptides Derived from $NME7_{AB}$ or NME7-X1 Competitively Inhibit the Binding of Intact $NME7_{AB}$ and NME7-X1 and are Anti-Cancer Agents.

In another aspect of the invention, therapeutic agents for the treatment or prevention of cancers are peptides derived from the NME7 sequence, which are administered to a patient for the treatment or prevention of cancers. In one aspect, the NME7-derived peptides are administered to a patient so that the peptides, which should be shorter than the entire NME7 and unable to confer the oncogenic activity of NME7, bind to the targets of NME7 and competitively inhibit the interaction of intact NME7 with its targets, wherein such interactions promote cancer. Since $NME7_{AB}$ is fully able to confer oncogenic activity, the sequence of NME7$_{AB}$ is preferred as the source for the shorter peptide(s), wherein it must be confirmed that the peptides themselves are not able to promote cancerous growth or other tumorigenic or oncogenic activity. In a preferred embodiment, one or more peptides having the sequence of a portion of NME7$_{AB}$ and being preferably about 12-56 amino acids in length are administered to a patient. To increase half-life, the peptides may be peptide mimics, such as peptides with unnatural backbone or D-form amino acids for L. In yet another case, the anti-cancer therapeutic agent is a peptide or peptide mimic wherein the peptide has a sequence highly homologous to at least a portion of NME7, NME7$_{AB}$, or NME7-X1 or its target the MUC1* extracellular domain, comprising the PSMGFR peptide, also called "FLR" in some cases herein.

FIG. 6-FIG. 9 provide a listing of preferred amino acid sequences that are predicted to inhibit NME7 binding to its cognate target. In a still more preferred embodiment, the peptides that are chosen for administration to a patient suffering from cancer or at risk of developing cancer are chosen because they bind to an NME7 binding partner and they do not themselves confer tumorigenic activity. In a yet more preferred embodiment, the NME7 binding partner is the extracellular domain of MUC1*. In a still more preferred embodiment, the NME7 binding partner is the PSMGFR peptide.

By the term "conferring tumorigenic activity or oncogenic activity", it is meant that the peptides themselves cannot support or promote the growth of cancers. Another way of testing whether or not a peptide or peptides derived from NME7 can promote tumorigenesis is to test whether or not the peptides can support pluripotent growth of human stem cells. NME proteins and peptides that support pluripotent human stem cell growth also support cancer growth. In yet another method, peptides are de-selected if they can cause somatic cells to revert to a less mature state.

Fragments of NME7$_{AB}$ inhibit cancer cell growth and the transition of cancer cells to a more metastatic state. As a demonstration, NME7 peptides A1, A2, B1, B2 and B3 added separately (FIG. 12) or in combinations (FIG. 13) inhibit the growth of cancer cells. In addition, NME7 peptides A1, A2, B1, B2 and B3 inhibited the transition of cancer cell to a more metastatic state (FIG. 15).

Thus, antibodies generated by immunizing with peptides specific to NME7, and specific to NME7$_{AB}$ or NME7-X1 will block the cancerous action of NME7 species and will be potent anti-cancer agents. Similarly, these results show that the peptides specific to NME7, and specific to NME7$_{AB}$ or NME7-X1 will block the cancerous action of NME7 species. In one aspect of the invention, the peptides are chosen from the list shown in FIG. 6. In one aspect of the invention the peptides are chosen from the list shown in FIG. 7. In one aspect of the invention the peptides are chosen from the list shown in FIG. 8. In yet another aspect of the invention the peptides are chosen from the list shown in FIG. 9. These antibodies may be generated by immunizing or may be generated or selected by other means, then selected for their ability to bind to NME7, NME7$_{AB}$, NME7-X1 or NME7 derived peptides, including but not limited to NME7 derived peptides A1 (SEQ ID NO: 141), A2 (SEQ ID NO: 142), B1 (SEQ ID NO: 143), B2 (SEQ ID NO: 144) or B3 (SEQ ID NO: 145). Such antibodies may be polyclonal, monoclonal, bispecific, bivalent, monovalent, single chain, scFv, human or humanized or may be an antibody mimic such as protein scaffolds that present recognition regions that bind to a specific target.

Anti-NME7 antibodies for use in the treatment or prevention of cancers can be generated by standard methods known to those skilled in the art wherein those methods are used to generate antibodies or antibody-like molecules that recognize NME7, NME7$_{AB}$ or a shorter form of NME7$_{AB}$ wherein an additional 10-25 amino acids form the N-terminus are not present. Such antibodies may be human or humanized. Such antibodies may be polyclonal, monoclonal, bispecific, bivalent, monovalent, single chain, scFv, human or humanized or may be an antibody mimic such as protein scaffolds that present recognition regions that bind to a specific target.

Anti-NME7 antibodies that are generated by immunization with the NME7 derived peptides A1 (SEQ ID NO: 141), A2 (SEQ ID NO: 142), B1 (SEQ ID NO: 143), B2 (SEQ ID NO: 144) or B3 (SEQ ID NO: 145) or antibodies that bind to the A1, A2, B1, B2 or B3 peptides are antibodies that bind to NME7$_{AB}$ and NME7-X1, but resist binding to NME1 which may be required for the function of some healthy cells. Such antibodies inhibit the binding of NME7$_{AB}$ or NME7-X1 to their target receptor, MUC1*. Antibodies that bind to A1, A2, B1, B2 or B3 peptides are antibodies can be administered to a patient diagnosed with or at risk of developing a cancer or metastasis. Such antibodies may be human or humanized. Such antibodies may be polyclonal, monoclonal, bispecific, bivalent, monovalent, single chain, scFv, or may be an antibody mimic such as protein scaffolds that present recognition regions that bind to a specific target.

Anti-NME7 antibodies that are generated by immunization with the B3 peptide or antibodies that bind to the B3 peptide are especially specific for the recognition of NME7$_{AB}$ and NME7-X1. Such antibodies are also very efficient at inhibiting the binding of NME7$_{AB}$ or NME7-X1 to their target receptor, MUC1*. Antibodies that bind to the B3 peptide are also exceptionally efficient at preventing, inhibiting and reversing cancer or cancer metastases. Such antibodies may be human or humanized. Such antibodies may be polyclonal, monoclonal, bispecific, bivalent, monovalent, single chain, scFv, or may be an antibody mimic such as protein scaffolds that present recognition regions that bind to a specific target.

Note that the polyclonal antibody #61, which was generated in rabbits immunized with the B3 peptide, inhibited the transformation of cancer cells to cancer stem cells as evidenced by antibody #61 blocking upregulation of metastatic marker CXCR4 (FIG. 15).

The B3 peptide (SEQ ID NO: 145) derived from NME7 has a Cysteine at position 14, which complicates the generation of anti-NME7 antibodies. We mutated Cysteine 14 to Serine to make AIFGKTKIQNAVHSTDLPEDG-LLEVQYFF (SEQ ID NO:169) and immunized animals to generate anti-NME7 monoclonal antibodies. The resultant antibodies bind to the native B3 sequence as well as the B3Cys14Ser peptide. Seven (7) high affinity and specific monoclonal antibodies were generated: 8F9A5A1, 8F9A4A3, 5F3A5D4, 5D9E2B11, 5D9E10E4, 5D9G2C4, and 8H5H5G4. However, various sequence alignments showed that there are only three (3) unique sequence antibodies: 8F9A5A1, 8F9A4A3, 8F9A4P3 and 5F3A5D4 as seen below. Bolded and underlined regions indicate CDR sequences.

HEAVY CHAIN ALIGNMENT

```
8F9A5A1H    IQLVQSGPELKKPGETVKISCKASGYTFTNYGMNWVKQAPGKGLKWMGWINTYTGEPTYV  60
8F9A4A3H    VQLQQSGPELVKPGASVKISCKTSGNTFTEYTMHWVKQSHGKSLEWIGGFNPNNGVTNYN  60
5D9E2B11H   VQLQQSGPDLVKPGTSVKISCKTSGNTFTEYTMHWVKQSHGKSLEWIGGENPNNGVTNYN  60
5D9E10E4H   VQLQQSGPDLVKPGTSVKISCKTSGNTFTEYTMHWVKQSHGKSLEWIGGFNPNNGVTNYN  60
5D9G2C4H    VQLQQSGPDLVKPGTSVKISCKTSGNTFTEYTMHWVKQSHGKSLEWIGGFNPNNGVTNYN  60
5F3A5D4H    VQLQQSGPDLVKPGTSVKISCKTSGNTFTEYTMHWVKQSHGKSLEWIGGENPNNGVTNYN  60
8H5H5G4H    VQLQQSGPDLVKPGTSVKISCKTSGNTFTEYTMHWVKQSHGKSLEWIGGFNPNNGVTNYN  60
            :** ****:* *** :******:** ***:* *:**** *  **.*:*:*  :* .* .*

8F9A5A1H    DDFKGRFAFSLETSATTAYLQINNLKNEDTSTYFCARLR--GIRPGPLAYWGQGTLVTVS  118
8FIA4A3H    QKFKGKATLTVDKSSSTAYMELRSLTSEDSAVYYCARRYYHSLYVFYFDYWGQGTTLTVS  120
            QKFKGKATLTVDKSSSTAYMELRSLTSEDSAVYYCARRYYHSTYVFYFDSWGQGTT----  116
            QKFKGKATLTVDKSSSTAYMELRSLTSEDSAVYYCARRYYHSTYVFYFDSWGQGTTLTVS  120
            QKFKGKATLTVDKSSSTAYMELRSLTSEDSAVYYCARRYYHSTYVFYFDSWGQGTTLTVS  120
            QKFKGKATLTVDKSSSTAYMELRSLTSEDSAVYYCARRYYHSTYVFYFDSWGQGTTLTVS  120
            QKFKGKATLTVDKSSSTAYMELRSLTSEDSAVYYCARRYYHSTYVFYFDSWGQGTTLTVS  120
            :.***:  ::::::.*::***:::..*..**::.*:***    :       : *****

8F9A4P3H    A 119 (SEQ ID NO: 172)
8F9A4A3H    S 121 (SEQ ID NO: 173)
5D9E2B11H   - 116 (SEQ ID NO: 174)
5D9E10E4H   S 121 (SEQ ID NO: 175)
5D9G2C4H    S 121 (SEQ ID NO: 175)
5F3A5D4H    S 121 (SEQ ID NO: 175)
8H5H5G4H    S 121 (SEQ ID NO: 175)

8F9A4P3H    VQLQQSGPELVKPGASVKISCKTSGNTFTEYTMHWVKQSHGKSLEWIGGFNPNNGVTNYN  60
8F9A4A3H    VQLQQSGPELVKPGASVKISCKTSGNTFTEYTMHWVKQSHGKSLEWIGGFNPNNGVTNYN  60
5D9E2B11H   VQLQQSGPDLVKPGTSVKISCKTSGNTFTEYTMHWVKQSHGKSLEWIGGFNPNNGVTNYN  60
5D9E10E4H   VQLQQSGPDLVKPGTSVKISCKTSGNTFTEYTMHWVKQSHGKSLEWIGGFNPNNGVTNYN  60
5D9G2C4H    VQLQQSGPDLVKPGTSVKISCKTSGNTFTEYTMHWVKQSHGKSLEWIGGFNPNNGVTNYN  60
5F3A5D4H    VQLQQSGPDLVKPGTSVKISCKTSGNTFTEYTMHWVKQSHGKSLEWIGGFNPNNGVTNYN  60
8H5H5G4H    VQLQQSGPDLVKPGTSVKISCKTSGNTFTEYTMHWVKQSHGKSLEWIGGFNPNNGVTNYN  60
            ********:*****:*********************************************

8F9A4P3H    QKFKGKATLTVDKSSSTAYMELRSLTSEDSAVYYCARRYYHSLYVFYFDYWGQGTTLTVS  120
8F9A4A3H    QKFKGKATLTVDKSSSTAYMELRSLTSEDSAVYYCARRYYHSLYVFYFDYWGQGTTLTVS  120
5D9E2B11H   QKFKGKATLTVDKSSSTAYMELRSLTSEDSAVYYCARRYYHSTYVFYFDSWGQGTT----  116
5D9E10E4H   QKFKGKATLTVDKSSSTAYMELRSLTSEDSAVYYCARRYYHSTYVFYFDSWGQGTTLTVS  120
5D9G2C4H    QKFKGKATLTVDKSSSTAYMELRSLTSEDSAVYYCARRYYHSTYVFYFDSWGQGTTLTVS  120
5F3A5D4H    QKFKGKATLTVDKSSSTAYMELRSLTSEDSAVYYCARRYYHSTYVFYFDSWGQGTTLTVS  120
8H5H5G4H    QKFKGKATLTVDKSSSTAYMELRSLTSEDSAVYYCARRYYHSTYVFYFDSWGQGTTLTVS  120
            ******************************************      ****** *****

8F9A4P3H    S 121 (SEQ ID NO: 173)
8F9A4A3H    S 121 (SEQ ID NO: 173)
5D9E2B11H   - 121 (SEQ ID NO: 174)
5D9E10E4H   S 121 (SEQ ID NO: 175)
5D9G2C4H    S 121 (SEQ ID NO: 175)
5F3A5D4H    S 121 (SEQ ID NO: 175)
8H5H5G4H    S 121 (SEQ ID NO: 175)
```

LIGHT CHAIN ALIGNMENT

```
8F9A4P3L    ETTVTQSPASLSMAIGEKVTIRCITSTDIDDDMNWYQQKPGEPPKLLISEGNTLRPGVPS  60
8F9A4A3L    DIQMTQTTSSLSASLGDRVTLSCSASQGISNYLNWYQQKPDGTVELLIFYTSSLHSGVPS  60
5D9E2B11L   DIQMTQTTSSLSASLGDRVTISCSASQGISNYLNWFQQKPDGTIKLLIYYTSSLHSGVPS  60
5D9E10E4L   DIQMTQTTSSLSASLGDRVTISCSASQGISNYLNWFQQKPDGTIKLLIYYTSSLHSGVPS  60
5D9G2C4L    DIQMTQTTSSLSASLGDRVTISCSASQGISNYLNWFQQKPDGTIKLLIYYTSSLHSGVPS  60
5F3A5D4L    DIQMTQTTSSLSASLGDRVTISCSASQGISNYLNWFQQKPDGTIKLLIYYTSSLHSGVPS  60
8H5H5G4L    DIQMTQTTSSLSASLGDRVTISCSASQGISNYLNWFQQKPDGTIKLLIYYTSSLHSGVPS  60
8F9A5A1L    EILLTQSPAIIAASPGEKVTITCSASSSV-SYMNWYQQKPGSSPKIWIYGISNLASGVPA  60
             : :**: :  ::  : *:*** *  .* :**:****. *  ..  ..*  ***:

8F9A4P3L    RFSSSGYGTDFVFPTIENMLSEDVADYYCLQSDNLPLTFGSGTKLEIKR  108 (SEQ ID NO: 185)
8F9A4A3L    RFSGSGSGTDYSLTISNLEPEDIATYYCQQYSKLPYTFGGGTKLEIK    108 (SEQ ID NO: 1109)
5D9E2B11L   RFSGSGSGTDYSLTISNVEPEDIATYYCQQYSKLPYTFGGGTKLEIKR  108 (SEQ ID NO: 186)
5D9E10E4L   RFSGSGSGTDYSLTISNVEPEDIATYYCQQYSKLPYTFGGGTKLEIKR  108 (SEQ ID NO: 186)
5D9G2C4L    RFSGSGSGTDYSLTISNVEPEDIATYYCQQYSKLPYTFGGGTKLEIKR  108 (SEQ ID NO: 186)
5F3A5D4L    RFSGSGSGTDYSLTISNVEPEDIATYYCQQYSKLPYTFGGGTKLEIKR  108 (SEQ ID NO: 186)
8H5H5G4L    RFSGSGSGTDYSLTISNVEPEDIATYYCQQYSKLPYTFGGGTKLEIKR  108 (SEQ ID NO: 186)
8F9A5A1L    RFSGSGSGTSFSFTINSMEAEDVATYYCQQRSSYPPTFGGGTKLEIKR  108 (SEQ ID NO: 191)
            ***.** **.:  :**..: :** *** *  . * ***.*******

5D9E2B11L   DIQMTQTTSSLSASLGDRVTISCSASQGISNYLNWFQQKPDGTIKLLIYYTSSLHSGVPS  60
5D9E10E4L   DIQMTQTTSSLSASLGDRVTISCSASQGISNYLNWFQQKPDGTIKLLIYYTSSLHSGVPS  60
5D9G2C4L    DIQMTQTTSSLSASLGDRVTISCSASQGISNYLNWFQQKPDGTIKLLIYYTSSLHSGVPS  60
5F3A5D4L    DIQMTQTTSSLSASLGDRVTISCSASQGISNYLNWFQQKPDGTIKLLIYYTSSLHSGVPS  60
8H5H5G4L    DIQMTQTTSSLSASLGDRVTISCSASQGISNYLNWFQQKPDGTIKLLIYYTSSLHSGVPS  60
```

```
                  ************************************************************
5D9E2B11L         RFSGSGSGTDYSLTISNVEPEDIATYYCQQYSKLPYTFGGGTKLEIKR              108  (SEQ ID NO: 186)
5D9E10E4L         RFSGSGSGTDYSLTISNVEPEDIATYYCQQYSKLPYTFGGGTKLEIKR              108  (SEQ ID NO: 186)
5D9G2C4L          RFSGSGSGTDYSLTISNVEPEDIATYYCQQYSKLPYTFGGGTKLEIKR              108  (SEQ ID NO: 186)
5F3A5D4L          RFSGSGSGTDYSLTISNVEPEDIATYYCQQYSKLPYTFGGGTKLEIKR              108  (SEQ ID NO: 186)
8H5H5G4L          RFSGSGSGTDYSLTISNVEPEDIATYYCQQYSKLPYTFGGGTKLEIKR              108  (SEQ ID NO: 186)
                  ******************************************************

8F9A4P3L          ETTVTQSPASLSMAIGEKVTIRCITSTDIDDDMNWYQQKPGEPPKLLISEGNTLRPGVPS   60
8F9A5A1L          EILLTQSPATIAASPGEKVTITCSASSSV-SYMNWYQQKPGSSPKIWIYGISNLASGVPA   60
                  * :***** :: : ****** * :*:O: O *********. **: *   ..* ***:

8F9A4P3L          RFSSSGYGTDFVFTIENMLSEDVADYYCLQSDNLPLTFGSGTKLEIKR              108  (SEQ ID NO: 185)
8F9A5A1L          RFSGSGSGTSFSFTINSMEAEDVATYYCQQRSSYPPTFGGGTKLEIKR              108  (SEQ ID NO: 191)
                  ***.** **.* ***:.* :**** *** *  ..  * ***.********
```

Monoclonal antibodies 5D9E2B11, 5D9E10E4, 5D9G2C4, and 8H5H5G4 all have the same sequence as 5F3A5D4, also known as 5D4. Herein, when we refer to antibody 5F3A5D4, aka 5D4, it is understood that it also applies to 5D9E2B11, 5D9E10E4, 5D9G2C4, and 8H5H5G4. As can be seen in FIG. 24 and FIG. 25 anti-NME7 antibodies 8F9A5A1, 8F9A4A3, and 5F3A5D4 all bind to NME7$_{AB}$ but not to NME1. This is important because the A domain of NME7 has high homology to NME1, which is required for normal cell function. For an anti-cancer therapeutic or an anti-metastasis therapeutic it will be imperative to inhibit NME7$_{AB}$ but not NME1.

FIG. 26, FIG. 27 and FIG. 28 show that these anti-NME7 antibodies are also able to disrupt the binding of NME7$_{AB}$ to the MUC1* PSMGFR peptide and the N-10 PSMGFR peptide. As can be seen, there is not a total displacement of NME7$_{AB}$ from the MUC1* peptides. However, recall that NME7$_{AB}$ is comprised of an A domain and a B domain, each of which are capable of binding to MUC1*. These antibodies were designed to disrupt binding of the B domain to MUC1*; the A domain of NME7$_{AB}$ would still be able to bind to the MUC1* peptide on the plate surface. For a useful therapeutic, the antibody would only need to disrupt the binding of one domain to MUC1* and in so doing ligand-induced dimerization and activation of MUC1* growth factor receptor would be blocked. Antibodies or antibody mimics that bind to the NME7 B3 peptide or the B3 Cys14Ser peptide (SEQ ID NO:169) are antibodies can be administered to a patient diagnosed with or at risk of developing a cancer or metastasis.

It is well known in the field that it is difficult to make cancer cells metastasize in an animal model. It is estimated that in a human tumor only about 1 in 100,000 or even 1 in 1,000,000 cancer cells is able to break away from the tumor and implant elsewhere to initiate a metastasis [Al-Hajj et al., 2003]. Some researchers report that T47D breast cancer cells injected into an immune compromised mouse will metastasize after about 12 weeks [Harrell et al 2006]. Other researchers report that AsPC-1 pancreatic cancer cells will metastasize after about 4 weeks [Suzuki et al, 2013].

Here, we show that T47D breast cancer cells grown for 10 days in a serum-free media containing recombinant NME7$_{AB}$ as the only growth factor. It was observed that when grown in NME7$_{AB}$, about 25% of the cancer cells began floating, stopped dividing but were still viable. PCR measurement showed that these "floating" cells greatly upregulated expression of the breast cancer metastatic factor CXCR4.

In some of the figures presented herein, these floater cells are referred to as cancer stem cells (CSCs). Immune compromised female nu/nu mice were implanted with 90-day release estrogen pellets. Either 500,000 T47D-wt cells or 10,000 T47D-CSCs (cancer stem cells) were injected into the tail vein (i.v.), sub-cutaneously (s.c.), or into the intra-peritoneal space (i.p.) of the nu/nu mice. These cancer cells were engineered to express Luciferase. To visualize the tumors or cancer cells, animals are injected with Luciferin, then visualized on an IVIS instrument 10 minutes later. As can be seen in the IVIS measurements of FIG. 33A-FIG. 33B, by Day 6 the 500,000 T47D-wt cells injected into the tail vein show no signs of live cancer cells or cancer cell engraftment.

In stark contrast, the 10,000 T47D-CSC injected into the tail vein have metastasized. Before the Day 6 IVIS measurement, the T47D-CSC mice were injected with 32 nM recombinant NME7$_{AB}$. The next day, one of the two CSC mice was injected with a cocktail of anti-NME7 monoclonal antibodies 8F9A5A1, 8F9A4A3, and 5F3A5D4 in a volume of 200 uL at a concentration that corresponds to 15 mgs/kg. The nearly coincident injection of NME7$_{AB}$ and anti-NME7 antibody likely nullified the effect of the antibody. FIG. 34 shows that by Day 10, the treated mouse is almost entirely metastatic. As can be seen in the figure, the mouse chosen for treatment is more metastatic than the comparable T47D-CSC mouse.

That animal was again injected with the anti-NME7 antibodies on Day 10. The IVIS measurement of Day 12 (FIG. 35) shows that the antibody treated mouse is beginning to clear the metastases. By Day 14 (FIG. 36) the untreated mouse has died from rampant metastases and the treated mouse has cleared the metastases. FIG. 37 shows the time course of IVIS measurements for the mouse injected with 500,000 T47D-wt cells and the mouse injected with T47D-CSCs that received anti-NME7 treatment until Day 17 when antibody treatment was suspended. As can be seen, on Day 17 there remained a small cluster of cancer cells, which by Day 19 had grown larger. By Day 21 the metastases had spread and antibody treatment was resumed. As is shown in the figure, after resumption of anti-NME7 antibody treatment, the animal was cleared of all metastases and shows no signs of ill health.

FIG. 38 shows the IVIS time course for animals that were injected sub-cutaneously or intra-peritoneally. Antibody injections for animals injected with CSCs sub-cutaneously or intra-peritoneally were also injected with anti-NME7 antibodies s.c. or i.p. In these animals, antibody injections stopped at Day 17 and did not resume. FIG. 39-FIG. 40 show that a polyclonal anti-NME7 antibody generated by immunization with the B3 peptide stains advanced cancers and metastatic cancers but not normal tissues or low-grade cancers, where only 1 in 100,000 or 1 in 1,000,000 cancer cells would be a metastatic cancer cells. Taken together, these data show that anti-NME7 antibodies 8F9A5A1, 8F9A4A3, and 5F3A5D4 or 8F9A5A1, or 8F9A4A3, or 5F3A5D4 administered to a patient diagnosed with or at risk of developing a cancer would prevent, inhibit the formation of, or reverse cancer metastases.

In addition to treating metastatic animals with a cocktail of anti-NME7$_{AB}$ antibodies, we also administered monoclonal anti-NME7$_{AB}$ antibodies individually and showed they were capable of preventing as well as reversing cancer metastases. In one demonstration, female nu/nu mice weighing approximately 20 g each, were implanted with 90-day estrogen release pellets between 8-10 weeks of age. Cancer cells were made metastatic by culturing for 10-15 days in a serum-free media supplemented with growth factor NME7$_{AB}$. Both adherent and floating cells show upregulation of metastatic markers and in animals are able to metastasize within 4-7 days. In this case, the floating cells were harvested on Day 11 of in vitro culture and injected into the tail vein of the test animals. To test a prevention model, one group of animals was injected into the tail vein, 24 hours before injection of the metastatic cancer cells, with anti-NME7$_{AB}$ antibody 8F9A4A3 at 15 mg/kg and injected thereafter with the same dosage approximately every 48 hours. FIG. 42A-FIG. 42F shows photographs of female nu/nu mice, which were injected into the tail vein with 10,000 Luciferase positive T47D metastatic breast cancer stem cells and treated with the anti-NME7$_{AB}$ antibody 4A3 also known as 8F9A4A3. To image cancer cells, the Luciferase substrate, Luciferin, is intraperitoneally injected 10 minutes before being photographed in IVIS instrument. FIG. 42A-42C show IVIS photographs with animals face down. FIG. 42D-42F show IVIS photographs with animals face up. FIGS. 42A and 42D show control animals injected with phosphate buffered saline solution. FIGS. 42B and 42E show a prevention model in which animals were injected with anti-NME7$_{AB}$ antibody 4A3 24 hrs before injection of the metastatic cancer cells, then approximately every other day for a total of 12 antibody injections over 22 days. FIGS. 42C and 42F show a reversal model in which animals were injected with anti-NME7$_{AB}$ antibody 4A3 24 hrs after injection of the metastatic cancer cells, then approximately every other day for a total of 11 antibody injections over 20 days. As can be seen in the figure, anti-NME7$_{AB}$ antibody 8F9A4A3 can prevent, as well as reverse an established metastasis.

Anti-NME7$_{AB}$ antibodies 5A1 and 5D4 were also tested in a metastasis prevention model and shown to greatly inhibit cancer metastasis. FIG. 43A-43F shows photographs of female nu/nu mice weighing approximately 20 g each, which were injected into the tail vein with 10,000 Luciferase positive T47D metastatic breast cancer stem cells and treated with the anti-NME7$_{AB}$ antibodies 5A1, also known as 8F9A5A1, and 5D4, also known as 5F3A5D4. To image cancer cells, the Luciferase substrate, Luciferin, is intraperitoneally injected 10 minutes before being photographed in IVIS instrument. FIG. 43A-43C show IVIS photographs with animals face down. FIG. 43D-43F show IVIS photographs with animals face up. FIGS. 43A and 43D show control animals injected with phosphate buffered saline solution. FIGS. 43B, 43E, 43C and 43F show a prevention model in which animals were injected with anti-NME7$_{AB}$ antibodies, at 15 mg/kg 24 hours before injection of the metastatic cancer cells, then approximately every other day for a total of 12 antibody injections over 22 days. Photographs were taken either at Day 24 or at Day 27. Specifically, mouse #1 in the group treated with antibody 5A1 was photographed at Day 27 while mouse #2 and #3 were photographed on Day 24 because animals died on Day 26.

Anti-NME7$_{AB}$ antibodies 5A1 and 5D4 were also tested in a metastasis reversal model and shown to greatly inhibit established cancer metastases. In this experiment, animals were injected on Day 0 into the tail vein with 10,000 T47D metastatic cancer cells mixed with NME7$_{AB}$ at a final concentration of 32 nM. Further, animals were injected twice, Day 3 and Day 4, with more NME7$_{AB}$ which our experiments have shown make the metastasis more difficult to reverse. The first antibody injection was on Day 7. Because the degree of metastasis in each test animal is somewhat variable, we wanted to make certain that the apparent clearance of metastatic cancer cells was due to the anti-NME7$_{AB}$ treatment. We therefore treated the animals with alternating high dose and low doses. As can clearly be seen in FIG. 44, high dose anti-NME7$_{AB}$ results in clearance of the metastasis, which if not completely eradicated comes back and even increases with lower dose. This experiment shows that all three anti-NME7$_{AB}$ antibodies tested, 5A1, 4A3 and 5D4, which are able to bind to the NME7-B3 peptide, inhibit cancer metastasis in a concentration dependent manner. FIG. 44A-44D show photographs of female nu/nu mice that were injected into the tail vein with 10,000 Luciferase positive T47D metastatic breast cancer stem cells mixed with NME7$_{AB}$ at a final concentration of 32 nM. Animals were then injected into the tail vein with 32 nM NME7$_{AB}$ before being treated with individual anti-NME7$_{AB}$ antibodies. FIG. 44A shows control animals injected with phosphate buffered saline solution. FIG. 44B shows animals treated with anti-NME7$_{AB}$ monoclonal antibody 8F9A5A1. FIG. 44C shows animals treated with anti-NME7$_{AB}$ monoclonal antibody 8F9A4A3. FIG. 44D shows animals treated with anti-NME7$_{AB}$ monoclonal antibody 5F3A5D4. Green arrows indicate low antibody dosage (5-7 mg/kg) over the indicated period and Red arrows indicate high dosage (15 mg/kg). As can be seen in the figure, the metastasis clears considerably when antibody is administered at 15 mg/kg.

In addition to demonstrating that the anti-NME7$_{AB}$ antibodies of the invention can inhibit metastasis, we tested their effect on metastasis from a primary tumor, which would more closely mimic the physiology of cancer metastasis. We generated T47D metastatic breast cancer cells, also known as cancer stem cells (CSCs) by culturing the cancer cells in a minimal serum-free media containing NME7$_{AB}$ for 10-15 days. These T47D CSCs were then implanted sub-cutaneously into the right flank of NSG mice into which had been implanted a 90-day estrogen release pellet. The implanted cancer cells were Luciferase positive so that after injection of the Luciferase substrate, Luciferin, the cancer cells emit photons and can be photographed in an IVIS instrument to measure and locate the implanted cancer cells. FIG. 45A-45B shows photographs of female nu/nu mice that on Day 0 were injected sub-cutaneously into the right flank with 10,000 Luciferase positive T47D metastatic breast cancer stem cells, mixed with NME7$_{AB}$ to a final concentration of 32 nM, then mixed in a 1:1 vol:vol with Matrigel. Tumor engraftment was allowed to progress Day 0-Day 6. Animals were then treated i.v. by tail vein injection with anti-NME7$_{AB}$ antibodies. Control animals were injected with PBS. FIG. 45A shows IVIS photographs of control animals. FIG. 45B shows IVIS photographs of animals injected into tail vein with a cocktail of anti-NME7$_{AB}$ antibodies 5A1, 4A3 and 5D4 to a total concentration of 15 mg/kg. Antibodies or PBS were administered 4 times between Day 7 and Day 18. As can be seen in the figure, the anti-NME7$_{AB}$ antibody treated animals show less metastases (blue dots in whole body) than the control group. In the treated group, 2 of the 5 animals have primary tumors that are larger than those in the control group. This could be because the anti-NME7$_{AB}$ antibodies prevented the spread of the cancer cells, so they remained concentrated in the primary tumor. In this experiment, PCR analysis, performed prior to injection of the cancer cells, showed that after 11 days in culture with NME7$_{AB}$, the T47D breast cancer cells had upregulated CXCR4 by 109-fold, OCT4 by 2-fold, NANOG by 3.5-fold and MUC1 by 2.7-fold.

In another experiment, we tested the effect of anti-NME7$_{AB}$ antibodies of the invention on metastasis from a primary tumor to organs that breast cancers typically metastasize to. Breast cancers commonly metastasize to liver, lung, bone and brain, in that order. We generated T47D metastatic breast cancer cells by culturing in a minimal serum-free media containing NME7$_{AB}$ for 11 days. These T47D CSCs were then implanted sub-cutaneously into the right flank of NSG mice into which had been implanted a 90-day estrogen release pellet. FIG. 46A-46P shows photographs of female nu/nu mice that on Day 0 were injected sub-cutaneously into the right flank with 10,000 Luciferase positive T47D metastatic breast cancer stem cells, mixed with NME7$_{AB}$ to a final concentration of 32 nM, then mixed in a 1:1 vol:vol with Matrigel. Tumor engraftment was allowed to progress Day 0-Day 6. Animals were then treated i.v., by tail vein injection, with anti-NME7$_{AB}$ antibodies. Control animals were injected with PBS. On Day 38 animals were sacrificed and livers harvested then analyzed by IVIS to detect cancer cells that had metastasized to the liver. FIG. 46A-46B show whole body IVIS photographs of control animals that were injected with only PBS. FIG. 46C-46D show whole body IVIS photographs of control animals that were injected with the anti-NME7$_{AB}$ antibody 5A1. FIG. 46E-46F show whole body IVIS photographs of control animals that were injected with the anti-NME7$_{AB}$ antibody 4A3. FIG. 46G-46H show whole body IVIS photographs of control animals that were injected with the anti-NME7$_{AB}$ antibody 5D4. FIGS. 46A, 46C, 46E, and 46G are IVIS photographs taken at Day 7 before any treatment. FIGS. 46B, 46D, 46F, and 46H are IVIS photographs taken at Day 31 after anti-NME7$_{AB}$ antibody treatment or mock treatment. As can be seen in the figure, animals in the PBS control group show metastasis (blue dots) in the whole body IVIS photographs, while animals treated with anti-NME7$_{AB}$ antibodies do not. FIG. 46I-46P show photographs and IVIS photographs of livers and lung harvested from animals after sacrifice. FIGS. 46I, 46K, 46M, and 46O are regular photographs. FIGS. 46J, 46L, 46N, and 46P are IVIS photographs, illuminating the cancer cells that have metastasized there. As can be seen in the figure, the anti-NME7$_{AB}$ antibodies greatly inhibited metastasis to the liver, which is a primary site for breast cancer metastasis. FIG. 46Q is a bar graph of the measured photons emitted and enumerated by IVIS instrument for livers harvested from control animals versus the treated animals. As can be seen in the inserted graph of IVIS measurements, the inhibition of metastasis to the liver follows the rank order of inhibition of metastasis when cells were injected into the tail vein, which also matches the rank order of potency in being able to disrupt the NME7$_{AB}$-MUC1* interaction.

We performed immunofluorescent imaging of many cancer cell lines to determine if cultured cancer cell lines express NME7$_{AB}$. As FIGS. 47A-47F and FIG. 48A-48I clearly show, each MUC1 positive cancer cell line we tested is positive for NME7$_{AB}$ and its binding is membranous, consistent with NME7$_{AB}$ being secreted from cancer cells whereupon it binds to the extra cellular domain of MUC1*. FIG. 47A-47F shows photographs of immunofluorescent experiments in which various cancer cell lines are stained for the presence of NME7$_{AB}$. FIG. 47A shows T47D breast cancer cells stained with varying concentrations of anti-NME7$_{AB}$ antibody 5D4. FIG. 47B shows ZR-75-1 breast cancer cells, also known as 1500s, stained with varying concentrations of anti-NME7$_{AB}$ antibody 5D4. FIG. 47C shows H1975 non-small cell lung cancer cells stained with varying concentrations of anti-NME7$_{AB}$ antibody 5D4. FIG. 47D shows H292 non-small cell lung cancer cells stained with varying concentrations of anti-NME7$_{AB}$ antibody 5D4. FIG. 47E shows HPAFII pancreatic cancer cells stained with varying concentrations of anti-NME7$_{AB}$ antibody 5D4. FIG. 47F shows DU145 prostate cancer cells stained with varying concentrations of anti-NME7$_{AB}$ antibody 5D4. As can be seen in the figure, all the cancer cell lines we tested show strong and membranous staining for NME7$_{AB}$. The monoclonal antibody used in these experiments was 5D4. In parallel, NME7$_{AB}$ antibodies 5A1 and 4A3 were used to stain the same cell lines and produced the same results.

FIG. 48A-48I shows photographs of immunofluorescent experiments in which various lung cancer cell lines are stained for the presence of NME7$_{AB}$. FIG. 48A-48C shows H1975 non-small cell lung cancer cells, which are an adenocarcinoma, stained with varying concentrations of anti-NME7$_{AB}$ antibody 5D4. FIG. 48A is an overlay of DAPI and anti-NME7$_{AB}$ staining. FIG. 48B shows anti-NME7$_{AB}$ staining alone. FIG. 48C is a magnified view of the overlay of DAPI and anti-NME7$_{AB}$ staining. FIG. 48D-48F shows H292 non-small cell lung cancer cells, which are a mucoepidermoid pulmonary carcinoma, stained with varying concentrations of anti-NME7$_{AB}$ antibody 5D4. FIG. 48D is an overlay of DAPI and anti-NME7$_{AB}$ staining. FIG. 48E shows anti-NME7$_{AB}$ staining alone. FIG. 48F is a magnified view of the overlay of DAPI and anti-NME7$_{AB}$ staining. FIG. 48G-48I shows H358 non-small cell lung cancer cells, which are a metastatic bronchioalveolar carcinoma, stained with varying concentrations of anti-NME7$_{AB}$ antibody 5D4. FIG. 48G is an overlay of DAPI and anti-NME7$_{AB}$ staining. FIG. 48H shows anti-NME7$_{AB}$ staining alone. FIG. 48I is a magnified view of the overlay of DAPI and anti-NME7$_{AB}$ staining.

In addition, culturing these cell lines in a serum-free media containing NME7$_{AB}$ even further increased their expression of stem cell and metastatic markers. In particular, the cells that became non-adherent, referred to here as floaters, have even higher expression of stem cell and metastatic markers than their adherent counterparts. FIG. 49A-49I shows PCR graphs of cancer cell lines, breast T47D, Lung H1975, lung H358 and pancreatic HPAFII before and after culture in NME7$_{AB}$. FIG. 49A measured breast metastatic marker CXCR4. FIG. 49B measured stem cell marker OCT4. FIG. 49C measured metastatic marker ALDH1. FIG. 49D measured stem cell marker SOX2. FIG. 49E measured stem cell marker NANOG. FIG. 49F measured marker CDH1, also known as E-cadherin. FIG. 49G measured metastatic marker CD133. FIG. 49H measured stem cell marker ZEB2. FIG. 49I measured stem, cancer and metastatic marker MUC1. The floater cells, also known as tumor spheres become able to grow anchorage independently and show markers of metastasis that are more elevated than the adherent cells. Animals injected with cancer stem cells are those injected with the NME7$_{AB}$ grown floater cells. As can be seen in the figure markers of metastasis, stem cell markers, or markers of epithelial to mesenchymal transition (EMT) are elevated after culture in NME7$_{AB}$, indicating a transition to a more metastatic state. FIG. 50 shows Day 6 IVIS photographs of NSG mice injected into the tail vein with either 10,000 H358 lung cancer parent cells or H358 cells after 10-12 days in culture with NME7$_{AB}$. As can be seen in the figure, the NCI-H358 lung cancer cells grown in NME7$_{AB}$ have greatly increased metastatic potential compared to the parent cells, which are themselves reportedly metastatic cells. The functional increase in metastasis in 6 days from the NCI-H358 NME7$_{AB}$ metastatic cancer stem cells from just 10,000 cells is consistent with FIG. 49, showing that H358 cells greatly increased expression of metastatic markers after culture in NME7$_{AB}$.

FIG. 51 shows PCR graph of a MUC1 negative prostate cancer line PC3 before and after 2 or 3 passages in culture in either dimeric NM23-H1, also known as NME1, or NME7$_{AB}$. The graph shows the fold difference in markers of stem cells, cancer cells as well as metastatic markers. As can be seen in the figure, repeated culture in NME1 or NME7$_{AB}$ induces upregulation of stem, cancer and metastatic markers but also upregulates expression of MUC1 by 5-8 times.

Collectively, these data have demonstrated that an NME7 that is devoid of the DM10 domain is secreted by cancer cells and binds to the extra cellular domain of a MUC1 that is devoid of tandem repeat domain, whereupon the NME7 dimerizes the MUC1* extra cellular domain which results in increased cancer cell growth and an increase in the cancer cells' metastatic potential. It stands to reason that antibodies that disrupt the interaction between NME7$_{AB}$ and MUC1* extra cellular domain would inhibit cancer cell growth and would inhibit cancer metastasis. Here, we have shown that anti-NME7$_{AB}$ antibodies that inhibit interaction between NME7$_{AB}$ and MUC1* extra cellular domain do in fact inhibit cancer cell growth and cancer metastasis. Therefore, it follows that anti-NME7$_{AB}$ antibodies can be administered to a patient, diagnosed with or at risk of developing a cancer or metastasis, for the treatment or prevention of cancers.

Because NME1 is expressed in the cytoplasm of all cells and can be lethal if knocked out, and importantly the NME1 A domain has high sequence homology to the NME7 A domain, it is critical that anti-NME7$_{AB}$ antibodies for therapeutic use bind to NME7$_{AB}$ or NME7-X1, but not to NME1. In one aspect of the invention antibodies that would be optimal for therapeutic use were selected for their ability to bind to peptides that were unique to NME7$_{AB}$ or NME7-X1 and were not present in the NME1 sequence. FIG. 6-FIG. 9 lists NME7$_{AB}$ unique peptides.

In a preferred embodiment, antibodies suitable for administration to a patient for the treatment or prevention of cancer or cancer metastasis are selected from the group of antibodies that bind to the NME7 B3 peptide. In yet a more preferred embodiment, antibodies suitable for administration to a patient for the treatment or prevention of cancer or cancer metastasis are selected from the group of antibodies that bind to the NME7 B3 peptide, bind to NME7$_{AB}$ but do not bind to NME1. Examples of antibodies suitable for therapeutic use for the treatment or prevention of cancers or cancer metastasis, which have demonstrated such anti-cancer activity and anti-metastatic activity in vitro and in vivo here, include anti-NME7 antibodies 5A1, 4A3 and 5D4. These are but examples and other antibodies generated as described here and selected as described here will have the same anti-cancer and anti-metastatic activity. Such antibodies may be full antibodies or fragment thereof, including scFvs or antibody mimics wherein the variable domains of the antibody are incorporated into a protein scaffold that mimic an antibody. The antibodies may be of human or non-human species, including murine, camelid, llama, human or humanized and may be monoclonal, polyclonal, scFvs or fragments thereof.

Anti-NME7 antibodies for treatment or prevention of cancers or metastases can be used in many different therapeutic formats. For example, any of the antibodies described herein, or a fragment thereof, can be administered to a patient as a stand-alone antibody or antibody fragment, or attached to a toxin such as an antibody drug conjugate (ADC), or incorporated into a bi-specific antibody or incorporated into a BiTE (bispecific T cell engager), or incorporated into a chimeric antigen receptor (CAR) or engineered to be expressed by a cell that also expresses a CAR. The cell may be an immune cell, a T cell, an NK cell or a stem or progenitor cell, which may then be differentiated into a T cell or an NK cell.

Any of the antibodies described herein, or a fragment thereof, can be used as a diagnostic reagent to probe a bodily fluid, cell, tissue or bodily specimen for the presence of NME7$_{AB}$ or NME7-X1, which would be an indicator of cancer or susceptibility to cancers. Antibodies for diagnostic uses may be connected to an imaging agent, a nucleic acid tag, may be of any species including camelid, and can be used in whole body applications or on a bodily fluid, such as blood, cell, or tissue, in vitro, in vivo or intra-operatively.

The selection criteria, for therapeutically useful or diagnostically useful anti-NME7 antibodies, depends on the format or modality of the therapeutic or diagnostic into which the antibody will be incorporated. If the antibody or antibody fragment is to be administered to a patient as a stand-alone agent for the treatment or prevention of cancers or cancer metastases, then the antibody is selected for its ability to: i) bind to NME7$_{AB}$ or NME7-X1, but not to NME1; ii) bind to the PSMGFR peptide; iii) bind to the N-10 peptide and iv) disrupt the interaction between NME7$_{AB}$ or NME7-X1 and the MUC1* extra cellular domain or the interaction between NME7$_{AB}$ or NME7-X1 and the N-10 peptide. The antibody may also be selected for its ability to bind to the NME7 B3 peptide. This therapeutic format also encompasses a cell that has been engineered to express a CAR and a secreted anti-NME7 antibody.

Other modalities require other selection criteria for anti-NME7 antibodies. If the anti-NME7 antibody is to be incorporated into an ADC, the ADC must be internalized by the target cell to trigger killing of the target cell. Recall that NME7$_{AB}$ or NME7-X1 will be bound to the extra cellular domain of MUC1*. If the antibody disrupts binding of the NME to MUC1* extra cellular domain, then the toxin-conjugated antibody will not be internalized and the cell will not be killed. Similarly, if the anti-NME7 antibody is to be incorporated into a CAR or a BiTE, the interaction between NME7$_{AB}$ or NME7-X1 cannot be disrupted or the immune cell will no longer be able to direct its killing agents to the cancer cell. If the anti-NME7 antibody is to be used as a diagnostic reagent, the interaction between NME7$_{AB}$ or NME7-X1 cannot be disrupted or antibody and associated label will be washed away. Therefore, for ADC, CAR T, or CAR-NK, BiTEs or diagnostic applications, the anti-NME7 antibody is selected for its ability to: i) bind to NME7$_{AB}$ or NME7-X1, but not to NME1; ii) bind to the PSMGFR peptide; iii) bind to the N-10 peptide and iv) bind to NME7$_{AB}$ or NME7-X1 without disrupting the interaction with the MUC1* extra cellular domain or the interaction between NME7$_{AB}$ or NME7-X1 and the N-10 peptide. The antibody may also be selected for its ability to bind to the NME7 B3 peptide.

In one aspect of the invention, a cell is engineered to express an anti-NME7$_{AB}$ antibody of the invention or fragment thereof. The cell may be an immune cell, such as a T cell or NK cell or it may be a stem or progenitor cell, which may be differentiated into a more mature immune cell such as a T cell or NK cell. In a preferred embodiment, the cell that is engineered to express an anti-NME7$_{AB}$ antibody is also engineered to express a chimeric antigen receptor (CAR). In a preferred embodiment, the CAR recognizes a tumor associated antigen. In a preferred embodiment, the CAR targets MUC1*. In a more preferred embodiment, the CAR is directed to the tumor by anti-MUC1* antibody MNC2. In another aspect of the invention, cell that is engineered to express a CAR is also engineered to inducibly express an anti-NME7 antibody. In one example, the nucleic acid encoding an anti-NME7$_{AB}$ antibody is inserted into the Foxp3 enhancer or promoter. In another example, the anti-NME7$_{AB}$ antibody is in an NFAT-inducible system. In one aspect, the NFAT-inducible system incorporates NFATc1 response elements inserted upstream of an anti-NME7$_{AB}$ antibody sequence. They may be inserted into an IL-2 promoter, a Foxp3 enhancer or promoter or other suitable promoter or enhancer.

In another aspect of the invention, peptides that are unique to NME7$_{AB}$ or NME7-X1 are incorporated into an entity used to immunize or vaccinate people against cancers or cancer metastases. In a preferred embodiment, the peptide comprises all or part of the NME7 B3 peptide, which may be the NME7 B3 peptide with Cys-14-Ser mutation.

Another aspect of the invention involves a method of generating anti-NME7$_{AB}$ antibodies in a host animal, where the animal is immunized with the NME7 B3 peptide. In a preferred embodiment, the NME7 B3 peptide has Cysteine 14 mutated to Serine (SEQ ID NO:169) to avoid disulfide bond formation which inhibits NME7 specific antibody generation.

Another aspect of the invention involves a method of generating cells with enhanced metastatic potential involving culturing the cells with NME7$_{AB}$ or NME7-X1. These cells can then be used in many aspects of drug discovery.

Another aspect of the invention involves a cell that is engineered to express NME7$_{AB}$ or NME7-X1. The NME7$_{AB}$ or NME7-X1 may be of human sequence. Their expression may be inducible. In one aspect the cell is an egg which is then developed into an animal that may be a transgenic animal able to express human NME7$_{AB}$ or NME7-X1.

NME7 binds to and dimerizes the extra cellular domain of the MUC1* growth factor receptor. Tissue studies show that MUC1* increases as tumor grade and metastasis increase. Here we show that NME7 expression increases as tumor grade and metastasis increases (FIG. 39-FIG. 41). Here, we have shown that antibodies that inhibit the interaction of NME7 and MUC1* inhibit tumor growth and metastases.

Other NME family members may bind to and dimerize the extra cellular domain of the MUC1* growth factor receptor. For example, we have shown that NME1, NME2 and NME6 can exist as dimers and that they bind to and dimerize the MUC1* extra cellular domain. NME7$_{AB}$ and NME7-X1 have two domains that can bind to the MUC1* extra cellular domain so as monomers they dimerize and activate the MUC1* growth factor receptor. We have now shown that anti-NME7 antibodies inhibit cancer and cancer metastases. Similarly, antibodies or antibody mimics that bind to these other NME proteins may be anti-cancer or anti-metastasis therapeutics that can be administered to a patient diagnosed with or at risk of developing a cancer or a metastasis. In one aspect of the invention, antibodies that can be used therapeutically for the treatment of cancers or metastases are antibodies that bind to NME1, NME2, NME3, NME4, NME5, NME6, NME7, NME8, NME9 or NME10. In one aspect of the invention, the therapeutic antibody or antibody mimic inhibits the binding of the NME protein and its cognate growth factor receptor. In one aspect of the invention, the therapeutic antibody or antibody mimic inhibits the interaction of the NME protein with the extra cellular domain of MUC1*. In another aspect of the invention, the therapeutic antibody or antibody mimic binds to a peptide, derived from NME1, NME2, NME3, NME4, NME5, NME6, NME7, NME8, NME9 or NME10, wherein the peptide is homologous to the NME7 A1, A2, B1, B2 or B3 peptide.

Below is a sequence alignment that shows a homology and identity alignment between NME7 and other NME family members. The underlined or underlined and bolded sequences correspond to NME7 peptides A1 (SEQ ID NO: 141), A2 (SEQ ID NO: 142), B1 (SEQ ID NO: 143), B2 (SEQ ID NO: 144) and B3 (SEQ ID NO: 145).

```
nucleoside diphosphate kinase 7 isoform a [Homo sapiens] (Hu_7)
MNHSERFVFIAEWYDPNASLLRRYELLFYPGDGSVEMHDVKNHRTFLKRTKYDNLHLEDLFIGNKVNVFSRQLVL
IDYGDQYTARQLGSRKEKTLALIKPDAISKAGEITEIINKAGFTITKLKMMMLSRKEALDFHVDHQSRPFFNELI
QFITTGPIIAMEILRDDAICEWKRLLGPANSGVARTDASESIRALFGTDGIRNAAHGPDSFASAAREMELFFPSS
GGCGPANTAKFTNCTCCIVKPHAVSEGLLGKILMAIRDAGFEISAMQMFNMDRVNVEEFYEVYKGVVTEYHDMVT
EMYSGPCVAMEIQQNNATKTFREFCGPADPEIARHLRPGTLRAIFGKTKIQNAVHCTDLPEDGLLEVQYFFKILD
N (SEQ ID NO: 1141)

NME2 Theoretical pI/Mw: 8.52/17298.04
MANLERTFIAIKPDGVQRGLVGEIIKRFEQKGFRLVAMKFLRASEEHLKQHYIDLKDRPFFPGLVKYMNSGPVVA
MVWEGLNVVKTGRVMLGETNPADSKPGTIRGDFCIQVGRNIIHGSDSVKSAEKEISLWFKPEELVDYKSCAHDWV
YE (SEQ ID NO: 19)

global/global (N-W) score: 171; 26.5% identity (56.8% similar) in 155 aa
overlap (1-131:1-152)
                   10        20        30        40        50
       7A      ----EKTLALIKPDAISKA--GEIIEIINKAGFTITKLKMMMLSRKEALDFHVDHQSRPF
                   :.:.  :::: .....  ::::.  ...  ::  .. .:..  :....  . ..:  ..:::
       2       MANLERTFIAIKPDGVQRGLVGEIIKRFEQKGFRLVAMKFLRASEEHLKQHYIDLKDRPF
                   10        20        30        40        50        60

60        70        80        90        100       110
       7A      FNELIQFITTGPIIAMEILRDDAICEWKRLLGPANSGVARTDASESIRALFGTDGIRNAA
                    :    :  ............ : ..::       ... .     . .::  .:  :  ...       .:::   :   .   ::
```

-continued

```
2    FPGLVKYMNSGPVVAMVWEGLNVVKTGRVMLGETNPADSKPG---TIRGDFCIQVGRNII
              70        80        90       100       110

120       130
7A   HGPDSFASAAREMELFF----------------- (SEQ ID NO: 199)
     ::  ::  :: .:. :.:
2    HGSDSVKSAEKEISLWFKPEELVDYKSCAHDWVYE (SEQ ID NO: 200)
     120       130       140       150 global/global (N-W) score: 104; 24.4% identity (51.3% similar) in 156 aa
overlap (1-134:1-152)
              10        20        30        40        50
7B   NC----TCCIVKPHAVSEGLLGKILMAIRDAGFEISAMQMFNMDRVNVEEFYEVYKGVVT
            :  : .:.:.::::. ...  ::: :::..  ..   .. ..: : :
2    MANLERTFIAIKPDGVQRGLVGEIIKRFEQKGFRLVAMKFLRASEEHLKQHYIDLKDR-P
     10        20        30        40        50

60        70        80        90       100       110
7B   EYHDMVTEMYSGPCVAMEIQQNNATKTFREFCGPADPEIARHLRPGTLRAIFGKTKIQNA
       .    . ::  ::: :::  . :...:: : .  :..   ..   :::::.:.  .:
2    FFPGLVKYMNSGPVVAMVWEGLNVVKTGRVMLGETNPADSK---PGTIRGDFCIQVGRNI
     60        70        80        90       100       110

120       130
7B   VHCTDLPEDGLLEVQYFF----------------- (SEQ ID NO: 201)
      .:  .:   ...  :.. .:
2    IHGSDSVKSAEKEISLWFKPEELVDYKSCAHDWVYE (SEQ ID NO: 202)
     120       130       140       150

>NME3 Theoretical pI/Mw: 5.96/19088.97
MICLVLTIFANLFPSAYSGVNERTFLAVKPDGVQRRLVGEIVRRFERKGFKLVALKLVQASEELLREHYVELRER
PFYSRLVKYMGSGPVVAMVWQGLDVVRASRALIGATDPGDATPGTIRGDFCVEVGKNVIHGSDSVESAQREIALW
FREDELLCWEDSAGHWLYE (SEQ ID NO: 206)

10        20        30        40        50
7A   EKTLALIKPDAISK--AGEIIEIINKAGFTITKLKMMMLSRKEALDFHVDHQSRPFFNEL
     :.:.  .:::..... .:::::. ...  ::  ::..  :...    .   . ::::.:
3    ERTFLAVKPDGVQRRLVGEIVRRFERKGFKLVALKLVQASEELLREHYVELRERPFYSRL
     30        40        50        60        70        80

60        70        80        90       100       110
7A   IQFITTGPIIAMEILRDDAICEWKRLLGPANSGVARTDASE-SIRALFGTDGIRNAAHGP
     ....  :::::: :::..::   :. ::::     :: ..: :: :: ::: :. : ::
3    VKYMGSGPVVAMVWQGLDVVRASRALIGATDPG----DATPGTIRGDFCVEVGKNVIHGS
              90       100       110       120       130

120       130
7A   DSFASAAREMELFF (SEQ ID NO: 203)
     ::  ::  :: .:.  :.:
3    DSVESAQREIALWF (SEQ ID NO: 204)
              140       150

10        20        30
7B   N-C-------------------TCCIVKPHAVSEGLLGKILMAIRDAGFEISAMQMFNM
       :            : :::  .:.  ::.:.. ..   ::.  :::.
3    MICLVLTIFANLFPSAYSGVNERTFLAVKPDGVQRRLVGEIVRRFERKGFKLVALKLVQA
     10        20        30        40        50        60

40        50        60        70        80        90
7B   DRVNVEEFYEVYKGVVTEYHDMVTEMYSGPCVAMEIQQNNATKTFREFCGPADPEIARHL
     ..   .: : :    :      . ::  ::: :::  . :...:: : .  :..
3    SEELLREHY-VELRERPFYSRLVKYMGSGPVVAMVWQGLDVVRASRALIGATDPGDAT--
              70        80        90       100       110

100       110       120       130
7B   RPGTLRAIFGKTKIQNAVHCTDLPEDGLLEVQYFF----------------- (SEQ ID NO: 205)
     :::::.: :    .:  .  .:  .:   ...  :..
3    -PGTIRGDFCVEVGKNVIHGSDSVESAQREIALWFREDELLCWEDSAGHWLYE (SEQ ID NO: 206)
              120       130       140       150       160

NME4 Theoretical pI/Mw: 10.30/20658.59
MGGLFWRSALRGLRCGPRAPGPSLLVRHGSGGPSWTRERTLVAVKPDGVQRRLVGDVIQRFERRGFTLVGMKMLQ
APESVLAEHYQDLRRKPFYPALIRYMSSGPVVAMVWEGYNVVRASRAMIGHTDSAEAAPGTIRGDFSVHISRNVI
HASDSVEGAQREIQLWFQSSELVSWADGGQHSSIHPA (SEQ ID NO: 1110)

29.3% identity (68.4% similar) in 133 aa overlap (1-131:56-185)
              10        20        30        40        50
7A   EKTLALIKPDAISK--AGEIIEIINKAGFTITKLKMMMLSRKEALDFHVDHQSRPFFNEL
     :.:.  .:::..... .:::::. ...  ::  ::..  :    .   . . .:::. :
```

-continued

```
4         ERTLVAVKPDGVQRRLVGDVIQRFERRGFTLVGMKMLQAPESVLAEHYQDLRRKPFYPAL
                  60        70        80        90       100       110

60        70        80        90       100       110
7A        IQFITTGPIIAMEILRDDAICEWKRLLGPANSGVARTDASESIRALFGTDGIRNAAHGPD
          :......:....: ..  ..  ..:  ::.. .   .       : ::.. ::. :.
4         IRYMSSGPVVAMVWEGYNVVRASRAMIGHTDSAEA---APGTIRGDFSVHISRNVIHASD
                 120       130       140       150       160       170

120       130
7A        SFASAAREMELFF  (SEQ ID NO: 207)
          :  .: ::..:.:
4         SVEGAQREIQLWE  (SEQ ID NO: 208)
                 180

28.8% identity (56.8% similar) in 132 aa overlap (3-134:40-167)
                  10        20        30        40        50        60
7B        TCCIVKPHAVSEGLLGKILMAIRDAGFEISAMQMFNMDRVNVEEFYEVYKGVVTEYHDMV
          :  :::.:. ..  :  :  :: .. ::  . . ..:..  .      .    :   ..
4         TLVAVKPDGVQRRLVGDVIQRFERRGFTLVGMKMLQAPESVLAEHYQDLRRK-PFYPALI
          40        50        60        70        80        90

70        80        90       100       110       120
7B        TEMYSGPCVAMEIQQNNATKTFREFCGPADPEIARHLRPGTLRAIFGKTKIQNAVHCTDL
           : :::.:::  .  .....  . :  .: :   : :  :::::.   ::   .: .:
4         RYMSSGPVVAMVWEGYNVVRASRAMIGHTDSAEAA---PGTIRGDFSVHISRNVIHASDS
         100       110       120       130       140       150

130
7B        PEDGLLEVQYFF  (SEQ ID NO: 209)
          :  . ..: .:
4         VEGAQREIQLWE  (SEQ ID NO: 210)
                160

NME5 Theoretical pI/Mw: 6.08/29296.23
MEISMPPPQIYVEKTLAIIKPDIVDKEEEIQDIILRSGFTIVQRRKLRLSPEQCSNFYVEKYGKMFFPNLTAYMS
SGPLVAMILARHKAISYWLELLGPNNSLVAKETHPDSLRAIYGTDDLRNALHGSNDFAAAEREIRFMFPEVIVEP
IPIGQAAKDYLNLHIMPTLLEGLTELCKQKPADPLFWYMCCRREHWTLRSILLVCMSGIRMSLPHCADYCSFVEG
FEIWLADWLLKNNPNKPKLCHHPIVEEPY  (SEQ ID NO: 1111)

44.3% identity (74.8% similar) in 131 aa overlap (1-131:13-143)
                   10        20        30        40        50        60
7A         EKTLALIKPDAISKAGEIIEIINKAGFTITKLKMMMLSRKEALDFHVDHQSRPFFNELIQ
           :::::.::::. :: ::. :: ::: :::::: :::: .  . ...::. .. :  . :
5          EKTLAIIKPDIVDKEEEIQDIILRSGFTIVQRRKLRLSPEQCSNFYVEKYGKMFFPNLTA
                   20        30        40        50        60        70

70        80        90       100       110       120
7A         FITTGPIIAMEILRDDAICEWKRLLGPANSGVARTDASESIRALFGTDGIRNAAHGPDSF
           .....:..:: . .  :: : ..:::: :::.  .: ::.  .:.: .::: .. . .:
5          YMSSGPLVAMILARHKAISYWLELLGPNNSLVAKETHPDSLRAIYGTDDLRNALHGSNDF
                   80        90       100       110       120       130

130
7A         ASAAREMELFF  (SEQ ID NO: 211)
           :.: ::.....:
5          AAAEREIRFMF  (SEQ ID NO: 212)
                 140

28.0% identity (58.3% similar) in 132 aa overlap (3-134:15-143)
                  10        20        30        40        50        60
7B        TCCIVKPHAVSEGLLGKILMAIRDAGFEISAMQMFNMDRVNVEEFYEVYKGVVTEYHDMV
          :  :.::..  ..   .:   :     :    . :. .  .      ..:   :.
5         TLAIIKPDIVDKEE--EIQDIILRSGFTIVQRRKLRLSPEQCSNFY-VEKYGKMFFPNLT
                 20        30        40        50        60

70        80        90       100       110       120
7B        TEMYSGPCVAMEIQQNNATKTFREFCGPADPEIARHLRPGTLRAIFGKTKIQNAVHCTDL
          . : :::.:: :.  :.. . . .   .   :: ::. .  :::.   ..:..:. .
5         AYMSSGPLVAMILARHKAISYWLELLGPNNSLVAKETHPDSLRAIYGTDDLRNALHGSND
                 80        90       100       110       120       130

130
7B        PEDGLLEVQYFF  (SEQ ID NO: 213)
           .  :.....
5         FAAAEREIRFMF  (SEQ ID NO: 214)
                140

NME6 Theoretical pI/Mw: 7.81 /22003.16
```

```
MTQNLGSEMASILRSPQALQLTLALIKPDAVAHPLILEAVHQQILSNKFLIVRMRELLWRKEDCQRFYREHEGRF
FYQRLVEFMASGPIRAYILAHKDAIQLWRTLMGPTRVFRARHVAPDSIRGSFGLTDTRNTTHGSDSVVSASREIA
AFFPDFSEQRWYEEEEPQLRCGPVCYSPEGGVHYVAGTGGLGPA (SEQ ID NO: 65)

37.6% identity (68.4% similar) in 133 aa overlap (3-131:22-153)
                10        20        30        40        50
7A      TLALIKPDAISKAGEIIEIINKA----GFTITKLKMMLSRKEALDFHVDHQSRPFFNEL
        ::::::::::...    ::  ...      :  :....  ..    ...   :. .:.:.:  :....:
6       TLALIKPDAVAHP-LILEAVHQQILSNKFLIVRMRELLWRKEDCQRFYREHEGRFFYQRL
             30         40        50        60        70        80

60        70        80        90       100       110
7A      IQFITTGPIIAMEILRDDAICEWKRLLGPANSGVARTDASESIRALFGTDGIRNAAHGPD
        ..:....::  :. .. ..:..  :: ... :.        ::       :. :...: .
6       VEFMASGPIRAYILAHKDAIQLWRTLMGPTRVFRARHVAPDSIRGSFGLTDTRNTTHGSD
             90       100       110       120       130       140

120       130
7A      SFASAAREMELFF (SEQ ID NO: 215)
        :  .::.::. ::
6       SVVSASREIAAFF (SEQ ID NO: 216)
            150

29.3% identity (57.9% similar) in 133 aa overlap (3-134:22-153)
                10        20        30        40        50        60
7B      TCCIVKPHAVSEGL-LGKILMAIRDAGFEISAMQMFNMDRVNVEEFYEVYKGVVTEYHDM
        :    ..::  :::.  :. .. .::.     : :       :.      :..
6       TLALIKPDAVAHPLILEAVHQQILSNKFLIVRMRELLWRKEDCQRFYREHEGRFF-YQRL
             30        40        50        60        70        80

70        80        90       100       110       120
7B      VTEMYSGPCVAMEIQQNNATKTFREFCGPADPEIARHLRPGTLRAIFGKTKIQNAVHCTD
        :  :  :::  :.   ..:    .: ::.         :::.    :  :   .:..  .:
6       VEFMASGPIRAYILAHKDAIQLWRTLMGPTRVFRARHVAPDSIRGSFGLTDTRNTTHGSD
             90       100       110       120       130       140

130
7B      LPEDGLLEVQYFF (SEQ ID NO: 217)
        ..  :.   ::
6       SVVSASREIAAFF (SEQ ID NO: 218)
            150

NME8 Theoretical pI/Mw: 4.90/67269.94
MASKKREVQLQTVINNQSLWDEMLQNKGLTVIDVYQAWCGPCRAMQPLFRKLKNELNEDEILHFAVAEADNIVTL
QPFRDKCEPVFLFSVNGKITEKIQGANAPLVNKKVINLIDEERKIAAGEMARPQYPEIPLVDSDSEVSEESPCES
VQELYSIAIIKPDAVISKKVLEIKRKITKAGFITEAEHKTVLTEEQVVNFYSRIADQCDFEEFVSFMTSGLSYIL
VVSQGSKHNPPSEETEPQTDTEPNERSEDQPEVEAQVTPGMMKNKQDSLQEYLERQHLAQLCDIEEDAANVAKFM
DAFFPDFKKMKSMKLEKTLALLRPNLFHERKDDVLRIIKDEDFKILEQRQVVLSEKEAQALCKEYENEDYFNKLI
ENMTSGPSLALVLLRDNGLQYWKQLLGPRTVEEAIEYFPESLCAQFAMDSLPVNQLYGSDSLETAEREIQHFFPL
QSTLGLIKPHATSEQREQILKIVKEAGFDLTQVKKMFLTPEQIEKIYPKVTGKDFYKDLLEMLSVGPSMVMILTK
WNAVAEWRRLMGPTDPEEAKLLSPDSIRAQFGISKLKNIVHGASNAYEAKEVVNRLFEDPEEN (SEQ ID NO:
1112)

36.1% identity (69.2% similar) in 133 aa overlap (1-131:316-448)
                10        20        30        40        50
7A      EKTLALIKPDAIS-KAGEIIEIINKAGFTITKLKMMLSRKEALDFHVDHQSRPFFNELI
        :::::::::..:  .  ...      : ::     :.  .::::: .  . .. .::.:
8       EKTLALLRPNLFHERKDDVLRIIKDEDFKILEQRQVVLSEKEAQALCKEYENEDYFNKLI
             320       330       340       350       360       370

60        70        80        90       100       110
7A      QFITTGPIIAMEILRDDAICEWKRLLGPANSGVARTDASESIRALFGTDGIR-NAAHGPD
         . :. :: : .. . .:..   :: ...  :.  :    :. : :.::  : .:..::
8       ENMTSGPSLALVLLRDNGLQYWKQLLGPRTVEEAIEYFPESLCAQFAMDSLPVNQLYGSD
             380       390       400       410       420       430

120       130
7A      SFASAAREMELFF (SEQ ID NO: 219)
        :.. .: .::.::
8       SLETAEREIQHFF (SEQ ID NO: 220)
               440

Waterman-Eggert score: 269; 85.9 bits; E(1) < 1.1e-21
33.6% identity (72.7% similar) in 128 aa overlap (1-127:451-577)
                10        20        30        40        50
7A      EKTLALIKPDAISKAGE-IIEIINKAGFTITKLKMMLSRKEALDFHVDHQSRPFFNELI
        ..:::::::  :  : ..  :.:::::::: .::::: .:..  ..    .. ::.:
8       QSTLGLIKPHATSEQREQILKIVKEAGFDLTQVKKMFLTPEQIEKIYPKVTGKDFYKDLL
             460       470       480       490       500       510
```

```
            60        70        80        90       100       110
7A   QFITTGPIIAMEILRDDAICEWKRLLGPANSGVARTDASESIRALFGTDGIRNAAHGPDS
     .......::  ...:. . .:. ::::::.:::..   :.  . .::::  ::  . ..: .::  ..
8    EMLSVGPSMVMILTKWNAVAEWRRLMGPTDPEEAKLLSPDSIRAQFGISKLKNIVHGASN
             520       530       540       550       560       570

120
7A   FASAAREM (SEQ ID NO: 221)
           :   :.:.
8    -AYEAKEV (SEQ ID NO: 222)

Waterman-Eggert score: 119; 40.4 bits; E(1) < 5.3e-08
33.8% identity (73.8% similar) in 65 aa overlap (3-65:156-220)
           10        20         30        40        50        60
7A   TLALIKPDAI--SKAGEIIEIINKAGFTITKLKMMMLSRKEALDFHVDHQSRPFFNELIQ
     ..::::::::.  .:: ::  . :.::::: :    . .:.........:. .. :.:..
8    SIAIIKPDAVISKKVLEIKRKITKAGFIIEAEHKTVLTEEQVVNFYSRIADQCDFEEFVS
            160       170       180       190       200       210

7A   FITTG (SEQ ID NO: 223)
     :.:.:
8    FMTSG (SEQ ID NO: 224)
         220

33.6% identity (65.5% similar) in 116 aa overlap (3-118:453-566)
           10        20        30        40        50        60
7B   TCCIVKPHAVSEGLLGKILMAIRDAGFEISAMQMFNMDRVNVEEFYEVYKGVVTEYHDMV
      :  ..:::::::.  .:: ...:::..  . .  .:::.:   :       :.:..
8    TLGLIKPHATSEQRE-QILKIVKEAGFDLTQVKKMFLTPEQIEKIYPKVTGK-DFYKDLL
            460       470       480       490       500       510

70        80        90       100       110
7B   TEMYSGPCVAMEIQQNNATKTFREFCGPADPEIARHLRPGTLRAIFGKTKIQNAVH (SEQ ID NO: 225)
      .  ::  ::::::::::...  .:  . : :  : .   :.::.:::::::  ::
8    EMLSVGPSMVMILTKWNAVAEWRRLMGPTDPEEAKLLSPDSIRAQFGISKLKNIVH (SEQ IDNO: 226)
            520       530       540       550       560

Waterman-Eggert score: 128; 41.3 bits; E(1) < 2.9e-08
23.3% identity (60.3% similar) in 116 aa overlap (20-134:334-448)
            20        30        40        50        60        70
7B   ILMAIRDAGFEISAMQMFNMDRVNVEEFYEVYKGVVTEYHDMVTEMYSGPCVAMEIQQNN
      .: :.:.:  :.: ::: ..   ..    ..    .:..:    ..   .:.
8    VLRIIKDEDFKILEQRQVVLSEKEAQALCKEYENE-DYFNKLIENMTSGPSLALVLLRDN
            340       350       360       370       380       390

80        90       100       110       120       130
7B   ATKTFREFCGPADPEIARHLRPGTLRAIFGKTKIQ-NAVHCTDLPEDGLLEVQYFF (SEQ ID NO: 227)
     .  .... ::  : :   :: . .:.  ..    .  . : : : .:    .:.::
8    GLQYWKQLLGPRTVEEAIEYFPESLCAQFAMDSLPVNQLYGSDSLETAEREIQHFF (SEQ ID NO: 228)
            400       410       420       430       440

Waterman-Eggert score: 76; 26.4 bits; E(1) < 0.00088
23.4% identity (46.8% similar) in 111 aa overlap (6-105:159-268)
           10        20        30        40        50        60
7B   IVKPHAVSEGLLGKILMAIRDAGFEISAMQMFNMDRVNVEEFYEVYKGVVTEYHDMVTEM
     :.:: ::   . .:  : : :  :::  :  .    . .::        ....... :
8    IIKPDAVISKKVLEIKRKITKAGFIIEAEHKTVLTEEQVVNFYSRIADQC-DFEEFVSFM
            160       170       180       190       200       210

70        80        90       100
7B   YSGPCVAMEIQQNNATKTFREFCGPA----------DPEIARHLRPGTLR (SEQ ID NO: 229)
     ::    . .::. .  :       :          .::  .. :: ::  :
8    TSGLSYILVVSQGSKHNPPSEETEPQTDTEPNERSEDQPEVEAQVTPGMMK (SEQ ID NO: 230)
            220       230       240       250       260

NME9
MLSSKGLTVVDVYQGWCGPCKPVVSLFQKMRIEVGLDLLHFALAEADRLDVLEKYRGKCE
PTFLFYAIKDEALSDEDECVSHGKNNGEDEDMVSSERTCTLAIIKPDAVAHGKTDEIIMK
IQEAGFEILTNEERTMTEAEVRLFYQHKAGESPSSVRHRNALQCRPWKPGQRRC (SEQ ID NO: 231)

41.3% identity (67.4% similar) in 46 aa overlap (3-46:100-145)
           10        20        30        40
7A   TLALIKPDAIS--KAGEIIEIINKAGFTITKLKMMMLSRKEALDFH
     ::.:::::::.  .:: ::  ..:::::. .  ::   . .:.
9    TLAIIKPDAVAHGKTDEIIMKIQEAGFEILTNEERTMTEAEVRLFY
            100       110       120       130       140

>--
```

```
Waterman-Eggert score: 30; 13.5 bits; E(1) < 0.85
28.6% identity (71.4% similar) in 14 aa overlap (69-82:100-113)
                70        80
         AMEILRDDAICEWK (SEQ ID NO: 232)
         .. :... ::. . :
         TLAIIKPDAVAHGK (SEQ ID NO: 233)
         100       110

Waterman-Eggert score: 29; 13.2 bits; E(1) < 0.91
25.8% identity (74.2% similar) in 31 aa overlap (12-42:121-149)
              20        30        40
7A     ISKAGEIIEIINKAGFTITKLKMMMLSRKEA (SEQ ID NO: 234)
       :..:: .::... .::. .. ....:
9      IQEAG--FEILTNEERTMTEAEVRLFYQHKA (SEQ ID NO: 235)
              130       140

39.6% identity (69.8% similar) in 53 aa overlap (1-53:98-150)
              10        20        30        40        50
7A    NCTCCIVKPHAVSEGLLGKILMAIRDAGFEISAMQMFNMDRVNVEEFYEVYKG (SEQ ID NO: 236)
      .::  :.:: ::..:   .:.: :..::::: ..   .: ..::. ::.   :
9     TCTLAIIKPDAVAHGKTDEIIMKIQEAGFEILTNEERTMTEAEVRLFYQHKAG (SEQ ID NO: 237)
          100       110       120       130       140       150

NME10 NP_008846.2 protein XRP2 [Homo sapiens]
MGCFFSKRRKADKESRPENEEERPKQYSWDQREKVDPKDYMFSGLKDETVGRLPGTVAGQQFLIQDCENC
NIYIFDHSATVTIDDCTNCIIFLGPVKGSVFFRNCRDCKCTLACQQFRVRDCRKLEVFLCCATQPIIESS
SNIKFGCFQWYYPELAFQFKDAGLSIFNNTWSNIHDFTPVSGELNWSLLPEDAVVQDYVPIPTTEELKAV
RVSTEANRSIVPISRGQRQKSSDESCLVVLFAGDYTIANARKLIDEMVGKGFFLVQTKEVSMKAEDAQRV
FREKAPDFLPLLNKGPVIALEFNGDGAVEVCQLIVNEIFNGTKMFVSESKETASGDVDSFYNFADIQMGI (SEQ
ID NO: 238)

23.58 identity (66.28 similar) in 68 aa overlap (11-78:246-308)
            20        30        40        50        60        70
7A   AISKAGEIIEIINKAGFTITKLKMMMLSRKEALDFHVDHQSRPFFNELIQFITTGPIIAM
     .:.:: ..:: .  ::  ::.      .:   .:  .   :   ... ... ::.:.
10   TIANARKLIDEMVGKGFFLVQTKEVSMKAEDAQ--RVFREKAP---DFLPLLNKGPVIAL
         250       260       270         280          290       300

7A   EILRDDAI (SEQ ID NO: 239)
     :.   : :.
10   EFNGDGAV (SEQ ID NO: 240)

Waterman-Eggert score: 35; 15.1 bits; E(1) < 0.73
28.9% identity (57.8% similar) in 45 aa overlap (66-108:200-244)
            70        80        90       100
7A   PIIAMEILRDDAIC-EWKRLLGPANSGVARTDASES-IRALFGTD (SEQ ID NO: 241)
     ::  .   :.: .. .   ....:: . ...::...  .
10   PIPTTEELKAVRVSTEANRSIVPISRGQRQKSSDESCLVVLFAGD (SEQ ID NO: 242)
         200       210       220       230       240

Waterman-Eggert score: 33; 14.4 bits; E(1) < 0.87
14.7% identity (52.0% similar) in 75 aa overlap (7-80:35-109)
             10        20        30        40        50        60
7A   IKPDAISKAGEIIEIINKAGFTITKLKMMMLSRKEALDFHVDHQSRPFFNELIQ-FITTG
     . :      :   : :...     . :::      ... ... . .
10   VDPKDYMFSGLKDETVGRLPGTVAGQQFLIQDCENCNIYIFDHSATVTIDDCTNCIIFLG
         40        50        60        70        80        90

70        80
7A   PIIAMEILRDDAICE (SEQ ID NO: 243)
     :.  . ...:.    :.
10   PVKGSVFFRNCRDCK (SEQ ID NO: 244)
            100

Waterman-Eggert score: 45; 17.5 bits; E (1) < 0.22
21.6% identity (58.8% similar) in 51 aa overlap (4-50:130-180)
           10        20        30        40        50
7B    CCIVKP--HAVSEGLLGKILMAIRDAGFEI--SAMQMFNMDRVNVEEFYEV (SEQ ID NO: 245)
      ::   .. .. .. :.  .  ........   :....:      :..: :
10    CCATQPIIESSSNIKFGCFQWYYPELAFQFKDAGLSIFNNTWSNIHDFTPV (SEQ ID NO: 246)
         130       140       150       160       170       180
```

As an example, antibodies or antibody mimics that bind to the NME7 homologous peptides ("homologous peptides") in particular homologous to A1, A2, B1, B2 or B3 peptides, may be administered to a patient diagnosed with or at risk of developing a cancer or cancer metastasis.

Homologous Peptides to A1, A2, B1, B2 or B3 Peptides

Homologous peptides to A1, A2, B1, B2 or B3 peptides may include without limitation the following:

```
NME2A1
(amino acids)
                                    (SEQ ID NO: 247)
RASEEHLKQHYIDLKD NME2A2
(amino acids)
                                    (SEQ ID NO: 248)
PADSKPGT NME2B1
(amino acids)
                                    (SEQ ID NO: 249)
QKGFRLVAMKFLRASEEHLK NME2B2
(amino acids)
                                    (SEQ ID NO: 250)
IDLKDRPFPGLVKY NME2B3
(amino acids)
                                    (SEQ ID NO: 251)
GDFCIQVGRNIIHGSDSVKSAEKEISLWF NME3A1
(amino acids)
                                    (SEQ ID NO: 252)
QASEELLREHYVELRE NME3A1
(amino acids)
                                    (SEQ ID NO: 253)
PGDATPGT NME3B1
(amino acids)
                                    (SEQ ID NO: 254)
RKGFKLVALKLVQASEELLR NME3B2
(amino acids)
                                    (SEQ ID NO: 255)
VELRERPFYSRLVKY NME3B3
(amino acids)
                                    (SEQ ID NO: 256)
GDFCVEVGKNVIHGSDSVESAQREIALWF NME4A1
(amino acids)
                                    (SEQ ID NO: 257)
QAPESVLAEHYQDLRR NME4A2
(amino acids)
                                    (SEQ ID NO: 258)
SAEAAPGT NME4B1
(amino acids)
                                    (SEQ ID NO: 259)
RRGFTLVGMKMLQAPESVLA NME4B2
(amino acids)
                                    (SEQ ID NO: 260)
QDLRRKPFYPALIRY NME4B3
(amino acids)
                                    (SEQ ID NO: 261)
GDFSVHISRNVIHASDSVEGAQREIQLWF NME5A1
(amino acids)
                                    (SEQ ID NO: 262)
RLSPEQCSNFYVEKYG NME5A2
(amino acids)
                                    (SEQ ID NO: 263)
SLVAKETHPDS NME5B1
(amino acids)
                                    (SEQ ID NO: 264)
RSGFTIVQRRKLRLSPEQCS NME5B2
(amino acids)
                                    (SEQ ID NO: 265)
VEKYGKMFFPNLTAY NME5B3
(amino acids)
                                    (SEQ ID NO: 266)
AIYGTDDLRNALHGSNDFAAAEREIRFMF NME6A1
(amino acids)
                                    (SEQ ID NO: 267)
LWRKEDCQRFYREHEG NME6A2
(amino acids)
                                    (SEQ ID NO: 268)
VFRARHVAPDS NME6B1
(amino acids)
                                    (SEQ ID NO: 269)
SNKFLIVRMRELLWRKEDCQ NME6B2
(amino acids)
                                    (SEQ ID NO: 270)
REHEGRFFYQRLVEF NME6B3
(amino acids)
                                    (SEQ ID NO: 271)
GSFGLTDTRNTTHGSDSVVSASREIAAFF NME8A1
(amino acids)
                                    (SEQ ID NO: 272)
VLSEKEAQALCKEYEN NME8A2
(amino acids)
                                    (SEQ ID NO: 273)
VEEAIEYFPES NME8A3
(amino acids)
                                    (SEQ ID NO: 274)
FLTPEQIEKIYPKVTG NME8A4
(amino acids)
                                    (SEQ ID NO: 275)
PEEAKLLSPDS NME8A5
(amino acids)
                                    (SEQ ID NO: 276)
VLTEEQVVNFYSRIAD
```

```
NME8B1
(amino acids)
                                  (SEQ ID NO: 277)
EAGFDLTQVKKMFLTPEQIE NME8B2
(amino acids)
                                  (SEQ ID NO: 278)
PKVTGKDFYKDLLEM NME8B3
(amino acids)
                                  (SEQ ID NO: 279)
AQFGISKLKNIVH NME8B4
(amino acids)
                                  (SEQ ID NO: 280)
DEDFKILEQRQVVLSEKEAQ NME8B5
(amino acids)
                                  (SEQ ID NO: 281)
KEYENEDYFNKLIEN NME8B6
(amino acids)
                                  (SEQ ID NO: 282)
AQFAMDSLPVNQLYGSDSLETAEREIQHFF NME8B7
(amino acids)
                                  (SEQ ID NO: 283)
KAGFIIEAEHKTVLTEEQVV NME8B8
(amino acids)
                                  (SEQ ID NO: 284)
SRIADQCDFEEFVSF NME9A1
(amino acids)
                                  (SEQ ID NO: 285)
TMTEAEVRLFY NME9B1
(amino acids)
                                  (SEQ ID NO: 286)
EAGFEILTNEERTMTEAEVR NME10A1
(amino acids)
                                  (SEQ ID NO: 287)
SMKAEDAQRVFREK NME10A2
(amino acids)
                                  (SEQ ID NO: 288)
GQRQKSSDES NME10A3
(amino acids)
                                  (SEQ ID NO: 289)
IQDCENCNIYIFDHSA NME10B1
                                  (SEQ ID NO: 290)
ELAFQFKDAGLSIFNNTWSNIH
```

In some cases, peptides derived from other NME proteins can be made more homologous to NME7 A1, A2, B1, B2 or B3 peptides by shifting the frame or extending the NME7 peptides such that the extended peptides are more homologous to the NME7 peptides that gave rise to antibodies that inhibit cancer or cancer metastases. As another example, antibodies or antibody mimics that bind to the NME7 homologous extended peptides ("extended peptides") may be administered to a patient diagnosed with or at risk of developing a cancer or cancer metastasis.

Homologous Extended Peptides to A1, A2, B1, B2 or B3 Peptides

Homologous peptides to A1, A2, B1, B2 or B3 peptides that are extended peptides may include without limitation the following:

```
NME2A1
(amino acids)
                                  (SEQ ID NO: 291)
RASEEHLKQHYIDLKDRPFFPGL NME2A2
(amino acids)
                                  (SEQ ID NO: 292)
LGETNPADSKPGTIRGDF NME2B1
(amino acids)
                                  (SEQ ID NO: 293)
GLVGEIIKRFEQKGFRLVAMKFLRASEEHLKQHY NME2B2
(amino acids)
                                  (SEQ ID NO: 294)
YIDLKDRPFFPGLVKYMNSGPVVAM NME2B3
(amino acids)
                                  (SEQ ID NO: 295)
PGTIRGDFCIQVGRNIIHGSDSVKSAEKEISLWF NME3A1
(amino acids)
                                  (SEQ ID NO: 296)
LKLVQASEELLREHYVELRERPFYSRL NME3A1
(amino acids)
                                  (SEQ ID NO: 297)
LIGATDPGDATPGTIRGDF NME3B1
(amino acids)
                                  (SEQ ID NO: 298)
LVGEIVRRFERKGFKLVALKLVQASEELLRE NME3B2
(amino acids)
                                  (SEQ ID NO: 299)
EHY-VELRERPFYSRLVKYMGSGPVVAM NME3B3
(amino acids)
                                  (SEQ ID NO: 300)
PGTIRGDFCVEVGKNVIHGSDSVESAQREIALWF NME4A1
(amino acids)
                                  (SEQ ID NO: 301)
GFTLVGMKMLQAPESVLAEHYQDLRRKPF NME4A2
(amino acids)
                                  (SEQ ID NO: 302)
GHTDSAEAAPGTIRGDF NME4B1
(amino acids)
                                  (SEQ ID NO: 303)
LVGDVIQRFERRGFTLVGMKMLQAPESVLAEHY NME4B2
(amino acids)
                                  (SEQ ID NO: 304)
EHYQDLRRKPFYPALIRYMSSGPVVAM NME 4B3
(amino acids)
                                  (SEQ ID NO: 305)
PGTIRGDFSVHISRNVIHASDS VEGAQREIQLWF
```

```
NME5A1
(amino acids)
                                  (SEQ ID NO: 306)
GFTIVQRRKLRLSPEQCSNFYVEKYGKMFF NME5A2
(amino acids)
                                  (SEQ ID NO: 307)
LLGPNNSLVAKETHPDSLRAIYGTD NME5B1
(amino acids)
                                  (SEQ ID NO: 308)
IQDIILRSGFTIVQRRKLRLSPEQCSNFY NME5B2
(amino acids)
                                  (SEQ ID NO: 309)
FYVEKYGKMFFPNLTAYMSSGPLVAM NME5B3
(amino acids)
                                  (SEQ ID NO: 310)
PDSLRAIYGTDDLRNALHGSNDFAAAEREIRFMF NME6A1
(amino acids)
                                  (SEQ ID NO: 311)
FLIVRMRELLWRKEDCQRFYREHEGRFFYQRL NME6A2
(amino acids)
                                  (SEQ ID NO: 312)
LMGPTRVFRARHVAPDSIRGSFG NME6B1
(amino acids)
                                  (SEQ ID NO: 313)
ILSNKFLIVRMRELLWRKEDCQRFY NME6B2
(amino acids)
                                  (SEQ ID NO: 314)
FYREHEGRFFYQRLVEFMASGPIRA NME6B3
(amino acids)
                                  (SEQ ID NO: 315)
ARHVAPDSIRGSFGLTDTRNTTHGSDSVVSASREIAAFF NME8A1
(amino acids)
                                  (SEQ ID NO: 316)
FKILEQRQVVLSEKEAQALCKEYENEDYFNKLI NME8A2
(amino acids)
                                  (SEQ ID NO: 317)
WKQLLGPRTVEEAIEYFPESLCAQFAMD NME8A3
(amino acids)
                                  (SEQ ID NO: 318)
AGFDLTQVKKMFLTPEQIEKIYPKVTGKDFYKDL NME8A4
(amino acids)
                                  (SEQ ID NO: 319)
EWRRLMGPTDPEEAKLLSPDSIRAQFG NME8A5
(amino acids)
                                  (SEQ ID NO: 320)
KAGFIIEAEHKTVLTEEQVVNFYSRIADQCDFEE NME8B1
(amino acids)
                                  (SEQ ID NO: 321)
ILKIVKEAGFDLTQVKKMFLTPEQIEKIY NME8B2
(amino acids)
                                  (SEQ ID NO: 322)
YPKVTGKDFYKDLLEMLSVGP NME8B3
(amino acids)
                                  (SEQ ID NO: 323)
DPEEAKLLSPDSIRAQFGISKLKNIVH NME8B4
(amino acids)
                                  (SEQ ID NO: 324)
LRIIKDEDFKILEQRQVVLSEKEAQ NME8B5
(amino acids)
                                  (SEQ ID NO: 325)
KEYENE-DYFNKLIENMTSGPSLA NME8B6
(amino acids)
                                  (SEQ ID NO: 326)
PESLCAQFAMDSLPVNQLYGSDSLETAEREIQHFF NME8B7
(amino acids)
                                  (SEQ ID NO: 327)
IKRKITKAGFIIEAEHKTVLTEEQVVNFY NME8B8
(amino acids)
                                  (SEQ ID NO: 328)
FYSRIADQCDFEEFVSFMTSG NME9A1
(amino acids)
                                  (SEQ ID NO: 329)
AGFEILTNEERTMTEAEVRLFY NME9B1
(amino acids)
                                  (SEQ ID NO: 330)
IIMKIQEAGFEILTNEERTMTEAEVRLFY NME10A1
(amino acids)
                                  (SEQ ID NO: 331)
GFFLVQTKEVSMKAEDAQRVFREKAP NME10A2
(amino acids)
                                  (SEQ ID NO: 332)
EANRSIVPISRGQRQKSSDESCLVVLFAGD NME10A3
(amino acids)
                                  (SEQ ID NO: 333)
IQDCENCNIYIFDHSA NME10B1
                                  (SEQ ID NO: 334)
ELAFQFKDAGLSIFNNTWSNIHDFTPVDCT
```

Some NME proteins exert a function that is necessary for normal cell growth or development. For example, NME1 is thought to be required for normal cell function. Other NME proteins have catalytic domains whose function is required in normal cells or tissues. In these cases, therapeutic antibodies can be selected based on their ability to bind to the targeted, cancer associated NME, but not to a non-targeted NME. For example, the anti-NME7 antibodies presented here, 8F9A5A1, 8F9A4A3, and 5F3A5D4, were selected for their ability to bind to NME7$_{AB}$ but not to NME1; they were further selected based on their ability to inhibit cancer and cancer metastases.

In another aspect of the invention, anti-NME7 antibodies, antibody fragments, for example scFvs, or fragments of antibody mimics are incorporated into chimeric antigen receptors (CARs) which are engineered to be expressed in immune cells. The immune cell can be engineered to express an anti-NME7 CAR, an anti-MUC1* CAR, or both. One of the CARs may be expressed off of an inducible promoter. Alternatively, an immune cell may be engineered to express a CAR such as an anti-MUC1* CAR and an inducible anti-NME7 antibody or antibody fragment. In some instances the inducible promoter may contain NFAT response elements. In one aspect, these engineered species are expressed in T cells, NK cells or dendritic cells. The immune cells may be obtained from the patient or from a donor. In some cases, immune molecules such as MHCs, checkpoint inhibitors or receptors for checkpoint inhibitors are mutated or cut out, for example using CrisPR or CrisPR-like technology. In another aspect, ITAM molecules, Fos, or Jun are mutated or genetically excised via Talens, Sleeping Beauty, CrisPR or CrisPR-like technologies in patient or donor derived immune cells.

In one aspect of the invention, the anti-NME7 antibodies or antibody mimics for use in CAR T format are chosen from among the group of antibodies or antibody mimics that are specific for NME7 but do not disrupt the binding of NME7 to the extra cellular domain of MUC1*. In this way, the anti-NME7 antibody or antibody mimic that targets the CART to the tumor will not simply pluck the ligand from the receptor, whereupon the T cell would be unable to inject the target cancer cell with Granzyme B. Such antibodies or antibody mimics are generated by immunizing an animal with an NME7 peptide, such as NME7 peptides A1, A2, B1, B2 or B3 or selected by virtue of their ability to bind to NME7 peptides A1, A2, B1, B2 or B3. Antibodies or antibody mimics can be screened for their ability to specifically bind to NME7, but not to NME1 or NME2, and also for their inability to disrupt binding between NME7 and MUC1* extra cellular domain. For example, in an ELISA setup, the PSMGFR peptide is immobilized to the surface. A labeled $NME7_{AB}$ is allowed to bind to the surface immobilized MUC1* extra cellular domain, and detection of the $NME7_{AB}$ label is measured in the presence or absence of the test antibody or antibody mimic. In one aspect of the invention, an antibody that does not diminish binding between $NME7_{AB}$ and surface-immobilized MUC1* extra cellular domain peptide is selected as an antibody that is incorporated into a CAR and engineered to be expressed in an immune cell and then administered to a patient for the treatment or prevention of cancer or cancer metastases.

In one aspect of the invention, an anti-NME7 antibody or fragment thereof is administered to a patient diagnosed with or at risk of developing a cancer or cancer metastasis. In one aspect, the anti-NME7 antibody or antibody fragment binds to an NME peptide discussed above in particular under sections "Homologous peptides to A1, A2, B1, B2 or B3 peptides" and the "Homologous extended peptides to A1, A2, B1, B2 or B3 peptides".

In another aspect, the antibody, antibody fragment or antibody mimic binds to an NME7 derived peptide chosen from among A1, A2, B1, B2 or B3 (SEQ ID NOS: 141-145). In yet another aspect, the antibody, antibody fragment or antibody mimic binds to an NME7 peptide comprising most or all of the B3 peptide. In one aspect of the invention, the anti-NME7 antibody, antibody fragment or antibody mimic comprises sequences derived from the variable domains of anti-NME7 antibodies 8F9A4A3 ("4A3") (SEQ ID NOS: 1001-1015), 8F9A5A1 ("5A1") (SEQ ID NOS: 1016-1030), or 8H5H5G4 ("5G4") (SEQ ID NOS: 1031-1045) shown below.

```
Anti-NME7 B3 peptide monoclonal antibodies
Monoclonal antibody 8F9A4A3 "4A3"
Heavy chain variable region sequence
Gaggtccagctgcaacagtctggacctgaactggtgaagcctggggcttcagtgaagatatcctgcaagacttctgg
aaacacattcactgaatacaccatgcactgggtgaagcagagccatggaaagagccttgagtggattggaggttttaatcctaacaatg
gtgttactaactacaaccagaagttcaagggcaaggccacattgactgtagacaagtcctccagcacagcctacatggagctccgcag
cctgacatctgaggattctgcagtctattactgtgcaagacggtactaccatagtctctacgtgttttactttgactactggggccaaggca
ccactctcacagtctcctca (SEQ ID NO: 1138)

Translated protein, wherein the underlined sequence is the complementarity
determining region (CDR):
EVQLQQSGPELVKPGASVKISCKTSGNTFTEYTMHWVKQSHGKSLEWIG
GFNPNNGVTNYNQKFKGKATLTVDKSSSTAYMELRSLTSEDSAVYYCARRYYHSLY
VFYFDYWGQGTTLTVSS (SEQ ID NO: 1139)

Mouse 8F9A4A3 heavy chain variable domain framework 1 (FR1) sequence
gaggtccagctgcaacagtctggacctgaactggtgaagcctggggcttcagtgaagatatcctgcaagacttctgg
a (SEQ ID NO: 1113)

EVQLQQSGPELVKPGASVKISCKTSG (SEQ ID NO: 1114)

Heavy chain variable region CDR1:
aacacattcactgaataccaccatgcac (SEQ ID NO: 1115)

NTFTEYTMH (SEQ ID NO: 388)

Mouse 8F9A4A3 heavy chain variable domain framework 2 (FR2) sequence
tgggtgaagcagagccatggaaagagccttgagtggattgga (SEQ ID NO: 1116)

WVKQSHGKSLEWIG (SEQ ID NO: 1117)

Mouse 8F9A4A3 Heavy chain variable region CDR2:
ggttttaatcctaacaatggtgttactaactacaaccagaagttcaagggc (SEQ ID NO: 1118)
```

GFNPNNGVTNYNQKFKG (SEQ ID NO: 389)

Mouse 4A3 heavy chain variable domain framework 3 (FR3) sequence aaggccacattgactgtagacaagtcctccagcacagcctacatggagctccgcagcctgacatctgaggattctgc
agtctattactgtgcaaga (SEQ ID NO: 1119)

KATLTVDKSSSTAYMELRSLTSEDSAVYYCAR (SEQ ID NO: 1120)

Mouse 8F9A4A3 Heavy chain variable region CDR3:
cggtactaccatagtctctacgtgttttactttgactac (SEQ ID NO: 1121)

RYYHSLYVFYFDY (SEQ ID NO: 390)

Mouse 8F9A4A3 Light chain variable region sequence
gatatccagatgacacagactacatcctccctgtctgcctctctgggagacagagtcaccctcagttgcagtgcaagtc
agggcattagcaattatttaaactggtatcagcagaaaccagatggaactgttgaactcctgatcttttacacatcaagtttacactcagga
gtcccatcaaggttcagtggcagtgggtctgggacagattattctctcaccatcagcaacctggaacctgaagatattgccacttactatt
gtcagcagtatagtaagcttccttacacgttcggaggggggaccaagctggaaataaaa (SEQ ID NO: 1136)

Translated protein, wherein the underlined sequence is the complementarity
determining region (CDR):
DIQMTQTTSSLSASLGDRVTLSCSASQGISNYLNWYQQKPDGTVELLIFYT
SSLHSGVPSRFSGSGSGTDYSLTISNLEPEDIATYYCQQYSKLPYTFGGGTKLEIK
(SEQ ID NO: 1109)

Mouse 8F9A4A3 light chain variable domain framework 1 (FR1) sequence
gatatccagatgacacagactacatcctccctgtctgcctctctgggagacagagtcaccctcagttgc (SEQ ID NO:
1122)

DIQMTQTTSSLSASLGDRVTLSC (SEQ ID NO: 1123)

Mouse 8F9A4A3 Light chain variable region CDR 1:
agtgcaagtcagggcattagcaattatttaaac (SEQ ID NO: 1124)

SASQGISNYLN (SEQ ID NO: 393)

Mouse 4A3 light chain variable domain framework 2 (FR2) sequence
tggtatcagcagaaaccagatggaactgttgaactcctgatcttt (SEQ ID NO: 1125)

WYQQKPDGTVELLIF (SEQ ID NO: 1126)

Mouse 8F9A4A3 Light chain variable region CDR2:
tacacatcaagtttacactca (SEQ ID NO: 1127)

YTSSLHS (SEQ ID NO: 394)

Mouse 8F9A4A3 light chain variable domain framework 3 (FR3) sequence
ggagtcccatcaaggttcagtggcagtgggtctgggacagattattctctcaccatcagcaacctggaacctgaagat
attgccacttactattgt (SEQ ID NO: 1128)

GVPSRFSGSGSGTDYSLTISNLEPEDIATYYC (SEQ ID NO: 1129)

Mouse 8F9A4A3 Light chain variable region CDR3:
Cagcagtatagtaagcttccttacacg (SEQ ID NO: 1130)

QQYSKLPYT (SEQ ID NO: 395)

Humanized 8F9A4A3 H-ori heavy chain variable domain sequence
caggttcagctggttcagtctggtgcagaagtgaagaaacctggcgcctctgtgaaggtgtcctgcaaggtgtccgg
aaataccttcaccgagtacaccatgcactgggtccgacaggcccctggcaaaggacttgaatggatgggcggcttcaaccccaacaa
cggcgtgaccaactacaaccagaaattcaagggccgcgtgaccatgaccgaggacacaagcacagacaccgcctacatggaactg
agcagcctgagaagcgaggacaccgccgtgtactactgcgccagaaggtactaccacagcctgtacgtgttctacttcgactactggg
gccagggcaccctggtcacagtttcttct (SEQ ID NO: 1131)

QVQLVQSGAEVKKPGASVKVSCKVSGNTFTEYTMHWVRQAPGKGLEW
MGGFNPNNGVTNYNQKFKGRVTMTEDTSTDTAYMELSSLRSEDTAVYYCARRYYH
SLYVFYFDYWGQGTLVTVSS (SEQ ID NO: 1004)

Humanized 8F9A4A3 H-1.46 heavy chain variable domain sequence
caagtgcagctggtgcagagcggcgccgaggtgaagaaacctggcgccagcgtgaaagtgtcctgcaaggccag
cggcaatacattcaccgagtacacaatgcactgggtcagacaggcccccggccagggcctggaatggatcggcggatttaacccca
acaacgcgtgacaaactacaaccagaagttcaagggcaaggtgaccatcacaagagacaccagcagcagcaccgtgtacatggaa
actgtcttctctgcggagcgaggataccgccgtgtactattgtgccagacgtactaccacagcctgtacgtgttctacttcgactactgg
ggacagggcaccctggttaccgtgtcctct (SEQ ID NO: 1101)

QVQLVQSGAEVKKPGASVKVSCKASGNTFTEYTMHWVRQAPGQGLEWI
GGFNPNNGVTNYNQKFKGKVTITRDTSSSTVYMELSSLRSEDTAVYYCARRYYHSL
YVFYFDYWGQGTLVTVSS (SEQ ID NO: 1102)

Humanized 8F9A4A3 H-3.15 heavy chain variable domain sequence
gaggtgcagctggtggaaagcggcggcggcctggttaagcctggcggatctctgagactgagctgtgccgcttctg
gcaataccttcaccgagtacaccatgcactgggtgcggcaggcccctggaaaaggcctggaatggatcggcggatttaaccccaac
aacggcgtgacaaattacaaccagaaattcaagggcaagttcaccatcacaagagataagagcaagaacaccctgtacctgcaaatg
aacagcctgaagtccgaggacacegeegtgtactactgcgccagacggtactaccacagcctctatgtgttctacttcgactactgggg
ccagggcacactggtcaccgtgtccagc (SEQ ID NO: 1132)

EVQLVESGGGLVKPGGSLRLSCAASGNTFTEYTMHWVRQAPGKGLEWIG
GFNPNNGVTNYNQKFKGKFTITRDKSKNTLYLQMNSLKSEDTAVYYCARRYYHSLY
VFYFDYWGQGTLVTVSS (SEQ ID NO: 1133)

Humanized 8F9A4A3 H-4.4 heavy chain variable domain sequence
caagtgcagctgcaggagagcggacctggcctggttaagcctggaggcaccctgtctctgacatgtgctgtgtctgg
caatacctttaccgagtacaccatgcactgggtgcggcagcctccaggcaagggcctggaatggatcggcggcttcaaccccaacaa
cggcgtgacaaattacaaccagaaattcaagggaaaagtgaccatcaccgtggataagtccaagaacaccttcagcctcaagctgag
cagcgtgacagccgccgacaccgccgtgtactactgcgccagaagatactatcacagcctgtacgtgttctacttcgactactggggc
cagggcacactggtcaccgtgtccagc (SEQ ID NO: 1105)

QVQLQESGPGLVKPGGTLSLTCAVSGNTFTEYTMHWVRQPPGKGLEWIG
GFNPNNGVTNYNQKFKGKVTITVDKSKNTFSLKLSSVTAADTAVYYCARRYYHSLY
VFYFDYWGQGTLVTVSS (SEQ ID NO: 1106)

Humanized 8F9A4A3 L-1.6 light chain variable domain sequence
gatatccagatgacacagagccctagctccctgagcgccagcgtgggcgaccgggtcaccattacatgcagcgctt
ctcagggcatctccaactacctgaactggtaccagcagaaaccggcaaggcccctaagctgctgatcttctacaccagctctctgca
cagcggcgtgccatctagattcagcggatctggcagcggcaccgactacaccctgaccatcagctccctccagcctgaggacttcgc
cacctactactgtcagcaatacagcaagctgccttataccttggcggcggaacaaaggtggaaatcaag
(SEQ ID NO: 1103)

DIQMTQSPSSLSASVGDRVTITCSASQGISNYLNWYQQKPGKAPKLLIFYT
SSLHSGVPSRFSGSGSGTDYTLTISSLQPEDFATYYCQQYSKLPYTFGGGTKVEIK
(SEQ ID NO: 1104)

Humanized 8F9A4A3 L-3.15 light chain variable domain sequence
gagatcgtgatgacccagagcccagctacacttagtgtgagtccaggtgaacgggctaccctgtcctgcagcgcca
gccagggcatcagcaactacctgaactggtaccagcagaaacctggccaggcccctagactgctgatcttctacaccagcagcctgc
acagcggcatccccgccagattcagcggcagcggctctggaacagactacaccctgacaatctctagcctgcagtctgaagattttgc
cgtctactactgtcagcaatacagcaagctgccttataccttcggcggcggaaccaaggtggaaattaag (SEQ ID NO: 1134)

EIVMTQSPATLSVSPGERATLSCSASQGISNYLNWYQQKPGQAPRLLIFYT
SSLHSGIPARFSGSGSGTDYTLTISSLQSEDFAVYYCQQYSKLPYTFGGGTKVEIK
(SEQ ID NO: 1135)

Humanized 8F9A4A3 L-4.1 light chain variable domain sequence
gatatcgtgatgacccagagcccagacgacctggcagtgagcctgctacaatcaactgcagcgcca
gccagggcatctccaactacctgaattggtatcagcagaaacctggccaggctcctaagctgctgatcttctacaccagcagcctgcac
agcggcgtgccagatagattcagcggcagcggatctggcaccgactacacactgaccatttcttctctcaggccgaggacgtggcc
gtctactactgtcagcaatacagcaagctgccttacacctttggcggaggcacaaaggtggaaatcaag (SEQ ID NO: 1107)

DIVMTQSPDSLAVSLGERATINCSASQGISNYLNWYQQKPGQAPKLLIFYT
SSLHSGVPDRFSGSGSGTDYTLTISSLQAEDVAVYYCQQYSKLPYTFGGGTKVEIK
(SEQ ID NO: 1108)

Monoclonal antibody 5D9E2B11
Heavy chain variable region sequence
H-1, 4, 7, 8, 12
gtccagctgcaacagtctggacctgatctggtgaagcctgggacttcagtgaagatatcctgtaagacttctggaaaca
cattcactgaatacaccatgcactgggtgaagcagagccatggaaagagccttgagtggattggagggtttaatcctaacaatggtgtta
ctaactacaaccagaagttcaagggcaaggccacattgactgtagacaagtcctccagcacagtctacatggagctccgcagcctga
catctgaggattctgcagtctattactgtgcaagacgttactaccatagtacctacgtgttctactttgactcctggggccaaggcaccact
ctcacagtctcctca (SEQ ID NO: 396)

Translated protein, wherein the underlined sequence is the complementarity
determining region (CDR):
VQLQQSGPDLVKPGTSVKISCKTSGNTFTEYTMHWVKQSHGKSLEWIGGF
NPNNGVTNYNQKFKGKATLTVDKSSSTAYMELRSLTSEDSAVYYCARRYYHSTYVF
YFDSWGQGTTLTVSS (SEQ ID NO: 397)

Heavy chain variable region CDR1:
NTFTEYTMH (SEQ ID NO: 398)

Heavy chain variable region CDR2:
GFNPNNGVTNYNQKFKG (SEQ ID NO: 399)

Heavy chain variable region CDR3:
RYYHSTYVFYFDS (SEQ ID NO: 400)

Light chain variable region sequence
K-3, 4, 5, 6, 12
gatatccagatgacacagactacatcctccctgtctgcctctctgggagacagagtcaccatcagttgcagtgcaagtc
agggcattagcaattatttaaactggtttcagcagaaaccagatggaactattaagctcctgatctattacacatcaagtttacattcagga
gtcccatcaaggttcagtggcagtgggtctgggacagattattctctcaccatcagtaatgtggaacctgaagatattgccacttactattg
tcagcagtatagtaagcttccttacacgttcggaggggggaccaagctggagataaaacgg (SEQ ID NO: 401)

Translated protein:
DIQMTQTTSSLSASLGDRVTISCSASQGISNYLNWFQQKPDGTIKLLIYYTS
SLHSGVPSRFSGSGSGTDYSLTISNVEPEDIATYYCQQYSKLPYTFGGGTKLEIKR
(SEQ ID NO: 402)

Translated protein, wherein the underlined sequence is the complementarity
determining region (CDR):
DIQMTQTTSSLSASLGDRVTISCSASQGISNYLNWFQQKPDGTIKLLIYYTS
SLHSGVPSRFSGSGSGTDYSLTISNVEPEDIATYYCQQYSKLPYTFGGGTKLEIKR
(SEQ ID NO: 403)

Light chain variable region CDR 1:
SASQGISNYLN (SEQ ID NO: 404)

Light chain variable region CDR2:
YTSSLHS (SEQ ID NO: 405)

Light chain variable region CDR3:
QQYSKLPYT (SEQ ID NO: 406)

Monoclonal antibody 5D9E10E4
Heavy chain variable region sequence
H-2, 4, 7, 10, 12
gtccagctgcaacagtctggacctgatctggtgaagcctggggacttcagtgaagatatcctgtaagacttctggaaaca
cattcactgaatacaccatgcactgggtgaagcagagccatggaaagagccttgagtggattggaggttttaatcctaacaatggtgtta
ctaactacaaccagaagttcaaggggcaaggccacattgactgtagacaagtcctccagcacagcctacatggagctccgcagcctga
catctgaggattctgcagtctattactgtgcaagacgttactaccatagtacctacgtgttctactttgactcctggggccaaggcaccact
ctcacagtctcctca (SEQ ID NO: 407)

Translated protein, wherein the underlined sequence is the complementarity
determining region (CDR):
VQLQQSGPDLVKPGTSVKISCKTSGNTFTEYTMHWVKQSHGKSLEWIGGF
NPNNGVTNYNQKFKGKATLTVDKSSSTAYMELRSLTSEDSAVYYCARRYYHSTYVF
YFDSWGQGTTLTVSS (SEQ ID NO: 408)

Heavy chain variable region CDR1:
NTFTEYTMH (SEQ ID NO: 409)

Heavy chain variable region CDR2:
GFNPNNGVTNYNQKFKG (SEQ ID NO: 410)

Heavy chain variable region CDR3:
RYYHSTYVFYFDS (SEQ ID NO: 411)

Light chain variable region sequence
K-2, 6, 8, 14, 15
gatatccagatgacacagactacatcctccctgtctgcctctctgggagacagagtcaccatcagttgcagtgcaagtc
agggcattagcaattatttaaactggtttcagcagaaaccagatggaactattaagctcctgatctattacacatcaagtttacattcagga
gtcccatcaaggttcagtggcagtgggtctgggacagattattctctcaccatcagtaatgtggaacctgaagatattgccacttactattg
tcagcagtatagtaagcttccttacacgttcggaggggggaccaagctggagataaaacgg (SEQ ID NO: 412)

Translated protein, wherein the underlined sequence is the complementarity
determining region (CDR):
DIQMTQTTSSLSASLGDRVTISCSASQGISNYLNWFQQKPDGTIKLLIYYTS
SLHSGVPSRFSGSGSGTDYSLTISNVEPEDIATYYCQQYSKLPYTFGGGTKLEIKR
(SEQ ID NO: 413)

Light chain variable region CDR 1:
SASQGISNYLN (SEQ ID NO: 414)

Light chain variable region CDR2:
YTSSLHS (SEQ ID NO: 415)

Light chain variable region CDR3:
QQYSKLPYT (SEQ ID NO: 416)

Monoclonal antibody 5D9G2C4
Heavy chain variable region sequence

H-4, 9, 10, 11, 13
gtccagctgcaacagtctggacctgatctggtgaagcctggggacttcagtgaagatatcctgtaagacttctggaaaca
cattcactgaatacaccatgcactgggtgaagcagagccatggaaagagccttgagtggattggaggttttaatcctaacaatggtgtta
ctaactacaaccagaagttcaagggcaaggccacattgactgtagacaagtcctccagcacagcctacatggagctccgcagcctga
catctgaggattctgcagtctattactgtgcaagacgttactaccatagtacctacgtgttctactttgactcctggggccaaggcaccact
ctcacagtctcctca (SEQ ID NO: 417)

Translated protein, wherein the underlined sequence is the complementarity
determining region (CDR):
VQLQQSGPDLVKPGTSVKISCKTSGNTFTEYTMHWVKQSHGKSLEWIGGF
NPNNGVTNYNQKFKGKATLTVDKSSSTAYMELRSLTSEDSAVYYCARRYYHSTYVF
YFDSWGQGTTLTVSS (SEQ ID NO: 418)

Heavy chain variable region CDR1:
NTFTEYTMH (SEQ ID NO: 419)

Heavy chain variable region CDR2:
GFNPNNGVTNYNQKFKG (SEQ ID NO: 420)

Heavy chain variable region CDR3:
RYYHSTYVFYFDS (SEQ ID NO: 421)

Light chain variable region sequence
K-4, 6, 7, 8, 10
gatatccagatgacacagactacatcctccctgtctgcctctctgggagacagagtcaccatcagttgcagtgcaagtc
agggcattagcaattatttaaactggtttcagcagaaaccagatggaactattaagctcctgatctattacacatcaagtttacattcagga
gtcccatcaaggttcagtggcagtgggtctgggacagattattctctcaccatcagtaatgtggaacctgaagatattgccacttactattg
tcagcagtatagtaagcttccttacacgttcggaggggggaccaagctggagataaaacgg (SEQ ID NO: 422)

Translated protein, wherein the underlined sequence is the complementarity
determining region (CDR):
DIQMTQTTSSLSASLGDRVTISCSASQGISNYLNWFQQKPDGTIKLLIYYTS
SLHSGVPSRFSGSGSGTDYSLTISNVEPEDIATYYCQQYSKLPYTFGGGTKLEIKR
(SEQ ID NO: 423)

Light chain variable region CDR 1:
SASQGISNYLN (SEQ ID NO: 424)

Light chain variable region CDR2:
YTSSLHS (SEQ ID NO: 425)

Light chain variable region CDR3:
QQYSKLPYT (SEQ ID NO: 426)

Monoclonal antibody 5F3A5D4
Heavy chain variable region sequence
H-2, 3 ,4, 13, 15
gtccagctgcaacagtctggacctgatctggtgaagcctggggacttcagtgaagatatcctgtaagacttctggaaaca
cattcactgaatacaccatgcactgggtgaagcagagccatggaaagagccttgagtggattggaggttttaatcctaacaatggtgtta
ctaactacaaccagaagttcaagggcaaggccacattgactgtagacaagtcctccagcacagcctacatggagctccgcagcctga
catctgaggattctgcagtctattactgtgcaagacgttactaccatagtacctacgtgttctactttgactcctggggccaaggcaccact
ctcacagtctcctca (SEQ ID NO: 427)

Translated protein, wherein the underlined sequence is the complementarity
determining region (CDR):
VQLQQSGPDLVKPGTSVKISCKTSGNTFTEYTMHWVKQSHGKSLEWIGGF
NPNNGVTNYNQKFKGKATLTVDKSSSTAYMELRSLTSEDSAVYYCARRYYHSTYVF
YFDSWGQGTTLTVSS (SEQ ID NO: 428)

Heavy chain variable region CDR1:
NTFTEYTMH (SEQ ID NO: 429)

Heavy chain variable region CDR2:
GFNPNNGVTNYNQKFKG (SEQ ID NO: 430)

Heavy chain variable region CDR3:
RYYHSTYVFYFDS (SEQ ID NO: 431)

Light chain variable region sequence
K-1, 2, 3, 4, 9
gatatccagatgacacagactacatcctccctgtctgcctctctgggagacagagtcaccatcagttgcagtgcaagtc
agggcattagcaattatttaaactggtttcagcagaaaccagatggaactattaagctcctgatctattacacatcaagtttacattcagga
gtcccatcaaggttcagtggcagtgggtctgggacagattattctctcaccatcagtaatgtggaacctgaagatattgccacttactattg
tcagcagtatagtaagcttccttacacgttcggaggggggaccaagctggagataaaacgg (SEQ ID NO: 432)

Translated protein, wherein the underlined sequence is the complementarity
determining region (CDR):
DIQMTQTTSSLSASLGDRVTISCSASQGISNYLNWFQQKPDGTIKLLIYYTS
SLHSGVPSRFSGSGSGTDYSLTISNVEPEDIATYYCQQYSKLPYTFGGGTKLEIKR (SEQ ID NO: 433)

Light chain variable region CDR 1:
SASQGISNYLN (SEQ ID NO: 434)

Light chain variable region CDR2:
YTSSLHS (SEQ ID NO: 435)

Light chain variable region CDR3:
QQYSKLPYT (SEQ ID NO: 436)

Monoclonal antibody 8F9A5A1
Heavy chain variable region sequence
H-3, 4, 6, 10, 11
atccagttggtgcagtctggacctgagctgaagaagcctggagagacagtcaagatctcctgcaaggcttctgggtat
accttcacaaactatggaatgaactgggtgaagcaggctccaggaaagggtttaaagtggatgggctggataaacacctacactgga
gagccaacatatgttgatgacttcaagggacggtttgccttctctttggaaacctctgccaccactgcctatttgcagatcaacaacctca
aaaatgaggacacgtctacatatttctgtgcaagattgaggggggatacgaccgggtcccttggcttactggggccaagggactctggtc
actgtctctgca (SEQ ID NO: 437)

Translated protein, wherein the underlined sequence is the complementarity
determining region (CDR):
IQLVQSGPELKKPGETVKISCKASGYTFTNYGMNWVKQAPGKGLKWMG
WINTYTGEPTYVDDFKGRFAFSLETSATTAYLQINNLKNEDTSTYFCARLRGIRPGPL
AYWGQGTLVTVSA (SEQ ID NO: 438)

Heavy chain variable region CDR1:
YTFTNYGMN (SEQ ID NO: 439)

Heavy chain variable region CDR2:
WINTYTGEPTYVDDFKG (SEQ ID NO: 440)

Heavy chain variable region CDR3:
LRGIRPGPLAY (SEQ ID NO: 441)

Light chain variable region sequence
K-1, 2, 3, 4, 5
gaaattttgctcacccagtctccagcaatcatagctgcatctcctggggagaaggtcaccatcacctgcagtgccagct
caagtgtaagttacatgaactggtaccagcagaaaccaggatcctcccccaaaatatggatttatggtatatccaacctggcttctggag
ttcctgctcgcttcagtggcagtgggtctgggacatctttctctttcacaatcaacagcatggaggctgaagatgttgccacttattactgtc
agcaaaggagtagttacccacccacgttcggaggggggaccaagctggaaataaaacgg (SEQ ID NO: 442)

Translated protein, wherein the underlined sequence is the complementarity
determining region (CDR):
EILLTQSPANIAASPGEKVTITCSASSSVSYMNWYQQKPGSSPKIWIYGISNL
ASGVPARFSGSGSGTSFSFTINSMEAEDVATYYCQQRSSYPPTFGGGTKLEIKR (SEQ
ID NO: 443)

Light chain variable region CDR 1:
SASSSVSYMN (SEQ ID NO: 444)

Light chain variable region CDR2:
GISNLAS (SEQ ID NO: 445)

Light chain variable region CDR3:
QQRSSYPPT (SEQ ID NO: 446)

Monoclonal antibody 8H5H5G4
Heavy chain variable region sequence
H-1, 3, 5, 6, 10
gtccagctgcaacagtctggacctgatctggtgaagcctggggacttcagtgaagatatcctgtaagacttctggaaaca
cattcactgaatacaccatgcactgggtgaagcagagccatggaaagagccttgagtggattggaggttttaatcctaacaatggtgtta
ctaactacaaccagaagttcaagggcaaggccacattgactgtagacaagtcctccagcacagcctacatggagctccgcagcctga
catctgaggattctgcagtctattactgtgcaagacgttactaccatagtacctacgtgttctactttgactcctggggccaaggcaccact
ctcacagtctcctca (SEQ ID NO: 447)

Translated protein, wherein the underlined sequence is the complementarity
determining region (CDR):
VQLQQSGPDLVKPGTSVKISCKTSGNTFTEYTMHWVKQSHGKSLEWIGGF
NPNNGVTNYNQKFKGKATLTVDKSSSTAYMELRSLTSEDSAVYYCARRYYHSTYVF
YFDSWGQGTTLTVSS (SEQ ID NO: 448)

Heavy chain variable region CDR1:
NTFTEYTMH (SEQ ID NO: 449)

Heavy chain variable region CDR2:
GFNPNNGVTNYNQKFKG (SEQ ID NO: 450)

Heavy chain variable region CDR3:
RYYHSTYVFYFDS (SEQ ID NO: 451)

Light chain variable region sequence
K-2, 5, 8, 9, 15
gatatccagatgacacagactacatcctcctgtctgcctctctgggagacagagtcaccatcagttgcagtgcaagtc
agggcattagcaattatttaaactggtttcagcagaaaccagatggaactattaagctcctgatctattacacatcaagtttacattcagga
gtcccatcaaggttcagtggcagtgggtctgggacagattattctctcaccatcagtaatgtggaacctgaagatattgccacttactattg
tcagcagtatagtaagcttccttacacgttcggaggggggaccaagctggagataaaacgg (SEQ ID NO: 452)

Translated protein, wherein the underlined sequence is the complementarity
determining region (CDR):
DIQMTQTTSSLSASLGDRVTISCSASQGISNYLNWFQQKPDGTIKLLIYYTS
SLHSGVPSRFSGSGSGTDYSLTISNVEPEDIATYYCQQYSKLPYTFGGGTKLEIKR
(SEQ ID NO: 453)

Light chain variable region CDR 1:
SASQGISNYLN (SEQ ID NO: 454)

Light chain variable region CDR2:
YTSSLHS (SEQ ID NO: 455)

Light chain variable region CDR3:
QQYSKLPYT (SEQ ID NO: 456)

8F9A4P3 Heavy chain variable region sequence mouse
Gtccagctgcaacagtctggacctgaactggtgaagcctggggcttcagtgaagatatcctgcaagacttctggaaa
cacattcactgaatacaccatgcactgggtgaagcagagccatggaaagagccttgagtggattggaggttttaatcctaacaatggtg
ttactaactacaaccagaagttcaagggcaaggccacattgactgtagacaagtcctccagcacagcctacatggagctccgcagcct
gacatctgaggattctgcagtctattactgtgcaagacggtactaccatagtctctacgtgttttactttgactactggggccaaggcacca
ctctcacagtctcctca (SEQ ID NO: 335)

VQLQQSGPELVKPGASVKISCKTSGNTFTEYTMHWVKQSHGKSLEWIGGF
NPNNGVTNYNQKFKGKATLTVDKSSSTAYMELRSLTSEDSAVYYCARRYYHSLYVF
YFDYWGQGTTLTVSS (SEQ ID NO: 1001)

IGHV1-24*01 V-REGION sequence human (closest match hu antibody sequence)
Caggtccagctggtacagtctggggctgaggtgaagaagcctggggcctcagtgaaggtctcctgcaaggtttccg
gatacaccctcactgaattatccatgcactgggtgcgacaggctcctggaaaagggcttgagtggatgggaggttttgatcctgaagat
ggtgaaacaatctacgcacagaagttccagggcagagtcaccatgaccgaggacacatctacagacacagcctacatggagctgag
cagcctgagatctgaggacacggccgtgtattactgtgcaaca (SEQ ID NO: 336)

QVQLVQSGAEVKKPGASVKVSCKVSGYTLTELSMHWVRQAPGKGLEW
MGGFDPEDGETIYAQKFQGRVTMTEDTSTDTAYMELSSLRSEDTAVYYCAT (SEQ ID
NO: 1002)

human (closest match hu antibody sequence)
IGHJ4*01 J-REGION sequence
tactttgactactggggccaaggaaccctggtcaccgtctcctca (SEQ ID NO: 337)

YFDYWGQGTLVTVSS (SEQ ID NO: 1003)

humanized heavy chain variable seq (SEQ ID NO: 1001 + SEQ ID NO: 1002 +
SEQ ID NO: 1003)
humanized 8F9A4P3 Heavy chain variable region sequence
(DNA)
caggtccagctggtacagtctggggctgaggtgaagaagcctggggcctcagtgaaggtctcctgcaaggtttccg
gaaacacattcactgaatacaccatgggtgcgacaggctcctggaaaagggcttgagtggatgggaggttttaatcctaacaat
ggtgttactaactacaaccagaagttcaagggcagagtcaccatgaccgaggacacatctacagacacagcctacatggagctgagc
agcctgagatctgaggacacggccgtgtattactgtgcaagacggtactaccatagtctctacgtgttttactttgactactggggccaag
gaaccctggtcaccgtctcctca (SEQ ID NO: 338)

QVQLVQSGAEVKKPGASVKVSCKVSGNTFTEYTMHWVRQAPGKGLEW
MGGFNPNNGVTNYNQKFKGRVTMTEDTSTDTAYMELSSLRSEDTAVYYCARRYYH
SLYVFYFDYWGQGTLVTVSS (SEQ ID NO: 1004)

humanized heavy chain variable seq (codon optimized version of 1004)
humanized 8F9A4P3 Heavy chain variable region sequence (codon optimized)
(DNA)
caggttcagctggttcagtctggcgccgaagtgaagaaacctggcgcctctgtgaaggtgtcctgcaaggtgtccgg
aaataccttcaccgagtacaccatgcactgggtccgacaggcccctggcaaaggacttgaatggatgggcggcttcaaccccaacaa
cggcgtgaccaactacaaccagaaattcaagggccgcgtgaccatgaccgaggacacaagcacagacaccgcctacatggaactg
agcagcctgagaagcgaggacaccgccgtgtactactgcgccagaaggtactaccacagcctgtacgtgttctacttcgactactggg
gccagggcacactggtcacagttttcttct (SEQ ID NO: 339)

QVQLVQSGAEVKKPGASVKVSCKVSGNTFTEYTMHWVRQAPGKGLEW
MGGFNPNNGVTNYNQKFKGRVTMTEDTSTDTAYMELSSLRSEDTAVYYCARRYYH
SLYVFYFDYWGQGTLVTVSS (SEQ ID NO: 1005)

humanized heavy chain variable seq ("modified" SEQ ID NO: 1005 sequence,
where modified means certain amino acids that are thought to be critical for binding or
structure have been reverted to the mouse sequence).
Modified humanized 8F9A4P3 Heavy chain variable region sequence
caggtccagctggtacagtctggggctgaggtgaagaagcctggggcctcagtgaaggtctcctgcaaggtttccg
gaaacacattcactgaatacaccatgcactgggtgcgacaggctcctggaaaagggcttgagtggattggaggttttaatcctaacaat
ggtgttactaactacaaccagaagttcaagggcaaagtcaccctgaccgtggacacatctagcagcacagcctacatggagctgagc
agcctgagatctgaggacacggccgtgtattactgtgcaagacggtactaccatagtctctacgtgttttactttgactactggggccaag
gaaccctggtcaccgtctcctca (SEQ ID NO: 340)

QVQLVQSGAEVKKPGASVKVSCKVSGNTFTEYTMHWVRQAPGKGLEWI
GGFNPNNGVTNYNQKFKGKVTLTVDTSSSTAYMELSSLRSEDTAVYYCARRYYHSL
YVFYFDYWGQGTLVTVSS (SEQ ID NO: 1006)

humanized heavy chain variable seq (SEQ ID NO: 1006 codon optimized)
Modified humanized 8F9A4P3 Heavy chain variable region sequence (codon optimized)
caggttcagctggttcagtctggggcgaagtgaagaaacctggcgcctctgtgaaggtgtcctgcaaggtgtccgg
aaatacccttcaccgagtacaccatgcactgggtccgacaggcccctggcaaaggactggaatggatcggcggcttcaacccaaca
acggcgtgaccaactacaaccagaaattcaagggcaaagtgaccctgaccgtggacaccagcagcagcacagcctacatggaact
gagcagcctgagaagcgaggacaccgccgtgtactactgcgccagaaggtactaccacagcctgtacgtgttctacttcgactactgg
ggccagggcaccctggtcacagtttcttct (SEQ ID NO: 341)

QVQLVQSGAEVKKPGASVKVSCKVSGNTFTEYTMHWVRQAPGKGLEWI
GGFNPNNGVTNYNQKFKGKVTLTVDTSSSTAYMELSSLRSEDTAVYYCARRYYHSL
YVFYFDYWGQGTLVTVSS (SEQ ID NO: 1007)

8F9A4P3 Light chain variable region sequence mouse
gaaacaactgtgacccagtctccagcatccctgtccatggctataggagaaaaagtcaccatcagatgcataaccag
cactgatattgatgatgatatgaactggtaccagcagaagccaggggaacctcctaagctcctatttcagaaggcaatactcttcgtcct
ggagtcccatcccgattctccagcagtggctatggtacagattttgttttacaattgaaaacatgctctcagaagatgttgcagattactac
tgtttgcaaagtgataacttgcctctcacgttcggctcggggacaaagttggaaattaaacgg (SEQ ID NO: 342)

ETTVTQSPASLSMAIGEKVTIRCITSTDIDDDMNWYQQKPGEPPKLLISEGN
TLRPGVPSRFSSSGYGTDFVFTIENMLSEDVADYYCLQSDNLPLTFGSGTKLEIKR
(SEQ ID NO: 1008)

human (closest match hu antibody sequence)
IGKV5-2*01 V-REGION sequence
gaaacgacactcacgcagtctccagcattcatgtcagcgactccaggagacaaagtcaacatctcctgcaaagccag
ccaagacattgatgatgatatgaactggtaccaacagaaaccaggagaagctgctattttcattattcaagaagctactactctcgttcct
ggaatcccacctcgattcagtggcagcgggtatggaacagattttaccctcacaattaataacatagaatctgaggatgctgcatattact
tctgt (SEQ ID NO: 343)

ETTLTQSPAFMSATPGDKVNISCKASQDIDDDMNWYQQKPGEAAIFIIQEA
TTLVPGIPPRFSGSGYGTDFTLTINNIESEDAAYYFC (SEQ ID NO: 1009)

human (closest match hu antibody sequence)
IGKJ4*02 J-REGION sequence
ctcacgttcggcggagggaccaaggtggagatcaaa (SEQ ID NO: 344)

LTFGGGTKVEIK (SEQ ID NO: 1010)

humanized light chain variable seq (SEQ ID NO: 1008 + SEQ ID NO: 1009 + SEQ ID NO: 1)
humanized 8F9A4P3 Light chain variable region sequence
gaaacgacactcacgcagtctccagcattcatgtcagcgactccaggagacaaagtcaacatctcctgcataaccag
cactgatattgatgatgatatgaactggtaccaacagaaaccaggagaagctgctattttcattattcaagaaggcaatactcttcgtcctg
gaatcccacctcgattcagtggcagcgggtatggaacagattttaccctcacaattaataacatagaatctgaggatgctgcatattactt
ctgtttgcaaagtgataacttgcctctcacgttcggcggagggaccaaggtggagatcaaacgg (SEQ ID NO: 345)

ETTLTQSPAFMSATPGDKVNISCITSTDIDDDMNWYQQKPGEAAIFIIQEGN
TLRPGIPPRFSGSGYGTDFTLTINNIESEDAAYYFCLQSDNLPLTFGGGTKVEIKR (SEQ
ID NO: 1011)

humanized light chain variable seq (codon optimized version of SEQ ID NO: 1011)
humanized 8F9A4P3 Light chain variable region sequence (codon optimized)
Gagacaaccctgacacagagccctgccttcatgtctgccacacctggcgacaaagtgaacatcagctgcatcacca
gcaccgacatcgacgacgacatgaactggtatcagcagaagcctggcgaggccgccatcttcatcatccaagagggcaacacactg
cggcctggcatccctcctagatttctggcagcggctacggcaccgacttcaccctgaccatcaacaacatcgagagcgaggacgcc
gcctactacttctgcctgcaaagcgacaacctgcctctgacctttggcggaggcaccaaggtggaaatcaagcgg (SEQ ID
NO: 346)

ETTLTQSPAFMSATPGDKVNISCITSTDIDDDMNWYQQKPGEAAIFIIQEGN
TLRPGIPPRFSGSGYGTDFTLTINNIESEDAAYYFCLQSDNLPLTFGGGTKVEIKR (SEQ
ID NO: 1012)

humanized light chain variable seq ("modified" SEQ ID NO: 1012 sequence,
where modified means certain amino acids that are thought to be critical for binding or
structure have been reverted to the mouse sequence).

Modified humanized 8F9A4P3 Light chain variable region sequence
gaaacgacagtgacgcagtctccagcattcatgtcagcgactccaggagacaaagtcaccatctcctgcataaccag
cactgatattgatgatgatatgaactggtaccaacagaaaccaggagaagctgctattctgctgattagcgaaggcaatactcttcgtcct
ggaatcccacctcgattcagtagcagcgggtatggaacagattttaccctcacaattaataacatagaatctgaggatgctgcatattact
tctgtttgcaaagtgataacttgcctctcacgttcggcggagggaccaaggtggagatcaaacgg (SEQ ID NO: 347)

ETTVTQSPAFMSATPGDKVTISCITSTDIDDDMNWYQQKPGEAAILLISEG
NTLRPGIPPRFSSSGYGTDFTLTINNIESEDAAYYFCLQSDNLPLTFGGGTKVEIKR
(SEQ ID NO: 1013)

humanized light chain variable seq (SEQ ID NO: 1013 codon optimized)
Modified humanized 8F9A4P3 Light chain variable region sequence (codon optimized)
gagacaaccgtgacacagagccctgccttcatgtctgccacacctggcgacaaagtgaccatcagctgcatcacca
gcaccgacatcgacgacgacatgaactggtatcagcagaagcctggcgaggccgccatcctgctgatctctgagggaaacacactgc
ggcctggcatcc ctcctagattttccagcagcggctacggcaccgacttcacccctgaccatcaacaacatcgagagcgaggacgccg
cctactacttctgcctgcaaagcgacaacctgcctctgacctttggcggaggcaccaaggtggaaatcaagcgg
(SEQ ID NO: 348)

ETTVTQSPAFMSATPGDKVTISCITSTDIDDDMNWYQQKPGEAAILLISEG
NTLRPGIPPRFSSSGYGTDFTLTINNIESEDAAYYFCLQSDNLPLTFGGGTKVEIKR
(SEQ ID NO: 1014)

humanized heavy and light chains joined via a flexible linker.
Modified humanized 8F9A4P3 sequence (codon optimized)
Caggttcagctggttcagtctggcgccgaagtgaagaaacctggcgcctctgtgaaggtgtcctgcaaggtgtccgg
aaatacct tcaccgagtacaccatgcactgggtccgacaggcccctggcaaaggactggaatggattgggctggattcaacccca aca
acggcgtgaccaactacaaccagaaattcaagggcaaagtgaccctgaccgtggacaccagcagcagcacagcctacatggaact
gagcagcctgagaagcgaggacaccgccgtgtactactgcgccagaaggtactaccacagcctgtacgtgttctacttcgactactgg
ggccagggcaccctggtcacagtttcttctggcggtggcggaagcggaggcggtggctccggtggcggaggcagcgaaacgaca
gtgacgcagtctccagcattcatgtcagcgactccaggagacaaagtcaccatctcctgcataaccagcactgatattgatgatgatatg
aactggtaccaacagaaaccaggagaagctgctattctgctgattagcgaaggcaatactcttcgtcctggaatcccacctcgattcagt
agcagcgggtatggaacagattttaccctcacaattaataacatagaatctgaggatgctgcatattacttctgtttgcaaagtgataactt
gcctctcacgttcggcggagggaccaaggtggagatcaaacgg (SEQ ID NO: 349)

QVQLVQSGAEVKKPGASVKVSCKVSGNTFTEYTMHWVRQAPGKGLEWI
GGFNPNNGVTNYNQKFKGKVTLTVDTSSSTAYMELSSLRSEDTAVYYCARRYYHSL
YVFYFDYWGQGTLVTVSSGGGGSGGGGSGGGGSETTVTQSPAFMSATPGDKVTISCI
TSTDIDDDMNWYQQKPGEAAILLISEGNTLRPGIPPRFSSSGYGTDFTLTINNIESEDA
AYYFCLQSDNLPLTFGGGTKVEIKR (SEQ ID NO: 1015)

8F9A5A1 Heavy chain variable region sequence
atccagttggtgcagtctggacctgagctgaagaagcctggagagacagtcaagatctcctgcaaggcttctgggtat
accttcacaaactatggaatgaactgggtgaagcaggctccaggaaagggtttaaagtggatgggctggataaacacctacactgga
gagccaacatatgttgatgacttcaagggacggtttgccttctcttggaaacctctgccaccactgcctatttgcagatcaacaacctca
aaaatgaggacacgtctacatatttctgtgcaagattgaggggatacgacccgggtcccttggcttactggggccaagggactctggtc
actgtctctgca (SEQ ID NO: 350)

IQLVQSGPELKKPGETVKISCKASGYTFTNYGMNWVKQAPGKGLKWMG
WINTYTGEPTYVDDFKGRFAFSLETSATTAYLQINNLKNEDTSTYFCARLRGIRPGPL
AYWGQGTLVTVSA (SEQ ID NO: 1016)

IGHV7-81*01 V-REGION sequence
caggtgcagctggtgcagtctggccatgaggtgaagcagcctggggcctcagtgaaggtctcctgcaaggcttctg
gttacagtttcaccacctatggtatgaattgggtgccacaggcccctggacaagggcttgagtggatgggatggttcaacacctacact
gggaacccaacatatgcccagggcttcacaggacggtttgtcttctccatggacacctgccagcacagcatacctgcagatcagca
gcctaaaggctgaggacatggccatgtattactgtgcgaga (SEQ ID NO: 351)

QVQLVQSGHEVKQPGASVKVSCKASGYSFTTYGMNWVPQAPGQGLEW
MGWFNTYTGNPTYAQGFTGRFVFSMDTSASTAYLQISSLKAEDMAMYYCAR (SEQ
ID NO: 1017)

IGHJ4*03 J-REGION sequence
tactttgactactggggccaagggaccctggtcaccgtctcctca (SEQ ID NO: 352)

YFDYWGQGTLVTVSS (SEQ ID NO: 1018)

humanized 8F9A5A1 Heavy chain variable region sequence
Caggtgcagctggtgcagtctggccatgaggtgaagcagcctggggcctcagtgaaggtctcctgcaaggcttctg
ggtataccttcacaaactatggaactgggtgccacaggcccctggacaagggcttgagtggatgggatggataaacacctaca
ctggagagccaacatatgttgatgacttcaagggacggtttgtcttctccatggacacctgccagcacagcatacctgcagatcagc
agcctaaaggctgaggacatggccatgtattactgtgcaagattgaggggatacgacccgggtcccttggcttactggggccaaggg
accctggtcaccgtctcctca (SEQ ID NO: 353)

QVQLVQSGHEVKQPGASVKVSCKASGYTFTNYGMNWVPQAPGQGLEW
MGWINTYTGEPTYVDDFKGRFVFSMDTSASTAYLQISSLKAEDMAMYYCARLRGIR
PGPLAYWGQGTLVTVSS (SEQ ID NO: 1019)

humanized 8F9A5A1 Heavy chain variable region sequence (codon optimized)
caggttcagctggtgcagtctggccacgaagtgaaacagcctggcgcctctgtgaaggtgtcctgtaaagccagcg gctacacctttaccaactacggcatgaactgggtgcccccaggctcctggacaaggcttggaatggatgggctggatcaacacctacac
cggcgagcctacctacgtggacgacttcaagggcagattcgtgttcagcatggacaccagcgccagcacagcctacctgcagatca
gctctctgaaggccgaggatatggccatgtactactgcgccagactgagaggcatcagacctggacctctggcctattggggacagg
gcacactggtcacagtgtcctct (SEQ ID NO: 354)

QVQLVQSGHEVKQPGASVKVSCKASGYTFTNYGMNWVPQAPGQGLEW
MGWINTYTGEPTYVDDFKGRFVFSMDTSASTAYLQISSLKAEDMAMYYCARLRGIR
PGPLAYWGQGTLVTVSS (SEQ ID NO: 1020)

Modified humanized 8F9A5A1 Heavy chain variable region sequence
cagatccagctggtgcagtctggccccgaggtgaagcagcctgggcctcagtgaaggtctcctgcaaggcttctg
ggtataccttcacaaactatggaatgaactgggtgaagcaggcccctggacaagggcttgagtggatgggatggataaacacctaca
ctggagagccaacatatgttgatgacttcaagggacggtttgccttctccatggacacctctgccagcacagcatacctgcagatcagc
agcctaaaggctgaggacaccgccacctattactgtgcaagattgaggggggatacgacccgggtcccttggcttactggggccaaggg
accctggtcaccgtctcctca (SEQ ID NO: 355)

QIQLVQSGPEVKQPGASVKVSCKASGYTFTNYGMNWVKQAPGQGLEWM
GWINTYTGEPTYVDDFKGRFAFSMDTSASTAYLQISSLKAEDTATYYCARLRGIRPG
PLAYWGQGTLVTVSS (SEQ ID NO: 1021)

Modified humanized 8F9A5A1 Heavy chain variable region sequence (codon optimized)
cagattcagctggtgcagtctggccccgaagtgaaacaacctggcgcctcagtgaaggtctcctgcaaggccagcg
gctacacctttaccaactacggcatgaactgggtcaagcaggcccctggacaaggcctggaatggatggctggatcaacacctaca
ccggcgagcctacctacgtggacgacttcaagggcagattcgccttcagcatggacaccagcgccagcacagcctacctgcagatc
agctctctgaaggccgaggacaccgccacctactactgtgccagactgagaggcatcagacccggacctctggcctattggggaca
gggaacactggtcaccgtgtcctct (SEQ ID NO: 356)

QIQLVQSGPEVKQPGASVKVSCKASGYTFTNYGMNWVKQAPGQGLEWM
GWINTYTGEPTYVDDFKGRFAFSMDTSASTAYLQISSLKAEDTATYYCARLRGIRPG
PLAYWGQGTLVTVSS (SEQ ID NO: 1022)

8F9A5A1 Light chain variable region sequence
gaaattttgctcacccagtctccagcaatcatagctgcatctcctggggagaaggtcaccatcacctgcagtgccagct
caagtgtaagttacatgaactggtaccagcagaaaccaggatcctccccaaaatggatttatggtatatccaacctggcttctggag
ttcctgctcgttcagtggcagtgggtctgggacatctttctctttcacaatcaacagcagtgaggctgaagatgttgccacttattactgtc
agcaaaggagtagttacccacccacgttcggaggggggaccaagctggaaataaaacgg (SEQ ID NO: 357)

EILLTQSPANIAASPGEKVTITCSASSSVSYMNWYQQKPGSSPKIWIYGISNL
ASGVPARFSGSGSGTSFSFTINSMEAEDVATYYCQQRSSYPPTFGGGTKLEIKR (SEQ
ID NO: 1023)

IGKV3D-15*02 V-REGION sequence
gaaatagtgatgatgcagtctccagccacccctgtctgtgtctccaggggaaagagccaccctctcctgcagggccag
tcagagtgttagcagcaacttagcctggtaccagcagaaacctggccaggctcccaggctcctcatctatggtgcatccaccagggcc
actggcatcccagccaggttcagtggcagtgggtctgggacagagttcactctcaccatcagcagcctgcagtctgaagattttgcagt
ttattactgtcagcagtataataac (SEQ ID NO: 358)

EIVMMQSPATLSVSPGERATLSCRASQSVSSNLAWYQQKPGQAPRLLIYG
ASTRATGIPARFSGSGSGTEFTLTISSLQSEDFAVYYCQQYNN (SEQ ID NO: 1024)

IGKJ4*02 J-REGION sequence
ctcacgttcggcggagggaccaaggtggagatcaaa (SEQ ID NO: 359)

LTFGGGTKVEIK (SEQ ID NO: 1025)

humanized 8F9A5A1 Light chain variable region sequence
gaaatagtgatgatgcagtctccagccacccctgtctgtgtctccaggggaaagagccaccctctcctgcagtgccagc
tcaagtgtaagttacatgaactggtaccagcagaaacctggccaggctcccaggctcctcatctatggtatatccaacctggcttctggc
atcccagccaggttcagtggcagtgggtctgggacagagttcactctcaccatcagcagcctgcagtctgaagattttgcagtttattact
gtcagcaaaggagtagttacccacccacgttcggcggagggaccaaggtggagatcaaacgg (SEQ ID NO: 360)

EIVMMQSPATLSVSPGERATLSCSASSSVSYMNWYQQKPGQAPRLLIYGIS
NLASGIPARFSGSGSGTEFTLTISSLQSEDFAVYYCQQRSSYPPTFGGGTKVEIKR (SEQ
ID NO: 1026)

humanized 8F9A5A1 Light chain variable region sequence (codon optimized)
gagatcgtgatgatgcagagccccgccacactgagtgtgtctccaggcgaaagagccacactgtcctgtagcgcca
gcagcagcgtgtcctacatgaactggtatcagcagaagcccggacaggcccctagactgctgatctacggcatcagcaatctggcca
gcggcatccctgccagattttctggctctggctccggcaccgagttcaccctgacaatctctagcctgcagagcgaggacttcgccgtg
tactactgccagcagagaagcagctaccctcctacctttggcggaggcaccaaggtggaaatcaagcgg (SEQ ID NO: 361)

EIVMMQSPATLSVSPGERATLSCSASSSVSYMNWYQQKPGQAPRLLIYGIS
NLASGIPARFSGSGSGTEFTLTISSLQSEDFAVYYCQQRSSYPPTFGGGTKVEIKR (SEQ
ID NO: 1027)

Modified humanized 8F9A5A1 Light chain variable region sequence
gaaatagtgctgacccagtctccagccacccctgtctgtgtctccaggggaaagagccaccctctcctgcagtgccag
ctcaagtgtaagttacatgaactggtaccagcagaaacctggccaggctcccaggctctggatctatggtatatccaacctggcttctgg catcccagccaggttcagtggcagtgggtctgggacaagcttcagcctcaccatcagcagcctgcagtctgaagattttgcagtttatta
ctgtcagcaaaggagtagttacccacccacgttcggcggagggaccaaggtggagatcaaacgg (SEQ ID NO: 362)

EIVLTQSPATLSVSPGERATLSCSASSSVSYMNWYQQKPGQAPRLWIYGIS
NLASGIPARFSGSGSGTSFSLTISSLQSEDFAVYYCQQRSSYPPTFGGGTKVEIKR (SEQ
ID NO: 1028)

Modified humanized 8F9A5A1 Light chain variable region sequence (codon optimized)
gagatcgtgctgacacagtctcccgccacactgagtgtgtctccaggcgaaagagccacactgtcctgtagcgccag
cagcagcgtgtcctacatgaactggtatcagcagaagcccggacaggcccctagactgtggatctacggcatcagcaatctggccag
cggcatccctgccagattttctggctctggctccggcaccagcttcagcctgacaatcagcagcctgcagagcgaggacttcgccgtg
tactactgccagcagagaagcagctaccctcctacctttggcggaggcaccaaggtggaaatcaagcgg (SEQ ID NO: 363)

(amino acids)
EIVLTQSPATLSVSPGERATLSCSASSSVSYMNWYQQKPGQAPRLWIYGIS
NLASGIPARFSGSGSGTSFSLTISSLQSEDFAVYYCQQRSSYPPTFGGGTKVEIKR (SEQ
ID NO: 1029)

Modified humanized 8F9A5A1 scFV sequence (codon optimized)
Cagattcagctggtgcagtctggccccgaagtgaaacaacctggcgcctctgtgaaggtgtcctgcaaggccagcg
gctacacctttaccaactacggcatgaactgggtcaagcaggcccctggacaaggcctggaatggatgggctggatcaacacctaca
ccggcgagcctacctacgtggacgacttcaagggcagattcgccttcagcatggacaccagcgccagcacagcctacctgcagatc
agctctctgaaggccgaggacaccgccacctactactgtgccagactgagaggcatcagaccccgagacctctggcctattgggggaca
gggaacactggtcaccgtgtcctctggcggtggcggaagcggaggcggtggctccggtggcggaggcagcgagatcgtgctgac
acagtctcccgccacactgagtgtgtctccaggcgaaagagccacactgtcctgtagcgccagcagcagcgtgtcctacatgaactg
gtatcagcagaagcccggacaggcccctagactgtggatctacggcatcagcaatctggccagcggcatccctgccagattttctggc
tctggctccggcaccagcttcagcctgacaatcagcctgcagagcgaggacttcgccgtgtactactgccagcagagaagcag
ctaccctcctacctttggcggaggcaccaaggtggaaatcaagcgg (SEQ ID NO: 364)

QIQLVQSGPEVKQPGASVKVSCKASGYTFTNYGMNWVKQAPGQGLEWM
GWINTYTGEPTYVDDFKGRFAFSMDTSASTAYLQISSLKAEDTATYYCARLRGIRPG
PLAYWGQGTLVTVSSGGGGSGGGGSGGGGSEIVLTQSPATLSVSPGERATLSCSASS
SVSYMNWYQQKPGQAPRLWIYGISNLASGIPARFSGSGSGTSFSLTISSLQSEDFAVY
YCQQRSSYPPTFGGGTKVEIKR (SEQ ID NO: 1030)

8H5H5G4 Heavy chain variable region sequence
gtccagctgcaacagtctggacctgatctggtgaagcctgggacttcagtgaagatatcctgtaagacttctggaaaca
cattcactgaatacaccatgcactgggtgaagcagagccatggaaagagccttgagtggattggaggttttaatcctaacaatggtgtta
ctaactacaaccagaagttcaagggcaaggccacattgactgtagacaagtcctccagcacagcctacatggagctccgcagcctga
catctgaggattctgcagtctattactgtgcaagacgttactaccatagtacctacgtgttctactttgactcctggggccaaggcaccact
ctcacagtctcctca (SEQ ID NO: 365)

VQLQQSGPDLVKPGTSVKISCKTSGNTFTEYTMHWVKQSHGKSLEWIGGF
NPNNGVTNYNQKFKGKATLTVDKSSSTAYMELRSLTSEDSAVYYCARRYYHSTYVF
YFDSWGQGTTLTVSS (SEQ ID NO: 1031)

IGHV1-24*01 V-REGION sequence
(DNA)
caggtccagctggtacagtctggggctgaggtgaagaagcctggggcctcagtgaaggtctcctgcaaggtttccg
gatacacccctcactgaattatccatgcactgggtgcgacaggctcctggaaaagggcttgagtggatgggaggttttgatcctgaagat
ggtgaaacaatctacgcacagaagttccagggcagagtcaccatgaccgaggacacatctacagacacagcctacatggagctgag
cagcctgagatctgaggacacggccgtgtattactgtgcaaca (SEQ ID NO: 366)

(amino acids)
QVQLVQSGAEVKKPGASVKVSCKVSGYTLTELSMHWVRQAPGKGLEW
MGGFDPEDGETIYAQKFQGRVTMTEDTSTDTAYMELSSLRSEDTAVYYCAT (SEQ ID
NO: 1032)

IGHJ4*03 J-REGION sequence
(DNA)
tactttgactactggggccaagggaccctggtcaccgtctcctca (SEQ ID NO: 367)

(amino acids)
YFDYWGQGTLVTVSS (SEQ ID NO: 1033)

Humanized 8H5H5G4 Heavy chain variable region sequence
(DNA)
caggtccagctggtacagtctggggctgaggtgaagaagcctggggcctcagtgaaggtctcctgcaaggtttccg
gaaacacattcactgaatacaccatgcacTgggtgcgacaggctcctggaaaagggcttgagtggatgggaggttttaatcctaacaa
tggtgttactaactacaaccagaagttcaagggcAgagtcaccatgaccgaggacacatctacagacacagcctacatggagctgag
cagcctgagatctgaggacacggccgtgtattactgtGcaagacgttactaccatagtacctacgtgttctactttgactcctggggcca
agggaccctggtcaccgtctcctca (SEQ ID NO: 368)

(amino acids)
QVQLVQSGAEVKKPGASVKVSCKVSGNTFTEYTMHWVRQAPGKGLEW
MGGFNPNNGVTNYNQKFKGRVTMTEDTSTDTAYMELSSLRSEDTAVYYCARRYYH
STYVFYFDSWGQGTLVTVSS (SEQ ID NO: 1034)

Humanized 8H5H5G4 Heavy chain variable region sequence (codon optimized)
(DNA)
caggttcagctggttcagtctggcgccgaagtgaagaaacctggcgcctctgtgaaggtgtcctgcaaggtgtccgg
aaataccttcaccgagtacaccatgcactgggtccgacaggccctggcaaaggacttgaatggatgggcggcttcaacccccaacaa
cggcgtgaccaactacaaccagaaattcaagggccgcgtgaccatgaccgaggacacaagcacagacaccgcctacatggaactg
agcagcctgagaagcgaggacaccgccgtgtactactgcgccagaaggtactaccacagcacctacgtgttctacttcgacagctgg
ggccagggcacactggtcacagtttcttct (SEQ ID NO: 369)

(amino acids)
QVQLVQSGAEVKKPGASVKVSCKVSGNTFTEYTMHWVRQAPGKGLEW
MGGFNPNNGVTNYNQKFKGRVTMTEDTSTDTAYMELSSLRSEDTAVYYCARRYYH
STYVFYFDSWGQGTLVTVSS (SEQ ID NO: 1035)

Modified Humanized 8H5H5G4 Heavy chain variable region sequence
(DNA)
caggtccagctggtacagtctggggctgaggtgaagaagcctggggcctcagtgaaggtctcctgcaaggtttccg
gaaacacattcactgaatacaccatgcactgggtgcgacaggctcctggaaaagggcttgagtggatcggaggttttaatcctaacaat
ggtgttactaactacaaccagaagttcaagggcaaggtcaccgtgaccgtggacacatctagcagcacagcctacatggagctgagc
agcctgagatctgaggacacggccgtgtattactgtgcaagacgttactaccatagtacctacgtgttctactttgactcctggggccaa
gggaccctggtcaccgtctcctca (SEQ ID NO: 370)

(amino acids)
QVQLVQSGAEVKKPGASVKVSCKVSGNTFTEYTMHWVRQAPGKGLEWI
GGFNPNNGVTNYNQKFKGKVTLTVDTSSSTAYMELSSLRSEDTAVYYCARRYYHST
YVFYFDSWGQGTLVTVSS (SEQ ID NO: 1036)

Modified Humanized 8H5H5G4 Heavy chain variable region sequence (codon optimized)
(DNA)
caggttcagctggttcagtctggcgccgaagtgaagaaacctggcgcctctgtgaaggtgtcctgcaaggtgtccgg
aaataccttcaccgagtacaccatgcactgggtccgacaggcccctggcaaaggactggaatggatcggcggcttcaacccccaaca
acggcgtgaccaactacaaccagaaattcaagggcaaagtgaccctgaccgtggacaccagcagcagcacagcctacatggaact
gagcagcctgagaagcgaggacaccgccgtgtactactgcgccagaaggtactaccacagcacctacgtgttctacttcgacagctg
gggccagggcacactggtcacagtttcttct (SEQ ID NO: 371)

(amino acids)
QVQLVQSGAEVKKPGASVKVSCKVSGNTFTEYTMHWVRQAPGKGLEWI
GGFNPNNGVTNYNQKFKGKVTLTVDTSSSTAYMELSSLRSEDTAVYYCARRYYHST
YVFYFDSWGQGTLVTVSS (SEQ ID NO: 1037)

8H5H5G4 Light chain variable region sequence
(DNA)
gatatccagatgacacagactacatcctccctgtctgcctctctgggagacagagtcaccatcagttgcagtgcaagtc
agggcattagcaattatttaaactggtttcagcagaaaccagatggaactattaagctcctgatctattacacatcaagtttacattcagga
gtcccatcaaggttcagtggcagtgggtctgggacagattattctctcaccatcagtaatgtggaacctgaagatattgccacttactattg
tcagcagtatagtaagcttccttacacgttcggaggggggaccaagctggagataaaacgg (SEQ ID NO: 372)

(amino acids)
DIQMTQTTSSLSASLGDRVTISCSASQGISNYLNWFQQKPDGTIKLLIYYTS
SLHSGVPSRFSGSGSGTDYSLTISNVEPEDIATYYCQQYSKLPYTFGGGTKLEIKR
(SEQ ID NO: 1038)

IGKV1-27*01 V-REGION sequence
(DNA)
gacatccagatgacccagtctccatcctccctgtctgcatctgtaggagacagagtcaccatcacttgccgggcgagt
cagggcattagcaattatttagcctggtatcagcagaaaccagggaaagttcctaagctcctgatctatgctgcatccactttgcaatcag
gggtcccatctcggttcagtggcagtggatctgggacagatttcactctcaccatcagcagcctgcagcctgaagatgttgcaacttatt
actgtcaaaagtataacagtgcccct (SEQ ID NO: 373)

(amino acids)
DIQMTQSPSSLSASVGDRVTITCRASQGISNYLAWYQQKPGKVPKLLIYAA
STLQSGVPSRFSGSGSGTDFTLTISSLQPEDVATYYCQKYNSAP (SEQ ID NO: 1039)

IGKJ4*02 J-REGION sequence
(DNA)
ctcacgttcggcggagggaccaaggtggagatcaaa (SEQ ID NO: 374)

(amino acids)
LTFGGGTKVEIK (SEQ ID NO: 1040)

humanized 8H5H5G4 Light chain variable region sequence
(DNA)
gacatccagatgacccagtctccatcctccctgtctgcatctgtaggagacagagtcaccatcacttgcagtgcaagtc
agggcattagcaattatttaaacTggtatcagcagaaaccagggaaagttcctaagctcctgatctattacacatcaagtttacattcagg
ggtcccatctcggttcagtggcagtggatctgggacagatttcactctcaccatcagcagcctgcagcctgaagatgttgcaacttatta
ctgtcagcagtatagtaagcttccttacacgttcggcggagggaccaaggtggagatcaaacgg (SEQ ID NO: 375)

(amino acids)
DIQMTQSPSSLSASVGDRVTITCSASQGISNYLNWYQQKPGKVPKLLIYYT
SSLHSGVPSRFSGSGSGTDFTLTISSLQPEDVATYYCQQYSKLPYTFGGGTKVEIKR
(SEQ ID NO: 1041)

humanized 8H5H5G4 Light chain variable region sequence (codon optimized)
(DNA)
gacatccagatgacacagagccctagcagcctgtctgccagcgtgggagacagagtgaccatcacatgtagcgcca
gccagggcatcagcaactacctgaactggtatcagcagaaacccggcaaggtgcccaagctgctgatctactacaccagcagcctg
cacagcggcgtgccaagcagatttctggcagcggctctggcaccgacttcaccctgaccatatctagcctgcagcctgaggacgtg
gccacctactactgtcagcagtacagcaagctgccctacacctttggcggaggcaccaaggtggaaatcaagcgg (SEQ ID
NO: 376)

(amino acids)
DIQMTQSPSSLSASVGDRVTITCSASQGISNYLNWYQQKPGKVPKLLIYYT
SSLHSGVPSRFSGSGSGTDFTLTISSLQPEDVATYYCQQYSKLPYTFGGGTKVEIKR
(SEQ ID NO: 1042)

Modified humanized 8H5H5G4 Light chain variable region sequence
(DNA)
gacatccagatgacccagtctccatcctccctgtctgcatctgtaggagacagagtcaccatcacttgcagtcaagtc
agggcattagcaattatttaaactggtatcagcagaaaccagggaaagttcctaagctcctgatctattacacatcaagtttacattcagg
ggtcccatctcggttcagtggcagtggatctgggacagattacactctcaccatcagcagcctgcagcctgaagatgttgcaacttatta
ctgtcagcagtatagtaagcttccttacacgttcggcggagggaccaaggtggagatcaaacgg (SEQ ID NO: 377)

(amino acids)
DIQMTQSPSSLSASVGDRVTITCSASQGISNYLNWYQQKPGKVPKLLIYYT
SSLHSGVPSRFSGSGSGTDYTLTISSLQPEDVATYYCQQYSKLPYTFGGGTKVEIKR
(SEQ ID NO: 1043)

Modified humanized 8H5H5G4 Light chain variable region sequence (codon optimized)
(DNA)
gacatccagatgacacagagccctagcagcctgtctgccagcgtgggagacagagtgaccatcacatgtagcgcca
gccagggcatcagcaactacctgaactggtatcagcagaaacccggcaaggtgcccaagctgctgatctactacaccagcagcctg
cacagcggcgtgccaagcagatttctggcagcggctctggcaccgactacaccctgaccatatctagcctgcagcctgaggacgtg
gccacctactactgtcagcagtacagcaagctgccctacacctttggcggaggcaccaaggtggaaatcaagcgg (SEQ ID
NO: 378)

(amino acids)
DIQMTQSPSSLSASVGDRVTITCSASQGISNYLNWYQQKPGKVPKLLIYYT
SSLHSGVPSRFSGSGSGTDYTLTISSLQPEDVATYYCQQYSKLPYTFGGGTKVEIKR
(SEQ ID NO: 1044)

Modified humanized 8H5H5G4 scFV sequence (codon optimized)
(DNA)
Caggttcagctggttcagtctggcgccgaagtgaagaaacctggcgcctctgtgaaggtgtcctgcaaggtgtccgg
aaataccttcaccgagtacaccatgcactgggtccgacaggcccctggcaaaggactggaatggatcggcggcttcaaccccaaca
acggcgtgaccaactacaaccagaaattcaagggcaaagtgaccctgaccgtggacaccagcagcagcacagcctacatggaact
gagcagcctgagaagcgaggacaccgccgtgtactactgcgcacgataccaccagcaccacctacgtgttctacttcgacagctg
gggccagggcacactggtcacagtttcttctggcggtggcggaagcggaggcggtggctccggtggcggaggcagcgacatcca
gatgacacagagccctagcagcctgtctgccagcgtgggagacagagtgaccatcacatgtagcgccagccagggcatcagcaact
acctgaactggtatcagcagaaacccggcaaggtgcccaagctgctgatctactacaccagcagcctgcacagcggcgtgccaagc
agatttctggcagcggctctggcaccgactacaccctgaccatatctagcctgcagcctgaggacgtggccacctactactgtcagca
gtacagcaagctgccctacacctttggcggaggcaccaaggtggaaatcaagcgg (SEQ ID NO: 379)

(amino acids)
QVQLVQSGAEVKKPGASVKVSCKVSGNTFTEYTMHWVRQAPGKGLEWI
GGFNPNNGVTNYNQKFKGKVTLTVDTSSSTAYMELSSLRSEDTAVYYCARRYYHST
YVFYFDSWGQGTLVTVSSGGGGSGGGGSGGGGSDIQMTQSPSSLSASVGDRVTITCS
ASQGISNYLNWYQQKPGKVPKLLIYYTSSLHSGVPSRFSGSGSGTDYTLTISSLQPED
VATYYCQQYSKLPYTFGGGTKVEIKR (SEQ ID NO: 1045)

Human IgG1 heavy chain constant region sequence: (for making full antibody-
pair with either kappa or lambda constant region; 2 plasmids, express together)
(DNA)
gctagcaccaagggcccatcggtcttccccctggcaccctcctccaagagcacctctgggggcacagcggccctgg
gctgcctggtcaaggactacttccccgaaccggtgacggtgtcgtggaactcaggcgccctgaccagcggcgtgcacaccttccccg
getgtcctacagtcctcaggactctactccctcagcagcgtggtgacagtgccctccagcagcttgggcacccagacctacatctgca
acgtgaatcacaagcccagcaacaccaaggtggacaagaaagttgagcccaaatcttgtgacaaaactcacacatgcccaccgtgcc
cagcacctgaactcctggggggaccgtcagtcttcctcttccccccaaaacccaaggacaccctcatgatctcccggacccctgaggt
cacatgcgtggtggtggacgtgagccacgaagaccctgaggtcaagttcaactggtacgtggacggcgtggaggtgcataatgcca
agacaaagccgcgggaggagcagtacaacagcacgtaccgtgtggtcagcgtcctcaccgtcctgcaccaggactggctgaatgg
caaggagtacaagtgcaaggtctccaacaaagccctcccagcccccatcgagaaaaccatctccaaagccaaagggcagccccga
gaaccacaggtgtacaccctgcccccatcccgggaggagatgaccaagaaccaggtcagcctgacctgcctggtcaaaggcttctat
cccagcgacatcgccgtggagtgggagagcaatgggcagccggagaacaactacaagaccacgcctcccgtgctggactccgac
ggctccttcttcctctacagcaagctcaccgtggacaagagcaggtggcagcaggggaacgtcttctcatgctccgtgatgcatgagg
ctctgcacaaccactacacgcagaagagcctctccctgtctccgggtaaatga (SEQ ID NO: 380)

(amino acids)
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKTTP
PVLDSDGSFFLYSKLTVDKSRWQQGNVFSCSVMHEALHNHYTQKSLSLSPGK (SEQ
ID NO: 1046)

Human IgG2 heavy chain constant region sequence: (for making full antibody-
pair with either kappa or lambda constant region; 2 plasmids, express together)
(DNA)
gcctccaccaagggcccatcggtcttccccctggcgccctgctccaggagcacctccgagagcacagcgccctg
ggctgcctggtcaaggactacttccccgaaccggtgacggtgtcgtggaactcaggcgctctgaccagcggcgtgcacaccttccca
gctgtcctacagtcctcaggactctactccctcagcagcgtggtgaccgtgcctccagcaacttcggcacccagacctacacctgca
acgtagatcacaagcccagcaacaccaaggtggacaagacagttgagcgcaaatgttgtgtcgagtgcccaccgtgcccagcacca
cctgtggcaggaccgtcagtcttcctcttccccccaaaacccaaggacaccctcatgatctcccggacccctgaggtcacgtgcgtgg
tggtggacgtgagccacgaagaccccgaggtccagttcaactggtacgtggacggcgtggaggtgcataatgccaagacaaagcc
acgggaggagcagttcaacagcacgttccgtgtggtcagcgtcctcaccgttgtgcaccaggactggctgaacggcaaggagtaca
agtgcaaggtctccaacaaaggcctcccagcccccatcgagaaaaccatctccaaaaccaaagggcagccccgagaaccacaggt
gtacaccctgcccccatcccgggaggagatgaccaagaaccaggtcagctgacctgcctggtcaaaggcttctaccccagcgaca
tcgccgtggagtgggagagcaatgggcagccggagaacaactacaagaccacacctcccatgctggactccgacggctccttcttc
ctctacagcaagctcaccgtggacaagagcaggtggcagcaggggaacgtcttctcatgctccgtgatgcatgaggctctgcacaac
cactacacgcagaagagcctctccctgtctccgggtaaatag (SEQ ID NO: 381)

(amino acids)
ASTKGPSVFPLAPCSRSTSESTAALGCLVKDYFPEPVTVSWNSGALTSGVH
TFPAVLQSSGLYSLSSVVTVPSSNFGTQTYTCNVDHKPSNTKVDKTVERKCCVECPP
CPAPPVAGPSVFLFPPKPKDTLMISRTPEVTCVVVDVSHEDPEVQFNWYVDGVEHN
AKTKPREEQFNSTFRVVSVLTVVHQDWLNGKEYKCKVSNKGLPAPIEKTISKTKGQP
REPQVYTLPPSREEMTKNQVSLTCLVKGFYPSDIAVEWESNGQPENNYKTTPPMLDS
DGSFFLYSKLTVDKSRWQQGNVFSCSVMHEALHNHYTQKSLSLSPGK (SEQ ID
NO: 1047)

Human Kappa light chain constant region sequence:
(DNA)
aggacggtggctgcaccatctgtcttcatcttcccgccatctgatgagcagttgaaatctggaactgcctctgttgtgtg
cctgctgaataacttctatcccagagaggccaaagtacagtggaaggtggataacgccctccaatcgggtaactcccaggagagtgtc
acagagcaggacagcaaggacagcacctacagcctcagcagcaccctgacgctgagcaaagcagactacgagaaacacaaagtc
tacgcctgcgaagtcacccatcagggcctgagctcgcccgtcacaaagagcttcaacaggggagagtgttag
(SEQ ID NO: 382)

(amino acids)
RTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTKSFNRGEC
(SEQ ID NO: 1048)

Human Lambda light chain constant region sequence:
(DNA)
ggtcagcccaaggctgcccctcggtcactctgttcccgccctcctctgaggagcttcaagccaacaaggccacact
ggtgtgtctcataagtgacttctaccggggagccgtgacagtggcctggaaggcagatagcagccccgtcaaggcgggagtggaga
ccaccacccctccaaacaaagcaacaacaagtacgcggccagcagctatctgagcctgacgcctgagcagtggaagtcccacag
aagctacagctgccaggtcacgcatgaagggagcaccgtggagaagacagtggcccctacagaatgttcatag
(SEQ ID NO: 383)

(amino acids)
GQPKAAPSVTLFPPSSEELQANKATLVCLISDFYPGAVTVAWKADSSPVK
AGVETTTPSKQSNNKYAASSYLSLTPEQWKSHRSYSCQVTHEGSTVEKTVAPTECS
(SEQ ID NO: 1049)

Human IgG1 Fc region sequence: (to be fused to scFv for homo-dimerizes)
(DNA)
gagcccaaatcttgtgacaaaactcacacatgcccaccgtgcccagcacctgaactcctggggggaccgtcagtctt
cctcttccccccaaaacccaaggacaccctcatgatctcccggacccctgaggtcacatgcgtggtggtggacgtgagccacgaaga
ccctgaggtcaagttcaactggtacgtggacggcgtggaggtgcataatgccaagacaaagccgcgggaggagcagtacaacagc
acgtaccgtgtggtcagcgtcctcaccgtcctgcaccaggactggctgaatggcaaggagtacaagtgcaaggtctccaacaaagcc
ctcccagcccccatcgagaaaaccatctccaaagccaaagggcagccccgagaaccacaggtgtacaccctgcccccatcccggg
aggagatgaccaagaaccaggtcagcctgacctgcctggtcaaaggcttctatcccagcgacatcgccgtggagtgggagagcaat
gggcagccggagaacaactacaagaccacgcctcccgtgctggactccgacggctccttcttcctctacagcaagctcaccgtggac
aagagcaggtggcagcaggggaacgtcttctcatgctccgtgatgcatgaggctctgcacaaccactacacgcagaagagcctctcc
ctgtctccgggtaaatga (SEQ ID NO: 384)

(amino acids)
EPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKC
KVSNKALPAPIEKTISKAKGQPREPQVYTLPPSREEMTKNQVSLTCLVKGFYPSDIAV
EWESNGQPENNYKTTPPVLDSDGSFFLYSKLTVDKSRWQQGNVFSCSVMHEALHNH
YTQKSLSLSPGK* (SEQ ID NO: 1050)

-continued

Human IgG2 Fc region sequence:
(DNA)
gagcgcaaatgttgtgtcgagtgcccaccgtgcccagcaccacctgtggcaggaccgtcagtcttcctcttcccccca
aaacccaaggacaccctcatgatctcccggacccctgaggtcacgtgcgtggtggtggacgtgagccacgaagacccccgaggtcca
gttcaactggtacgtggacggcgtggaggtgcataatgccaagacaaagccacgggaggagcagttcaacagcacgttccgtgtgg
tcagcgtcctcaccgttgtgcaccaggactggctgaacggcaaggagtacaagtgcaaggtctccaacaaaggcctcccagccccc
atcgagaaaaccatctccaaaaccaaagggcagccccgagaaccacaggtgtacaccctgcccccatcccgggaggagatgacca
agaaccaggtcagcctgacctgcctggtcaaaggcttctacccagcgacatcgccgtggagtgggagagcaatgggcagccgga
gaacaactacaagaccacacctcccatgctggactccgacggctccttcttcctctacagcaagctcaccgtggacaagagcaggtg
gcagcaggggaacgtcttctcatgctccgtgatgcatgaggctctgcacaaccactacacgcagaagagcctctccctgtctccgggt
aaatag (SEQ ID NO: 385)

(amino acids)
ERKCCVECPPCPAPPVAGPSVFLFPPKPKDTLMISRTPEVTCVVVDVSHED
PEVQFNWYVDGVEVHNAKTKPREEQFNSTFRVVSVLTVVHQDWLNGKEYKCKVSN
KGLPAPIEKTISKTKGQPREPQVYTLPPSREEMTKNQVSLTCLVKGFYPSDIAVEWES
NGQPENNYKTTPPMLDSDGSFFLYSKLTVDKSRWQQGNVFSCSVMHEALHNHYTQ
KSLSLSPGK* (SEQ ID NO: 1051)

In another aspect of the invention, an immune cell engineered to express a CAR is administered to a patient diagnosed with or at risk of developing a cancer or cancer metastasis, wherein the immune cell is also engineered to express an anti-NME7 antibody or antibody fragment, which may be expressed off of an inducible promoter. In one aspect, the CAR is guided by an anti-MUC1* antibody fragment. In one case, the CAR is huMNC2-CAR44. In one aspect, the anti-NME7 antibody or antibody fragment binds to an NME peptide listed under sections "Homologous peptides to A1, A2, B1, B2 or B3 peptides" and the "Homologous extended peptides to A1, A2, B1, B2 or B3 peptides" above. In another aspect, the antibody or antibody fragment binds to an NME7 derived peptide chosen from among A1, A2, B1, B2 or B3 (SEQ ID NOS: 141-145). In yet another aspect, the antibody, antibody fragment or antibody mimic binds to an NME7 peptide comprising the B3 peptide. In one aspect of the invention, the anti-NME7 antibody, antibody fragment or antibody mimic comprises sequences derived from the variable domains of anti-NME7 antibodies 8F9A4A3, 8F9A5A1, or 8H5H5G4.

Such antibodies may be human or humanized. Such antibodies may be polyclonal, monoclonal, bispecific, bivalent, monovalent, single chain, scFv, or may be an antibody mimic such as protein scaffolds that present recognition regions that bind to a specific target. As is appreciated by those skilled in the art, antibodies can be of non-human origin, human or humanized. Methods for humanizing antibodies include fusing all or some of the mouse variable regions to V- and J-regions of a closest match human antibody sequence, for example, as shown in sequences listed as SEQ ID NOS:1001-1045. Full antibodies, rather than single chain constructs, can also be made. For example, the heavy chain variable mouse sequence is fused to human V- and J-regions then fused to the human heavy chain constant regions of IgG1, IgG2 or IgG3. Similarly, the light chain variable mouse sequences are fused to human V- and J-regions then fused to either the human Kappa or Lambda constant regions of IgG1, IgG2 or IgG3. Plasmids are expressed together and associate to form the full antibody (SEQ ID NOS:1047-1051).

In another aspect of the invention, small molecules are anti-cancer agents that are selected for their ability to inhibit the tumorigenic effects of NME7, NME7$_{AB}$ or NME7-X1. For example, a high throughput screen identifies small molecules that will treat cancer. In a multi-well plate, small molecules are separately added to wells in which cancer cells are cultured in a medium containing NME7$_{AB}$. If the small molecule diminishes the amount of cells that become floaters and/or reduces the expression of metastatic markers such as CXCR4, CHD1 or pluripotent stem cell markers, then that small molecule is an anti-cancer drug candidate. Another method of identifying small molecules that are anti-cancer agents is to select those small molecules that bind to NME7, NME7$_{AB}$ or NME7-X1 or suppresses expression of the NME7 species. Yet another high throughput screen is to select for small molecules that inhibit the binding of NME7$_{AB}$ to the PSMGFR peptide of the MUC1* extracellular domain and those small molecules will be anti-cancer agents.

The sequences of NME7$_{AB}$ and NME7-X1 differ only in that NME7-X1 is missing some of the N-terminal sequence that NME7$_{AB}$ has. Experiments show that there is a naturally occurring NME7 species that is nearly identical to NME7$_{AB}$, which we call NME7$_{AB}$-like species. Antibodies that bind to NME7-X1 may also bind to the naturally occurring species that mimics NME7$_{AB}$, unless there are conformational differences that an antibody can differentiate. Therefore, if it is desired to inhibit NME7-X1 but not NME7$_{AB}$-like species, or vice versa, siRNA, anti-sense nucleic acids, or genetic editing techniques can be used to inhibit expression of one but not the other.

In one case, the anti-cancer therapeutic agent is a nucleic acid that directly or indirectly suppresses specific expression of NME7, NME7-X1 or NME7$_{AB}$-like species. Such nucleic acids can be siRNA, RNAi, anti-sense nucleic acids and the like that directly suppress the NME7 species. In another aspect of the invention, the nucleic acid can indirectly suppress the NME7 species for example by altering the expression of a molecule that regulates it. For example, the super enhancer BRD4 suppresses expression of NME7. Therefore, an effective therapeutic for the treatment or prevention of cancer is an agent that increases expression of BRD4. An effective therapeutic may be an agent that increases expression of BRD4's co-factor, JMJD6.

Peptides derived from NME7$_{AB}$ or NME7-X1, or the entire protein, are used to generate anti-NME7 or anti-NME7-X1 antibodies in animals that we have demonstrated inhibit cancer growth and inhibit transition of cancer cells to metastatic cancer cells. Similarly, NME7 derived peptides can be administered to a human such that they generate antibodies that treat or prevent cancer or inhibit transition of cancer cells to metastatic cancer cells. NME7 peptides or proteins are administered to a person as a type of vaccine to stimulate the production of anti-NME7, anti-NME7$_{AB}$ or anti-NME7-X1 antibodies in the recipient. The results shown in FIG. 12 and FIG. 13 indicate that immunizing a person with a collection of peptides derived from NME7, especially in the NME7-X1 or NME7$_{AB}$ sequences may be a more effective vaccine than immunizing with a single peptide. Said peptides or proteins may further be conjugated to a carrier protein or other adjuvant, known to those skilled in the art to aid in the stimulation of an immune response.

NME7 peptides that lie outside of the DM10 domain are preferred to generate antibodies for the treatment or prevention of cancer. Peptides that can be administered to a patient for the prevention of cancer or metastasis contain sequences of the peptides listed in FIG. 6-FIG. 9. A1, A2, B1, B2 and B3 are examples of peptides that generate antibodies that bind to NME7$_{AB}$ and NME7-X1 and are administered to a patient for the treatment or prevention of cancer. The invention is not limited to peptides of the exact sequence as is naturally occurring in NME7 or NME7-X1. As is known to those skilled in the art, substitution of several amino acids of a peptide sequence can still give rise to antibodies that specifically recognize the natural protein sequence. It is not intended that the invention be limited to the peptides demonstrated herein to inhibit cancer growth or inhibit the transition of regular cancer cells to metastatic cancer cells. The methods used here to identify peptides A1, A2, B1, B2 and B3 can also be used to identify other peptide sequences that could be equally or more effective than the peptides demonstrated here.

Chimeric antigen receptor molecules comprising portions of human NME7$_{AB}$ or NME7-X1 or comprising an antibody fragment that binds to NME7$_{AB}$ or NME7-X1 are anticancer therapeutics and are administered to a patient for the treatment or prevention of cancers or cancer metastases.

In one instance, the recognition units or variable regions of anti-NME7 antibodies are fused to molecules of T cells using the technology known as CAR (chimeric antigen receptor) technology or CAR T technology. The salient feature of antibodies or fragments thereof that can be used therapeutically to treat or prevent cancers is the identification of antibody-like variable regions that recognize NME7 and prevent its interaction with targets that promote cancers. In one case, the target is the PSMGFR region of MUC1*.

Antibodies, antibody fragments or single chain antibodies can be engineered into chimeric molecules, including chimeric antigen receptors, also known as CARs, which molecules are then transfected or transduced into an immune system cell, such as a T cell, and administered to a patient. The humanized antibodies or antibody fragments, typically an scFv, comprises much of the extracellular domain of a CAR. The antibody fragment is biochemically fused to immune system signaling molecules, such as CD8 as the transmembrane domain and cytoplasmic signaling motifs such as T cell receptor signaling molecules also called activation domains, or co-stimulatory domains including but not limited to CD3-zeta, CD28, 41bb, OX40. CARs can be transfected into T cells or other cells, preferably immune system cells and administered to a patient. Here we describe CARs in which the extracellular portion contains an anti-NME7, anti-NME7$_{AB}$ or anti-NME7-X1 antibody, antibody fragment or single chain, scFv antibody fragment. In a preferred embodiment, the antibody or antibody fragment is human or humanized.

Effective anti-NME7 or anti-NME7-X1 antibodies or fragments will have the ability to bind to native NME7, NME7$_{AB}$ or NME7-X1. In practice, the parent antibody, from which the extracellular domain of the CAR is engineered, is generated by immunizing an animal with an NME7, NME7$_{AB}$ or NME7-X1 derived peptide. In one aspect of the invention, the immunizing peptide is comprised of NME7 amino acids 1-376. In one aspect of the invention, the immunizing peptide is comprised of NME7 amino acids 92-376. In another aspect of the invention, the immunizing peptide is comprised of NME7 amino acids 125-376. In yet another aspect of the invention, the immunizing peptide is made up of sequences listed in FIG. 6-FIG. 8. In another aspect of the invention, the immunizing peptide is made up of sequences listed in FIG. 9. Alternatively, the parent antibody or the antibody fragment is selected from a library or pool of antibodies, which may be natural, synthetic or fragments of either, wherein they are selected for their ability to bind to NME7, NME7$_{AB}$ or NME7-X1, peptides listed in FIG. 6-FIG. 8, or peptides listed in FIG. 9.

The targeting portion of a CAR need not be an antibody or antibody fragment. Here we describe a CAR wherein the extracellular domain contains an NME7 fragment. NME7-derived peptide(s) are engineered into a different sort of CAR wherein the targeting portion of the extracellular domain is a protein fragment or peptide rather than an antibody or antibody fragment. The peptide CARs are transfected or transduced into an immune system cell, typically a T cell. The NME7 fragments or NME7 derived peptides are selected for their ability to bind to their cognate binding partners but should not be able to function as intact NME7, NME7$_{AB}$ or NME7-X1 and confer tumorigenic activity. NME7 fragments or NME7 derived peptides are biochemically fused to immune system signaling molecules, such as CD8 as the transmembrane domain and cytoplasmic signaling motifs such as T cell receptor signaling molecules also called activation domains, or co-stimulatory domains including but not limited to CD3-zeta, CD28, 41bb, OX40.

In one aspect of the invention, the NME7 fragment is most or all of the NME7 NDPK B domain. In another aspect of the invention, the NME7 fragment is an NME7 peptide that contains one or more of the peptide sequences listed in FIG. 6-FIG. 9. Experiments indicate that, for strategies that use NME7 or fragments of NME7, NME7$_{AB}$, or NME7-X1 as the targeting portion of a chimeric antigen receptor (CAR) for engineered immune cell therapeutics, fairly large fragments of NME7$_{AB}$ or NME7-X1 would be more effective than shorter peptides, for example peptides less than 15 amino acids in length. Alternatively, a collection of CARs, each bearing a different NME7$_{AB}$ derived peptide can collectively be transfected or transduced into an immune system cell and administered to a patient for the treatment or prevention of cancers. Experiments shown in FIG. 12-FIG. 13 support the validity of this approach.

CARs that contain an NME7 fragment in its extracellular domain are transfected or transduced into an immune system cell, typically a T cell, and administered to a patient for the treatment or prevention of cancers. In one aspect, the cancer is a MUC1*-positive cancer. In another aspect, the cancer is a metastatic cancer.

Agents that inhibit an enzyme that cleaves NME7 can be used to treat or prevent cancers. Some forms of NME7 are sequestered within the cell and therefore are not secreted from the cell whereupon they can act as growth factors to promote cancers. Full-length NME7 is 42 kDa. However, we found that a ~33kDaNME7 species that is devoid of the DM10 domain and appears to be essentially identical to the recombinant NME7$_{AB}$ that we generated, is secreted from cancer cells and stem cells. This ~33 kDa NME7 species and another ~25 kDa NME7 species may be cleavage products that would be eliminated by an agent that inhibited cleavage of NME7.

The detection of elevated levels of NME7, or an ~33 kDa NME7 species, which we call NME7$_{AB}$-like species, or NME7-X1 in a patient sample is diagnostic of the presence of cancer or its progression to a more aggressive or metastatic state. The inventors have discovered that both early stage, naïve stem cells and cancer cells, especially MUC1*-positive cancer cells, express high levels of a ~33 kDa NME7 that is devoid of the DM10 domain and NME7-X1.

NME7-X1 was recently listed in a protein database as being a theoretical alternative isoform of NME7, however, it had never been detected in tissues or cells. We designed primers that differentiate NME7-X1 from NME7 by PCR. The expression levels of human NME7, NME7a, NME7b and NME7-X1 were measured by PCR in a panel of cells that included fibroblast cells, human embryonic stem cells, human iPS cells, T47D human breast cancer cells, DU145 human prostate cancer cells, PC3 human prostate cancer cells, HEK295 human fetal liver cells, and other human stem cell lines. NME7 is expressed at higher levels in cancer cells than in stem cells. Particularly, NME7-X1 is expressed 10-fold higher in prostate cancer cells and 3-fold higher in breast cancer cells, than it is in fibroblast cells or stem cells. NME7-X1 is expressed ~5-fold higher in HEK293 fetal liver cells than it is in fibroblast cells or stem cells and therefore predicts that NME7-X1 is elevated in liver cancers. NME7b is expressed 17-25-times higher in prostate cancer cells than in stem cells.

Detection of elevated levels of NME7 species in a patient sample will be indicators that the patient has a cancer or is at risk of developing a cancer. Levels of NME7 species levels can be measured or assessed by PCR, hybridization schemes, cycling probe technologies, FISH, immunocytochemistry, IHC, Western blot, immunoprecipitation, sandwich assays, ELISA assays and the like. The patient sample may be a fluid sample, a blood sample, milk, urine, cells, liquid biopsy, biopsy and the like. In a patient diagnosed with cancer, elevated levels of NME7 species are indicators of increased metastatic potential. Elevated levels of NME7-X1 are indicators of prostate cancer. Antibodies of the invention are used to detect and distinguish NME7 species and are used as a diagnostic tool.

Because adult cells and tissues do not express significant levels of NME7 or secrete NME7, an effective way to diagnose cancer or to diagnose a more aggressive or metastatic form, or a shift to a more aggressive form, is to measure levels of NME7 in a sample from a patient, from a collection of cells or tissues or from cultured cells, compared to NME7 levels in a healthy sample or compared to levels of NME7 known to exist in healthy adult cells or tissues. Increased levels of NME7 indicate the presence of cancer, the presence of a metastatic cancer or the onset of metastasis. Increased levels of NME7 is also indicative of a MUC1*-positive cancer. The sample assayed for the presence of NME7 may be a collection of cells that may be cultured cell lines or cells from a patient, a bodily fluid, a blood sample, a tissue specimen, or a biopsy specimen. Therefore, a diagnostic assay that will detect the presence of cancer or the progression of cancer, comprises the steps of: 1) obtaining a sample from a patient having cancer or at risk of developing a cancer; 2) subjecting that sample to an assay capable of detecting or measuring levels of NME7, or levels of nucleic acids encoding NME7; 3) comparing levels of the measured NME7 protein or NME7-encoding nucleic acids in the test sample to levels in control patients or control cells; 4) determining that the levels of NME7 or nucleic acids encoding NME7 are elevated compared to the controls; and 5) concluding that the donor of the test sample has cancer or has had a progression of cancer if the control to which the test was compared came from a donor previously diagnosed with a cancer.

In this assay, the control sample to which the test sample is compared can be non-cancerous cells, cultured cells, a sample from a healthy donor, a non-cancerous sample from the donor, or a sample from the donor of the test sample wherein the control sample was taken from the donor at a previous point in time. The source of such samples may be any specimen taken from the patient being tested for the presence or progression of cancer, including bodily fluids, cerebrospinal fluid, bone marrow samples, blood, tissues, cells, biopsy tissues or cells, cultured cells derived from a patient's cells and the like. The source of the sample to which the test sample is compared can be bodily fluids, cerebrospinal fluid, bone marrow samples, blood, tissues, cells, biopsy tissues or cells, or cultured cells that may be derived from a healthy donor or the test patient wherein the samples were taken at a previous point in time. The measured levels to which the test sample is compared may be from previously recorded data and compiled into lists for comparison to test samples.

Theranostics

Patients diagnosed with elevated levels of NME7 protein or nucleic acids encoding NME7 are then treated with therapeutic agents that suppress expression of NME7, inhibit cleavage of NME7 or inhibit NME7 binding to its targets, wherein such interaction promotes cancers. An important target of NME7 or a cleavage product of NME7, is MUC1*. NME7 binds to and dimerizes the extracellular domain of MUC1*. Therefore, patients diagnosed with elevated levels of NME7 will benefit from treatment with therapeutic agents that inhibit NME7 and/or therapeutic agents that inhibit the dimerization of a cleaved form of MUC1, whose extracellular domain is comprised of some or all of the PSMGFR sequence. Thus assessing suitability of cancer treatments and administration of an effective amount of a therapeutic for the treatment or prevention of cancers would consists of the steps of: 1) obtaining a sample from a patient suspected of having a cancer or at risk of developing a cancer or at risk of developing a metastatic cancer; 2) measuring an amount of NME7 or a cleavage product thereof or an NME7 encoding nucleic acid wherein the measured levels are significantly above those measured in a control sample; 3) determining that the patient has a cancer or has developed a more aggressive or a metastatic cancer; 4) administering to the patient an effective amount of a therapeutic agent that suppresses expression of NME7, inhibits cleavage of NME7 or inhibits NME7 binding to its targets and/or administering to the patient an effective amount of a therapeutic agent that suppresses expression of MUC1, inhibits cleavage of MUC1 to MUC1* or inhibits MUC1* binding to its targets. In a preferred embodiment, the therapeutic agent that inhibits NME7 binding to its targets, inhibits its interaction with MUC1*. In a more preferred embodiments, it inhibits its interaction with the extracellular domain of MUC1* comprised essentially of the PSMGFR sequence. In a preferred embodiment, the therapeutic agent that inhibits MUC1* binding to its targets, inhibits the interaction between MUC1* and NME7. In a more preferred embodiment, the therapeutic agent that inhibits the interaction between MUC1* and NME7 inhibits the binding of MUC1* to the portion of NME7 that is comprised essentially of the sequence of NME7&B.

Chemically Modified Peptides

Polypeptide or antibody therapeutics may suffer from short circulating half-life, and proteolytic degradation and low solubility. To improve the pharmacokinetics and pharmacodynamics properties of the inventive biopharmaceuticals, methods such as manipulation of the amino acid sequence may be made to decrease or increase immunogenicity and decrease proteolytic cleavage; fusion or conjugation of the peptides to immunoglobulins and serum proteins, such as albumin may be made; incorporation into drug delivery vehicles for the biopharmaceuticals such as the inventive peptides and antibodies for protection and slow release may also be made; and conjugating to natural or synthetic polymers are also contemplated. In particular, for synthetic polymer conjugation, pegylation or acylation, such as N-acylation, S-acylation and so forth are also contemplated.

Nucleic Acid Constructs

Also provided is an expression vector comprising a nucleic acid molecule of the invention as described herein, wherein the nucleic acid molecule is operatively linked to an expression control sequence. Also provided is a host-vector system for the production of a polypeptide which comprises the expression vector of the invention which has been introduced into a host cell suitable for expression of the polypeptide. The suitable host cell may be a bacterial cell such as E. coli, a yeast cell, such as Pichia pastoris, an insect cell, such as Spodoptera frugiperda, or a mammalian cell, such as a COS, HEK or CHO cell.

The present invention also provides for methods of producing the polypeptides of the invention by growing cells of the host-vector system described herein, under conditions permitting production of the polypeptide and recovering the polypeptide so produced. The polypeptides useful for practicing the present invention may be prepared by expression in a prokaryotic or eukaryotic expression system.

The recombinant gene may be expressed and the polypeptide purified utilizing any number of methods. The gene may be subcloned into a bacterial expression vector, such as for example, but not by way of limitation, pZErO.

The polypeptides may be purified by any technique which allows for the subsequent formation of a stable, biologically active protein. For example, and not by way of limitation, the factors may be recovered from cells either as soluble proteins or as inclusion bodies, from which they may be extracted quantitatively by 8M guanidinium hydrochloride and dialysis. In order to further purify the factors, any number of purification methods may be used, including but not limited to conventional ion exchange chromatography, affinity chromatography, different sugar chromatography, hydrophobic interaction chromatography, reverse phase chromatography or gel filtration.

When used herein, polypeptide includes functionally equivalent molecules in which amino acid residues are substituted for residues within the sequence resulting in a silent or conservative change. For example, one or more amino acid residues within the sequence can be substituted by another amino acid of a similar polarity, which acts as a functional equivalent, resulting in a silent or conservative alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. The potential glycosylation amino acids include serine, threonine, and asparagine. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, etc.

Any of the methods known to one skilled in the art for the insertion of DNA fragments into a vector may be used to construct expression vectors encoding the polypeptides of the invention using appropriate transcriptional/translational control signals and protein coding sequences. These methods may include in vitro recombinant DNA and synthetic techniques and in vivo recombinations (genetic recombination). Expression of nucleic acid sequence encoding the polypeptides of the invention may be regulated by a second nucleic acid sequence so that the polypeptide is expressed in a host transformed with the recombinant DNA molecule. For example, expression of the polypeptides described herein may be controlled by any promoter/enhancer element known in the art. Promoters which may be used to control expression of the polypeptide include, but are not limited to the long terminal repeat as described in Squinto et al., (1991, Cell 65:1-20); the SV40 early promoter region (Bernoist and Chambon, 1981, Nature 290:304-310), the CMV promoter, the M-MuLV 5' terminal repeat the promoter contained in the 3'long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:144-1445), the regulatory sequences of the metallothionein gene (Brinster et al., 1982, Nature 296:39-42); prokaryotic expression vectors such as the β-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25), see also "Useful proteins from recombinant bacteria" in Scientific American, 1980, 242:74-94; promoter elements from yeast or other fungi such as the Gal 4 promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), Sendai virus, lenti virus, albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58); alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94); myelin basic protein gene control region which is active in oligodendrocyte cells in the brain (Readhead et al., 1987, Cell 48:703-712); myosin light chain-2 gene control region which is active in skeletal muscle (Shani, 1985, Nature 314:283-286), and gonadotropic releasing hormone gene control region which is active in the hypothalamus (Mason et al., 1986, Science 234:1372-1378).

Thus, according to the invention, expression vectors capable of being replicated in a bacterial or eukaryotic host comprising nucleic acids encoding a polypeptide as described herein, are used to transfect the host and thereby direct expression of such nucleic acid to produce polypeptides which may then be recovered in biologically active form. As used herein, a biologically active form includes a form capable of binding to the relevant receptor and causing a differentiated function and/or influencing the phenotype of the cell expressing the receptor.

Expression vectors containing the nucleic acid inserts can be identified by without limitation, at least three general approaches: (a) DNA-DNA hybridization, (b) presence or absence of "marker" gene functions, and (c) expression of inserted sequences. In the first approach, the presence of foreign nucleic acids inserted in an expression vector can be detected by DNA-DNA hybridization using probes comprising sequences that are homologous to an inserted nucleic acid sequences. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign nucleic acid sequences in the vector. For example, if an eft nucleic acid sequence is inserted within the marker gene sequence of the vector, recombinants containing the insert can be identified by the absence of the marker gene function. In the third approach, recombinant expression vectors can be identified by assaying the foreign nucleic acid product expressed by the recombinant constructs. Such assays can be based, for example, on the physical or functional properties of the nucleic acid product of interest, for example, by binding of a ligand to a receptor or portion thereof which may be tagged with, for example, a detectable antibody or portion thereof or binding to antibodies produced against the protein of interest or a portion thereof.

The polypeptide, in particular modified of the present invention, may be expressed in the host cells transiently, constitutively or permanently.

Effective doses useful for treating the diseases or disorders indicated in the present application may be determined using methods known to one skilled in the art (see, for example, Fingl, et al., The Pharmacological Basis of Therapeutics, Goodman and Gilman, eds. Macmillan Publishing Co, New York, pp. 1-46 (1975). Pharmaceutical compositions for use according to the invention include the polypeptides described above in a pharmacologically acceptable liquid, solid or semi-solid carrier, linked to a carrier or targeting molecule (e.g., antibody, hormone, growth factor, etc.) and/or incorporated into liposomes, microcapsules, and controlled release preparation prior to administration in vivo. For example, the pharmaceutical composition may comprise a polypeptide in an aqueous solution, such as sterile water, saline, phosphate buffer or dextrose solution. Alternatively, the active agents may be comprised in a solid (e.g. wax) or semi-solid (e.g. gelatinous) formulation that may be implanted into a patient in need of such treatment. The administration route may be any mode of administration known in the art, including but not limited to intravenously, intrathecally, subcutaneously, intrauterinely, by injection into involved tissue, intraarterially, intranasally, orally, or via an implanted device.

Administration may result in the distribution of the active agent of the invention throughout the body or in a localized area. For example, in some conditions, which involve distant regions of the nervous system, intravenous or intrathecal administration of agent may be desirable. In some situations, an implant containing active agent may be placed in or near the lesioned area. Suitable implants include, but are not limited to, gelfoam, wax, spray, or microparticle-based implants.

The present invention also provides for pharmaceutical compositions comprising the polypeptides described herein, in a pharmacologically acceptable vehicle. The compositions may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

Gene Therapy

Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, N Y (1993); and Kriegler, Gene Transfer and Expression, A Laboratory Manual, Stockton Press, NY (1990).

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors, or by direct injection of naked DNA, or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors) and so on. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor. Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contain nucleic acid sequences encoding the polypeptide are used. The nucleic acid sequences encoding the polypeptide to be used in gene therapy are cloned into one or more vectors, which facilitates delivery of the gene into a patient. Lentiviral vectors, such as retroviral vectors, and other vectors such as adenoviral vectors and adeno-associated viruses are examples of viral vectors that may be used. Retroviral vectors contain the components necessary for the correct packaging of the viral genome and integration into the host cell DNA.

Adenoviruses are especially attractive vehicles for delivering genes to respiratory epithelia because they naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. In addition, adeno-associated virus (AAV) has also been proposed for use in gene therapy.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion and so on. Numerous techniques are known in the art for the introduction of foreign genes into cells and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T-lymphocytes, B-lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, and so on.

In a preferred embodiment, the cell used for gene therapy is autologous to the patient.

In an embodiment in which recombinant cells are used in gene therapy, nucleic acid sequences encoding the polypeptide are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention.

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Therapeutic Composition

The formulation of therapeutic compounds is generally known in the art and reference can conveniently be made to Remington's Pharmaceutical Sciences, 17th ed., Mack Publishing Co., Easton, Pa., USA. For example, from about 0.05 ng to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intra nasal, intra ocular, intradermal or suppository routes or implanting (eg using slow release molecules by the intraperitoneal route or by using cells e.g. monocytes or dendrite cells sensitized in vitro and adoptively transferred to the recipient). Depending on the route of administration, the peptide may be required to be coated in a material to protect it from the action of enzymes, acids and other natural conditions which may inactivate said ingredients.

For example, the low lipophilicity of the peptides will allow them to be destroyed in the gastrointestinal tract by enzymes capable of cleaving peptide bonds and in the stomach by acid hydrolysis. In order to administer peptides by other than parenteral administration, they will be coated by, or administered with, a material to prevent its inactivation. For example, peptides may be administered in an adjuvant, co-administered with enzyme inhibitors or in liposomes. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes.

The active compounds may also be administered parenterally or intraperitoneally. Dispersions can also be prepared in glycerol liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, chlorobutanol, phenol, sorbic acid, theomersal and the like. In many cases, it will be preferable to include isotonic agents, for example, sugars or sodium chloride. Prolonged absorption of the injectable compositions can be brought about by the use in the composition of agents delaying absorption, for example, aluminium monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterile active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof When the peptides are suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 2000 mg of active compound.

The tablets, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

Delivery Systems

Various delivery systems are known and can be used to administer a compound of the invention, e.g., encapsulation in liposomes, microparticles, microcapsules, recombinant cells capable of expressing the compound, receptor-mediated endocytosis, construction of a nucleic acid as part of a retroviral or other vector, etc. Methods of introduction include but are not limited to intradermal, intramuscular, intraperitoneal, intravenous, subcutaneous, intranasal, intra ocular, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody or a peptide of the invention, care must be taken to use materials to which the protein does not absorb. In another embodiment, the compound or composition can be delivered in a vesicle, in particular a liposome. In yet another embodiment, the compound or composition can be delivered in a controlled release system. In one embodiment, a pump may be used. In another embodiment, polymeric materials can be used. In yet another embodiment, a controlled release system can be placed in proximity of the therapeutic target, thus requiring only a fraction of the systemic dose.

Sequence Listing Free Text

As regards the use of nucleotide symbols other than a, g, c, t, they follow the convention set forth in WIPO Standard ST.25, Appendix 2, Table 1, wherein k represents t or g; n represents a, c, t or g; m represents a or c; r represents a or g; s represents c or g; w represents a or t and y represents c or t.

MTPGTQSPFF LLLLLTVLTV VTGSGHASST PGGEKETSAT QRSSVPSSTE KNAVSMTSSV LSSHSPGSGS STTQGQDVTL APATEPASGS AATWGQDVTS VPVTRPALGS TTPPAHDVTS APDNKPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTR-

PAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDTRPAPGS TAPPAHGVTS APDNRPALGS TAPPVHNVTS ASGSASGSAS TLVHNGTSAR ATTTPASKST PFSIPSHHSD TPTTLASHST KTDASSTHHS SVPPLTSSNH STSPQLSTGV SFFFLSFHIS NLQFNSSLED PSTDYYQELQ RDISEMFLQI YKQGGFLGLS NIKFRPGSVV VQLTLAFREG TINVHDVETQ FNQYKTEAAS RYNLTISDVS VSDVPFPFSA QSGAGVPGWG IALLVLVCVL VALAIVYLIA LAVCQCRRKN YGQLDIFPAR DTYHPMSEYP TYHTHGRYVP PSSTDRSPYE KVSAGNGGSS LSYTNPAVAA ASANL (SEQ ID NO:1) describes full-length MUC1 Receptor (Mucin 1 precursor, Genbank Accession number: P15941).

```
                                          (SEQ ID NO: 2)
MTPGTQSPFFLLLLLTVLT (SEQ ID NO: 3)
MTPGTQSPFFLLLLLTVLT VVTA (SEQ ID NO: 4)
MTPGTQSPFFLLLLLTVLT VVTG
```

SEQ ID NOS:2, 3 and 4 describe N-terminal MUC-1 signaling sequence for directing MUC1 receptor and truncated isoforms to cell membrane surface. Up to 3 amino acid residues may be absent at C-terminal end as indicated by variants in SEQ ID NOS:2, 3 and 4.

GTINVHDVETQFNQYKTEAASRYNLTISDVSVSDVPFPFSAQSGAGVPGW GIALLVLVCVLVALAIVYLIALAVCQCRRKNYGQLDIFPARDTYHPMSEYPTYHTHG RYVPPSSTDRSPYEKVSAGNGGSSLSYTNPAVAAASANL (SEQ ID NO:5) describes a truncated MUC1 receptor isoform having nat-PSMGFR at its N-terminus and including the transmembrane and cytoplasmic sequences of a full-length MUC1 receptor.

GTINVHDVETQFNQYKTEAASRYNLTISDVSVSDVPFPFSAQSGA (SEQ ID NO:6) describes the extracellular domain of Native Primary Sequence of the MUC1 Growth Factor Receptor (nat-PSMGFR—an example of "PSMGFR"): TINVHDVETQFNQYKTEAASRYNLTISDVSVSDVPFPFSAQSGA (SEQ ID NO:7) describes the extracellular domain of Native Primary Sequence of the MUC1 Growth Factor Receptor (nat-PSMGFR—An example of "PSMGFR"), having a single amino acid deletion at the N-terminus of SEQ ID NO: 6).

GTINVHDVETQFNQYKTEAASPYNLTISDVSVSDVPFPFSAQSGA (SEQ ID NO:8) describes the extracellular domain of "SPY" functional variant of the native Primary Sequence of the MUC1 Growth Factor Receptor having enhanced stability (var-PSMGFR—An example of "PSMGFR").

TINVHDVETQFNQYKTEAASPYNLTISDVSVSDVPFPFSAQSGA (SEQ ID NO:9) describes the extracellular domain of "SPY" functional variant of the native Primary Sequence of the MUC1 Growth Factor Receptor having enhanced stability (var-PSMGFR—An example of "PSMGFR"), having a single amino acid deletion at the C-terminus of SEQ ID NO:8).

```
                                                              (SEQ ID NO: 10)
        tgtcagtgccgccgaaagaactacgggcagctggacatctttccagcccgggatacctaccatcctatgagcgagta ccccacctaccacacccatgggcgctatgtgcccctagcagtaccgatcgtagcccctatgagaaggtttctgcaggtaacggtggc agcagcctctcttacacaaacccagcagtggcagccgcttctgccaacttg
        describes MUC1 cytoplasmic domain nucleotide sequence.

(SEQ ID NO: 11)
CQCRRKNYGQLDIFPARDTYHPMSEYPTYHTHGRYVPPSSTDRSPYEKVS

AGNGGSSLSYTNPAVAAASANL
describes MUC1 cytoplasmic domain amino acid sequence.

(SEQ ID NO: 12)
        gagatcctgagacaatgaatcatagtgaaagattcgttttcattgcagagtggtatgatccaaatgcttcacttcttcgac gttatgagctttatttacccaggggatggatctgttgaaatgcatgatgtaaagaatcatcgcaccttttaaagcggaccaaatatgata acctgcacttggaagatttatttataggcaacaaagtgaatgtcttttctcgacaactggtattaattgactatggggatcaatatacagctc gccagctgggcagtaggaaagaaaaaacgctagccctaattaaaccagatgcaatatcaaaggctggagaaataattgaaataataa acaaagctggatttactataaccaaactcaaaatgatgatgctttcaaggaaagaagcattggattttcatgtagatcaccagtcaagacc cttttcaatgagctgatccagtttattacaactggtcctattattgccatgagattttaagagatgatgctatatgtgaatggaaaagactg ctgggacctgcaaactctggagtggcacgcacagatgcttctgaaagcattagagccctctttggaacagatggcataagaaatgcag cgcatggccctgattcttttgcttctgcggccagagaaatggagttgttttttccttcaagtggaggttgtgggccggcaaacactgctaa atttactaattgtacctgttgcattgttaaaccccatgctgtcagtgaaggtatgttgaatacactatattcagtacattttgttaataggagag caatgtttattttcttgatgtactttatgtatagaaaataa
        describes NME7 nucleotide sequence (NME7: GENBANK ACCESSION AB209049).
```

```
                                                                     (SEQ ID NO: 13)
DPETMNHSERFVFIAEWYDPNASLLRRYELLFYPGDGSVEMHDVKNHRT

FLKRTKYDNLHLEDLFIGNKVNVFSRQLVLIDYGDQYTARQLGSRKEKTLALIKPDAI

SKAGENIEIINKAGFTITKLKMMMLSRKEALDFHVDHQSRPFFNELIQFITTGPIIAMEIL

RDDAICEWKRLLGPANSGVARTDASESIRALFGTDGIRNAAHGPDSFASAAREMELF

FPSSGGCGPANTAKFTNCTCCIVKPHAVSEGMLNTLYSVHFVNRRAMFIFLMYFMYRK
describes NME7 amino acid sequence (NME7: GENBANK ACCESSION AB209049).

(SEQ ID NO: 14)
atggtgctactgtctactttagggatcgtctttcaaggcgaggggcctcctatctcaagctgtgatacaggaaccatggc caactgtgagcgtaccttcattgcgatcaaaccagatggggtccagcggggtcttgtgggagagattatcaagcgttttgagcagaaag gattccgccttgttggtctgaaattcatgcaagcttccgaagatcttctcaaggaacactacgttgacctgaaggaccgtccattctttgcc ggcctggtgaaatacatgcactcagggccggtagttgccatggtctgggaggggctgaatgtggtgaagacgggccgagtcatgctc ggggagaccaaccctgcagactccaagcctgggaccatccgtggagacttctgcatacaagttggcaggaacattatacatggcagt gattctgtggagagtgcagagaaggagatcggcttgtggtttcaccctgaggaactggtagattacacgagctgtgctcagaactggat ctatgaatga
describes NM23-H1 nucleotide sequence (NM23-H1: GENBANK ACCESSION AF487339).

(SEQ ID NO: 15)
MVLLSTLGIVFQGEGPPISSCDTGTMANCERTFIAIKPDGVQRGLVGEIIKR

FEQKGFRLVGLKFMQASEDLLKEHYVDLKDRPFFAGLVKYMHSGPVVAMVWEGL

NVVKTGRVMLGETNPADSKPGTIRGDFCIQVGRNIIHGSDSVESAEKEIGLWFHPEEL

VDYTSCAQNWIYE
NM23-H1 describes amino acid sequence (NM23-H1: GENBANK ACCESSION AF487339).

(SEQ ID NO: 16)
atggtgctactgtctactttagggatcgtctttcaaggcgaggggcctcctatctcaagctgtgatacaggaaccatggc caactgtgagcgtaccttcattgcgatcaaaccagatggggtccagcggggtcttgtgggagagattatcaagcgttttgagcagaaag gattccgccttgttggtctgaaattcatgcaagcttccgaagatcttctcaaggaacactacgttgacctgaaggaccgtccattctttgcc ggcctggtgaaatacatgcactcagggccggtagttgccatggtctgggaggggctgaatgtggtgaagacgggccgagtcatgctc ggggagaccaaccctgcagactccaagcctgggaccatccgtggagacttctgcatacaagttggcaggaacattatacatggcggt gattctgtggagagtgcagagaaggagatcggcttgtggtttcaccctgaggaactggtagattacacgagctgtgctcagaactggat ctatgaatga
describes NM23-H1 S120G mutant nucleotide sequence (NM23-H1: GENBANK ACCESSION AF487339).

(SEQ ID NO: 17)
MVLLSTLGIVFQGEGPPISSCDTGTMANCERTFIAIKPDGVQRGLVGEIIKR

FEQKGFRLVGLKFMQASEDLLKEHYVDLKDRPFFAGLVKYMHSGPVVAMVWEGL

NVVKTGRVMLGETNPADSKPGTIRGDFCIQVGRNIIHGGDSVESAEKEIGLWFHPEEL

VDYTSCAQNWIYE
describes NM23-H1 S120G mutant amino acid sequence (NM23-H1: GENBANK ACCESSION AF487339).

(SEQ ID NO: 18)
atggccaacctggagcgcaccttcatcgccatcaagccggacggcgtgcagcgcggcctggtgggcgagatcatc aagcgcttcgagcagaagggattccgcctcgtggccatgaagttcctccgggcctctgaagaacacctgaagcagcactacattgac ctgaaagaccgaccattcttccctgggctggtgaagtacatgaactcagggccggttgtggccatggtctgggaggggctgaacgtg gtgaagacaggccgagtgatgcttggggagaccaatccagcagattcaaagccaggcaccattcgtgggacttctgcattcaggtt ggcaggaacatcattcatggcagtgattcagtaaaaagtgctgaaaaagaaatcagcctatggtttaagcctgaagaactggttgacta caagtcttgtgctcatgactgggtctatgaataa
describes NM23-H2 nucleotide sequence (NM23-H2: GENBANK ACCESSION AK313448).
```

(SEQ ID NO: 19)
MANLERTFIAIKPDGVQRGLVGEIIKRFEQKGFRLVAMKFLRASEEHLKQH

YIDLKDRPFFPGLVKYMNSGPVVAMVWEGLNVVKTGRVMLGETNPADSKPGTIRG

DFCIQVGRNIIHGSDSVKSAEKEISLWFKPEELVDYKSCAHDWVYE
describes NM23-H2 amino acid sequence (NM23-H2: GENBANK ACCESSION AK313448).

Human NM23-H7-2 sequence optimized for *E. coli* expression:
(DNA)
(SEQ ID NO: 20)
atgcatgacgttaaaaatcaccgtaccttctgaaacgcacgaaatatgataatctgcatctggaagacctgtttattggc aacaaagtcaatgtgttctctcgtcagctggtgctgatcgattatggcgaccagtacaccgcgcgtcaactgggtagtcgcaaagaaaa aacgctggccctgattaaaccggatgcaatctccaaagctggcgaaattatcgaaattatcaacaaagcgggtttcaccatcacgaaac tgaaaatgatgatgctgagccgtaaagaagccctggattttcatgtcgaccaccagtctcgcccgttttcaatgaactgattcaattcatc accacgggtccgattatcgcaatggaaattctgcgtgatgacgctatctgcgaatggaaacgcctgctgggcccggcaaactcaggtg ttgcgcgtaccgatgccagtgaatccattgcgctctgtttggcaccgatggtatccgtaatgcagcacatggtccggactcattcgcat cggcagctcgtgaaatggaactgttttttcccgagctctggccggttgcggtccggcaaacaccgccaaatttaccaattgtacgtgctgta ttgtcaaaccgcacgcagtgtcagaaggcctgctgggtaaaattctgatggcaatccgtgatgctggctttgaaatctcggccatgcag atgttcaacatggaccgcgttaacgtcgaagaattctacgaagtttacaaaggcgtggttaccgaatatcacgatatggttacgaaatg tactccggtccgtgcgtcgcgatggaaattcagcaaaacaatgccaccaaaacgtttcgtgaattctgtggtccggcagatccggaaat cgcacgtcatctgcgtccgggtaccctgcgcgcaattttttggtaaaacgaaaatccagaacgctgtgcactgtaccgatctgccggaa gacggtctgctggaagttcaatactttttcaaaattctggataattga (amino acids)
(SEQ ID NO: 21)
MHDVKNHRTFLKRTKYDNLHLEDLFIGNKVNVFSRQLVLIDYGDQYTAR

QLGSRKEKTLALIKPDAISKAGEIIEIINKAGFTITKLKMMMLSRKEALDFHVDHQSRP

FFNELIQFITTGPIIAMEILRDDAICEWKRLLGPANSGVARTDASESIRALFGTDGIRNA

AHGPDSFASAAREMELFFPSSGGCGPANTAKFTNCTCCIVKPHAVSEGLLGKILMAIR

DAGFEISAMQMFNMDRVNVEEFYEVYKGVVTEYHDMVTEMYSGPCVAMEIQQNN

ATKTFREFCGPADPEIARHLRPGTLRAIFGKTKIQNAVHCTDLPEDGLLEVQYFFKILDN-

Human NME7-A:
(DNA)
(SEQ ID NO: 22)
atggaaaaaacgctagccctaattaaaccagatgcaatatcaaaggctggagaaataattgaaataataaacaaagct ggatttactataaccaaactcaaaatgatgatgcttcaaggaaagaagcattggattcatgtagatcaccagtcaagacccttttcaat gagctgatccagttattacaactggtcctattattgccatggagattttaagagatgatgctatatgtgaatggaaaagactgctgggacc tgcaaactctggagtggcacgcacagatgcttctgaaagcattagagccctcttggaacagatggcataagaaatgcagcgcatggc cctgattcttttgcttctgcgccagagaaatggagttgtttttttga (amino acids)
(SEQ ID NO: 23)
MEKTLALIKPDAISKAGEIIEIINKAGFTITKLKMMMLSRKEALDFHVDHQS

RPFFNELIQFITTGPIIAMEILRDDAICEWKRLLGPANSGVARTDASESIRALFGTDGIR

NAAHGPDSFASAAREMELFF-

Human NME7-A1:
(DNA)
(SEQ ID NO: 24)
atggaaaaaacgctagccctaattaaaccagatgcaatatcaaaggctggagaaataattgaaataataaacaaagct ggatttactataaccaaactcaaaatgatgatgcttcaaggaaagaagcattggattcatgtagatcaccagtcaagacccttttcaat gagctgatccagttattacaactggtcctattattgccatggagattttaagagatgatgctatatgtgaatggaaaagactgctgggacc -continued tgcaaactctggagtggcacgcacagatgcttctgaaagcattagagccctctttggaacagatggcataagaaatgcagcgcatggc cctgattcttttgcttctgcggccagagaaatggagttgttttttccttcaagtggaggttgtgggccggcaaacactgctaaatttacttga (amino acids)

(SEQ ID NO: 25)

MEKTLALIKPDAISKAGEIIEIINKAGFTITKLKMMMLSRKEALDFHVDHQS

RPFFNELIQFITTGPIIAMEILRDDAICEWKRLLGPANSGVARTDASESIRALFGTDGIR

NAAHGPDSFASAAREMELFFPSSGGCGPANTAKFT-

Human NME7-A2:
(DNA)

(SEQ ID NO: 26)

atgaatcatagtgaaagattcgttttcattgcagagtggtatgatccaaatgcttcacttcttcgacgttatgagcttttatttt acccaggggatggatctgttgaaatgcatgatgtaaagaatcatcgcaccttttaaagcggaccaaatatgataacctgcacttggaag atttattataggcaacaaagtgaatgtcttttctcgacaactggtattaattgactatggggatcaatatacagctcgccagctgggcagta ggaaagaaaaaacgctagccctaattaaaccagatgcaatatcaaaggctggagaaataattgaataataaacaaagctggatttact ataaccaaactcaaaatgatgatgctttcaaggaaagaagcattggattttcatgtagatcaccagtcaagaccttttcaatgagctgat ccagtttattacaactggtcctattattgccatggagattttaagagatgatgctatatgtgaatggaaaagactgctgggacctgcaaact ctggagtggcacgcacagatgcttctgaaagcattagagccctctttggaacagatggcataagaaatgcagcgcatggccctgattct tttgcttctgcggccagagaaatggagttgttttttga (amino acids)

(SEQ ID NO: 27)

MNHSERFVFIAEWYDPNASLLRRYELLFYPGDGSVEMHDVKNHRTFLKR

TKYDNLHLEDLFIGNKVNVFSRQLVLIDYGDQYTARQLGSRKEKTLALIKPDAISKA

GEIIEIINKAGFTITKLKMMMLSRKEALDFHVDHQSRPFFNELIQFITTGPIIAMEILRDD

AICEWKRLLGPANSGVARTDASESIRALFGTDGIRNAAHGPDSFASAAREMELFF-

Human NME7-A3:
(DNA)

(SEQ ID NO: 28)

atgaatcatagtgaaagattcgttttcattgcagagtggtatgatccaaatgcttcacttcttcgacgttatgagcttttatttt acccaggggatggatctgttgaaatgcatgatgtaaagaatcatcgcaccttttaaagcggaccaaatatgataacctgcacttggaag atttattataggcaacaaagtgaatgtcttttctcgacaactggtattaattgactatggggatcaatatacagctcgccagctgggcagta ggaaagaaaaaacgctagccctaattaaaccagatgcaatatcaaaggctggagaaataattgaataataaacaaagctggatttact ataaccaaactcaaaatgatgatgctttcaaggaaagaagcattggattttcatgtagatcaccagtcaagaccttttcaatgagctgat ccagtttattacaactggtcctattattgccatggagattttaagagatgatgctatatgtgaatggaaaagactgctgggacctgcaaact ctggagtggcacgcacagatgcttctgaaagcattagagccctctttggaacagatggcataagaaatgcagcgcatggccctgattct tttgcttctgcggccagagaaatggagttgttttttccttcaagtggaggttgtgggccggcaaacactgctaaatttacttga (amino acids)

(SEQ ID NO: 29)

MNHSERFVFIAEWYDPNASLLRRYELLFYPGDGSVEMHDVKNHRTFLKR

TKYDNLHLEDLFIGNKVNVFSRQLVLIDYGDQYTARQLGSRKEKTLALIKPDAISKA

GEIIEIINKAGFTITKLKMMMLSRKEALDFHVDHQSRPFFNELIQFITTGPIIAMEILRDD

AICEWKRLLGPANSGVARTDASESIRALFGTDGIRNAAHGPDSFASAAREMELFFPSS

GGCGPANTAKFT-

Human NME7-B:
(DNA)

(SEQ ID NO: 30)

atgaattgtacctgttgcattgttaaacccatgctgtcagtgaaggactgttgggaaagatcctgatggctatccgaga tgcaggttttgaaatctcagctatgcagatgttcaatatggatcgggttaatgttgaggaattctatgaagtttataaaggagtagtgaccg aatatcatgacatggtgacagaaatgtattctggccccttgtgtagcaatggagattcaacagaataatgctacaaagacatttcgagaattt -continued tgtggacctgctgatcctgaaattgcccggcatttacgccctggaactctcagagcaatctttggtaaaactaagatccagaatgctgttc actgtactgatctgccagaggatggcctattagaggttcaatacttcttctga (amino acids)
(SEQ ID NO: 31)
MNCTCCIVKPHAVSEGLLGKILMAIRDAGFEISAMQMFNMDRVNVEEFY

EVYKGVVTEYHDMVTEMYSGPCVAMEIQQNNATKTFREFCGPADPEIARHLRPGTL

RAIFGKTKIQNAVHCTDLPEDGLLEVQYFF-

Human NME7-B1:
(DNA)
(SEQ ID NO: 32)
atgaattgtacctgttgcattgttaaacccatgctgtcagtgaaggactgttgggaaagatcctgatggctatccgaga tgcaggttttgaaatctcagctatgcagatgttcaatatggatcgggttaatgttgaggaattctatgaagtttataaaggagtagtgaccg aatatcatgacatggtgacagaaatgtattctggcccttgtgtagcaatggagattcaacagaataatgctacaaagacatttcgagaattt tgtggacctgctgatcctgaaattgcccggcatttacgccctggaactctcagagcaatctttggtaaaactaagatccagaatgctgttc actgtactgatctgccagaggatggcctattagaggttcaatacttcttcaagatcttggataattagtga (amino acids)
(SEQ ID NO: 33)
MNCTCCIVKPHAVSEGLLGKILMAIRDAGFEISAMQMFNMDRVNVEEFY

EVYKGVVTEYHDMVTEMYSGPCVAMEIQQNNATKTFREFCGPADPEIARHLRPGTL

RAIFGKTKIQNAVHCTDLPEDGLLEVQYFFKILDN-

Human NME7-B2:
(DNA)
(SEQ ID NO: 34)
atgccttcaagtggaggttgtgggccggcaaacactgctaaatttactaattgtacctgttgcattgttaaacccatgct gtcagtgaaggactgttgggaaagatcctgatggctatccgagatgcaggttttgaaatctcagctatgcagatgttcaatatggatcgg gttaatgttgaggaattctatgaagtttataaaggagtagtgaccgaatatcatgacatggtgacagaaatgtattctggcccttgtgtagc aatggagattcaacagaataatgctacaaagacatttcgagaattttgtggacctgctgatcctgaaattgcccggcatttacgccctgga actctcagagcaatctttggtaaaactaagatccagaatgctgttcactgtactgatctgccagaggatggcctattagaggttcaatactt cttctga (amino acids)
(SEQ ID NO: 35)
MPSSGGCGPANTAKFTNCTCCIVKPHAVSEGLLGKILMAIRDAGFEISAM

QMFNMDRVNVEEFYEVYKGVVTEYHDMVTEMYSGPCVAMEIQQNNATKTFREFC

GPADPEIARHLRPGTLRAIFGKTKIQNAVHCTDLPEDGLLEVQYFF-

Human NME7-B3:
(DNA)
(SEQ ID NO: 36)
atgccttcaagtggaggttgtgggccggcaaacactgctaaatttactaattgtacctgttgcattgttaaacccatgct gtcagtgaaggactgttgggaaagatcctgatggctatccgagatgcaggttttgaaatctcagctatgcagatgttcaatatggatcgg gttaatgttgaggaattctatgaagtttataaaggagtagtgaccgaatatcatgacatggtgacagaaatgtattctggcccttgtgtagc aatggagattcaacagaataatgctacaaagacatttcgagaattttgtggacctgctgatcctgaaattgcccggcatttacgccctgga actctcagagcaatctttggtaaaactaagatccagaatgctgttcactgtactgatctgccagaggatggcctattagaggttcaatactt cttcaagatcttggataattagtga (amino acids)
(SEQ ID NO: 37)
MPSSGGCGPANTAKFTNCTCCIVKPHAVSEGLLGKILMAIRDAGFEISAM

QMFNMDRVNVEEFYEVYKGVVTEYHDMVTEMYSGPCVAMEIQQNNATKTFREFC

GPADPEIARHLRPGTLRAIFGKTKIQNAVHCTDLPEDGLLEVQYFFKILDN--

-continued

Human NME7-AB, also known as NME7$_{AB}$:
(DNA)

(SEQ ID NO: 38)

atggaaaaaacgctagccctaattaaaccagatgcaatatcaaaggctggagaaataattgaaataataaacaaagct ggatttactataaccaaactcaaaatgatgatgctttcaaggaaagaagcattggattttcatgtagatcaccagtcaagaccttttcaat gagctgatccagtttattacaactggtcctattattgccatggagattttaagagatgatgctatatgtgaatggaaaagactgctgggacc tgcaaactctggagtggcacgcacagatgcttctgaaagcattagagccctctttggaacagatggcataagaaatgcagcgcatggc cctgattcttttgcttctgcggccagagaaatggagttgttttttccttcaagtggaggttgtgggccggcaaacactgctaaatttactaatt gtacctgttgcattgttaaaccccatgctgtcagtgaaggactgttgggaaagatcctgatggctatccgagatgcaggttttgaaatctc agctatgcagatgttcaatatggatcgggttaatgttgaggaattctatgaagtttataaaggagtagtgaccgaatatcatgacatggtga cagaaatgtattctggcccttgtgtagcaatggagattcaacagaataatgctacaaagacatttcgagaattttgtggacctgctgatcct gaaattgcccggcatttacgccctggaactctcagagcaatctttggtaaaactaagatccagaatgctgttcactgtactgatctgccag aggatggcctattagaggttcaatacttcttcaagatcttggataattagtga (amino acids)

(SEQ ID NO: 39)

MEKTLALIKPDAISKAGEIIEIINKAGFTITKLKMMMLSRKEALDFHVDHQS

RPFFNELIQFITTGPIIAMEILRDDAICEWKRLLGPANSGVARTDASESIRALFGTDGIR

NAAHGPDSFASAAREMELFFPSSGGCGPANTAKFTNCTCCIVKPHAVSEGLLGKILM

AIRDAGFEISAMQMFNMDRVNVEEFYEVYKGVVTEYHDMVTEMYSGPCVAMEIQQ

NNATKTFREFCGPADPEIARHLRPGTLRAIFGKTKIQNAVHCTDLPEDGLLEVQYFFK

ILDN--

Human NME7-AB1:
(DNA)

(SEQ ID NO: 40)

atggaaaaaacgctagccctaattaaaccagatgcaatatcaaaggctggagaaataattgaaataataaacaaagct ggatttactataaccaaactcaaaatgatgatgctttcaaggaaagaagcattggattttcatgtagatcaccagtcaagaccttttcaat gagctgatccagtttattacaactggtcctattattgccatggagattttaagagatgatgctatatgtgaatggaaaagactgctgggacc tgcaaactctggagtggcacgcacagatgcttctgaaagcattagagccctctttggaacagatggcataagaaatgcagcgcatggc cctgattcttttgcttctgcggccagagaaatggagttgttttttccttcaagtggaggttgtgggccggcaaacactgctaaatttactaatt gtacctgttgcattgttaaaccccatgctgtcagtgaaggactgttgggaaagatcctgatggctatccgagatgcaggttttgaaatctc agctatgcagatgttcaatatggatcgggttaatgttgaggaattctatgaagtttataaaggagtagtgaccgaatatcatgacatggtga cagaaatgtattctggcccttgtgtagcaatggagattcaacagaataatgctacaaagacatttcgagaattttgtggacctgctgatcct gaaattgcccggcatttacgccctggaactctcagagcaatctttggtaaaactaagatccagaatgctgttcactgtactgatctgccag aggatggcctattagaggttcaatacttcttctga (amino acids)

(SEQ ID NO: 41)

MEKTLALIKPDAISKAGEIIEIINKAGFTITKLKMMMLSRKEALDFHVDHQS

RPFFNELIQFITTGPIIAMEILRDDAICEWKRLLGPANSGVARTDASESIRALFGTDGIR

NAAHGPDSFASAAREMELFFPSSGGCGPANTAKFTNCTCCIVKPHAVSEGLLGKILM

AIRDAGFEISAMQMFNMDRVNVEEFYEVYKGVVTEYHDMVTEMYSGPCVAMEIQQ

NNATKTFREFCGPADPEIARHLRPGTLRAIFGKTKIQNAVHCTDLPEDGLLEVQYFF-

Human NME7-A sequence optimized for *E. coli* expression:
(DNA)

(SEQ ID NO: 42)

atggaaaaaacgctggccctgattaaaccggatgcaatctccaaagctggcgaaattatcgaaattatcaacaaagcg ggtttcaccatcacgaaactgaaaatgatgatgctgagccgtaaagaagccctggattttcatgtcgaccaccagtctcgcccgttttca atgaactgattcaattcatcaccacgggtccgattatcgcaatggaaattctgcgtgatgacgctatctgcgaatggaaacgcctgctgg

```
gcccggcaaactcaggtgttgcgcgtaccgatgccagtgaatccattcgcgctctgtttggcaccgatggtatccgtaatgcagcacat ggtccggactcattcgcatcggcagctcgtgaaatggaactgttttttctga
```

(amino acids)                                                                                          (SEQ ID NO: 43)

```
MEKTLALIKPDAISKAGEIIEIINKAGFTITKLKMMMLSRKEALDFHVDHQS

RPFFNELIQFITTGPIIAMEILRDDAICEWKRLLGPANSGVARTDASESIRALFGTDGIR

NAAHGPDSFASAAREMELFF-
```

Human NME7-A1 sequence optimized for *E. coli* expression:
(DNA)
                                                                                                       (SEQ ID NO: 44)
```
atggaaaaaacgctggccctgattaaaccggatgcaatctccaaagctggcgaaattatcgaaattatcaacaaagcg ggtttcaccatcacgaaactgaaaatgatgatgctgagccgtaaagaagccctggattttcatgtcgaccaccagtctcgcccgttttca atgaactgattcaattcatcaccacgggtccgattatcgcaatggaaattctgcgtgatgacgctatctgcgaatggaaacgcctgctgg gcccggcaaactcaggtgttgcgcgtaccgatgccagtgaatccattcgcgctctgtttggcaccgatggtatccgtaatgcagcacat ggtccggactcattcgcatcggcagctcgtgaaatggaactgttttttcccgagctctggcggttgcggtccggcaaacaccgccaaatt tacctga
```

(amino acids)                                                                                          (SEQ ID NO: 45)

```
MEKTLALIKPDAISKAGEIIEIINKAGFTITKLKMMMLSRKEALDFHVDHQS

RPFFNELIQFITTGPIIAMEILRDDAICEWKRLLGPANSGVARTDASESIRALFGTDGIR

NAAHGPDSFASAAREMELFFPSSGGCGPANTAKFT-
```

Human NME7-A2 sequence optimized for *E. coli* expression:
(DNA)
                                                                                                       (SEQ ID NO: 46)
```
atgaatcactccgaacgctttgttttatcgccgaatggtatgaccgaatgcttccctgctgcgccgctacgaactgct gttttatccgggcgatggtagcgtggaaatgcatgacgttaaaaatcaccgtacctttctgaaacgcacgaaatatgataatctgcatctg gaagacctgtttattggcaacaaagtcaatgtgttctctcgtcagctggtgctgatcgattatggcgaccagtacaccgcgcgtcaactg ggtagtcgcaaagaaaaaacgctggccctgattaaaccggatgcaatctccaaagctggcgaaattatcgaaattatcaacaaagcgg gtttcaccatcacgaaactgaaaatgatgatgctgagccgtaaagaagccctggattttcatgtcgaccaccagtctcgcccgttttcaa tgaactgattcaattcatcaccacgggtccgattatcgcaatggaaattctgcgtgatgacgctatctgcgaatggaaacgcctgctggg cccggcaaactcaggtgttgcgcgtaccgatgccagtgaatccattcgcgctctgtttggcaccgatggtatccgtaatgcagcacatg gtccggactcattcgcatcggcagctcgtgaaatggaactgttttttctga
```

(amino acids)                                                                                          (SEQ ID NO: 47)

```
MNHSERFVFIAEWYDPNASLLRRYELLFYPGDGSVEMHDVKNHRTFLKR

TKYDNLHLEDLFIGNKVNVFSRQLVLIDYGDQYTARQLGSRKEKTLALIKPDAISKA

GEIIEIINKAGFTITKLKMMMLSRKEALDFHVDHQSRPFFNELIQFITTGPIIAMEILRDD

AICEWKRLLGPANSGVARTDASESIRALFGTDGIRNAAHGPDSFASAAREMELFF-
```

Human NME7-A3 sequence optimized for *E. coli* expression:
(DNA)
                                                                                                       (SEQ ID NO: 48)
```
atgaatcactccgaacgctttgttttatcgccgaatggtatgaccgaatgcttccctgctgcgccgctacgaactgct gttttatccgggcgatggtagcgtggaaatgcatgacgttaaaaatcaccgtacctttctgaaacgcacgaaatatgataatctgcatctg gaagacctgtttattggcaacaaagtcaatgtgttctctcgtcagctggtgctgatcgattatggcgaccagtacaccgcgcgtcaactg ggtagtcgcaaagaaaaaacgctggccctgattaaaccggatgcaatctccaaagctggcgaaattatcgaaattatcaacaaagcgg gtttcaccatcacgaaactgaaaatgatgatgctgagccgtaaagaagccctggattttcatgtcgaccaccagtctcgcccgttttcaa tgaactgattcaattcatcaccacgggtccgattatcgcaatggaaattctgcgtgatgacgctatctgcgaatggaaacgcctgctggg cccggcaaactcaggtgttgcgcgtaccgatgccagtgaatccattcgcgctctgtttggcaccgatggtatccgtaatgcagcacatg
```

-continued gtccggactcattcgcatcggcagctcgtgaaatggaactgttttttcccgagctctggcggttgcggtccggcaaacaccgccaaattt acctga (amino acids)
(SEQ ID NO: 49)
MNHSERFVFIAEWYDPNASLLRRYELLFYPGDGSVEMHDVKNHRTFLKR

TKYDNLHLEDLFIGNKVNVFSRQLVLIDYGDQYTARQLGSRKEKTLALIKPDAISKA

GEIIEIINKAGFTITKLKMMMLSRKEALDFHVDHQSRPFFNELIQFITTGPIIAMEILRDD

AICEWKRLLGPANSGVARTDASESIRALFGTDGIRNAAHGPDSFASAAREMELFFPSS

GGCGPANTAKFT-

Human NME7-B sequence optimized for *E. coli* expression:
(DNA)
(SEQ ID NO: 50)
atgaattgtacgtgctgtattgtcaaaccgcacgcagtgtcagaaggcctgctgggtaaaattctgatggcaatccgtg atgctggctttgaaatctcggccatgcagatgttcaacatggaccgcgttaacgtcgaagaattctacgaagtttacaaaggcgtggtta ccgaatatcacgatatggttacggaaatgtactccggtccgtgcgtcgcgatggaaattcagcaaaacaatgccaccaaaacgtttcgt gaattctgtggtccggcagatccggaaatcgcacgtcatctgcgtccgggtaccctgcgcgcaattttttggtaaaacgaaaatccagaa cgctgtgcactgtaccgatctgccggaagacggtctgctggaagttcaatacttttttctga (amino acids)
(SEQ ID NO: 51)
MNCTCCIVKPHAVSEGLLGKILMAIRDAGFEISAMQMFNMDRVNVEEFY

EVYKGVVTEYHDMVTEMYSGPCVAMEIQQNNATKTFREFCGPADPEIARHLRPGTL

RAIFGKTKIQNAVHCTDLPEDGLLEVQYFF-

Human NME7-B1 sequence optimized for *E. coli* expression:
(DNA)
(SEQ ID NO: 52)
atgaattgtacgtgctgtattgtcaaaccgcacgcagtgtcagaaggcctgctgggtaaaattctgatggcaatccgtg atgctggctttgaaatctcggccatgcagatgttcaacatggaccgcgttaacgtcgaagaattctacgaagtttacaaaggcgtggtta ccgaatatcacgatatggttacggaaatgtactccggtccgtgcgtcgcgatggaaattcagcaaaacaatgccaccaaaacgtttcgt gaattctgtggtccggcagatccggaaatcgcacgtcatctgcgtccgggtaccctgcgcgcaattttttggtaaaacgaaaatccagaa cgctgtgcactgtaccgatctgccggaagacggtctgctggaagttcaatacttttttcaaaattctggataattga (amino acids)
(SEQ ID NO: 53)
MNCTCCIVKPHAVSEGLLGKILMAIRDAGFEISAMQMFNMDRVNVEEFY

EVYKGVVTEYHDMVTEMYSGPCVAMEIQQNNATKTFREFCGPADPEIARHLRPGTL

RAIFGKTKIQNAVHCTDLPEDGLLEVQYFFKILDN-

Human NME7-B2 sequence optimized for *E. coli* expression:
(DNA)
(SEQ ID NO: 54)
atgccgagctctggcggttgcggtccggcaaacaccgccaaatttaccaattgtacgtgctgtattgtcaaaccgcac gcagtgtcagaaggcctgctgggtaaaattctgatggcaatccgtgatgctggctttgaaatctcggccatgcagatgttcaacatggac cgcgttaacgtcgaagaattctacgaagtttacaaaggcgtggttaccgaatatcacgatatggttacggaaatgtactccggtccgtgc gtcgcgatggaaattcagcaaaacaatgccaccaaaacgtttcgtgaattctgtggtccggcagatccggaaatcgcacgtcatctgcg tccgggtaccctgcgcgcaattttttggtaaaacgaaaatccagaacgctgtgcactgtaccgatctgccggaagacggtctgctggaa gttcaatacttttttctga (amino acids)
(SEQ ID NO: 55)
MPSSGGCGPANTAKFTNCTCCIVKPHAVSEGLLGKILMAIRDAGFEISAM

QMFNMDRVNVEEFYEVYKGVVTEYHDMVTEMYSGPCVAMEIQQNNATKTFREFC

GPADPEIARHLRPGTLRAIFGKTKIQNAVHCTDLPEDGLLEVQYFF-

Human NME7-B3 sequence optimized for *E. coli* expression:
(DNA)

(SEQ ID NO: 56)

atgccgagctctggcggttgcggtccggcaaacaccgccaaatttaccaattgtacgtgctgtattgtcaaaccgcac gcagtgtcagaaggcctgctgggtaaaattctgatggcaatccgtgatgctggctttgaaatctcggccatgcagatgttcaacatggac cgcgttaacgtcgaagaattctacgaagtttacaaaggcgtggttaccgaatatcacgatatggttacggaaatgtactccggtccgtgc gtcgcgatggaaattcagcaaaacaatgccaccaaaacgtttcgtgaattctgtggtccggcagatccggaaatcgcacgtcatctgcg tccgggtaccctgcgcgcaattttggtaaaacgaaaatccagaacgctgtgcactgtaccgatctgccggaagacggtctgctggaa gttcaatacttttcaaaattctggataattga (amino acids)

(SEQ ID NO: 57)

MPSSGGCGPANTAKFTNCTCCIVKPHAVSEGLLGKILMAIRDAGFEISAM

QMFNMDRVNVEEFYEVYKGVVTEYHDMVTEMYSGPCVAMEIQQNNATKTFREFC

GPADPEIARHLRPGTLRAIFGKTKIQNAVHCTDLPEDGLLEVQYFFKILDN-

Human NME7-AB, also known as NME7$_{AB}$ sequence optimized for *E. coli* expression:
(DNA)

(SEQ ID NO: 58)

atggaaaaaacgctggccctgattaaaccggatgcaatctccaaagctggcgaaattatcgaaattatcaacaaagcg gtttcaccatcacgaaactgaaaatgatgatgctgagccgtaaagaagccctggattttcatgtcgaccaccagtctcgcccgttttca atgaactgattcaattcatcaccacgggtccgattatcgcaatggaaattctgcgtgatgacgctatctgcgaatggaaacgctgctgg gcccggcaaactcaggtgttgcgcgtaccgatgccagtgaatccattcgcgctctgtttggcaccgatggtatccgtaatgcagcacat ggtccggactcattcgcatcggcagctcgtgaaatggaactgttttttccgagctctggcggttgcggtccggcaaacaccgccaaatt taccaattgtacgtgctgtattgtcaaaccgcacgcagtgtcagaaggcctgctgggtaaaattctgatggcaatccgtgatgctggcttt gaaatctcggccatgcagatgttcaacatggaccgcgttaacgtcgaagaattctacgaagtttacaaaggcgtggttaccgaatatca cgatatggttacggaaatgtactccggtccgtgcgtcgcgatggaaattcagcaaaacaatgccaccaaaacgtttcgtgaattctgtgg tccggcagatccggaaatcgcacgtcatctgcgtccgggtaccctgcgcgcaattttggtaaaacgaaaatccagaacgctgtgcact gtaccgatctgccggaagacggtctgctggaagttcaatacttttcaaaattctggataattga (amino acids)

(SEQ ID NO: 59)

MEKTLALIKPDAISKAGEIIEIINKAGFTITKLKMMMLSRKEALDFHVDHQS

RPFFNELIQFITTGPIIAMEILRDDAICEWKRLLGPANSGVARTDASESIRALFGTDGIR

NAAHGPDSFASAAREMELFFPSSGGCGPANTAKFTNCTCCIVKPHAVSEGLLGKILM

AIRDAGFEISAMQMFNMDRVNVEEFYEVYKGVVTEYHDMVTEMYSGPCVAMEIQQ

NNATKTFREFCGPADPEIARHLRPGTLRAIFGKTKIQNAVHCTDLPEDGLLEVQYFFK

ILDN-

Human NME7-AB1, also known as NME7$_{AB}$1 sequence optimized for *E. coli* expression:
(DNA)

(SEQ ID NO: 60)

Atggaaaaaacgctggccctgattaaaccggatgcaatctccaaagctggcgaaattatcgaaattatcaacaaagc gggtttcaccatcacgaaactgaaaatgatgatgctgagccgtaaagaagccctggattttcatgtcgaccaccagtctcgcccgttttc aatgaactgattcaattcatcaccacgggtccgattatcgcaatggaaattctgcgtgatgacgctatctgcgaatggaaacgctgctg ggcccggcaaactcaggtgttgcgcgtaccgatgccagtgaatccattcgcgctctgtttggcaccgatggtatccgtaatgcagcaca tggtccggactcattcgcatcggcagctcgtgaaatggaactgttttttccgagctctggcggttgcggtccggcaaacaccgccaaat taccaattgtacgtgctgtattgtcaaaccgcacgcagtgtcagaaggcctgctgggtaaaattctgatggcaatccgtgatgctggctt tgaaatctcggccatgcagatgttcaacatggaccgcgttaacgtcgaagaattctacgaagtttacaaaggcgtggttaccgaatatca cgatatggttacggaaatgtactccggtccgtgcgtcgcgatggaaattcagcaaaacaatgccaccaaaacgtttcgtgaattctgtgg -continued tccggcagatccggaaatcgcacgtcatctgcgtccgggtaccctgcgcgcaatttttggtaaaacgaaaatccagaacgctgtgcact gtaccgatctgccggaagacggtctgctggaagttcaatacttttctga (amino acids)

(SEQ ID NO: 61)

MEKTLALIKPDAISKAGEIIEIINKAGFTITKLKMMMLSRKEALDFHVDHQS

RPFFNELIQFITTGPIIAMEILRDDAICEWKRLLGPANSGVARTDASESIRALFGTDGIR

NAAHGPDSFASAAREMELFFPSSGGCGPANTAKFTNCTCCIVKPHAVSEGLLGKILM

AIRDAGFEISAMQMFNMDRVNVEEFYEVYKGVVTEYHDMVTEMYSGPCVAMEIQQ

NNATKTFREFCGPADPEIARHLRPGTLRAIFGKTKIQNAVHCTDLPEDGLLEVQYFF-

Mouse NME6
(DNA)

(SEQ ID NO: 62)

Atgacctccatcttgcgaagtccccaagctcttcagctcacactagccctgatcaagcctgatgcagttgcccaccca ctgatcctggaggctgttcatcagcagattctgagcaacaagttcctcattgtacgaacagggaactgcagtggaagctggaggact gccggaggttttaccgagagcatgaagggcgttttttctatcagcggctggtggagttcatgacaagtgggccaatccgagcctatatc cttgcccacaaagatgccatccaactttggaggacactgatgggacccaccagagtatttcgagcacgctatatagcccagattcaat tcgtggaagtttgggcctcactgacacccgaaatactacccatggctcagactccgtggtttccgccagcagagagattgcagcttctt ccctgacttcagtgaacagcgctggtatgaggaggaggaaccccagctgcggtgtggtcctgtgcactacagtccagaggaaggtat ccactgtgcagctgaaacaggaggccacaaacaacctaacaaaacctag (amino acids)

(SEQ ID NO: 63)

MTSILRSPQALQLTLALIKPDAVAHPLILEAVHQQILSNKFLIVRTRELQWK

LEDCRRFYREHEGRFFYQRLVEFMTSGPIRAYILAHKDAIQLWRTLMGPTRVFRARY

IAPDSIRGSLGLTDTRNTTHGSDSVVSASREIAAFFPDFSEQRWYEEEEPQLRCGPVHY

SPEEGIHCAAETGGHKQPNKT-

Human NME6:
(DNA)

(SEQ ID NO: 64)

Atgacccagaatctggggagtgagatggcctcaatcttgcgaagccctcaggctctccagctcactctagccctgat caagcctgacgcagtcgcccatccactgattctggaggctgttcatcagcagattctaagcaacaagttcctgattgtacgaatgagag aactactgtggagaaaggaagattgccagaggttttaccgagagcatgaagggcgttttttctatcagaggctggtggagttcatggcc agcgggccaatccgagcctacatccttgcccacaaggatgccatccagctctggaggacgctcatgggacccaccagagtgttccga gcacgccatgtggccccagattctatccgtgggagtttcggcctcactgacacccgcaacaccacccatggttcggactctgtggtttc agccagcagagagattgcagcttcttccctgacttcagtgaacagcgctggtatgaggaggaagagccccagttgcgctgtggccct gtgtgctatagcccagagggaggtgtccactatgtagctggaacaggaggcctaggaccagcctga (amino acids)

(SEQ ID NO: 65)

MTQNLGSEMASILRSPQALQLTLALIKPDAVAHPLILEAVHQQILSNKFLIV

RMRELLWRKEDCQRFYREHEGRFFYQRLVEFMASGPIRAYILAHKDAIQLWRTLMG

PTRVFRARHVAPDSIRGSFGLTDTRNTTHGSDSVVSASREIAAFFPDFSEQRWYEEEE

PQLRCGPVCYSPEGGVHYVAGTGGLGPA-

Human NME6 1:
(DNA)

(SEQ ID NO: 66)

Atgacccagaatctggggagtgagatggcctcaatcttgcgaagccctcaggctctccagctcactctagccctgat caagcctgacgcagtcgcccatccactgattctggaggctgttcatcagcagattctaagcaacaagttcctgattgtacgaatgagag aactactgtggagaaaggaagattgccagaggttttaccgagagcatgaagggcgttttttctatcagaggctggtggagttcatggcc agcgggccaatccgagcctacatccttgcccacaaggatgccatccagctctggaggacgctcatgggacccaccagagtgttccga -continued gcacgccatgtggcccagattctatccgtgggagtttcggcctcactgacacccgcaacaccacccatggttcggactctgtggtttc agccagcagagagattgcagccttcttccctgacttcagtgaacagcgctggtatgaggaggaagagccccagttgcgctgtggccct gtgtga (amino acids) (SEQ ID NO: 67)

MTQNLGSEMASILRSPQALQLTLALIKPDAVAHPLILEAVHQQILSNKFLIV

RMRELLWRKEDCQRFYREHEGRFFYQRLVEFMASGPIRAYILAHKDAIQLWRTLMG

PTRVFRARHVAPDSIRGSFGLTDTRNTTHGSDSVVSASREIAAFFPDFSEQRWYEEEE

PQLRCGPV-

Human NME6 2:
(DNA) (SEQ ID NO: 68)

Atgctcactctagccctgatcaagcctgacgcagtcgcccatccactgattctggaggctgttcatcagcagattctaa gcaacaagttcctgattgtacgaatgagagaactactgtggagaaaggaagattgccagaggttttaccgagagcatgaagggcgtttt ttctatcagaggctggtggagttcatggccagcgggccaatccgagcctacatccttgcccacaaggatgccatccagctctggagga cgctcatgggacccaccagagtgttccgagcacgccatgtggccccagattctatccgtgggagtttcggcctcactgacacccgcaa caccacccatggttcggactctgtggtttcagccagcagagagattgcagccttcttccctgacttcagtgaacagcgctggtatgagg aggaagagccccagttgcgctgtggccctgtgtga (amino acids) (SEQ ID NO: 69)

MLTLALIKPDAVAHPLILEAVHQQILSNKFLIVRMRELLWRKEDCQRFYRE

HEGRFFYQRLVEFMASGPIRAYILAHKDAIQLWRTLMGPTRVFRARHVAPDSIRGSF

GLTDTRNTTHGSDSVVSASREIAAFFPDFSEQRWYEEEEPQLRCGPV-

Human NME6 3:
(DNA) (SEQ ID NO: 70)

Atgctcactctagccctgatcaagcctgacgcagtcgcccatccactgattctggaggctgttcatcagcagattctaa gcaacaagttcctgattgtacgaatgagagaactactgtggagaaaggaagattgccagaggttttaccgagagcatgaagggcgtttt ttctatcagaggctggtggagttcatggccagcgggccaatccgagcctacatccttgcccacaaggatgccatccagctctggagga cgctcatgggacccaccagagtgttccgagcacgccatgtggccccagattctatccgtgggagtttcggcctcactgacacccgcaa caccacccatggttcggactctgtggtttcagccagcagagagattgcagccttcttccctgacttcagtgaacagcgctggtatgagg aggaagagccccagttgcgctgtggccctgtgtgctatagcccagagggaggtgtccactatgtagctggaacaggaggcctagga ccagcctga (amino acids) (SEQ ID NO: 71)

MLTLALIKPDAVAHPLILEAVHQQILSNKFLIVRMRELLWRKEDCQRFYRE

HEGRFFYQRLVEFMASGPIRAYILAHKDAIQLWRTLMGPTRVFRARHVAPDSIRGSF

GLTDTRNTTHGSDSVVSASREIAAFFPDFSEQRWYEEEEPQLRCGPVCYSPEGGVHY

VAGTGGLGPA-

Human NME6 sequence optimized for *E. coli* expression:
(DNA) (SEQ ID NO: 72)

Atgacgcaaaatctgggctcggaaatggcaagtatcctgcgctccccgcaagcactgcaactgaccctggctctgat caaaccggacgctgttgctcatccgctgattctggaagcggtccaccagcaaattctgagcaacaaatttctgatcgtgcgtatgcgcg aactgctgtggcgtaaagaagattgccagcgtttttatcgcgaacatgaaggccgtttctttttatcaacgcctggttgaattcatggcctct ggtccgattcgcgcatatatcctggctcacaaagatgcgattcagctgtggcgtaccctgatgggtccgacgcgcgtctttcgtgcacgt catgtggcaccggactcaatccgtggctcgttcggtctgaccgatacgcgcaataccacgcacggtagcgactctgttgttagtgcgtc -continued ccgtgaaatcgcggccttttcccggacttctccgaacagcgttggtacgaagaagaagaaccgcaactgcgctgtggcccggtctgtt attctccggaaggtggtgtccattatgtggcgggcacgggtggtctgggtccggcatga (amino acids)

(SEQ ID NO: 73)

MTQNLGSEMASILRSPQALQLTLALIKPDAVAHPLILEAVHQQILSNKFLIV

RMRELLWRKEDCQRFYREHEGRFFYQRLVEFMASGPIRAYILAHKDAIQLWRTLMG

PTRVFRARHVAPDSIRGSFGLTDTRNTTHGSDSVVSASREIAAFFPDFSEQRWYEEEE

PQLRCGPVCYSPEGGVHYVAGTGGLGPA-

Human NME6 1 sequence optimized for *E. coli* expression:
(DNA)

(SEQ ID NO: 74)

Atgacgcaaaatctgggctcggaaatggcaagtatcctgcgctccccgcaagcactgcaactgaccctggctctgat caaaccggacgctgttgctcatccgctgattctggaagcggtccaccagcaaattctgagcaacaaatttctgatcgtgcgtatgcgcg aactgctgtggcgtaaagaagattgccagcgttttttatcgcgaacatgaaggccgtttcttttatcaacgcctggttgaattcatggcctct ggtccgattcgcgcatatatcctggctcacaaagatgcgattcagctgtggcgtaccctgatgggtccgacgcgcgtctttcgtgcacgt catgtggcaccggactcaatccgtggctcgttcggtctgaccgatacgcgcaataccacgcacggtagcgactctgttgttagtgcgtc ccgtgaaatcgcggccttttcccggacttctccgaacagcgttggtacgaagaagaagaaccgcaactgcgctgtggcccggtctga (amino acids)

(SEQ ID NO: 75)

MTQNLGSEMASILRSPQALQLTLALIKPDAVAHPLILEAVHQQILSNKFLIV

RMRELLWRKEDCQRFYREHEGRFFYQRLVEFMASGPIRAYILAHKDAIQLWRTLMG

PTRVFRARHVAPDSIRGSFGLTDTRNTTHGSDSVVSASREIAAFFPDFSEQRWYEEEE

PQLRCGPV-

Human NME6 2 sequence optimized for *E. coli* expression:
(DNA)

(SEQ ID NO: 76)

Atgctgaccctggctctgatcaaaccggacgctgttgctcatccgctgattctggaagcggtccaccagcaaattctg agcaacaaatttctgatcgtgcgtatgcgcgaactgctgtggcgtaaagaagattgccagcgttttttatcgcgaacatgaaggccgtttct tttatcaacgcctggttgaattcatggcctctggtccgattcgcgcatatatcctggctcacaaagatgcgattcagctgtggcgtaccctg atgggtccgacgcgcgtctttcgtgcacgtcatgtggcaccggactcaatccgtggctcgttcggtctgaccgatacgcgcaataccac gcacggtagcgactctgttgttagtgcgtcccgtgaaatcgcggccttttcccggacttctccgaacagcgttggtacgaagaagaag aaccgcaactgcgctgtggcccggtctga (amino acids)

(SEQ ID NO: 77)

MLTLALIKPDAVAHPLILEAVHQQILSNKFLIVRMRELLWRKEDCQRFYRE

HEGRFFYQRLVEFMASGPIRAYILAHKDAIQLWRTLMGPTRVFRARHVAPDSIRGSF

GLTDTRNTTHGSDSVVSASREIAAFFPDFSEQRWYEEEEPQLRCGPV-

Human NME6 3 sequence optimized for *E. coli* expression:
(DNA)

(SEQ ID NO: 78)

Atgctgaccctggctctgatcaaaccggacgctgttgctcatccgctgattctggaagcggtccaccagcaaattctg agcaacaaatttctgatcgtgcgtatgcgcgaactgctgtggcgtaaagaagattgccagcgttttttatcgcgaacatgaaggccgtttct tttatcaacgcctggttgaattcatggcctctggtccgattcgcgcatatatcctggctcacaaagatgcgattcagctgtggcgtaccctg atgggtccgacgcgcgtctttcgtgcacgtcatgtggcaccggactcaatccgtggctcgttcggtctgaccgatacgcgcaataccac gcacggtagcgactctgttgttagtgcgtcccgtgaaatcgcggccttttcccggacttctccgaacagcgttggtacgaagaagaag aaccgcaactgcgctgtggcccggtctgttattctccggaaggtggtgtccattatgtggcgggcacgggtggtctgggtccggcatga (amino acids)

(SEQ ID NO: 79)

MLTLALIKPDAVAHPLILEAVHQQILSNKFLIVRMRELLWRKEDCQRFYRE

HEGRFFYQRLVEFMASGPIRAYILAHKDAIQLWRTLMGPTRVFRARHVAPDSIRGSF

GLTDTRNTTHGSDSVVSASREIAAFFPDFSEQRWYEEEEPQLRCGPVCYSPEGGVHY

VAGTGGLGPA-

OriGene-NME7-1 full length
(DNA)

(SEQ ID NO: 80)

gacgttgtatacgactcctatagggcggccgggaattcgtcgactggatccggtaccgaggagatctgccgccgcg atcgccatgaatcatagtgaaagattcgttttcattgcagagtggtatgatccaaatgcttcacttcttcgacgttatgagcttttattttaccc aggggatggatctgttgaaatgcatgatgtaaagaatcatcgcacctttttaaagcggaccaaatatgataacctgcacttggaagattta tttataggcaacaaagtgaatgtcttctctcgacaactggtattaattgactatggggatcaatatacagctcgccagctgggcagtagga agaaaaaacgctagccctaattaaaccagatgcaatatcaaaggctggagaaataattgaaataataaacaaagctggatttactataa ccaaactcaaaatgatgatgctttcaaggaaagaagcattggattttcatgtagatcaccagtcaagaccctttttcaatgagctgatcca gtttattacaactggtcctattattgccatggagattttaagagatgatgctatatgtgaatggaaaagactgctgggacctgcaaactctg gagtggcacgcacagatgcttctgaaagcattagagccctctttggaacagatggcataagaaatgcagcgcatggccctgattctttt gcttctgcggccagagaaatggagttgttttttccttcaagtggaggttgtgggccggcaaacactgctaaatttactaattgtacctgttg cattgttaaaccccatgctgtcagtgaaggactgttgggaaagatcctgatggctatccgagatgcaggttttgaaatctcagctatgcag atgttcaatatggatcgggttaatgttgaggaattctatgaagtttataaggagtagtgaccgaatatcatgacatggtgacagaaatgta ttctggcccttgtgtagcaatggagattcaacagaataatgctacaaagacatttcgagaattttgtggacctgctgatcctgaaattgccc ggcatttacgccctggaactctcagagcaatctttggtaaaactaagatccagaatgctgttcactgtactgatctgccagaggatggcct attagaggttcaatacttcttcaagatcttggataatacgcgtacgcggccgctcgagcagaaactcatctcagaagaggatctggcag caaatgatatcctggattacaaggatgacgacgataaggtttaa (amino acids)

(SEQ ID NO: 81)

MNHSERFVFIAEWYDPNASLLRRYELLFYPGDGSVEMHDVKNHRTFLKR

TKYDNLHLEDLFIGNKVNVFSRQLVLIDYGDQYTARQLGSRKEKTLALIKPDAISKA

GEIIEIINKAGFTITKLKMMMLSRKEALDFHVDHQSRPFFNELIQFITTGPIIAMEILRDD

AICEWKRLLGPANSGVARTDASESIRALFGTDGIRNAAHGPDSFASAAREMELFFPSS

GGCGPANTAKFTNCTCCIVKPHAVSEGLLGKILMAIRDAGFEISAMQMFNMDRVNV

EEFYEVYKGVVTEYHDMVTEMYSGPCVAMEIQQNNATKTFREFCGPADPEIARHLR

PGTLRAIFGKTKIQNAVHCTDLPEDGLLEVQYFFKILDNTRTRRLEQKLISEEDLAAN

DILDYKDDDDKV

Abnova NME7-1 Full length
(amino acids)

(SEQ ID NO: 82)

MNHSERFVFIAEWYDPNASLLRRYELLFYPGDGSVEMHDVKNHRTFLKR

TKYDNLHLEDLFIGNKVNVFSRQLVLIDYGDQYTARQLGSRKEKTLALIKPDAISKA

GEIIEIINKAGFTITKLKMMMLSRKEALDFHVDHQSRPFFNELIQFITTGPIIAMEILRDD

AICEWKRLLGPANSGVARTDASESIRALFGTDGIRNAAHGPDSFASAAREMELFFPSS

GGCGPANTAKFTNCTCCIVKPHAVSEGLLGKILMAIRDAGFEISAMQMFNMDRVNV

EEFYEVYKGVVTEYHDMVTEMYSGPCVAMEIQQNNATKTFREFCGPADPEIARHLR

PGTLRAIFGKTKIQNAVHCTDLPEDGLLEVQYFFKILDN

```
Abnova Partial NME7-B
(amino acids)
                                                          (SEQ ID NO: 83)
DRVNVEEFYEVYKGVVTEYHDMVTEMYSGPCVAMEIQQNNATKTFREF

CGPADPEIARHLRPGTLRAIFGKTKIQNAVHCTDLPEDGLLEVQYFFKIL

Histidine Tag
                                                          (SEQ ID NO: 84)
(ctcgag)caccaccaccaccaccactga Strept II Tag
                                                          (SEQ ID NO: 85)
(accggt)tggagccatcctcagttcgaaaagtaatga N-10 peptide:
                                                          (SEQ ID NO: 86)
QFNQYKTEAASRYNLTISDVSVSDVPFPFSAQSGA C-10 peptide
                                                          (SEQ ID NO: 87)
GTINVHDVETQFNQYKTEAASRYNLTISDVSVSDV (SEQ ID NO: 88)
LALIKPDA (SEQ ID NO: 89)
MMMLSRKEALDFHVDHQS (SEQ ID NO: 90)
ALDFHVDHQS (SEQ ID NO: 91)
EILRDDAICEWKRL (SEQ ID NO: 92)
FNELIQFITTGP (SEQ ID NO: 93)
RDDAICEW (SEQ ID NO: 94)
SGVARTDASESIRALFGTDGIRNAA (SEQ ID NO: 95)
ELFFPSSGG (SEQ ID NO: 96)
KFTNCTCCIVKPHAVSEGLLGKILMA (SEQ ID NO: 97)
LMAIRDAGFEISAMQMFNMDRVNVEEFYEVYKGVVT (SEQ ID NO: 98)
EFYEVYKGVVTEYHD (SEQ ID NO: 99)
EIQQNNATKTFREFCGPADPEIARHLRPGTLRAIFGKTKIQNA (SEQ ID NO: 100)
YSGPCVAM (SEQ ID NO: 101)
FREFCGP (SEQ ID NO: 102)
VHCTDLPEDGLLEVQYFFKILDN (SEQ ID NO: 103)
IQNAVHCTD (SEQ ID NO: 104)
TDLPEDGLLEVQYFFKILDN (SEQ ID NO: 105)
PEDGLLEVQYFFK (SEQ ID NO: 106)
EIINKAGFTITK
```

```
MLSRKEALDFHVDHQS                                        (SEQ ID NO: 107)

NELIQFITT                                               (SEQ ID NO: 108)

EILRDDAICEWKRL                                          (SEQ ID NO: 109)

SGVARTDASESIRALFGTDGI                                   (SEQ ID NO: 110)

SGVARTDASES                                             (SEQ ID NO: 111)

ALFGTDGI                                                (SEQ ID NO: 112)

NCTCCIVKPHAVSE                                          (SEQ ID NO: 113)

LGKILMAIRDA                                             (SEQ ID NO: 114)

EISAMQMFNMDRVNVE                                        (SEQ ID NO: 115)

EVYKGVVT                                                (SEQ ID NO: 116)

EYHDMVTE                                                (SEQ ID NO: 117)

EFCGPADPEIARHLR                                         (SEQ ID NO: 118)

AIFGKTKIQNAV                                            (SEQ ID NO: 119)

LPEDGLLEVQYFFKILDN                                      (SEQ ID NO: 120)

GPDSFASAAREMELFFP                                       (SEQ ID NO: 121)
```

Immunizing peptides derived from human NME7

```
ICEWKRL                                                 (SEQ ID NO: 122)

LGKILMAIRDA                                             (SEQ ID NO: 123)

HAVSEGLLGK                                              (SEQ ID NO: 124)

VTEMYSGP                                                (SEQ ID NO: 125)

NATKTFREF                                               (SEQ ID NO: 126)

AIRDAGFEI                                               (SEQ ID NO: 127)

AICEWKRLLGPAN                                           (SEQ ID NO: 128)

DHQSRPFF                                                (SEQ ID NO: 129)

AICEWKRLLGPAN                                           (SEQ ID NO: 130)

VDHQSRPF                                                (SEQ ID NO: 131)
```

```
                                                        (SEQ ID NO: 132)
PDSFAS
                                                        (SEQ ID NO: 133)
KAGEIIEIINKAGFTITK

Immunizing peptides derived from human NME1
                                                        (SEQ ID NO: 134)
MANCERTFIAIKPDGVQRGLVGEIIKRFE (SEQ ID NO: 135)
VDLKDRPF (SEQ ID NO: 136)
HGSDSVESAEKEIGLWF (SEQ ID NO: 137)
ERTFIAIKPDGVQRGLVGEIIKRFE (SEQ ID NO: 138)
VDLKDRPFFAGLVKYMHSGPVVAMVWEGLN (SEQ ID NO: 139)
NIIHGSDSVESAEKEIGLWFHPEELV (SEQ ID NO: 140)
KPDGVQRGLVGEII Immunizing peptide derived from human NME7, but which does not bind NME1
                                                        (SEQ ID NO: 141)
MLSRKEALDFHVDHQS
peptide A1

(SEQ ID NO: 142)
SGVARTDASES
peptide A2

(SEQ ID NO: 143)
DAGFEISAMQMFNMDRVNVE
peptide B1

(SEQ ID NO: 144)
EVYKGVVTEYHDMVTE
peptide B2

(SEQ ID NO: 145)
AIFGKTKIQNAVHCTDLPEDGLLEVQYFF
peptide B3

Human NME7 a
(DNA)
                                                        (SEQ ID NO: 146)
atgaatcatagtgaaagattcgttttcattgcagagtggtatgatccaaatgcttcacttcttcgacgttatgagcttttatttt acccaggggatggatctgttgaaatgcatgatgtaaagaatcatcgcacctttttaaagcggaccaaatatgataacctgcacttggaag atttatttataggcaacaaagtgaatgtcttttctcgacaactggtattaattgactatggggatcaatatacagctcgccagctgggcagta ggaaagaaaaaacgctagccctaattaaaccagatgcaatatcaaaggctggagaaataattgaaataataaacaaagctggatttact ataaccaaactcaaaatgatgatgctttcaaggaaagaagcattggattttcatgtagatcaccagtcaagaccctttttcaatgagctgat ccagtttattacaactggtcctattattgccatgagattttaagagatgatgctatatgtgaatggaaaagactgctgggacctgcaaact ctggagtggcacgcacagatgcttctgaaagcattagagccctctttggaacagatggcataagaaatgcagcgcatggccctgattct tttgcttctgcggccagagaaatggagttgttttttccttcaagtggaggttgtgggccggcaaacactgctaaatttactaattgtacctgtt gcattgttaaacccccatgctgtcagtgaaggactgttgggaaagatcctgatggctatccgagatgcaggttttgaaatctcagctatgca gatgttcaatatggatcgggttaatgttgaggaattctatgaagtttataaaggagtagtgaccgaatatcatgacatggtgacagaaatgt attctggcccttgtgtagcaatggagattcaacagaataatgctacaaagacatttcgagaattttgtggacctgctgatcctgaaattgcc cggcatttacgccctggaactctcagagcaatctttggtaaaactaagatccagaatgctgttcactgtactgatctgccagaggatggc ctattagaggttcaatacttcttcaagatcttggataattag
```

(amino acids)

(SEQ ID NO: 147)

MNHSERFVFIAEWYDPNASLLRRYELLFYPGDGSVEMHDVKNHRTFLKR

TKYDNLHLEDLFIGNKVNVFSRQLVLIDYGDQYTARQLGSRKEKTLALIKPDAISKA

GEIIEIINKAGFTITKLKMMMLSRKEALDFHVDHQSRPFFNELIQFITTGPIIAMEILRDD

AICEWKRLLGPANSGVARTDASESIRALFGTDGIRNAAHGPDSFASAAREMELFFPSS

GGCGPANTAKFTNCTCCIVKPHAVSEGLLGKILMAIRDAGFEISAMQMFNMDRVNV

EEFYEVYKGVVTEYHDMVTEMYSGPCVAMEIQQNNATKTFREFCGPADPEIARHLR

PGTLRAIFGKTKIQNAVHCTDLPEDGLLEVQYFFKILDN

Human NME7 b
(DNA)

(SEQ ID NO: 148)

atgcatgatgtaaagaatcatcgcacctttttaaagcggaccaaatatgataacctgcacttggaagatttatttataggc aacaaagtgaatgtcttttctcgacaactggtattaattgactatggggatcaatatacagctcgccagctgggcagtaggaaagaaaaa acgctagccctaattaaaccagatgcaatatcaaaggctggagaaataattgaaataataaacaaagctggatttactataaccaaactc aaaatgatgatgctttcaaggaagaagcattggattttcatgtagatcaccagtcaagaccctttttcaatgagctgatccagtttattaca actggtcctattattgccatggagattttaagagatgatgctatatgtgaatggaaaagactgctgggacctgcaaactctggagtggca cgcacagatgcttctgaaagcattagagccctctttggaacagatggcataagaaatgcagcgcatggccctgattcttttgcttctgcg gccagagaaatggagttgttttttccttcaagtggaggttgtgggccggcaaacactgctaaatttactaattgtacctgttgcattgttaaa ccccatgctgtcagtgaaggactgttgggaaagatcctgatggctatccgagatgcaggttttgaaatctcagctatgcagatgttcaata tggatcgggttaatgttgaggaattctatgaagtttataaaggagtagtgaccgaatatcatgacatggtgacagaaatgtattctggccct tgtgtagcaatggagattcaacagaataatgctacaaagacatttcgagaattttgtggacctgctgatcctgaaattgcccggcatttac gccctggaactctcagagcaatctttggtaaaactaagatccagaatgctgttcactgtactgatctgccagaggatggcctattagagg ttcaatacttcttcaagatcttggataattag (amino acids)

(SEQ ID NO: 149)

MHDVKNHRTFLKRTKYDNLHLEDLFIGNKVNVFSRQLVLIDYGDQYTAR

QLGSRKEKTLALIKPDAISKAGEIIEIINKAGFTITKLKMMMLSRKEALDFHVDHQSRP

FFNELIQFITTGPIIAMEILRDDAICEWKRLLGPANSGVARTDASESIRALFGTDGIRNA

AHGPDSFASAAREMELFFPSSGGCGPANTAKFTNCTCCIVKPHAVSEGLLGKILMAIR

DAGFEISAMQMFNMDRVNVEEFYEVYKGVVTEYHDMVTEMYSGPCVAMEIQQNN

ATKTFREFCGPADPEIARHLRPGTLRAIFGKTKIQNAVHCTDLPEDGLLEVQYFFKILDN

Human NME7-AB also known as NME7$_{AB}$
(DNA)

(SEQ ID NO: 150)

atggaaaaaacgctagccctaattaaaccagatgcaatatcaaaggctggagaaataattgaaataataaacaaagct ggatttactataaccaaactcaaaatgatgatgctttcaaggaagaagcattggattttcatgtagatcaccagtcaagaccctttttcaat gagctgatccagtttattacaactggtcctattattgccatggagattttaagagatgatgctatatgtgaatggaaaagactgctgggacc tgcaaactctggagtggcacgcacagatgcttctgaaagcattagagccctctttggaacagatggcataagaaatgcagcgcatggc cctgattcttttgcttctgcggccagagaaatggagttgttttttccttcaagtggaggttgtgggccggcaaacactgctaaatttactaatt gtacctgttgcattgttaaaccccatgctgtcagtgaaggactgttgggaaagatcctgatggctatccgagatgcaggttttgaaatctc agctatgcagatgttcaatatggatcgggttaatgttgaggaattctatgaagtttataaaggagtagtgaccgaatatcatgacatggtga cagaaatgtattctggcccttgtgtagcaatggagattcaacagaataatgctacaaagacatttcgagaattttgtggacctgctgatcct gaaattgcccggcatttacgccctggaactctcagagcaatctttggtaaaactaagatccagaatgctgttcactgtactgatctgccag aggatggcctattagaggttcaatacttcttcaagatcttggataattag (amino acids)

(SEQ ID NO: 151)

MEKTLALIKPDAISKAGEIIEIINKAGFTITKLKMMMLSRKEALDFHVDHQS

RPFFNELIQFITTGPIIAMEILRDDAICEWKRLLGPANSGVARTDASESIRALFGTDGIR

NAAHGPDSFASAAREMELFFPSSGGCGPANTAKFTNCTCCIVKPHAVSEGLLGKILM

AIRDAGFEISAMQMFNMDRVNVEEFYEVYKGVVTEYHDMVTEMYSGPCVAMEIQQ

NNATKTFREFCGPADPEIARHLRPGTLRAIFGKTKIQNAVHCTDLPEDGLLEVQYFFK

ILDN

Human NME7-X1
(DNA)

(SEQ ID NO: 152)

atgatgatgctttcaaggaaagaagcattggattttcatgtagatcaccagtcaagacccttttcaatgagctgatccag tttattacaactggtcctattattgccatggagattttaagagatgatgctatatgtgaatggaaaagactgctgggacctgcaaactctgg agtggcacgcacagatgcttctgaaagcattagagccctctttggaacagatggcataagaaatgcagcgcatggccctgattcttttgc ttctgcggccagagaaatggagttgttttttccttcaagtggaggttgtgggccggcaaacactgctaaatttactaattgtacctgttgcat tgttaaacccatgctgtcagtgaaggactgttgggaaagatcctgatggctatccgagatgcaggttttgaaatctcagctatgcagat gttcaatatggatcgggttaatgttgaggaattctatgaagtttataaaggagtagtgaccgaatatcatgacatggtgacagaaatgtatt ctggcccttgtgtagcaatggagattcaacagaataatgctacaaagacatttcgagaattttgtggacctgctgatcctgaaattgcccg gcatttacgccctggaactctcagagcaatctttggtaaaactaagatccagaatgctgttcactgtactgatctgccagaggatggccta ttagaggttcaatacttcttcaagatcttggataattag (amino acids)

(SEQ ID NO: 153)

MMMLSRKEALDFHVDHQSRPFFNELIQFITTGPIIAMEILRDDAICEWKRL

LGPANSGVARTDASESIRALFGTDGIRNAAHGPDSFASAAREMELFFPSSGGCGPANT

AKFTNCTCCIVKPHAVSEGLLGKILMAIRDAGFEISAMQMFNMDRVNVEEFYEVYK

GVVTEYHDMVTEMYSGPCVAMEIQQNNATKTFREFCGPADPEIARHLRPGTLRAIFG

KTKIQNAVHCTDLPEDGLLEVQYFFKILDN*

Human NME7 a (optimized for *E coli* expression)
(DNA)

(SEQ ID NO: 154)

atgaatcactccgaacgctttgttttatcgccgaatggtatgacccgaatgcttccctgctgcgccgctacgaactgct gttttatccgggcgatggtagcgtggaaatgcatgacgttaaaaatcaccgtacctttctgaaacgcacgaaatatgataatctgcatctg gaagacctgtttattggcaacaaagtcaatgtgttctctcgtcagctggtgctgatcgattatggcgaccagtacaccgcgcgtcaactg ggtagtcgcaaagaaaaaacgctggccctgattaaaccggatgcaatctccaaagctggcgaaattatcgaaattatcaacaaagcgg gtttcaccatcacgaaactgaaaatgatgatgctgagccgtaaagaagccctggattttcatgtcgaccaccagtctcgcccgttttcaa tgaactgattcaattcatcaccacgggtccgattatcgcaatggaaattctgcgtgatgacgctatctgcgaatggaaacgcctgctggg cccggcaaactcaggtgttgcgcgtaccgatgccagtgaatccattcgcgctctgtttggcaccgatggtatccgtaatgcagcacatg gtccggactcattcgcatcggcagctcgtgaaatggaactgtttttcccgagctctggcggttgcggtccggcaaacaccgccaaattt accaattgtacgtgctgtattgtcaaaccgcacgcagtgtcagaaggcctgctgggtaaaattctgatggcaatccgtgatgctggcttt gaaatctcggccatgcagatgttcaacatggaccgcgttaacgtcgaagaattctacgaagtttacaaaggcgtggttaccgaatatca cgatatggttacggaaatgtactccggtccgtgcgtcgcgatggaaattcagcaaaacaatgccaccaaaacgtttcgtgaattctgtgg tccggcagatccggaaatcgcacgtcatctgcgtccgggtaccctgcgcgcaattttggtaaaacgaaaatccagaacgctgtgcact gtaccgatctgccggaagacggtctgctggaagttcaatacttttttcaaaattctggataat (amino acids)

(SEQ ID NO: 155)

MNHSERFVFIAEWYDPNASLLRRYELLFYPGDGSVEMHDVKNHRTFLKR

TKYDNLHLEDLFIGNKVNVFSRQLVLIDYGDQYTARQLGSRKEKTLALIKPDAISKA

GEIIEIINKAGFTITKLKMMMLSRKEALDFHVDHQSRPFFNELIQFITTGPIIAMEILRDD

AICEWKRLLGPANSGVARTDASESIRALFGTDGIRNAAHGPDSFASAAREMELFFPSS

GGCGPANTAKFTNCTCCIVKPHAVSEGLLGKILMAIRDAGFEISAMQMFNMDRVNV

EEFYEVYKGVVTEYHDMVTEMYSGPCVAMEIQQNNATKTFREFCGPADPEIARHLR

PGTLRAIFGKTKIQNAVHCTDLPEDGLLEVQYFFKILDNTG

Human NME7 b (optimized for *E coli* expression)
(DNA)

(SEQ ID NO: 156)

atgcatgacgttaaaaatcaccgtacctttctgaaacgcacgaaatatgataatctgcatctggaagacctgtttattggc aacaaagtcaatgtgttctctcgtcagctggtgctgatcgattatggcgaccagtacaccgcgcgtcaactgggtagtcgcaaagaaaa aacgctggccctgattaaaccggatgcaatctccaaagctggcgaaattatcgaaattatcaacaaagcgggtttcaccatcacgaaac tgaaaatgatgatgctgagccgtaaagaagccctggattttcatgtcgaccaccagtctcgcccgttttcaatgaactgattcaattcatc accacgggtccgattatcgcaatggaaattctgcgtgatgacgctatctgcgaatggaaacgcctgctgggcccggcaaactcaggtg ttgcgcgtaccgatgccagtgaatccattcgcgctctgtttggcaccgatggtatccgtaatgcagcacatggtccggactcattcgcat cggcagctcgtgaaatggaactgttttttcccgagctctggcggttgcggtccggcaaacaccgccaaatttaccaattgtacgtgctgta ttgtcaaaccgcacgcagtgtcagaaggcctgctgggtaaaattctgatggcaatccgtgatgctggctttgaaatctcggccatgcag atgttcaacatggaccgcgttaacgtcgaagaattctacgaagtttacaaaggcgtggttaccgaatatcacgatatggttacggaaatg tactccggtccgtgcgtcgcgatggaaattcagcaaaacaatgccaccaaaacgtttcgtgaattctgtggtccggcagatccggaaat cgcacgtcatctgcgtccgggtaccctgcgcgcaattttggtaaaacgaaaatccagaacgctgtgcactgtaccgatctgccggaa gacggtctgctggaagttcaatacttttcaaaattctggataat (amino acids)

(SEQ ID NO: 157)

MHDVKNHRTFLKRTKYDNLHLEDLFIGNKVNVFSRQLVLIDYGDQYTAR

QLGSRKEKTLALIKPDAISKAGEIIEIINKAGFTITKLKMMMLSRKEALDFHVDHQSRP

FFNELIQFITTGPIIAMEILRDDAICEWKRLLGPANSGVARTDASESIRALFGTDGIRNA

AHGPDSFASAAREMELFFPSSGGCGPANTAKFTNCTCCIVKPHAVSEGLLGKILMAIR

DAGFEISAMQMFNMDRVNVEEFYEVYKGVVTEYHDMVTEMYSGPCVAMEIQQNN

ATKTFREFCGPADPEIARHLRPGTLRAIFGKTKIQNAVHCTDLPEDGLLEVQYFFKILD

NTG

Human NME7-AB also known as NME7$_{AB}$ (optimized for *E coli* expression)
(DNA)

(SEQ ID NO: 158)

atggaaaaaacgctggccctgattaaaccggatgcaatctccaaagctggcgaaattatcgaaattatcaacaaagcg ggtttcaccatcacgaaactgaaaatgatgatgctgagccgtaaagaagccctggattttcatgtcgaccaccagtctcgcccgttttca atgaactgattcaattcatcaccacgggtccgattatcgcaatggaaattctgcgtgatgacgctatctgcgaatggaaacgcctgctgg gcccggcaaactcaggtgttgcgcgtaccgatgccagtgaatccattcgcgctctgtttggcaccgatggtatccgtaatgcagcacat ggtccggactcattcgcatcggcagctcgtgaaatggaactgttttttcccgagctctggcggttgcggtccggcaaacaccgccaaatt taccaattgtacgtgctgtattgtcaaaccgcacgcagtgtcagaaggcctgctgggtaaaattctgatggcaatccgtgatgctggcttt gaaatctcggccatgcagatgttcaacatggaccgcgttaacgtcgaagaattctacgaagtttacaaaggcgtggttaccgaatatca cgatatggttacggaaatgtactccggtccgtgcgtcgcgatggaaattcagcaaaacaatgccaccaaaacgtttcgtgaattctgtgg tccggcagatccggaaatcgcacgtcatctgcgtccgggtaccctgcgcgcaattttggtaaaacgaaaatccagaacgctgtgcact gtaccgatctgccggaagacggtctgctggaagttcaatacttttcaaaattctggataat (amino acids)

(SEQ ID NO: 159)

MEKTLALIKPDAISKAGEIIEIINKAGFTITKLKMMMLSRKEALDFHVDHQS

RPFFNELIQFITTGPIIAMEILRDDAICEWKRLLGPANSGVARTDASESIRALFGTDGIR

NAAHGPDSFASAAREMELFFPSSGGCGPANTAKFTNCTCCIVKPHAVSEGLLGKILM

AIRDAGFEISAMQMFNMDRVNVEEFYEVYKGVVTEYHDMVTEMYSGPCVAMEIQQ

NNATKTFREFCGPADPEIARHLRPGTLRAIFGKTKIQNAVHCTDLPEDGLLEVQYFFK

ILDNTG

Human NME7-X1 (optimized for *E coli* expression)
(DNA)

(SEQ ID NO: 160)

atgatgatgctgagccgtaaagaagccctggattttcatgtcgaccaccagtctcgcccgttttcaatgaactgattcaa ttcatcaccacgggtccgattatcgcaatggaaattctgcgtgatgacgctatctgcgaatggaaacgcctgctgggcccggcaaactc aggtgttgcgcgtaccgatgccagtgaatccattcgcgctctgtttggcaccgatggtatccgtaatgcagcacatggtccggactcatt cgcatcggcagctcgtgaaatggaactgttttttcccgagctctggcggttgcggtccggcaaacaccgccaaatttaccaattgtacgt gctgtattgtcaaaccgcacgcagtgtcagaaggcctgctgggtaaaattctgatggcaatccgtgatgctggctttgaaatctcggcca tgcagatgttcaacatggaccgcgttaacgtcgaagaattctacgaagtttacaaaggcgtggttaccgaatatcacgatatggttacgg aaatgtactccggtccgtgcgtcgcgatggaaattcagcaaaacaatgccaccaaaacgtttcgtgaattctgtggtccggcagatccg gaaatcgcacgtcatctgcgtccgggtaccctgcgcgcaatttttggtaaaacgaaaatccagaacgctgtgcactgtaccgatctgcc ggaagacggtctgctggaagttcaatactttttcaaaattctggataat (amino acids)

(SEQ ID NO: 161)

MMMLSRKEALDFHVDHQSRPFFNELIQFITTGPIIAMEILRDDAICEWKRL

LGPANSGVARTDASESIRALFGTDGIRNAAHGPDSFASAAREMELFFPSSGGCGPANT

AKFTNCTCCIVKPHAVSEGLLGKILMAIRDAGFEISAMQMFNMDRVNVEEFYEVYK

GVVTEYHDMVTEMYSGPCVAMEIQQNNATKTFREFCGPADPEIARHLRPGTLRAIFG

KTKIQNAVHCTDLPEDGLLEVQYFFKILDNTG

DM10 domain of NME7
(amino acids)

(SEQ ID NO: 162)

MNHSERFVFIAEWYDPNASLLRRYELLFYPGDGSVEMHDVKNHRTFLKR

TKYDNLHLEDLFIGNKVNVFSRQLVLIDYGDQYTARQLGSRK a fragment or variation of PSMGFR peptide (SEQ ID NO: 163)

SNIKFRPGSVVVQLTLAFREGTINVHDVETQFNQYKTEAASRY;

a fragment or variation of PSMGFR peptide (SEQ ID NO: 164)

SVVVQLTLAFREGTINVHDVETQFNQYKTEAASRY;

a fragment or variation of PSMGFR peptide (SEQ ID NO: 165)

VQLTLAFREGTINVHDVETQFNQY;

a fragment or variation of PSMGFR peptide (SEQ ID NO: 166)

SNIKFRPGSVVVQLTLAFREGTIN;

a fragment or variation of PSMGFR peptide (SEQ ID NO: 167)

SNIKFRPGSVVVQLTLAFREGTINVHDVETQFNQYKTE;

a fragment or variation of PSMGFR peptide (SEQ ID NO: 168)

VQLTLAFREGTINVHDVETQFNQYKTEAASRYNLTISDVSVSDVP.

Cys at residue 14 is mutated to Ser of NME7B peptide 3 (B domain):

(SEQ ID NO: 169)

AIFGKTKIQNAVHSTDLPEDGLLEVQYFF

N-10 peptide (SEQ ID NO: 170)

QFNQYKTEAASRYNLTISDVSVSDVPFPFSAQSGA

C-10 peptide (SEQ ID NO: 171)

GTINVHDVETQFNQYKTEAASRYNLTISDVSVSDV

EXAMPLES

Example 1—Components of Minimal Serum-Free Base ("MM") (500 mls)

400 ml DME/F12/GlutaMAX I (Invitrogen #10565-018)
100 ml Knockout Serum Replacement (KO-SR, Invitrogen #10828-028)
5 ml 100×MEM Non-essential Amino Acid Solution (Invitrogen #11140-050)
0.9 ml (0.1 mM) β-mercaptoethanol (55 mM stock, Invitrogen #21985-023.

Example 2—Generation of Protein Constructs

For generating recombinant NME7, first, constructs were made to make a recombinant NME7 that could be expressed efficiently and in soluble form. The first approach was to make a construct that would encode the native NME7 (a) or an alternative splice variant NME7 (b), which has an N-terminal deletion. In some cases, the constructs carried a histidine tag or a strep tag to aid in purification. NME7-a, full-length NME7 expressed poorly in E. coli and NME7-b did not express at all in E. coli. However, a novel construct was made in which the DM10 sequence was deleted and the NME7 comprised essentially the NDPK A and B domains having a calculated molecular weight of 33 kDa.

This novel NME7$_{AB}$ expressed very well in E. coli and existed as the soluble protein. NME7$_{AB}$ was first purified over an NTA-Ni column and then further purified by size exclusion chromatography (FPLC) over a Sephadex 200 column. Fractions were collected and tested by SDS-PAGE to identify fractions with the highest and purest expression of NME7$_{AB}$. The FPLC trace for the combined fractions that were the most pure were combined. The purified NME7$_{AB}$ protein was then tested and shown to fully support the growth of human stem cells and further reverts them to the most naïve, pre-X-inactivation state. The purified NME7$_{AB}$ was also shown to accelerate the growth of cancer cells.

Example 3—ELISA Assay Showing NME7$_{AB}$ Simultaneously Binds to Two MUC1* Extra Cellular Domain Peptides Results are shown in FIG. 1. The PSMGFR peptide bearing a C-terminal Cysteine (PSMGFR-Cys) was covalently coupled to BSA using Imject Maleimide activated BSA kit (Thermo Fisher). PSMGFR-Cys coupled BSA was diluted to 10 ug/mL in 0.1M carbonate/bicarbonate buffer pH 9.6 and 50 uL was added to each well of a 96 well plate. After overnight incubation at 4° C., the plate was washed twice with PBS-T and a 3% BSA solution was added to block remaining binding site on the well. After 1 h at RT the plate was washed twice with PBS-T and NME7, diluted in PBS-T+1% BSA, was added at different concentrations. After 1 h at RT the plate was washed 3× with PBS-T and anti-NM23-H7 (B-9, Santa Cruz Biotechnology), diluted in PBS-T+1% BSA, was added at 1/500 dilution. After 1 h at RT the plate was washed 3× with PBS-T and goat anti mouse-HRP, diluted in PBS-T+1% BSA, was added at 1/3333 dilution. After 1 h at RT the plate was washed 3× with PBS-T and binding of NME7 was measured at 415 nm using ABTS solution (Pierce).

ELISA MUC1* dimerization: The protocol for NME7 binding was used, and NME7 was used at 11.6 ug/mL. After 1 h at RT the plate was washed 3× with PBS-T and His-Tagged PSMGFR peptide (PSMGFR-His) or biotinylated PSMGFR peptide (PSMGFR-biotin), diluted in PBS-T+1% BSA, was added at different concentration. After 1 h at RT the plate was washed 3× with PBS-T and anti-Histag-HRP (Abcam) or streptavidin-HRP (Pierce), diluted in PBS-T+1% BSA, was added at a concentration of 1/5000. After 1 h at RT the plate was washed 3× with PBS-T and binding of PSMGFR peptide to NME7 already bound to another PSMGFR peptide (which could not signal by anti-His antibody or by streptavidin) coupled BSA was measured at 415 nm using a ABTS solution (Pierce).

Example 4—Functional Testing of Human Recombinant NME7$_{AB}$

For testing recombinant NME7$_{AB}$ for ability to maintain pluripotency and inhibit differentiation, a soluble variant of NME7, NME7$_{AB}$, was generated and purified. Human stem cells (iPS cat #SC101a-1, System Biosciences) were grown per the manufacturer's directions in 4 ng/ml bFGF over a layer of mouse fibroblast feeder cells for four passages. These source stem cells were then plated into 6-well cell culture plates (Vita™, Thermo Fisher) that had been coated with 12.5 ug/well of a monoclonal anti-MUC1* antibody, MN-C3. Cells were plated at a density of 300,000 cells per well. The base media was Minimal Stem Cell Media consisting of: 400 ml DME/F12/GlutaMAX I (Invitrogen #10565-018), 100 ml Knockout Serum Replacement (KO-SR, Invitrogen #10828-028), 5 ml 100×MEM Non-essential Amino Acid Solution (Invitrogen #11140-050) and 0.9 ml (0.1 mM) β-mercaptoethanol (55 mM stock, Invitrogen #21985-023). The base media can be any media. In a preferred embodiment, the base media is free of other growth factors and cytokines. To the base media was added either 8 nM of NME7$_{AB}$ or 8 nM NM23-H1 refolded and purified as stable dimers. Media was changed every 48 hours and due to accelerated growth, had to be harvested and passaged at Day 3 post-plating. Comparable pluripotent stem cell growth was achieved when stem cells were grown in NM23-H1 dimers or in NME7 monomers.

NME7 and NM23-H1 (NME1) dimers both grew pluripotently and had no differentiation even when 100% confluent. As can be seen in the photos, NME7 cells grew faster than the cells grown in NM23-H1 dimers. Cell counts at the first harvest verified that culture in NME7 produced 1.4-times more cells than culture in NM23-H1 dimers. ICC staining for the typical pluripotent markers confirmed that NME7$_{AB}$ fully supported human stem cell growth, pluripotency, and resisted differentiation.

The NME7 species of ~30-33 kDa may be an alternative splice isoform or a post translational modification such as cleavage, which may enable secretion from the cell.

Example 5—Inducing Transition of Cancer Cells to Metastatic Cancer Cells by Culturing Cells Under Conditions that Revert Stem Cells to a More Naïve State Cancer cells are normally cultured in a serum-containing media such as RPMI. We discovered that culturing cancer cells in the presence of reagents that make stem cells revert to a more naïve state, makes the cancer cells transform to a more metastatic state.

We demonstrated that NME7$_{AB}$, human NME1 dimers, bacterial NME1 dimers, NME7-X1 and "2i" inhibitors were each able to transform regular cancer cells into metastatic cancer cells, which are also called cancer stem cells "CSCs" or tumor initiating cells "TICs". 2i is the name given to two biochemical inhibitors that researchers found made human stem cells revert to a more naïve state. 2i are MEK and GSK3-beta inhibitors PD0325901 and CHIR99021, which are added to culture medium to final concentrations of about 1 mM and 3 mM, respectively.

NME7$_{AB}$ and NME7-X1 are at a final concentration of about 4 nM when added to separate batches of minimal medium to make cancer cells transform to metastatic cells, although lower and higher concentrations also work well in the range of about 1 nM to 16 nM. Human or bacterial NME1 dimers are used at a final concentration of 4 nM to 32 nM, with 16 nM typically used in these experiments, wherein the human NME bears the S120G mutation. Lower concentrations may be required if using wild type. It is not intended that these exact concentrations are important. It is important that the NME1 proteins are dimers and the range of concentrations over which this happens is in the low nanomolar range although certain mutations allow higher concentrations to remain as dimers.

Similarly, the concentrations of NME7 proteins can vary. NME7$_{AB}$ and NME7-X1 are monomers and concentrations used to transform cancer cells to metastatic cells should allow the proteins to remain as monomers. Various molecular markers have been proposed as being indicators of metastatic cancer cells. Different cancer types may have different molecules that are up-regulated. For example, the receptor CXCR4 is up-regulated in metastatic breast cancers while E-cadherin, also known as CHD1, is up-regulated more in metastatic prostate cancers.

In addition to these specific metastasis markers, typical markers of pluripotency such as OCT4, SOX2, NANOG, and KLF4 are up-regulated as cancers become metastatic. The starting cancer cells and the later metastatic cancer cells can be assayed by PCR to measure expression levels of these genes.

FIG. 2 shows a graph of RT-PCR measurements of T47D breast cancer cells that were cultured in a media that contained NME7$_{AB}$. A rho I kinase inhibitor, ROCi, ROCKi or Ri, was added to prevent the transformed cells from floating off the plate. Expression levels of various metastatic markers as well as pluripotent stem cell markers were measured for the parent cells and for the NME7$_{AB}$ cultured cells. The results show that the floater cells express higher amounts of metastatic and pluripotency markers compared to the cells that received ROCi. We reasoned it was because those measurements were the average of cells that did not transform and those that did but the ROCi made them remain adherent. This can clearly be seen in figures wherein "—Ri" means adherent cells that did not receive ROCi and so were not mixed with the highly metastatic cells that float.

Prostate cancer cells also transitioned to a more metastatic state when cultured in media containing NM23, aka NME1, or NME7$_{AB}$. Here we show that for every cell line tested so far, culture in NME7$_{AB}$, human NME1 dimers, or bacterial NMEs that have high sequence homology to human, induces transition to a more metastatic state.

Figure 4:
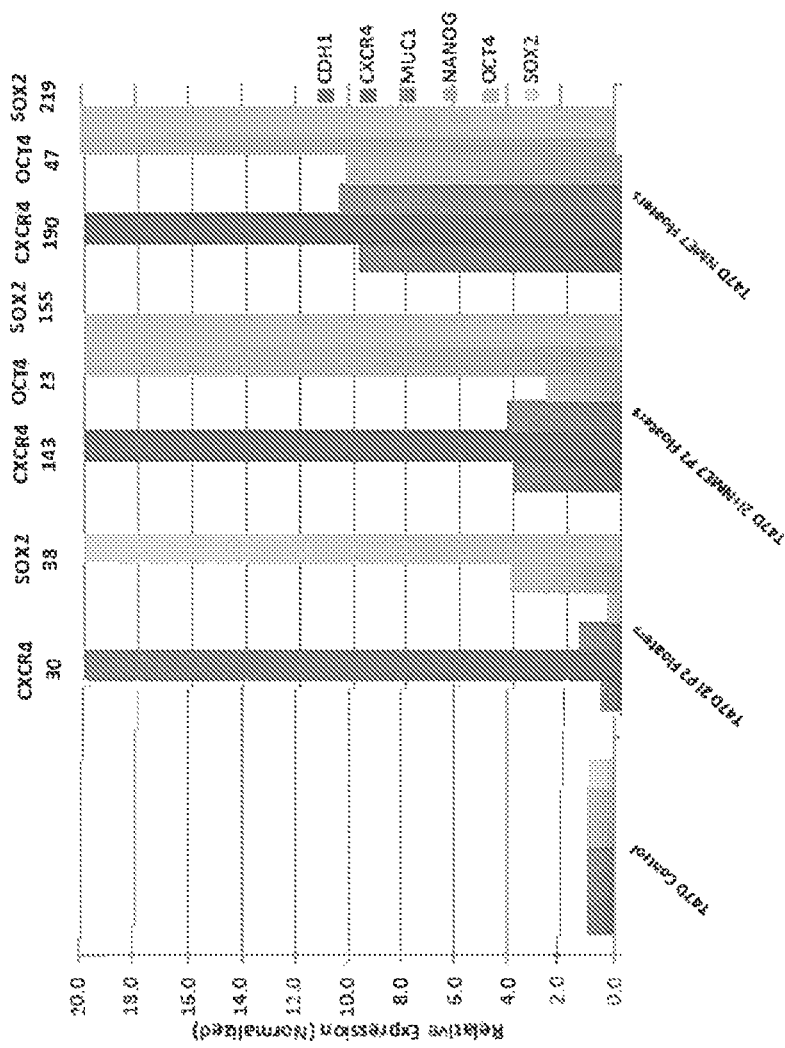
FIG. 4 is a graph of RT-PCR measurement of the metastatic markers and pluripotent stem cell markers showing that the 2i inhibitors (GSK3-beta and MEK inhibitors), which were previously shown to revert stem cells to a more naïve state, also induce cancer cells to a more metastatic state although not as well as NME7$_{AB}$.

FIG. 4 shows a graph of RT-PCR measurements of expression levels of metastatic and pluripotency markers for breast cancer cells that are cultured in media containing either 2i inhibitors, NME7$_{AB}$ or both. As can be seen, 2i inhibitors are also able to induce the transition of cancer cells to a more metastatic state. Ovarian cancer cell lines SK-OV3, OV-90, pancreatic cancer cell lines CAPAN-2 and PANC-1, breast cancer cell line MDA-MB all displayed the morphological transition of going from adherent to non-adherent when cultured in NME7$_{AB}$ and or 2i inhibitors.

FIG. 20 shows graphs of RT-PCR measurement of metastatic or pluripotency markers for various cancer cell lines cultured for 72 or 144 hours in NME7$_{AB}$. FIG. 20A shows that SK-OV3 cells increase expression of metastatic markers CHD1, SOX2 and NME7-X1 when cultured in NME7$_{AB}$. FIG. 20B shows that OV-90 cells increase expression of metastatic markers CXCR4 and NME7-X1 after culture in NME7$_{AB}$.

Example 6—Demonstration that Cancer Cells Cultured in NME7 Become Metastatic

A functional test of whether or not a population of cancer cells is metastatic is to implant very low numbers, e.g. 200, of the cells in immuno-compromised mice and see if they develop into a tumor. Typically 5-6 million cancer cells are required to form a tumor in an immuno-compromised mouse. We showed that as few as 50 of the NME-induced metastatic cancer cells formed tumors in mice. In addition, mice that were injected throughout the test period with human NME7$_{AB}$, NME1, or NME7-X1 developed remote metastases.

T47D human breast cancer cells were cultured in standard RPMI media for 14 days with media changes every 48 hours and passed by trypsinization when approximately 75% confluent. The cells were then plated into 6-well plates and cultured in minimal stem cell media (see Example 1) that was supplemented with 4 nM NME7$_{AB}$. Media was changed every 48 hours. By about Day 4, some cells become detached from the surface and float. Media is carefully changed so as to retain the "floaters" as these are the cells that have the highest metastatic potential as evidenced by RT-PCR measurement of metastatic markers. On Day 7 or 8, the floaters are harvested and counted. Samples are retained for RT-PCR measurement. The key marker measured is CXCR4 which is up-regulated by 40-200 times after being briefly cultured in NME7$_{AB}$.

The freshly harvested floater metastatic cells are xeno-grafted into the flank of female nu/nu athymic mice that have been implanted with 90-day slow release estrogen pellets. Floater cells were xenografted as 10,000, 1,000, 100 or 50 cells each. Half of the mice in each group of 6 were also injected daily with 32 nM NME7$_{AB}$ near the original implantation site. The parent T47D cells that were cultured in RPMI media without NME7$_{AB}$ were also implanted into mice as 6 million, 10,000 or 100 as controls. Mice implanted with the NME7-induced floater cells developed tumors even when as few as 50 cells were implanted. Mice that were implanted with the floater cells and that received daily injections of NME7$_{AB}$ also developed remote tumors or remote metastases in various organs. 11 out of the 12 mice, or 92%, that were injected with human NME7$_{AB}$ after implantation of the NME7$_{AB}$ cultured cancer cells, developed tumors at the injection site. Only 7 out of the 12 mice, or 58%, that were not injected with human NME7$_{AB}$ after implantation developed tumors. 9 out of the 11 mice, or 82%, that got tumors and were injected with human NME7$_{AB}$ developed multiple tumors remote from the injection site. None of the mice that were not injected with NME7$_{AB}$ developed multiple, visible tumors.

After sacrifice, RT-PCR and Western blots showed that the remote bumps on the mice injected with NME7$_{AB}$ were indeed human breast tumors. Similar analysis of their organs showed that in addition to remote bumps, mice had randomly metastasized to the liver and lung with human breast cancer characteristic of the human breast cancer cells that were implanted. As expected, only the mice implanted with 6 million cells grew tumors.

Several experiments like the one described above were performed with essentially the same results. In each experiment, there were either 24 or 52 mice, including all proper controls.

Example 7—Peptides Selected Because their Sequence is Unique to NME7, A1, A2, B1, B2 and B3, Inhibit the Binding of NME7 Species to MUC1* Extracellular Domain Peptide NME7 peptides were selected as immunizing agents for antibody production. NME7 peptides A1, A2, B1, B2 and B3 (FIG. 9) were chosen using a process of sequence alignment among human NME1, human NME7 and several bacterial NMEs that were homologous to human NME1 or human NME7. Five regions that had high sequence homology among all were identified. However, to prevent selecting peptides that would give rise to antibodies that would inhibit human NME1 as well as human NME7, we chose NME7 sequences that were adjacent to the homologous regions wherein those peptides had sequences that were different from human NME1. We did ELISA assays to see if the peptides on their own could bind to a synthetic MUC1* peptide on the surface and inhibit the binding of human NME7 or human NME1 to the immobilized peptide (FIG. 11). FIG. 11 shows that the peptides inhibited the binding of NME7 and NME1 to the immobilized PSMGFR peptide. Recall that each of the NME7 A domain and B domain can bind to a PSMGFR peptide. Therefore complete inhibition of NME7$_{AB}$ binding to a PSMGFR peptide cannot be accomplished with a single antibody or peptide that is derived from just one domain. This showed that those regions from which the peptides were derived were the regions that interacted with MUC1* and would give rise to antibodies that would bind to those regions of NME7 and inhibit its binding to MUC1* receptor.

In another experiment, the free peptides A1, A2, B1, B2 and B3 were added to cancer cells in culture that were undergoing transition to a more metastatic state by culturing in either NME7$_{AB}$ or 2i. FIG. 14 shows a table of scientist observations when cancer cells are grown in either NME7$_{AB}$ or 2i inhibitors, and shows that the free peptides inhibited the morphological change from adherent cells to floaters, which for breast cancer cells is directly correlated to increased expression of metastatic markers, especially CXCR4. RT-PCR measurements confirm that the NME7$_{AB}$ peptides inhibited the increase in expression of metastasis marker CXCR4.

FIG. 15 shows a graph of RT-PCR measurements of CXCR4 expression in T47D breast cancer cells that were grown in either NME7$_{AB}$ or 2i inhibitors, each of which transform cancer cells to a more metastatic state, and the inhibitory effect of NME7-derived peptides, A1, A2, B1, B2 and B3, on the metastatic transformation. FIG. 32 shows a table of recorded RNA levels in samples that were used for RT-PCR measurement of CXCR4 in FIG. 15 as well as the threshold cycle number for CXCR4 expression as well as for the control housekeeping gene.

Example 8—Anti-NME7 Antibodies Specifically Bind to Human NME7 but not to Human NME1

A standard ELISA assay was performed to determine whether or not the NME7 antibodies we generated by immunization with NME7$_{AB}$ peptides A1, A2, B1, B2, and B3 would bind specifically to NME7$_{AB}$, but not to human NME1 as it has healthy functions and it may be detrimental to a human to block it with an antibody. The ELISAs of FIG. 24-25 show that all of the NME7 antibodies that were generated from peptides A1, A2, B1, B2, and B3 bind to human NME7$_{AB}$ (FIG. 24) but not to human NME1 (FIG. 25). The peptides used to generate these antibodies are common to both NME7$_{AB}$ and NME7-X1. This assays show that the antibodies generated from peptides A1, A2, B1, B2, and B3 specifically bind to NME7$_{AB}$ and by extension will bind to NME7-X1.

```
NME7A peptide 1 (A domain):
                                            (SEQ ID NO: 141)
MLSRKEALDFHVDHQS NME7A peptide 2 (A domain):
                                            (SEQ ID NO: 142)
SGVARTDASES NME7B peptide 1 (B domain):
                                            (SEQ ID NO: 143)
DAGFEISAMQMFNMDRVNVE NME7B peptide 2 (B domain):
                                            (SEQ ID NO: 144)
EVYKGVVTEYHDMVTE NME7B peptide 3 (B domain):
                                            (SEQ ID NO: 145)
AIFGKTKIQNAVHCTDLPEDGLLEVQYFF
```

Example 9—Anti-NME7 Specific Antibodies and the Peptides that Generated them Inhibit Cancer Cell Growth Rabbits were immunized with NME7 peptides A1, A2, B1, B2, and B3 and antibodies were generated, collected and purified over a column to which the immunizing peptide had been conjugated. T47D breast cancer cells were plated and cultured according to ATCC protocols in RPMI media supplemented with serum. Antibodies generated from immunization with peptides A1, A2, B1, B2, and B3 were added at the concentrations indicated in FIG. 12. Immunizing peptides A1, A2, B1, B2, and B3, and the PSMGFR extracellular domain peptide of MUC1*, "FLR" here, were also added separately to growing T47D breast cancer cells. Taxol and the E6 anti-MUC1* Fab were added as controls. The graph of FIG. 12 shows that the antibodies generated, as well as the free peptides, potently inhibited the growth of the cancer cells. Note the comparison to inhibition using Taxol, which is a chemotherapy agent that kills healthy and cancer cells alike. Also, for comparison, a polyclonal antibody generated using a large stretch of NME7 from amino acid 100 to 376 is shown. Although this antibody is a potent inhibitor of cancer growth it could have non-specific effects since it can bind to NME1 as well as to NME7.

In a similar experiment, combinations of the antibodies generated from immunization with peptides A1, A2, B1, B2, and B3 as well as the peptides themselves were added to growing cancer cells at the concentrations indicated. The graphs of cell growth shown in FIG. 13 show that the combinations of antibodies and peptides potently inhibited the growth of cancer cells. In these two experiments, the cells were MUC1* positive breast cancer cells.

Example 10—Anti-NME7 Antibodies Inhibit the Transition of Cancer Cells to Metastatic Cancer Cells Cancer cells transform to a more metastatic state when cultured in the presence of agents that revert stem cells to a more naïve state. We have demonstrated that culturing cancer cells in $NME7_{AB}$, human NME1 dimers, bacterial NME1 dimers or MEK and GSK3-beta inhibitors, called "2i", causes the cells to become more metastatic. As the cells transition to a more metastatic state, they become non-adherent and float off of the culture plate. These floating cells, "floaters" were collected separately from those that were adherent and were shown to: a) express much higher levels of metastatic genes; and b) when xenografted into mice, the floater cells were able to generate tumors when implanted at very low numbers. RT-PCR measurement of specific metastatic markers such as CXCR4 in breast cancers, CHD1 in prostate cancer, and other pluripotent stem cell markers such as OCT4, SOX2, NANOG, KLF4, c-Myc and others were dramatically over-expressed in cancer cells that were cultured in $NME7_{AB}$ and most over-expressed in the cells that became non-adherent, called "floaters" here and in figures.

Here we show that the NME7-specific antibodies, generated by immunization with NME7-derived peptides A1, A2, B1, B2 and B3, as well as the peptides themselves, inhibit the transition from cancer cell to metastatic cancer cells. In the first of these experiments, the antibodies generated by immunization with A1, A2, B1, B2 and B3 were tested for their ability to inhibit the metastatic transition induced by culture of T47D breast cancer cells in $NME7_{AB}$ or in 2i inhibitors. The most striking observation was that the antibodies and the peptides dramatically reduced the number of floater cells, which was the first indication that the antibodies and peptides had inhibited the transformation to metastatic cancer cells. In particular, cells to which the antibody generated from immunization with the B3 peptide barely generated any floater cells.

FIG. 14 shows the recorded observations of the percentage of floater cells visible for each antibody relative to the control wells that did not receive any antibody treatment. mRNA was extracted from both the floater cells and the adherent cells. RT-PCR was used to measure expression levels of metastatic markers, including CXCR4. Treatment with the anti-NME7 antibodies greatly reduced the amount of metastatic markers, such as CXCR4, indicating the antibodies inhibited the transition to metastatic cancer. (See FIG. 15). Notably, the antibody generated by immunization with peptide B3, aka antibody #61, essentially completely inhibited the transition to a more metastatic state. FIG. 15B shows that breast cancer cells that were treated with the $NME7_{AB}$ peptides, A1, A2, B1, B2 and B3, alone were able to potently inhibit the transition to a more metastatic state induced by culturing the cells in a media containing the 2i inhibitors. Peptide B3 was especially effective as was antibody #61 that it generated. FIG. 15C shows the same graph but with the Y-axis expanded to show the peptide inhibition of metastatic markers. The amount of mRNA, which indicates cell viability and growth, was measured. Cells that were treated with antibody had much less mRNA, indicating that in addition to inhibiting the transition to a more metastatic state, the anti-$NME7_{AB}$ antibodies inhibited the growth of the cancer cells. FIG. 16 shows a table of the amounts of RNA recovered for the inhibition experiment shown in FIG. 15A.

Example 11—Anti-NME7 Antibodies Generated with NME7-Derived Peptides A1, A2, B1, B2 and B3 Identify Novel NME7 Species not Detectable Using any Commercially Available Antibodies As is known to those skilled in the art, some antibodies recognize a linear portion of the target protein and can be used in Western blot assays while other antibodies recognize a non-linear conformational motif and can be used in pull-down or immunoprecipitation assays. Previous to this application, cleaved NME7 or isoform NME7-X1 was not known to exist. Using antibodies that were commercially available at the time of filing shows that existing antibodies could not specifically detect these important NME7 species. B9 (Santa Cruz Biotechnology) is a monoclonal antibody raised against NME7 amino acids 100-376. FIG. 19D-19F shows that it only detects full-length 42 kDa NME7. Another commercially available antibody, H278, is a rabbit polyclonal raised against NME7 amino acids 100-376, which includes amino acid sequences that are not unique to NME7. FIG. 19D-19F shows that this antibody also stains NME1, which is 17 kDa as well as full-length NME7 and other bands that do not appear to be specific to $NME7_{AB}$.

NME7 antibodies generated by immunization with $NME7_{AB}$ peptides A1, A2, B1, B2 or B3 identify new NME7 species including the full-length 42 kDa protein, a ~33kDaNME7 species that may be a cleavage product or alternative isoform, a ~30 kDa NME7 species that may be a cleavage product or alternative isoform, wherein the ~30 kDa species appears to be NME7-X1. FIG. 19A-C shows that antibodies generated by peptides A1, B1 and B3 identify the secreted forms of NME7, $NME7_{AB}$ and NME7-X1 in a wide range of cancer cell lines, including T47D breast cancer cells, PC3 and DU145 prostate cancer cells, HEK293 fetal liver cells, and leukemia cells IM-9, K562, and MV411.

Example 12—Generation of Anti-NME7 Antibodies

A synthetic peptide having the sequence of the B3 region of NME7, AIFGKTKIQNAVHCTDLPEDGLLEVQYFFC (SEQ ID NO: 1142), was used to immunize rabbits. Antibodies that resulted from immunization with NME7 peptide B3 inhibited the growth of MUC1* positive cancer cells and also inhibited the formation of cancer stem cells, which are characterized by upregulation of metastatic markers, ability to grow anchorage independently, and are able to form tumors in animals from as few as 200 cells, whereas regular cancer cells typically require implantation of about 4 million cells for tumor engraftment.

In some cases, the NME7 B3 peptide was made with a C14A or C14V mutation. This sequence more reproducibly generated anti-NME7 antibodies.

Monoclonal antibodies were generated in mice according to standard methods by immunizing with NME7 B3, B3 with C14A mutation, or B3 with C14V mutation. The antibodies listed were selected because of their ability to bind to NME7, NME7-X1, $NME7_{AB}$, but importantly did not bind to NME1, which is thought to be required for some normal cellular functions. These antibodies also bind to the NME7 derived peptides B3, B3 with C14A mutation, and B3 with C14V mutation.

Experiments showed that these anti-NME7 antibodies inhibited the binding of NME7 to the MUC1* extra cellular domain, but did not block the binding of NME1 to the MUC1* extra cellular domain peptide. Further, the antibodies inhibited the formation of cancer stem cells.

CITED REFERENCES LIST

Al-Hajj et al. (2003) Prospective identification of tumorigenic breast cancer cells. PNAS. April 1; 100(7):3983-3988.

Clarke M F, Dick J E, Dirks P B, Eaves C J, Jamieson C H, Jones D L, Visvader J, Weissman I L, Wahl G M. (2006) Cancer stem cells—perspectives on current status and future directions: AACR Workshop on cancer stem cell. Cancer Res. October 1; 66(19):9339-44. Epub 2006 Sep. 21.

Chen K, Huang Y H, Chen J L. (2013) Understanding and targeting cancer stem cells: therapeutic implications and challenges. Acta Pharmacologica Sinica 34: 732-740; Review Darash-Yahana M, Pikarsky E, Abramovitch R, Zeira E, Pal B, Karplus R, Beider K, Avniel S, Kasem S, Galun E, Peled A (2004) Role of high expression levels of CXCR4 in tumor growth, vascularization, and metastasis. FASEB J 18(11): 1240-1242

Mahanta S, Fessler S, Park J, Bamdad C. A Minimal Fragment of MUC1 Mediates Growth of Cancer Cells, 2008 PLoS ONE 3:e2054-2065.

Hikita S, Clegg O, Kosik K, Bamdad C. MUC1* Mediates the Growth of Human Pluripotent Stem Cells, 2008 PLoS ONE 3:e3312-3325.

Kumar S M, Liu S, Lu H, Zhang H, Zhang P J, Gimotty P A, Guerra M, Guo W, Xu X. (2012) Acquired cancer stem cell phenotypes through Oct4-mediated dedifferentiation. Oncogene. November 22; 31(47):4898-911.

Liu K, Lin B, Zhao M, Yang X, Chen M, Gao A, Liu F, Que J, Lan X. (2013) The multiple roles for Sox2 in stem cell maintenance and tumorigenesis. Cellular Signaling May; 25(5): 1264-71. Review Wang M L, Chiou S H, Wu C W. (2013) Targeting cancer stem cells: emerging role of Nanog transcription factor. Onco targets and Therapy. September 4; 6:1207-20. Review.

Xu C, Rosler E, Jiang J, Lebkowski J S, Gold J D, et al. (2005) Basic Fibroblast Growth Factor Supports Undifferentiated Human Embryonic Stem Cell Growth Without Conditioned Medium. STEM CELLS 23: 315-323.

Fessler S, Wotkowicz M, Mahanta S, Bamdad C (2009) MUC1* is a determinant of trastuzumab (Herceptin) resistance in breast cancer cells, Breast Cancer Res Treat 118:113-124 DOI 10.1007/s10549-009-0412-3

Miki J, Furusato B, Li H, Gu Y, Takahashi H, Egawa S, Sesterhenn I A, McLeod D G, Srivastava S, Rhim J S. Identification of putative stem cell markers, CD133 and CXCR4, in hTERT-immortalized primary nonmalignant and malignant tumor-derived human prostate epithelial cell lines and in prostate cancer specimens. Cancer Res. 2007 Apr. 1; 67(7):3153-61.

Jeter C R, Liu B, Liu X, Chen X, Liu C, Calhoun-Davis T, Repass J, Zaehres H, Shen J J, Tang D G. NANOG promotes cancer stem cell characteristics and prostate cancer resistance to androgen deprivation. Oncogene. 2011 Sep. 8; 30(36):3833-45. PMCID:

Faber A, Goessler U R, Hoermann K, Schultz J D, Umbreit C, Stern-Straeter J. SDF-1-CXCR4 axis: cell trafficking in the cancer stem cell niche of head and neck squamous cell carcinoma. Oncol. Rep. 2013 June; 29(6):2325-31.

Mukherjee D, Zhao J. The Role of chemokine receptor CXCR4 in breast cancer metastasis. Am J Cancer Res. 2013; 3(1):46-57. PMCID: PMC3555200

Herreros-Villanueva M, Zhang J-S, Koenig A, Abel E V, Smyrk T C, Bamlet W R, de Narvaj as AA-M, Gomez T S, Simeone D M, Bujanda L, Billadeau D D. SOX2 promotes dedifferentiation and imparts stem cell-like features to pancreatic cancer cells. Oncogenesis. 2013; 2:e61. PMCID: PMC3759123

Hanna J, Cheng A W, Saha K, Kim J, Lengner C J, et al. (2010) Human embryonic stem cells with biological and epigenetic characteristics similar to those of mouse ESCs. Proc Natl Acad Sci USA 107: 9222-9227.

Smagghe, B. J. Stewart A. K., Carter M. G., Shelton L. S., Bernier K. J., Hartman E. J., Calhoun A. K., Hatziioannou V. M., Lillacci G., Kirk B. A., DiNardo B. A., Kosik K. S., Bamdad C. (2013) MUC1* Ligand, NM23-H1, Is a Novel Growth Factor That Maintains Human Stem Cells in a More Naïve State. PLoS ONE 8(3): e58601

Theunissen T W, Powell B E, Wang H, Mitalipova M, Faddah D A, Reddy J, Fan Z P, Maetzel D, Ganz K, Shi L, Lungjangwa T, Imsoonthornruksa S, Stelzer Y, Rangarajan S, D'Alessio A, Zhang J, Gao Q, Dawlaty M M, Young R A, Gray N S, Jaenisch R. (2014) Systematic Identification of Culture Conditions for Induction and Maintenance of Naive Human Pluripotency. Cell Stem Cell. 2014 Jul. 24, S1934-5909(14)00298-7.

Rais Y1, Zviran A, Geula S, Gafni O, Chomsky E, Viukov S, Mansour A A, Caspi I, Krupalnik V, Zerbib M, Maza I, Mor N, Baran D, Weinberger L, Jaitin D A, Lara-Astiaso D, Blecher-Gonen R, Shipony Z, Mukamel Z, Hagai T, Gilad S, Amann-Zalcenstein D, Tanay A, Amit I, Novershtern N, Hanna J H (2013). Deterministic direct reprogramming of somatic cells to pluripotency., 502(7469): 65-70.

Xu R H, Peck R M, Li D S, Feng X, Ludwig T, et al. (2005) Basic FGF and suppression of BMP signaling sustain undifferentiated proliferation of human ES cells. Nat Methods 2: 185-190.

Liu W, Ma Q, Wong K, Li W, Ohgi K, Zhang J, Aggarwal A K, Rosenfeld M G. Brd4 and JMJD6-Associated Anti-Pause Enhancers in Regulation of Transcriptional Pause Release. Cell. 2013 Dec. 19; 155(7):1581-95. PMCID: PMC3886918.

Silva J, Barrandon O, Nichols J, Kawaguchi J, Theunissen T W, Smith A. Promotion of reprogramming to ground state pluripotency by signal inhibition. PLoS Biol. 2008 Oct. 21; 6(10): e253. PMCID: PMC2570424

Takahashi K and Yamanaka S (2006) Induction of pluripotent stem cells from mouse embryonic and adult fibroblast cultures by defined factors. Cell 126(4):663-676.

Porter D et al. (2011) Chimeric antigen receptor-modified T cells in chronic lymphoid leukemia. N Engl J Med 365: 725-733 DOI: 10.1056/NEJMoa1103849

Tiller T et al. (2013) A fully synthetic human Fab antibody library based on fixed VH/VL framework pairings with favorable biophysical properties. MABs 9:5(3) PMID: 23571156

Webb P A, Perisic O, Mendola C E, Backer J M and Williams R L. The crystal structure of a human nucleoside diphosphate kinase, NM23-H2. J Mol Biol. 1995, 251: 574-587.

Min K, Song H K, Chang C, Kim S Y, Lee K J and Suh S W. Crystal structure of human nucleoside diphosphate kinase A, a metastasis suppressor. Proteins. 2002, 46:340-342.

Okabe-Kado et al., "A new function of Nm23/NDP kinase as a differentiation inhibitory factor, which does not require it's kinase activity", FEBS Letters 363: 311-315, 1995

Lombardi et al., "nm23: Unraveling Its Biological Function in Cell Differentiation" JOURNAL OF CELLULAR PHYSIOLOGY 182:144-149 (2000)

Harrell et al., Estrogen Receptor Positive Breast Cancer Metastasis: Altered Hormonal Sensitivity and Tumor Aggressiveness in Lymphatic Vessels and Lymph Nodes. Cancer Res 2006; 66: (18). Sep. 15, 2006.

Suzuki et al., Combined effect of dehydroxymethylepoxyquinomicin and gemcitabine in a mouse model of liver metastasis of pancreatic cancer. Clin Exp Metastasis (2013) 30:381-392.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A monoclonal antibody comprising:
    an amino acid sequence in the heavy chain variable region comprising the following:
        in the CDR1 region NTFTEYTMH (SEQ ID NO: 388);
        in the CDR2 region GFNPNNGVTNYNQKFKG (SEQ ID NO: 389); and
        in the CDR3 region RYYHSLYVFYFDY (SEQ ID NO: 390); and
    an amino acid sequence in the light chain variable region comprising the following:
        in the CDR1 region SASQGISNYLN (SEQ ID NO:393);
        in the CDR2 region YTSSLHS (SEQ ID NO: 394); and
        in the CDR3 region QQYSKLPYT (SEQ ID NO: 395).

2. The monoclonal antibody of claim 1, comprising:
    (a) an amino acid sequence in the heavy chain variable region comprising a sequence of SEQ ID NO: 1139; and
    (b) an amino acid sequence in the light chain variable region comprising a sequence of SEQ ID NO: 1109.

3. The monoclonal antibody of claim 1, comprising:
    (a) an amino acid sequence in the heavy chain variable region comprising a sequence of any one of SEQ ID NOs: 1102, 1106, or 1133; and
    (b) an amino acid sequence in the light chain variable region comprising a sequence of any one of SEQ ID NOs: 1104, 1108, or 1135.

4. The monoclonal antibody of claim 1, which is monovalent.

5. The monoclonal antibody of claim 1, which is an Fab or a single chain variable fragment antibody (scFv).

6. The monoclonal antibody of claim 1, which is bispecific.

7. A bispecific T-cell engager comprising the monoclonal antibody of claim 1.

8. The monoclonal antibody of claim 1, which is humanized or an engineered antibody mimic.

9. An isolated nucleic acid encoding the monoclonal antibody of claim 1.

10. A method of treating a MUC1*-dependent cancer comprising administering a pharmaceutical composition comprising the antibody of claim 1.

11. The method of claim 10, wherein the pharmaceutical composition inhibits cancer metastasis.

12. The method of claim 10, wherein the pharmaceutical composition inhibits growth of cancer cells that express MUC1*.

13. A method for diagnosing cancer or cancer metastasis comprising contacting cells of an individual suspected of having cancer or a cancer metastasis with the monoclonal antibody of claim 1.

14. The method of claim 13, wherein the cells are cells of a tissue or tissue sample.

15. The method of claim 13, wherein the cells are in vitro.

16. A cell comprising a nucleic acid encoding the monoclonal antibody of claim 1.

* * * * *